US011566001B2

(12) United States Patent
Burns et al.

(10) Patent No.: US 11,566,001 B2
(45) Date of Patent: Jan. 31, 2023

(54) HEPATITIS B CAPSID ASSEMBLY MODULATORS

(71) Applicant: Venatorx Pharmaceuticals, Inc., Malvern, PA (US)

(72) Inventors: Christopher J. Burns, Malvern, PA (US); Glen Coburn, Bethel, CT (US); Bin Liu, Plainsboro, NJ (US); Jiangchao Yao, Princeton, NJ (US); Christopher Benetatos, Chester Springs, PA (US); Steven A. Boyd, Chester Springs, PA (US); Stephen M. Condon, Glenmoore, PA (US); Thomas Haimowitz, Newtown, PA (US)

(73) Assignee: VENATORX PHARMACEUTICALS, INC., Malvern, PA (US)

( * ) Notice: Subject to any disclaimer, the term of this patent is extended or adjusted under 35 U.S.C. 154(b) by 0 days.

(21) Appl. No.: 17/514,578

(22) Filed: Oct. 29, 2021

(65) Prior Publication Data
US 2022/0298110 A1   Sep. 22, 2022

Related U.S. Application Data

(63) Continuation of application No. 17/209,726, filed on Mar. 23, 2021, now abandoned, which is a continuation of application No. 16/671,815, filed on Nov. 1, 2019, now Pat. No. 11,014,881, which is a continuation of application No. 16/438,361, filed on Jun. 11, 2019, now Pat. No. 10,590,076.

(60) Provisional application No. 62/683,557, filed on Jun. 11, 2018, provisional application No. 62/832,734, filed on Apr. 11, 2019.

(51) Int. Cl.
| | | |
|---|---|---|
| C07D 487/04 | (2006.01) | |
| C07D 207/34 | (2006.01) | |
| A61P 31/20 | (2006.01) | |
| C07D 401/12 | (2006.01) | |
| C07D 405/12 | (2006.01) | |
| C07D 417/12 | (2006.01) | |
| C07D 403/06 | (2006.01) | |
| C07D 498/04 | (2006.01) | |
| C07D 401/06 | (2006.01) | |
| C07D 403/12 | (2006.01) | |
| C07D 413/12 | (2006.01) | |
| C07D 413/14 | (2006.01) | |
| C07D 471/04 | (2006.01) | |
| C07D 513/04 | (2006.01) | |
| C07D 207/337 | (2006.01) | |
| C07D 401/14 | (2006.01) | |
| C07D 405/14 | (2006.01) | |
| C07D 409/12 | (2006.01) | |
| C07D 409/14 | (2006.01) | |
| C07F 5/02 | (2006.01) | |

(52) U.S. Cl.
CPC ............ *C07D 207/34* (2013.01); *A61P 31/20* (2018.01); *C07D 207/337* (2013.01); *C07D 401/06* (2013.01); *C07D 401/12* (2013.01); *C07D 401/14* (2013.01); *C07D 403/06* (2013.01); *C07D 403/12* (2013.01); *C07D 405/12* (2013.01); *C07D 405/14* (2013.01); *C07D 409/12* (2013.01); *C07D 409/14* (2013.01); *C07D 413/12* (2013.01); *C07D 413/14* (2013.01); *C07D 417/12* (2013.01); *C07D 471/04* (2013.01); *C07D 487/04* (2013.01); *C07D 498/04* (2013.01); *C07D 513/04* (2013.01); *C07F 5/025* (2013.01)

(58) Field of Classification Search
CPC .................................................... C07D 487/04
See application file for complete search history.

(56) References Cited

U.S. PATENT DOCUMENTS

| | | | |
|---|---|---|---|
| 10,590,076 B2 | 3/2020 | Burns et al. | |
| 10,836,769 B2 * | 11/2020 | Gutierrez | C07D 487/04 |
| 11,014,881 B2 | 5/2021 | Burns et al. | |
| 11,247,965 B2 | 2/2022 | Burns et al. | |
| 2009/0012075 A1 | 1/2009 | Miller et al. | |
| 2015/0259324 A1 | 9/2015 | Hartman et al. | |
| 2019/0292187 A1 | 9/2019 | Gutierrez et al. | |
| 2019/0375708 A1 | 12/2019 | Burns et al. | |
| 2020/0123105 A1 | 4/2020 | Burns et al. | |
| 2021/0171439 A1 | 6/2021 | Burns et al. | |

FOREIGN PATENT DOCUMENTS

| | | |
|---|---|---|
| AU | 2005320134 B2 | 4/2011 |
| WO | WO-2013006394 A1 | 1/2013 |
| WO | WO-2015011281 A1 | 1/2015 |
| WO | WO-2015118057 A1 | 8/2015 |
| WO | WO-2017001655 A1 | 1/2017 |

(Continued)

OTHER PUBLICATIONS

CAS registry No. 894855-11-9; STN entry date: Jul. 20, 2006; Chemical name: 6-[(3R)-3-Amino-1-piperidinyl]-5-[(2-chlorophenyl)methyl]-N-cyclobutyl-2,3,4,5-tetrahydro-1,3-dimethyl-2,4-dioxo-1H-pyrrolo[3,2-d]pyrimidine-7-carboxamide whole document.

(Continued)

*Primary Examiner* — Laura L Stockton
(74) *Attorney, Agent, or Firm* — Wilson Sonsini Goodrich & Rosati

(57) ABSTRACT

Described herein are hepatitis B capsid assembly modulators and pharmaceutical compositions comprising said compounds. The subject compounds and compositions are useful for the treatment of hepatitis B.

11 Claims, No Drawings

(56) References Cited

FOREIGN PATENT DOCUMENTS

| WO | WO-2017156255 A1 | 9/2017 |
|----|------------------|--------|
| WO | WO-2018039531 A1 | 3/2018 |
| WO | WO-2018121689 A1 | 7/2018 |
| WO | WO-2019118358 A1 | 6/2019 |
| WO | WO-2019165374 A1 | 8/2019 |
| WO | WO-2019185016 A1 | 10/2019 |
| WO | WO-2019223791 A1 | 11/2019 |
| WO | WO-2019241292 A1 | 12/2019 |
| WO | WO-2020156494 A1 | 8/2020 |
| WO | WO-2021058001 A1 | 4/2021 |
| WO | WO-2021058002 A1 | 4/2021 |
| WO | WO-2021098850 A1 | 5/2021 |
| WO | WO-2021119081 A1 | 6/2021 |
| WO | WO-2021178362 A1 | 9/2021 |
| WO | WO-2022095950 A1 | 5/2022 |

OTHER PUBLICATIONS

CAS registry No. 894855-18-6; STN entry date: Jul. 20, 2006; Chemical name: 6-[(3R)-3-Amino-1-piperidinyl]-5-[(2-chloro-5-fluorophenyl)methyl]-N-cyclopropyl-2,3,4,5-tetrahydro-1,3-dimethyl-2,4-dioxo-1H-pyrrolo[3,2-d]pyrimidine-7-carboxamide whole document.

CAS registry No. 894855-20-0; STN entry date: Jul. 20, 2006; Chemical name: 6-[(3R)-3-Amino-1-piperidinyl]-5-[(2-chloro-5-fluorophenyl)methyl]-N-cyclobutyl-2,3,4,5-tetrahydro-1,3-dimethyl-2,4-dioxo-1H-pyrrolo[3,2-d]pyrimidine-7-carboxamide whole document.

CAS registry No. 894855-23-3; STN entry date: Jul. 20, 2006; Chemical name: 6-[(3R)-3-Amino-1-piperidinyl]-5-[(2-chloro-5-fluorophenyl)methyl]-2,3,4,5-tetrahydro-N-(3-hydroxytricyclo[3.3.1.1.3,7]dec-1-yl)-1,3-dimethyl-2,4-dioxo-1H-pyrrolo[3,2-d]pyrimidine-7-carboxamide.

CAS registry No. 894855-25-5; STN entry date: Jul. 20, 2006; Chemical name: 6-[(3R)-3-Amino-1-piperidinyl]-5-[(2-cyanophenyl)methyl]-N-cyclobutyl-2,3,4,5-tetrahydro-1,3-dimethyl-2,4-dioxo-1H-pyrrolo[3,2-d]pyrimidine-7-carboxamide whole document.

CAS registry No. 894855-26-6; STN entry date: Jul. 20, 2006; Chemical name: 6-[(3R)-3-Amino-1-piperidinyl]-5-[(2-cyanophenyl)methyl]-N-cyclobutyl-2,3,4,5-tetrahydro-1,3-dimethyl-2,4-dioxo-1H-pyrrolo[3,2-d]pyrimidine-7-carboxamide whole document.

CAS registry No. 894855-28-8; STN entry date: Jul. 20, 2006; Chemical name: 6-[(3R)-3-Amino-1-piperidinyl]-5-(2-butyn-1-yl)-N-cyclopropyl-2,3,4,5-tetrahydro-1,3-dimethyl-2,4-dioxo-1H-pyrrolo[3,2-d]pyrimidine-7-carboxamide.

Okamoto et al.: Intramolecular cyclization of 6-amino-5-[(2-substituted-2-(cyanovinyl) amino]-1,3-dimethyluracil: synthesis of 9-deazaxanthine derivatives and 8-(cyanomethyl) theophylline. The Journal of Organic Chemistry 49(5):908-912 (1984).

PCT/US2018/64768 International Search Report and Written Opinion dated Apr. 29, 2019.

PCT/US2019/036611 International Search Report and Written Opinion dated Oct. 1, 2019.

PCT/US2020/063936 International Search Report and Written Opinion dated Mar. 12, 2021.

PCT/US2021/020397 International Search Report and Written Opinion dated May 14, 2021.

PubChem CID 130421434. Created Oct. 7, 2017. Accessed Mar. 18, 2019.

U.S. Appl. No. 16/438,361 Office Action dated Aug. 26, 2019.
U.S. Appl. No. 16/671,815 Office Action dated Oct. 15, 2020.
U.S. Appl. No. 16/771,387 Office Action dated Jun. 24, 2021.

* cited by examiner

HEPATITIS B CAPSID ASSEMBLY MODULATORS

CROSS-REFERENCE

This application is a continuation of U.S. patent application Ser. No. 17/209,726 filed on Mar. 23, 2021, which is a continuation of U.S. patent application Ser. No. 16/671,815 filed on Nov. 1, 2019, now U.S. Pat. No. 11,014,881, issued on May 25, 2021, which is a continuation of U.S. patent application Ser. No. 16/438,361 filed on Jun. 11, 2019, now U.S. Pat. No. 10,590,076, issued on Mar. 17, 2020, which claims the benefit of U.S. Provisional Application Ser. No. 62/683,557 filed Jun. 11, 2018 and U.S. Provisional Application Ser. No. 62/832,734 filed Apr. 11, 2019, which are hereby incorporated by reference in their entirety.

BACKGROUND OF THE INVENTION

The present invention relates to small-molecule compounds that modulate capsid assembly and block hepatitis B virus (HBV) replication with the potential to be used as a monotherapy or in combination with other antivirals for the treatment of chronic HBV infection.

HBV is a small enveloped DNA virus belonging to the Hepadnaviridae family that is distributed worldwide as ten geographically distinct genotypes. Infection with HBV is typically self-limiting in otherwise healthy adults; however, vertical transmission or exposure during early childhood often results in a chronic lifelong infection. Worldwide there are an estimated >400 million individuals chronically infected with HBV that are at risk for complications due to liver disease, including cirrhosis, fibrosis, hepatocellular carcinoma and death. Each year 500,000 to 1 million people die from end stage liver disease as a consequence of HBV infection The compact HBV genome utilizes four overlapping reading frames to encode the major structural and non-structural proteins: polymerase (P), envelope (S), core (C) and the X protein (X). HBV enters human hepatocytes via receptor mediated endocytosis, following binding of the envelope glycoprotein to its primary receptor, the bile acid transporter sodium taurocholate co-transporting polypeptide (NTCP). Following fusion with the endosome membrane, the capsid is ejected into the cytoplasm and translocated to the nucleus. The partially double-stranded, relaxed, circular HBV genome (RC DNA) is converted to a covalently closed circular DNA form (cccDNA) by host cellular DNA repair mechanisms. The HBV cccDNA serves as the template for RNA polymerase II-dependent transcription of multiple RNA species, including viral mRNAs and the 3.2-kbp pre-genomic RNA (pgRNA). During the maturation process, pgRNA is packaged into capsids along with the HBV polymerase. The pgRNA is then reverse transcribed into a negative-stranded DNA template that is subsequently converted into the partially double-stranded RC DNA species by the polymerase. Mature, enveloped HBV particles containing the RC DNA genome are secreted from the surface of the infected hepatocyte ready to initiate new cycles of infection.

The capsid is composed of 240 copies of the core protein that spontaneously self-assemble through a network of weak inter-subunit interactions. In vitro evidence suggests that a timer of core dimers initiates the nucleation event that rapidly recruits additional dimers to form the icosahedral core structure (T=4). In addition to its structural role, encapsidation of the pgRNA is an essential step required for HBV DNA synthesis and formation of the mature capsid particle. The core protein also plays an important role in shuttling the RC DNA into the nucleus to initiate and maintain the cccDNA pools and may also play a role in regulating interferon sensitive gene expression. Thus, capsid modulators may have the unique ability to intervene at multiple points in the HBV lifecycle.

Several chemotype series of HBV capsid assembly modulators have been reported in the literature including: phenylpropenamides (PP) (e.g., AT-130), heteroarylpyrimidines (HAP) (e.g. Bay 41-4109), and sulfamoylbenzamides (SBA) (e.g. NVR 3-778). Capsid modulators exert their effects on the assembly process through one of two different mechanisms of action. The HAP series induces the aberrant assembly of large capsid aggregates that subsequently triggers the degradation of the core protein. The PP and SBA series, on the other hand, appear to accelerate capsid assembly resulting in the production of authentic empty capsid particles that have failed to incorporate pgRNA. Assembly modulators representing both mechanisms have demonstrated the ability to reduce HBV DNA levels in mouse models of infection. More recently, NVR 3-778 (SBA) demonstrated clinical proof-of-concept in a Phase 1b clinical trial, resulting in a −1.7 log 10 reduction in HBV DNA following 600 mg bid dosing for 29 days.

SUMMARY OF THE INVENTION

Described herein are compounds of Formula (I), (Ia)-(Id) that modulate the normal capsid assembly of hepatitis B core proteins to inhibit the hepatitis B lifecycle, and thus act as antiviral agents toward HBV.

Disclosed herein are compounds of Formula (I), or a pharmaceutically acceptable salt, solvate, or stereoisomer thereof:

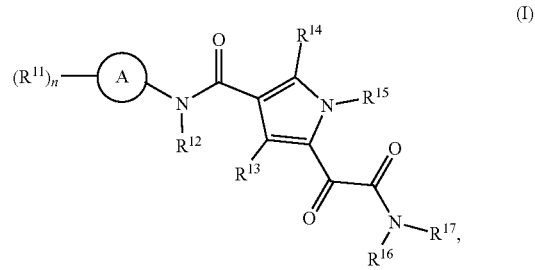

wherein:

Ring A is aryl, heteroaryl, cycloalkyl, or heterocycloalkyl;
each $R^{11}$ is independently halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, —$C_1$-$C_6$alkyl(aryl), —$C_1$-$C_6$alkyl(heteroaryl), —$C_1$-$C_6$alkyl(cycloalkyl), or —$C_1$-$C_6$alkyl(heterocycloalkyl); wherein each alkyl, alkenyl, alkynyl, cycloalkyl, heterocycloalkyl, aryl, and heteroaryl is independently optionally substituted with one, two, or three $R^1$;
or two $R^{11}$ on adjacent atoms are taken together with the atoms to which they are attached to form a cycloalkyl, heterocycloalkyl, aryl, or heteroaryl; each optionally substituted with one, two, or three $R^2$;

$R^{12}$ is hydrogen or $C_1$-$C_6$alkyl;

$R^{13}$ is hydrogen, halogen, —CN, —OH, —$OR^a$, —SH, —$SR^a$, —S(=O)$R^a$, —S(=O)$_2R^a$, —NO$_2$, —$NR^bR^c$, —NHS(=O)$_2R^a$, —S(=O)$_2NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^bC$(=O)$NR^bR^c$, —$NR^bC$(=O)$R^a$, —$NR^bC$(=O)$OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, —$C_1$-$C_6$alkyl(aryl), —$C_1$-$C_6$alkyl(heteroaryl), —$C_1$-$C_6$alkyl(cycloalkyl), or —$C_1$-$C_6$alkyl(heterocycloalkyl); wherein each alkyl, alkenyl, alkynyl, cycloalkyl, heterocycloalkyl, aryl, and heteroaryl is independently optionally substituted with one, two, or three $R^3$;

$R^{14}$ is hydrogen, halogen, —CN, —OH, —$OR^a$, —SH, —$SR^a$, —S(=O)$R^a$, —S(=O)$_2R^a$, —NO$_2$, —$NR^bR^c$, —NHS(=O)$_2R^a$, —S(=O)$_2NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^bC$(=O)$NR^bR^c$, —$NR^bC$(=O)$R^a$, —$NR^bC$(=O)$OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, —$C_1$-$C_6$alkyl(aryl), —$C_1$-$C_6$alkyl(heteroaryl), —$C_1$-$C_6$alkyl(cycloalkyl), or —$C_1$-$C_6$alkyl(heterocycloalkyl); wherein each alkyl, alkenyl, alkynyl, cycloalkyl, heterocycloalkyl, aryl, and heteroaryl is independently optionally substituted with one, two, or three $R^4$;

$R^{15}$ is hydrogen, —S(=O)$R^a$, —S(=O)$_2R^a$, —S(=O)$_2NR^bR^c$, —C(=O)$R^a$, —C(=O)$OR^b$, —C(=O)$NR^bR^c$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, —$C_1$-$C_6$alkyl(aryl), —$C_1$-$C_6$alkyl(heteroaryl), —$C_1$-$C_6$alkyl(cycloalkyl), or —$C_1$-$C_6$alkyl(heterocycloalkyl); wherein each alkyl, alkenyl, alkynyl, cycloalkyl, heterocycloalkyl, aryl, and heteroaryl is independently optionally substituted with one, two, or three $R^5$;

or $R^{14}$ and $R^{15}$ are taken together to form a heterocycloalkyl optionally substituted with one, two, three, or four $R^6$;

$R^{16}$ and $R^{17}$ are each independently hydrogen, —CN, —$OR^{20}$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, cycloalkenyl, heterocycloalkyl, heterocycloalkenyl, aryl, heteroaryl, —$C_1$-$C_6$alkyl(aryl), —$C_1$-$C_6$alkyl(heteroaryl), —$C_1$-$C_6$alkyl(cycloalkyl), or —$C_1$-$C_6$alkyl(heterocycloalkyl); wherein each alkyl, alkenyl, alkynyl, cycloalkyl, heterocycloalkyl, aryl, and heteroaryl is independently optionally substituted with one, two, or three $R^7$;

or $R^{16}$ and $R^{17}$ are taken together with the nitrogen atom to which they are attached to form a heterocycloalkyl or a heterocycloalkenyl; each optionally substituted with one, two, or three $R^8$;

each $R^{20}$ is independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^7$;

n is 0-4;

each $R'$, $R^2$, $R^3$, $R^4$, $R^5$, $R^6$, and $R^8$ is independently oxo, halogen, —CN, —OH, —$OR^a$, —SH, —$SR^a$, —S(=O)$R^a$, —S(=O)$_2R^a$, —NO$_2$, —$NR^bR^c$, —NHS(=O)$_2R^a$, —S(=O)$_2NR^bR^c$, —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^bC$(=O)$NR^bR^c$, —$NR^bC$(=O)$R^a$, —$NR^bC$(=O)$OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, —$C_1$-$C_6$alkyl(aryl), —$C_1$-$C_6$alkyl(heteroaryl), —$C_1$-$C_6$alkyl(cycloalkyl), or —$C_1$-$C_6$alkyl(heterocycloalkyl); wherein each alkyl, alkenyl, alkynyl, cycloalkyl, heterocycloalkyl, aryl, and heteroaryl is independently optionally substituted with one, two, or three oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl;

each $R^7$ is independently oxo, halogen, —CN, —OH, —$OR^a$, —SH, —$SR^a$, —S(=O)$R^a$, —S(=O)$_2R^a$, —NO$_2$, —$NR^bR^c$, —NHS(=O)$_2R^a$, —S(=O)$_2NR^bR^c$, —B($OR^b$)($OR^c$), —C(=O)$R^a$, —OC(=O)$R^a$, —C(=O)$OR^b$, —OC(=O)$OR^b$, —C(=O)$NR^bR^c$, —OC(=O)$NR^bR^c$, —$NR^bC$(=O)$NR^bR^c$, —$NR^bC$(=O)$R^a$, —$NR^bC$(=O)$OR^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, —$C_1$-$C_6$alkyl(aryl), —$C_1$-$C_6$alkyl(heteroaryl), —$C_1$-$C_6$alkyl(cycloalkyl), or —$C_1$-$C_6$alkyl(heterocycloalkyl); wherein each alkyl, alkenyl, alkynyl, cycloalkyl, heterocycloalkyl, aryl, and heteroaryl is independently optionally substituted with one, two, or three $R^{7a}$;

each $R^{7a}$ is independently oxo, halogen, —CN, —OH, —$OR^a$, —$NR^bR^c$, —C(=O)$R^a$, —C(=O)$OR^b$, —C(=O)$NR^bR^c$, $C_1$-$C_6$alkyl, $C_1$-$C_6$haloalkyl, $C_1$-$C_6$hydroxyalkyl, $C_1$-$C_6$aminoalkyl, cycloalkyl, heterocycloalkyl, aryl, or heteroaryl; wherein each alkyl, cycloalkyl, heterocycloalkyl, aryl, and heteroaryl is independently optionally substituted with one, two, or three oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl;

each $R^a$ is independently $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl; and each $R^b$ and $R^c$ are independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl;

or $R^b$ and $R^c$ are taken together with the atom to which they are attached to form a heterocycloalkyl optionally substituted with one, two, or three oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, C$_1$-C$_6$alkyl, C$_1$-C$_6$haloalkyl, C$_1$-C$_6$hydroxyalkyl, or C$_1$-C$_6$aminoalkyl.

Also disclosed herein are pharmaceutical compositions comprising a compound disclosed herein, or a pharmaceutically acceptable salt, solvate, or stereoisomer thereof, and a pharmaceutically acceptable excipient.

Also disclosed herein are methods of treating an infection in a subject, comprising administering to the subject a compound disclosed herein, or a pharmaceutically acceptable salt, solvate, or stereoisomer thereof or a pharmaceutical composition disclosed herein. In some embodiments of a method of treating an infection; the infection is a viral infection. In some embodiments of a method of treating an infection; the infection is caused by the hepatitis B virus. In some embodiments of a method of treating an infection; the infection is hepatitis B.

INCORPORATION BY REFERENCE

All publications, patents, and patent applications mentioned in this specification are herein incorporated by reference to the same extent as if each individual publication, patent, or patent application was specifically and individually indicated to be incorporated by reference.

DETAILED DESCRIPTION OF THE INVENTION

Chronic hepatitis B infection (CHB) is currently managed with interferon-alpha or nucleoside(tide) analog-based therapies that target the HBV encoded polymerase/reverse transcriptase. The effectiveness of interferon-alpha is limited by inadequate long term responses and severe side effects, while entecavir and tenofovir, are generally well-tolerated, possess a high barrier to resistance and potently suppress viral replication. None of the aforementioned frontline therapies are curative, however, and expensive lifelong therapy is required to maintain a virologic response and prevent the complications associated with liver disease. Novel therapies representing different treatment classes are therefore urgently required to improve functional cure rates (i.e. defined as the loss of HBsAg expression) and shorten treatment durations. Modulators of HBV capsid assembly represent one such class of antivirals with the potential to improve outcomes for chronically infected individuals.

Definitions

In the following description, certain specific details are set forth in order to provide a thorough understanding of various embodiments. However, one skilled in the art will understand that the invention may be practiced without these details. In other instances, well-known structures have not been shown or described in detail to avoid unnecessarily obscuring descriptions of the embodiments. Unless the context requires otherwise, throughout the specification and claims which follow, the word "comprise" and variations thereof, such as, "comprises" and "comprising" are to be construed in an open, inclusive sense, that is, as "including, but not limited to." Further, headings provided herein are for convenience only and do not interpret the scope or meaning of the claimed invention.

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. Also, as used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The terms below, as used herein, have the following meanings, unless indicated otherwise:

"oxo" refers to =O.

"Alkyl" refers to an optionally substituted straight-chain, or optionally substituted branched-chain saturated hydrocarbon monoradical having from one to about ten carbon atoms, more preferably one to six carbon atoms. Examples include, but are not limited to methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, n-butyl, isobutyl, sec-butyl, t-butyl, n-pentyl, isopentyl, neopentyl, tert-amyl and hexyl, and longer alkyl groups, such as heptyl, octyl and the like. Whenever it appears herein, a numerical range such as "C$_1$-C$_6$ alkyl" or "C$_{1-6}$alkyl", means that the alkyl group may consist of 1 carbon atom, 2 carbon atoms, 3 carbon atoms, 4 carbon atoms, 5 carbon atoms or 6 carbon atoms, although the present definition also covers the occurrence of the term "alkyl" where no numerical range is designated. In some embodiments, the alkyl is a C$_{1-10}$alkyl. In some embodiments, the alkyl is a C$_{1-6}$alkyl. In some embodiments, the alkyl is a C$_{1-5}$alkyl. In some embodiments, the alkyl is a C$_{1-4}$alkyl. In some embodiments, the alkyl is a C$_{1-3}$alkyl. Unless stated otherwise specifically in the specification, an alkyl group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkyl is optionally substituted with oxo, halogen, —CN, —OH, —OMe, —NH$_2$, or —NO$_2$. In some embodiments, the alkyl is optionally substituted with halogen, —CN, —OH, or —OMe. In some embodiments, the alkyl is optionally substituted with halogen.

"Alkenyl" refers to an optionally substituted straight-chain, or optionally substituted branched-chain hydrocarbon monoradical having one or more carbon-carbon double-bonds and having from two to about ten carbon atoms, more preferably two to about six carbon atoms. The group may be in either the cis or trans conformation about the double bond(s), and should be understood to include both isomers. Examples include, but are not limited to ethenyl (—CH=CH$_2$), 1-propenyl (—CH$_2$CH=CH$_2$), isopropenyl [—C(CH$_3$)=CH$_2$], butenyl, 1,3-butadienyl and the like. Whenever it appears herein, a numerical range such as "C$_2$-C$_6$ alkenyl" or "C$_{2-6}$alkenyl", means that the alkenyl group may consist of 2 carbon atoms, 3 carbon atoms, 4 carbon atoms, 5 carbon atoms or 6 carbon atoms, although the present definition also covers the occurrence of the term "alkenyl" where no numerical range is designated. Unless stated otherwise specifically in the specification, an alkenyl group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkenyl is optionally substituted with oxo, halogen, —CN, —OH, —OMe, —NH$_2$, or —NO$_2$. In some embodiments, the alkenyl is optionally substituted with halogen, —CN, —OH, or —OMe. In some embodiments, the alkenyl is optionally substituted with halogen.

"Alkynyl" refers to an optionally substituted straight-chain or optionally substituted branched-chain hydrocarbon monoradical having one or more carbon-carbon triple-bonds and having from two to about ten carbon atoms, more preferably from two to about six carbon atoms. Examples include, but are not limited to ethynyl, 2-propynyl, 2-butynyl, 1,3-butadiynyl and the like. Whenever it appears herein, a numerical range such as "C$_2$-C$_6$ alkynyl" or "C$_{2-6}$alkynyl", means that the alkynyl group may consist of 2 carbon atoms, 3 carbon atoms, 4 carbon atoms, 5 carbon atoms or 6 carbon atoms, although the present definition also covers the occurrence of the term "alkynyl" where no numerical range is designated. Unless stated otherwise specifically in the specification, an alkynyl group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkynyl is optionally substituted with oxo, halogen, —CN, —OH, —OMe, —NH$_2$, or —NO$_2$. In some embodiments, the alkynyl is optionally substituted with halogen, —CN, —OH, or —OMe. In some embodiments, the alkynyl is optionally substituted with halogen.

"Alkylene" refers to a straight or branched divalent hydrocarbon chain. Unless stated otherwise specifically in the specification, an alkylene group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkylene is optionally substituted with oxo, halogen, —CN, —OH, —OMe, —NH$_2$, or —NO$_2$. In some embodiments, the alkylene is optionally substituted with halogen, —CN, —OH, or —OMe. In some embodiments, the alkylene is optionally substituted with halogen.

"Alkoxy" refers to a radical of the formula —OR$_a$ where R$_a$ is an alkyl radical as defined. Unless stated otherwise specifically in the specification, an alkoxy group may be optionally substituted as described below, for example, with oxo, halogen, amino, nitrile, nitro, hydroxyl, haloalkyl, alkoxy, aryl, cycloalkyl, heterocycloalkyl, heteroaryl, and the like. In some embodiments, the alkoxy is optionally substituted with halogen, —CN, —OH, —OMe, —NH$_2$, or —NO$_2$. In some embodiments, the alkoxy is optionally substituted with halogen, —CN, —OH, or —OMe. In some embodiments, the alkoxy is optionally substituted with halogen.

"Aryl" refers to a radical derived from a hydrocarbon ring system comprising hydrogen, 6 to 30 carbon atoms and at least one aromatic ring. The aryl radical may be a monocyclic, bicyclic, tricyclic or tetracyclic ring system, which may include fused (when fused with a cycloalkyl or heterocycloalkyl ring, the aryl is bonded through an aromatic ring atom) or bridged ring systems. In some embodiments, the aryl is a 6- to 10-membered aryl. In some embodiments, the aryl is a 6-membered aryl (phenyl). Aryl radicals include, but are not limited to, aryl radicals derived from the hydrocarbon ring systems of anthrylene, naphthylene, phenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, an aryl may be optionally substituted as described below, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, the aryl is optionally substituted with halogen, methyl, ethyl, —CN, —CF$_3$, —OH, —OMe, —NH$_2$, or —NO$_2$. In some embodiments, the aryl is optionally substituted with halogen, methyl, ethyl, —CN, —CF$_3$, —OH, or —OMe. In some embodiments, the aryl is optionally substituted with halogen.

"Cycloalkyl" refers to a stable, partially or fully saturated, monocyclic or polycyclic carbocyclic ring, which may include fused (when fused with an aryl or a heteroaryl ring, the cycloalkyl is bonded through a non-aromatic ring atom) or bridged ring systems. Representative cycloalkyls include, but are not limited to, cycloalkyls having from three to fifteen carbon atoms (C$_3$-C$_{15}$ cycloalkyl), from three to ten carbon atoms (C$_3$-C$_{10}$ cycloalkyl), from three to eight carbon atoms (C$_3$-C$_8$ cycloalkyl), from three to six carbon atoms (C$_3$-C$_6$ cycloalkyl), from three to five carbon atoms (C$_3$-C$_5$ cycloalkyl), or three to four carbon atoms (C$_3$-C$_4$ cycloalkyl). In some embodiments, the cycloalkyl is a 3- to 10-membered cycloalkyl. In some embodiments, the cycloalkyl is a 3- to 6-membered cycloalkyl. In some embodiments, the cycloalkyl is a 5- to 6-membered cycloalkyl. Monocyclic cycloalkyls include, for example, cyclopropyl, cyclobutyl, cyclopentyl, cyclohexyl, cycloheptyl, and cyclooctyl. Polycyclic cycloalkyls include, for example, adamantyl, norbornyl, decalinyl, bicyclo[3.3.0]octane, bicyclo[4.3.0]nonane, cis-decalin, trans-decalin, bicyclo[2.1.1]hexane, bicyclo[2.2.1]heptane, bicyclo[2.2.2]octane, bicyclo[3.2.2]nonane, and bicyclo[3.3.2]decane, and 7,7-dimethyl-bicyclo[2.2.1]heptanyl. Partially saturated cycloalkyls include, for example cyclopentenyl, cyclohexenyl, cycloheptenyl, and cyclooctenyl. Unless stated otherwise specifically in the specification, a cycloalkyl is optionally substituted, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, a cycloalkyl is optionally substituted with oxo, halogen, methyl, ethyl, —CN, —CF$_3$, —OH, —OMe, —NH$_2$, or —NO$_2$. In some embodiments, a cycloalkyl is optionally substituted with oxo, halogen, methyl, ethyl, —CN, —CF$_3$, —OH, or —OMe. In some embodiments, the cycloalkyl is optionally substituted with halogen.

"Cycloalkenyl" refers to a partially unsaturated, monocyclic or polycyclic carbocyclic ring, which may include fused (when fused with an aryl or a heteroaryl ring, the cycloalkenyl is bonded through a non-aromatic ring atom) or bridged ring systems. Representative cycloalkenyl include, but are not limited to, cycloalkenyls having from three to fifteen carbon atoms (C$_3$-C$_{15}$ cycloalkenyl), from three to ten carbon atoms (C$_3$-C$_{10}$ cycloalkenyl), from three to eight carbon atoms (C$_3$-C$_8$ cycloalkenyl), from three to six carbon atoms (C$_3$-C$_6$ cycloalkenyl), from three to five carbon atoms (C$_3$-C$_5$ cycloalkenyl), four to six carbon atoms (C$_4$-C$_6$ cycloalkenyl), four to eight carbon atoms (C$_4$-C$_8$ cycloalkenyl), or four to ten carbon atoms (C$_4$-C$_{10}$ cycloalkenyl). Monocyclic cycloalkenyl include, for example, cyclopentene, cyclohexene, cycloheptene, cyclopentadiene, cyclohexadiene, cycloheptadiene, and cycloheptatriene. Unless stated otherwise specifically in the specification, a cycloalkenyl may be optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, the cycloalkenyl is optionally substituted with oxo, halogen, methyl, ethyl, —CN, —CF$_3$, —OH, —OMe, —NH$_2$, or —NO$_2$. In some embodiments, the cycloalkenyl is optionally substituted with halogen, methyl, ethyl, —CN, —CF$_3$, —OH, or —OMe. In some embodiments, the cycloalkenyl is optionally substituted with halogen.

"Halo" or "halogen" refers to bromo, chloro, fluoro or iodo. In some embodiments, halogen is fluoro or chloro. In some embodiments, halogen is fluoro.

"Haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

"Heterocycloalkyl" refers to a stable 3- to 24-membered fully saturated ring radical comprising 2 to 23 carbon atoms and from one to 8 heteroatoms selected from the group consisting of nitrogen, oxygen, phosphorous and sulfur. In some embodiments, the heterocycloalkyl comprises one to three heteroatoms selected from the group consisting of nitrogen, oxygen, and sulfur. In some embodiments, the heterocycloalkyl comprises one to three heteroatoms selected from the group consisting of nitrogen and oxygen. In some embodiments, the heterocycloalkyl comprises one to three nitrogens. In some embodiments, the heterocycloalkyl comprises one or two nitrogens. In some embodiments, the heterocycloalkyl comprises one nitrogen. In some embodiments, the heterocycloalkyl comprises one nitrogen and one oxygen. Unless stated otherwise specifically in the specification, the heterocycloalkyl radical may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon, or sulfur atoms in the heterocycloalkyl radical may be optionally oxidized; the nitrogen atom may be optionally quaternized. Representative heterocycloalkyls include, but are not limited to, heterocycloalkyls having from two to fifteen carbon atoms (C$_2$-C$_{15}$ heterocycloalkyl), from two to ten carbon atoms (C$_2$-C$_{10}$ heterocycloalkyl), from two to eight carbon atoms (C$_2$-C$_8$ heterocycloalkyl), from two to seven carbon atoms (C$_2$-C$_7$ heterocycloalkyl), from two to six carbon atoms (C$_2$-C$_6$ heterocycloalkyl), from two to five carbon atoms (C$_2$-O$_5$ heterocycloalkyl), or two to four carbon atoms (C$_2$-C$_4$ heterocycloalkyl). Examples of such heterocycloalkyl radicals include, but are not limited to, aziridinyl, azetidinyl, oxetanyl, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, 1,1-dioxo-thiomorpholinyl, 1,3-dihydroisobenzofuran-1-yl, 3-oxo-1,3-dihydroisobenzofuran-1-yl, methyl-2-oxo-1,3-dioxol-4-yl, and 2-oxo-1,3-dioxol-4-yl. The term heterocycloalkyl also includes all ring forms of the carbohydrates, including but not limited to the monosaccharides, the disaccharides and the oligosaccharides. Unless otherwise noted, heterocycloalkyls have from 2 to 10 carbons in the ring. It is understood that when referring to the number of carbon atoms in a heterocycloalkyl, the number of carbon atoms in the heterocycloalkyl is not the same as the total number of atoms (including the heteroatoms) that make up the heterocycloalkyl (i.e. skeletal atoms of the heterocycloalkyl ring). In some embodiments, the heterocycloalkyl is a 3- to 8-membered heterocycloalkyl. In some embodiments, the heterocycloalkyl is a 3- to 7-membered heterocycloalkyl. In some embodiments, the heterocycloalkyl is a 3- to 6-membered heterocycloalkyl. In some embodiments, the heterocycloalkyl is a 4- to 6-membered heterocycloalkyl. In some embodiments, the heterocycloalkyl is a 5- to 6-membered heterocycloalkyl. Unless stated otherwise specifically in the specification, a heterocycloalkyl may be optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, the heterocycloalkyl is optionally substituted with oxo, halogen, methyl, ethyl, —CN, —CF$_3$, —OH, —OMe, —NH$_2$, or —NO$_2$. In some embodiments, the heterocycloalkyl is optionally substituted with halogen, methyl, ethyl, —CN, —CF$_3$, —OH, or —OMe. In some embodiments, the heterocycloalkyl is optionally substituted with halogen.

"Heterocycloalkenyl" refers to a stable 3- to 24-membered partially unsaturated ring radical comprising 2 to 23 carbon atoms and from one to 8 heteroatoms selected from the group consisting of nitrogen, oxygen, phosphorous and sulfur. In some embodiments, the heterocycloalkenyl comprises one to three heteroatoms selected from the group consisting of nitrogen, oxygen, and sulfur. In some embodiments, the heterocycloalkenyl comprises one to three heteroatoms selected from the group consisting of nitrogen and oxygen. In some embodiments, the heterocycloalkenyl comprises one to three nitrogens. In some embodiments, the heterocycloalkenyl comprises one or two nitrogens. In some embodiments, the heterocycloalkenyl comprises one nitrogen. Unless stated otherwise specifically in the specification, the heterocycloalkenyl may be a monocyclic, bicyclic, tricyclic or tetracyclic ring system, which may include fused (when fused with an aryl or a heteroaryl ring, the heterocycloalkyl is bonded through a non-aromatic ring atom) or bridged ring systems; and the nitrogen, carbon or sulfur atoms in the heterocycloalkenyl radical may be optionally oxidized; the nitrogen atom may be optionally quaternized. Representative heterocycloalkenyls include, but are not limited to, heterocycloalkenyls having from two to ten carbon atoms (C$_2$-C$_{10}$ heterocycloalkenyl), from two to eight carbon atoms (C$_2$-C$_8$ heterocycloalkenyl), from two to seven carbon atoms (C$_2$-C$_7$ heterocycloalkenyl), from two to six carbon atoms (C$_2$-C$_6$ heterocycloalkenyl), from two to five carbon atoms (C$_2$-C$_5$ heterocycloalkenyl), or two to four carbon atoms (C$_2$-C$_4$ heterocycloalkenyl). Examples of such heterocycloalkenyls include, but are not limited to, 2,3-dihydro-1H-pyrrole, 1,2,3,6-tetrahydropyridine, 1,2-dihydropyridine, 1,2,3,4-tetrahydropyrazine, and 3,4-dihydro-2H-1,4-oxazine. Unless otherwise noted, heterocycloalkenyls have from 2 to 10 carbons in the ring. It is understood that when referring to the number of carbon atoms in a heterocycloalkenyl, the number of carbon atoms in the heterocycloalkenyl is not the same as the total number of atoms (including the heteroatoms) that make up the heterocycloalkenyl (i.e. skeletal atoms of the heterocycloalkenyl ring). In some embodiments, the heterocycloalkenyl is a 3- to 8-membered heterocycloalkenyl. In some embodiments, the heterocycloalkenyl is a 3- to 7-membered heterocycloalkenyl. In some embodiments, the heterocycloalkenyl is a 3- to 6-membered heterocycloalkenyl. In some embodiments, the heterocycloalkenyl is a 4- to 6-membered heterocycloalkenyl. In some embodiments, the heterocycloalkenyl is a 5- to 6-membered heterocycloalkenyl. Unless stated otherwise specifically in the specification, a heterocycloalkenyl may be optionally substituted as described below, for example, with oxo, halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, the heterocycloalkenyl is optionally substituted with oxo, halogen, methyl, ethyl, —CN, —CF$_3$, —OH, —OMe, —NH$_2$, or —NO$_2$. In some embodiments, the heterocycloalkenyl is optionally substituted with halogen, methyl, ethyl, —CN, —CF$_3$, —OH, or —OMe. In some embodiments, the heterocycloalkenyl is optionally substituted with halogen.

"Heteroaryl" refers to a 5- to 14-membered ring system radical comprising hydrogen atoms, one to thirteen carbon atoms, one to six heteroatoms selected from the group consisting of nitrogen, oxygen, phosphorous and sulfur, and at least one aromatic ring. In some embodiments, the heteroaryl comprises one to three heteroatoms selected from the group consisting of nitrogen, oxygen, and sulfur. In some embodiments, the heteroaryl comprises one to three heteroatoms selected from the group consisting of nitrogen and oxygen. In some embodiments, the heteroaryl comprises one to three nitrogens. In some embodiments, the heteroaryl comprises one or two nitrogens. In some embodiments, the heteroaryl comprises one nitrogen. The heteroaryl radical may be a monocyclic, bicyclic, tricyclic or tetracyclic ring system, which may include fused (when fused with a cycloalkyl or heterocycloalkyl ring, the heteroaryl is bonded through an aromatic ring atom) or bridged ring systems; and the nitrogen, carbon or sulfur atoms in the heteroaryl radical may be optionally oxidized; the nitrogen atom may be optionally quaternized. In some embodiments, the heteroaryl is a 5- to 10-membered heteroaryl. In some embodiments, the heteroaryl is a 5- to 6-membered heteroaryl. In some embodiments, the heteroaryl is a 6-membered heteroaryl. In some embodiments, the heteroaryl is a 5-membered heteroaryl. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl may be optionally substituted as described below, for example, with halogen, amino, nitrile, nitro, hydroxyl, alkyl, alkenyl, alkynyl, haloalkyl, alkoxy, aryl, cycloalkyl, heterocycloalkyl, heteroaryl, and the like. In some embodiments, the heteroaryl is optionally substituted with halogen, methyl, ethyl, —CN, —CF$_3$, —OH, —OMe, —NH$_2$, or —NO$_2$. In some embodiments, the heteroaryl is optionally substituted with halogen, methyl, ethyl, —CN, —CF$_3$, —OH, or —OMe. In some embodiments, the heteroaryl is optionally substituted with halogen.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl" as defined above. Further, an optionally substituted group may be un-substituted (e.g., —CH$_2$CH$_3$), fully substituted (e.g., —CF$_2$CF$_3$), mono-substituted (e.g., —CH$_2$CH$_2$F) or substituted at a level anywhere in-between fully substituted and mono-substituted (e.g., —CH$_2$CHF$_2$, —CH$_2$CF$_3$, —CF$_2$CH$_3$, —CFHCHF$_2$, etc.). It will be understood by those skilled in the art with respect to any group containing one or more substituents that such groups are not intended to introduce any substitution or substitution patterns (e.g., substituted alkyl includes optionally substituted cycloalkyl groups, which in turn are defined as including optionally substituted alkyl groups, potentially ad infinitum) that are sterically impractical and/or synthetically non-feasible. Thus, any substituents described should generally be understood as having a maximum molecular weight of about 1,000 daltons, and more typically, up to about 500 daltons.

An "effective amount" or "therapeutically effective amount" refers to an amount of a compound administered to a mammalian subject, either as a single dose or as part of a series of doses, which is effective to produce a desired therapeutic effect.

"Treatment" of an individual (e.g. a mammal, such as a human) or a cell is any type of intervention used in an attempt to alter the natural course of the individual or cell. In some embodiments, treatment includes administration of a pharmaceutical composition, subsequent to the initiation of a pathologic event or contact with an etiologic agent and includes stabilization of the condition (e.g., condition does not worsen) or alleviation of the condition. In some embodiments, treatment also includes prophylactic treatment (e.g., administration of a composition described herein when an individual is suspected to be suffering from a viral infection, e.g., hepatitis B).

Compounds

Described herein are compounds of Formula (I), (Ia)-(Id), or a pharmaceutically acceptable salt, solvate, or stereoisomer thereof useful in the treatment of viral infections. In some embodiments, the viral infection is a chronic hepatitis B infection.

Disclosed herein is a compound of Formula (I), or a pharmaceutically acceptable salt, solvate, or stereoisomer thereof:

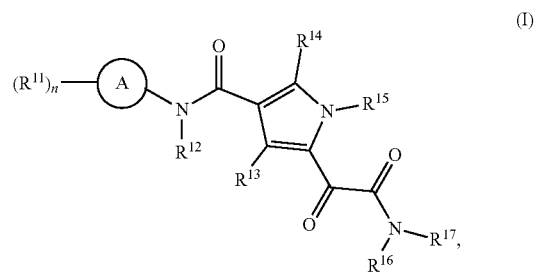

wherein:
Ring A is aryl, heteroaryl, cycloalkyl, or heterocycloalkyl;
each $R^{11}$ is independently halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, —C$_1$-C$_6$alkyl (aryl), —C$_1$-C$_6$alkyl(heteroaryl), —C$_1$-C$_6$alkyl(cycloalkyl), or —C$_1$-C$_6$alkyl(heterocycloalkyl); wherein each alkyl, alkenyl, alkynyl, cycloalkyl, heterocycloalkyl, aryl, and heteroaryl is independently optionally substituted with one, two, or three R';

or two R$^{11}$ on adjacent atoms are taken together with the atoms to which they are attached to form a cycloalkyl, heterocycloalkyl, aryl, or heteroaryl; each optionally substituted with one, two, or three R$^2$;

R$^{12}$ is hydrogen or C$_1$-C$_6$alkyl;

R$^{13}$ is hydrogen, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, —C$_1$-C$_6$alkyl(aryl), —C$_1$-C$_6$alkyl(heteroaryl), —C$_1$-C$_6$alkyl(cycloalkyl), or —C$_1$-C$_6$alkyl(heterocycloalkyl); wherein each alkyl, alkenyl, alkynyl, cycloalkyl, heterocycloalkyl, aryl, and heteroaryl is independently optionally substituted with one, two, or three R$^3$;

R$^{14}$ is hydrogen, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, —C$_1$-C$_6$alkyl(aryl), —C$_1$-C$_6$alkyl(heteroaryl), —C$_1$-C$_6$alkyl(cycloalkyl), or —C$_1$-C$_6$alkyl(heterocycloalkyl); wherein each alkyl, alkenyl, alkynyl, cycloalkyl, heterocycloalkyl, aryl, and heteroaryl is independently optionally substituted with one, two, or three R$^4$;

R$^{15}$ is hydrogen, —S(=O)R$^a$, —S(=O)$_2$R$^a$, —S(=O)$_2$NR$^b$R$^c$, —C(=O)R$^a$, —C(=O)OR$^b$, —C(=O)NR$^b$R$^c$, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, —C$_1$-C$_6$alkyl(aryl), —C$_1$-C$_6$alkyl(heteroaryl), —C$_1$-C$_6$alkyl(cycloalkyl), or —C$_1$-C$_6$alkyl(heterocycloalkyl); wherein each alkyl, alkenyl, alkynyl, cycloalkyl, heterocycloalkyl, aryl, and heteroaryl is independently optionally substituted with one, two, or three R$^5$;

or R$^{14}$ and R$^{15}$ are taken together to form a heterocycloalkyl optionally substituted with one, two, three, or four R$^6$;

R$^{16}$ and R$^{17}$ are each independently hydrogen, —CN, —OR$^{20}$, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, cycloalkenyl, heterocycloalkyl, heterocycloalkenyl, aryl, heteroaryl, —C$_1$-C$_6$alkyl(aryl), —C$_1$-C$_6$alkyl(heteroaryl), —C$_1$-C$_6$alkyl(cycloalkyl), or —C$_1$-C$_6$alkyl(heterocycloalkyl); wherein each alkyl, alkenyl, alkynyl, cycloalkyl, heterocycloalkyl, aryl, and heteroaryl is independently optionally substituted with one, two, or three R$^7$;

or R$^{16}$ and R$^{17}$ are taken together with the nitrogen atom to which they are attached to form a heterocycloalkyl or a heterocycloalkenyl; each optionally substituted with one, two, or three R$^8$;

each R$^{20}$ is independently hydrogen, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^7$;

n is 0-4;

each R', R$^2$, R$^3$, R$^4$, R$^5$, R$^6$, and R$^8$ is independently oxo, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, —C$_1$-C$_6$alkyl(aryl), —C$_1$-C$_6$alkyl(heteroaryl), —C$_1$-C$_6$alkyl(cycloalkyl), or —C$_1$-C$_6$alkyl(heterocycloalkyl); wherein each alkyl, alkenyl, alkynyl, cycloalkyl, heterocycloalkyl, aryl, and heteroaryl is independently optionally substituted with one, two, or three oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, C$_1$-C$_6$alkyl, C$_1$-C$_6$haloalkyl, C$_1$-C$_6$hydroxyalkyl, or C$_1$-C$_6$aminoalkyl;

each R$^7$ is independently oxo, halogen, —CN, —OH, —OR$^a$, —SH, —SW, —S(=O)R$^a$, —S(=O)$_2$R$^a$, —NO$_2$, —NR$^b$R$^c$, —NHS(=O)$^2$R$^a$, —S(=O)$_2$NR$^b$R$^c$, —B(OR$^b$)(OR$^c$), —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, —C$_1$-C$_6$alkyl(aryl), —C$_1$-C$_6$alkyl(heteroaryl), —C$_1$-C$_6$alkyl(cycloalkyl), or —C$_1$-C$_6$alkyl(heterocycloalkyl); wherein each alkyl, alkenyl, alkynyl, cycloalkyl, heterocycloalkyl, aryl, and heteroaryl is independently optionally substituted with one, two, or three R$^{7a}$;

each R$^{7a}$ is independently oxo, halogen, —CN, —OH, —OR$^a$, —NR$^b$R$^c$, —C(=O)$_2$R$^a$, —C(=O)OR$^b$, —C(=O)NR$^b$R$^c$, C$_1$-C$_6$alkyl, C$_1$-C$_6$haloalkyl, C$_1$-C$_6$hydroxyalkyl, C$_1$-C$_6$aminoalkyl, cycloalkyl, heterocycloalkyl, aryl, or heteroaryl; wherein each alkyl, cycloalkyl, heterocycloalkyl, aryl, and heteroaryl is independently optionally substituted with one, two, or three oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, C$_1$-C$_6$alkyl, C$_1$-C$_6$haloalkyl, C$_1$-C$_6$hydroxyalkyl, or C$_1$-C$_6$aminoalkyl;

each R$^a$ is independently C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, C$_1$-C$_6$alkyl, C$_1$-C$_6$haloalkyl, C$_1$-C$_6$hydroxyalkyl, or C$_1$-C$_6$aminoalkyl; and each R$^b$ and R$^c$ are independently hydrogen, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, C$_1$-C$_6$alkyl, C$_1$-C$_6$haloalkyl, C$_1$-C$_6$hydroxyalkyl, or C$_1$-C$_6$aminoalkyl;

or R$^b$ and R$^c$ are taken together with the atom to which they are attached to form a heterocycloalkyl optionally substituted with one, two, or three oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, C$_1$-C$_6$alkyl, C$_1$-C$_6$haloalkyl, C$_1$-C$_6$hydroxyalkyl, or C$_1$-C$_6$aminoalkyl.

In some embodiment of a compound of Formula (I), R$^{14}$ is hydrogen, halogen, —CN, —OH, —OR$^a$, —NR$^b$R$^c$, —C(=O)OR$^b$, —C(=O)NR$^b$R$^c$, C$_1$-C$_6$alkyl, C$_1$-C$_6$haloalkyl, or cycloalkyl.

Disclosed herein is a compound of Formula (I), or a pharmaceutically acceptable salt, solvate, or stereoisomer thereof:

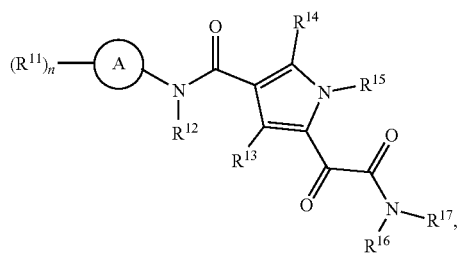

(I)

wherein:
Ring A is aryl, heteroaryl, cycloalkyl, or heterocycloalkyl;
each R$^{11}$ is independently halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, —C$_1$-C$_6$alkyl(aryl), —C$_1$-C$_6$alkyl(heteroaryl), —C$_1$-C$_6$alkyl(cycloalkyl), or —C$_1$-C$_6$alkyl(heterocycloalkyl); wherein each alkyl, alkenyl, alkynyl, cycloalkyl, heterocycloalkyl, aryl, and heteroaryl is independently optionally substituted with one, two, or three R$^1$;
or two R$^{11}$ on adjacent atoms are taken together with the atoms to which they are attached to form a cycloalkyl, heterocycloalkyl, aryl, or heteroaryl; each optionally substituted with one, two, or three R$^2$;
R$^{12}$ is hydrogen or C$_1$-C$_6$alkyl;
R$^{13}$ is hydrogen, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, —C$_1$-C$_6$alkyl(aryl), —C$_1$-C$_6$alkyl(heteroaryl), —C$_1$-C$_6$alkyl(cycloalkyl), or —C$_1$-C$_6$alkyl(heterocycloalkyl); wherein each alkyl, alkenyl, alkynyl, cycloalkyl, heterocycloalkyl, aryl, and heteroaryl is independently optionally substituted with one, two, or three R$^3$;
R$^{14}$ is hydrogen, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, —C$_1$-C$_6$alkyl(aryl), —C$_1$-C$_6$alkyl(heteroaryl), —C$_1$-C$_6$alkyl(cycloalkyl), or —C$_1$-C$_6$alkyl(heterocycloalkyl); wherein each alkyl, alkenyl, alkynyl, cycloalkyl, heterocycloalkyl, aryl, and heteroaryl is independently optionally substituted with one, two, or three R$^4$;
R$^{15}$ is hydrogen, —S(=O)R$^a$, —S(=O)$_2$R$^a$, —S(=O)$_2$NR$^b$R$^c$, —C(=O)R$^a$, —C(=O)OR$^b$, —C(=O)NR$^b$R$^c$, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, —C$_1$-C$_6$alkyl(aryl), —C$_1$-C$_6$alkyl(heteroaryl), —C$_1$-C$_6$alkyl(cycloalkyl), or —C$_1$-C$_6$alkyl(heterocycloalkyl); wherein each alkyl, alkenyl, alkynyl, cycloalkyl, heterocycloalkyl, aryl, and heteroaryl is independently optionally substituted with one, two, or three R$^5$;
or R$^{14}$ and R$^{15}$ are taken together to form a heterocycloalkyl optionally substituted with one, two, three, or four R$^6$;
R$^{16}$ and R$^{17}$ are each independently hydrogen, —CN, —OR$^{20}$, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, —C$_1$-C$_6$alkyl(aryl), —C$_1$-C$_6$alkyl(heteroaryl), —C$_1$-C$_6$alkyl(cycloalkyl), or —C$_1$-C$_6$alkyl(heterocycloalkyl); wherein each alkyl, alkenyl, alkynyl, cycloalkyl, heterocycloalkyl, aryl, and heteroaryl is independently optionally substituted with one, two, or three R$^7$;
or R$^{16}$ and R$^{17}$ are taken together with the nitrogen atom to which they are attached to form a heterocycloalkyl or a heterocycloalkenyl; each optionally substituted with one, two, or three R$^8$;
each R$^{20}$ is independently hydrogen, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three R$^7$;
n is 0-4;
each R', R$^2$, R$^3$, R$^4$, R$^5$, R$^6$, and R$^8$ is independently oxo, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, C$_1$-C$_6$alkyl, C$_1$-C$_6$haloalkyl, C$_1$-C$_6$hydroxyalkyl, C$_1$-C$_6$aminoalkyl, C$_2$-C$_6$alkenyl, C$_2$-C$_6$alkynyl, cycloalkyl, heterocycloalkyl, aryl, heteroaryl, —C$_1$-C$_6$alkyl(aryl), —C$_1$-C$_6$alkyl(heteroaryl), —C$_1$-C$_6$alkyl(cycloalkyl), or —C$_1$-C$_6$alkyl(heterocycloalkyl); wherein each alkyl, alkenyl, alkynyl, cycloalkyl, heterocycloalkyl, aryl, and heteroaryl is independently optionally substituted with one, two, or three oxo, halogen, —CN, —OH, —OMe, —S(=O)Me, —S(=O)$_2$Me, —NH$_2$, —S(=O)$_2$NH$_2$, —C(=O)Me, —C(=O)

OH, —C(=O)OMe, $C_1$-$C_6$alkyl, $C_1$-$C_6$haloalkyl, $C_1$-$C_6$hydroxyalkyl, or $C_1$-$C_6$aminoalkyl;

each $R^7$ is independently oxo, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —B(OR$^b$)(OR$^c$), —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, heteroaryl, —$C_1$-$C_6$alkyl(aryl), —$C_1$-$C_6$alkyl(heteroaryl), —$C_1$-$C_6$alkyl(cycloalkyl), or —$C_1$-$C_6$alkyl(heterocycloalkyl); wherein each alkyl, alkenyl, alkynyl, cycloalkyl, heterocycloalkyl, aryl, and heteroaryl is independently optionally substituted with one, two, or three $R^{7a}$;

each $R^{7a}$ is independently oxo, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, $C_1$-$C_6$haloalkyl, $C_1$-$C_6$hydroxyalkyl, or $C_1$-$C_6$aminoalkyl;

each $R^a$ is independently $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl; and each $R^b$ and $R^c$ are independently hydrogen, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl;

or $R^b$ and $R^c$ are taken together with the atom to which they are attached to form a heterocycloalkyl optionally substituted with one, two, or three oxo, halogen, —CN, —OH, —OMe, —S(=O)Me, —S(=O)$_2$Me, —NH$_2$, —S(=O)$_2$NH$_2$, —C(=O)Me, —C(=O)OH, —C(=O)OMe, $C_1$-$C_6$alkyl, $C_1$-$C_6$haloalkyl, $C_1$-$C_6$hydroxyalkyl, or $C_1$-$C_6$aminoalkyl.

In some embodiment of a compound of Formula (I), $R^{14}$ is hydrogen, halogen, —CN, —OH, —OR$^a$, —NR$^b$R$^c$, —C(=O)OR$^b$, —C(=O)NR$^b$R$^c$, $C_1$-$C_6$alkyl, $C_1$-$C_6$haloalkyl, or cycloalkyl.

In some embodiment of a compound of Formula (I), $R^{14}$ is hydrogen, halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, $C_1$-$C_6$haloalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one, two, or three $R^4$. In some embodiment of a compound of Formula (I), $R^{14}$ is hydrogen, halogen, —CN, —OH, —OR$^a$, —NR$^b$R$^c$, $C_1$-$C_6$alkyl, $C_1$-$C_6$haloalkyl, $C_1$-$C_6$hydroxyalkyl, or $C_1$-$C_6$aminoalkyl; wherein each alkyl is independently optionally substituted with one, two, or three $R^4$. In some embodiment of a compound of Formula (I), $R^{14}$ is hydrogen, halogen, $C_1$-$C_6$alkyl, $C_1$-$C_6$haloalkyl; wherein each alkyl is independently optionally substituted with one, two, or three $R^4$. In some embodiment of a compound of Formula (I), $R^{14}$ is hydrogen, halogen, $C_1$-$C_6$alkyl optionally substituted with one, two, or three $R^4$. In some embodiment of a compound of Formula (I), $R^{14}$ is hydrogen or $C_1$-$C_6$alkyl. In some embodiment of a compound of Formula (I), $R^{14}$ is $C_1$-$C_6$alkyl.

In some embodiment of a compound of Formula (I), each alkyl, cycloalkyl, heterocycloalkyl, aryl, and heteroaryl in $R^{14}$ is optionally substituted with one, two, or three $R^4$. In some embodiment of a compound of Formula (I), each alkyl, cycloalkyl, heterocycloalkyl, aryl, and heteroaryl in $R^{14}$ is optionally substituted with one or two $R^4$. In some embodiment of a compound of Formula (I), each alkyl, cycloalkyl, heterocycloalkyl, aryl, and heteroaryl in $R^{14}$ is optionally substituted with one $R^4$. In some embodiment of a compound of Formula (I), each alkyl, cycloalkyl, heterocycloalkyl, aryl, and heteroaryl in $R^{14}$ is optionally substituted with two $R^4$. In some embodiment of a compound of Formula (I), each alkyl, cycloalkyl, heterocycloalkyl, aryl, and heteroaryl in $R^{14}$ is optionally substituted with three $R^4$.

In some embodiment of a compound of Formula (I), each $R^4$ is independently oxo, halogen, —CN, —OH, —OR$^a$, —NR$^b$R$^c$, —C(=O)R$^a$, —C(=O)OR$^b$, $C_1$-$C_6$alkyl, $C_1$-$C_6$haloalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one, two, or three oxo, halogen, —CN, —OH, —OMe, —NH$_2$, $C_1$-$C_6$alkyl, $C_1$-$C_6$haloalkyl, $C_1$-$C_6$hydroxyalkyl, or $C_1$-$C_6$aminoalkyl. In some embodiment of a compound of Formula (I), each $R^4$ is independently oxo, halogen, —CN, —OH, —OR$^a$, —NR$^b$R$^c$, $C_1$-$C_6$alkyl, $C_1$-$C_6$haloalkyl, $C_1$-$C_6$hydroxyalkyl, or $C_1$-$C_6$aminoalkyl; wherein each alkyl is independently optionally substituted with one, two, or three oxo, halogen, —CN, —OH, —OMe, —NH$_2$, $C_1$-$C_6$alkyl, or $C_1$-$C_6$haloalkyl. In some embodiment of a compound of Formula (I), each $R^4$ is independently oxo, halogen, —CN, —OH, —OR$^a$, —NR$^b$R$^c$, $C_1$-$C_6$alkyl, $C_1$-$C_6$haloalkyl; wherein each alkyl is independently optionally substituted with one, two, or three oxo, halogen, —CN, —OH, —OMe, —NH$_2$, $C_1$-$C_6$alkyl, or $C_1$-$C_6$haloalkyl. In some embodiment of a compound of Formula (I), each $R^4$ is independently oxo, halogen, —CN, —OH, —OR$^a$, —NR$^b$R$^c$, $C_1$-$C_6$alkyl, $C_1$-$C_6$haloalkyl. In some embodiment of a compound of Formula (I), each $R^4$ is independently oxo, halogen, —CN, —OH, —OMe, —NH$_2$, Me, or CF$_3$. In some embodiment of a compound of Formula (I), each $R^4$ is independently halogen.

In some embodiment of a compound of Formula (I), $R^{15}$ is hydrogen, —S(=O)$_2$R$^a$, —S(=O)$_2$NR$^b$R$^a$, —C(=O)R$^a$, —C(=O)OR$^b$, —C(=O)NR$^b$R$^c$, $C_1$-$C_6$alkyl, $C_1$-$C_6$haloalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one, two, or three $R^5$. In some embodiment of a compound of Formula (I), $R^{15}$ is hydrogen, —S(=O)$_2$R$^a$, —S(=O)$_2$NR$^b$R$^c$, —C(=O)R$^a$, —C(=O)OR$^b$, —C(=O)NR$^b$R$^c$, $C_1$-$C_6$alkyl, $C_1$-$C_6$haloalkyl, $C_1$-$C_6$hydroxyalkyl, or $C_1$-$C_6$aminoalkyl; wherein each alkyl is independently optionally substituted with one, two, or three $R^5$. In some embodiment of a compound of Formula (I), $R^{15}$ is hydrogen, $C_1$-$C_6$alkyl, $C_1$-$C_6$haloalkyl, $C_1$-$C_6$hydroxyalkyl, or $C_1$-$C_6$aminoalkyl; wherein each alkyl is independently optionally substituted with one, two, or three $R^5$. In some embodiment of a compound of Formula (I), $R^{15}$ is hydrogen, —S(=O)$_2R^a$, —S(=O)$_2NR^bR^c$, —C(=O)$R^a$, —C(=O)OR$^b$, —C(=O)NR$^bR^c$, $C_1$-$C_6$alkyl, $C_1$-$C_6$haloalkyl, $C_1$-$C_6$hydroxyalkyl, or cycloalkyl. In some embodiment of a compound of Formula (I), $R^{15}$ is hydrogen, $C_1$-$C_6$alkyl, $C_1$-$C_6$haloyalkyl, or $C_1$-$C_6$hydroxyalkyl. In some embodiment of a compound of Formula (I), $R^{15}$ is hydrogen, $C_1$-$C_6$alkyl, or $C_1$-$C_6$hydroxyalkyl. In some embodiment of a compound of Formula (I), $R^{15}$ is hydrogen or $C_1$-$C_6$alkyl. In some embodiment of a compound of Formula (I), $R^{15}$ is $C_1$-$C_6$alkyl.

In some embodiment of a compound of Formula (I), each alkyl, cycloalkyl, heterocycloalkyl, aryl, and heteroaryl in $R^{15}$ is optionally substituted with one, two, or three $R^5$. In some embodiment of a compound of Formula (I), each alkyl, cycloalkyl, heterocycloalkyl, aryl, and heteroaryl in $R^{15}$ is optionally substituted with one or two $R^5$. In some embodiment of a compound of Formula (I), each alkyl, cycloalkyl, heterocycloalkyl, aryl, and heteroaryl is $R^{15}$ in optionally substituted with one $R^5$. In some embodiment of a compound of Formula (I), each alkyl, cycloalkyl, heterocycloalkyl, aryl, and heteroaryl in $R^{15}$ is optionally substituted with two $R^5$. In some embodiment of a compound of Formula (I), each alkyl, cycloalkyl, heterocycloalkyl, aryl, and heteroaryl in $R^{15}$ is optionally substituted with three $R^5$.

In some embodiment of a compound of Formula (I), each $R^5$ is independently oxo, halogen, —CN, —OH, —OR$^a$, —NR$^bR^c$, —C(=O)$R^a$, —C(=O)OR$^b$, $C_1$-$C_6$alkyl, $C_1$-$C_6$haloalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one, two, or three oxo, halogen, —CN, —OH, —OMe, —NH$_2$, $C_1$-$C_6$alkyl, $C_1$-$C_6$haloalkyl, $C_1$-$C_6$hydroxyalkyl, or $C_1$-$C_6$aminoalkyl. In some embodiment of a compound of Formula (I), each $R^5$ is independently oxo, halogen, —CN, —OH, —OR$^a$, —NR$^bR^c$, $C_1$-$C_6$alkyl, $C_1$-$C_6$haloalkyl, $C_1$-$C_6$hydroxyalkyl, or $C_1$-$C_6$aminoalkyl; wherein each alkyl is independently optionally substituted with one, two, or three oxo, halogen, —CN, —OH, —OMe, —NH$_2$, $C_1$-$C_6$alkyl, or $C_1$-$C_6$haloalkyl. In some embodiment of a compound of Formula (I), each $R^5$ is independently oxo, halogen, —CN, —OH, —OR$^a$, —NR$^bR^c$, $C_1$-$C_6$alkyl, $C_1$-$C_6$haloalkyl; wherein each alkyl is independently optionally substituted with one, two, or three oxo, halogen, —CN, —OH, —OMe, —NH$_2$, $C_1$-$C_6$alkyl, or $C_1$-$C_6$haloalkyl. In some embodiment of a compound of Formula (I), each $R^5$ is independently oxo, halogen, —CN, —OH, —OR$^a$, —NR$^bR^c$, $C_1$-$C_6$alkyl, $C_1$-$C_6$haloalkyl. In some embodiment of a compound of Formula (I), each $R^5$ is independently oxo, halogen, —CN, —OH, —OMe, —NH$_2$, Me, or CF$_3$. In some embodiment of a compound of Formula (I), each $R^5$ is independently halogen.

In some embodiment of a compound of Formula (I), $R^{14}$ and $R^{15}$ are taken together to form a heterocycloalkyl optionally substituted with one, two, three, or four $R^6$. In some embodiment of a compound of Formula (I), $R^{14}$ and $R^{15}$ are taken together to form a heterocycloalkyl optionally substituted with one, two, three, or four $R^6$; wherein the heterocycloalkyl is a 5-, 6-, or 7-membered heterocycloalkyl.

In some embodiment of a compound of Formula (I), $R^{14}$ and $R^{15}$ are taken together to form a heterocycloalkyl optionally substituted with one, two, three, or four $R^6$; wherein the heterocycloalkyl is a 5-membered heterocycloalkyl. In some embodiment of a compound of Formula (I), $R^{14}$ and $R^{15}$ are taken together to form a heterocycloalkyl optionally substituted with one, two, three, or four $R^6$; wherein the heterocycloalkyl is a 6-membered heterocycloalkyl. In some embodiment of a compound of Formula (I), $R^{14}$ and $R^{15}$ are taken together to form a heterocycloalkyl optionally substituted with one, two, three, or four $R^6$; wherein the heterocycloalkyl is a 7-membered heterocycloalkyl.

In some embodiment of a compound of Formula (I), the heterocycloalkyl formed when $R^{14}$ and $R^{15}$ are taken together is optionally substituted with one, two, or three $R^6$. In some embodiment of a compound of Formula (I), the heterocycloalkyl formed when $R^{14}$ and $R^{15}$ are taken together is optionally substituted with one or two $R^6$. In some embodiment of a compound of Formula (I), the heterocycloalkyl formed when $R^{14}$ and $R^{15}$ are taken together is optionally substituted with one $R^6$. In some embodiment of a compound of Formula (I), the heterocycloalkyl formed when $R^{14}$ and $R^{15}$ are taken together is optionally substituted with two $R^6$. In some embodiment of a compound of Formula (I), the heterocycloalkyl formed when $R^{14}$ and $R^{15}$ are taken together is optionally substituted with three $R^6$.

In some embodiment of a compound of Formula (I), each $R^6$ is independently oxo, halogen, —CN, —OH, —OR$^a$, —NR$^bR^c$, —C(=O)$R^a$, —C(=O)OR$^b$, $C_1$-$C_6$alkyl, $C_1$-$C_6$haloalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one, two, or three oxo, halogen, —CN, —OH, —OMe, —NH$_2$, $C_1$-$C_6$alkyl, $C_1$-$C_6$haloalkyl, $C_1$-$C_6$hydroxyalkyl, or $C_1$-$C_6$aminoalkyl. In some embodiment of a compound of Formula (I), each $R^6$ is independently oxo, halogen, —CN, —OH, —OR$^a$, —NR$^bR^c$, $C_1$-$C_6$alkyl, $C_1$-$C_6$haloalkyl, $C_1$-$C_6$hydroxyalkyl, or $C_1$-$C_6$aminoalkyl; wherein each alkyl is independently optionally substituted with one, two, or three oxo, halogen, —CN, —OH, —OMe, —NH$_2$, $C_1$-$C_6$alkyl, or $C_1$-$C_6$haloalkyl. In some embodiment of a compound of Formula (I), each $R^6$ is independently oxo, halogen, —CN, —OH, —OR$^a$, —NR$^bR^c$, $C_1$-$C_6$alkyl, $C_1$-$C_6$haloalkyl; wherein each alkyl is independently optionally substituted with one, two, or three oxo, halogen, —CN, —OH, —OMe, —NH$_2$, $C_1$-$C_6$alkyl, or $C_1$-$C_6$haloalkyl. In some embodiment of a compound of Formula (I), each $R^6$ is independently oxo, halogen, —CN, —OH, —OR$^a$, —NR$^bR^c$, $C_1$-$C_6$alkyl, $C_1$-$C_6$haloalkyl. In some embodiment of a compound of Formula (I), each $R^6$ is independently halogen, —CN, —OH, —OR$^a$, —NR$^bR^c$, —S(=O)$_2R^a$, —S(=O)$_2$NR$^bR^c$, —C(=O)$R^a$, $C_1$-$C_6$alkyl, $C_1$-$C_6$haloalkyl, $C_1$-$C_6$hydroxyalkyl, or cycloalkyl. In some embodiment of a compound of Formula (I), each $R^6$ is independently halogen —S(=O)$_2R^a$, —C(=O)$R^a$, or $C_1$-$C_6$alkyl. In some embodiment of a compound of Formula (I), each $R^6$ is independently oxo, halogen, —CN, —OH, —OMe, —NH$_2$, Me, or CF$_3$. In some embodiment of a compound of Formula (I), each $R^6$ is independently halogen.

In some embodiment of a compound of Formula (I), is

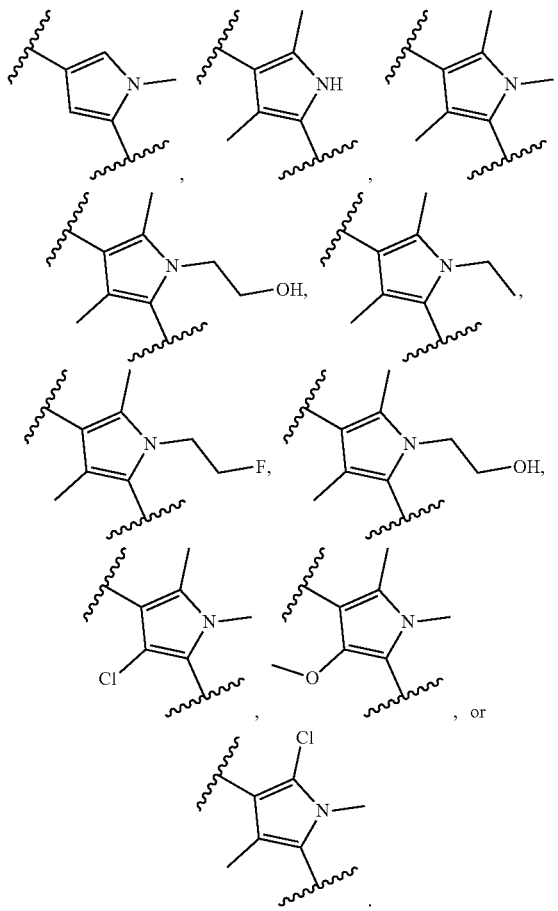

In some embodiment of a compound of Formula (I),

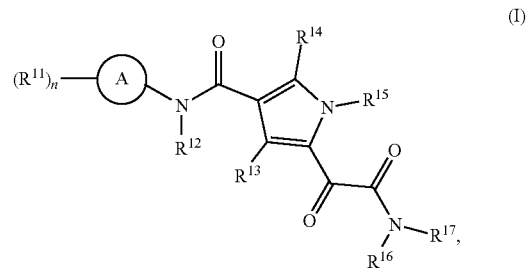

is

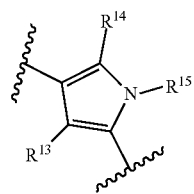

In some embodiment of a compound of Formula (Ia), each $R^6$ is independently halogen, —CN, —OH, —OR$^a$, —NR$^b$R$^c$, —S(=O)$_2$R$^a$, —S(=O)$_2$NR$^b$R$^c$, —C(=O)R$^a$, $C_1$-$C_6$alkyl, $C_1$-$C_6$haloalkyl, $C_1$-$C_6$hydroxyalkyl, or cycloalkyl. In some embodiment of a compound of Formula (Ia), each $R^6$ is independently halogen, —CN, —OH, —OR$^a$, —NR$^b$R$^c$, —S(=O)$_2$R$^a$, —S(=O)$_2$NR$^b$R$^c$, —C(=O)R$^a$, $C_1$-$C_6$alkyl, $C_1$-$C_6$haloalkyl, $C_1$-$C_6$hydroxyalkyl, or cycloalkyl. In some embodiment of a compound of Formula (Ia), each $R^6$ is independently halogen, —OH, —S(=O)$_2$R$^a$, —C(=O)R$^a$, or $C_1$-$C_6$alkyl. In some embodiment of a compound of Formula (Ia), each $R^6$ is independently halogen, —S(=O)$_2$R$^a$, —C(=O)R$^a$, or $C_1$-$C_6$alkyl.

In some embodiment of a compound of Formula (I), the compound or a pharmaceutically acceptable salt, solvate, or stereoisomer thereof is of Formula (Ia):

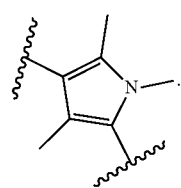 [SMILES: *c1c(C)c(*)n(C)c1C]

(I)

wherein:

Ring B is heterocycloalkyl;

each $R^6$ is independently oxo, halogen, —CN, —OH, —OR$^a$, —SH, —SR$^a$, —S(=O)R$^a$, —S(=O)$_2$R$^a$, —NO$_2$, —NR$^b$R$^c$, —NHS(=O)$_2$R$^a$, —S(=O)$_2$NR$^b$R$^c$, —C(=O)R$^a$, —OC(=O)R$^a$, —C(=O)OR$^b$, —OC(=O)OR$^b$, —C(=O)NR$^b$R$^c$, —OC(=O)NR$^b$R$^c$, —NR$^b$C(=O)NR$^b$R$^c$, —NR$^b$C(=O)R$^a$, —NR$^b$C(=O)OR$^b$, $C_1$-$C_6$alkyl, $C_1$-$C_6$haloalkyl, $C_1$-$C_6$hydroxyalkyl, $C_2$-$C_6$alkenyl, $C_2$-$C_6$alkynyl, cycloalkyl, heterocycloalkyl, aryl, heteroaryl, —$C_1$-$C_6$alkyl(aryl), —$C_1$-$C_6$alkyl(heteroaryl), —$C_1$-$C_6$alkyl(cycloalkyl), or —$C_1$-$C_6$alkyl(heterocycloalkyl); and m is 0-4.

In some embodiment of a compound of Formula (Ia), Ring B is a 4-, 5-, 6-, or 7-membered heterocycloalkyl. In some embodiment of a compound of Formula (Ia), Ring B is a 5-, 6-, or 7-membered heterocycloalkyl. In some embodiment of a compound of Formula (Ia), Ring B is a 5-membered heterocycloalkyl. In some embodiment of a compound of Formula (Ia), Ring B is a 6-membered heterocycloalkyl. In some embodiment of a compound of Formula (Ia), Ring B is a 7-membered heterocycloalkyl. In some embodiment of a compound of Formula (Ia),

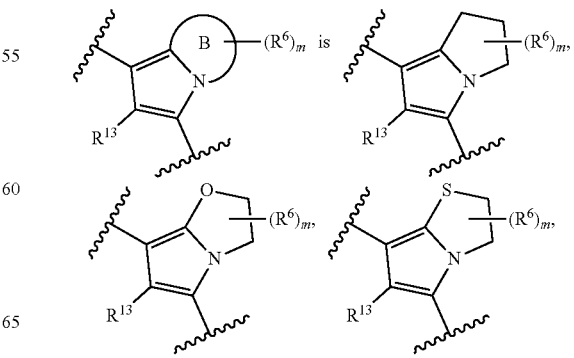

-continued

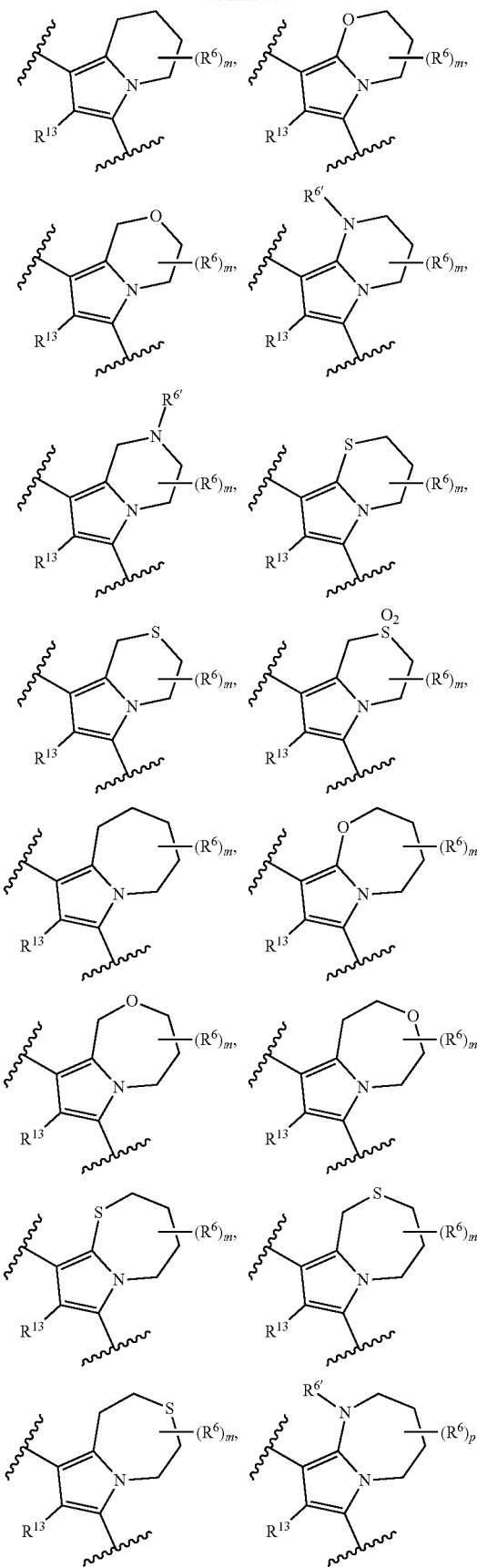

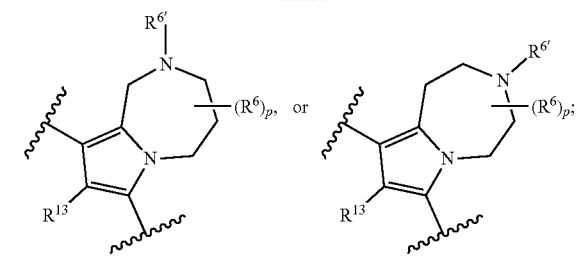

wherein
R[6'] is hydrogen, —S(=O)R[a], —S(=O)$_2$R[a], —S(=O)$_2$NR[b]R[c], —C(=O)R[a], —C(=O)OR[b], —C(=O)NR[b]R[c], $C_1$-$C_6$alkyl, $C_1$-$C_6$haloalkyl, $C_1$-$C_6$hydroxyalkyl, $C_2$-$C_6$alkenyl, $C_2$-$C_6$alkynyl, cycloalkyl, heterocycloalkyl, aryl, heteroaryl, —$C_1$-$C_6$alkyl(aryl), —$C_1$-$C_6$alkyl(heteroaryl), —$C_1$-$C_6$alkyl(cycloalkyl), or —$C_1$-$C_6$alkyl(heterocycloalkyl); and p is 0-3.

In some embodiment of a compound of Formula (Ia), is

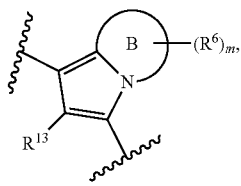

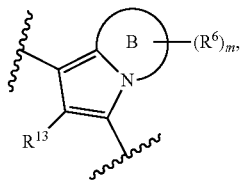

In some embodiment of a compound of Formula (Ia), is

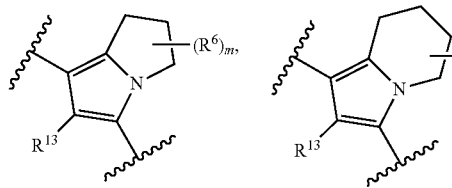 or 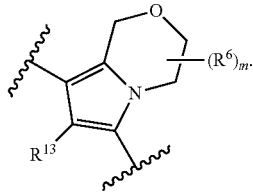

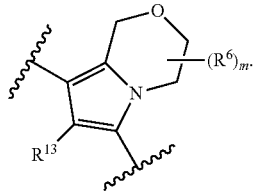

In some embodiment of a compound of Formula (Ia),

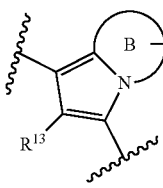 is 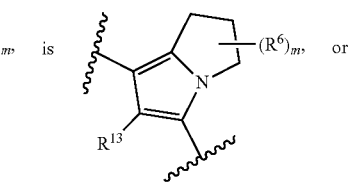 or

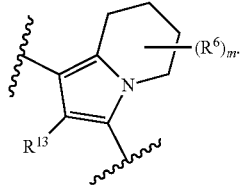

In some embodiment of a compound of Formula (Ia),

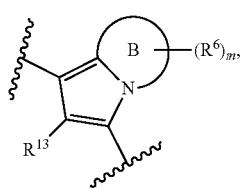

is

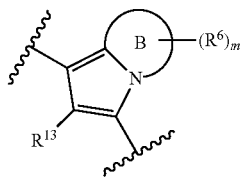

In some embodiment of a compound of Formula (Ia),

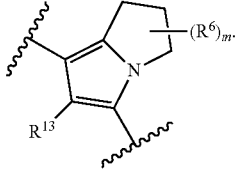

is

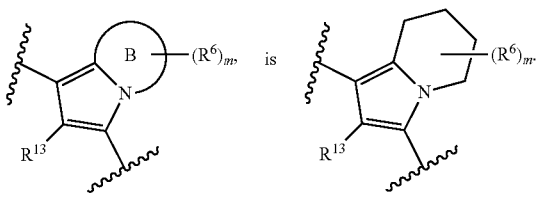

In some embodiment of a compound of Formula (Ia), m is 0-3. In some embodiment of a compound of Formula (Ia), m is 0-2. In some embodiment of a compound of Formula (Ia), m is 0 or 1. In some embodiment of a compound of Formula (Ia), m is 1 or 2. In some embodiment of a compound of Formula (Ia), m is 1-3. In some embodiment of a compound of Formula (Ia), m is 0. In some embodiment of a compound of Formula (Ia), m is 1. In some embodiment of a compound of Formula (Ia), m is 2. In some embodiment of a compound of Formula (Ia), m is 3. In some embodiment of a compound of Formula (Ia), m is 4.

In some embodiment of a compound of Formula (Ia), each $R^6$ is independently oxo, halogen, —CN, —OH, —$OR^a$, —$NR^bR^c$, —C(=O)$R^a$, —C(=O)$OR^b$, $C_1$-$C_6$alkyl, $C_1$-$C_6$haloalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one, two, or three oxo, halogen, —CN, —OH, —OMe, —$NH_2$, $C_1$-$C_6$alkyl, $C_1$-$C_6$haloalkyl, $C_1$-$C_6$hydroxyalkyl, or $C_1$-$C_6$aminoalkyl. In some embodiment of a compound of Formula (Ia), each $R^6$ is independently oxo, halogen, —CN, —OH, —$OR^a$, —$NR^bR^c$, $C_1$-$C_6$alkyl, $C_1$-$C_6$haloalkyl, $C_1$-$C_6$hydroxyalkyl, or $C_1$-$C_6$aminoalkyl; wherein each alkyl is independently optionally substituted with one, two, or three oxo, halogen, —CN, —OH, —OMe, —$NH_2$, $C_1$-$C_6$alkyl, or $C_1$-$C_6$haloalkyl. In some embodiment of a compound of Formula (Ia), each $R^6$ is independently oxo, halogen, —CN, —OH, —$OR^a$, —$NR^bR^c$, $C_1$-$C_6$alkyl, $C_1$-$C_6$haloalkyl; wherein each alkyl is independently optionally substituted with one, two, or three oxo, halogen, —CN, —OH, —OMe, —$NH_2$, $C_1$-$C_6$alkyl, or $C_1$-$C_6$haloalkyl. In some embodiment of a compound of Formula (Ia), each $R^6$ is independently oxo, halogen, —CN, —OH, —OMe, —$NH_2$, Me, or $CF_3$. In some embodiment of a compound of Formula (Ia), each $R^6$ is independently oxo, halogen, —CN, —OH, —$OR^a$, —$NR^bR^c$, $C_1$-$C_6$alkyl, $C_1$-$C_6$haloalkyl. In some embodiment of a compound of Formula (Ia), each $R^6$ is independently halogen.

In some embodiment of a compound of Formula (Ia), each $R^6$ is independently halogen, —CN, —OH, —$OR^a$, —$NR^bR^c$, —$S(=O)_2R^a$, —$S(=O)_2NR^bR^c$, —$C(=O)R^a$, $C_1$-$C_6$alkyl, $C_1$-$C_6$haloalkyl, $C_1$-$C_6$hydroxyalkyl, or cycloalkyl. In some embodiment of a compound of Formula (Ia), each $R^6$ is independently halogen, —OH, —$S(=O)_2R^a$, —$C(=O)R^a$, or $C_1$-$C_6$alkyl. In some embodiment of a compound of Formula (Ia), each $R^6$ is independently halogen, —$S(=O)_2R^a$, —$C(=O)R^a$, or $C_1$-$C_6$alkyl. In some embodiment of a compound of Formula (Ia), each $R^6$ is independently halogen, —CN, —OH, —$OR^a$, —$NR^bR^c$, $C_1$-$C_6$alkyl, $C_1$-$C_6$haloalkyl, $C_1$-$C_6$hydroxyalkyl, or cycloalkyl. In some embodiment of a compound of Formula (Ia), each $R^6$ is independently halogen or $C_1$-$C_6$alkyl.

In some embodiment of a compound of Formula (Ia), p is 0-2. In some embodiment of a compound of Formula (Ia), p is 0 or 1. In some embodiment of a compound of Formula (Ia), p is 1 or 2. In some embodiment of a compound of Formula (Ia), p is 1-3. In some embodiment of a compound of Formula (Ia), p is 0. In some embodiment of a compound of Formula (Ia), p is 1. In some embodiment of a compound of Formula (Ia), p is 2. In some embodiment of a compound of Formula (Ia), p is 3.

In some embodiment of a compound of Formula (Ia), $R^{6'}$ is hydrogen, —$S(=O)_2R^a$, —$S(=O)_2NR^bR^c$, —$C(=O)R^a$, $C_1$-$C_6$haloalkyl, $C_1$-$C_6$hydroxyalkyl, or cycloalkyl. In some embodiment of a compound of Formula (Ia), $R^{6'}$ is hydrogen, —$S(=O)_2R^a$, —$C(=O)R^a$, or $C_1$-$C_6$alkyl. In some embodiment of a compound of Formula (Ia), $R^{6'}$ is hydrogen or $C_1$-$C_6$alkyl.

In some embodiment of a compound of Formula (I) or (Ia), the compound or a pharmaceutically acceptable salt, solvate, or stereoisomer thereof is of Formula (Ib):

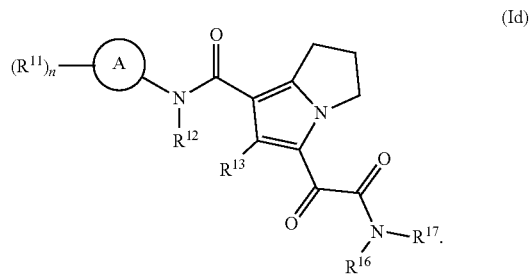

(Ib)

In some embodiment of a compound of Formula (I) or (Ia), the compound or a pharmaceutically acceptable salt, solvate, or stereoisomer thereof is of Formula (Ic):

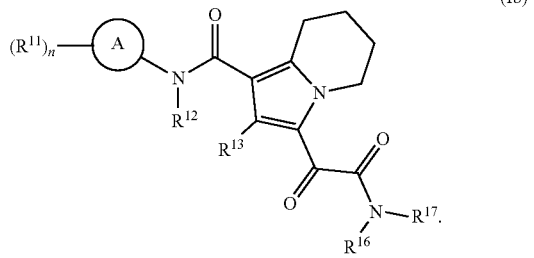

(Ic)

In some embodiment of a compound of Formula (I) or (Ia), the compound or a pharmaceutically acceptable salt, solvate, or stereoisomer thereof is of Formula (Id):

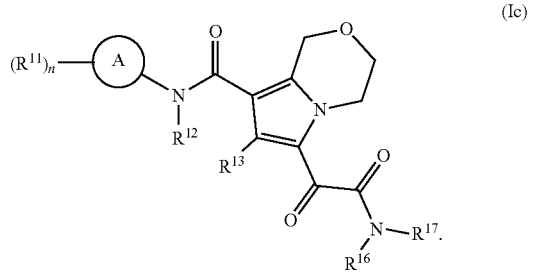

(Id)

In some embodiment of a compound of Formula (I), (Ia)-(Id), $R^{12}$ is hydrogen or $C_1$-$C_6$alkyl. In some embodiment of a compound of Formula (I), (Ia)-(Id), $R^u$ is hydrogen. In some embodiment of a compound of Formula (I), (Ia)-(Id), $R^u$ is $C_1$-$C_6$alkyl.

In some embodiment of a compound of Formula (I), (Ia)-(Id), IV is hydrogen, halogen, —CN, —OH, —$OR^a$, —$NR^bR^c$, —$C(=O)OR^b$, —$C(=O)NR^bR^c$, $C_1$-$C_6$alkyl, $C_1$-$C_6$haloalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one, two, or three $R^3$. In some embodiment of a compound of Formula (I), (Ia)-(Id), $R^{13}$ is hydrogen, halogen, $C_1$-$C_6$alkyl, $C_1$-$C_6$haloalkyl, $C_1$-$C_6$hydroxyalkyl, $C_1$-$C_6$aminoalkyl, or cycloalkyl; wherein each alkyl or cycloalkyl is independently optionally substituted with one, two, or three $R^3$. In some embodiment of a compound of Formula (I), (Ia)-(Id), $R^{13}$ is hydrogen, halogen, $C_1$-$C_6$alkyl, or $C_1$-$C_6$haloalkyl; wherein each alkyl is independently optionally substituted with one, two, or three $R^3$. In some embodiment of a compound of Formula (I), (Ia)-(Id), $R^{13}$ is hydrogen, halogen, —CN, —OH, —$OR^a$, —$NR^bR^c$, —$C(=O)OR^b$, —$C(=O)NR^bR^c$, $C_1$-$C_6$alkyl, $C_1$-$C_6$haloalkyl, or cycloalkyl. In some embodiment of a compound of Formula (I), (Ia)-(Id), $R^{13}$ is hydrogen, halogen, or $C_1$-$C_6$alkyl. In some embodiment of a compound of Formula (I), (Ia)-(Id), $R^{13}$ is hydrogen or $C_1$-$C_6$alkyl. In some embodiment of a compound of Formula (I), (Ia)-(Id), $R^{13}$ is $C_1$-$C_6$alkyl.

In some embodiment of a compound of Formula (I), (Ia)-(Id), each alkyl, alkenyl, alkynyl, cycloalkyl, heterocycloalkyl, aryl, or heteroaryl in $R^{13}$ is optionally substituted with one, two, or three $R^3$. In some embodiment of a compound of Formula (I), (Ia)-(Id), each alkyl, alkenyl, alkynyl, cycloalkyl, heterocycloalkyl, aryl, or heteroaryl in $R^{13}$ is optionally substituted with one or two $R^3$. In some embodiment of a compound of Formula (I), (Ia)-(Id), each alkyl, alkenyl, alkynyl, cycloalkyl, heterocycloalkyl, aryl, or heteroaryl in $R^{13}$ is optionally substituted with one $R^3$. In some embodiment of a compound of Formula (I), (Ia)-(Id), each alkyl, alkenyl, alkynyl, cycloalkyl, heterocycloalkyl, aryl, or heteroaryl in $R^{13}$ is optionally substituted with two $R^3$. In some embodiment of a compound of Formula (I), (Ia)-(Id), each alkyl, alkenyl, alkynyl, cycloalkyl, heterocycloalkyl, aryl, or heteroaryl in $R^{13}$ is optionally substituted with three $R^3$.

In some embodiment of a compound of Formula (I), (Ia)-(Id), each $R^3$ is independently oxo, halogen, —CN, —OH, —$OR^a$, —$NR^bR^c$, —$C(=O)R^a$, —$C(=O)OR^b$, $C_1$-$C_6$alkyl, $C_1$-$C_6$haloalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one, two, or three oxo, halogen, —CN, —OH, —OMe, —NH$_2$, $C_1$-$C_6$alkyl, $C_1$-$C_6$haloalkyl, $C_1$-$C_6$hydroxyalkyl, or $C_1$-$C_6$aminoalkyl. In some embodiment of a compound of Formula (I), (Ia)-(Id), each $R^3$ is independently oxo, halogen, —CN, —OH, —OR$^a$, —NR$^b$R$^c$, $C_1$-$C_6$alkyl, $C_1$-$C_6$haloalkyl, $C_1$-$C_6$hydroxyalkyl, or $C_1$-$C_6$aminoalkyl; wherein each alkyl is independently optionally substituted with one, two, or three oxo, halogen, —CN, —OH, —OMe, —NH$_2$, $C_1$-$C_6$alkyl, or $C_1$-$C_6$haloalkyl. In some embodiment of a compound of Formula (I), (Ia)-(Id), each $R^3$ is independently oxo, halogen, —CN, —OH, —OR$^a$, —NR$^b$R$^c$, $C_1$-$C_6$alkyl, $C_1$-$C_6$haloalkyl; wherein each alkyl is independently optionally substituted with one, two, or three oxo, halogen, —CN, —OH, —OMe, —NH$_2$, $C_1$-$C_6$alkyl, or $C_1$-$C_6$haloalkyl. In some embodiment of a compound of Formula (I), (Ia)-(Id), each $R^3$ is independently oxo, halogen, —CN, —OH, —OR$^a$, —NR$^b$R$^c$, $C_1$-$C_6$alkyl, $C_1$-$C_6$haloalkyl. In some embodiment of a compound of Formula (I), (Ia)-(Id), each $R^3$ is independently oxo, halogen, —CN, —OH, —OMe, —NH$_2$, Me, or CF$_3$. In some embodiment of a compound of Formula (I), (Ia)-(Id), each $R^3$ is independently halogen.

In some embodiment of a compound of Formula (I), (Ia)-(Id), Ring A is cycloalkyl or heterocycloalkyl. In some embodiment of a compound of Formula (I), (Ia)-(Id), Ring A is cycloalkyl, aryl or heteroaryl. In some embodiment of a compound of Formula (I), (Ia)-(Id), Ring A is aryl or heteroaryl. In some embodiment of a compound of Formula (I), (Ia)-(Id), Ring A is phenyl or 5- or 6-membered heteroaryl. In some embodiment of a compound of Formula (I), (Ia)-(Id), Ring A is phenyl or 6-membered heteroaryl. In some embodiment of a compound of Formula (I), (Ia)-(Id), Ring A is phenyl or pyridyl. In some embodiment of a compound of Formula (I), (Ia)-(Id), Ring A is phenyl.

In some embodiment of a compound of Formula (I), (Ia)-(Id), n is 0-3. In some embodiment of a compound of Formula (I), (Ia)-(Id), n is 0-2. In some embodiment of a compound of Formula (I), (Ia)-(Id), n is 0 or 1. In some embodiment of a compound of Formula (I), (Ia)-(Id), n is 1-3. In some embodiment of a compound of Formula (I), (Ia)-(Id), n is 1 or 2. In some embodiment of a compound of Formula (I), (Ia)-(Id), n is 0. In some embodiment of a compound of Formula (I), (Ia)-(Id), n is 1. In some embodiment of a compound of Formula (I), (Ia)-(Id), n is 2. In some embodiment of a compound of Formula (I), (Ia)-(Id), n is 3. In some embodiment of a compound of Formula (I), (Ia)-(Id), n is 4.

In some embodiment of a compound of Formula (I), (Ia)-(Id), each $R^{11}$ is independently halogen, —CN, —OH, —OR$^a$, —NR$^b$R$^c$, —C(=O)R$^a$, —C(=O)OR$^b$, —C(=O)NR$^b$R$^c$, $C_1$-$C_6$alkyl, $C_1$-$C_6$haloalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one, two, or three R'. In some embodiment of a compound of Formula (I), (Ia)-(Id), each $R^{11}$ is independently halogen, —CN, $C_1$-$C_6$alkyl, $C_1$-$C_6$haloalkyl, $C_1$-$C_6$hydroxyalkyl, $C_1$-$C_6$aminoalkyl, or cycloalkyl; wherein each alkyl and cycloalkyl is independently optionally substituted with one, two, or three R'. In some embodiment of a compound of Formula (I), (Ia)-(Id), each $R^{11}$ is independently halogen, —CN, $C_1$-$C_6$alkyl, $C_1$-$C_6$haloalkyl, $C_1$-$C_6$hydroxyalkyl, $C_1$-$C_6$aminoalkyl; wherein each alkyl is independently optionally substituted with one, two, or three R'. In some embodiment of a compound of Formula (I), (Ia)-(Id), each $R^{11}$ is independently halogen, —CN, $C_1$-$C_6$alkyl, or $C_1$-$C_6$haloalkyl; wherein each alkyl is independently optionally substituted with one, two, or three R'. In some embodiment of a compound of Formula (I), (Ia)-(Id), each $R^{11}$ is independently halogen, —CN, —OH, —OR$^a$, —C(=O)OR$^b$, —C(=O)NR$^b$R$^c$, $C_1$-$C_6$alkyl, $C_1$-$C_6$haloalkyl, or cycloalkyl. In some embodiment of a compound of Formula (I), (Ia)-(Id), each $R^{11}$ is independently halogen, —CN, $C_1$-$C_6$alkyl, or $C_1$-$C_6$haloalkyl. In some embodiment of a compound of Formula (I), (Ia)-(Id), each $R^{11}$ is independently halogen or $C_1$-$C_6$alkyl.

In some embodiment of a compound of Formula (I), (Ia)-(Id), each alkyl, alkenyl, alkynyl, cycloalkyl, heterocycloalkyl, aryl, or heteroaryl in $R^{11}$ is optionally substituted with one, two, or three R'. In some embodiment of a compound of Formula (I), (Ia)-(Id), each alkyl, alkenyl, alkynyl, cycloalkyl, heterocycloalkyl, aryl, or heteroaryl in $R^{11}$ is optionally substituted with one or two R'. In some embodiment of a compound of Formula (I), (Ia)-(Id), each alkyl, alkenyl, alkynyl, cycloalkyl, heterocycloalkyl, aryl, or heteroaryl in $R^{11}$ is optionally substituted with one R'. In some embodiment of a compound of Formula (I), (Ia)-(Id), each alkyl, alkenyl, alkynyl, cycloalkyl, heterocycloalkyl, aryl, or heteroaryl in $R^{11}$ is optionally substituted with two $R^1$. In some embodiment of a compound of Formula (I), (Ia)-(Id), each alkyl, alkenyl, alkynyl, cycloalkyl, heterocycloalkyl, aryl, or heteroaryl in $R^{11}$ is optionally substituted with three $R^1$.

In some embodiment of a compound of Formula (I), (Ia)-(Id), each $R^1$ is independently oxo, halogen, —CN, —OH, —OR$^a$, —NR$^b$R$^c$, —C(=O)R$^a$, —C(=O)OR$^b$, $C_1$-$C_6$alkyl, $C_1$-$C_6$haloalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one, two, or three oxo, halogen, —CN, —OH, —OMe, —NH$_2$, $C_1$-$C_6$alkyl, $C_1$-$C_6$haloalkyl, $C_1$-$C_6$hydroxyalkyl, or $C_1$-$C_6$aminoalkyl. In some embodiment of a compound of Formula (I), (Ia)-(Id), each $R^1$ is independently oxo, halogen, —CN, —OH, —OR$^a$, —NR$^b$R$^c$, $C_1$-$C_6$alkyl, $C_1$-$C_6$haloalkyl, $C_1$-$C_6$hydroxyalkyl, or $C_1$-$C_6$aminoalkyl; wherein each alkyl is independently optionally substituted with one, two, or three oxo, halogen, —CN, —OH, —OMe, —NH$_2$, $C_1$-$C_6$alkyl, or $C_1$-$C_6$haloalkyl. In some embodiment of a compound of Formula (I), (Ia)-(Id), each $R^1$ is independently oxo, halogen, —CN, —OH, —OR$^a$, —NR$^b$R$^c$, $C_1$-$C_6$alkyl, $C_1$-$C_6$haloalkyl; wherein each alkyl is independently optionally substituted with one, two, or three oxo, halogen, —CN, —OH, —OMe, —NH$_2$, $C_1$-$C_6$alkyl, or $C_1$-$C_6$haloalkyl. In some embodiment of a compound of Formula (I), (Ia)-(Id), each $R^1$ is independently oxo, halogen, —CN, —OH, —OR$^a$, —NR$^b$R$^c$, $C_1$-$C_6$alkyl, $C_1$-$C_6$haloalkyl. In some embodiment of a compound of Formula (I), (Ia)-(Id), each $R^1$ is independently oxo, halogen, —CN, —OH, —OMe, —NH$_2$, Me, or CF$_3$. In some embodiment of a compound of Formula (I), (Ia)-(Id), each $R^1$ is independently halogen.

In some embodiment of a compound of Formula (I), (Ia)-(Id), two $R^{11}$ on adjacent atoms are taken together with the atoms to which they are attached to form a cycloalkyl, heterocycloalkyl, aryl, or heteroaryl; each optionally substituted with one, two, or three $R^2$. In some embodiment of a compound of Formula (I), (Ia)-(Id), two $R^{11}$ on adjacent atoms are taken together with the atoms to which they are attached to form a cycloalkyl optionally substituted with one, two, or three $R^2$. In some embodiment of a compound of Formula (I), (Ia)-(Id), two $R^{11}$ on adjacent atoms are taken together with the atoms to which they are attached to form a heterocycloalkyl optionally substituted with one, two, or three R². In some embodiment of a compound of Formula (I), (Ia)-(Id), two R¹¹ on adjacent atoms are taken together with the atoms to which they are attached to form an aryl optionally substituted with one, two, or three R². In some embodiment of a compound of Formula (I), (Ia)-(Id), two R¹¹ on adjacent atoms are taken together with the atoms to which they are attached to form a heteroaryl optionally substituted with one, two, or three R².

In some embodiment of a compound of Formula (I), (Ia)-(Id), each cycloalkyl, heterocycloalkyl, aryl, or heteroaryl formed when two R¹¹ are taken together is optionally substituted with one, two, or three R². In some embodiment of a compound of Formula (I), (Ia)-(Id), each cycloalkyl, heterocycloalkyl, aryl, or heteroaryl formed when two R¹¹ are taken together is optionally substituted with one or two R². In some embodiment of a compound of Formula (I), (Ia)-(Id), each cycloalkyl, heterocycloalkyl, aryl, or heteroaryl formed when two R¹¹ are taken together is optionally substituted with one R². In some embodiment of a compound of Formula (I), (Ia)-(Id), each cycloalkyl, heterocycloalkyl, aryl, or heteroaryl formed when two R¹¹ are taken together is optionally substituted with two R². In some embodiment of a compound of Formula (I), (Ia)-(Id), R¹¹ is optionally substituted with three R².

In some embodiment of a compound of Formula (I), (Ia)-(Id), each R² is independently oxo, halogen, —CN, —OH, —OR$^a$, —NR$^b$R$^c$, —C(=O)R$^a$, —C(=O)OR$^b$, $C_1$-$C_6$alkyl, $C_1$-$C_6$haloalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one, two, or three oxo, halogen, —CN, —OH, —OMe, —NH₂, $C_1$-$C_6$alkyl, $C_1$-$C_6$haloalkyl, $C_1$-$C_6$hydroxyalkyl, or $C_1$-$C_6$aminoalkyl. In some embodiment of a compound of Formula (I), (Ia)-(Id), each R² is independently oxo, halogen, —CN, —OH, —OR$^a$, —NR$^b$R$^c$, $C_1$-$C_6$alkyl, $C_1$-$C_6$haloalkyl, $C_1$-$C_6$hydroxyalkyl, or $C_1$-$C_6$aminoalkyl; wherein each alkyl is independently optionally substituted with one, two, or three oxo, halogen, —CN, —OH, —OMe, —NH₂, $C_1$-$C_6$alkyl, or $C_1$-$C_6$haloalkyl. In some embodiment of a compound of Formula (I), (Ia)-(Id), each R² is independently oxo, halogen, —CN, —OH, —OR$^a$, —NR$^b$R$^c$, $C_1$-$C_6$alkyl, $C_1$-$C_6$haloalkyl; wherein each alkyl is independently optionally substituted with one, two, or three oxo, halogen, —CN, —OH, —OMe, —NH₂, $C_1$-$C_6$alkyl, or $C_1$-$C_6$haloalkyl. In some embodiment of a compound of Formula (I), (Ia)-(Id), each R² is independently oxo, halogen, —CN, —OH, —OR$^a$, —NR$^b$R$^c$, $C_1$-$C_6$alkyl, $C_1$-$C_6$haloalkyl. In some embodiment of a compound of Formula (I), (Ia)-(Id), each R² is independently oxo, halogen, —CN, —OH, —OMe, —NH₂, Me, or CF₃. In some embodiment of a compound of Formula (I), (Ia)-(Id), each R² is independently halogen.

In some embodiment of a compound of Formula (I), (Ia)-(Id),

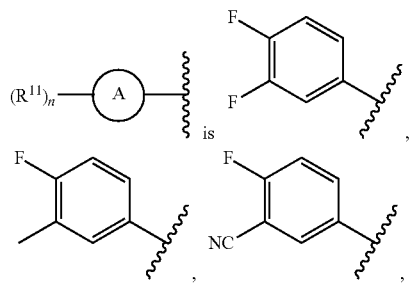

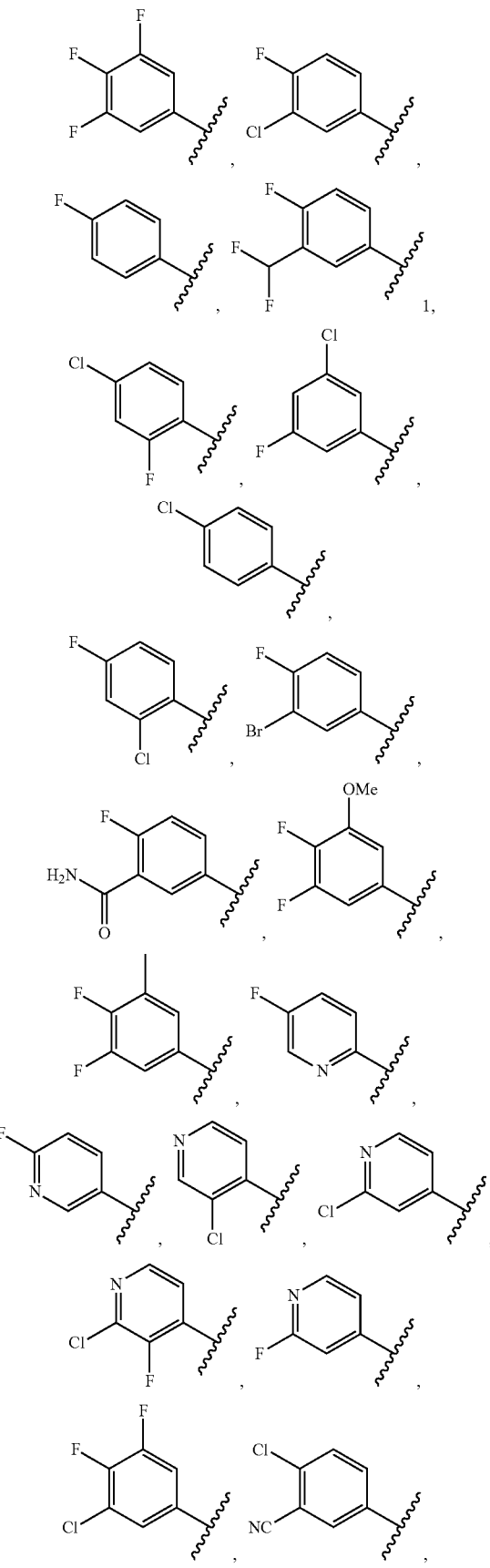

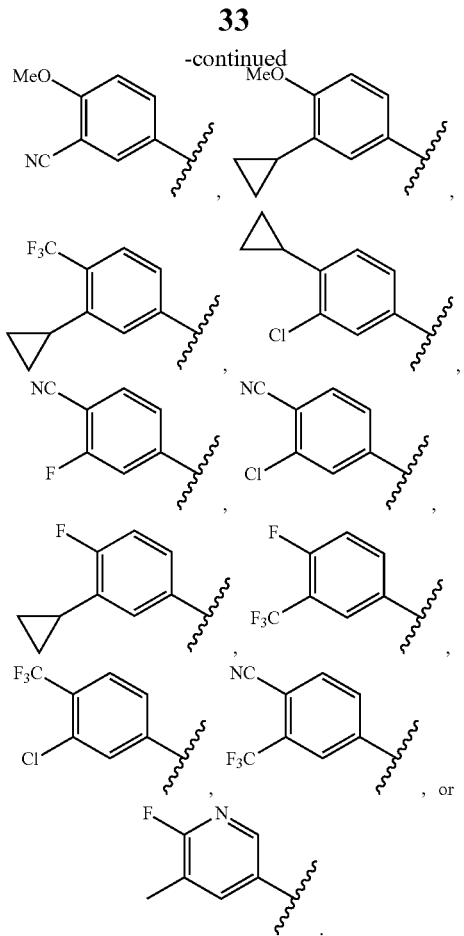
In some embodiment of a compound of Formula (I), (Ia)-(Id),
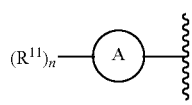
is
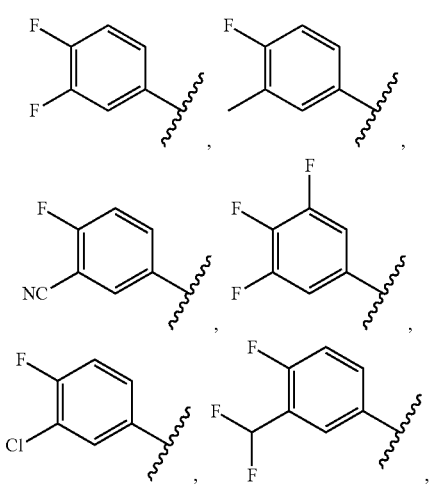
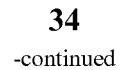
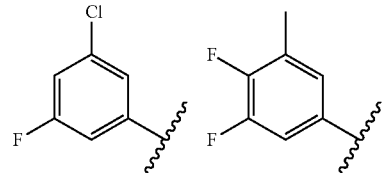
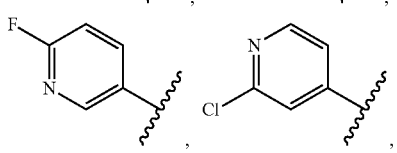
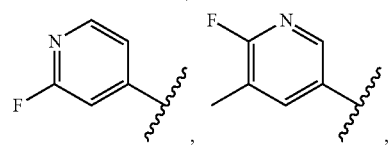
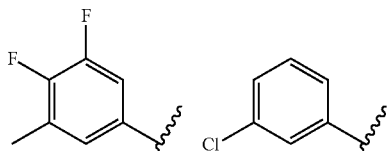
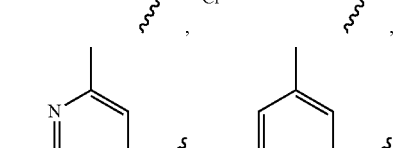
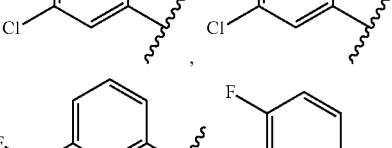
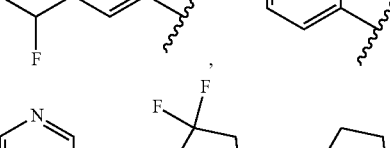
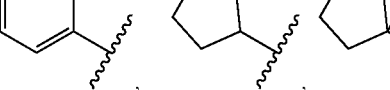
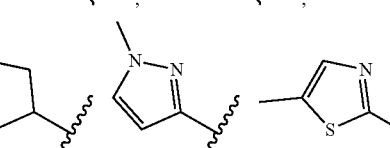
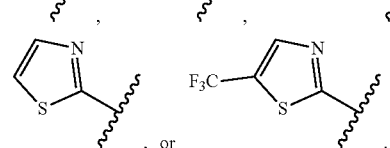
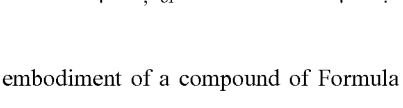
In some embodiment of a compound of Formula (I), (Ia)-(Id),
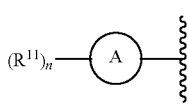

is

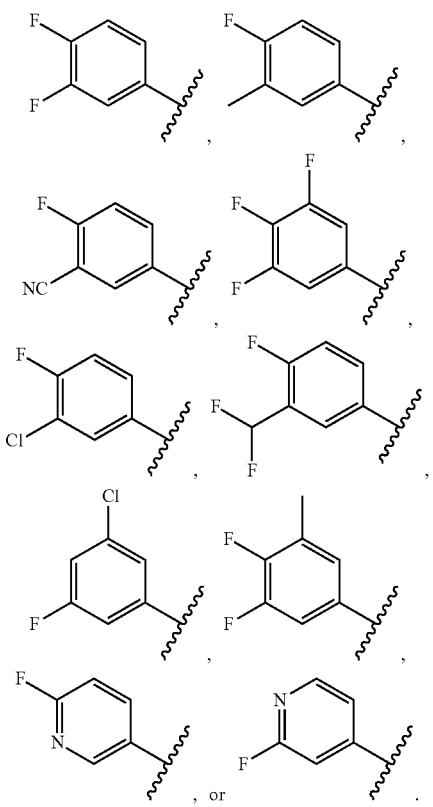

In some embodiment of a compound of Formula (I), (Ia)-(Id),

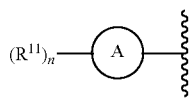

is

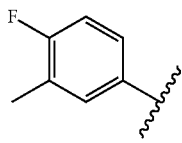

In some embodiment of a compound of Formula (I), (Ia)-(Id), $R^{16}$ is hydrogen, $C_1$-$C_6$alkyl, $C_1$-$C_6$haloalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one, two, or three $R^7$. In some embodiment of a compound of Formula (I), (Ia)-(Id), $R^{16}$ is hydrogen, $C_1$-$C_6$alkyl, $C_1$-$C_6$haloalkyl, $C_1$-$C_6$hydroxyalkyl, or $C_1$-$C_6$aminoalkyl; wherein each alkyl is independently optionally substituted with one, two, or three $R^7$. In some embodiment of a compound of Formula (I), (Ia)-(Id), $R^{16}$ is hydrogen, $C_1$-$C_6$alkyl, or $C_1$-$C_6$haloalkyl; wherein each alkyl is independently optionally substituted with one, two, or three $R^7$. In some embodiment of a compound of Formula (I), (Ia)-(Id), $R^{16}$ is hydrogen or $C_1$-$C_6$alkyl. In some embodiment of a compound of Formula (I), (Ia)-(Id), $R^{16}$ is hydrogen.

In some embodiment of a compound of Formula (I), (Ia)-(Id), $R^{17}$ is hydrogen, —CN, —OR$^{20}$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, $C_3$-$C_{15}$cycloalkyl, $C_2$-$C_{15}$heterocycloalkyl, phenyl, 5- or 6-membered heteroaryl, —$C_1$-$C_6$alkyl(phenyl), —$C_1$-$C_6$alkyl(5- or 6-membered heteroaryl), —$C_1$-$C_6$alkyl($C_3$-$C_{15}$cycloalkyl), or —$C_1$-$C_6$alkyl($C_2$-$C_{15}$heterocycloalkyl); wherein each alkyl, alkenyl, alkynyl, cycloalkyl, heterocycloalkyl, aryl, and heteroaryl is independently optionally substituted with one, two, or three $R^7$.

In some embodiment of a compound of Formula (I), (Ia)-(Id), $R^{17}$ is hydrogen, —CN, —OR$^{20}$, $C_1$-$C_6$alkyl, $C_1$-$C_6$haloalkyl, $C_1$-$C_6$hydroxyalkyl, $C_1$-$C_6$aminoalkyl, $C_2$-$C_6$alkenyl, $C_2$-$C_6$alkynyl, $C_3$-$C_{10}$cycloalkyl, $C_2$-$C_{10}$heterocycloalkyl, phenyl, 5- or 6-membered heteroaryl, —$C_1$-$C_6$alkyl(phenyl), —$C_1$-$C_6$alkyl(5- or 6-membered heteroaryl), —$C_1$-$C_6$alkyl($C_3$-$C_{10}$cycloalkyl), or —$C_1$-$C_6$alkyl($C_2$-$C_{10}$heterocycloalkyl); wherein each alkyl, alkenyl, alkynyl, cycloalkyl, heterocycloalkyl, aryl, and heteroaryl is independently optionally substituted with one, two, or three $R^7$.

In some embodiment of a compound of Formula (I), (Ia)-(Id), $R^{17}$ is —OR$^{20}$, $C_1$-$C_6$alkyl, $C_1$-$C_6$haloalkyl, $C_1$-$C_6$hydroxyalkyl, $C_1$-$C_6$aminoalkyl, $C_2$-$C_6$alkynyl, $C_3$-$C_{10}$cycloalkyl, $C_2$-$C_{10}$cycloalkenyl, $C_3$-$C_{10}$heterocycloalkyl, $C_2$-$C_{10}$heterocycloalkenyl, phenyl, 5- or 6-membered heteroaryl, —$C_1$-$C_6$alkyl(phenyl), —$C_1$-$C_6$alkyl(5- or 6-membered heteroaryl), —$C_1$-$C_6$alkyl($C_3$-$C_{10}$cycloalkyl), or —$C_1$-$C_6$alkyl($C_2$-$C_{10}$heterocycloalkyl); wherein each alkyl, alkynyl, cycloalkyl, cycloalkenyl, heterocycloalkyl, heterocycloalkenyl, aryl, and heteroaryl is independently optionally substituted with one, two, or three $R^7$.

In some embodiment of a compound of Formula (I), (Ia)-(Id), $R^{17}$ is —OR$^{20}$, $C_1$-$C_6$alkyl, $C_1$-$C_6$haloalkyl, $C_1$-$C_6$hydroxyalkyl, $C_1$-$C_6$aminoalkyl, $C_2$-$C_6$alkynyl, $C_3$-$C_{10}$cycloalkyl, $C_3$-$C_{10}$cycloalkenyl, $C_2$-$C_{10}$heterocycloalkyl, phenyl, 5- or 6-membered heteroaryl, —$C_1$-$C_6$alkyl(5- or 6-membered heteroaryl), —$C_1$-$C_6$alkyl($C_3$-$C_{10}$cycloalkyl), or —$C_1$-$C_6$alkyl($C_2$-$C_{10}$heterocycloalkyl); wherein each alkyl, alkynyl, cycloalkyl, cycloalkenyl, heterocycloalkyl, aryl, and heteroaryl is independently optionally substituted with one, two, or three $R^7$.

In some embodiment of a compound of Formula (I), (Ia)-(Id), $R^{17}$ is —OR$^{20}$, $C_1$-$C_6$alkyl, $C_1$-$C_6$haloalkyl, $C_1$-$C_6$hydroxyalkyl, $C_1$-$C_6$aminoalkyl, $C_2$-$C_6$alkynyl, cycloalkyl, cycloalkenyl, heterocycloalkyl, heterocycloalkenyl, aryl, heteroaryl, —$C_1$-$C_6$alkyl(aryl), —$C_1$-$C_6$alkyl(heteroaryl), —$C_1$-$C_6$alkyl(cycloalkyl), or —$C_1$-$C_6$alkyl(heterocycloalkyl); wherein each alkyl, alkynyl, cycloalkyl, cycloalkeny, heterocycloalkyl, heterocycloalkenyl, aryl, and heteroaryl is independently optionally substituted with one, two, or three $R^7$.

In some embodiment of a compound of Formula (I), (Ia)-(Id), $R^{17}$ is —OR$^{20}$, $C_1$-$C_6$alkyl, $C_1$-$C_6$haloalkyl, $C_1$-$C_6$hydroxyalkyl, $C_1$-$C_6$aminoalkyl, $C_2$-$C_6$alkynyl, cycloalkyl, cycloalkenyl, heterocycloalkyl, aryl, heteroaryl, —$C_1$-$C_6$alkyl(heteroaryl), —$C_1$-$C_6$alkyl(cycloalkyl), or —$C_1$-$C_6$alkyl(heterocycloalkyl); wherein each alkyl, alkynyl, cycloalkyl, cycloalkenyl, heterocycloalkyl, aryl, and heteroaryl is independently optionally substituted with one, two, or three $R^7$.

In some embodiment of a compound of Formula (I), (Ia)-(Id), $R^{17}$ is —OR$^{20}$, $C_1$-$C_6$alkyl, $C_1$-$C_6$haloalkyl, $C_1$-$C_6$hydroxyalkyl, $C_1$-$C_6$aminoalkyl, $C_2$-$C_6$alkynyl, cycloalkyl, heterocycloalkyl, aryl, heteroaryl, —$C_1$-$C_6$alkyl(aryl), —$C_1$-$C_6$alkyl(heteroaryl), —$C_1$-$C_6$alkyl(cycloalkyl), or —$C_1$-$C_6$alkyl(heterocycloalkyl); wherein each alkyl, cycloalkyl, heterocycloalkyl, aryl, and heteroaryl is independently optionally substituted with one, two, or three $R^7$.

In some embodiment of a compound of Formula (I), (Ia)-(Id), $R^{17}$ is —$OR^{20}$, $C_1$-$C_6$alkyl, $C_1$-$C_6$haloalkyl, $C_1$-$C_6$hydroxyalkyl, $C_1$-$C_6$aminoalkyl, cycloalkyl, heterocycloalkyl, —$C_1$-$C_6$alkyl(aryl), —$C_1$-$C_6$alkyl(heteroaryl), —$C_1$-$C_6$alkyl(cycloalkyl), or —$C_1$-$C_6$alkyl(heterocycloalkyl); wherein each alkyl, cycloalkyl, heterocycloalkyl, aryl, and heteroaryl is independently optionally substituted with one, two, or three $R^7$.

In some embodiment of a compound of Formula (I), (Ia)-(Id), $R^{17}$ is —$OR^{20}$, $C_1$-$C_6$alkyl, $C_1$-$C_6$haloalkyl, $C_1$-$C_6$hydroxyalkyl, cycloalkyl, heterocycloalkyl, —$C_1$-$C_6$alkyl(heteroaryl), or —$C_1$-$C_6$alkyl(cycloalkyl); wherein each alkyl, cycloalkyl, heterocycloalkyl, and heteroaryl is independently optionally substituted with one, two, or three $R^7$.

In some embodiment of a compound of Formula (I), (Ia)-(Id), $R^{17}$ is $C_1$-$C_6$alkyl, $C_1$-$C_6$haloalkyl, $C_1$-$C_6$hydroxyalkyl, or cycloalkyl; each optionally substituted with one, two, or three $R^7$.

In some embodiment of a compound of Formula (I), (Ia)-(Id), $R^{17}$ is $C_1$-$C_6$hydroxyalkyl, cycloalkyl, or heterocycloalkyl; each optionally substituted with one, two, or three $R^7$.

In some embodiment of a compound of Formula (I), (Ia)-(Id), $R^{17}$ is $C_1$-$C_6$alkyl or cycloalkyl; each optionally substituted with one, two, or three $R^7$. In some embodiment of a compound of Formula (I), (Ia)-(Id), $R^{17}$ is $C_1$-$C_6$alkyl optionally substituted with one, two, or three $R^7$.

In some embodiment of a compound of Formula (I), (Ia)-(Id), $R^{17}$ is $C_1$-$C_6$haloalkyl, $C_1$-$C_6$hydroxyalkyl or cycloalkyl; each optionally substituted with one, two, or three $R^7$. In some embodiment of a compound of Formula (I), (Ia)-(Id), $R^{17}$ is $C_1$-$C_6$haloalkyl optionally substituted with one, two, or three $R^7$. In some embodiment of a compound of Formula (I), (Ia)-(Id), $R^{17}$ is $C_1$-$C_6$hydroxyalkyl optionally substituted with one, two, or three $R^7$. In some embodiment of a compound of Formula (I), (Ia)-(Id), $R^{17}$ is cycloalkyl optionally substituted with one, two, or three $R^7$.

In some embodiment of a compound of Formula (I), (Ia)-(Id), each alkyl, alkenyl, alkynyl, cycloalkyl, cycloalkenyl, heterocycloalkyl, heterocycloalkenyl, aryl, or heteroaryl in $R^{16}$ or $R^{17}$ is optionally substituted with one, two, or three $R^7$. In some embodiment of a compound of Formula (I), (Ia)-(Id), each alkyl, alkenyl, alkynyl, cycloalkyl, cycloalkenyl, heterocycloalkyl, heterocycloalkenyl, aryl, or heteroaryl in $R^{16}$ or $R^{17}$ is optionally substituted with one or two $R^7$. In some embodiment of a compound of Formula (I), (Ia)-(Id), each alkyl, alkenyl, alkynyl, cycloalkyl, cycloalkenyl, heterocycloalkyl, heterocycloalkenyl, aryl, or heteroaryl in $R^{16}$ or $R^{17}$ is optionally substituted with one $R^7$. In some embodiment of a compound of Formula (I), (Ia)-(Id), each alkyl, alkenyl, alkynyl, cycloalkyl, cycloalkenyl, heterocycloalkyl, heterocycloalkenyl, aryl, or heteroaryl in $R^{16}$ or $R^{17}$ is optionally substituted with two $R^7$. In some embodiment of a compound of Formula (I), (Ia)-(Id), each each alkyl, alkenyl, alkynyl, cycloalkyl, cycloalkenyl, heterocycloalkyl, heterocycloalkenyl, aryl, or heteroaryl in $R^{16}$ or $R^{17}$ is optionally substituted with three $R^7$.

In some embodiment of a compound of Formula (I), (Ia)-(Id), each $R^7$ is independently oxo, halogen, —CN, —OH, —$OR^a$, —$S(=O)_2R^a$, —$NR^bR^c$, —$NHS(=O)_2R^a$, —$S(=O)_2NR^bR^c$, —$B(OR^b)(OR^c)$, —$C(=O)R^a$, —$C(=O)OR^b$, —$C(=O)NR^bR^c$, —$NR^bC(=O)R^a$, $C_1$-$C_6$alkyl, $C_1$-$C_6$haloalkyl, $C_1$-$C_6$hydroxyalkyl, $C_1$-$C_6$aminoalkyl, cycloalkyl, heterocycloalkyl, aryl, or heteroaryl; wherein each alkyl, alkenyl, alkynyl, cycloalkyl, heterocycloalkyl, aryl, and heteroaryl is independently optionally substituted with one, two, or three $R^{7a}$.

In some embodiment of a compound of Formula (I), (Ia)-(Id), each $R^7$ is independently oxo, halogen, —CN, —OH, —$OR^a$, —$S(=O)_2R^a$, —$NR^bR^c$, —$NHS(=O)_2R^a$, —$B(OR^b)(OR^c)$, —$C(=O)R^a$, —$C(=O)OR^b$, —$C(=O)NR^bR^c$, —$NR^bC(=O)R^a$, $C_1$-$C_6$alkyl, $C_1$-$C_6$haloalkyl, $C_1$-$C_6$hydroxyalkyl, cycloalkyl, heterocycloalkyl, or heteroaryl; wherein each alkyl, alkenyl, alkynyl, cycloalkyl, heterocycloalkyl, aryl, and heteroaryl is independently optionally substituted with one, two, or three $R^{7a}$.

In some embodiment of a compound of Formula (I), (Ia)-(Id), each $R^7$ is independently halogen, —CN, —OH, —$OR^a$, —$NR^bR^c$, —$B(OR^b)(OR^c)$, —$C(=O)R^a$, —$C(=O)OR^b$, —$C(=O)NR^bR^a$, $C_1$-$C_6$alkyl, $C_1$-$C_6$haloalkyl, $C_1$-$C_6$hydroxyalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{7a}$.

In some embodiment of a compound of Formula (I), (Ia)-(Id), each $R^7$ is independently halogen, —CN, —OH, —$OR^a$, —$NR^bR^c$, —$C(=O)R^a$, —$C(=O)OR^b$, —$C(=O)NR^bR^c$, $C_1$-$C_6$alkyl, $C_1$-$C_6$haloalkyl, $C_1$-$C_6$hydroxyalkyl, cycloalkyl, heterocycloalkyl, aryl, or heteroaryl; wherein each alkyl, cycloalkyl, heterocycloalkyl, aryl, and heteroaryl is independently optionally substituted with one, two, or three $R^{7a}$.

In some embodiment of a compound of Formula (I), (Ia)-(Id), each $R^7$ is independently halogen, —CN, —OH, —$OR^a$, —$NR^bR^c$, —$C(=O)OR^b$, —$C(=O)NR^bR^c$, $C_1$-$C_6$alkyl, $C_1$-$C_6$haloalkyl, $C_1$-$C_6$hydroxyalkyl, cycloalkyl, or heteroaryl; wherein each alkyl, cycloalkyl, heterocycloalkyl, and heteroaryl is independently optionally substituted with one, two, or three $R^{7a}$. In some embodiment of a compound of Formula (I), (Ia)-(Id), each $R^7$ is independently halogen, —OH, —$OR^a$, —$C(=O)OR^b$, —$C(=O)NR^bR^c$, $C_1$-$C_6$alkyl, or heteroaryl; wherein each alkyl, cycloalkyl and heteroaryl is independently optionally substituted with one, two, or three $R^{7a}$. In some embodiment of a compound of Formula (I), (Ia)-(Id), each $R^7$ is independently halogen, —$C(=O)OR^b$, —$C(=O)NR^bR^c$, $C_1$-$C_6$alkyl, or heteroaryl; wherein each alkyl, cycloalkyl and heteroaryl is independently optionally substituted with one, two, or three $R^{7a}$. In some embodiment of a compound of Formula (I), (Ia)-(Id), each $R^7$ is independently halogen, —$C(=O)OR^b$, —$C(=O)NR^bR^c$, or heteroaryl optionally substituted with one, two, or three $R^{7a}$. In some embodiment of a compound of Formula (I), (Ia)-(Id), each $R^7$ is independently halogen, —$C(=O)OR^b$, or —$C(=O)NR^bR^c$. In some embodiment of a compound of Formula (I), (Ia)-(Id), each $R^7$ is independently —$C(=O)OR^b$ or —$C(=O)NR^bR^c$.

In some embodiment of a compound of Formula (I), (Ia)-(Id), each alkyl, alkenyl, alkynyl, cycloalkyl, heterocycloalkyl, aryl, or heteroaryl in $R^7$ is optionally substituted with one, two, or three $R^{7a}$. In some embodiment of a compound of Formula (I), (Ia)-(Id), each alkyl, alkenyl, alkynyl, cycloalkyl, heterocycloalkyl, aryl, or heteroaryl in $R^7$ is optionally substituted with one or two $R^{7a}$. In some embodiment of a compound of Formula (I), (Ia)-(Id), each alkyl, alkenyl, alkynyl, cycloalkyl, heterocycloalkyl, aryl, or heteroaryl in $R^7$ is optionally substituted with one $R^{7a}$. In some embodiment of a compound of Formula (I), (Ia)-(Id), each alkyl, alkenyl, alkynyl, cycloalkyl, heterocycloalkyl, aryl, or heteroaryl in $R^7$ is optionally substituted with two $R^{7a}$. In some embodiment of a compound of Formula (I), (Ia)-(Id), each alkyl, alkenyl, alkynyl, cycloalkyl, heterocycloalkyl, aryl, or heteroaryl in $R^7$ is optionally substituted with three $R^{7a}$.

In some embodiments, when $R^7$ is —B(OR$^b$)(OR$^c$); one of the oxygen on the boron can form a cyclic structure with one of the carbonyl group:

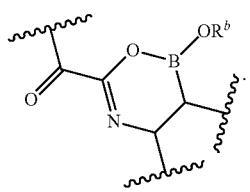

In some embodiment of a compound of Formula (I), (Ia)-(Id), each $R^{7a}$ is independently halogen, —CN, —OH, —OR$^a$, —NR$^b$R$^c$, $C_1$-$C_6$alkyl, or $C_1$-$C_6$haloalkyl. In some embodiment of a compound of Formula (I), (Ia)-(Id), each $R^{7a}$ is independently oxo, halogen, —CN, —OH, —OMe, —NH$_2$, Me, or CF$_3$. In some embodiment of a compound of Formula (I), (Ia)-(Id), each $R^{7a}$ is independently halogen, $C_1$-$C_6$alkyl, or $C_1$-$C_6$haloalkyl. In some embodiment of a compound of Formula (I), (Ia)-(Id), each $R^{7a}$ is independently halogen.

In some embodiment of a compound of Formula (I), (Ia)-(Id), $R^{16}$ and $R^{17}$ are taken together with the nitrogen atom to which they are attached to form a heterocycloalkyl optionally substituted with one, two, or three $R^8$. In some embodiment of a compound of Formula (I), (Ia)-(Id), $R^{16}$ and $R^{17}$ are taken together with the nitrogen atom to which they are attached to form a heterocycloalkyl optionally substituted with one, two, or three $R^8$; wherein the heterocycloalkyl is pyrrolidine, piperidine, morpholine, or piperazine. In some embodiment of a compound of Formula (I), (Ia)-(Id), $R^{16}$ and $R^{17}$ are taken together with the nitrogen atom to which they are attached to form a heterocycloalkyl optionally substituted with one, two, or three $R^8$; wherein the heterocycloalkyl is piperidine.

In some embodiment of a compound of Formula (I), (Ia)-(Id), the heterocycloalkyl or heterocycloalkenyl formed when $R^{16}$ and $R^{17}$ are taken together is optionally substituted with one, two, or three $R^8$. In some embodiment of a compound of Formula (I), (Ia)-(Id), the heterocycloalkyl or heterocycloalkenyl formed when $R^{16}$ and $R^{17}$ are taken together is optionally substituted with one or two $R^8$. In some embodiment of a compound of Formula (I), (Ia)-(Id), the heterocycloalkyl or heterocycloalkenyl formed when $R^{16}$ and $R^{17}$ are taken together is optionally substituted with one $R^8$. In some embodiment of a compound of Formula (I), (Ia)-(Id), the heterocycloalkyl or heterocycloalkenyl formed when $R^{16}$ and $R^{17}$ are taken together is optionally substituted with two $R^8$. In some embodiment of a compound of Formula (I), (Ia)-(Id), the heterocycloalkyl or heterocycloalkenyl formed when $R^{16}$ and $R^{17}$ are taken together is optionally substituted with three $R^8$.

In some embodiment of a compound of Formula (I), (Ia)-(Id), each $R^8$ is independently oxo, halogen, —CN, —OH, —OR$^a$, —NR$^b$R$^c$, —C(=O)R$^a$, —C(=O)OR$^b$, $C_1$-$C_6$alkyl, $C_1$-$C_6$haloalkyl, $C_1$-$C_6$hydroxyalkyl, $C_1$-$C_6$aminoalkyl, cycloalkyl, or heterocycloalkyl; wherein each alkyl, cycloalkyl, and heterocycloalkyl is independently optionally substituted with one, two, or three oxo, halogen, —CN, —OH, —OMe, —NH$_2$, $C_1$-$C_6$alkyl, $C_1$-$C_6$haloalkyl, $C_1$-$C_6$hydroxyalkyl, or $C_1$-$C_6$aminoalkyl. In some embodiment of a compound of Formula (I), (Ia)-(Id), each $R^8$ is independently oxo, halogen, —CN, —OH, —OR$^a$, —NR$^b$R$^c$, $C_1$-$C_6$alkyl, $C_1$-$C_6$haloalkyl, $C_1$-$C_6$hydroxyalkyl, or $C_1$-$C_6$aminoalkyl; wherein each alkyl is independently optionally substituted with one, two, or three oxo, halogen, —CN, —OH, —OMe, —NH$_2$, $C_1$-$C_6$alkyl, or $C_1$-$C_6$haloalkyl. In some embodiment of a compound of Formula (I), (Ia)-(Id), each $R^8$ is independently oxo, halogen, —CN, —OH, —OR$^a$, —NR$^b$R$^c$, $C_1$-$C_6$alkyl, $C_1$-$C_6$haloalkyl; wherein each alkyl is independently optionally substituted with one, two, or three oxo, halogen, —CN, —OH, —OMe, —NH$_2$, $C_1$-$C_6$alkyl, or $C_1$-$C_6$haloalkyl. In some embodiment of a compound of Formula (I), (Ia)-(Id), each $R^8$ is independently oxo, halogen, —CN, —OH, —OR$^a$, —NR$^b$R$^c$, $C_1$-$C_6$alkyl, $C_1$-$C_6$haloalkyl. In some embodiment of a compound of Formula (I), (Ia)-(Id), each $R^8$ is independently halogen, —CN, —OH, —OR$^a$, —NR$^b$R$^c$, $C_1$-$C_6$alkyl, $C_1$-$C_6$haloalkyl, or $C_1$-$C_6$hydroxyalkyl. In some embodiment of a compound of Formula (I), (Ia)-(Id), each $R^8$ is independently oxo, halogen, —CN, —OH, —OMe, —NH$_2$, Me, or CF$_3$. In some embodiment of a compound of Formula (I), (Ia)-(Id), each $R^8$ is independently —OH or $C_1$-$C_6$alkyl. In some embodiment of a compound of Formula (I), (Ia)-(Id), each $R^8$ is independently oxo, halogen, —CN, —OH, —OR$^a$, —NR$^b$R$^c$, $C_1$-$C_6$alkyl, $C_1$-$C_6$haloalkyl, or $C_1$-$C_6$hydroxyalkyl.

In some embodiment of a compound of Formula (I), (Ia)-(Id),

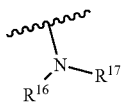

is

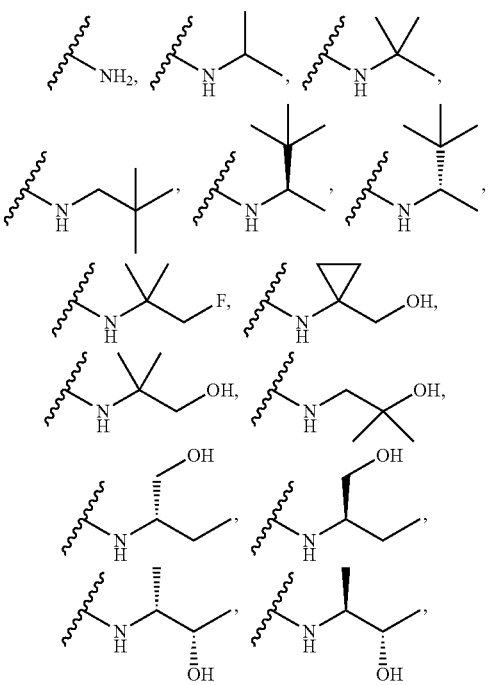

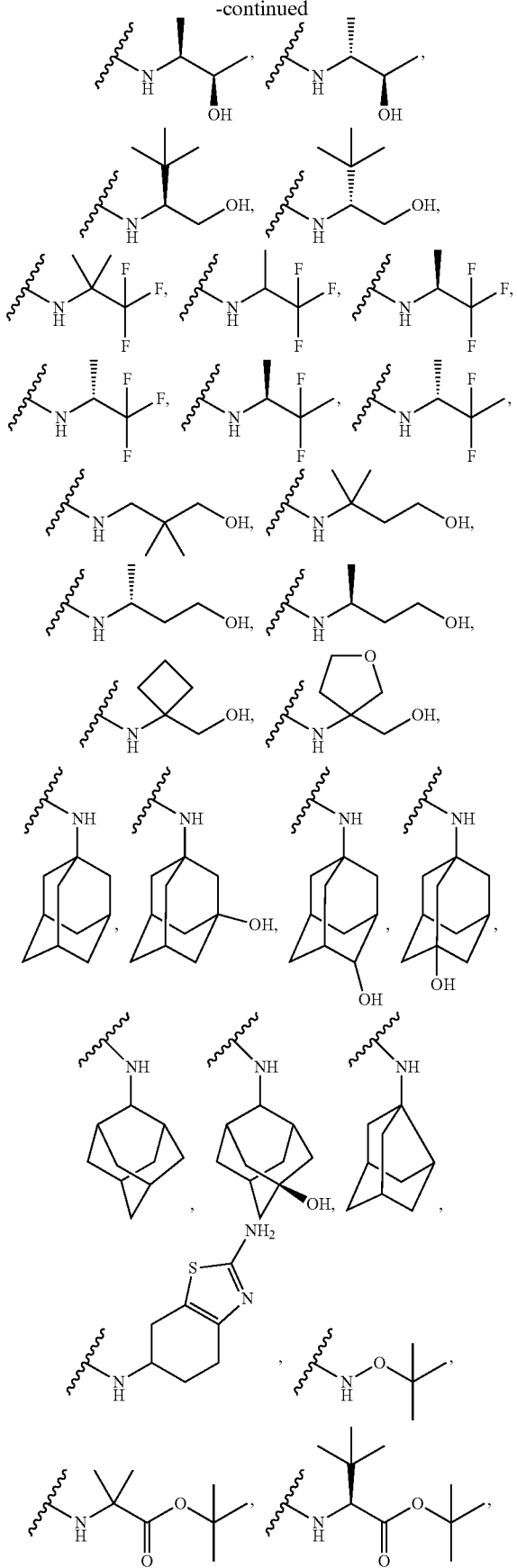
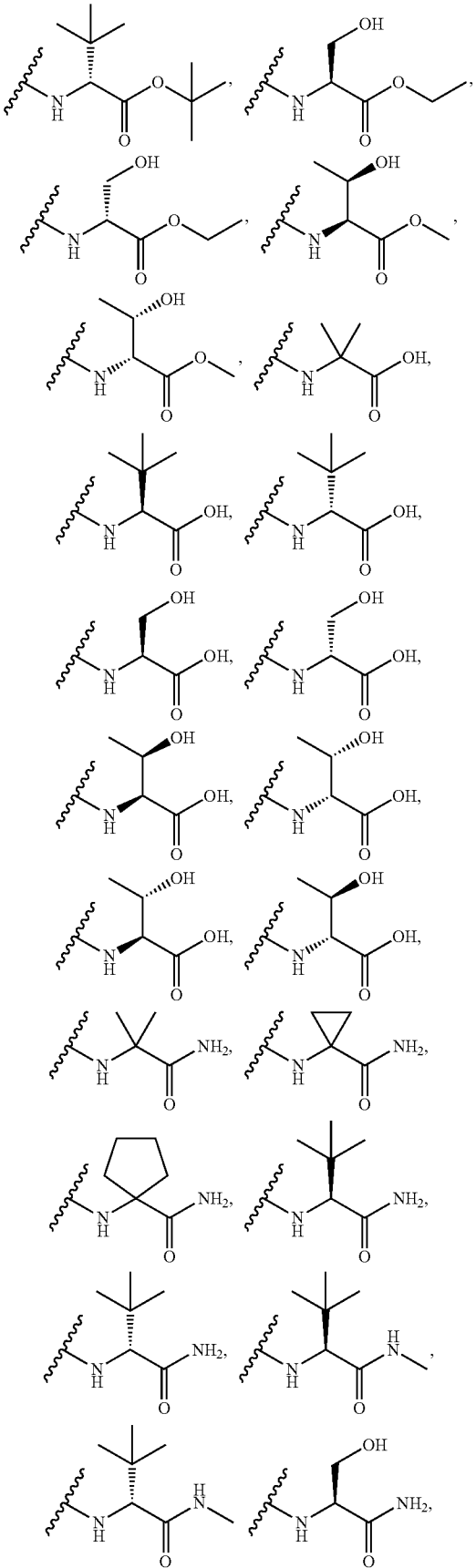

-continued
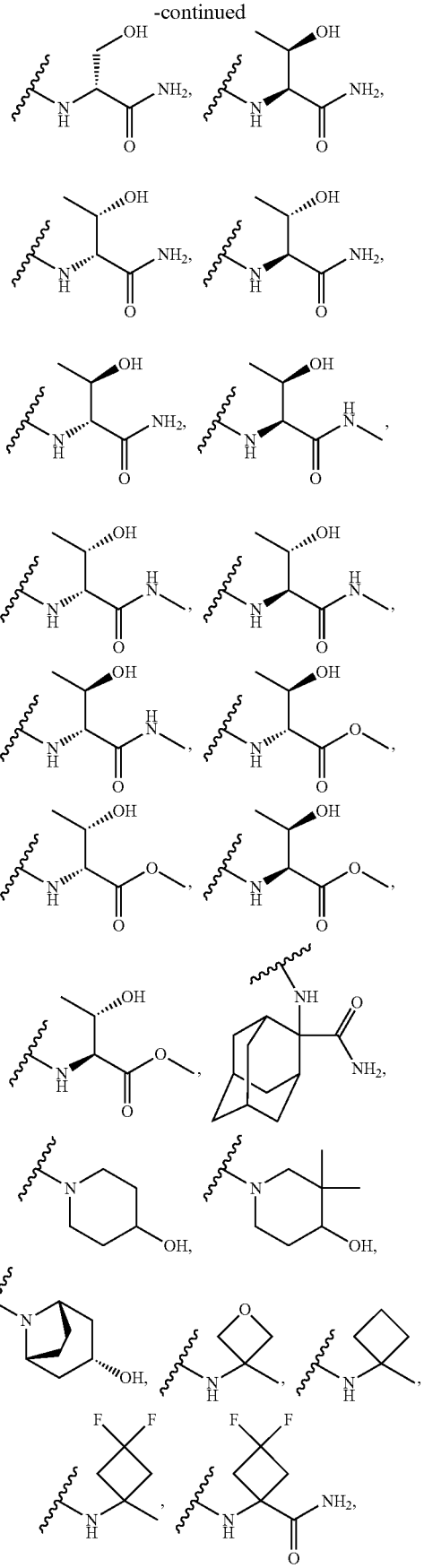
-continued
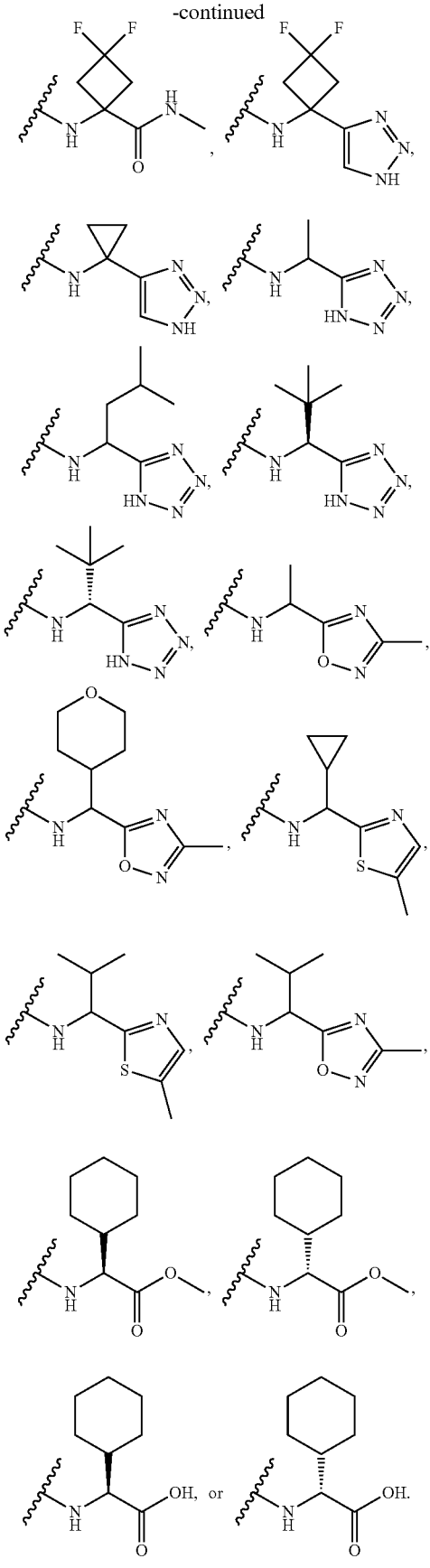

In some embodiment of a compound of Formula (I), (Ia)-(Id),
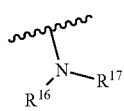
is
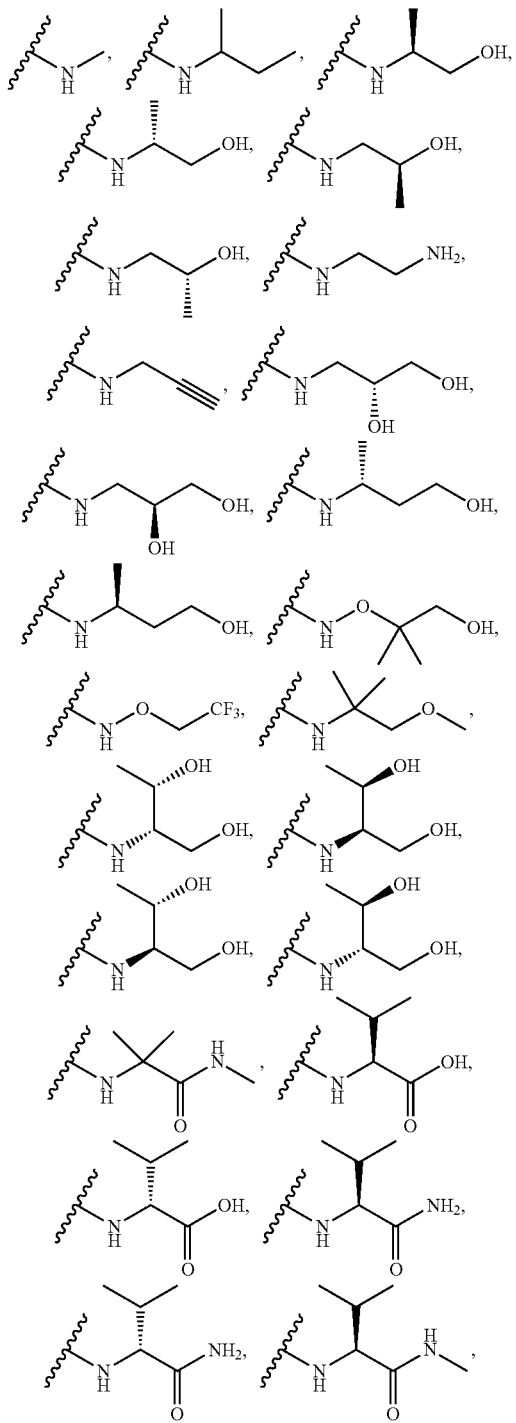
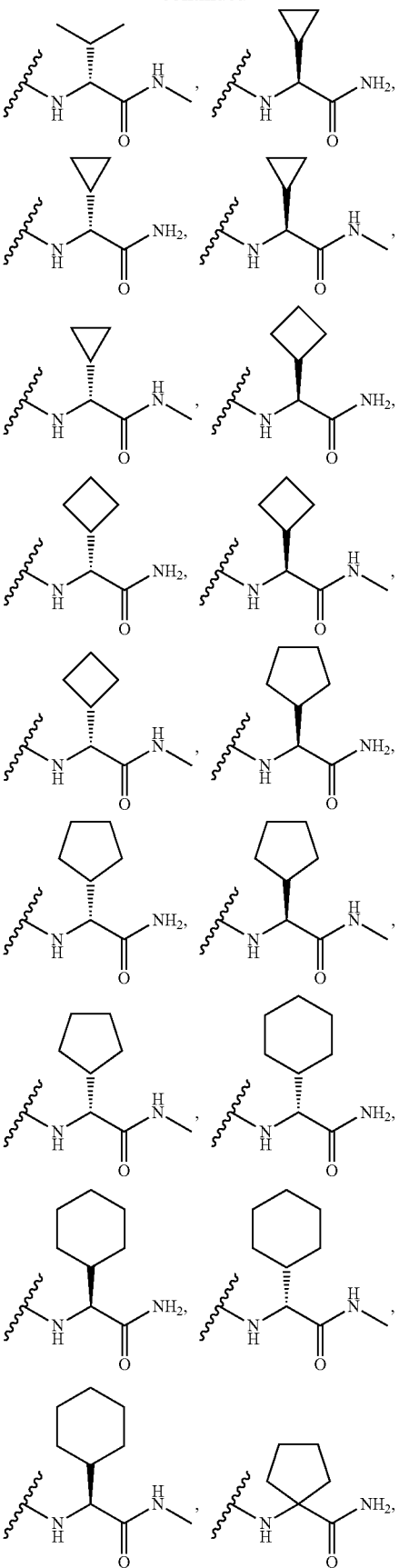

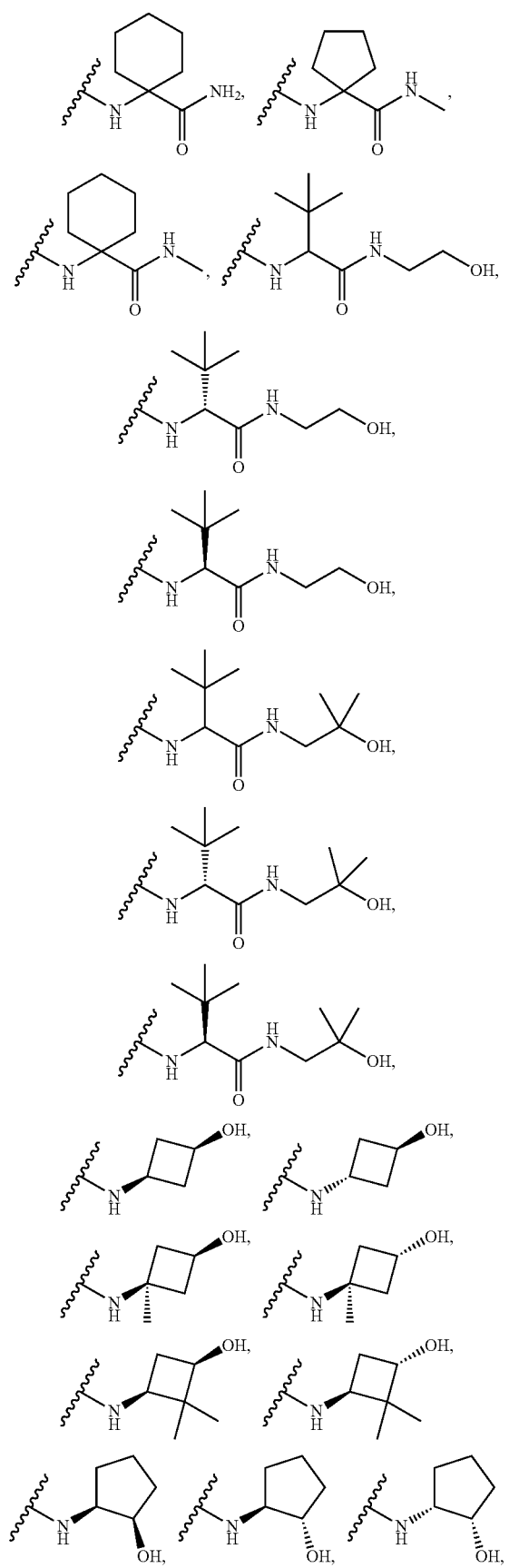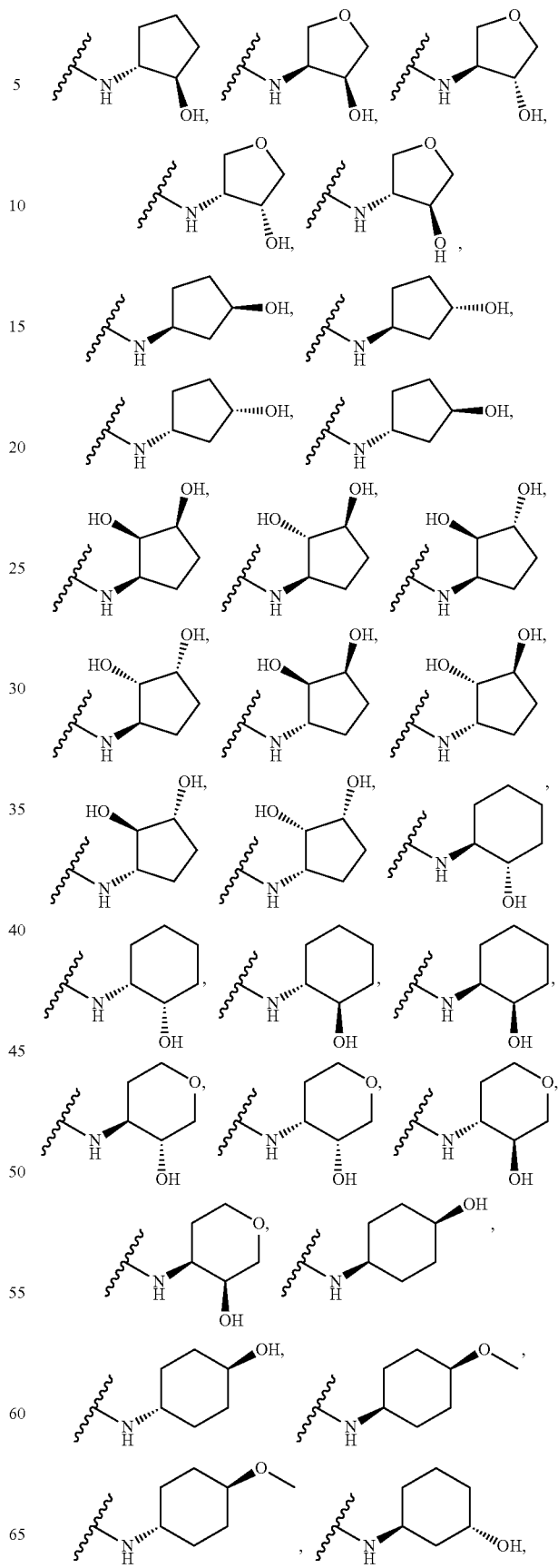

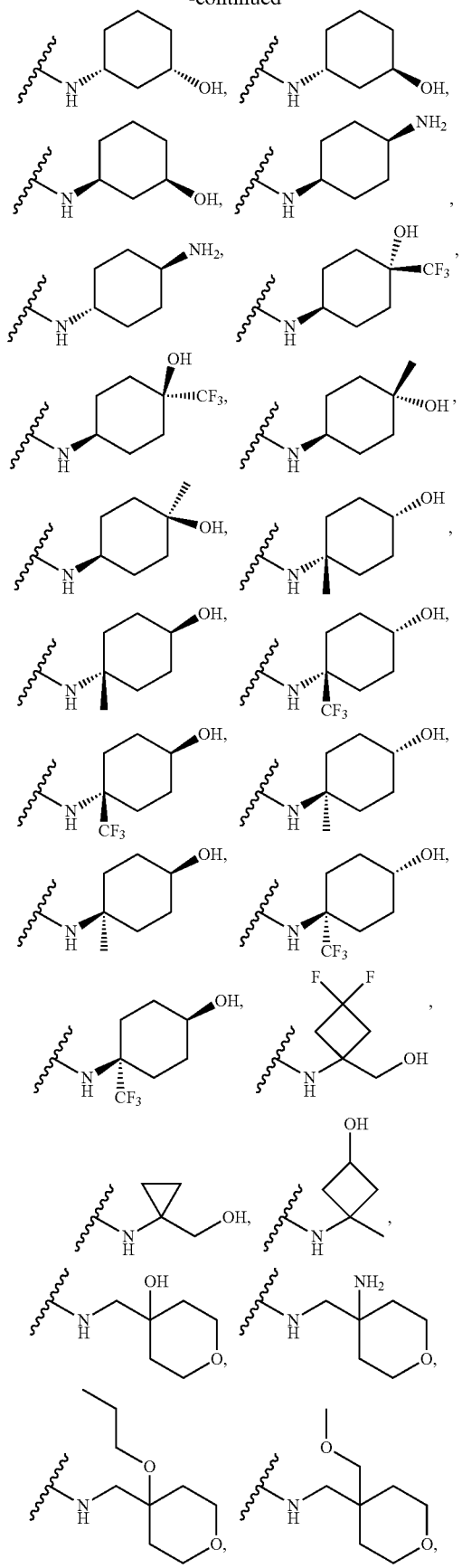
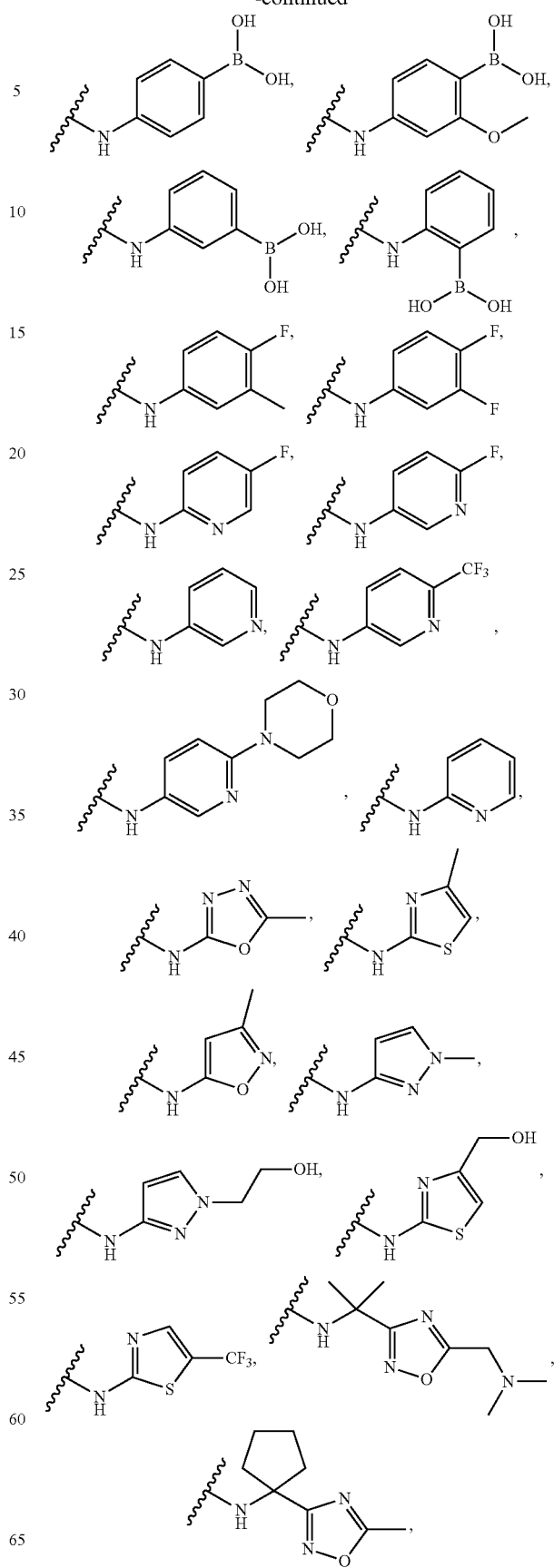

51
-continued
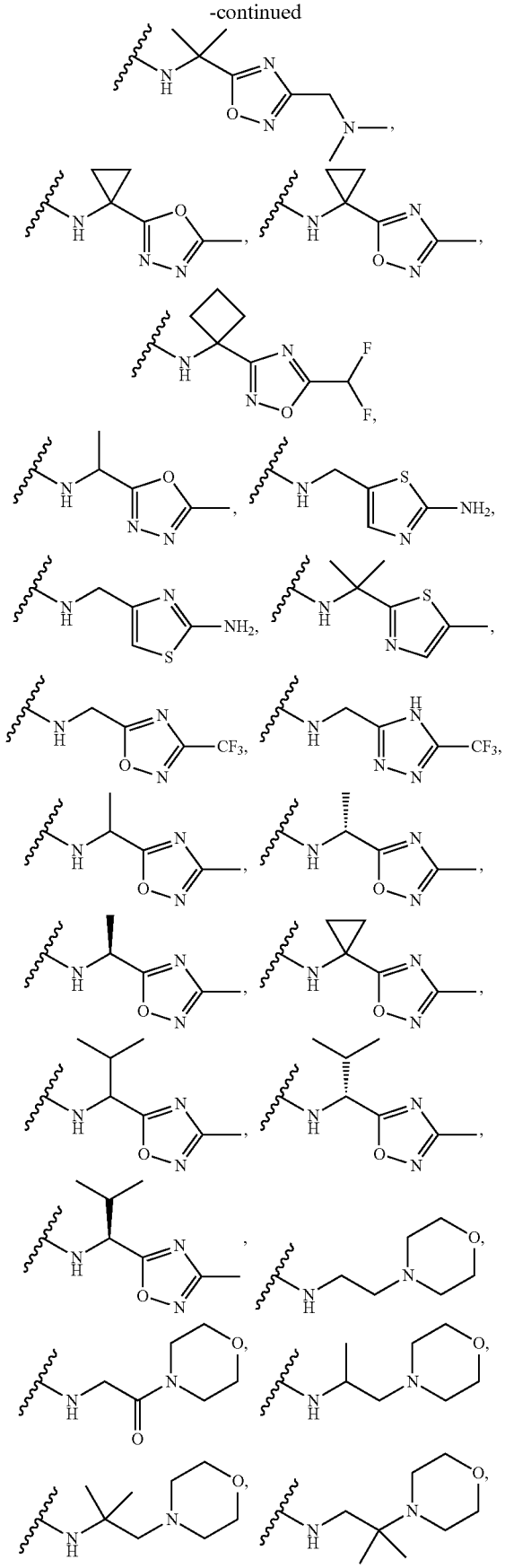
52
-continued
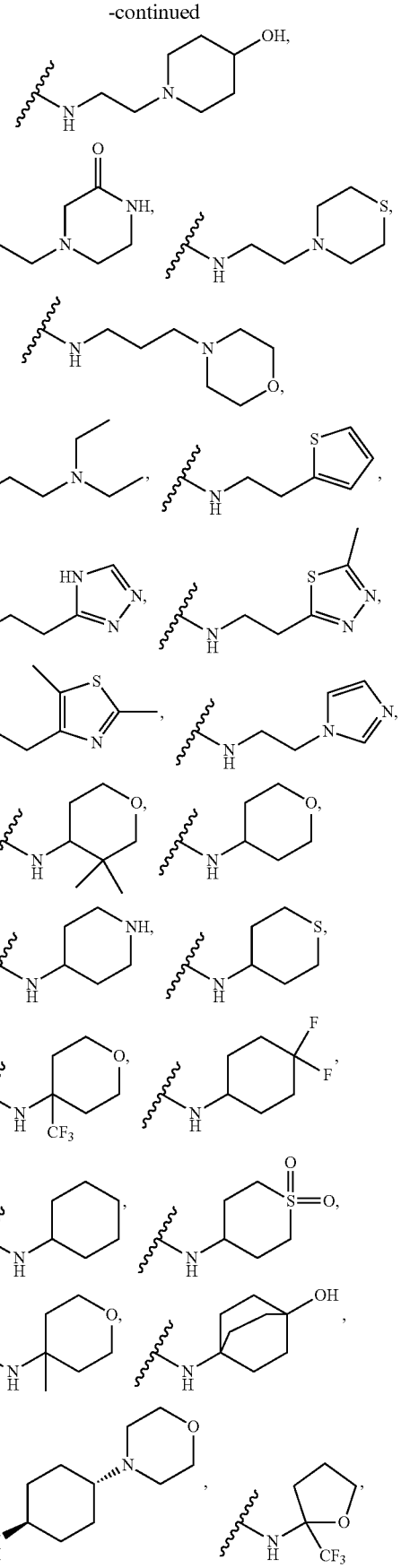

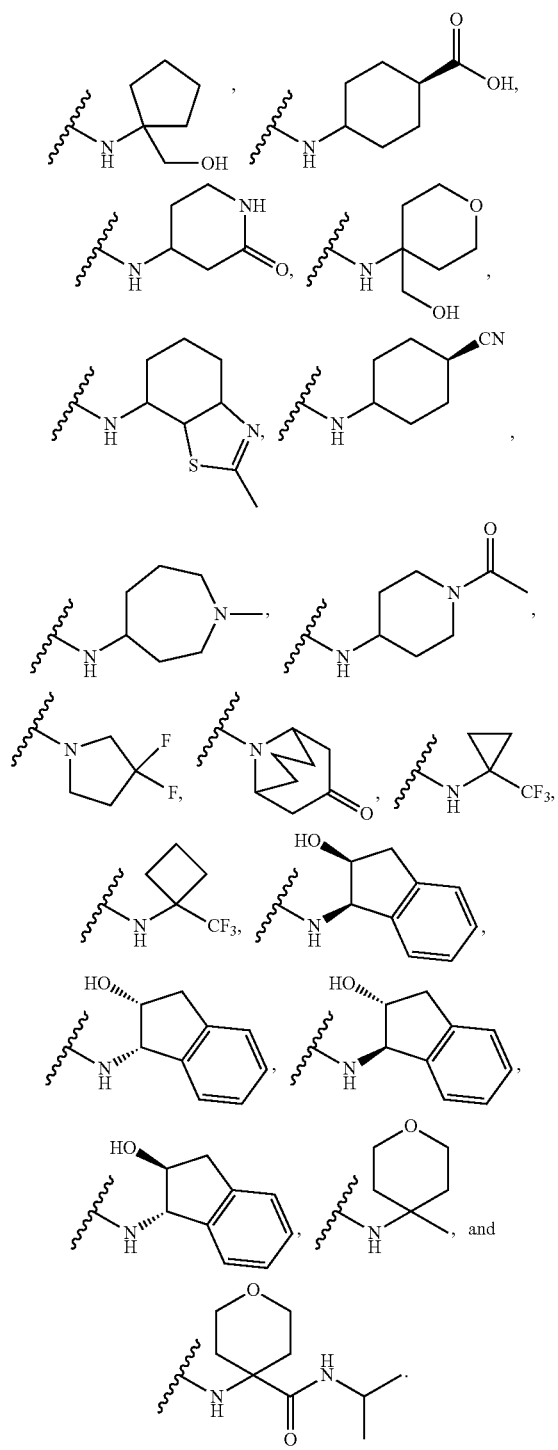
In some embodiment of a compound of Formula (I), (Ia)-(Id),
is

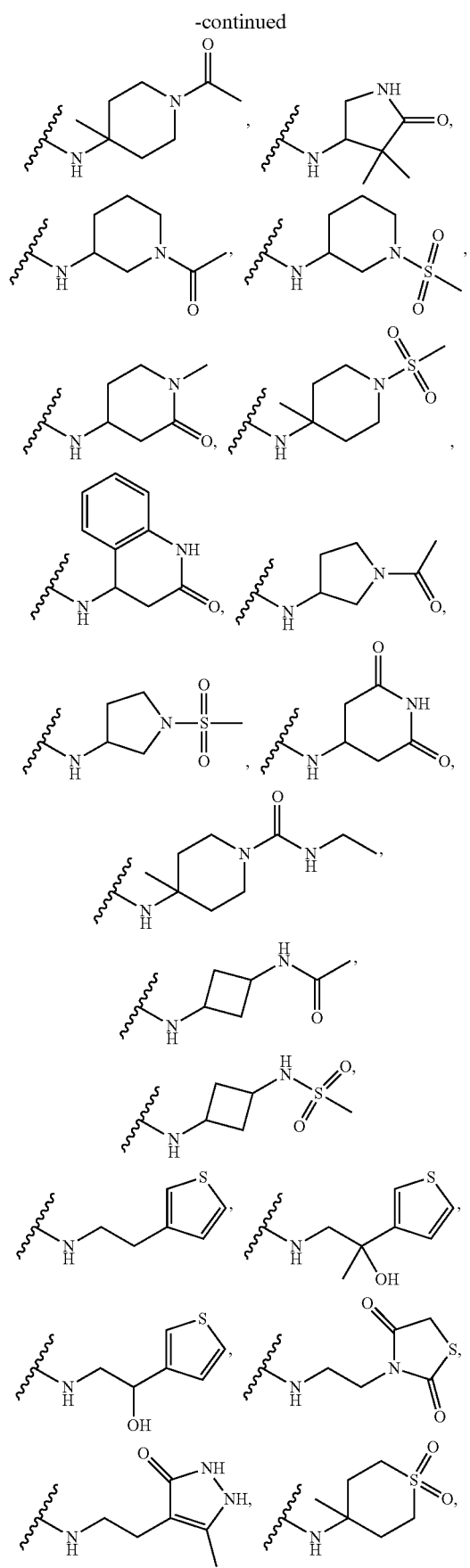
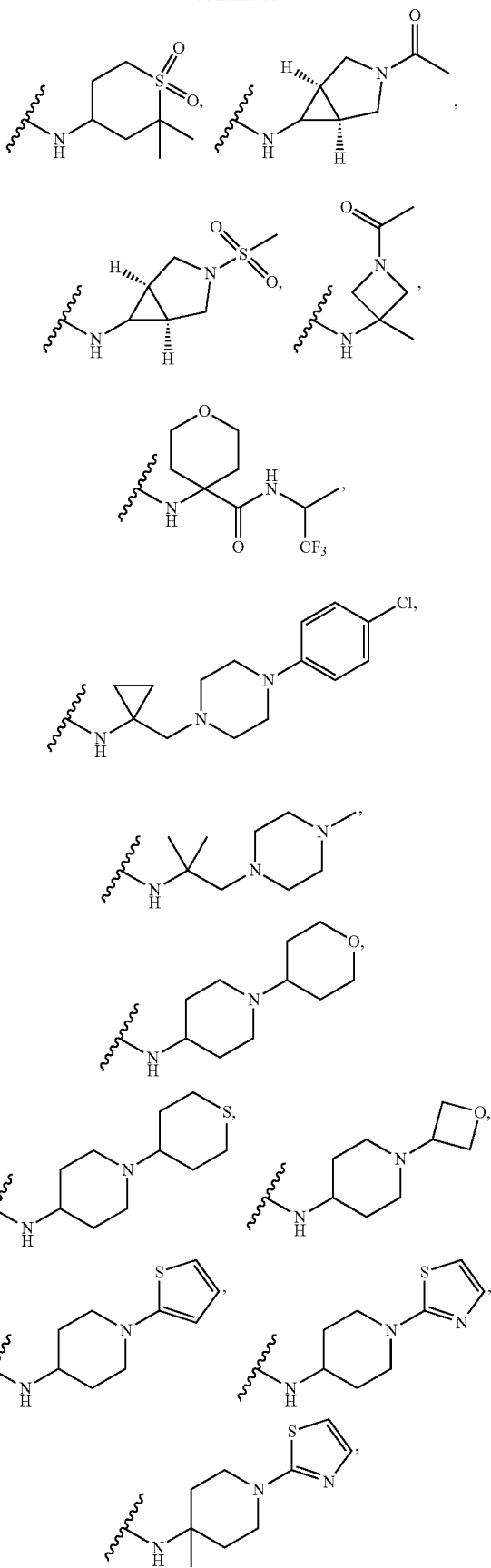

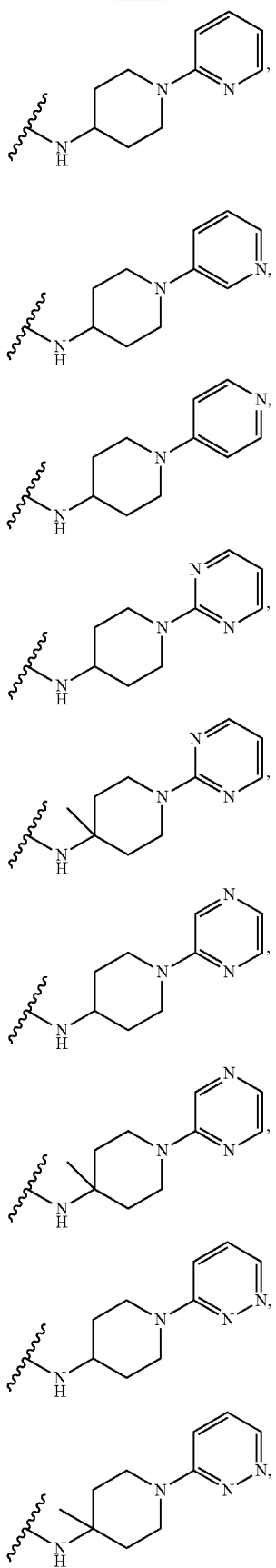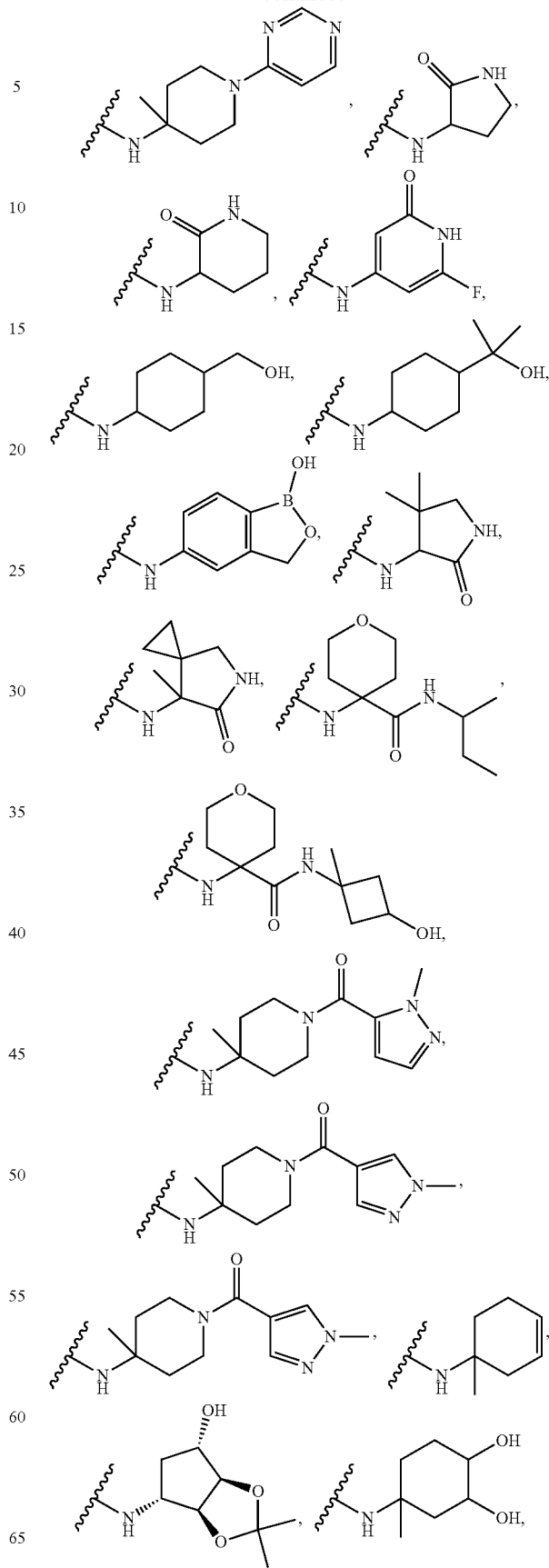

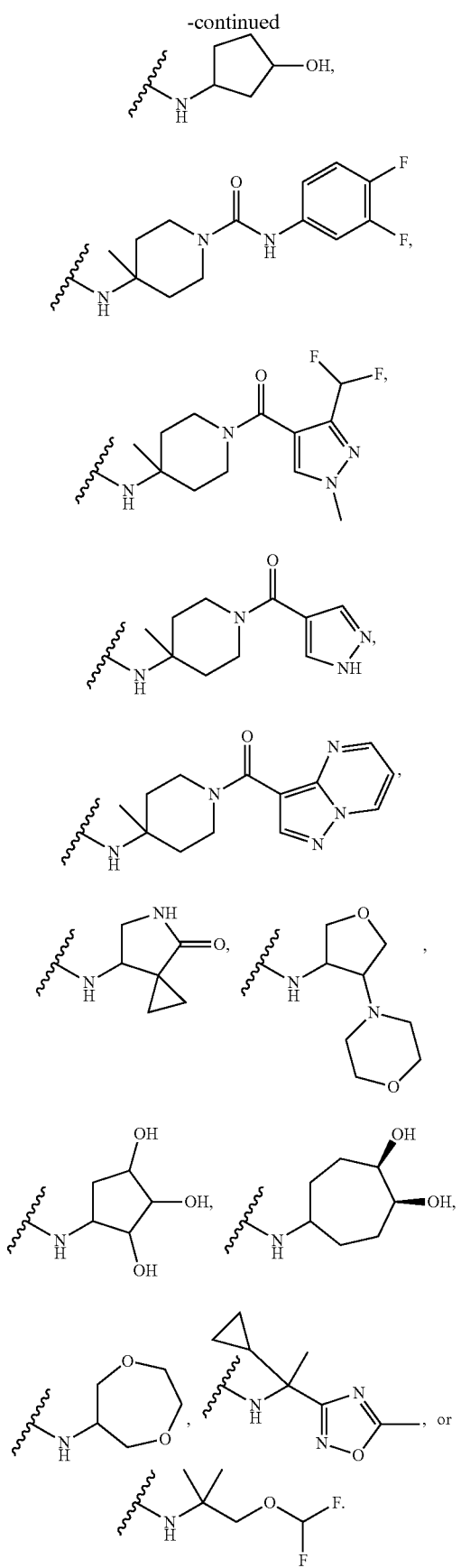

In some embodiments of a compound of Formula (I), (Ia)-(Id), or a pharmaceutically acceptable salt, solvate, or stereoisomer thereof, each $R^a$ is independently $C_1$-$C_6$alkyl, $C_1$-$C_6$haloalkyl, $C_1$-$C_6$hydroxyalkyl, $C_1$-$C_6$aminoalkyl, cycloalkyl, heterocycloalkyl, aryl, or heteroaryl. In some embodiments of a compound of Formula (I), (Ia)-(Id), or a pharmaceutically acceptable salt, solvate, or stereoisomer thereof, each $R^a$ is independently $C_1$-$C_6$alkyl, $C_1$-$C_6$haloalkyl, cycloalkyl, or heterocycloalkyl. In some embodiments of a compound of Formula (I), (Ia)-(Id), or a pharmaceutically acceptable salt, solvate, or stereoisomer thereof, each $R^a$ is independently $C_1$-$C_6$alkyl, $C_1$-$C_6$haloalkyl, or cycloalkyl. In some embodiments of a compound of Formula (I), (Ia)-(Id), or a pharmaceutically acceptable salt, solvate, or stereoisomer thereof, each $R^a$ is independently $C_1$-$C_6$alkyl or $C_1$-$C_6$haloalkyl. In some embodiments of a compound of Formula (I), (Ia)-(Id), or a pharmaceutically acceptable salt, solvate, or stereoisomer thereof; each $R^a$ is independently $C_1$-$C_6$alkyl.

In some embodiments of a compound of Formula (I), (Ia)-(Id), or a pharmaceutically acceptable salt, solvate, or stereoisomer thereof, each $R^b$ and $R^c$ is independently hydrogen, $C_1$-$C_6$alkyl, $C_1$-$C_6$haloalkyl, $C_1$-$C_6$hydroxyalkyl, $C_1$-$C_6$aminoalkyl, cycloalkyl, heterocycloalkyl, aryl, or heteroaryl. In some embodiments of a compound of Formula (I), (Ia)-(Id), or a pharmaceutically acceptable salt, solvate, or stereoisomer thereof, each $R^b$ and $R^c$ is independently hydrogen, $C_1$-$C_6$alkyl, $C_1$-$C_6$haloalkyl, cycloalkyl, or heterocycloalkyl. In some embodiments of a compound of Formula (I), (Ia)-(Id), or a pharmaceutically acceptable salt, solvate, or stereoisomer thereof, each $R^b$ and $R^c$ is independently hydrogen, $C_1$-$C_6$alkyl, $C_1$-$C_6$haloalkyl, or cycloalkyl. In some embodiments of a compound of Formula (I), (Ia)-(Id), or a pharmaceutically acceptable salt, solvate, or stereoisomer thereof, each $R^b$ and $R^c$ is independently hydrogen, $C_1$-$C_6$alkyl, or $C_1$-$C_6$haloalkyl. In some embodiments of a compound of Formula (I), (Ia)-(Id), or a pharmaceutically acceptable salt, solvate, or stereoisomer thereof, each $R^b$ and $R^c$ is independently hydrogen or $C_1$-$C_6$alkyl. In some embodiments of a compound of Formula (I), (Ia)-(Id), or a pharmaceutically acceptable salt, solvate, or stereoisomer thereof, each $R^b$ and $R^c$ is hydrogen.

In some embodiments of a compound of Formula (I), (Ia)-(Id), or a pharmaceutically acceptable salt, solvate, or stereoisomer thereof, $R^b$ and $R^c$ are taken together with the atom to which they are attached to form a heterocycloalkyl optionally substituted with one, two, or three halogen, $C_1$-$C_6$alkyl, or $C_1$-$C_6$haloalkyl.

Any combination of the groups described above for the various variables is contemplated herein. Throughout the specification, groups and substituents thereof are chosen by one skilled in the field to provide stable moieties and compounds.

Described herein is a compound of Formula (I), (Ia)-(Id), or a pharmaceutically acceptable salt, solvate, or stereoisomer thereof; selected from a compound in Table 1.

TABLE 1

Exemplary compounds

| Ex. | Structure | Chemical Name | ESI-MS (M + H)+ (m/z) |
| --- | --- | --- | --- |
| 1 | 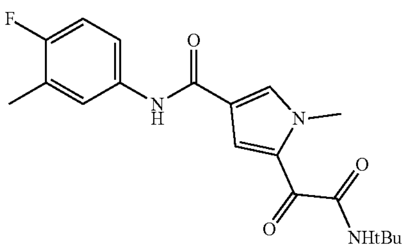 | 5-(2-(tert-butylamino)-2-oxoacetyl)-N-(4-fluoro-3-methylphenyl)-1-methyl-1H-pyrrole-3-carboxamide | 360.1 |
| 2 | 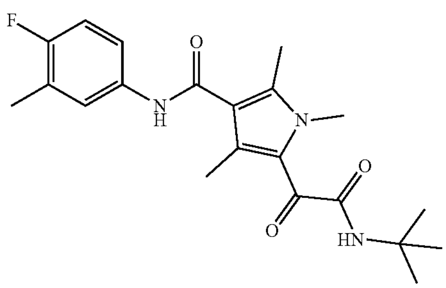 [SMILES: Cc1cc(NC(=O)c2c(C)c(C(=O)C(=O)NC(C)(C)C)n(C)c2C)ccc1F] | 5-(2-(tert-butylamino)-2-oxoacetyl)-N-(4-fluoro-3-methylphenyl)-1,2,4-trimethyl-1H-pyrrole-3-carboxamide | 388.2 |
| 3 | 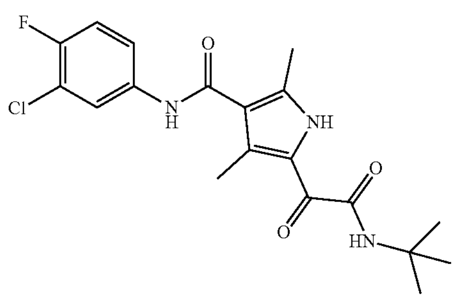 [SMILES: Cc1[nH]c(C(=O)C(=O)NC(C)(C)C)c(C)c1C(=O)Nc1ccc(F)c(Cl)c1] | 5-(2-(tert-butylamino)-2-oxoacetyl)-N-(3-chloro-4-fluorophenyl)-2,4-dimethyl-1H-pyrrole-3-carboxamide | 394 |
| 4 | 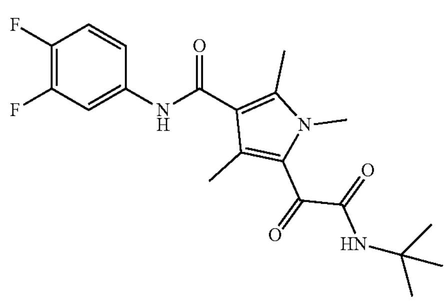 [SMILES: Cc1c(C(=O)Nc2ccc(F)c(F)c2)c(C)n(C)c1C(=O)C(=O)NC(C)(C)C] | 5-(2-(tert-butylamino)-2-oxoacetyl)-N-(3,4-difluorophenyl)-1,2,4-trimethyl-1H-pyrrole-3-carboxamide | 392.2 |
| 5 | 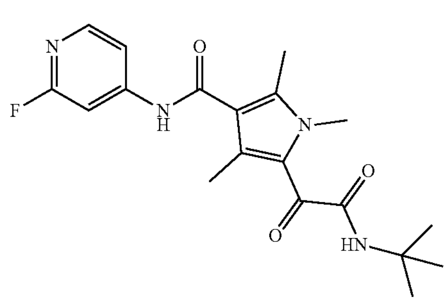 [SMILES: Cc1c(C(=O)Nc2ccnc(F)c2)c(C)n(C)c1C(=O)C(=O)NC(C)(C)C] | 5-(2-(tert-butylamino)-2-oxoacetyl)-N-(2-fluoropyridin-4-yl)-1,2,4-trimethyl-1H-pyrrole-3-carboxamide | 375.2 |

TABLE 1-continued

Exemplary compounds

| Ex. | Structure | Chemical Name | ESI-MS (M + H)+ (m/z) |
|---|---|---|---|
| 6 | 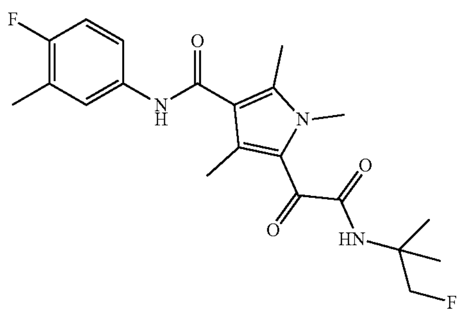 [SMILES: Cc1cc(NC(=O)c2c(C)c(C(=O)C(=O)NC(C)(C)CF)n(C)c2C)ccc1F] | 5-(2-((1-fluoro-2-methylpropan-2-yl)amino)-2-oxoacetyl)-N-(4-fluoro-3-methylphenyl)-1,2,4-trimethyl-1H-pyrrole-3-carboxamide | 428.2 |
| 7 | 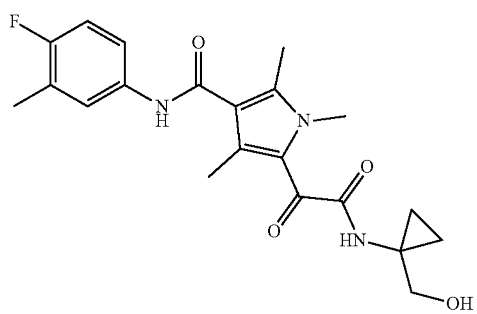 [SMILES: Cc1cc(NC(=O)c2c(C)c(C(=O)C(=O)NC3(CO)CC3)n(C)c2C)ccc1F] | N-(4-fluoro-3-methylphenyl)-5-(2-((1-(hydroxymethyl)cyclopropyl)amino)-2-oxoacetyl)-1,2,4-trimethyl-1H-pyrrole-3-carboxamide | 402.2 |
| 8 | 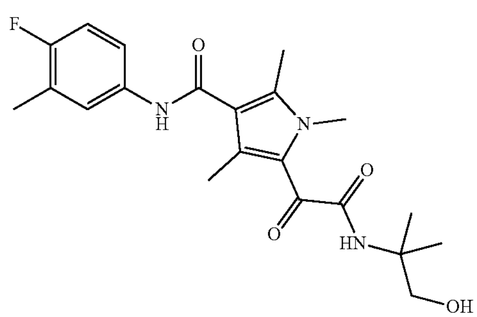 [SMILES: Cc1cc(NC(=O)c2c(C)c(C(=O)C(=O)NC(C)(C)CO)n(C)c2C)ccc1F] | N-(4-fluoro-3-methylphenyl)-5-(2-((1-hydroxy-2-methylpropan-2-yl)amino)-2-oxoacetyl)-1,2,4-trimethyl-1H-pyrrole-3-carboxamide | 404.2 |
| 9 | 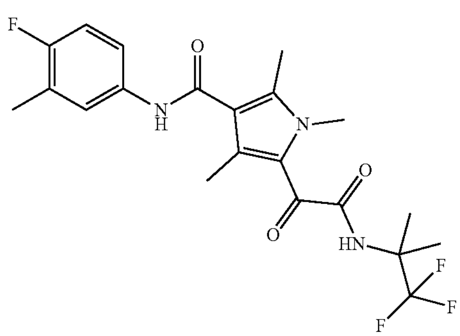 [SMILES: Cc1cc(NC(=O)c2c(C)c(C(=O)C(=O)NC(C)(C)C(F)(F)F)n(C)c2C)ccc1F] | N-(4-fluoro-3-methylphenyl)-1,2,4-trimethyl-5-(2-oxo-2-((1,1,1-trifluoro-2-methylpropan-2-yl)amino)acetyl)-1H-pyrrole-3-carboxamide | 442.2 |

TABLE 1-continued

Exemplary compounds

| Ex. | Structure | Chemical Name | ESI-MS (M + H)+ (m/z) |
|---|---|---|---|
| 10 | 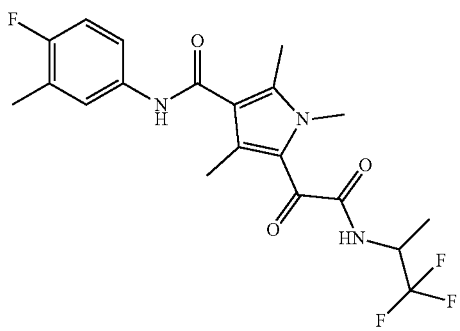 [SMILES: Cc1cc(NC(=O)c2c(C)c(C(=O)C(=O)NC(C)C(F)(F)F)n(C)c2C)ccc1F] | N-(4-fluoro-3-methylphenyl)-1,2,4-trimethyl-5-(2-oxo-2-((1,1,1-trifluoropropan-2-yl)amino)acetyl)-1H-pyrrole-3-carboxamide | 428.2 |
| 11 | 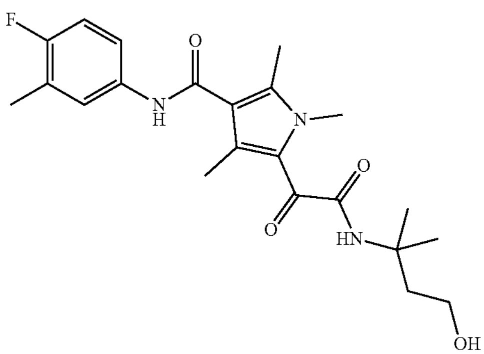 [SMILES: Cc1cc(NC(=O)c2c(C)c(C(=O)C(=O)NC(C)(C)CCO)n(C)c2C)ccc1F] | N-(4-fluoro-3-methylphenyl)-5-(2-((4-hydroxy-2-methylbutan-2-yl)amino)-2-oxoacetyl)-1,2,4-trimethyl-1H-pyrrole-3-carboxamide | 418.2 |
| 12 | 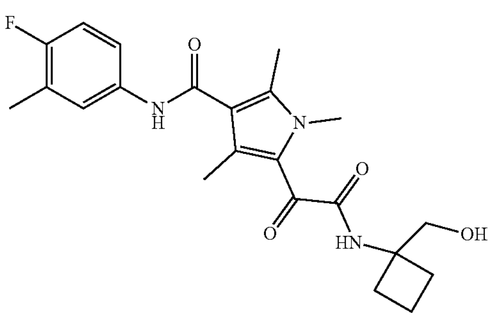 [SMILES: Cc1cc(NC(=O)c2c(C)c(C(=O)C(=O)NC3(CO)CCC3)n(C)c2C)ccc1F] | N-(4-fluoro-3-methylphenyl)-5-(2-((1-(hydroxymethyl)cyclobutyl)amino)-2-oxoacetyl)-1,2,4-trimethyl-1H-pyrrole-3-carboxamide | 416.2 |
| 13 | 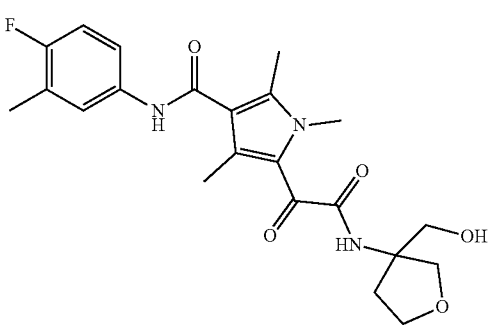 [SMILES: Cc1cc(NC(=O)c2c(C)c(C(=O)C(=O)NC3(CO)CCOC3)n(C)c2C)ccc1F] | N-(4-fluoro-3-methylphenyl)-5-(2-((3-(hydroxymethyl)tetrahydrofuran-3-yl)amino)-2-oxoacetyl)-1,2,4-trimethyl-1H-pyrrole-3-carboxamide | 432.2 |

TABLE 1-continued

Exemplary compounds

| Ex. | Structure | Chemical Name | ESI-MS (M + H)+ (m/z) |
|---|---|---|---|
| 14 | 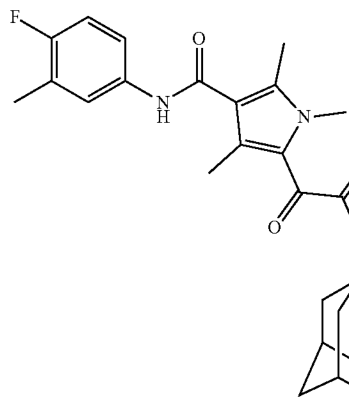 | 5-(2-(((3s,5s,7s)-adamantan-1-yl)amino)-2-oxoacetyl)-N-(4-fluoro-3-methylphenyl)-1,2,4-trimethyl-1H-pyrrole-3-carboxamide | 466.2 |
| 15 | 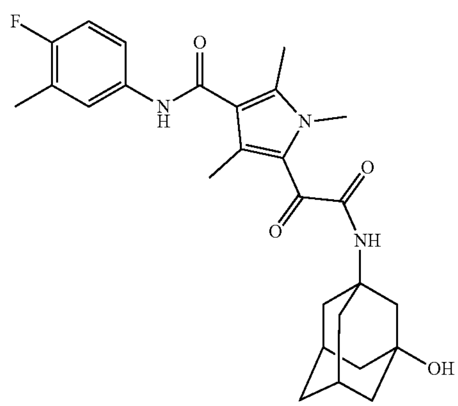 [SMILES: Cc1cc(NC(=O)c2c(C)c(C(=O)C(=O)NC34CC5CC(CC(O)(C5)C3)C4)n(C)c2C)ccc1F] | N-(4-fluoro-3-methylphenyl)-5-(2-(((1r,3s,5R,7S)-3-hydroxyadamantan-1-yl)amino)-2-oxoacetyl)-1,2,4-trimethyl-1H-pyrrole-3-carboxamide | 482.2 |
| 16 | 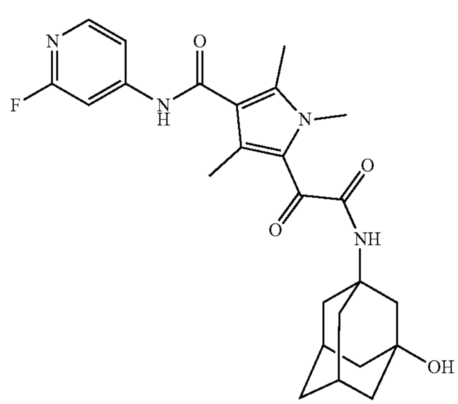 [SMILES: Cc1c(C(=O)Nc2ccnc(F)c2)c(C)n(C)c1C(=O)C(=O)NC12CC3CC(CC(O)(C3)C1)C2] | N-(2-fluoropyridin-4-yl)-5-(2-(((1r,3s,5R,7S)-3-hydroxyadamantan-1-yl)amino)-2-oxoacetyl)-1,2,4-trimethyl-1H-pyrrole-3-carboxamide | 469.2 |

TABLE 1-continued

Exemplary compounds

| Ex. | Structure | Chemical Name | ESI-MS (M + H)+ (m/z) |
|---|---|---|---|
| 17 | 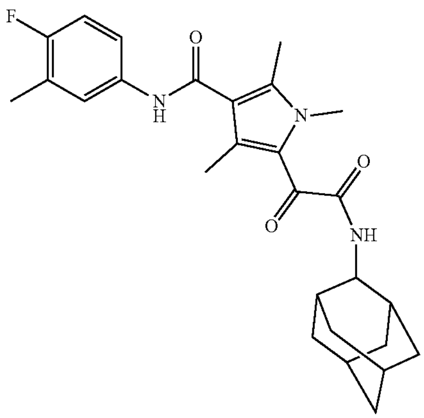 [SMILES: Cc1cc(NC(=O)c2c(C)c(C(=O)C(=O)NC3C4CC5CC(C4)CC3C5)n(C)c2C)ccc1F] | 5-(2-(((1r,3r)-adamantan-2-yl)amino)-2-oxoacetyl)-N-(4-fluoro-3-methylphenyl)-1,2,4-trimethyl-1H-pyrrole-3-carboxamide | 466.1 |
| 18 | 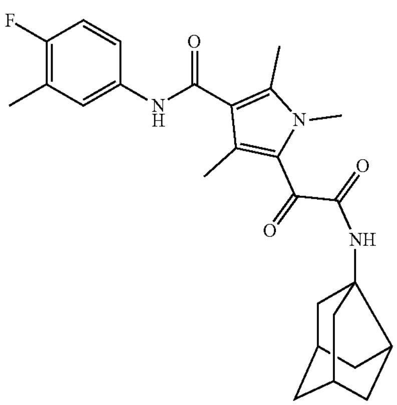 [SMILES: Cc1cc(NC(=O)c2c(C)c(C(=O)C(=O)NC34CC5CC(CC3C5)C4)n(C)c2C)ccc1F] | N-(4-fluoro-3-methylphenyl)-5-(2-(((2R,3as,5S,6as)-hexahydro-2,5-methanopentalen-3a(1H)-yl)amino)-2-oxoacetyl)-1,2,4-trimethyl-1H-pyrrole-3-carboxamide | 452.2 |
| 19 | 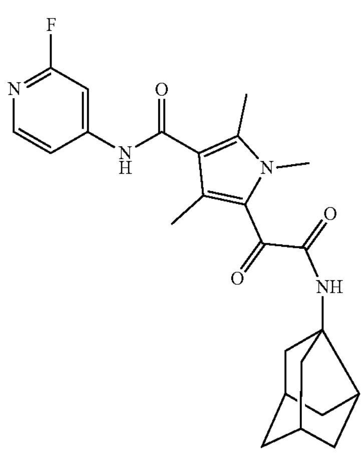 [SMILES: Cc1c(C(=O)Nc2ccnc(F)c2)c(C)n(C)c1C(=O)C(=O)NC12CC3CC(CC1C3)C2] | N-(2-fluoropyridin-4-yl)-5-(2-(((2R,3as,5S,6as)-hexahydro-2,5-methanopentalen-3a(1H)-yl)amino)-2-oxoacetyl)-1,2,4-trimethyl-1H-pyrrole-3-carboxamide | 439.2 |

TABLE 1-continued

Exemplary compounds

| Ex. | Structure | Chemical Name | ESI-MS (M + H)+ (m/z) |
|---|---|---|---|
| 20 | 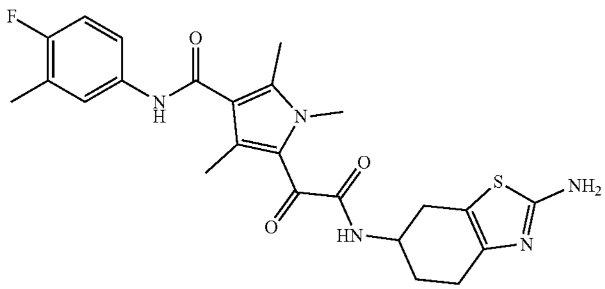 [SMILES: Cc1cc(NC(=O)c2c(C)c(C(=O)C(=O)NC3CCc4nc(N)sc4C3)n(C)c2C)ccc1F] | 5-(2-((2-amino-4,5,6,7-tetrahydrobenzo[d]thiazol-6-yl)amino)-2-oxoacetyl)-N-(4-fluoro-3-methylphenyl)-1,2,4-trimethyl-1H-pyrrole-3-carboxamide | 484.1 |
| 21 | 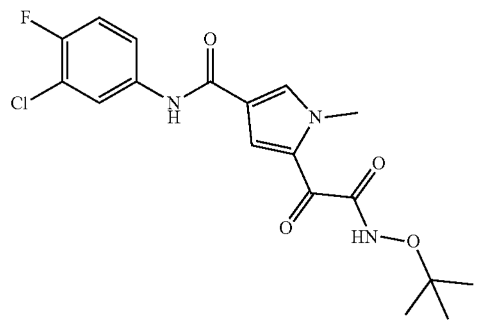 [SMILES: Cn1cc(C(=O)Nc2ccc(F)c(Cl)c2)cc1C(=O)C(=O)NOC(C)(C)C] | 5-(2-(tert-butoxyamino)-2-oxoacetyl)-N-(3-chloro-4-fluorophenyl)-1-methyl-1H-pyrrole-3-carboxamide | 396 |
| 22 | 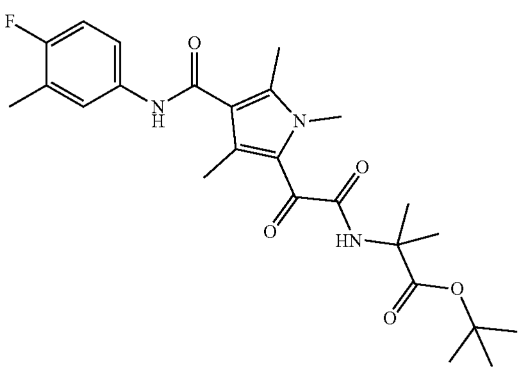 [SMILES: Cc1cc(NC(=O)c2c(C)c(C(=O)C(=O)NC(C)(C)C(=O)OC(C)(C)C)n(C)c2C)ccc1F] | tert-butyl 2-(2-(4-((4-fluoro-3-methylphenyl)carbamoyl)-1,3,5-trimethyl-1H-pyrrol-2-yl)-2-oxoacetamido)-2-methylpropanoate | 474.2 |
| 23 | 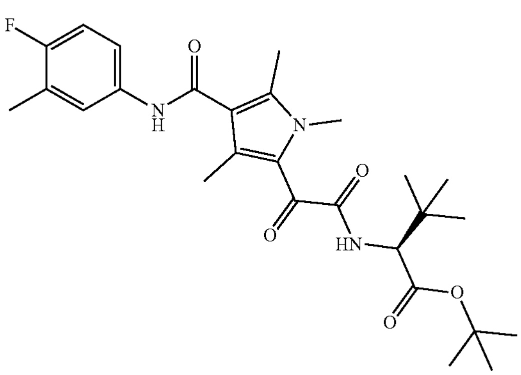 [SMILES: Cc1cc(NC(=O)c2c(C)c(C(=O)C(=O)N[C@H](C(=O)OC(C)(C)C)C(C)(C)C)n(C)c2C)ccc1F] | tert-butyl (S)-2-(2-(4-((4-fluoro-3-methylphenyl)carbamoyl)-1,3,5-trimethyl-1H-pyrrol-2-yl)-2-oxoacetamido)-3,3-dimethylbutanoate | 502.2 |

TABLE 1-continued

Exemplary compounds

| Ex. | Structure | Chemical Name | ESI-MS (M + H)+ (m/z) |
|---|---|---|---|
| 24 | 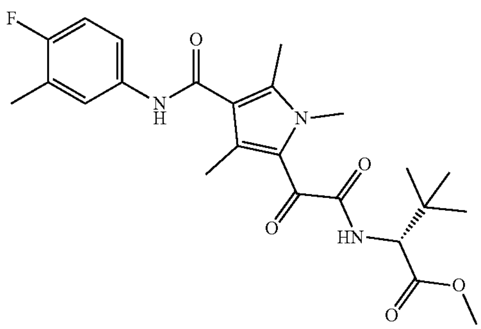 [SMILES: COC(=O)[C@H](NC(=O)C(=O)c1c(C)c(C(=O)Nc2ccc(F)c(C)c2)c(C)n1C)C(C)(C)C] | methyl (R)-2-(2-(4-((4-fluoro-3-methylphenyl)carbamoyl)-1,3,5-trimethyl-1H-pyrrol-2-yl)-2-oxoacetamido)-3,3-dimethylbutanoate | 460.2 |
| 25 | 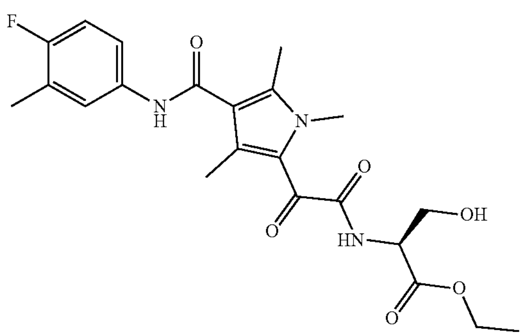 [SMILES: CCOC(=O)[C@H](CO)NC(=O)C(=O)c1c(C)c(C(=O)Nc2ccc(F)c(C)c2)c(C)n1C] | ethyl (2-(4-((4-fluoro-3-methylphenyl)carbamoyl)-1,3,5-trimethyl-1H-pyrrol-2-yl)-2-oxoacetyl)-L-serinate | 448.2 |
| 26 | 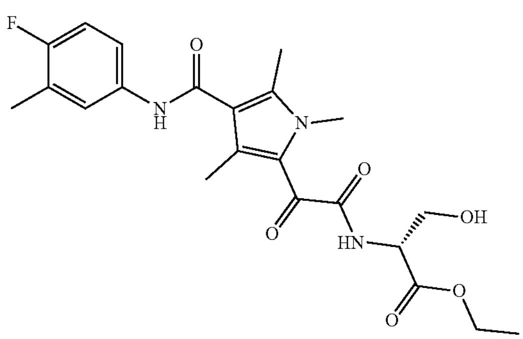 [SMILES: CCOC(=O)[C@@H](CO)NC(=O)C(=O)c1c(C)c(C(=O)Nc2ccc(F)c(C)c2)c(C)n1C] | ethyl (2-(4-((4-fluoro-3-methylphenyl)carbamoyl)-1,3,5-trimethyl-1H-pyrrol-2-yl)-2-oxoacetyl)-D-serinate | 448.2 |
| 27 | 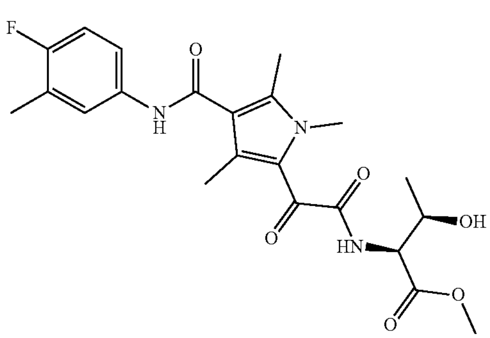 [SMILES: COC(=O)[C@@H](NC(=O)C(=O)c1c(C)c(C(=O)Nc2ccc(F)c(C)c2)c(C)n1C)[C@@H](C)O] | methyl (2-(4-((4-fluoro-3-methylphenyl)carbamoyl)-1,3,5-trimethyl-1H-pyrrol-2-yl)-2-oxoacetyl)-L-threoninate | 448.2 |

TABLE 1-continued

Exemplary compounds

| Ex. | Structure | Chemical Name | ESI-MS (M + H)+ (m/z) |
|---|---|---|---|
| 28 | 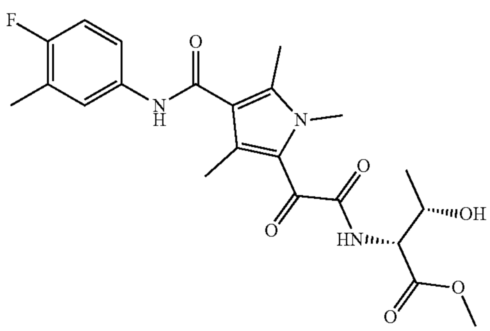 [SMILES: COC(=O)[C@H](NC(=O)C(=O)c1c(C)c(C(=O)Nc2ccc(F)c(C)c2)c(C)n1C)[C@H](C)O] | methyl (2-(4-((4-fluoro-3-methylphenyl)carbamoyl)-1,3,5-trimethyl-1H-pyrrol-2-yl)-2-oxoacetyl)-D-threoninate | 448.2 |
| 29 | 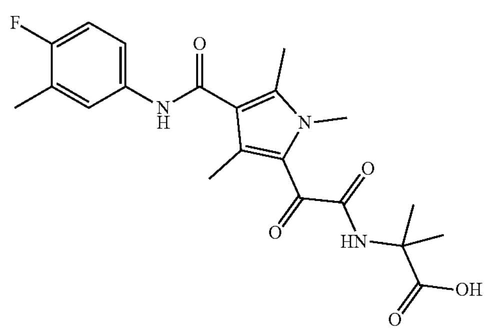 [SMILES: Cc1cc(NC(=O)c2c(C)c(C(=O)C(=O)NC(C)(C)C(=O)O)n(C)c2C)ccc1F] | 2-(2-(4-((4-fluoro-3-methylphenyl)carbamoyl)-1,3,5-trimethyl-1H-pyrrol-2-yl)-2-oxoacetamido)-2-methylpropanoic acid | 418.2 |
| 30 | 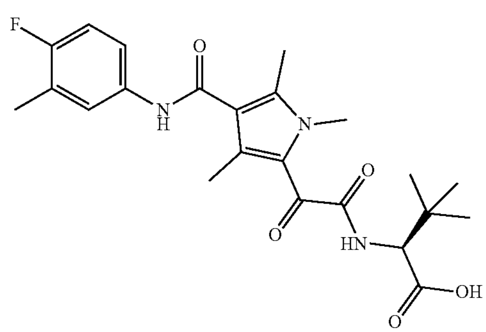 [SMILES: Cc1cc(NC(=O)c2c(C)c(C(=O)C(=O)N[C@H](C(=O)O)C(C)(C)C)n(C)c2C)ccc1F] | (S)-2-(2-(4-((4-fluoro-3-methylphenyl)carbamoyl)-1,3,5-trimethyl-1H-pyrrol-2-yl)-2-oxoacetamido)-3,3-dimethylbutanoic acid | 446.2 |
| 31 | 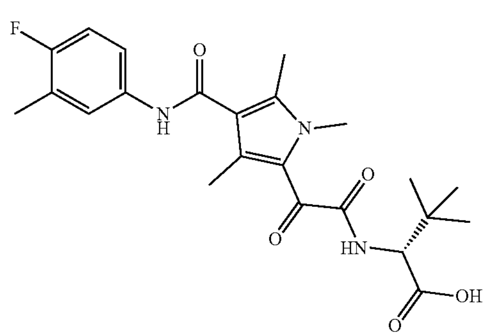 [SMILES: Cc1cc(NC(=O)c2c(C)c(C(=O)C(=O)N[C@@H](C(=O)O)C(C)(C)C)n(C)c2C)ccc1F] | (R)-2-(2-(4-((4-fluoro-3-methylphenyl)carbamoyl)-1,3,5-trimethyl-1H-pyrrol-2-yl)-2-oxoacetamido)-3,3-dimethylbutanoic acid | 446.2 |

TABLE 1-continued

Exemplary compounds

| Ex. | Structure | Chemical Name | ESI-MS (M + H)+ (m/z) |
|---|---|---|---|
| 32 | 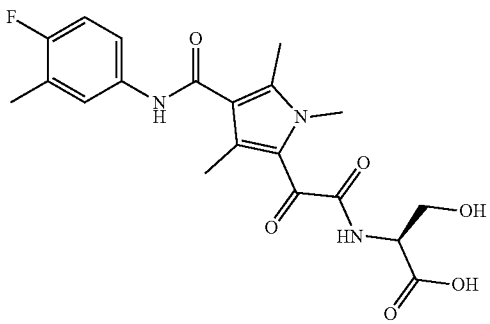 [SMILES: Cc1cc(NC(=O)c2c(C)c(C(=O)C(=O)N[C@@H](CO)C(=O)O)n(C)c2C)ccc1F] | (2-(4-((4-fluoro-3-methylphenyl)carbamoyl)-1,3,5-trimethyl-1H-pyrrol-2-yl)-2-oxoacetyl)-L-serine | 420.2 |
| 33 | 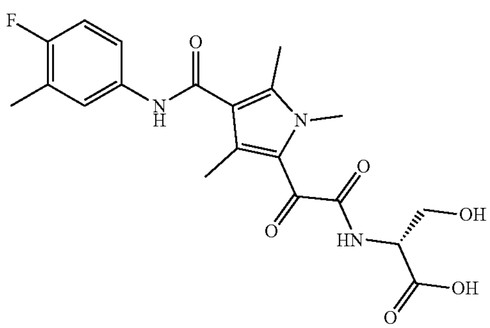 [SMILES: Cc1cc(NC(=O)c2c(C)c(C(=O)C(=O)N[C@H](CO)C(=O)O)n(C)c2C)ccc1F] | (2-(4-((4-fluoro-3-methylphenyl)carbamoyl)-1,3,5-trimethyl-1H-pyrrol-2-yl)-2-oxoacetyl)-D-serine | 420.2 |
| 34 | 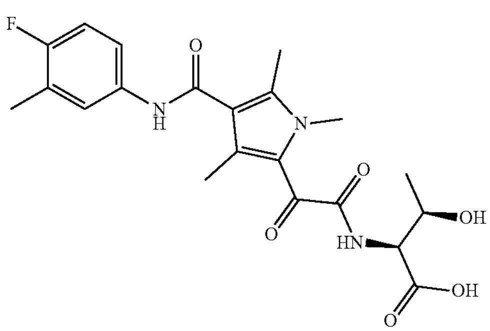 [SMILES: Cc1cc(NC(=O)c2c(C)c(C(=O)C(=O)N[C@H](C(=O)O)[C@@H](C)O)n(C)c2C)ccc1F] | (2-(4-((4-fluoro-3-methylphenyl)carbamoyl)-1,3,5-trimethyl-1H-pyrrol-2-yl)-2-oxoacetyl)-L-threonine | 434.2 |
| 35 | 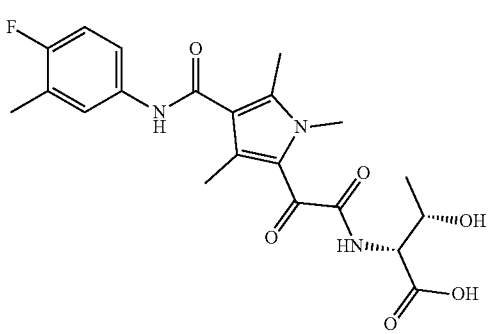 [SMILES: Cc1cc(NC(=O)c2c(C)c(C(=O)C(=O)N[C@@H](C(=O)O)[C@H](C)O)n(C)c2C)ccc1F] | (2-(4-((4-fluoro-3-methylphenyl)carbamoyl)-1,3,5-trimethyl-1H-pyrrol-2-yl)-2-oxoacetyl)-D-threonine | 434.2 |

TABLE 1-continued

Exemplary compounds

| Ex. | Structure | Chemical Name | ESI-MS (M + H)+ (m/z) |
|---|---|---|---|
| 36 | 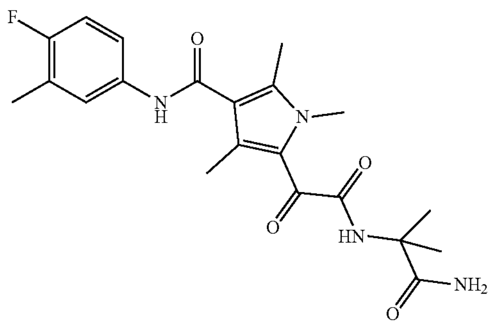 [SMILES: Cc1cc(NC(=O)c2c(C)c(C(=O)C(=O)NC(C)(C)C(N)=O)n(C)c2C)ccc1F] | 5-(2-((1-amino-2-methyl-1-oxopropan-2-yl)amino)-2-oxoacetyl)-N-(4-fluoro-3-methylphenyl)-1,2,4-trimethyl-1H-pyrrole-3-carboxamide | 439.2 |
| 37 | 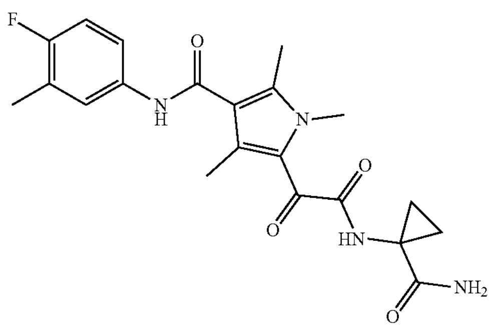 [SMILES: Cc1cc(NC(=O)c2c(C)c(C(=O)C(=O)NC3(C(N)=O)CC3)n(C)c2C)ccc1F] | 5-(2-((1-carbamoylcyclopropyl)amino)-2-oxoacetyl)-N-(4-fluoro-3-methylphenyl)-1,2,4-trimethyl-1H-pyrrole-3-carboxamide | 415.2 |
| 38 | 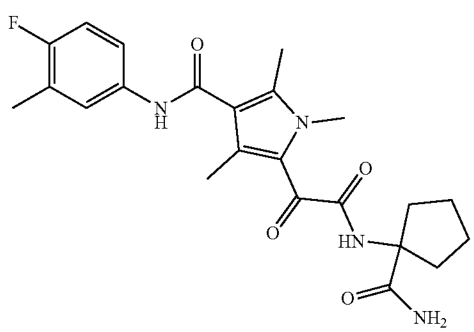 [SMILES: Cc1cc(NC(=O)c2c(C)c(C(=O)C(=O)NC3(C(N)=O)CCCC3)n(C)c2C)ccc1F] | 5-(2-((1-carbamoylcyclopentyl)amino)-2-oxoacetyl)-N-(4-fluoro-3-methylphenyl)-1,2,4-trimethyl-1H-pyrrole-3-carboxamide | 443.2 |
| 39 | 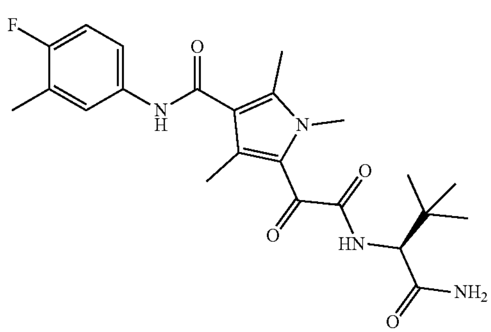 [SMILES: Cc1cc(NC(=O)c2c(C)c(C(=O)C(=O)N[C@H](C(N)=O)C(C)(C)C)n(C)c2C)ccc1F] | (S)-5-(2-((1-amino-3,3-dimethyl-1-oxobutan-2-yl)amino)-2-oxoacetyl)-N-(4-fluoro-3-methylphenyl)-1,2,4-trimethyl-1H-pyrrole-3-carboxamide | 445.2 |

TABLE 1-continued

Exemplary compounds

| Ex. | Structure | Chemical Name | ESI-MS (M + H)+ (m/z) |
|---|---|---|---|
| 40 | 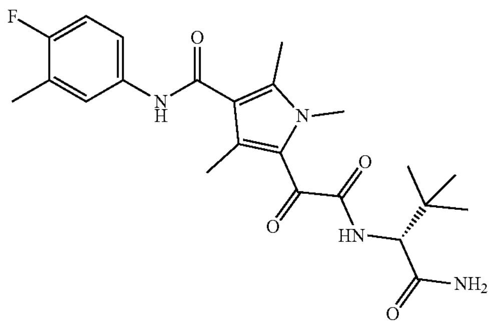 [SMILES: Cc1cc(NC(=O)c2c(C)c(C(=O)C(=O)N[C@@H](C(N)=O)C(C)(C)C)n(C)c2C)ccc1F] | (R)-5-(2-((1-amino-3,3-dimethyl-1-oxobutan-2-yl)amino)-2-oxoacetyl)-N-(4-fluoro-3-methylphenyl)-1,2,4-trimethyl-1H-pyrrole-3-carboxamide | 445.2 |
| 41 | 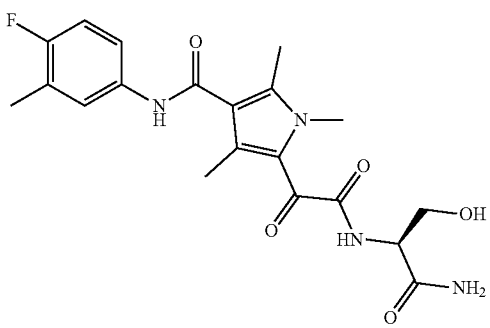 [SMILES: Cc1cc(NC(=O)c2c(C)c(C(=O)C(=O)N[C@@H](CO)C(N)=O)n(C)c2C)ccc1F] | (S)-5-(2-((1-amino-3-hydroxy-1-oxopropan-2-yl)amino)-2-oxoacetyl)-N-(4-fluoro-3-methylphenyl)-1,2,4-trimethyl-1H-pyrrole-3-carboxamide | 419.2 |
| 42 | 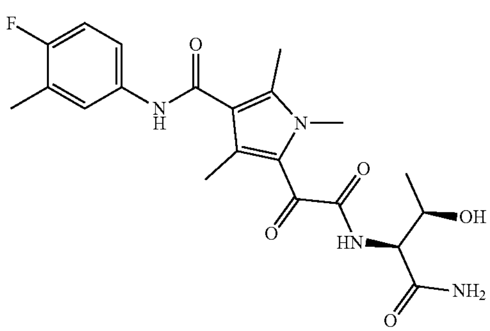 [SMILES: Cc1cc(NC(=O)c2c(C)c(C(=O)C(=O)N[C@H](C(N)=O)[C@@H](C)O)n(C)c2C)ccc1F] | 5-(2-(((2S,3R)-1-amino-3-hydroxy-1-oxobutan-2-yl)amino)-2-oxoacetyl)-N-(4-fluoro-3-methylphenyl)-1,2,4-trimethyl-1H-pyrrole-3-carboxamide | 433.2 |
| 43 | 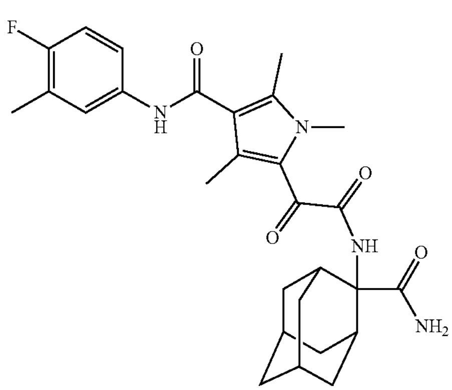 [SMILES: Cc1cc(NC(=O)c2c(C)c(C(=O)C(=O)NC3(C(N)=O)C4CC5CC(C4)CC3C5)n(C)c2C)ccc1F] | 5-(2-(((1r,3r,5r,7r)-2-carbamoyladamantan-2-yl)amino)-2-oxoacetyl)-N-(4-fluoro-3-methylphenyl)-1,2,4-trimethyl-1H-pyrrole-3-carboxamide | 509.2 |

TABLE 1-continued

Exemplary compounds

| Ex. | Structure | Chemical Name | ESI-MS (M + H)+ (m/z) |
|---|---|---|---|
| 44 | 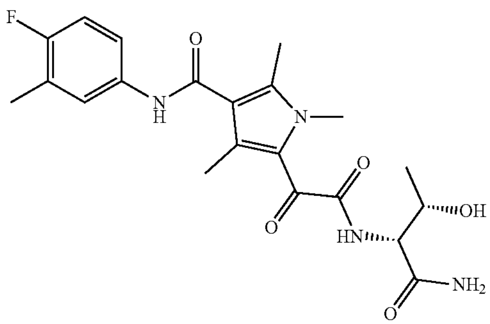 [SMILES: Cc1cc(NC(=O)c2c(C)c(C(=O)C(=O)N[C@@H](C(N)=O)[C@H](C)O)n(C)c2C)ccc1F] | 5-(2-(((2R,3S)-1-amino-3-hydroxy-1-oxobutan-2-yl)amino)-2-oxoacetyl)-N-(4-fluoro-3-methylphenyl)-1,2,4-trimethyl-1H-pyrrole-3-carboxamide | 433.2 |
| 45 | 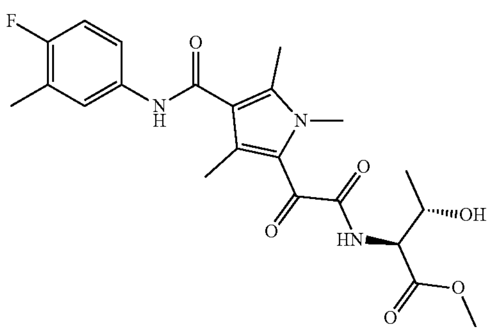 [SMILES: COC(=O)[C@@H](NC(=O)C(=O)c1c(C)c(C(=O)Nc2ccc(F)c(C)c2)c(C)n1C)[C@H](C)O] | methyl (2-(4-((4-fluoro-3-methylphenyl)carbamoyl)-1,3,5-trimethyl-1H-pyrrol-2-yl)-2-oxoacetyl)-L-allothreoninate | 448.2 |
| 46 | 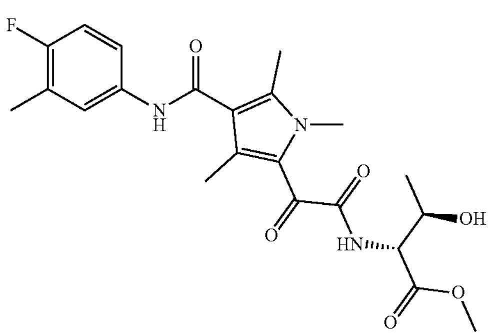 [SMILES: COC(=O)[C@H](NC(=O)C(=O)c1c(C)c(C(=O)Nc2ccc(F)c(C)c2)c(C)n1C)[C@@H](C)O] | methyl (2-(4-((4-fluoro-3-methylphenyl)carbamoyl)-1,3,5-trimethyl-1H-pyrrol-2-yl)-2-oxoacetyl)-D-allothreoninate | 448.2 |
| 47 | 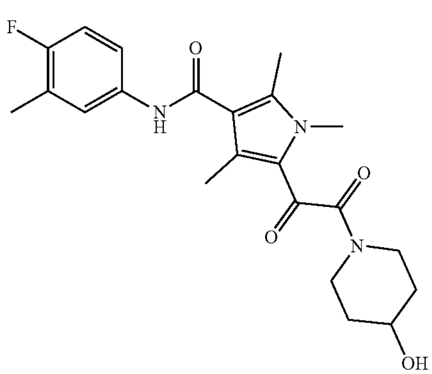 [SMILES: Cc1cc(NC(=O)c2c(C)c(C(=O)C(=O)N3CCC(O)CC3)n(C)c2C)ccc1F] | N-(4-fluoro-3-methylphenyl)-5-(2-(4-hydroxypiperidin-1-yl)-2-oxoacetyl)-1,2,4-trimethyl-1H-pyrrole-3-carboxamide | 416.2 |

TABLE 1-continued

Exemplary compounds

| Ex. | Structure | Chemical Name | ESI-MS (M + H)+ (m/z) |
|---|---|---|---|
| 48 | 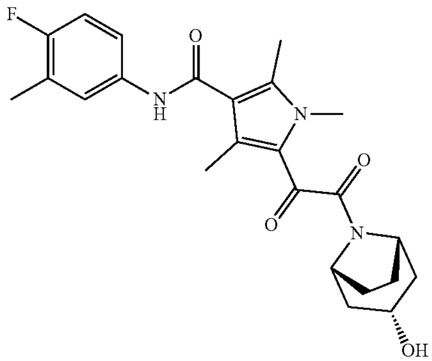 [SMILES: Cc1cc(NC(=O)c2c(C)c(C(=O)C(=O)N3[C@@H]4CC[C@H]3C[C@H](O)C4)n(C)c2C)ccc1F] | N-(4-fluoro-3-methylphenyl)-5-(2-((1R,3s,5S)-3-hydroxy-8-azabicyclo[3.2.1]octan-8-yl)-2-oxoacetyl)-1,2,4-trimethyl-1H-pyrrole-3-carboxamide | 442.2 |
| 49 | 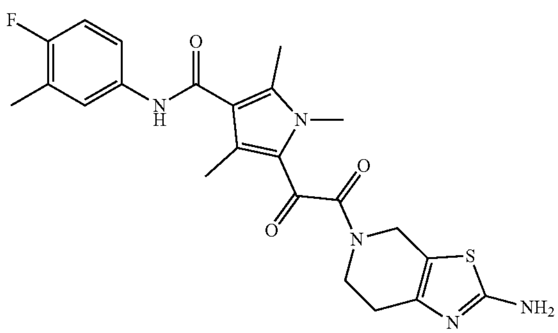 [SMILES: Cc1cc(NC(=O)c2c(C)c(C(=O)C(=O)N3CCc4nc(N)sc4C3)n(C)c2C)ccc1F] | 5-(2-(2-amino-6,7-dihydrothiazolo[5,4-c]pyridin-5(4H)-yl)-2-oxoacetyl)-N-(4-fluoro-3-methylphenyl)-1,2,4-trimethyl-1H-pyrrole-3-carboxamide | 470.1 |
| 50 | 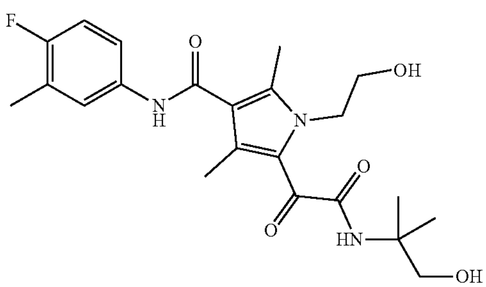 [SMILES: Cc1cc(NC(=O)c2c(C)c(C(=O)C(=O)NC(C)(C)CO)n(CCO)c2C)ccc1F] | N-(4-fluoro-3-methylphenyl)-5-(2-((1-hydroxy-2-methylpropan-2-yl)amino)-2-oxoacetyl)-1-(2-hydroxyethyl)-2,4-dimethyl-1H-pyrrole-3-carboxamide | 434.2 |
| 51 | 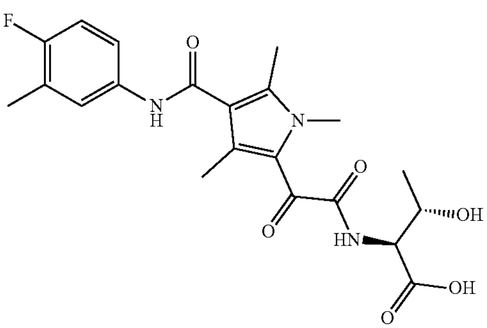 [SMILES: Cc1cc(NC(=O)c2c(C)c(C(=O)C(=O)N[C@H](C(=O)O)[C@H](C)O)n(C)c2C)ccc1F] | (2-(4-((4-fluoro-3-methylphenyl)carbamoyl)-1,3,5-trimethyl-1H-pyrrol-2-yl)-2-oxoacetyl)-L-allothreonine | 434.2 |

TABLE 1-continued

Exemplary compounds

| Ex. | Structure | Chemical Name | ESI-MS (M + H)+ (m/z) |
|---|---|---|---|
| 52 | 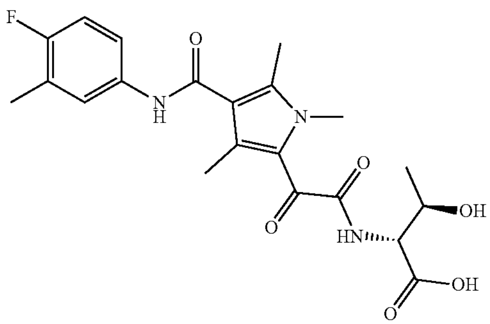 [SMILES: Cc1cc(NC(=O)c2c(C)c(C(=O)C(=O)N[C@@H](C(=O)O)[C@@H](C)O)n(C)c2C)ccc1F] | (2-(4-((4-fluoro-3-methylphenyl)carbamoyl)-1,3,5-trimethyl-1H-pyrrol-2-yl)-2-oxoacetyl)-D-allothreonine | 434.2 |
| 53 | 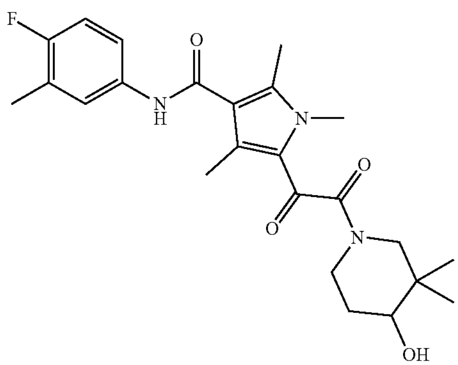 [SMILES: Cc1cc(NC(=O)c2c(C)c(C(=O)C(=O)N3CCC(O)C(C)(C)C3)n(C)c2C)ccc1F] | N-(4-fluoro-3-methylphenyl)-5-(2-(4-hydroxy-3,3-dimethylpiperidin-1-yl)-2-oxoacetyl)-1,2,4-trimethyl-1H-pyrrole-3-carboxamide | 444.2 |
| 54 | 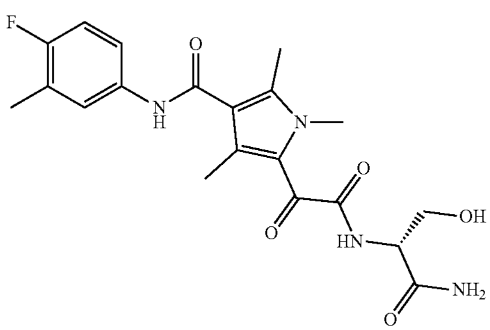 [SMILES: Cc1cc(NC(=O)c2c(C)c(C(=O)C(=O)N[C@H](CO)C(N)=O)n(C)c2C)ccc1F] | (R)-5-(2-((1-amino-3-hydroxy-1-oxopropan-2-yl)amino)-2-oxoacetyl)-N-(4-fluoro-3-methylphenyl)-1,2,4-trimethyl-1H-pyrrole-3-carboxamide | 419.2 |
| 55 | 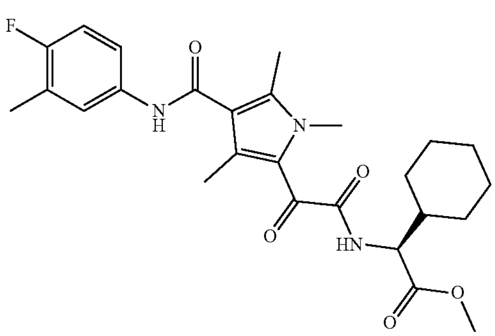 [SMILES: COC(=O)[C@@H](NC(=O)C(=O)c1c(C)c(C(=O)Nc2ccc(F)c(C)c2)c(C)n1C)C1CCCCC1] | methyl (S)-2-cyclohexyl-2-(2-(4-((4-fluoro-3-methylphenyl)carbamoyl)-1,3,5-trimethyl-1H-pyrrol-2-yl)-2-oxoacetamido)acetate | 486.2 |

TABLE 1-continued

Exemplary compounds

| Ex. | Structure | Chemical Name | ESI-MS (M + H)+ (m/z) |
|---|---|---|---|
| 56 | 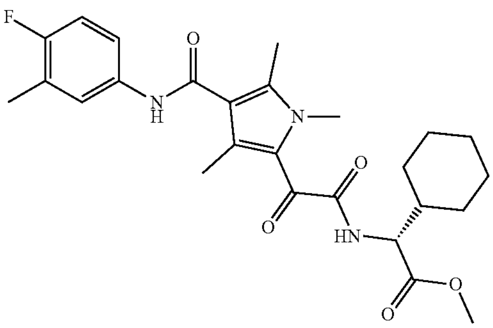 [SMILES: COC(=O)[C@H](NC(=O)C(=O)c1c(C)c(C(=O)Nc2ccc(F)c(C)c2)c(C)n1C)C1CCCCC1] | methyl (R)-2-cyclohexyl-2-(2-(4-((4-fluoro-3-methylphenyl)carbamoyl)-1,3,5-trimethyl-1H-pyrrol-2-yl)-2-oxoacetamido)acetate | 486.2 |
| 57 | 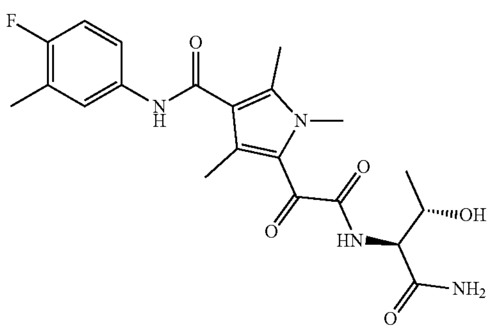 [SMILES: Cc1cc(NC(=O)c2c(C)c(C(=O)C(=O)N[C@H](C(N)=O)[C@H](C)O)n(C)c2C)ccc1F] | 5-(2-(((2S,3S)-1-amino-3-hydroxy-1-oxobutan-2-yl)amino)-2-oxoacetyl)-N-(4-fluoro-3-methylphenyl)-1,2,4-trimethyl-1H-pyrrole-3-carboxamide | 433.2 |
| 58 | 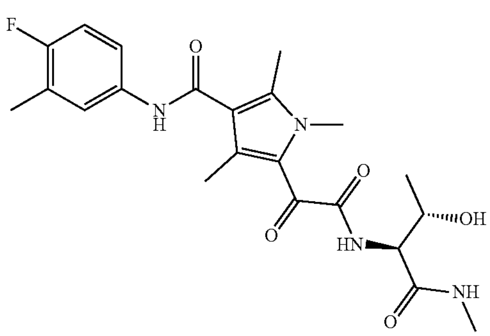 [SMILES: CNC(=O)[C@@H](NC(=O)C(=O)c1c(C)c(C(=O)Nc2ccc(F)c(C)c2)c(C)n1C)[C@H](C)O] | N-(4-fluoro-3-methylphenyl)-5-(2-(((2S,3S)-3-hydroxy-1-(methylamino)-1-oxobutan-2-yl)amino)-2-oxoacetyl)-1,2,4-trimethyl-1H-pyrrole-3-carboxamide | 447.2 |
| 59 | 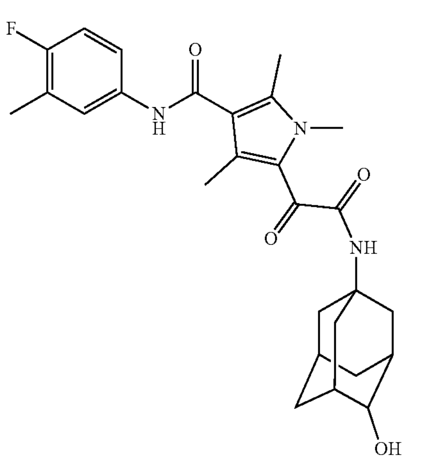 [SMILES: Cc1cc(NC(=O)c2c(C)c(C(=O)C(=O)NC34CC5CC(C3)C(O)C(C5)C4)n(C)c2C)ccc1F] | N-(4-fluoro-3-methylphenyl)-5-(2-(((1s,3R,4s,5S,7s)-4-hydroxyadamantan-1-yl)amino)-2-oxoacetyl)-1,2,4-trimethyl-1H-pyrrole-3-carboxamide | 482.2 |

TABLE 1-continued

Exemplary compounds

| Ex. | Structure | Chemical Name | ESI-MS (M + H)+ (m/z) |
|---|---|---|---|
| 60 | 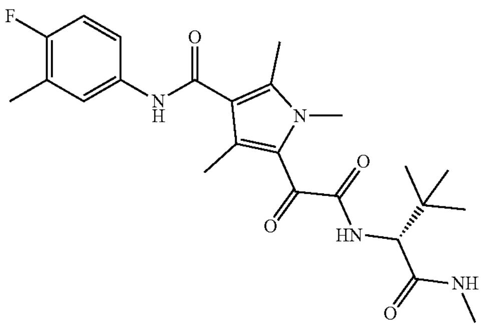 [SMILES: CNC(=O)[C@H](NC(=O)C(=O)c1c(C)c(C(=O)Nc2ccc(F)c(C)c2)c(C)n1C)C(C)(C)C] | (R)-5-(2-((3,3-dimethyl-1-(methylamino)-1-oxobutan-2-yl)amino)-2-oxoacetyl)-N-(4-fluoro-3-methylphenyl)-1,2,4-trimethyl-1H-pyrrole-3-carboxamide | 459.2 |
| 61 | 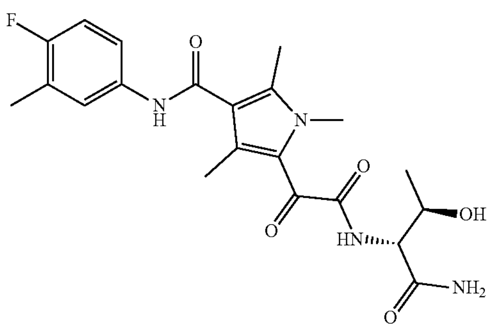 [SMILES: Cc1cc(NC(=O)c2c(C)c(C(=O)C(=O)N[C@@H](C(N)=O)[C@@H](C)O)n(C)c2C)ccc1F] | 5-(2-(((2R,3R)-1-amino-3-hydroxy-1-oxobutan-2-yl)amino)-2-oxoacetyl)-N-(4-fluoro-3-methylphenyl)-1,2,4-trimethyl-1H-pyrrole-3-carboxamide | 433.2 |
| 62 | 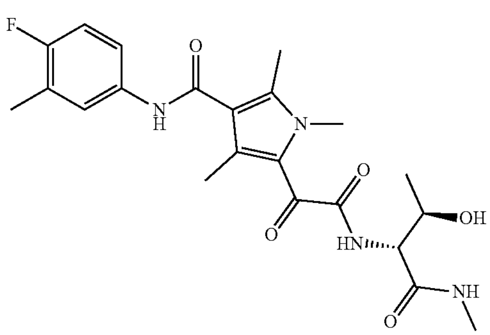 [SMILES: CNC(=O)[C@H](NC(=O)C(=O)c1c(C)c(C(=O)Nc2ccc(F)c(C)c2)c(C)n1C)[C@@H](C)O] | N-(4-fluoro-3-methylphenyl)-5-(2-(((2R,3R)-3-hydroxy-1-(methylamino)-1-oxobutan-2-yl)amino)-2-oxoacetyl)-1,2,4-trimethyl-1H-pyrrole-3-carboxamide | 447.2 |
| 63 | 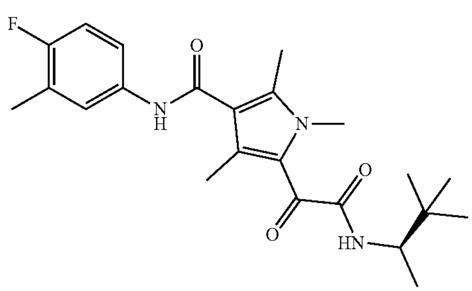 [SMILES: Cc1cc(NC(=O)c2c(C)c(C(=O)C(=O)N[C@H](C)C(C)(C)C)n(C)c2C)ccc1F] | (R)-5-(2-((3,3-dimethylbutan-2-yl)amino)-2-oxoacetyl)-N-(4-fluoro-3-methylphenyl)-1,2,4-trimethyl-1H-pyrrole-3-carboxamide | 416.2 |

TABLE 1-continued

Exemplary compounds

| Ex. | Structure | Chemical Name | ESI-MS (M + H)+ (m/z) |
|---|---|---|---|
| 54 | 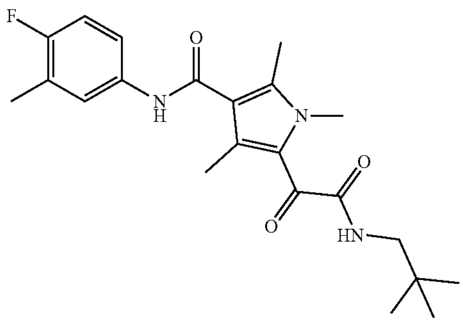 [SMILES: Cc1cc(NC(=O)c2c(C)c(C(=O)C(=O)NCC(C)(C)C)n(C)c2C)ccc1F] | N-(4-fluoro-3-methylphenyl)-1,2,4-trimethyl-5-(2-(neopentylamino)-2-oxoacetyl)-1H-pyrrole-3-carboxamide | 402.2 |
| 65 | 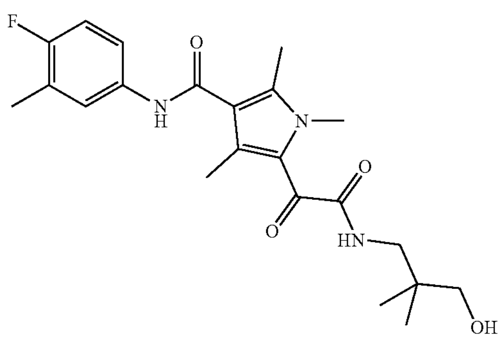 [SMILES: Cc1cc(NC(=O)c2c(C)c(C(=O)C(=O)NCC(C)(C)CO)n(C)c2C)ccc1F] | N-(4-fluoro-3-methylphenyl)-5-(2-((3-hydroxy-2,2-dimethylpropyl)amino)-2-oxoacetyl)-1,2,4-trimethyl-1H-pyrrole-3-carboxamide | 418.2 |
| 66 | 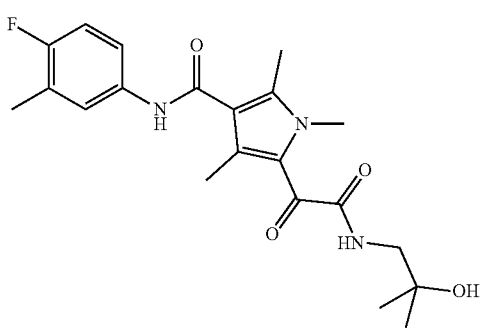 [SMILES: Cc1cc(NC(=O)c2c(C)c(C(=O)C(=O)NCC(C)(C)O)n(C)c2C)ccc1F] | N-(4-fluoro-3-methylphenyl)-5-(2-((2-hydroxy-2-methylethyl)amino)-2-oxoacetyl)-1,2,4-trimethyl-1H-pyrrole-3-carboxamide | 404.2 |
| 67 | 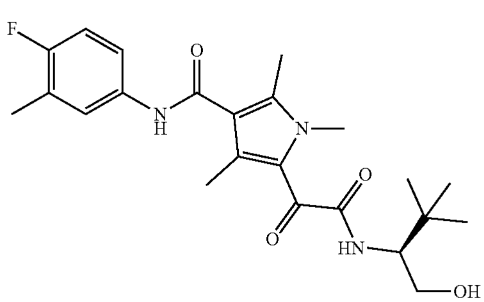 [SMILES: Cc1cc(NC(=O)c2c(C)c(C(=O)C(=O)N[C@H](CO)C(C)(C)C)n(C)c2C)ccc1F] | (S)-N-(4-fluoro-3-methylphenyl)-5-(2-((1-hydroxy-3,3-dimethylbutan-2-yl)amino)-2-oxoacetyl)-1,2,4-trimethyl-1H-pyrrole-3-carboxamide | 432.2 |

TABLE 1-continued

Exemplary compounds

| Ex. | Structure | Chemical Name | ESI-MS (M + H)+ (m/z) |
|---|---|---|---|
| 68 | 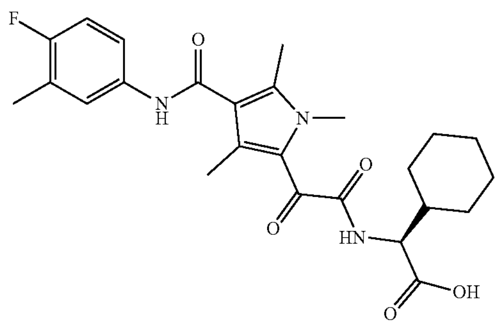 [SMILES: Cc1cc(NC(=O)c2c(C)c(C(=O)C(=O)N[C@H](C(=O)O)C3CCCCC3)n(C)c2C)ccc1F] | (S)-2-cyclohexyl-2-(2-(4-((4-fluoro-3-methylphenyl)carbamoyl)-1,3,5-trimethyl-1H-pyrrol-2-yl)-2-oxoacetamido)acetic acid | 472.2 |
| 69 | 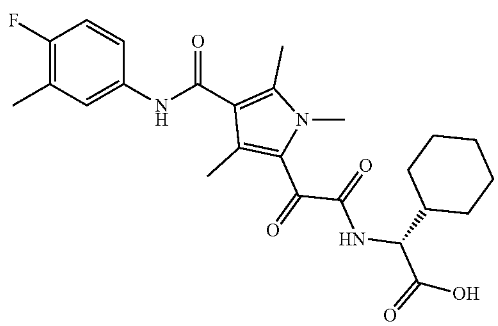 [SMILES: Cc1cc(NC(=O)c2c(C)c(C(=O)C(=O)N[C@@H](C(=O)O)C3CCCCC3)n(C)c2C)ccc1F] | (R)-2-cyclohexyl-2-(2-(4-((4-fluoro-3-methylphenyl)carbamoyl)-1,3,5-trimethyl-1H-pyrrol-2-yl)-2-oxoacetamido)acetic acid | 472.2 |
| 70 | 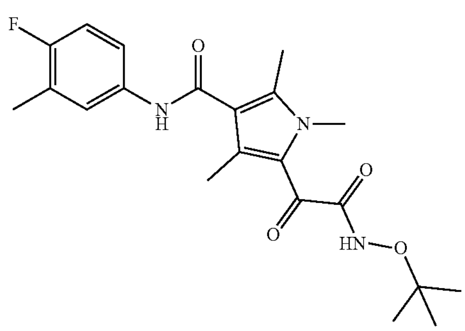 [SMILES: Cc1cc(NC(=O)c2c(C)c(C(=O)C(=O)NOC(C)(C)C)n(C)c2C)ccc1F] | 5-(2-(tert-butoxyamino)-2-oxoacetyl)-N-(4-fluoro-3-methylphenyl)-1,2,4-trimethyl-1H-pyrrole-3-carboxamide | 404 |
| 71 | 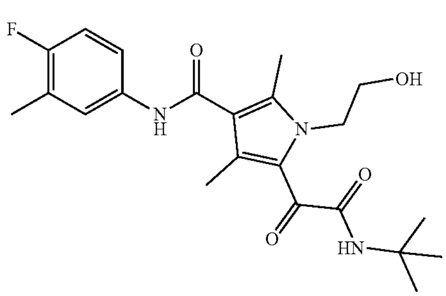 [SMILES: Cc1cc(NC(=O)c2c(C)c(C(=O)C(=O)NC(C)(C)C)n(CCO)c2C)ccc1F] | 5-(2-(tert-butylamino)-2-oxoacetyl)-N-(4-fluoro-3-methylphenyl)-1-(2-hydroxyethyl)-2,4-dimethyl-1H-pyrrole-3-carboxamide | 418.2 |

TABLE 1-continued

Exemplary compounds

| Ex. | Structure | Chemical Name | ESI-MS (M + H)+ (m/z) |
|---|---|---|---|
| 72 | 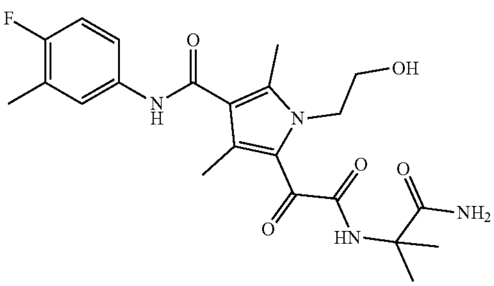 [SMILES: Cc1cc(NC(=O)c2c(C)c(C(=O)C(=O)NC(C)(C)C(N)=O)n(CCO)c2C)ccc1F] | 5-(2-((1-amino-2-methyl-1-oxopropan-2-yl)amino)-2-oxoacetyl)-N-(4-fluoro-3-methylphenyl)-1-(2-hydroxyethyl)-2,4-dimethyl-1H-pyrrole-3-carboxamide | 447.2 |
| 73 | 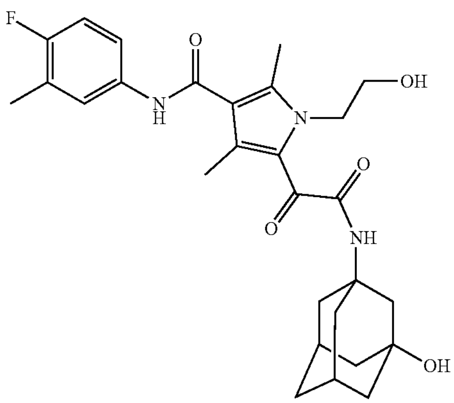 [SMILES: Cc1cc(NC(=O)c2c(C)c(C(=O)C(=O)NC34CC5CC(CC(O)(C5)C3)C4)n(CCO)c2C)ccc1F] | N-(4-fluoro-3-methylphenyl)-5-(2-(((1r,3s,5R,7S)-3-hydroxyadamantan-1-yl)amino)-2-oxoacetyl)-1-(2-hydroxyethyl)-2,4-dimethyl-1H-pyrrole-3-carboxamide | 512.2 |
| 74 | 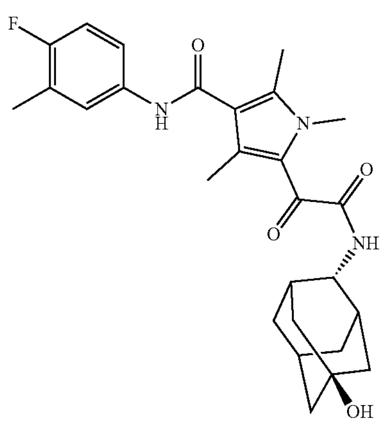 [SMILES: Cc1cc(NC(=O)c2c(C)c(C(=O)C(=O)N[C@H]3C4CC5CC3C[C@](O)(C5)C4)n(C)c2C)ccc1F] | N-(4-fluoro-3-methylphenyl)-5-(2-(((1R,2s,3S,5s,7s)-5-hydroxyadamantan-2-yl)amino)-2-oxoacetyl)-1,2,4-trimethyl-1H-pyrrole-3-carboxamide | 482.2 |
| 75 | 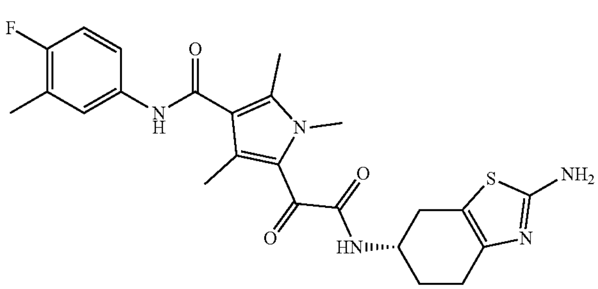 [SMILES: Cc1cc(NC(=O)c2c(C)c(C(=O)C(=O)N[C@H]3CCc4nc(N)sc4C3)n(C)c2C)ccc1F] | (S)-5-(2-((2-amino-4,5,6,7-tetrahydrobenzo[d]thiazol-6-yl)amino)-2-oxoacetyl)-N-(4-fluoro-3-methylphenyl)-1,2,4-trimethyl-1H-pyrrole-3-carboxamide | 484.2 |

TABLE 1-continued

Exemplary compounds

| Ex. | Structure | Chemical Name | ESI-MS (M + H)+ (m/z) |
|---|---|---|---|
| 76 | 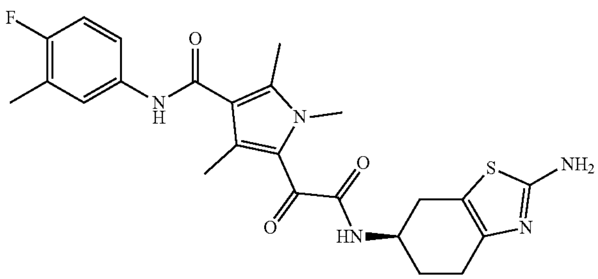 [SMILES: Cc1cc(NC(=O)c2c(C)c(C(=O)C(=O)N[C@@H]3CCc4nc(N)sc4C3)n(C)c2C)ccc1F] | (R)-5-(2-((2-amino-4,5,6,7-tetrahydrobenzo[d]thiazol-6-yl)amino)-2-oxoacetyl)-N-(4-fluoro-3-methylphenyl)-1,2,4-trimethyl-1H-pyrrole-3-carboxamide | 484.2 |
| 77 | 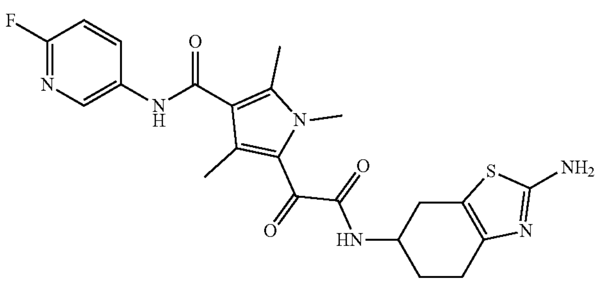 [SMILES: Cc1c(C(=O)Nc2ccc(F)nc2)c(C)n(C)c1C(=O)C(=O)NC1CCc2nc(N)sc2C1] | 5-(2-((2-amino-4,5,6,7-tetrahydrobenzo[d]thiazol-6-yl)amino)-2-oxoacetyl)-N-(6-fluoropyridin-3-yl)-1,2,4-trimethyl-1H-pyrrole-3-carboxamide | 471.1 |
| 78 | 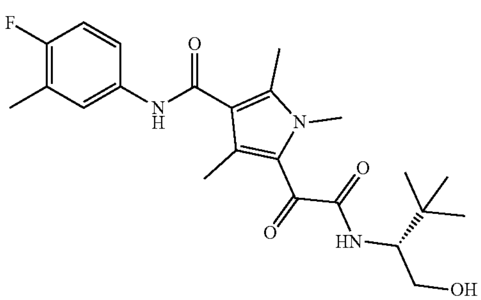 [SMILES: Cc1cc(NC(=O)c2c(C)c(C(=O)C(=O)N[C@@H](CO)C(C)(C)C)n(C)c2C)ccc1F] | (R)-N-(4-fluoro-3-methylphenyl)-5-(2-((1-hydroxy-3,3-dimethylbutan-2-yl)amino)-2-oxoacetyl)-1,2,4-trimethyl-1H-pyrrole-3-carboxamide | 432.2 |
| 79 | 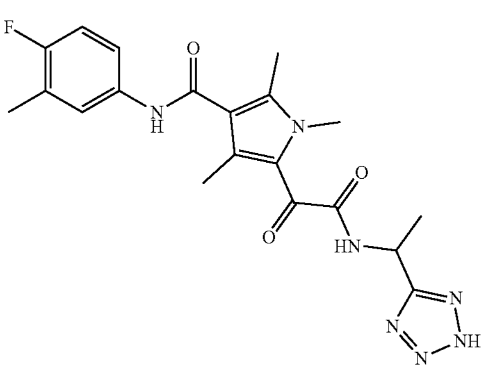 [SMILES: Cc1cc(NC(=O)c2c(C)c(C(=O)C(=O)NC(C)c3nn[nH]n3)n(C)c2C)ccc1F] | 5-(2-((1-(2H-tetrazol-5-yl)ethyl)amino)-2-oxoacetyl)-N-(4-fluoro-3-methylphenyl)-1,2,4-trimethyl-1H-pyrrole-3-carboxamide | 428 |

TABLE 1-continued

Exemplary compounds

| Ex. | Structure | Chemical Name | ESI-MS (M + H)+ (m/z) |
|---|---|---|---|
| 80 | 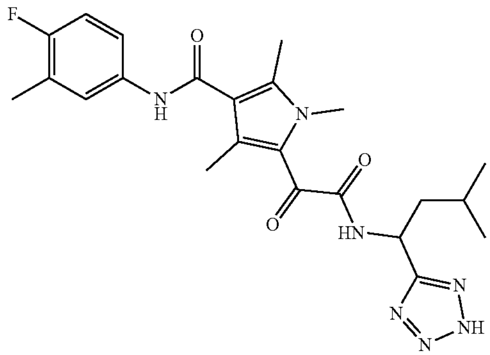 [SMILES: Cc1cc(NC(=O)c2c(C)c(C(=O)C(=O)NC(CC(C)C)c3nn[nH]n3)n(C)c2C)ccc1F] | N-(4-fluoro-3-methylphenyl)-1,2,4-trimethyl-5-(2-((3-methyl-1-(2H-tetrazol-5-yl)butyl)amino)-2-oxoacetyl)-1H-pyrrole-3-carboxamide | 470 |
| 81 | 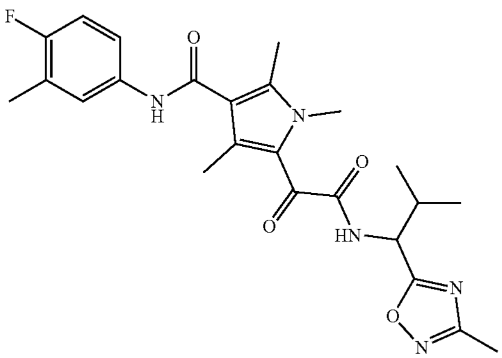 [SMILES: Cc1noc(C(NC(=O)C(=O)c2c(C)c(C(=O)Nc3ccc(F)c(C)c3)c(C)n2C)C(C)C)n1] | N-(4-fluoro-3-methylphenyl)-1,2,4-trimethyl-5-(2-((2-methyl-1-(3-methyl-1,2,4-oxadiazol-5-yl)propyl)amino)-2-oxoacetyl)-1H-pyrrole-3-carboxamide | 470 |
| 82 | 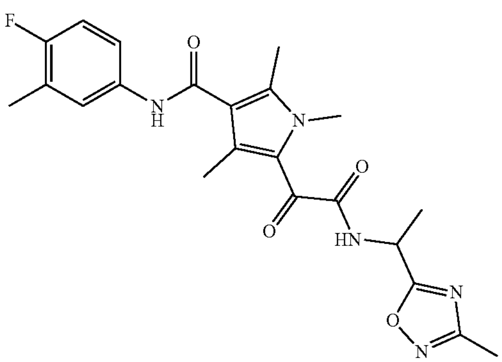 [SMILES: Cc1noc(C(C)NC(=O)C(=O)c2c(C)c(C(=O)Nc3ccc(F)c(C)c3)c(C)n2C)n1] | 5-(2-((cyclopropyl(5-methylthiazol-2-yl)methyl)amino)-2-oxoacetyl)-N-(4-fluoro-3-methylphenyl)-1,2,4-trimethyl-1H-pyrrole-3-carboxamide | 442.2 |
| 83 | 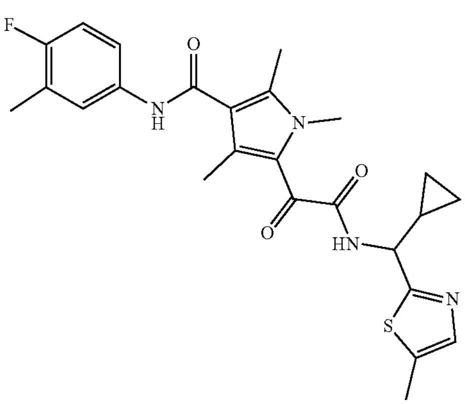 [SMILES: Cc1cnc(C(NC(=O)C(=O)c2c(C)c(C(=O)Nc3ccc(F)c(C)c3)c(C)n2C)C2CC2)s1] | N-(4-fluoro-3-methylphenyl)-1,2,4-trimethyl-5-(2-((2-(5-methylthiazol-2-yl)propan-2-yl)amino)-2-oxoacetyl)-1H-pyrrole-3-carboxamide | 483 |

TABLE 1-continued

Exemplary compounds

| Ex. | Structure | Chemical Name | ESI-MS (M + H)+ (m/z) |
|---|---|---|---|
| 84 | 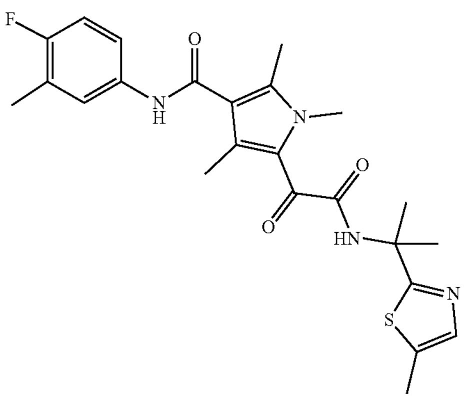 [SMILES: Cc1cnc(C(C)(C)NC(=O)C(=O)c2c(C)c(C(=O)Nc3ccc(F)c(C)c3)c(C)n2C)s1] | N-(4-fluoro-3-methylphenyl)-1,2,4-trimethyl-5-(2-(((3-methyl-1,2,4-oxadiazol-5-yl)(tetrahydro-2H-pyran-4-yl)methyl)amino)-2-oxoacetyl)-1H-pyrrole-3-carboxamide | 471 |
| 85 | 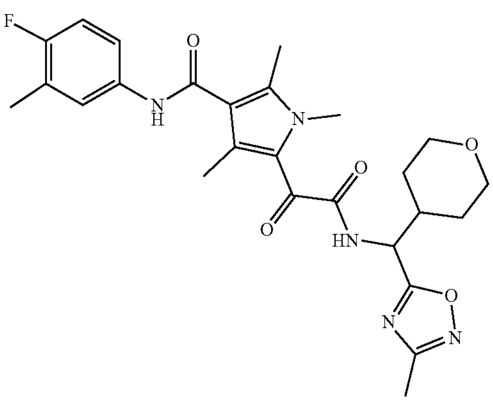 [SMILES: Cc1noc(C(NC(=O)C(=O)c2c(C)c(C(=O)Nc3ccc(F)c(C)c3)c(C)n2C)C2CCOCC2)n1] | 5-(2-((cyclopropyl(5-methylthiazol-2-yl)methyl)amino)-2-oxoacetyl)-N-(4-fluoro-3-methylphenyl)-1,2,4-trimethyl-1H-pyrrole-3-carboxamide | 512 |
| 86 | 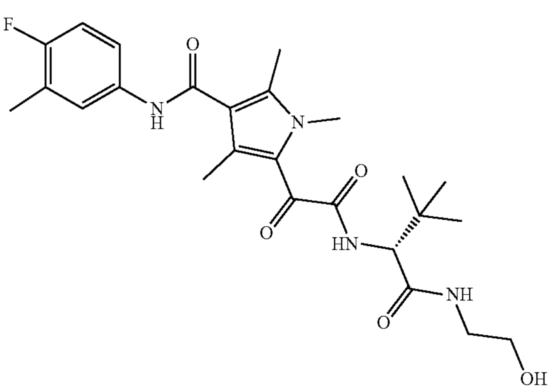 [SMILES: Cc1cc(NC(=O)c2c(C)c(C(=O)C(=O)N[C@@H](C(=O)NCCO)C(C)(C)C)n(C)c2C)ccc1F] | (R)-N-(4-fluoro-3-methylphenyl)-5-(2-((1-((2-hydroxyethyl)amino)-3,3-dimethyl-1-oxobutan-2-yl)amino)-2-oxoacetyl)-1,2,4-trimethyl-1H-pyrrole-3-carboxamide | 490 |

TABLE 1-continued

Exemplary compounds

| Ex. | Structure | Chemical Name | ESI-MS (M + H)+ (m/z) |
|---|---|---|---|
| 87 | 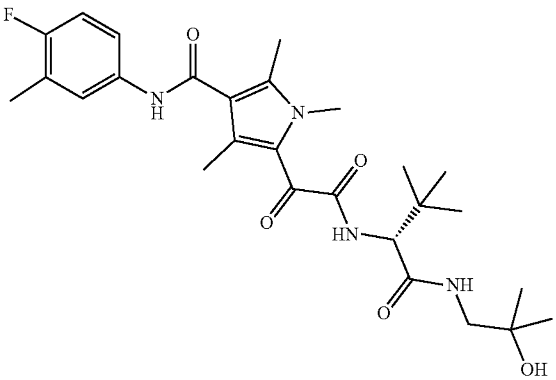 [SMILES: Cc1cc(NC(=O)c2c(C)c(C(=O)C(=O)N[C@@H](C(=O)NCC(C)(C)O)C(C)(C)C)n(C)c2C)ccc1F] | (R)-N-(4-fluoro-3-methylphenyl)-5-(2-((1-((2-hydroxy-2-methylpropyl)amino)-3,3-dimethyl-1-oxobutan-2-yl)amino)-2-oxoacetyl)-1,2,4-trimethyl-1H-pyrrole-3-carboxamide | 518 |
| 88 | 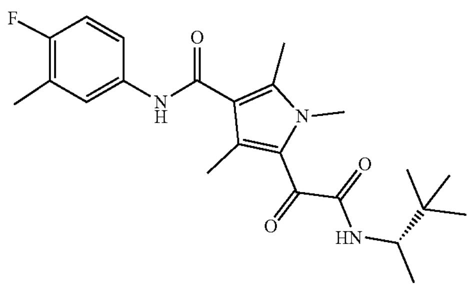 [SMILES: Cc1cc(NC(=O)c2c(C)c(C(=O)C(=O)N[C@@H](C)C(C)(C)C)n(C)c2C)ccc1F] | (S)-5-(2-((3,3-dimethylbutan-2-yl)amino)-2-oxoacetyl)-N-(4-fluoro-3-methylphenyl)-1,2,4-trimethyl-1H-pyrrole-3-carboxamide | 417 |
| 89 | 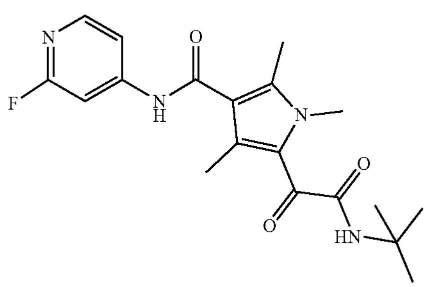 [SMILES: Cc1c(C(=O)Nc2ccnc(F)c2)c(C)n(C)c1C(=O)C(=O)NC(C)(C)C] | 5-(2-(tert-butylamino)-2-oxoacetyl)-N-(2-fluoropyridin-4-yl)-1,2,4-trimethyl-1H-pyrrole-3-carboxamide | 375.2 |
| 90 | 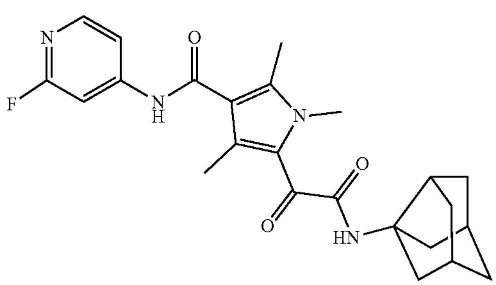 [SMILES: Cc1c(C(=O)Nc2ccnc(F)c2)c(C)n(C)c1C(=O)C(=O)NC12CC3CC(CC1C3)C2] | N-(2-fluoropyridin-4-yl)-5-(2-(((2R,3as,5S,6as)-hexahydro-2,5-methanopentalen-3a(1H)-yl)amino)-2-oxoacetyl)-1,2,4-trimethyl-1H-pyrrole-3-carboxamide | 439.2 |
| 91 | 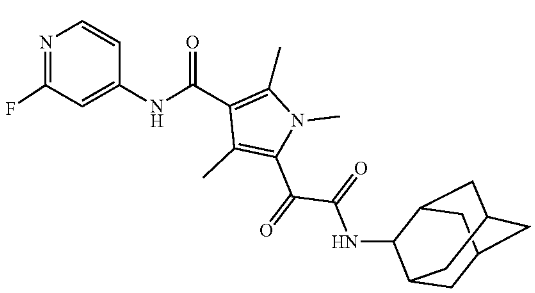 [SMILES: Cc1c(C(=O)Nc2ccnc(F)c2)c(C)n(C)c1C(=O)C(=O)NC1C2CC3CC(C2)CC1C3] | 5-(2-(((1r,3r)-adamantan-2-yl)amino)-2-oxoacetyl)-N-(6-fluoropyridin-3-yl)-1,2,4-trimethyl-1H-pyrrole-3-carboxamide | 453.2 |

TABLE 1-continued

Exemplary compounds

| Ex. | Structure | Chemical Name | ESI-MS (M + H)+ (m/z) |
|---|---|---|---|
| 92 | 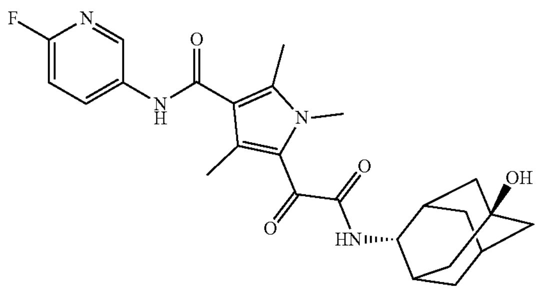 [SMILES: Cc1c(C(=O)Nc2ccc(F)nc2)c(C)n(C)c1C(=O)C(=O)N[C@H]1C2CC3CC1C[C@](O)(C3)C2] | N-(6-fluoropyridin-3-yl)-5-(2-(((1R,2s,3S,5s,7s)-5-hydroxyadamantan-2-yl)amino)-2-oxoacetyl)-1,2,4-trimethyl-1H-pyrrole-3-carboxamide | 469.1 |
| 93 | 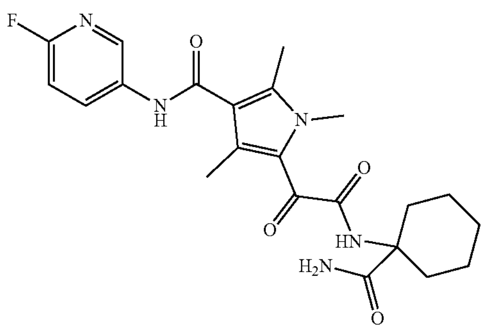 [SMILES: Cc1c(C(=O)Nc2ccc(F)nc2)c(C)n(C)c1C(=O)C(=O)NC1(C(N)=O)CCCCC1] | 5-(2-((1-carbamoylcyclohexyl)amino)-2-oxoacetyl)-N-(6-fluoropyridin-3-yl)-1,2,4-trimethyl-1H-pyrrole-3-carboxamide | 444.2 |
| 94 | 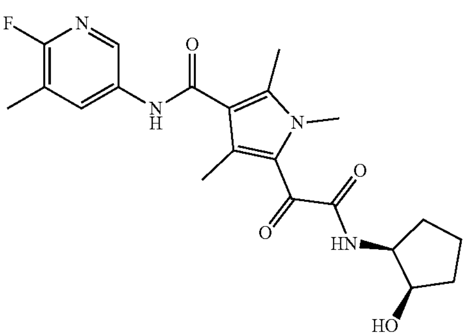 [SMILES: Cc1cc(NC(=O)c2c(C)c(C(=O)C(=O)N[C@H]3CCC[C@H]3O)n(C)c2C)cnc1F] | N-(4-fluoro-3-methylphenyl)-5-(2-(((1S,2R)-2-hydroxycyclopentyl)amino)-2-oxoacetyl)-1,2,4-trimethyl-1H-pyrrole-3-carboxamide | 416.2 |
| 95 | 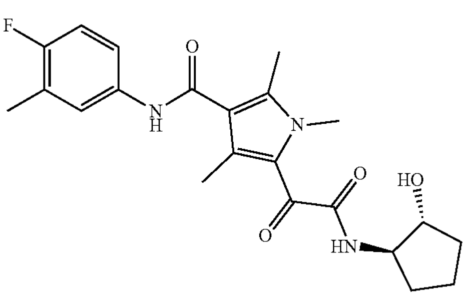 [SMILES: Cc1cc(NC(=O)c2c(C)c(C(=O)C(=O)N[C@@H]3CCC[C@H]3O)n(C)c2C)ccc1F] | N-(4-fluoro-3-methylphenyl)-5-(2-(((1R,2R)-2-hydroxycyclopentyl)amino)-2-oxoacetyl)-1,2,4-trimethyl-1H-pyrrole-3-carboxamide | 416.2 |

TABLE 1-continued

Exemplary compounds

| Ex. | Structure | Chemical Name | ESI-MS (M + H)+ (m/z) |
|---|---|---|---|
| 96 | 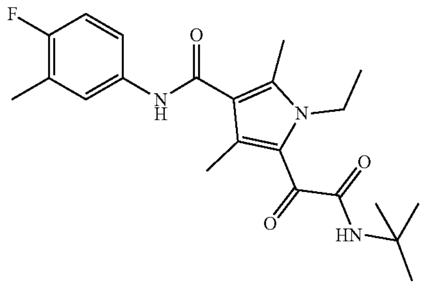 [SMILES: CCn1c(C)c(C(=O)Nc2ccc(F)c(C)c2)c(C)c1C(=O)C(=O)NC(C)(C)C] | 5-(2-(tert-butylamino)-2-oxoacetyl)-1-ethyl-N-(4-fluoro-3-methylphenyl)-2,4-dimethyl-1H-pyrrole-3-carboxamide | 402.2 |
| 97 | 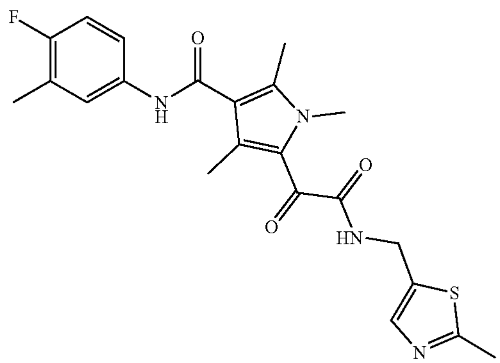 [SMILES: Cc1ncc(CNC(=O)C(=O)c2c(C)c(C(=O)Nc3ccc(F)c(C)c3)c(C)n2C)s1] | 5-(2-(((2-aminothiazol-5-yl)methyl)amino)-2-oxoacetyl)-N-(4-fluoro-3-methylphenyl)-1,2,4-trimethyl-1H-pyrrole-3-carboxamide | 444.1 |
| 98 | 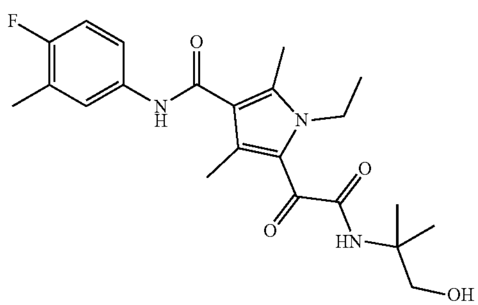 [SMILES: CCn1c(C)c(C(=O)Nc2ccc(F)c(C)c2)c(C)c1C(=O)C(=O)NC(C)(C)CO] | 1-ethyl-N-(4-fluoro-3-methylphenyl)-5-(2-((1-hydroxy-2-methylpropan-2-yl)amino)-2-oxoacetyl)-2,4-dimethyl-1H-pyrrole-3-carboxamide | 418.2 |
| 99 | 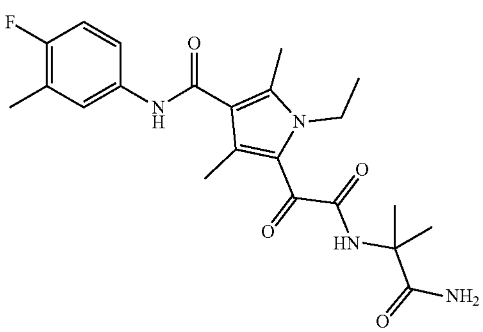 [SMILES: CCn1c(C)c(C(=O)Nc2ccc(F)c(C)c2)c(C)c1C(=O)C(=O)NC(C)(C)C(N)=O] | 5-(2-((1-amino-2-methyl-1-oxopropan-2-yl)amino)-2-oxoacetyl)-1-ethyl-N-(4-fluoro-3-methylphenyl)-2,4-dimethyl-1H-pyrrole-3-carboxamide | 431.2 |

TABLE 1-continued

Exemplary compounds

| Ex. | Structure | Chemical Name | ESI-MS (M + H)+ (m/z) |
|---|---|---|---|
| 100 | 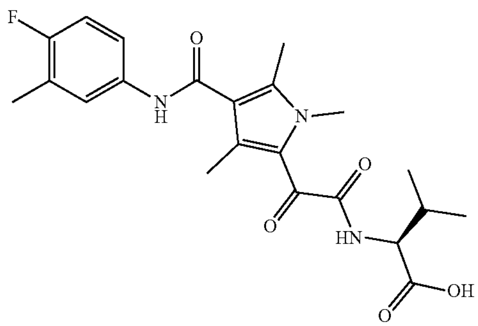 [SMILES: Cc1cc(NC(=O)c2c(C)c(C(=O)C(=O)N[C@H](C(=O)O)C(C)C)n(C)c2C)ccc1F] | (2-(4-((4-fluoro-3-methylphenyl)carbamoyl)-1,3,5-trimethyl-1H-pyrrol-2-yl)-2-oxoacetyl)-L-valine | 432 |
| 101 | 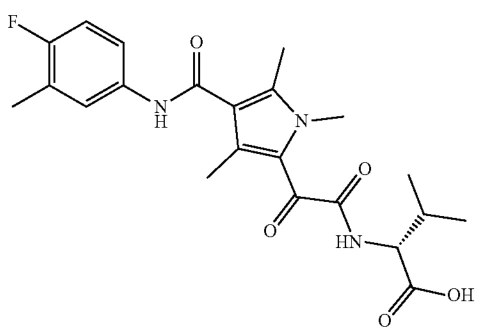 [SMILES: Cc1cc(NC(=O)c2c(C)c(C(=O)C(=O)N[C@@H](C(=O)O)C(C)C)n(C)c2C)ccc1F] | (2-(4-((4-fluoro-3-methylphenyl)carbamoyl)-1,3,5-trimethyl-1H-pyrrol-2-yl)-2-oxoacetyl)-D-valine | 432 |
| 102 | 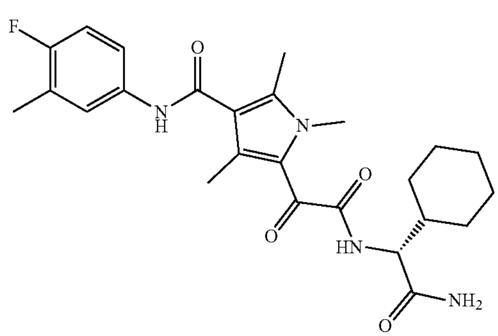 [SMILES: Cc1cc(NC(=O)c2c(C)c(C(=O)C(=O)N[C@@H](C(N)=O)C3CCCCC3)n(C)c2C)ccc1F] | (R)-5-(2-((2-amino-1-cyclohexyl-2-oxoethyl)amino)-2-oxoacetyl)-N-(4-fluoro-3-methylphenyl)-1,2,4-trimethyl-1H-pyrrole-3-carboxamide | 472 |
| 103 | 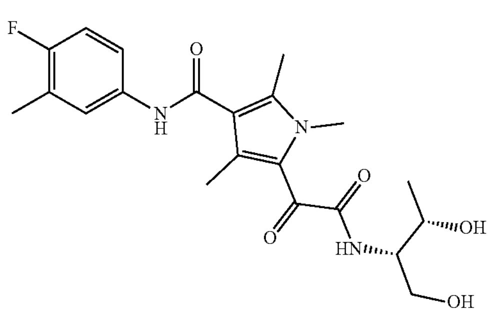 [SMILES: Cc1cc(NC(=O)c2c(C)c(C(=O)C(=O)N[C@@H](CO)[C@H](C)O)n(C)c2C)ccc1F] | 5-(2-(((2S,3S)-1,3-dihydroxybutan-2-yl)amino)-2-oxoacetyl)-N-(4-fluoro-3-methylphenyl)-1,2,4-trimethyl-1H-pyrrole-3-carboxamide | 420 |

TABLE 1-continued

Exemplary compounds

| Ex. | Structure | Chemical Name | ESI-MS (M + H)+ (m/z) |
|---|---|---|---|
| 104 | 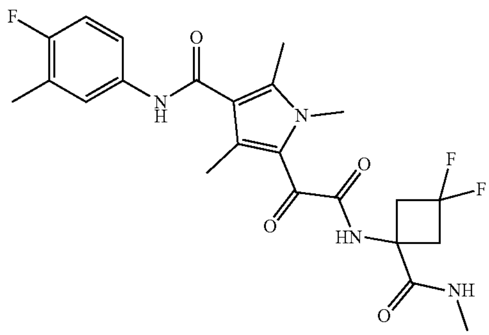 [SMILES: CNC(=O)C1(NC(=O)C(=O)c2c(C)c(C(=O)Nc3ccc(F)c(C)c3)c(C)n2C)CC(F)(F)C1] | 5-(2-((3,3-difluoro-1-(methylcarbamoyl)cyclobutyl)amino)-2-oxoacetyl)-N-(4-fluoro-3-methylphenyl)-1,2,4-trimethyl-1H-pyrrole-3-carboxamide | 479 |
| 105 | 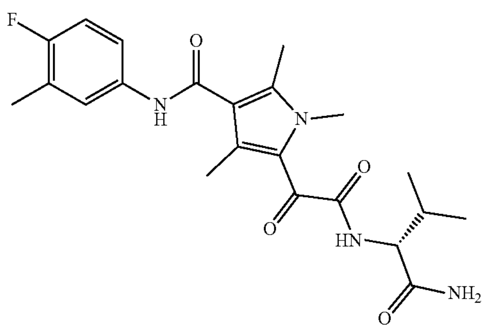 [SMILES: Cc1cc(NC(=O)c2c(C)c(C(=O)C(=O)N[C@@H](C(N)=O)C(C)C)n(C)c2C)ccc1F] | (R)-5-(2-((1-amino-3-methyl-1-oxobutan-2-yl)amino)-2-oxoacetyl)-N-(4-fluoro-3-methylphenyl)-1,2,4-trimethyl-1H-pyrrole-3-carboxamide | 431 |
| 106 | 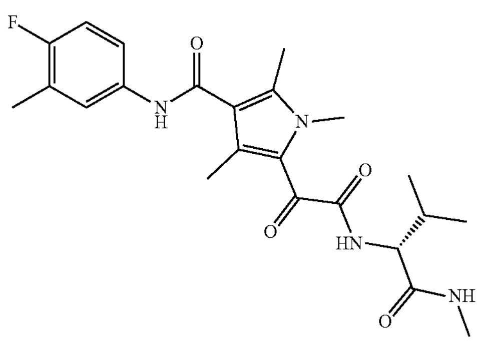 [SMILES: CNC(=O)[C@H](NC(=O)C(=O)c1c(C)c(C(=O)Nc2ccc(F)c(C)c2)c(C)n1C)C(C)C] | (R)-N-(4-fluoro-3-methylphenyl)-1,2,4-trimethyl-5-(2-((3-methyl-1-(methylamino)-1-oxobutan-2-yl)amino)-2-oxoacetyl)-1H-pyrrole-3-carboxamide | 446 |
| 107 | 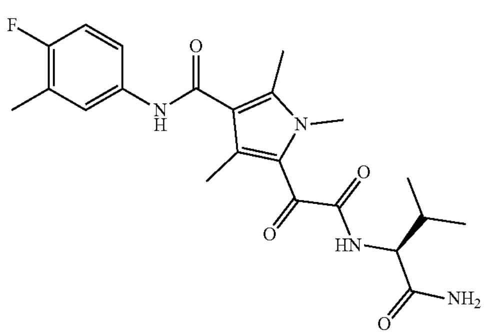 [SMILES: Cc1cc(NC(=O)c2c(C)c(C(=O)C(=O)N[C@H](C(N)=O)C(C)C)n(C)c2C)ccc1F] | (S)-5-(2-((1-amino-3-methyl-1-oxobutan-2-yl)amino)-2-oxoacetyl)-N-(4-fluoro-3-methylphenyl)-1,2,4-trimethyl-1H-pyrrole-3-carboxamide | 431 |

TABLE 1-continued

Exemplary compounds

| Ex. | Structure | Chemical Name | ESI-MS (M + H)+ (m/z) |
|---|---|---|---|
| 108 | 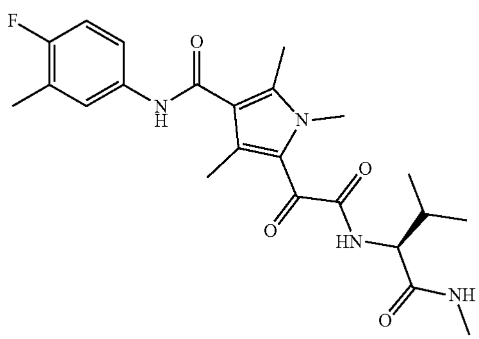 [SMILES: CNC(=O)[C@@H](NC(=O)C(=O)c1c(C)c(C(=O)Nc2ccc(F)c(C)c2)c(C)n1C)C(C)C] | (S)-N-(4-fluoro-3-methylphenyl)-1,2,4-trimethyl-5-(2-((3-methyl-1-(methylamino)-1-oxobutan-2-yl)amino)-2-oxoacetyl)-1H-pyrrole-3-carboxamide | 446 |
| 109 | 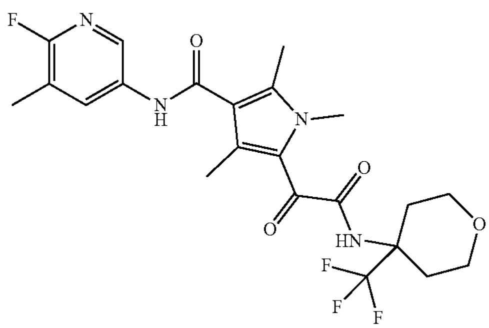 [SMILES: Cc1cc(NC(=O)c2c(C)c(C(=O)C(=O)NC3(C(F)(F)F)CCOCC3)n(C)c2C)cnc1F] | N-(4-fluoro-3-methylphenyl)-1,2,4-trimethyl-5-(2-oxo-2-((4-(trifluoromethyl)tetrahydro-2H-pyran-4-yl)amino)acetyl)-1H-pyrrole-3-carboxamide | 484.1 |
| 110 | 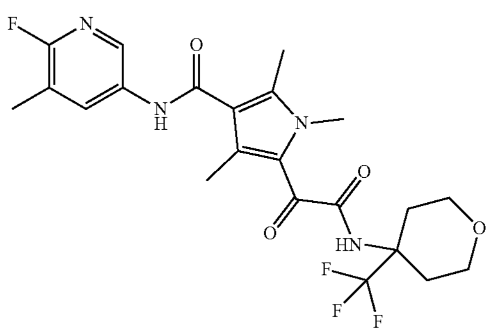 [SMILES: Cc1cc(NC(=O)c2c(C)c(C(=O)C(=O)NC3(C(F)(F)F)CCOCC3)n(C)c2C)cnc1F] | N-(6-fluoropyridin-3-yl)-1,2,4-trimethyl-5-(2-oxo-2-((4-(trifluoromethyl)tetrahydro-2H-pyran-4-yl)amino)acetyl)-1H-pyrrole-3-carboxamide | 471.1 |
| 111 | 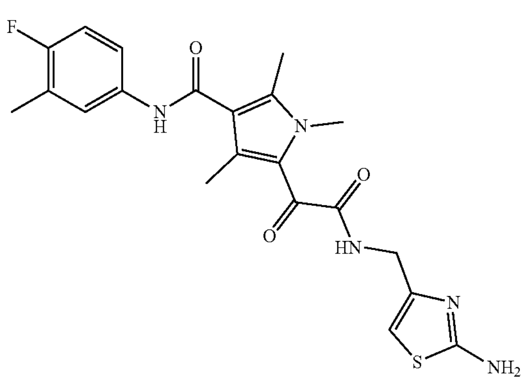 [SMILES: Cc1cc(NC(=O)c2c(C)c(C(=O)C(=O)NCc3csc(N)n3)n(C)c2C)ccc1F] | 5-(2-(((2-aminothiazol-4-yl)methyl)amino)-2-oxoacetyl)-N-(4-fluoro-3-methylphenyl)-1,2,4-trimethyl-1H-pyrrole-3-carboxamide | 444.1 |

TABLE 1-continued

Exemplary compounds

| Ex. | Structure | Chemical Name | ESI-MS (M + H)+ (m/z) |
|---|---|---|---|
| 112 | 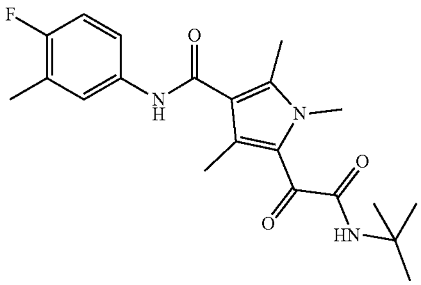 [SMILES: Cc1cc(NC(=O)c2c(C)c(C(=O)C(=O)NC(C)(C)C)n(C)c2C)ccc1F] | 5-(2-(tert-butylamino)-2-oxoacetyl)-N-(6-fluoro-5-methylpyridin-3-yl)-1,2,4-trimethyl-1H-pyrrole-3-carboxamide | 389.2 |
| 113 | 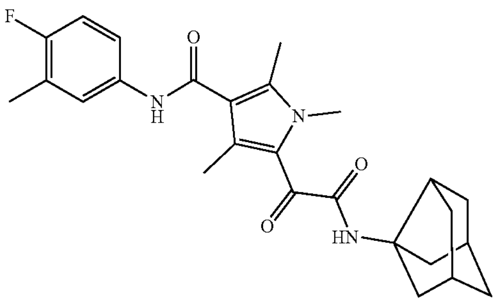 [SMILES: Cc1cc(NC(=O)c2c(C)c(C(=O)C(=O)NC34CC5CC(CC3C5)C4)n(C)c2C)ccc1F] | N-(6-fluoro-5-methylpyridin-3-yl)-5-(2-(((2R,3as,5S,6as)-hexahydro-2,5-methanopentalen-3a(1H)-yl)amino)-2-oxoacetyl)-1,2,4-trimethyl-1H-pyrrole-3-carboxamide | 453.2 |
| 114 | 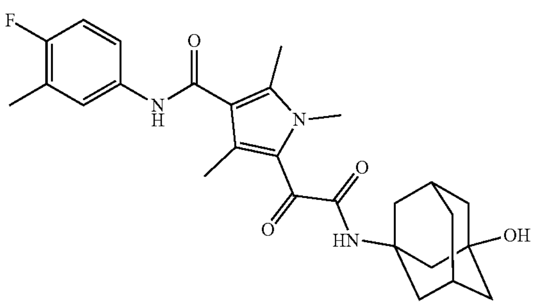 [SMILES: Cc1cc(NC(=O)c2c(C)c(C(=O)C(=O)NC34CC5CC(CC(O)(C5)C3)C4)n(C)c2C)ccc1F] | N-(6-fluoro-5-methylpyridin-3-yl)-5-(2-(((1r,3s,5R,7S)-3-hydroxyadamantan-1-yl)amino)-2-oxoacetyl)-1,2,4-trimethyl-1H-pyrrole-3-carboxamide | 483.2 |
| 115 | 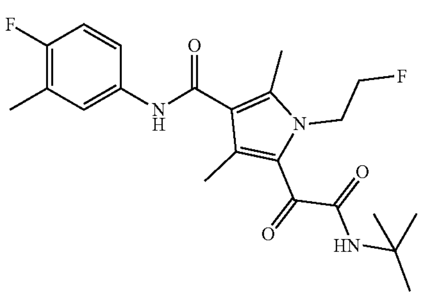 [SMILES: Cc1cc(NC(=O)c2c(C)c(C(=O)C(=O)NC(C)(C)C)n(CCF)c2C)ccc1F] | 5-(2-(tert-butylamino)-2-oxoacetyl)-N-(4-fluoro-3-methylphenyl)-1-(2-fluoroethyl)-2,4-dimethyl-1H-pyrrole-3-carboxamide | 420.2 |
| 116 | 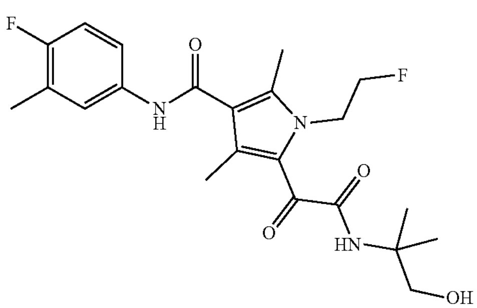 [SMILES: Cc1cc(NC(=O)c2c(C)c(C(=O)C(=O)NC(C)(C)CO)n(CCF)c2C)ccc1F] | N-(4-fluoro-3-methylphenyl)-1-(2-fluoroethyl)-5-(2-((1-hydroxy-2-methylpropan-2-yl)amino)-2-oxoacetyl)-2,4-dimethyl-1H-pyrrole-3-carboxamide | 436.2 |

TABLE 1-continued

Exemplary compounds

| Ex. | Structure | Chemical Name | ESI-MS (M + H)+ (m/z) |
|---|---|---|---|
| 117 | 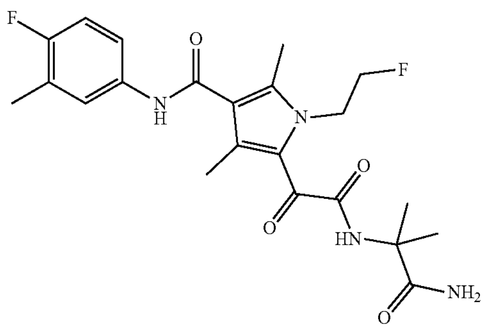 [SMILES: Cc1cc(NC(=O)c2c(C)c(C(=O)C(=O)NC(C)(C)C(N)=O)n(CCF)c2C)ccc1F] | 5-(2-((1-amino-2-methyl-1-oxopropan-2-yl)amino)-2-oxoacetyl)-N-(4-fluoro-3-methylphenyl)-1-(2-fluoroethyl)-2,4-dimethyl-1H-pyrrole-3-carboxamide | 449.2 |
| 118 | 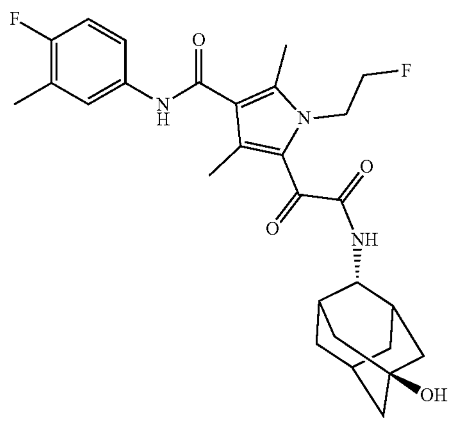 [SMILES: Cc1cc(NC(=O)c2c(C)c(C(=O)C(=O)N[C@H]3C4CC5CC3C[C@](O)(C5)C4)n(CCF)c2C)ccc1F] | N-(4-fluoro-3-methylphenyl)-1-(2-fluoroethyl)-5-(2-(((1R,2s,3S,5s,7s)-5-hydroxyadamantan-2-yl)amino)-2-oxoacetyl)-2,4-dimethyl-1H-pyrrole-3-carboxamide | 514.1 |
| 119 | 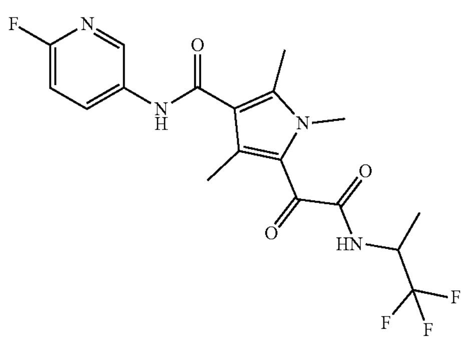 [SMILES: Cc1c(C(=O)Nc2ccc(F)nc2)c(C)n(C)c1C(=O)C(=O)NC(C)C(F)(F)F] | N-(6-fluoropyridin-3-yl)-1,2,4-trimethyl-5-(2-oxo-2-(((1,1,1-trifluoropropan-2-yl)amino)acetyl)-1H-pyrrole-3-carboxamide | 415.1 |
| 120 | 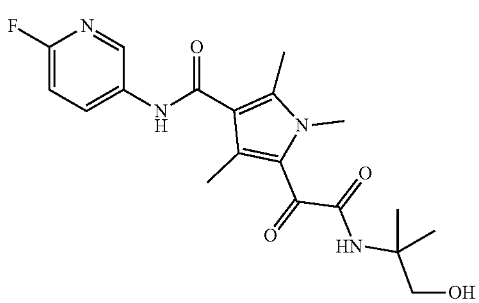 [SMILES: Cc1c(C(=O)Nc2ccc(F)nc2)c(C)n(C)c1C(=O)C(=O)NC(C)(C)CO] | N-(6-fluoropyridin-3-yl)-5-(2-((1-hydroxy-2-methylpropan-2-yl)amino)-2-oxoacetyl)-1,2,4-trimethyl-1H-pyrrole-3-carboxamide | 391.1 |

TABLE 1-continued

Exemplary compounds

| Ex. | Structure | Chemical Name | ESI-MS (M + H)+ (m/z) |
|---|---|---|---|
| 121 | 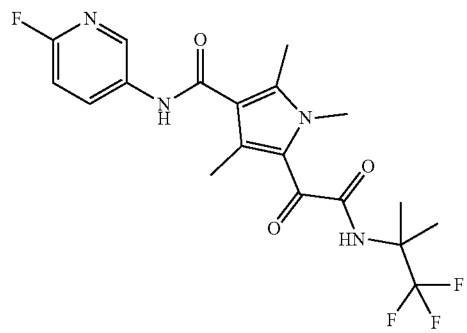 [SMILES: Cc1c(C(=O)Nc2ccc(F)nc2)c(C)n(C)c1C(=O)C(=O)NC(C)(C)C(F)(F)F] | N-(6-fluoropyridin-3-yl)-1,2,4-trimethyl-5-(2-oxo-2-((1,1,1-trifluoro-2-methylpropan-2-yl)amino)acetyl)-1H-pyrrole-3-carboxamide | 429.1 |
| 122 | 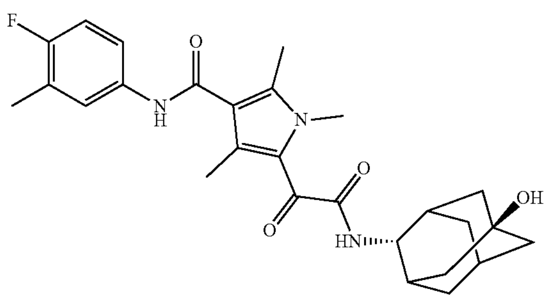 [SMILES: Cc1cc(NC(=O)c2c(C)c(C(=O)C(=O)N[C@H]3C4CC5CC3C[C@](O)(C5)C4)n(C)c2C)ccc1F] | N-(6-fluoro-5-methylpyridin-3-yl)-5-(2-(((1R,2s,3S,5s,7s)-5-hydroxyadamantan-2-yl)amino)-2-oxoacetyl)-1,2,4-trimethyl-1H-pyrrole-3-carboxamide | 483.1 |
| 123 | 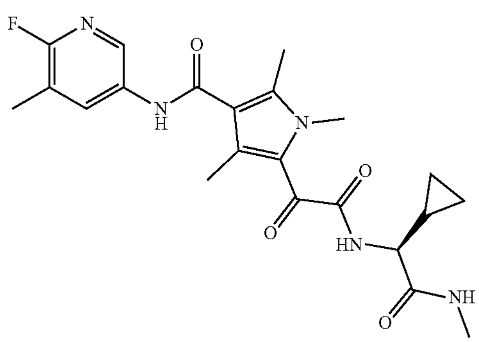 [SMILES: CNC(=O)[C@@H](NC(=O)C(=O)c1c(C)c(C(=O)Nc2cnc(F)c(C)c2)c(C)n1C)C1CC1] | (S)-5-(2-((1-cyclopropyl-2-(methylamino)-2-oxoethyl)amino)-2-oxoacetyl)-N-(4-fluoro-3-methylphenyl)-1,2,4-trimethyl-1H-pyrrole-3-carboxamide | 443 |
| 124 | 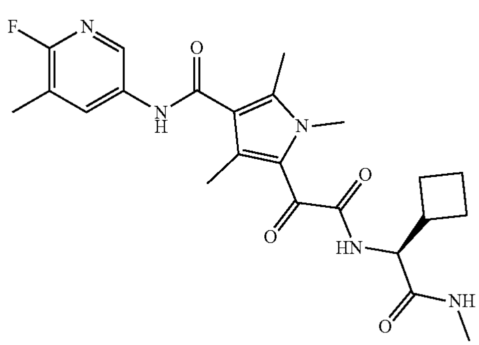 [SMILES: CNC(=O)[C@@H](NC(=O)C(=O)c1c(C)c(C(=O)Nc2cnc(F)c(C)c2)c(C)n1C)C1CCC1] | (S)-5-(2-((1-cyclobutyl-2-(methylamino)-2-oxoethyl)amino)-2-oxoacetyl)-N-(4-fluoro-3-methylphenyl)-1,2,4-trimethyl-1H-pyrrole-3-carboxamide | 458 |

TABLE 1-continued

Exemplary compounds

| Ex. | Structure | Chemical Name | ESI-MS (M + H)+ (m/z) |
|---|---|---|---|
| 125 | 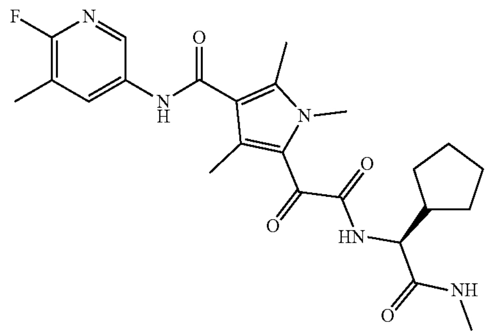 [SMILES: CNC(=O)[C@@H](NC(=O)C(=O)c1c(C)c(C(=O)Nc2cnc(F)c(C)c2)c(C)n1C)C1CCCC1] | (S)-5-(2-(((1-cyclopentyl-2-(methylamino)-2-oxoethyl)amino)-2-oxoacetyl)-N-(4-fluoro-3-methylphenyl)-1,2,4-trimethyl-1H-pyrrole-3-carboxamide | 472 |
| 126 | 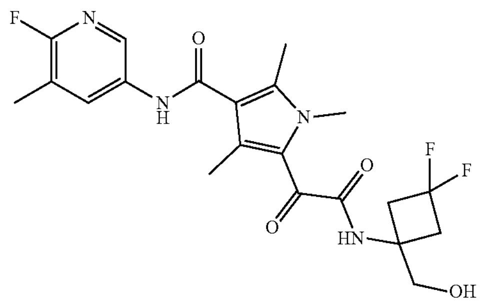 [SMILES: Cc1cc(NC(=O)c2c(C)c(C(=O)C(=O)NC3(CO)CC(F)(F)C3)n(C)c2C)cnc1F] | 5-(2-((3,3-difluoro-1-(hydroxymethyl)cyclobutyl)amino)-2-oxoacetyl)-N-(4-fluoro-3-methylphenyl)-1,2,4-trimethyl-1H-pyrrole-3-carboxamide | 452 |
| 127 | 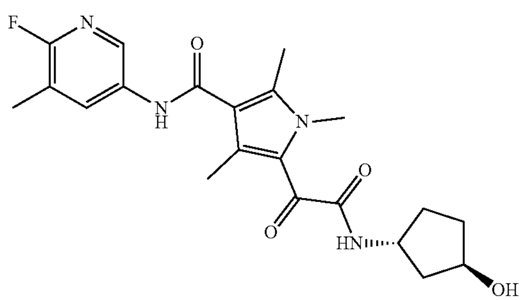 [SMILES: Cc1cc(NC(=O)c2c(C)c(C(=O)C(=O)N[C@@H]3CC[C@@H](O)C3)n(C)c2C)cnc1F] | N-(4-fluoro-3-methylphenyl)-5-(2-(((1R,3R)-3-hydroxycyclopentyl)amino)-2-oxoacetyl)-1,2,4-trimethyl-1H-pyrrole-3-carboxamide | 416.1 |
| 128 | 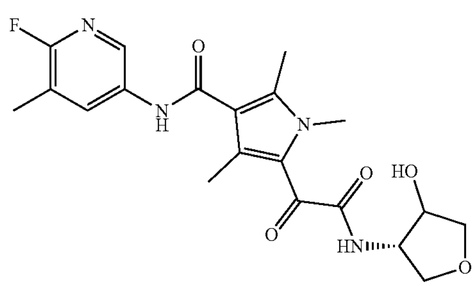 [SMILES: Cc1cc(NC(=O)c2c(C)c(C(=O)C(=O)N[C@H]3COCC3O)n(C)c2C)cnc1F] | N-(4-fluoro-3-methylphenyl)-5-(2-(((3S,4R)-4-hydroxytetrahydrofuran-3-yl)amino)-2-oxoacetyl)-1,2,4-trimethyl-1H-pyrrole-3-carboxamide | 418.1 |
| 129 | 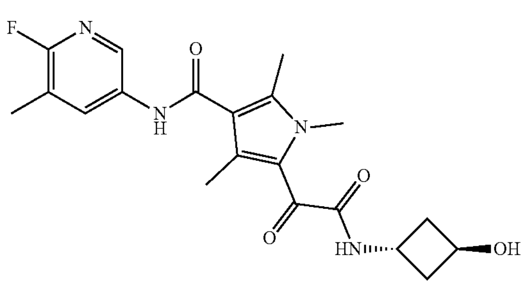 [SMILES: Cc1cc(NC(=O)c2c(C)c(C(=O)C(=O)N[C@H]3C[C@H](O)C3)n(C)c2C)cnc1F] | N-(4-fluoro-3-methylphenyl)-5-(2-(((1r,3r)-3-hydroxycyclobutyl)amino)-2-oxoacetyl)-1,2,4-trimethyl-1H-pyrrole-3-carboxamide | 402.1 |

TABLE 1-continued

Exemplary compounds

| Ex. | Structure | Chemical Name | ESI-MS (M + H)+ (m/z) |
|---|---|---|---|
| 130 | 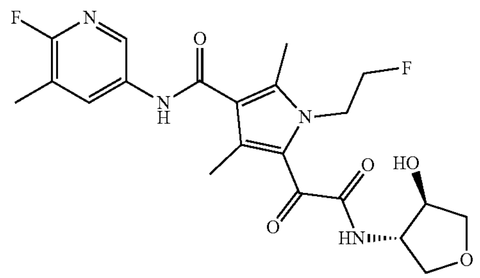 [SMILES: Cc1cc(NC(=O)c2c(C)c(C(=O)C(=O)N[C@H]3COC[C@@H]3O)n(CCF)c2C)cnc1F] | N-(4-fluoro-3-methylphenyl)-1-(2-fluoroethyl)-5-(2-(((3S,4R)-4-hydroxytetrahydrofuran-3-yl)amino)-2-oxoacetyl)-2,4-dimethyl-1H-pyrrole-3-carboxamide | 450.1 |
| 131 | 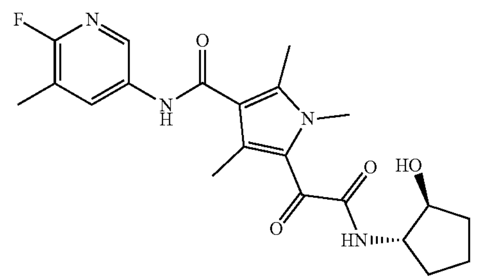 [SMILES: Cc1cc(NC(=O)c2c(C)c(C(=O)C(=O)N[C@H]3CCC[C@@H]3O)n(C)c2C)cnc1F] | N-(6-fluoro-5-methylpyridin-3-yl)-5-(2-(((1S,2S)-2-hydroxycyclopentyl)amino)-2-oxoacetyl)-1,2,4-trimethyl-1H-pyrrole-3-carboxamide | 417.1 |
| 132 | 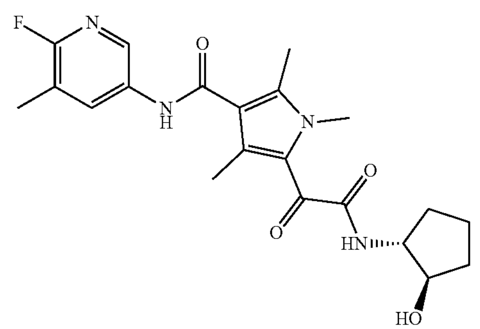 [SMILES: Cc1cc(NC(=O)c2c(C)c(C(=O)C(=O)N[C@@H]3CCC[C@H]3O)n(C)c2C)cnc1F] | N-(6-fluoro-5-methylpyridin-3-yl)-5-(2-(((1R,2R)-2-hydroxycyclopentyl)amino)-2-oxoacetyl)-1,2,4-trimethyl-1H-pyrrole-3-carboxamide | 417.1 |
| 133 | 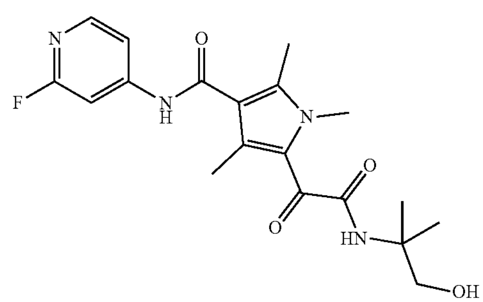 [SMILES: Cc1c(C(=O)Nc2ccnc(F)c2)c(C)n(C)c1C(=O)C(=O)NC(C)(C)CO] | N-(2-fluoropyridin-4-yl)-5-(2-((1-hydroxy-2-methylpropan-2-yl)amino)-2-oxoacetyl)-1,2,4-trimethyl-1H-pyrrole-3-carboxamide | 391.1 |
| 134 | 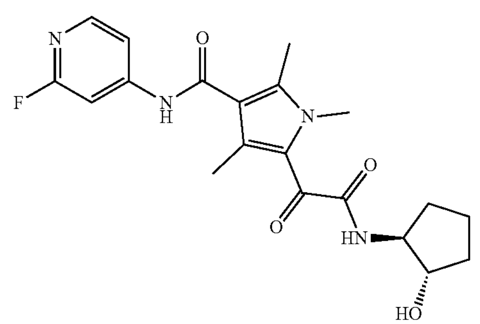 [SMILES: Cc1c(C(=O)Nc2ccnc(F)c2)c(C)n(C)c1C(=O)C(=O)N[C@H]1CCC[C@@H]1O] | N-(2-fluoropyridin-4-yl)-5-(2-(((1S,2S)-2-hydroxycyclopentyl)amino)-2-oxoacetyl)-1,2,4-trimethyl-1H-pyrrole-3-carboxamide | 403.1 |

TABLE 1-continued

Exemplary compounds

| Ex. | Structure | Chemical Name | ESI-MS (M + H)+ (m/z) |
|---|---|---|---|
| 135 | 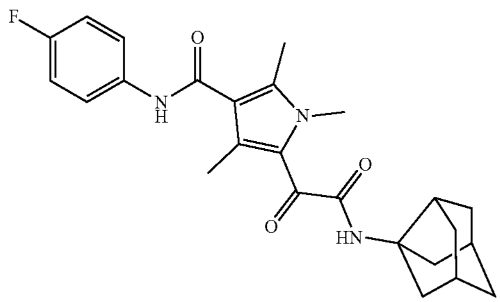 [SMILES: Cc1c(C(=O)Nc2ccc(F)cc2)c(C)n(C)c1C(=O)C(=O)NC12CC3CC(CC1C3)C2] | N-(5-fluoropyridin-2-yl)-5-(2-((((2R,3as,5S,6as)-hexahydro-2,5-methanopentalen-3a(1H)-yl)amino)-2-oxoacetyl)-1,2,4-trimethyl-1H-pyrrole-3-carboxamide | 439.2 |
| 136 | 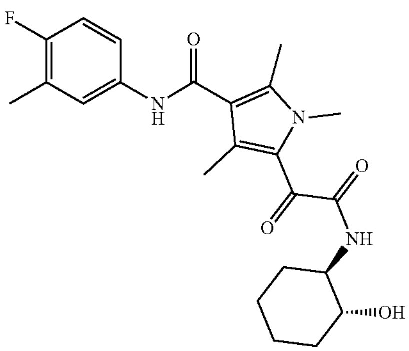 [SMILES: Cc1cc(NC(=O)c2c(C)c(C(=O)C(=O)N[C@@H]3CCCC[C@H]3O)n(C)c2C)ccc1F] | N-(4-fluoro-3-methylphenyl)-5-(2-(((1R,2R)-2-hydroxycyclohexyl)amino)-2-oxoacetyl)-1,2,4-trimethyl-1H-pyrrole-3-carboxamide | 430.1 |
| 137 | 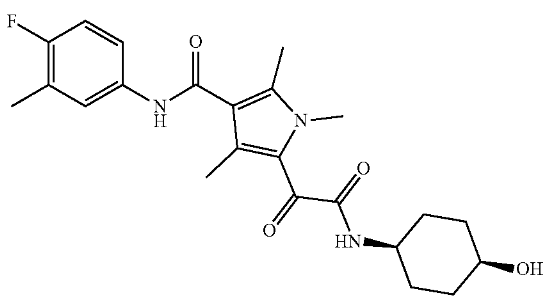 [SMILES: Cc1cc(NC(=O)c2c(C)c(C(=O)C(=O)N[C@H]3CC[C@@H](O)CC3)n(C)c2C)ccc1F] | N-(4-fluoro-3-methylphenyl)-5-(2-(((1s,4s)-4-hydroxycyclohexyl)amino)-2-oxoacetyl)-1,2,4-trimethyl-1H-pyrrole-3-carboxamide | 430.1 |
| 138 | 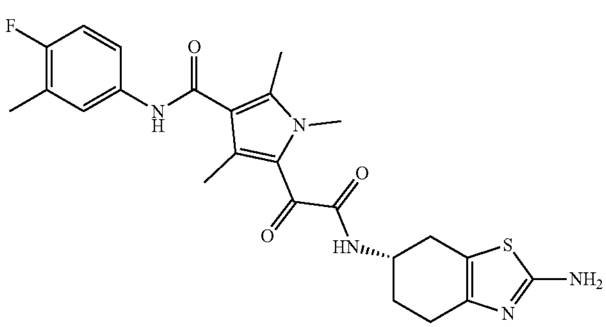 [SMILES: Cc1cc(NC(=O)c2c(C)c(C(=O)C(=O)N[C@H]3CCc4nc(N)sc4C3)n(C)c2C)ccc1F] | (S)-5-(2-((2-amino-4,5,6,7-tetrahydrobenzo[d]thiazol-6-yl)amino)-2-oxoacetyl)-N-(6-fluoro-5-methylpyridin-3-yl)-1,2,4-trimethyl-1H-pyrrole-3-carboxamide | 485.1 |

TABLE 1-continued

Exemplary compounds

| Ex. | Structure | Chemical Name | ESI-MS (M + H)+ (m/z) |
|---|---|---|---|
| 139 | 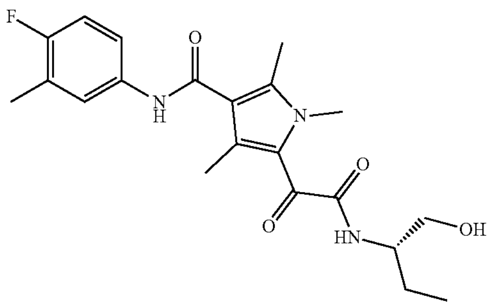 [SMILES: CC[C@@H](CO)NC(=O)C(=O)c1c(C)c(C(=O)Nc2ccc(F)c(C)c2)c(C)n1C] | (S)-N-(4-fluoro-3-methylphenyl)-5-(2-((1-hydroxybutan-2-yl)amino)-2-oxoacetyl)-1,2,4-trimethyl-1H-pyrrole-3-carboxamide | 404 |
| 140 | 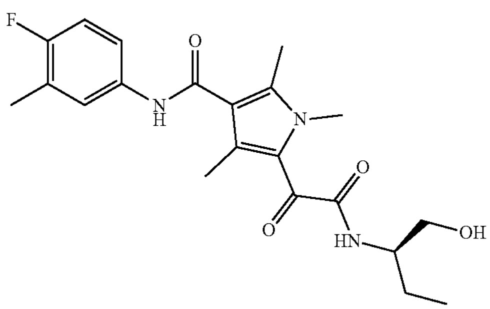 [SMILES: CC[C@H](CO)NC(=O)C(=O)c1c(C)c(C(=O)Nc2ccc(F)c(C)c2)c(C)n1C] | (R)-N-(4-fluoro-3-methylphenyl)-5-(2-((1-hydroxybutan-2-yl)amino)-2-oxoacetyl)-1,2,4-trimethyl-1H-pyrrole-3-carboxamide | 404 |
| 141 | 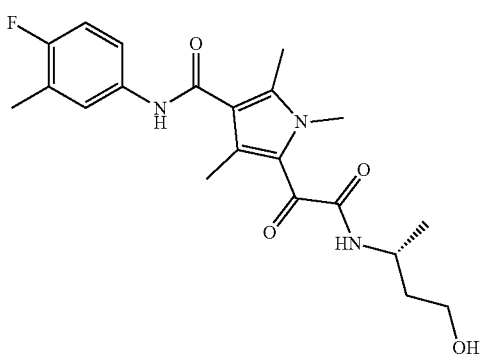 [SMILES: Cc1cc(NC(=O)c2c(C)c(C(=O)C(=O)N[C@H](C)CCO)n(C)c2C)ccc1F] | (R)-N-(4-fluoro-3-methylphenyl)-5-(2-((4-hydroxybutan-2-yl)amino)-2-oxoacetyl)-1,2,4-trimethyl-1H-pyrrole-3-carboxamide | 404 |
| 142 | 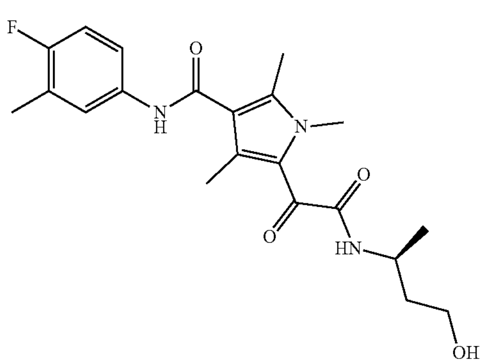 [SMILES: Cc1cc(NC(=O)c2c(C)c(C(=O)C(=O)N[C@@H](C)CCO)n(C)c2C)ccc1F] | (S)-N-(4-fluoro-3-methylphenyl)-5-(2-((4-hydroxybutan-2-yl)amino)-2-oxoacetyl)-1,2,4-trimethyl-1H-pyrrole-3-carboxamide | 404 |

TABLE 1-continued

Exemplary compounds

| Ex. | Structure | Chemical Name | ESI-MS (M + H)+ (m/z) |
|---|---|---|---|
| 143 | 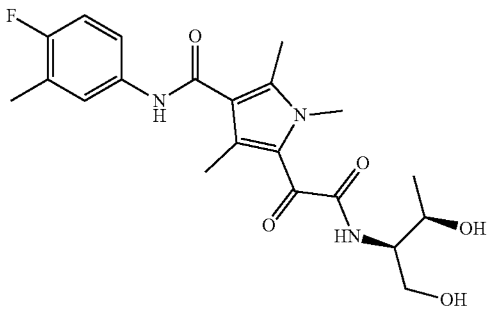 [SMILES: Cc1cc(NC(=O)c2c(C)c(C(=O)C(=O)N[C@H](CO)[C@@H](C)O)n(C)c2C)ccc1F] | 5-(2-(((2R,3R)-1,3-dihydroxybutan-2-yl)amino)-2-oxoacetyl)-N-(4-fluoro-3-methylphenyl)-1,2,4-trimethyl-1H-pyrrole-3-carboxamide | 420 |
| 144 | 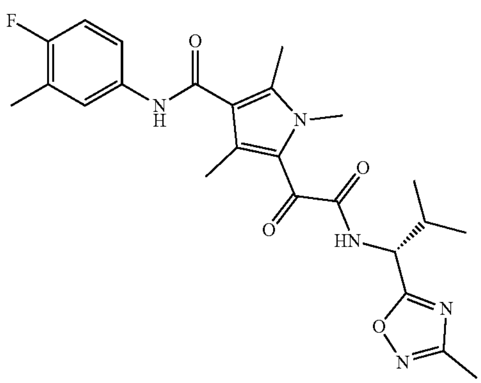 [SMILES: Cc1noc([C@H](NC(=O)C(=O)c2c(C)c(C(=O)Nc3ccc(F)c(C)c3)c(C)n2C)C(C)C)n1] | (R)-N-(4-fluoro-3-methylphenyl)-1,2,4-trimethyl-5-(2-((2-methyl-1-(3-methyl-1,2,4-oxadiazol-5-yl)propyl)amino)-2-oxoacetyl)-1H-pyrrole-3-carboxamide | 471 |
| 145 | 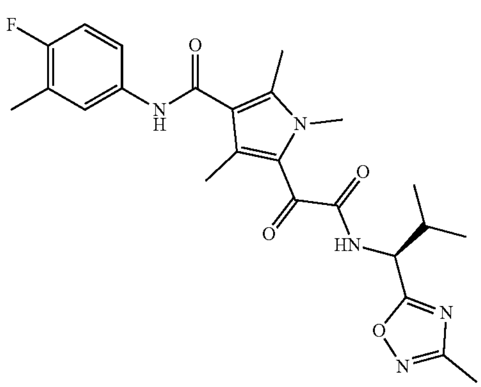 [SMILES: Cc1noc([C@@H](NC(=O)C(=O)c2c(C)c(C(=O)Nc3ccc(F)c(C)c3)c(C)n2C)C(C)C)n1] | (S)-N-(4-fluoro-3-methylphenyl)-1,2,4-trimethyl-5-(2-((2-methyl-1-(3-methyl-1,2,4-oxadiazol-5-yl)propyl)amino)-2-oxoacetyl)-1H-pyrrole-3-carboxamide | 471 |
| 146 | 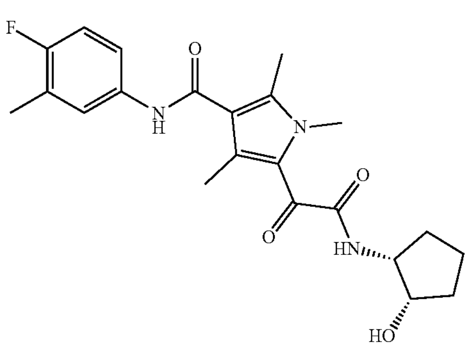 [SMILES: Cc1cc(NC(=O)c2c(C)c(C(=O)C(=O)N[C@@H]3CCC[C@@H]3O)n(C)c2C)ccc1F] | N-(4-fluoro-3-methylphenyl)-5-(2-(((1R,2S)-2-hydroxycyclopentyl)amino)-2-oxoacetyl)-1,2,4-trimethyl-1H-pyrrole-3-carboxamide | 416.1 |

TABLE 1-continued

Exemplary compounds

| Ex. | Structure | Chemical Name | ESI-MS (M + H)+ (m/z) |
|---|---|---|---|
| 147 | 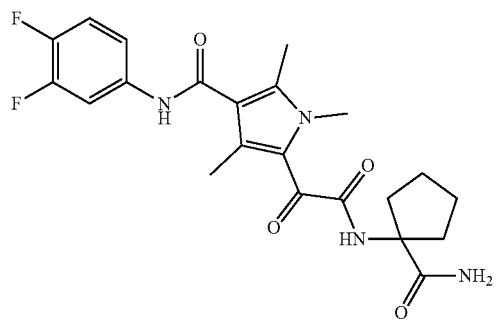 [SMILES: Cc1c(C(=O)Nc2ccc(F)c(F)c2)c(C)n(C)c1C(=O)C(=O)NC1(C(N)=O)CCCC1] | 5-(2-(((1-carbamoylcyclopentyl)amino)-2-oxoacetyl)-N-(3,4-difluorophenyl)-1,2,4-trimethyl-1H-pyrrole-3-carboxamide | 447.2 |
| 148 | 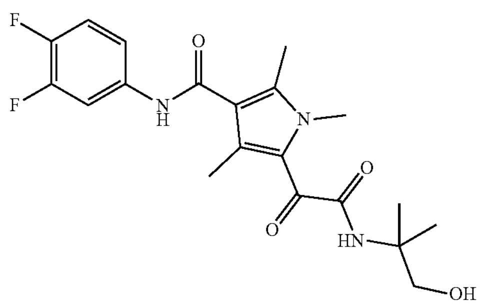 [SMILES: Cc1c(C(=O)Nc2ccc(F)c(F)c2)c(C)n(C)c1C(=O)C(=O)NC(C)(C)CO] | N-(3,4-difluorophenyl)-5-(2-(((1-hydroxy-2-methylpropan-2-yl)amino)-2-oxoacetyl)-1,2,4-trimethyl-1H-pyrrole-3-carboxamide | 408.2 |
| 149 | 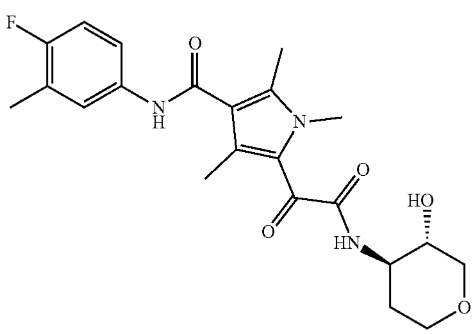 [SMILES: Cc1cc(NC(=O)c2c(C)c(C(=O)C(=O)N[C@@H]3CCOC[C@H]3O)n(C)c2C)ccc1F] | N-(4-fluoro-3-methylphenyl)-5-(2-(((3S,4R)-3-hydroxytetrahydro-2H-pyran-4-yl)amino)-2-oxoacetyl)-1,2,4-trimethyl-1H-pyrrole-3-carboxamide | 432.1 |
| 150 | 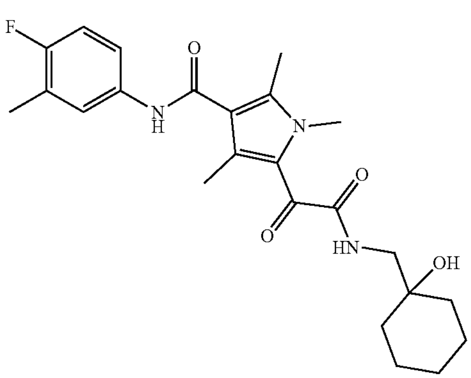 [SMILES: Cc1cc(NC(=O)c2c(C)c(C(=O)C(=O)NCC3(O)CCCCC3)n(C)c2C)ccc1F] | N-(4-fluoro-3-methylphenyl)-5-(2-(((4-hydroxytetrahydro-2H-pyran-4-yl)methyl)amino)-2-oxoacetyl)-1,2,4-trimethyl-1H-pyrrole-3-carboxamide | 446.1 |

TABLE 1-continued

Exemplary compounds

| Ex. | Structure | Chemical Name | ESI-MS (M + H)+ (m/z) |
|---|---|---|---|
| 151 | 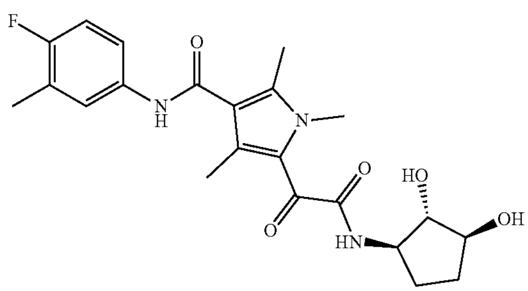 [SMILES: Cc1cc(NC(=O)c2c(C)c(C(=O)C(=O)N[C@@H]3CC[C@H](O)[C@H]3O)n(C)c2C)ccc1F] | 5-(2-(((1R,2S,3S)-2,3-dihydroxycyclopentyl)amino)-2-oxoacetyl)-N-(4-fluoro-3-methylphenyl)-1,2,4-trimethyl-1H-pyrrole-3-carboxamide | 432.1 |
| 152 | 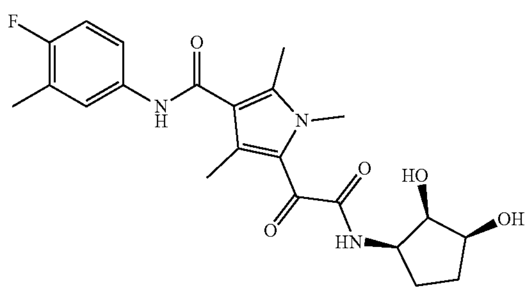 [SMILES: Cc1cc(NC(=O)c2c(C)c(C(=O)C(=O)N[C@@H]3CC[C@H](O)[C@@H]3O)n(C)c2C)ccc1F] | 5-(2-(((1R,2R,3S)-2,3-dihydroxycyclopentyl)amino)-2-oxoacetyl)-N-(4-fluoro-3-methylphenyl)-1,2,4-trimethyl-1H-pyrrole-3-carboxamide | 432.1 |
| 153 | 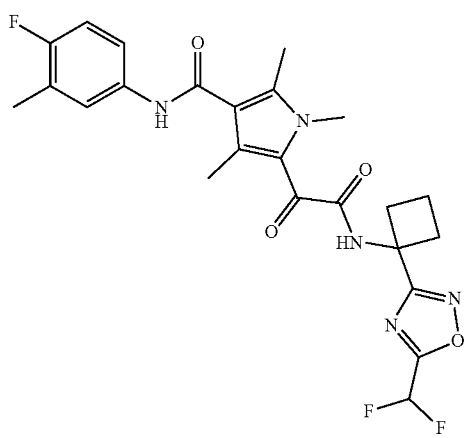 [SMILES: Cc1cc(NC(=O)c2c(C)c(C(=O)C(=O)NC3(c4noc(C(F)F)n4)CCC3)n(C)c2C)ccc1F] | 5-(2-((1-(5-(difluoromethyl)-1,2,4-oxadiazol-3-yl)cyclobutyl)amino)-2-oxoacetyl)-N-(4-fluoro-3-methylphenyl)-1,2,4-trimethyl-1H-pyrrole-3-carboxamide | 504 |
| 154 | 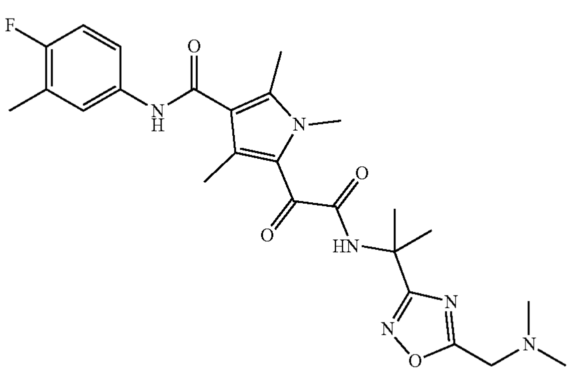 | 5-(2-((2-(5-((dimethylamino)methyl)-1,2,4-oxadiazol-3-yl)propan-2-yl)amino)-2-oxoacetyl)-N-(4-fluoro-3-methylphenyl)-1,2,4-trimethyl-1H-pyrrole-3-carboxamide | 500 |

TABLE 1-continued

Exemplary compounds

| Ex. | Structure | Chemical Name | ESI-MS (M + H)+ (m/z) |
|---|---|---|---|
| 155 | 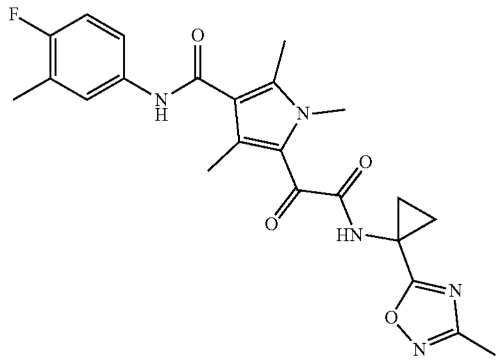 | N-(4-fluoro-3-methylphenyl)-1,2,4-trimethyl-5-(2-((1-(3-methyl-1,2,4-oxadiazol-5-yl)cyclopropyl)amino)-2-oxoacetyl)-1H-pyrrole-3-carboxamide | 454 |
| 156 | 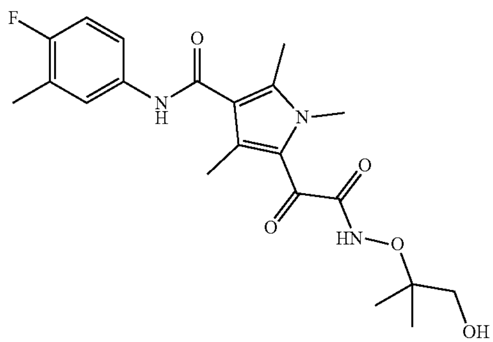 [SMILES: Cc1cc(NC(=O)c2c(C)c(C(=O)C(=O)NOC(C)(C)CO)n(C)c2C)ccc1F] | N-(4-fluoro-3-methylphenyl)-5-(2-(((1-hydroxy-2-methylpropan-2-yl)oxy)amino)-2-oxoacetyl)-1,2,4-trimethyl-1H-pyrrole-3-carboxamide | 420 |
| 157 | 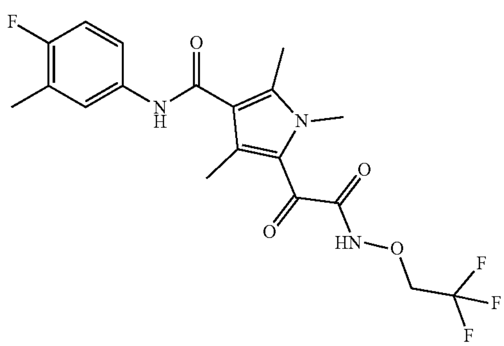 [SMILES: Cc1cc(NC(=O)c2c(C)c(C(=O)C(=O)NOCC(F)(F)F)n(C)c2C)ccc1F] | N-(4-fluoro-3-methylphenyl)-1,2,4-trimethyl-5-(2-oxo-2-((2,2,2-trifluoroethoxy)amino)acetyl)-1H-pyrrole-3-carboxamide | 430 |
| 158 | 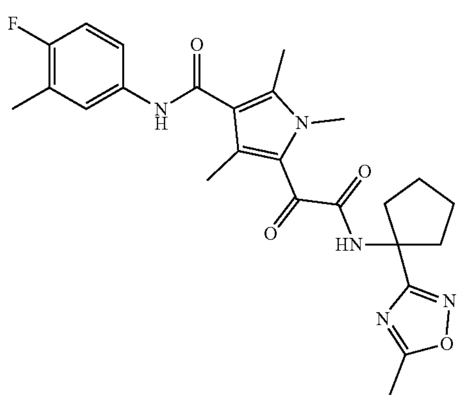 [SMILES: Cc1nc(C2(NC(=O)C(=O)c3c(C)c(C(=O)Nc4ccc(F)c(C)c4)c(C)n3C)CCCC2)no1] | N-(4-fluoro-3-methylphenyl)-1,2,4-trimethyl-5-(2-((1-(5-methyl-1,2,4-oxadiazol-3-yl)cyclopentyl)amino)-2-oxoacetyl)-1H-pyrrole-3-carboxamide | 483 |

TABLE 1-continued

Exemplary compounds

| Ex. | Structure | Chemical Name | ESI-MS (M + H)+ (m/z) |
|---|---|---|---|
| 159 | 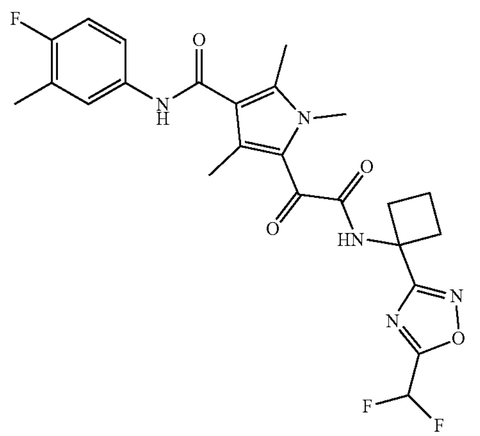 [SMILES: Cc1cc(NC(=O)c2c(C)c(C(=O)C(=O)NC3(c4noc(C(F)F)n4)CCC3)n(C)c2C)ccc1F] | 5-(2-((1-(5-(difluoromethyl)-1,2,4-oxadiazol-3-yl)cyclobutyl)amino)-2-oxoacetyl)-N-(6-fluoro-5-methylpyridin-3-yl)-1,2,4-trimethyl-1H-pyrrole-3-carboxamide | 505 |
| 160 | 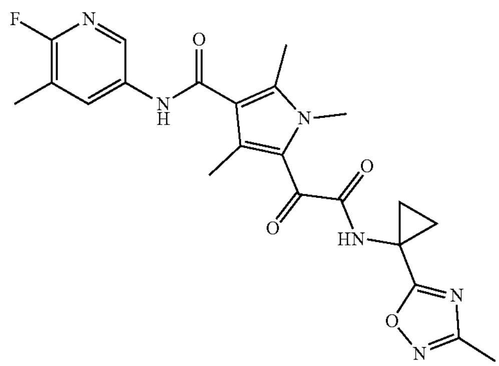 | N-(6-fluoro-5-methylpyridin-3-yl)-1,2,4-trimethyl-5-(2-(((1-(3-methyl-1,2,4-oxadiazol-5-yl)cyclopropyl)amino)-2-oxoacetyl)-1H-pyrrole-3-carboxamide | 455 |
| 161 | 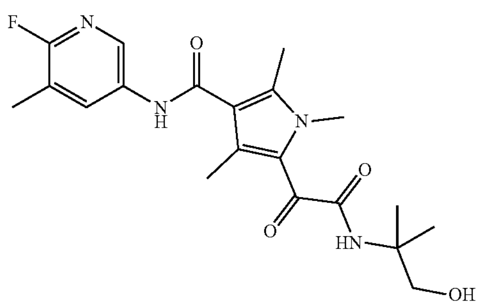 [SMILES: Cc1cc(NC(=O)c2c(C)c(C(=O)C(=O)NC(C)(C)CO)n(C)c2C)cnc1F] | N-(6-fluoro-5-methylpyridin-3-yl)-5-(2-((1-hydroxy-2-methylpropan-2-yl)amino)-2-oxoacetyl)-1,2,4-trimethyl-1H-pyrrole-3-carboxamide | 405.2 |
| 162 | 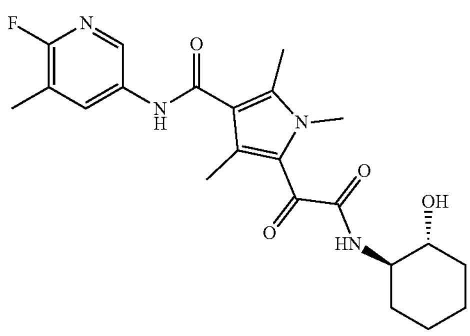 [SMILES: Cc1cc(NC(=O)c2c(C)c(C(=O)C(=O)N[C@@H]3CCCC[C@H]3O)n(C)c2C)cnc1F] | N-(6-fluoro-5-methylpyridin-3-yl)-5-(2-(((1R,2R)-2-hydroxycyclohexyl)amino)-2-oxoacetyl)-1,2,4-trimethyl-1H-pyrrole-3-carboxamide | 431.3 |

TABLE 1-continued

Exemplary compounds

| Ex. | Structure | Chemical Name | ESI-MS (M + H)+ (m/z) |
|---|---|---|---|
| 163 | 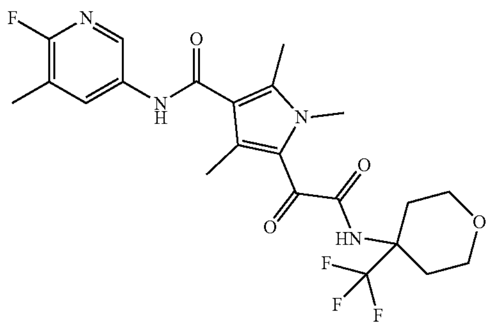 [SMILES: Cc1cc(NC(=O)c2c(C)c(C(=O)C(=O)NC3(C(F)(F)F)CCOCC3)n(C)c2C)cnc1F] | N-(6-fluoro-5-methylpyridin-3-yl)-1,2,4-trimethyl-5-(2-oxo-2-((4-(trifluoromethyl)tetrahydro-2H-pyran-4-yl)amino)acetyl)-1H-pyrrole-3-carboxamide | 485.2 |
| 164 | 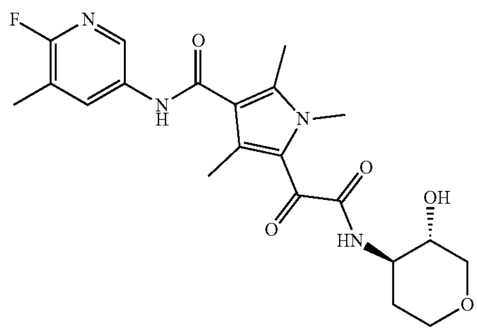 [SMILES: Cc1cc(NC(=O)c2c(C)c(C(=O)C(=O)N[C@@H]3CCOC[C@H]3O)n(C)c2C)cnc1F] | N-(6-fluoro-5-methylpyridin-3-yl)-5-(2-(((3S,4R)-3-hydroxytetrahydro-2H-pyran-4-yl)amino)-2-oxoacetyl)-1,2,4-trimethyl-1H-pyrrole-3-carboxamide | 433.2 |
| 165 | 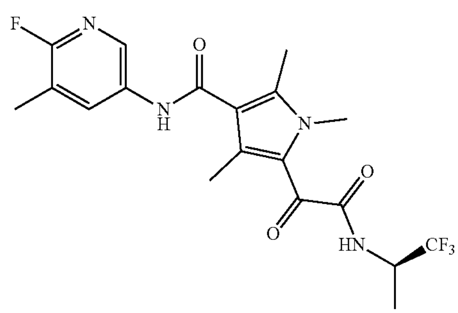 [SMILES: Cc1cc(NC(=O)c2c(C)c(C(=O)C(=O)N[C@H](C)C(F)(F)F)n(C)c2C)cnc1F] | (R)-N-(6-fluoro-5-methylpyridin-3-yl)-1,2,4-trimethyl-5-(2-oxo-2-((1,1,1-trifluoropropan-2-yl)amino)acetyl)-1H-pyrrole-3-carboxamide | 429.1 |
| 166 | 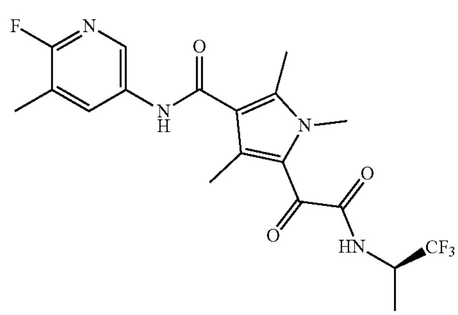 [SMILES: Cc1cc(NC(=O)c2c(C)c(C(=O)C(=O)N[C@H](C)C(F)(F)F)n(C)c2C)cnc1F] | (R)-N-(6-fluoropyridin-3-yl)-1,2,4-trimethyl-5-(2-oxo-2-((1,1,1-trifluoropropan-2-yl)amino)acetyl)-1H-pyrrole-3-carboxamide | 415.1 |

TABLE 1-continued

Exemplary compounds

| Ex. | Structure | Chemical Name | ESI-MS (M + H)+ (m/z) |
|---|---|---|---|
| 167 | 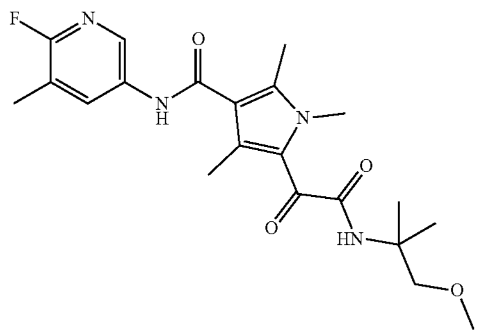 [SMILES: COCC(C)(C)NC(=O)C(=O)c1c(C)c(C(=O)Nc2cnc(F)c(C)c2)c(C)n1C] | N-(6-fluoro-5-methylpyridin-3-yl)-5-(2-((1-methoxy-2-methylpropan-2-yl)amino)-2-oxoacetyl)-1,2,4-trimethyl-1H-pyrrole-3-carboxamide | 419.1 |
| 168 | 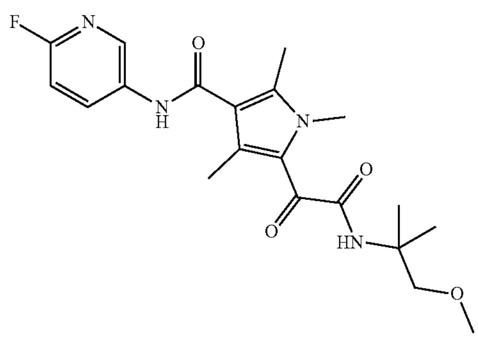 [SMILES: COCC(C)(C)NC(=O)C(=O)c1c(C)c(C(=O)Nc2ccc(F)nc2)c(C)n1C] | N-(6-fluoropyridin-3-yl)-5-(2-((1-methoxy-2-methylpropan-2-yl)amino-2-oxoacetyl)-1,2,4-trimethyl-1H-pyrrole-3-carboxamide | 405.1 |
| 169 | 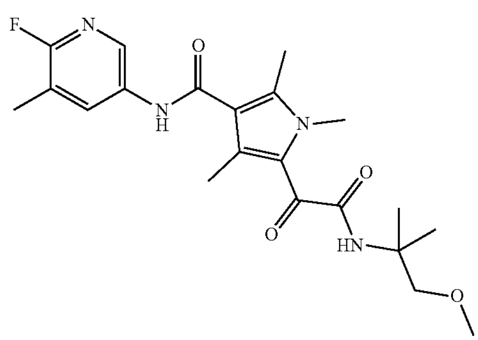 [SMILES: COCC(C)(C)NC(=O)C(=O)c1c(C)c(C(=O)Nc2cnc(F)c(C)c2)c(C)n1C] | N-(4-fluoro-3-methylphenyl)-5-(2-((1-methoxy-2-methylpropan-2-yl)amino)-2-oxoacetyl)-1,2,4-trimethyl-1H-pyrrole-3-carboxamide | 418.2 |
| 170 | 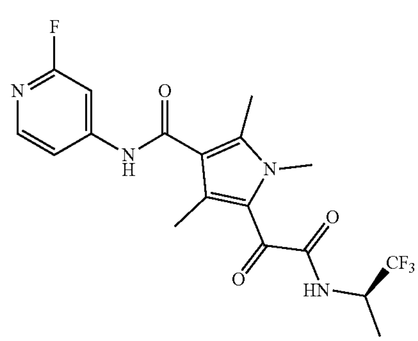 [SMILES: Cc1c(C(=O)Nc2ccnc(F)c2)c(C)n(C)c1C(=O)C(=O)N[C@H](C)C(F)(F)F] | (R)-N-(2-fluoropyridin-4-yl)-1,2,4-trimethyl-5-(2-oxo-2-((1,1,1-trifluoropropan-2-yl)amino)acetyl)-1H-pyrrole-3-carboxamide | 415.1 |

TABLE 1-continued

Exemplary compounds

| Ex. | Structure | Chemical Name | ESI-MS (M + H)+ (m/z) |
|---|---|---|---|
| 171 | 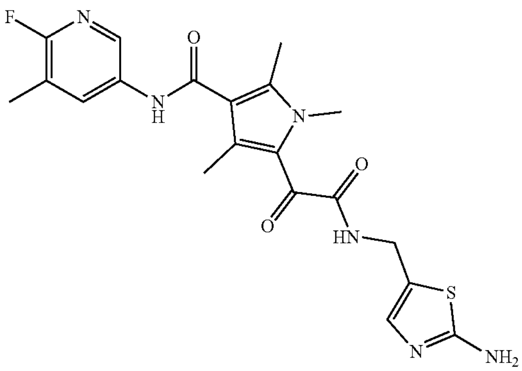 [SMILES: Cc1cc(NC(=O)c2c(C)c(C(=O)C(=O)NCc3cnc(N)s3)n(C)c2C)cnc1F] | 5-(2-(((2-aminothiazol-5-yl)methyl)amino)-2-oxoacetyl)-N-(6-fluoro-5-methylpyridin-3-yl)-1,2,4-trimethyl-1H-pyrrole-3-carboxamide | 445.1 |
| 172 | 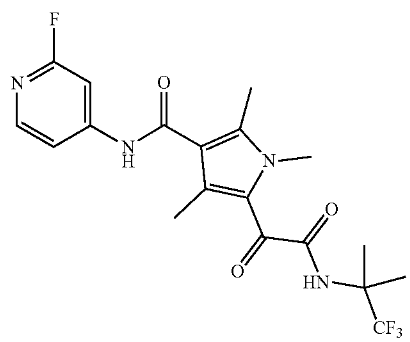 [SMILES: Cc1c(C(=O)Nc2ccnc(F)c2)c(C)n(C)c1C(=O)C(=O)NC(C)(C)C(F)(F)F] | N-(2-fluoropyridin-4-yl)-1,2,4-trimethyl-5-(2-oxo-2-((1,1,1-trifluoro-2-methylpropan-2-yl)amino)acetyl)-1H-pyrrole-3-carboxamide | 429.1 |
| 173 | 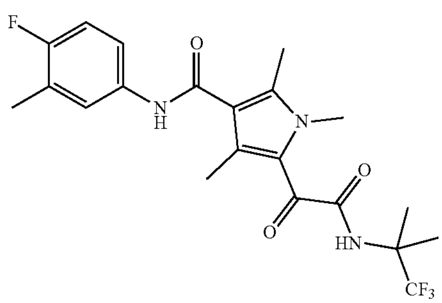 [SMILES: Cc1cc(NC(=O)c2c(C)c(C(=O)C(=O)NC(C)(C)C(F)(F)F)n(C)c2C)ccc1F] | N-(6-fluoro-5-methylpyridin-3-yl)-1,2,4-trimethyl-5-(2-oxo-2-((1,1,1-trifluoro-2-methylpropan-2-yl)amino)acetyl)-1H-pyrrole-3-carboxamide | 443.1 |
| 174 | 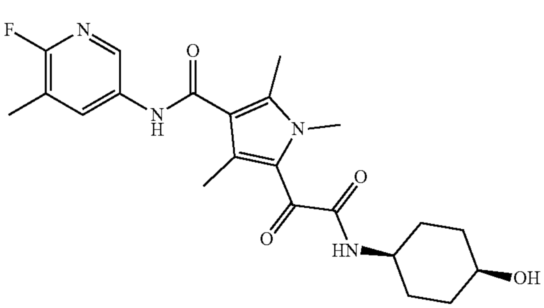 [SMILES: Cc1cc(NC(=O)c2c(C)c(C(=O)C(=O)N[C@H]3CC[C@@H](O)CC3)n(C)c2C)cnc1F] | N-(6-fluoro-5-methylpyridin-3-yl)-5-(2-(((1s,4s)-4-hydroxycyclohexyl)amino)-2-oxoacetyl)-1,2,4-trimethyl-1H-pyrrole-3-carboxamide | 431.1 |

TABLE 1-continued

Exemplary compounds

| Ex. | Structure | Chemical Name | ESI-MS (M + H)+ (m/z) |
|---|---|---|---|
| 175 | 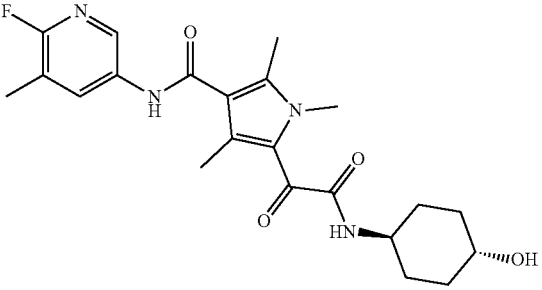 [SMILES: Cc1cc(NC(=O)c2c(C)c(C(=O)C(=O)N[C@H]3CC[C@H](O)CC3)n(C)c2C)cnc1F] | N-(6-fluoro-5-methylpyridin-3-yl)-5-(2-(((1r,4r)-4-hydroxycyclohexyl)amino)-2-oxoacetyl)-1,2,4-trimethyl-1H-pyrrole-3-carboxamide | 431.1 |
| 176 | 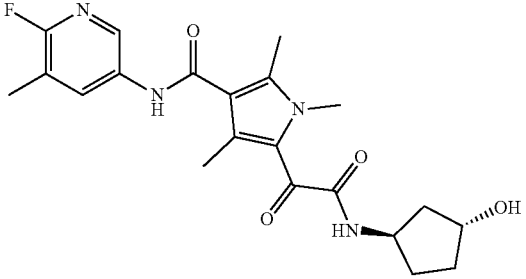 [SMILES: Cc1cc(NC(=O)c2c(C)c(C(=O)C(=O)N[C@@H]3CC[C@@H](O)C3)n(C)c2C)cnc1F] | N-(6-fluoro-5-methylpyridin-3-yl)-5-(2-(((1R,3R)-3-hydroxycyclopentyl)amino)-2-oxoacetyl)-1,2,4-trimethyl-1H-pyrrole-3-carboxamide | 417.1 |
| 177 | 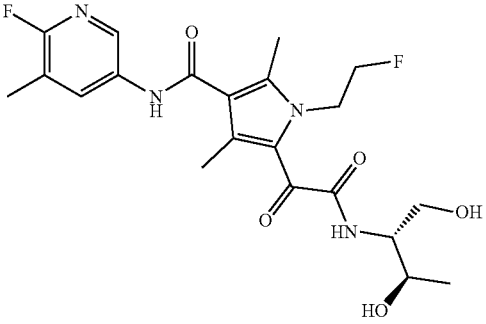 [SMILES: Cc1cc(NC(=O)c2c(C)c(C(=O)C(=O)N[C@H](CO)[C@@H](C)O)n(CCF)c2C)cnc1F] | 5-(2-(((2R,3R)-1,3-dihydroxybutan-2-yl)amino)-2-oxoacetyl)-N-(4-fluoro-3-methylphenyl)-1-(2-fluoroethyl)-2,4-dimethyl-1H-pyrrole-3-carboxamide | 452 |
| 178 | 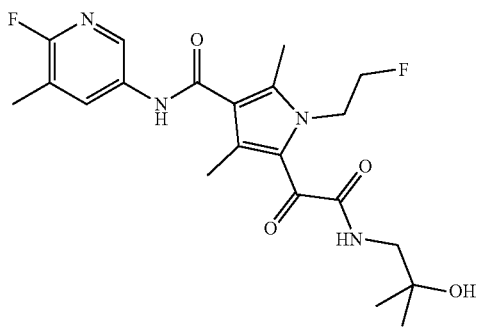 [SMILES: Cc1cc(NC(=O)c2c(C)c(C(=O)C(=O)NCC(C)(C)O)n(CCF)c2C)cnc1F] | N-(4-fluoro-3-methylphenyl)-1-(2-fluoroethyl)-5-(2-((2-hydroxy-2-methylpropyl)amino)-2-oxoacetyl)-2,4-dimethyl-1H-pyrrole-3-carboxamide | 436 |

TABLE 1-continued

Exemplary compounds

| Ex. | Structure | Chemical Name | ESI-MS (M + H)+ (m/z) |
|---|---|---|---|
| 179 | 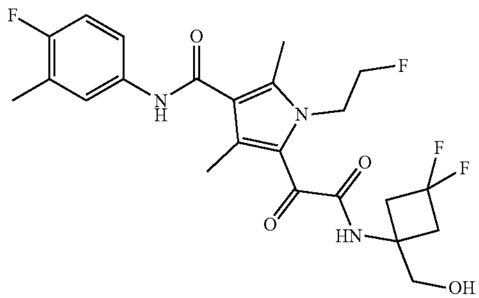 [SMILES: Cc1cc(NC(=O)c2c(C)c(C(=O)C(=O)NC3(CO)CC(F)(F)C3)n(CCF)c2C)ccc1F] | 5-(2-((3,3-difluoro-1-(hydroxymethyl)cyclobutyl)amino)-2-oxoacetyl)-N-(4-fluoro-3-methylphenyl)-1-(2-fluoroethyl)-2,4-dimethyl-1H-pyrrole-3-carboxamide | 484 |
| 180 | 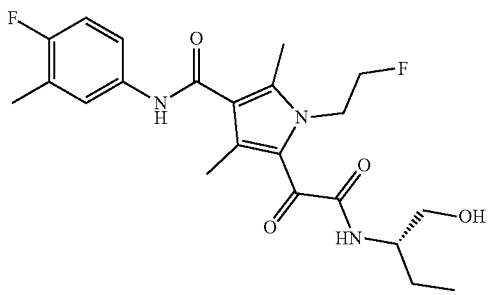 [SMILES: CC[C@@H](CO)NC(=O)C(=O)c1c(C)c(C(=O)Nc2ccc(F)c(C)c2)c(C)n1CCF] | (S)-N-(4-fluoro-3-methylphenyl)-1-(2-fluoroethyl)-5-(2-((1-hydroxybutan-2-yl)amino)-2-oxoacetyl)-2,4-dimethyl-1H-pyrrole-3-carboxamide | 436 |
| 181 | 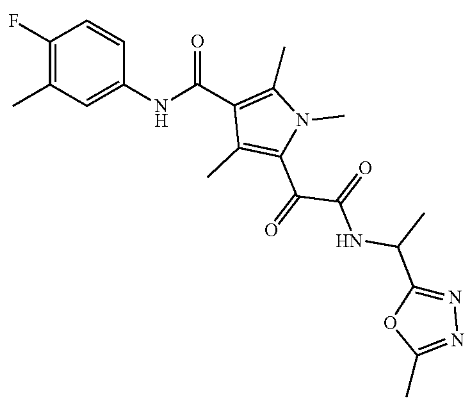 [SMILES: Cc1nnc(C(C)NC(=O)C(=O)c2c(C)c(C(=O)Nc3ccc(F)c(C)c3)c(C)n2C)o1] | N-(4-fluoro-3-methylphenyl)-1,2,4-trimethyl-5-(2-((1-(5-methyl-1,3,4-oxadiazol-2-yl)ethyl)amino)-2-oxoacetyl)-1H-pyrrole-3-carboxamide | 442 |
| 182 | 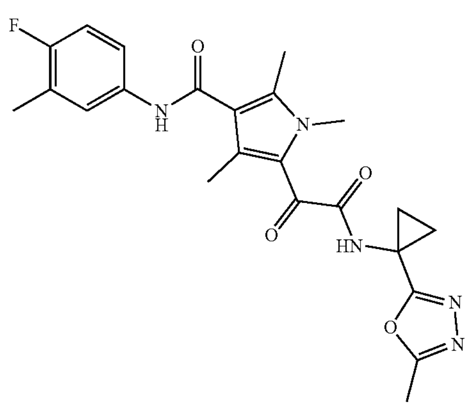 [SMILES: Cc1nnc(C2(NC(=O)C(=O)c3c(C)c(C(=O)Nc4ccc(F)c(C)c4)c(C)n3C)CC2)o1] | N-(4-fluoro-3-methylphenyl)-1,2,4-trimethyl-5-(2-((1-(5-methyl-1,3,4-oxadiazol-2-yl)cyclopropyl)amino)-2-oxoacetyl)-1H-pyrrole-3-carboxamide | 454 |

TABLE 1-continued

Exemplary compounds

| Ex. | Structure | Chemical Name | ESI-MS (M + H)+ (m/z) |
|---|---|---|---|
| 183 | 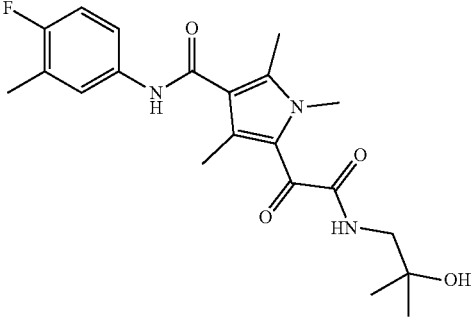 [SMILES: Cc1cc(NC(=O)c2c(C)c(C(=O)C(=O)NCC(C)(C)O)n(C)c2C)ccc1F] | N-(6-fluoro-5-methylpyridin-3-yl)-5-(2-((2-hydroxy-2-methylpropyl)amino)-2-oxoacetyl)-1,2,4-trimethyl-1H-pyrrole-3-carboxamide | 405 |
| 184 | 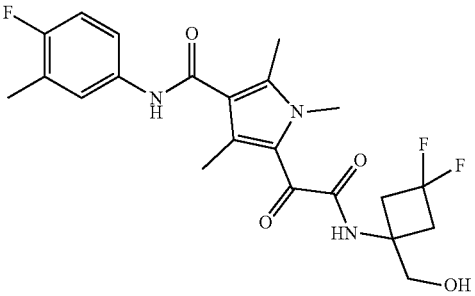 [SMILES: Cc1cc(NC(=O)c2c(C)c(C(=O)C(=O)NC3(CO)CC(F)(F)C3)n(C)c2C)ccc1F] | 5-(2-((3,3-difluoro-1-(hydroxymethyl)cyclobutyl)amino)-2-oxoacetyl)-N-(6-fluoro-5-methylpyridin-3-yl)-1,2,4-trimethyl-1H-pyrrole-3-carboxamide | 453 |
| 185 | 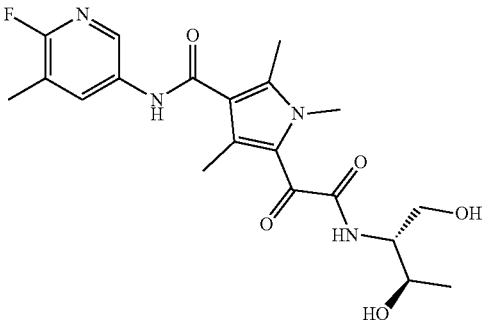 [SMILES: Cc1cc(NC(=O)c2c(C)c(C(=O)C(=O)N[C@H](CO)[C@@H](C)O)n(C)c2C)cnc1F] | 5-(2-(((2R,3R)-1,3-dihydroxybutan-2-yl)amino)-2-oxoacetyl)-N-(6-fluoro-5-methylpyridin-3-yl)-1,2,4-trimethyl-1H-pyrrole-3-carboxamide | 421 |
| 186 | 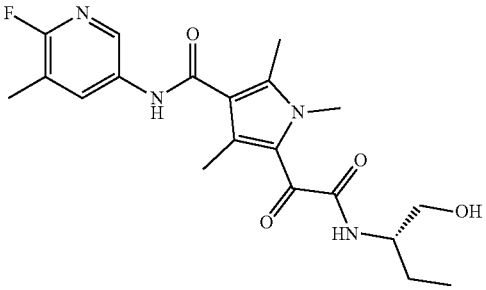 [SMILES: CC[C@@H](CO)NC(=O)C(=O)c1c(C)c(C(=O)Nc2cnc(F)c(C)c2)c(C)n1C] | (S)-N-(6-fluoro-5-methylpyridin-3-yl)-5-(2-((1-hydroxybutan-2-yl)amino)-2-oxoacetyl)-1,2,4-trimethyl-1H-pyrrole-3-carboxamide | 405 |

TABLE 1-continued

Exemplary compounds

| Ex. | Structure | Chemical Name | ESI-MS (M + H)+ (m/z) |
|---|---|---|---|
| 187 | 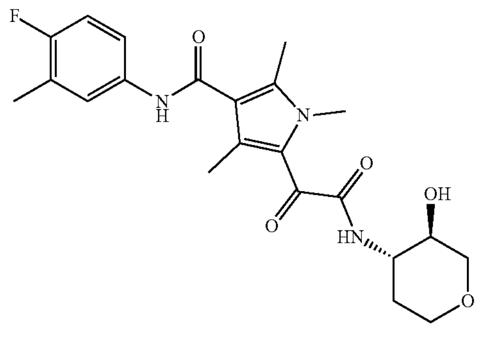 [SMILES: Cc1cc(NC(=O)c2c(C)c(C(=O)C(=O)N[C@H]3CCOC[C@@H]3O)n(C)c2C)ccc1F] | N-(4-fluoro-3-methylphenyl)-5-(2-(((3R,4S)-3-hydroxytetrahydro-2H-pyran-4-yl)amino)-2-oxoacetyl)-1,2,4-trimethyl-1H-pyrrole-3-carboxamide | 432.2 |
| 188 | 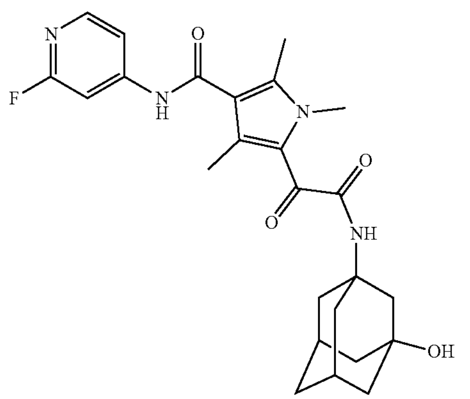 [SMILES: Cc1c(C(=O)Nc2ccnc(F)c2)c(C)n(C)c1C(=O)C(=O)NC12CC3CC(CC(O)(C3)C1)C2] | N-(2-fluoropyridin-4-yl)-5-(2-(((1r,3s,5R,7S)-3-hydroxyadamantan-1-yl)amino)-2-oxoacetyl)-1,2,4-trimethyl-1H-pyrrole-3-carboxamide | 469.2 |
| 189 | 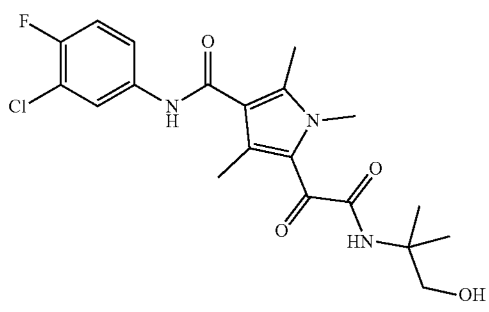 [SMILES: Cc1c(C(=O)Nc2ccc(F)c(Cl)c2)c(C)n(C)c1C(=O)C(=O)NC(C)(C)CO] | N-(3-chloro-4-fluorophenyl)-5-(2-((1-hydroxy-2-methylpropan-2-yl)amino)-2-oxoacetyl)-1,2,4-trimethyl-1H-pyrrole-3-carboxamide | 424.1 |
| 190 | 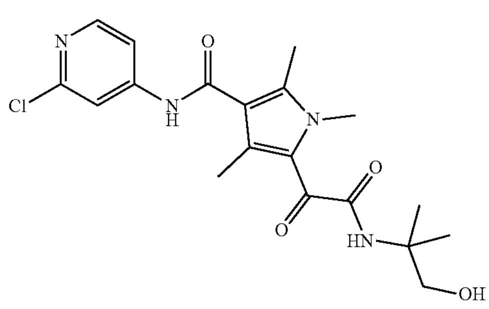 [SMILES: Cc1c(C(=O)Nc2ccnc(Cl)c2)c(C)n(C)c1C(=O)C(=O)NC(C)(C)CO] | N-(2-chloropyridin-4-yl)-5-(2-((1-hydroxy-2-methylpropan-2-yl)amino)-2-oxoacetyl)-1,2,4-trimethyl-1H-pyrrole-3-carboxamide | 407.1 |

TABLE 1-continued

Exemplary compounds

| Ex. | Structure | Chemical Name | ESI-MS (M + H)+ (m/z) |
|---|---|---|---|
| 191 | 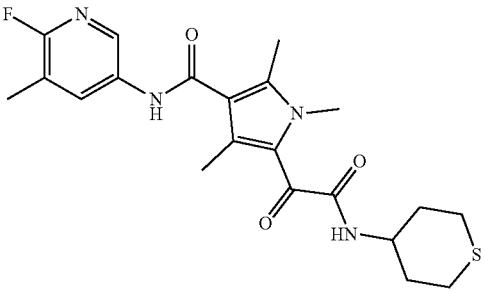 [SMILES: Cc1cc(NC(=O)c2c(C)c(C(=O)C(=O)NC3CCSCC3)n(C)c2C)cnc1F] | N-(6-fluoro-5-methylpyridin-3-yl)-1,2,4-trimethyl-5-(2-oxo-2-((tetrahydro-2H-thiopyran-4-yl)amino)acetyl)-1H-pyrrole-3-carboxamide | 433.1 |
| 192 | 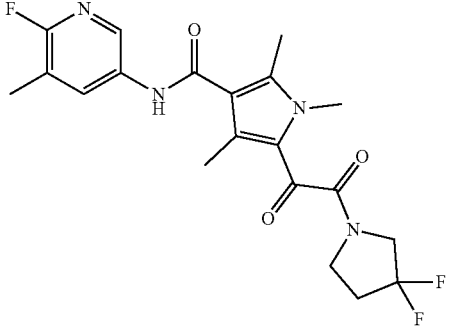 [SMILES: Cc1cc(NC(=O)c2c(C)c(C(=O)C(=O)N3CCC(F)(F)C3)n(C)c2C)cnc1F] | 5-(2-(3,3-difluoropyrrolidin-1-yl)-2-oxoacetyl)-N-(6-fluoro-5-methylpyridin-3-yl)-1,2,4-trimethyl-1H-pyrrole-3-carboxamide | 423.1 |
| 193 | 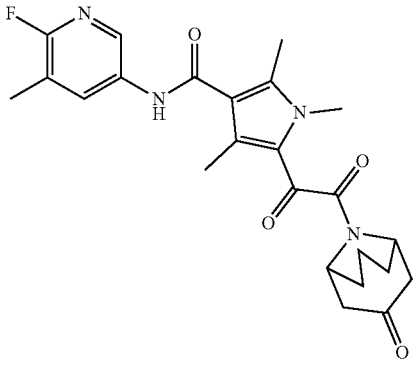 [SMILES: Cc1cc(NC(=O)c2c(C)c(C(=O)C(=O)N3C4CCCC3CC(=O)C4)n(C)c2C)cnc1F] | N-(6-fluoro-5-methylpyridin-3-yl)-1,2,4-trimethyl-5-(2-oxo-2-(3-oxo-9-azabicyclo[3.3.1]nonan-9-yl)acetyl)-1H-pyrrole-3-carboxamide | 455.1 |
| 194 | 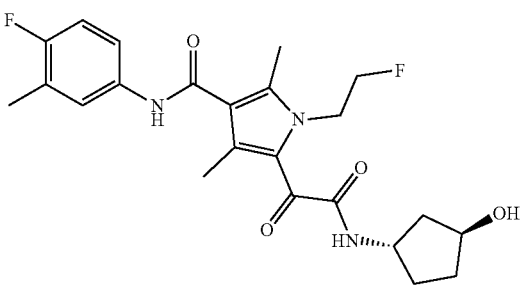 [SMILES: Cc1cc(NC(=O)c2c(C)c(C(=O)C(=O)N[C@H]3CC[C@H](O)C3)n(CCF)c2C)ccc1F] | N-(4-fluoro-3-methylphenyl)-1-(2-fluoroethyl)-5-(2-(((1S,3S)-3-hydroxycyclopentyl)amino)-2-oxoacetyl)-2,4-dimethyl-1H-pyrrole-3-carboxamide | 448.2 |

TABLE 1-continued

Exemplary compounds

| Ex. | Structure | Chemical Name | ESI-MS (M + H)+ (m/z) |
|---|---|---|---|
| 195 | 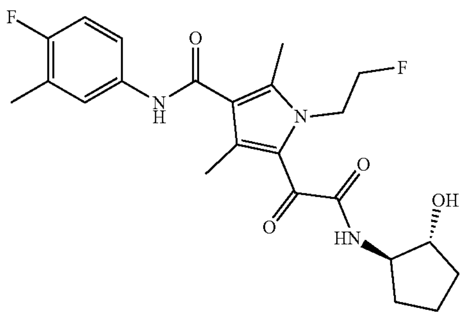 [SMILES: Cc1cc(NC(=O)c2c(C)c(C(=O)C(=O)N[C@@H]3CCC[C@H]3O)n(CCF)c2C)ccc1F] | N-(4-fluoro-3-methylphenyl)-1-(2-fluoroethyl)-5-(2-(((1R,2R)-2-hydroxycyclopentyl)amino)-2-oxoacetyl)-2,4-dimethyl-1H-pyrrole-3-carboxamide | 448.2 |
| 196 | 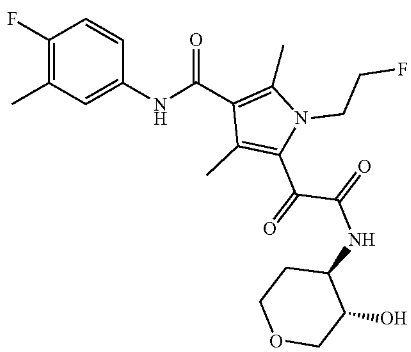 [SMILES: Cc1cc(NC(=O)c2c(C)c(C(=O)C(=O)N[C@@H]3CCOC[C@H]3O)n(CCF)c2C)ccc1F] | N-(4-fluoro-3-methylphenyl)-1-(2-fluoroethyl)-5-(2-(((3S,4R)-3-hydroxytetrahydro-2H-pyran-4-yl)amino)-2-oxoacetyl)-2,4-dimethyl-1H-pyrrole-3-carboxamide | 464.1 |
| 197 | 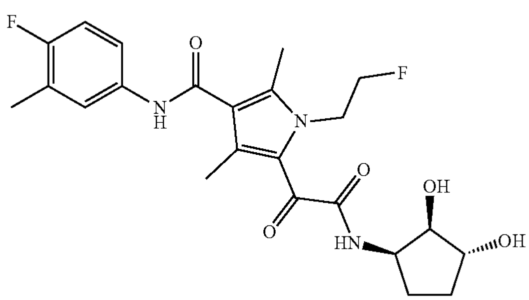 [SMILES: Cc1cc(NC(=O)c2c(C)c(C(=O)C(=O)N[C@@H]3CC[C@@H](O)[C@@H]3O)n(CCF)c2C)ccc1F] | 5-(2-(((1R,2R,3R)-2,3-dihydroxycyclopentyl)amino)-2-oxoacetyl)-N-(4-fluoro-3-methylphenyl)-1-(2-fluoroethyl)-2,4-dimethyl-1H-pyrrole-3-carboxamide | 464.2 |
| 198 | 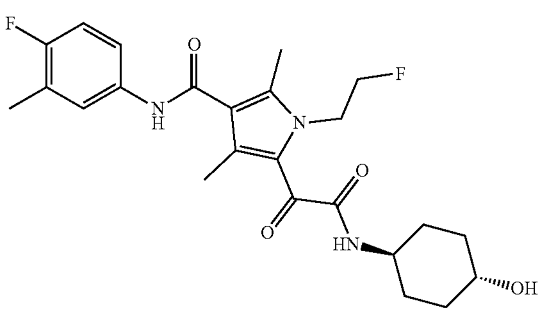 [SMILES: Cc1cc(NC(=O)c2c(C)c(C(=O)C(=O)N[C@H]3CC[C@H](O)CC3)n(CCF)c2C)ccc1F] | N-(4-fluoro-3-methylphenyl)-1-(2-fluoroethyl)-5-(2-(((1r,4r)-4-hydroxycyclohexyl)amino)-2-oxoacetyl)-2,4-dimethyl-1H-pyrrole-3-carboxamide | 462.2 |

TABLE 1-continued

Exemplary compounds

| Ex. | Structure | Chemical Name | ESI-MS (M + H)+ (m/z) |
|---|---|---|---|
| 199 | 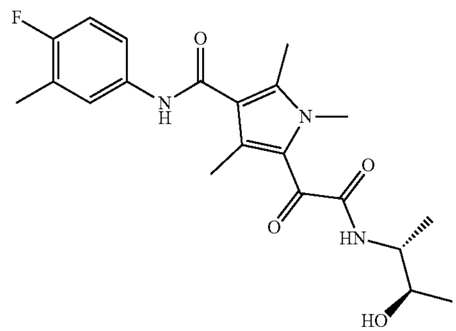 [SMILES: Cc1cc(NC(=O)c2c(C)c(C(=O)C(=O)N[C@H](C)[C@@H](C)O)n(C)c2C)ccc1F] | N-(4-fluoro-3-methylphenyl)-5-(2-(((2R,3R)-3-hydroxybutan-2-yl)amino)-2-oxoacetyl)-1,2,4-trimethyl-1H-pyrrole-3-carboxamide | 404 |
| 200 | 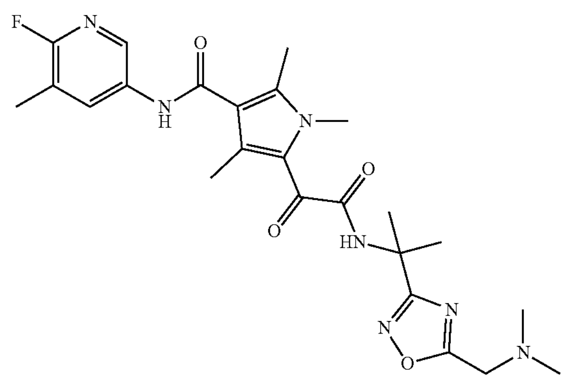 [SMILES: Cc1cc(NC(=O)c2c(C)c(C(=O)C(=O)NC(C)(C)c3noc(CN(C)C)n3)n(C)c2C)cnc1F] | 5-(2-((2-(5-((dimethylamino)methyl)-1,2,4-oxadiazol-3-yl)propan-2-yl)amino)-2-oxoacetyl)-N-(6-fluoro-5-methylpyridin-3-yl)-1,2,4-trimethyl-1H-pyrrole-3-carboxamide | 501 |
| 201 | 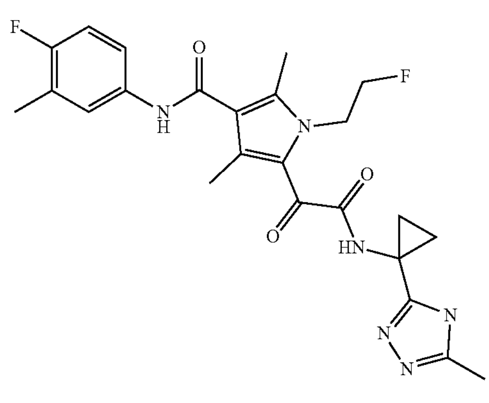 [SMILES: Cc1nnc(C2(NC(=O)C(=O)c3c(C)c(C(=O)Nc4ccc(F)c(C)c4)c(C)n3CCF)CC2)[nH]1] | N-(4-fluoro-3-methylphenyl)-1-(2-fluoroethyl)-2,4-dimethyl-5-(2-((1-(5-methyl-1,3,4-oxadiazol-2-yl)cyclopropyl)amino)-2-oxoacetyl)-1H-pyrrole-3-carboxamide | 486 |

TABLE 1-continued

Exemplary compounds

| Ex. | Structure | Chemical Name | ESI-MS (M + H)+ (m/z) |
|---|---|---|---|
| 202 | 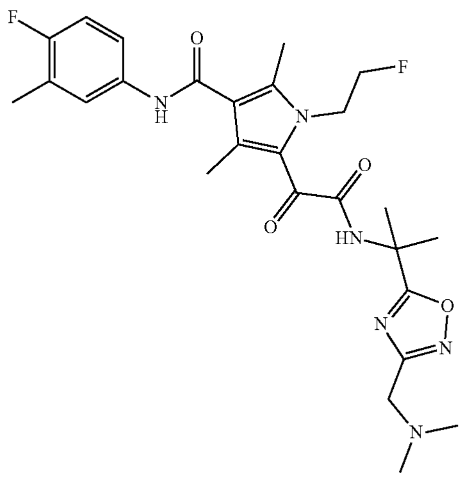 [SMILES: Cc1cc(NC(=O)c2c(C)c(C(=O)C(=O)NC(C)(C)c3nc(CN(C)C)no3)n(CCF)c2C)ccc1F] | 5-(2-((2-(3-((dimethylamino)methyl)-1,2,4-oxadiazol-5-yl)propan-2-yl)amino)-2-oxoacetyl)-N-(4-fluoro-3-methylphenyl)-1-(2-fluoroethyl)-2,4-dimethyl-1H-pyrrole-3-carboxamide | 532 |
| 203 | 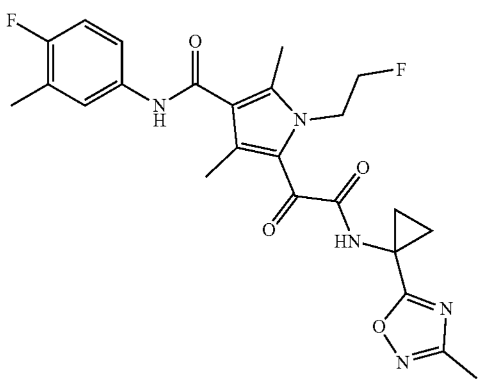 [SMILES: Cc1noc(C2(NC(=O)C(=O)c3c(C)c(C(=O)Nc4ccc(F)c(C)c4)c(C)n3CCF)CC2)n1] | N-(4-fluoro-3-methylphenyl)-1-(2-fluoroethyl)-2,4-dimethyl-5-(2-((1-(3-methyl-1,2,4-oxadiazol-5-yl)cyclopropyl)amino)-2-oxoacetyl)-1H-pyrrole-3-carboxamide | 486 |
| 204 | 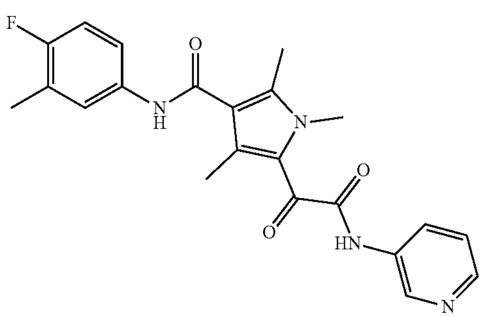 [SMILES: Cc1cc(NC(=O)c2c(C)c(C(=O)C(=O)Nc3cccnc3)n(C)c2C)ccc1F] | N-(4-fluoro-3-methylphenyl)-1,2,4-trimethyl-5-(2-oxo-2-(pyridin-3-ylamino)acetyl)-1H-pyrrole-3-carboxamide | 409 |
| 205 | 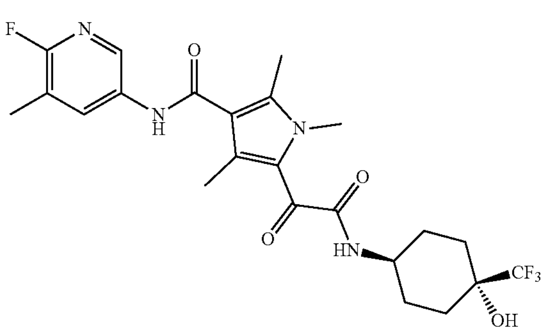 [SMILES: Cc1cc(NC(=O)c2c(C)c(C(=O)C(=O)N[C@H]3CC[C@@](O)(C(F)(F)F)CC3)n(C)c2C)cnc1F] | N-(6-fluoro-5-methylpyridin-3-yl)-5-(2-(((1r,4r)-4-hydroxy-4-(trifluoromethyl)cyclohexyl)amino)-2-oxoacetyl)-1,2,4-trimethyl-1H-pyrrole-3-carboxamide | 499.2 |

TABLE 1-continued

Exemplary compounds

| Ex. | Structure | Chemical Name | ESI-MS (M + H)+ (m/z) |
|---|---|---|---|
| 206 | 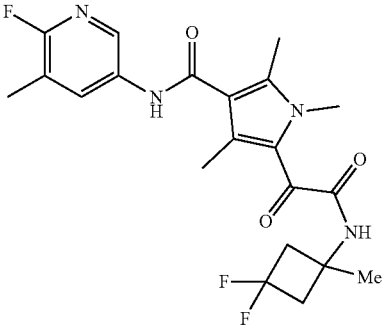 [SMILES: Cc1cc(NC(=O)c2c(C)c(C(=O)C(=O)NC3(C)CC(F)(F)C3)n(C)c2C)cnc1F] | 5-(2-((3,3-difluoro-1-methylcyclobutyl)amino)-2-oxoacetyl)-N-(6-fluoro-5-methylpyridin-3-yl)-1,2,4-trimethyl-1H-pyrrole-3-carboxamide | 437.1 |
| 207 | 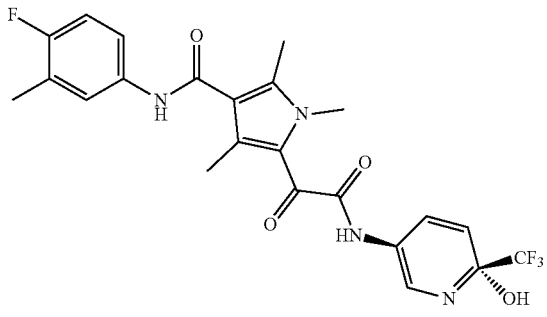 | N-(4-fluoro-3-methylphenyl)-5-(2-(((1r,4r)-4-hydroxy-4-(trifluoromethyl)cyclohexyl)amino)-2-oxoacetyl)-1,2,4-trimethyl-1H-pyrrole-3-carboxamide | 498.2 |
| 208 | 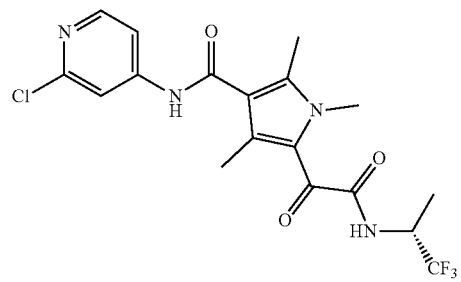 [SMILES: Cc1c(C(=O)Nc2ccnc(Cl)c2)c(C)n(C)c1C(=O)C(=O)N[C@H](C)C(F)(F)F] | (R)-N-(2-chloropyridin-4-yl)-1,2,4-trimethyl-5-(2-oxo-2-(((1,1,1-trifluoropropan-2-yl)amino)acetyl)-1H-pyrrole-3-carboxamide | 431.1 |
| 209 | 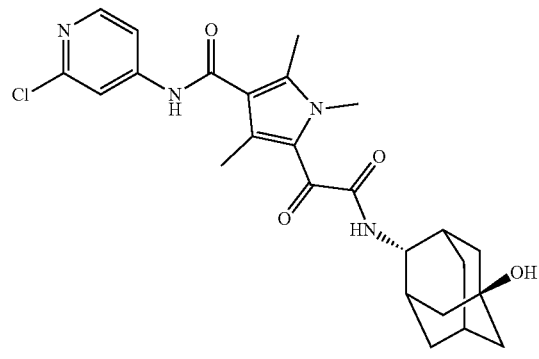 [SMILES: Cc1c(C(=O)Nc2ccnc(Cl)c2)c(C)n(C)c1C(=O)C(=O)N[C@H]1C2CC3CC1C[C@](O)(C3)C2] | N-(2-chloropyridin-4-yl)-5-(2-((((1R,2s,3S,5s,7s)-5-hydroxyadamantan-2-yl)amino)-2-oxoacetyl)-1,2,4-trimethyl-1H-pyrrole-3-carboxamide | 485.1 |

TABLE 1-continued

Exemplary compounds

| Ex. | Structure | Chemical Name | ESI-MS (M + H)+ (m/z) |
|---|---|---|---|
| 210 | 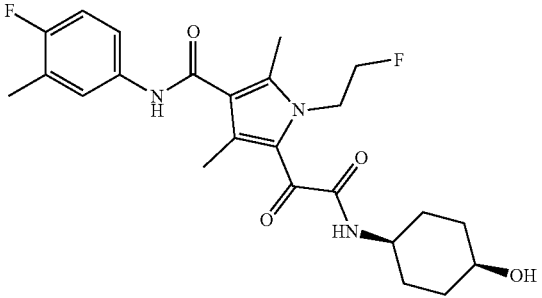 [SMILES: Cc1cc(NC(=O)c2c(C)c(C(=O)C(=O)N[C@H]3CC[C@@H](O)CC3)n(CCF)c2C)ccc1F] | N-(4-fluoro-3-methylphenyl)-1-(2-fluoroethyl)-5-(2-(((1s,4s)-4-hydroxycyclohexyl)amino)-2-oxoacetyl)-2,4-dimethyl-1H-pyrrole-3-carboxamide | 462.1 |
| 211 | 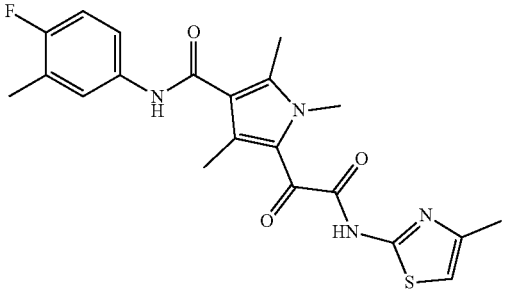 [SMILES: Cc1csc(NC(=O)C(=O)c2c(C)c(C(=O)Nc3ccc(F)c(C)c3)c(C)n2C)n1] | N-(4-fluoro-3-methylphenyl)-1,2,4-trimethyl-5-(2-((4-methylthiazol-2-yl)amino)-2-oxoacetyl)-1H-pyrrole-3-carboxamide | 429 |
| 212 | 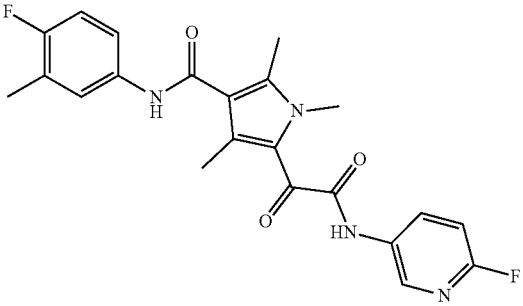 [SMILES: Cc1cc(NC(=O)c2c(C)c(C(=O)C(=O)Nc3ccc(F)nc3)n(C)c2C)ccc1F] | N-(4-fluoro-3-methylphenyl)-5-(2-((6-fluoropyridin-3-yl)amino)-2-oxoacetyl)-1,2,4-trimethyl-1H-pyrrole-3-carboxamide | 427 |
| 213 | 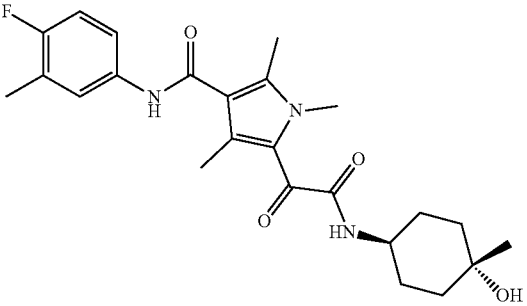 [SMILES: Cc1cc(NC(=O)c2c(C)c(C(=O)C(=O)N[C@H]3CC[C@](C)(O)CC3)n(C)c2C)ccc1F] | N-(4-fluoro-3-methylphenyl)-5-(2-(((1r,4r)-4-hydroxy-4-methylcyclohexyl)amino)-2-oxoacetyl)-1,2,4-trimethyl-1H-pyrrole-3-carboxamide | 444.2 |

TABLE 1-continued

Exemplary compounds

| Ex. | Structure | Chemical Name | ESI-MS (M + H)+ (m/z) |
|---|---|---|---|
| 214 | 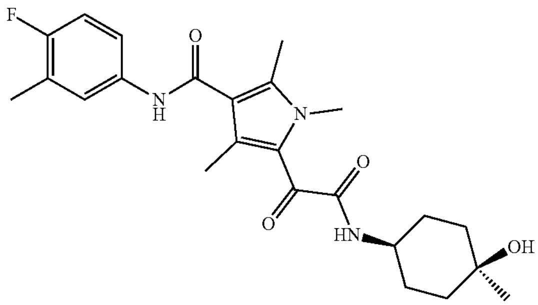 [SMILES: Cc1cc(NC(=O)c2c(C)c(C(=O)C(=O)N[C@H]3CC[C@@](C)(O)CC3)n(C)c2C)ccc1F] | N-(4-fluoro-3-methylphenyl)-5-(2-(((1s,4s)-4-hydroxy-4-methylcyclohexyl)amino)-2-oxoacetyl)-1,2,4-trimethyl-1H-pyrrole-3-carboxamide | 445 |
| 215 | 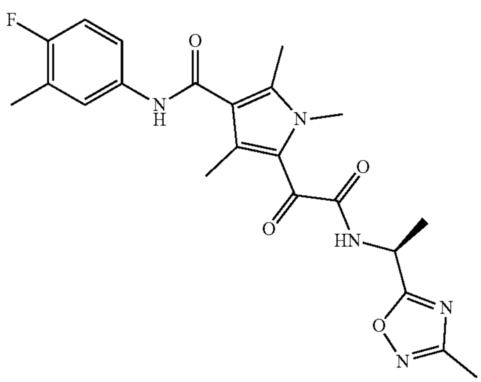 [SMILES: Cc1noc([C@H](C)NC(=O)C(=O)c2c(C)c(C(=O)Nc3ccc(F)c(C)c3)c(C)n2C)n1] | (S)-N-(4-fluoro-3-methylphenyl)-1,2,4-trimethyl-5-(2-((1-(3-methyl-1,2,4-oxadiazol-5-yl)ethyl)amino)-2-oxoacetyl)-1H-pyrrole-3-carboxamide | 442 |
| 216 | 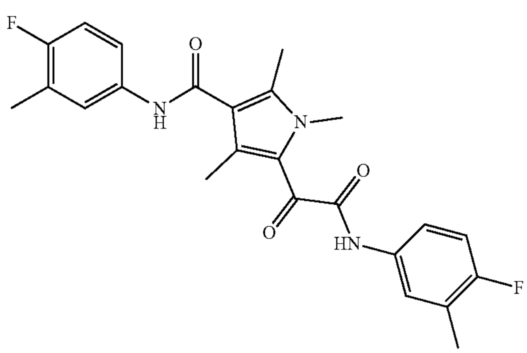 [SMILES: Cc1cc(NC(=O)C(=O)c2c(C)c(C(=O)Nc3ccc(F)c(C)c3)c(C)n2C)ccc1F] | N-(4-fluoro-3-methylphenyl)-5-(2-((4-fluoro-3-methylphenyl)amino)-2-oxoacetyl)-1,2,4-trimethyl-1H-pyrrole-3-carboxamide | 440 |
| 217 | 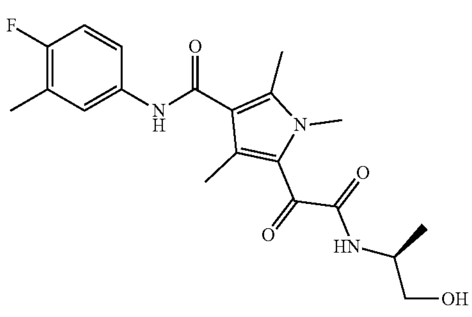 [SMILES: Cc1cc(NC(=O)c2c(C)c(C(=O)C(=O)N[C@@H](C)CO)n(C)c2C)ccc1F] | (S)-N-(4-fluoro-3-methylphenyl)-5-(2-((1-hydroxypropan-2-yl)amino)-2-oxoacetyl)-1,2,4-trimethyl-1H-pyrrole-3-carboxamide | 390 |

TABLE 1-continued

Exemplary compounds

| Ex. | Structure | Chemical Name | ESI-MS (M + H)+ (m/z) |
|---|---|---|---|
| 218 | 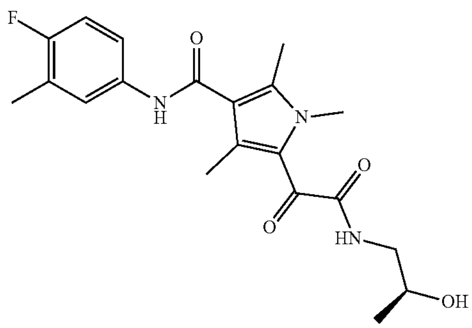 [SMILES: Cc1cc(NC(=O)c2c(C)c(C(=O)C(=O)NC[C@H](C)O)n(C)c2C)ccc1F] | (S)-N-(4-fluoro-3-methylphenyl)-5-(2-((2-hydroxypropyl)amino)-2-oxoacetyl)-1,2,4-trimethyl-1H-pyrrole-3-carboxamide | 390 |
| 219 | 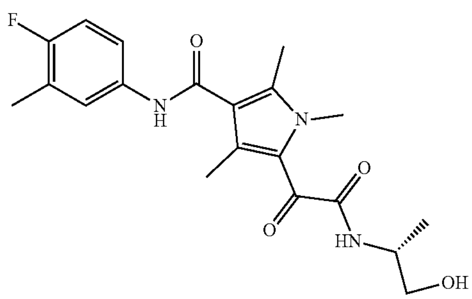 [SMILES: Cc1cc(NC(=O)c2c(C)c(C(=O)C(=O)N[C@H](C)CO)n(C)c2C)ccc1F] | (R)-N-(4-fluoro-3-methylphenyl)-5-(2-(((1-hydroxypropan-2-yl)amino)-2-oxoacetyl)-1,2,4-trimethyl-1H-pyrrole-3-carboxamide | 390 |
| 220 | 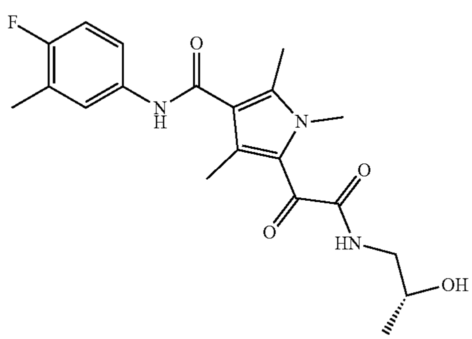 [SMILES: Cc1cc(NC(=O)c2c(C)c(C(=O)C(=O)NC[C@@H](C)O)n(C)c2C)ccc1F] | (R)-N-(4-fluoro-3-methylphenyl)-5-(2-((2-hydroxypropyl)amino)-2-oxoacetyl)-1,2,4-trimethyl-1H-pyrrole-3-carboxamide | 390 |
| 221 | 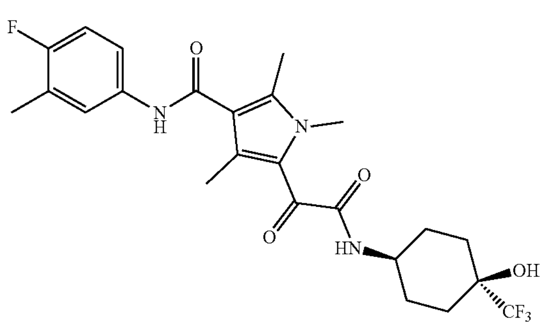 [SMILES: Cc1cc(NC(=O)c2c(C)c(C(=O)C(=O)N[C@H]3CC[C@](O)(C(F)(F)F)CC3)n(C)c2C)ccc1F] | N-(4-fluoro-3-methylphenyl)-5-(2-(((1s,4s)-4-hydroxy-4-(trifluoromethyl)cyclohexyl)amino)-2-oxoacetyl)-1,2,4-trimethyl-1H-pyrrole-3-carboxamide | 498.2 |

TABLE 1-continued

Exemplary compounds

| Ex. | Structure | Chemical Name | ESI-MS (M + H)+ (m/z) |
|---|---|---|---|
| 222 | 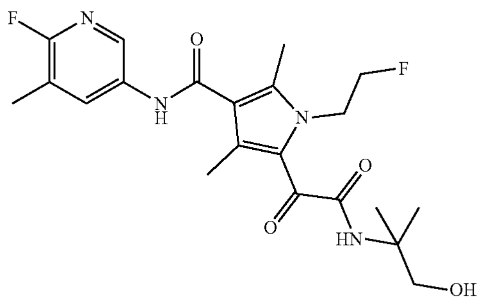 [SMILES: Cc1cc(NC(=O)c2c(C)c(C(=O)C(=O)NC(C)(C)CO)n(CCF)c2C)cnc1F] | N-(6-fluoro-5-methylpyridin-3-yl)-1-(2-fluoroethyl)-5-(2-((1-hydroxy-2-methylpropan-2-yl)amino)-2-oxoacetyl)-2,4-dimethyl-1H-pyrrole-3-carboxamide | 437.2 |
| 223 | 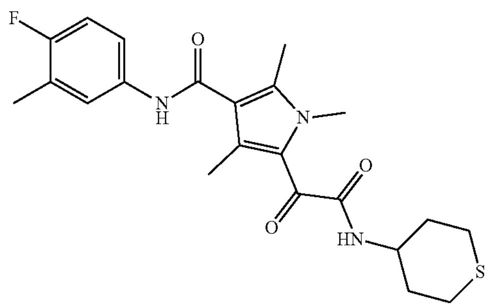 [SMILES: Cc1cc(NC(=O)c2c(C)c(C(=O)C(=O)NC3CCSCC3)n(C)c2C)ccc1F] | N-(4-fluoro-3-methylphenyl)-1,2,4-trimethyl-5-(2-oxo-2-((tetrahydro-2H-thiopyran-4-yl)amino)acetyl)-1H-pyrrole-3-carboxamide | 432.1 |
| 224 | 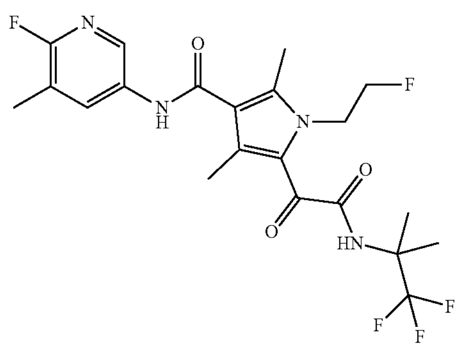 [SMILES: Cc1cc(NC(=O)c2c(C)c(C(=O)C(=O)NC(C)(C)C(F)(F)F)n(CCF)c2C)cnc1F] | N-(6-fluoro-5-methylpyridin-3-yl)-1-(2-fluoroethyl)-2,4-dimethyl-5-(2-oxo-2-((1,1,1-trifluoro-2-methylpropan-2-yl)amino)acetyl)-1H-pyrrole-3-carboxamide | 475.2 |
| 225 | 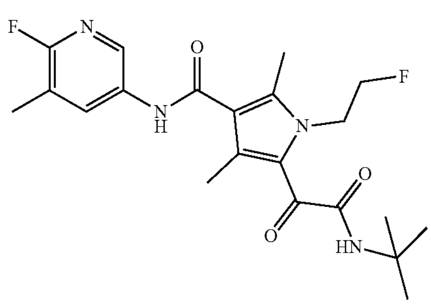 [SMILES: Cc1cc(NC(=O)c2c(C)c(C(=O)C(=O)NC(C)(C)C)n(CCF)c2C)cnc1F] | 5-(2-(tert-butylamino)-2-oxoacetyl)-N-(6-fluoro-5-methylpyridin-3-yl)-1-(2-fluoroethyl)-2,4-dimethyl-1H-pyrrole-3-carboxamide | 421.2 |

TABLE 1-continued

Exemplary compounds

| Ex. | Structure | Chemical Name | ESI-MS (M + H)+ (m/z) |
|---|---|---|---|
| 226 | 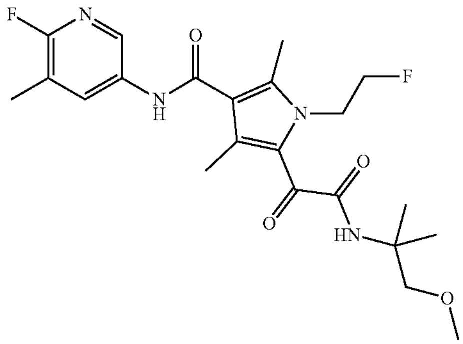 [SMILES: COCC(C)(C)NC(=O)C(=O)c1c(C)c(C(=O)Nc2cnc(F)c(C)c2)c(C)n1CCF] | N-(6-fluoro-5-methylpyridin-3-yl)-1-(2-fluoroethyl)-5-(2-((1-methoxy-2-methylpropan-2-yl)amino)-2-oxoacetyl)-2,4-dimethyl-1H-pyrrole-3-carboxamide | 451.3 |
| 227 | 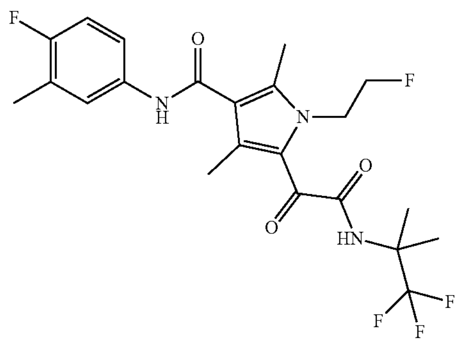 [SMILES: Cc1cc(NC(=O)c2c(C)c(C(=O)C(=O)NC(C)(C)C(F)(F)F)n(CCF)c2C)ccc1F] | N-(4-fluoro-3-methylphenyl)-1-(2-fluoroethyl)-2,4-dimethyl-5-(2-oxo-2-((1,1,1-trifluoro-2-methylpropan-2-yl)amino)acetyl)-1H-pyrrole-3-carboxamide | 474.2 |
| 228 | 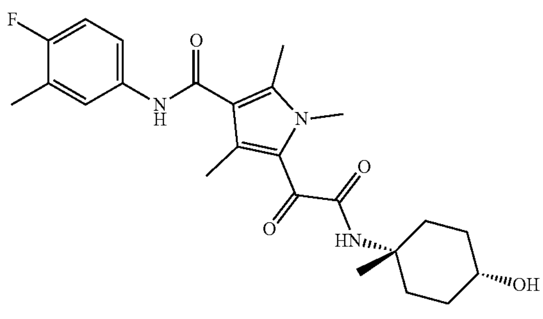 [SMILES: Cc1cc(NC(=O)c2c(C)c(C(=O)C(=O)N[C@]3(C)CC[C@H](O)CC3)n(C)c2C)ccc1F] | N-(4-fluoro-3-methylphenyl)-5-(2-(((1s,4s)-4-hydroxy-1-methylcyclohexyl)amino)-2-oxoacetyl)-1,2,4-trimethyl-1H-pyrrole-3-carboxamide | 444.2 |
| 229 | 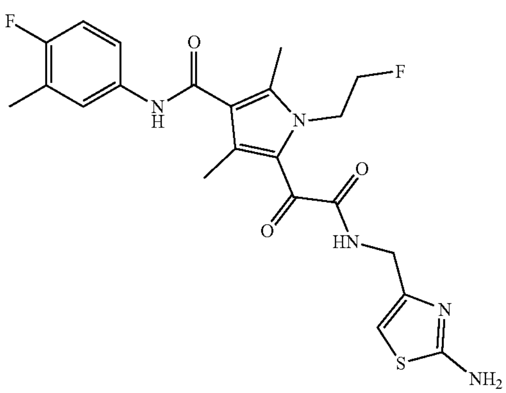 [SMILES: Cc1cc(NC(=O)c2c(C)c(C(=O)C(=O)NCc3csc(N)n3)n(CCF)c2C)ccc1F] | 5-(2-(((2-aminothiazol-4-yl)methyl)amino)-2-oxoacetyl)-N-(4-fluoro-3-methylphenyl)-1-(2-fluoroethyl)-2,4-dimethyl-1H-pyrrole-3-carboxamide | 476.2 |

TABLE 1-continued

Exemplary compounds

| Ex. | Structure | Chemical Name | ESI-MS (M + H)+ (m/z) |
|---|---|---|---|
| 230 | 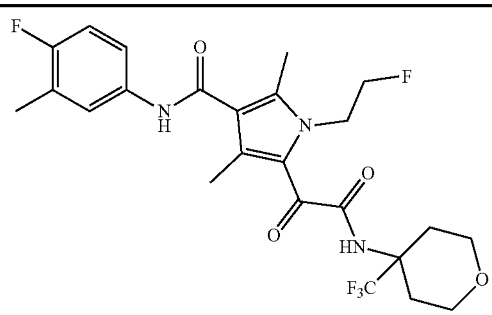 | N-(4-fluoro-3-methylphenyl)-1-(2-fluoroethyl)-2,4-dimethyl-5-(2-oxo-2-((4-(trifluoromethyl)tetrahydro-2H-pyran-4-yl)amino)acetyl)-1H-pyrrole-3-carboxamide | 516.1 |
| 231 | 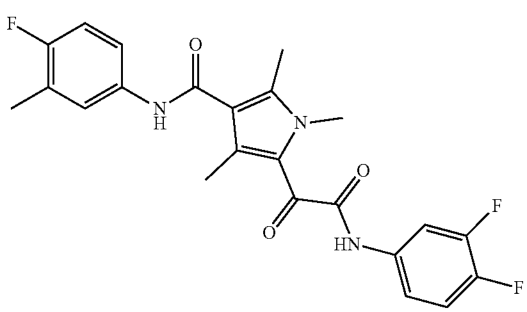 [SMILES: Cc1cc(NC(=O)c2c(C)c(C(=O)C(=O)Nc3ccc(F)c(F)c3)n(C)c2C)ccc1F] | 5-(2-((3,4-difluorophenyl)amino)-2-oxoacetyl)-N-(4-fluoro-3-methylphenyl)-1,2,4-trimethyl-1H-pyrrole-3-carboxamide | 444 |
| 232 | 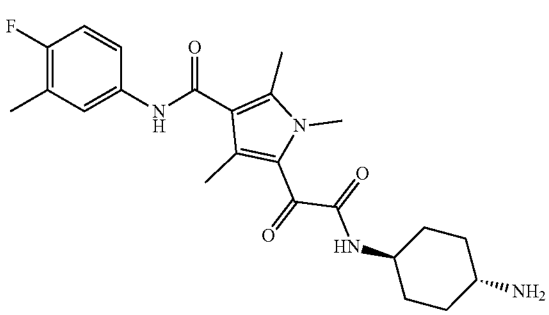 [SMILES: Cc1cc(NC(=O)c2c(C)c(C(=O)C(=O)N[C@H]3CC[C@H](N)CC3)n(C)c2C)ccc1F] | 5-(2-(((1r,4r)-4-aminocyclohexyl)amino)-2-oxoacetyl)-N-(4-fluoro-3-methylphenyl)-1,2,4-trimethyl-1H-pyrrole-3-carboxamide | 430 |
| 233 | 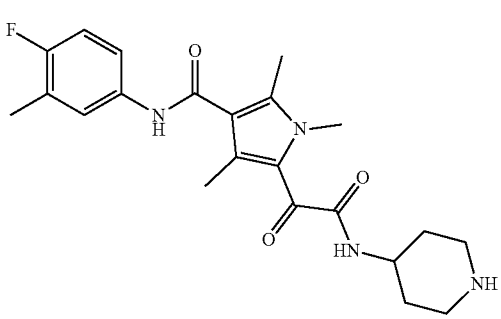 [SMILES: Cc1cc(NC(=O)c2c(C)c(C(=O)C(=O)NC3CCNCC3)n(C)c2C)ccc1F] | N-(4-fluoro-3-methylphenyl)-1,2,4-trimethyl-5-(2-oxo-2-(piperidin-4-ylamino)acetyl)-1H-pyrrole-3-carboxamide | 415 |
| 234 | 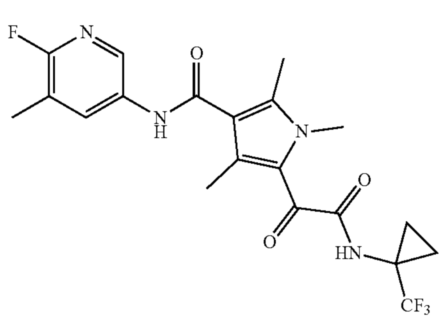 [SMILES: Cc1cc(NC(=O)c2c(C)c(C(=O)C(=O)NC3(C(F)(F)F)CC3)n(C)c2C)cnc1F] | N-(6-fluoro-5-methylpyridin-3-yl)-1,2,4-trimethyl-5-(2-oxo-2-((1-(trifluoromethyl)cyclopropyl)amino)acetyl)-1H-pyrrole-3-carboxamide | 441 |

TABLE 1-continued

Exemplary compounds

| Ex. | Structure | Chemical Name | ESI-MS (M + H)+ (m/z) |
|---|---|---|---|
| 235 | 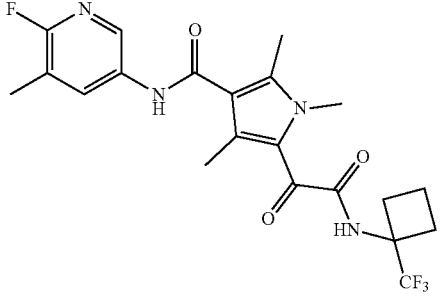 [SMILES: Cc1cc(NC(=O)c2c(C)c(C(=O)C(=O)NC3(C(F)(F)F)CCC3)n(C)c2C)cnc1F] | N-(6-fluoro-5-methylpyridin-3-yl)-1,2,4-trimethyl-5-(2-oxo-2-((1-(trifluoromethyl)cyclobutyl)amino)acetyl)-1H-pyrrole-3-carboxamide | 455 |
| 236 | 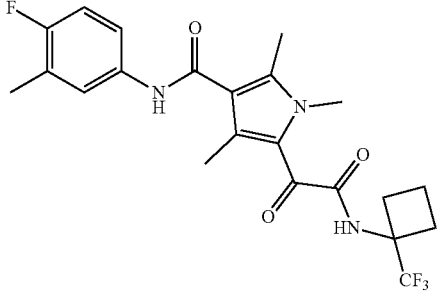 [SMILES: Cc1cc(NC(=O)c2c(C)c(C(=O)C(=O)NC3(C(F)(F)F)CCC3)n(C)c2C)ccc1F] | N-(4-fluoro-3-methylphenyl)-1,2,4-trimethyl-5-(2-oxo-2-((1-(trifluoromethyl)cyclobutyl)amino)acetyl)-1H-pyrrole-3-carboxamide | 454 |
| 237 | 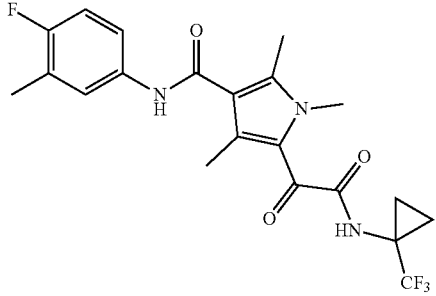 [SMILES: Cc1cc(NC(=O)c2c(C)c(C(=O)C(=O)NC3(C(F)(F)F)CC3)n(C)c2C)ccc1F] | N-(4-fluoro-3-methylphenyl)-1,2,4-trimethyl-5-(2-oxo-2-((1-(trifluoromethyl)cyclopropyl)amino)acetyl)-1H-pyrrole-3-carboxamide | 440 |
| 238 | 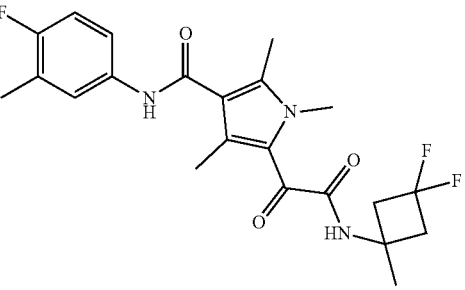 [SMILES: Cc1cc(NC(=O)c2c(C)c(C(=O)C(=O)NC3(C)CC(F)(F)C3)n(C)c2C)ccc1F] | 5-(2-((3,3-difluoro-1-methylcyclobutyl)amino)-2-oxoacetyl)-N-(4-fluoro-3-methylphenyl)-1,2,4-trimethyl-1H-pyrrole-3-carboxamide | 436 |

TABLE 1-continued

Exemplary compounds

| Ex. | Structure | Chemical Name | ESI-MS (M + H)+ (m/z) |
|---|---|---|---|
| 239 | 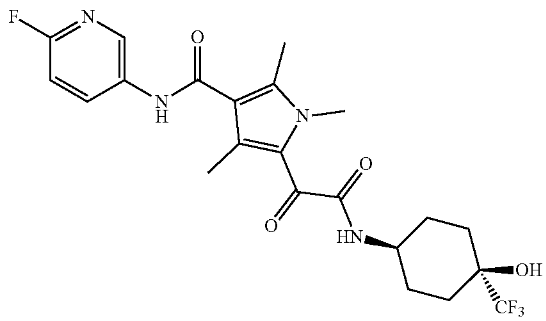 [SMILES: Cc1c(C(=O)Nc2ccc(F)nc2)c(C)n(C)c1C(=O)C(=O)N[C@H]1CC[C@](O)(C(F)(F)F)CC1] | N-(6-fluoropyridin-3-yl)-5-(2-(((1s,4s)-4-hydroxy-4-(trifluoromethyl)cyclohexyl)amino)-2-oxoacetyl)-1,2,4-trimethyl-1H-pyrrole-3-carboxamide | 485.1 |
| 240 | 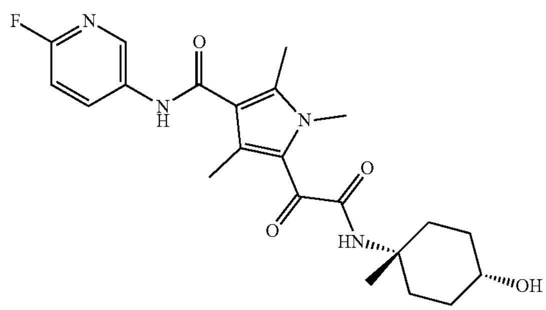 [SMILES: Cc1c(C(=O)Nc2ccc(F)nc2)c(C)n(C)c1C(=O)C(=O)N[C@]1(C)CC[C@H](O)CC1] | N-(6-fluoropyridin-3-yl)-5-(2-(((1s,4s)-4-hydroxy-1-methylcyclohexyl)amino)-2-oxoacetyl)-1,2,4-trimethyl-1H-pyrrole-3-carboxamide | 431.2 |
| 241 | 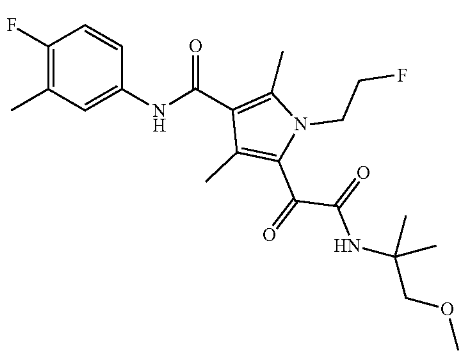 [SMILES: COCC(C)(C)NC(=O)C(=O)c1c(C)c(C(=O)Nc2ccc(F)c(C)c2)c(C)n1CCF] | N-(4-fluoro-3-methylphenyl)-1-(2-fluoroethyl)-5-(2-((1-methoxy-2-methylpropan-2-yl)amino)-2-oxoacetyl)-2,4-dimethyl-1H-pyrrole-3-carboxamide | 150.2 |
| 242 | 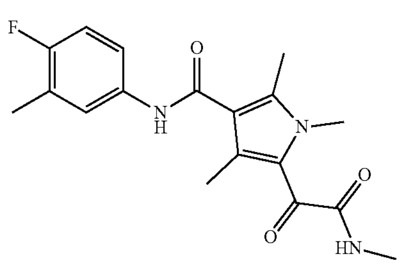 [SMILES: CNC(=O)C(=O)c1c(C)c(C(=O)Nc2ccc(F)c(C)c2)c(C)n1C] | N-(4-fluoro-3-methylphenyl)-1,2,4-trimethyl-5-(2-(methylamino)-2-oxoacetyl)-1H-pyrrole-3-carboxamide | 346 |

TABLE 1-continued

Exemplary compounds

| Ex. | Structure | Chemical Name | ESI-MS (M + H)+ (m/z) |
|---|---|---|---|
| 243 | 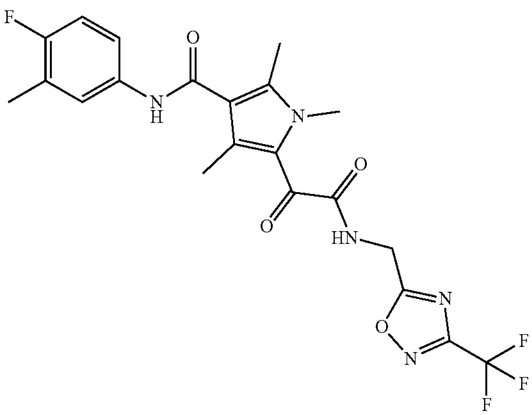 [SMILES: Cc1cc(NC(=O)c2c(C)c(C(=O)C(=O)NCc3nc(C(F)(F)F)no3)n(C)c2C)ccc1F] | N-(4-fluoro-3-methylphenyl)-1,2,4-trimethyl-5-(2-oxo-2-(((3-(trifluoromethyl)-1,2,4-oxadiazol-5-yl)methyl)amino)acetyl)-1H-pyrrole-3-carboxamide | 482 |
| 244 | 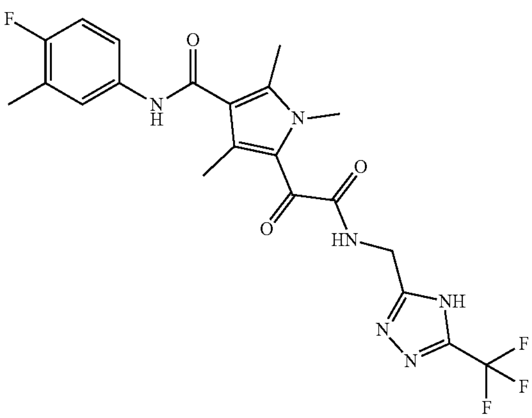 [SMILES: Cc1cc(NC(=O)c2c(C)c(C(=O)C(=O)NCc3nnc(C(F)(F)F)[nH]3)n(C)c2C)ccc1F] | N-(4-fluoro-3-methylphenyl)-1,2,4-trimethyl-5-(2-oxo-2-(((5-(trifluoromethyl)-4H-1,2,4-triazol-3-yl)methyl)amino)acetyl)-1H-pyrrole-3-carboxamide | 481 |
| 245 | 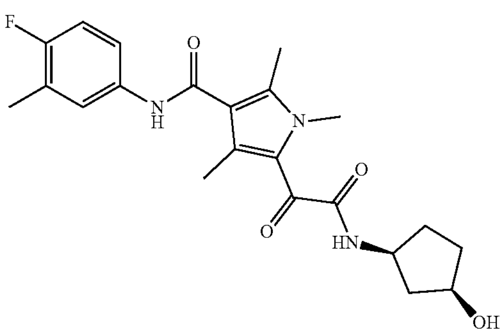 [SMILES: Cc1cc(NC(=O)c2c(C)c(C(=O)C(=O)N[C@H]3CC[C@@H](O)C3)n(C)c2C)ccc1F] | N-(4-fluoro-3-methylphenyl)-5-(2-(((1S,3R)-3-hydroxycyclopentyl)amino)-2-oxoacetyl)-1,2,4-trimethyl-1H-pyrrole-3-carboxamide | 416.1 |
| 246 | 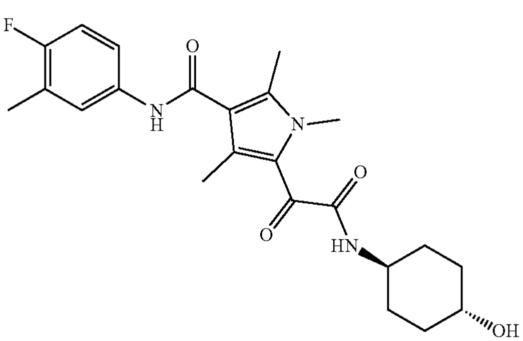 [SMILES: Cc1cc(NC(=O)c2c(C)c(C(=O)C(=O)N[C@H]3CC[C@H](O)CC3)n(C)c2C)ccc1F] | N-(4-fluoro-3-methylphenyl)-5-(2-(((1r,4r)-4-hydroxycyclohexyl)amino)-2-oxoacetyl)-1,2,4-trimethyl-1H-pyrrole-3-carboxamide | 430.2 |

TABLE 1-continued

Exemplary compounds

| Ex. | Structure | Chemical Name | ESI-MS (M + H)+ (m/z) |
|---|---|---|---|
| 247 | 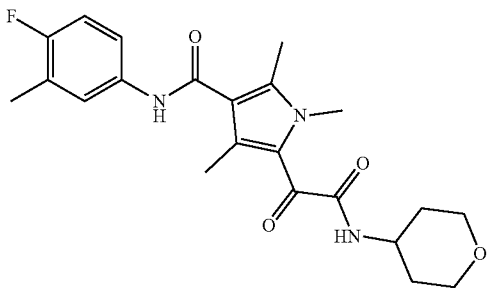 [SMILES: Cc1cc(NC(=O)c2c(C)c(C(=O)C(=O)NC3CCOCC3)n(C)c2C)ccc1F] | N-(4-fluoro-3-methylphenyl)-1,2,4-trimethyl-5-(2-oxo-2-((tetrahydro-2H-pyran-4-yl)amino)acetyl)-1H-pyrrole-3-carboxamide | 416.2 |
| 248 | 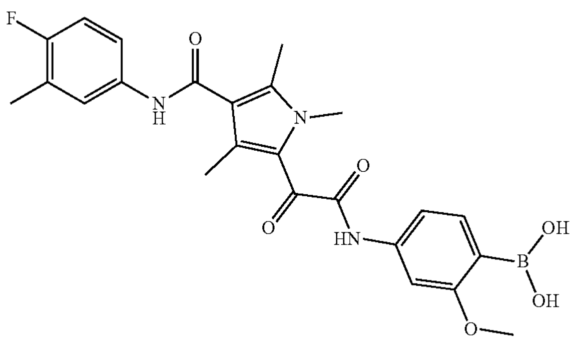 [SMILES: COc1cc(NC(=O)C(=O)c2c(C)c(C(=O)Nc3ccc(F)c(C)c3)c(C)n2C)ccc1B(O)O] | (4-(2-(4-((4-fluoro-3-methylphenyl)carbamoyl)-1,3,5-trimethyl-1H-pyrrol-2-yl)-2-oxoacetamido)-2-methoxyphenyl)boronic acid | 482.1 |
| 249 | 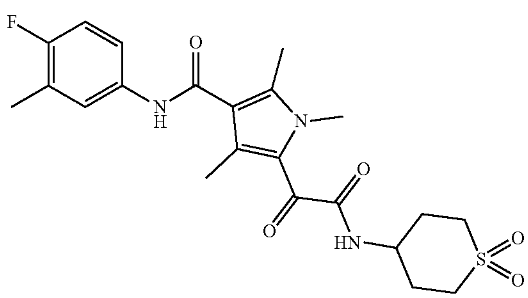 [SMILES: Cc1cc(NC(=O)c2c(C)c(C(=O)C(=O)NC3CCS(=O)(=O)CC3)n(C)c2C)ccc1F] | 5-(2-((1,1-dioxidotetrahydro-2H-thiopyran-4-yl)amino)-2-oxoacetyl)-N-(4-fluoro-3-methylphenyl)-1,2,4-trimethyl-1H-pyrrole-3-carboxamide | 464.1 |
| 250 | 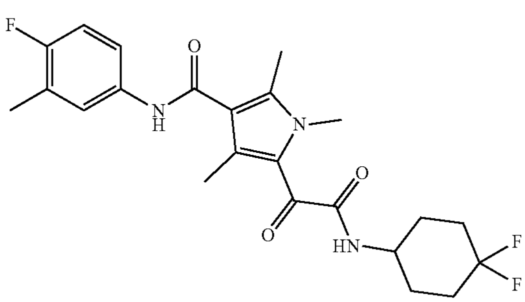 [SMILES: Cc1cc(NC(=O)c2c(C)c(C(=O)C(=O)NC3CCC(F)(F)CC3)n(C)c2C)ccc1F] | 5-(2-((4,4-difluorocyclohexyl)amino)-2-oxoacetyl)-N-(4-fluoro-3-methylphenyl)-1,2,4-trimethyl-1H-pyrrole-3-carboxamide | 450.2 |
| 251 | 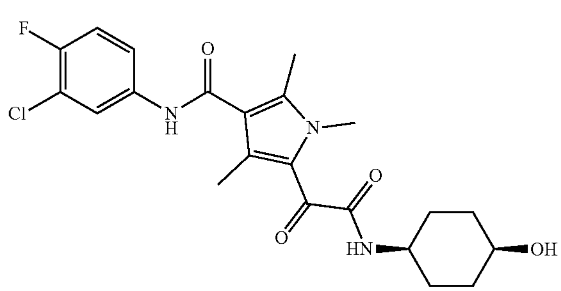 [SMILES: Cc1c(C(=O)Nc2ccc(F)c(Cl)c2)c(C)n(C)c1C(=O)C(=O)N[C@H]1CC[C@@H](O)CC1] | N-(3-chloro-4-fluorophenyl)-5-(2-(((1s,4s)-4-hydroxycyclohexyl)amino)-2-oxoacetyl)-1,2,4-trimethyl-1H-pyrrole-3-carboxamide | 450.1 |

TABLE 1-continued

Exemplary compounds

| Ex. | Structure | Chemical Name | ESI-MS (M + H)+ (m/z) |
|---|---|---|---|
| 252 | 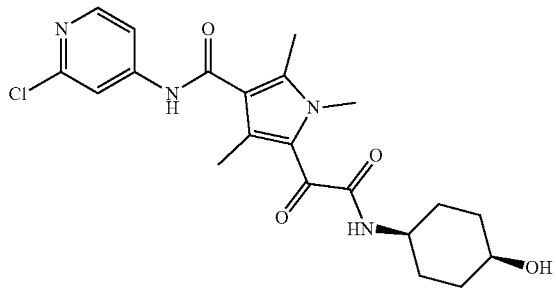 [SMILES: Cc1c(C(=O)Nc2ccnc(Cl)c2)c(C)n(C)c1C(=O)C(=O)N[C@H]1CC[C@@H](O)CC1] | N-(2-chloropyridin-4-yl)-5-(2-(((1s,4s)-4-hydroxycyclohexyl)amino)-2-oxoacetyl)-1,2,4-trimethyl-1H-pyrrole-3-carboxamide | 433.1 |
| 253 | 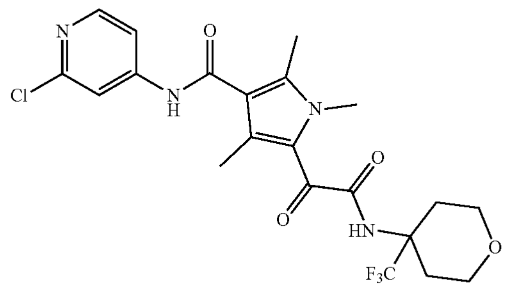 [SMILES: Cc1c(C(=O)Nc2ccnc(Cl)c2)c(C)n(C)c1C(=O)C(=O)NC1(C(F)(F)F)CCOCC1] | N-(2-chloropyridin-4-yl)-1,2,4-trimethyl-5-(2-oxo-2-((4-(trifluoromethyl)tetrahydro-2H-pyran-4-yl)amino)acetyl)-1H-pyrrole-3-carboxamide | 487.1 |
| 254 | 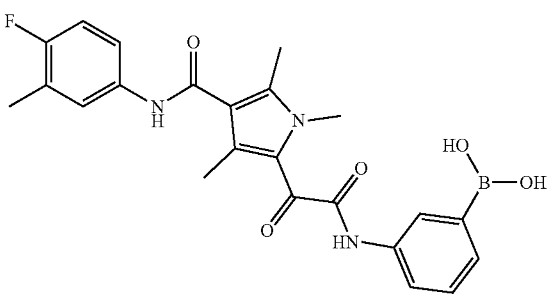 [SMILES: Cc1cc(NC(=O)c2c(C)c(C(=O)C(=O)Nc3cccc(B(O)O)c3)n(C)c2C)ccc1F] | (3-(2-(4-((4-fluoro-3-methylphenyl)carbamoyl)-1,3,5-trimethyl-1H-pyrrol-2-yl)-2-oxoacetamido)phenyl)boronic acid | 452 |
| 255 | 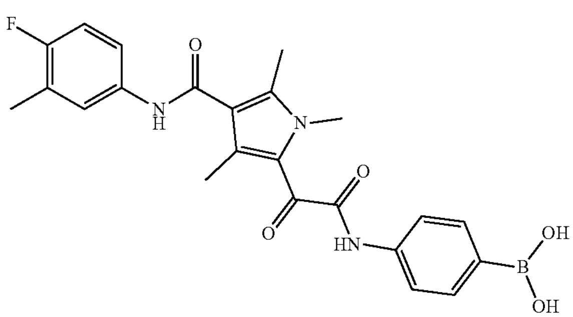 [SMILES: Cc1cc(NC(=O)c2c(C)c(C(=O)C(=O)Nc3ccc(B(O)O)cc3)n(C)c2C)ccc1F] | (4-(2-(4-((4-fluoro-3-methylphenyl)carbamoyl)-1,3,5-trimethyl-1H-pyrrol-2-yl)-2-oxoacetamido)phenyl)boronic acid | 452 |
| 256 | 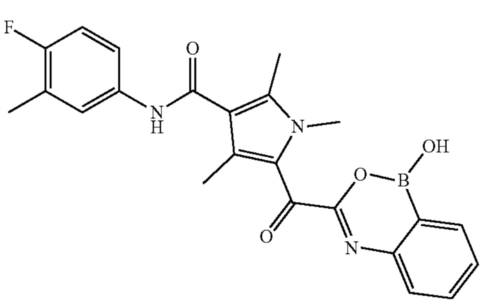 [SMILES: Cc1cc(NC(=O)c2c(C)c(C(=O)C3=Nc4ccccc4B(O)O3)n(C)c2C)ccc1F] | N-(4-fluoro-3-methylphenyl)-5-(1-hydroxy-1H-benzo[c][1,5,2]oxazaborinine-3-carbonyl)-1,2,4-trimethyl-1H-pyrrole-3-carboxamide | 434 |

TABLE 1-continued

Exemplary compounds

| Ex. | Structure | Chemical Name | ESI-MS (M + H)+ (m/z) |
|---|---|---|---|
| 257 | 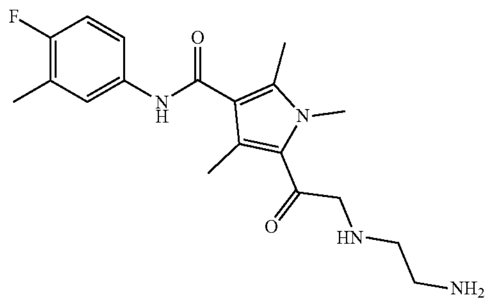 [SMILES: Cc1cc(NC(=O)c2c(C)c(C(=O)CNCCN)n(C)c2C)ccc1F] | 5-(2-((2-aminoethyl)amino)-2-oxoacetyl)-N-(4-fluoro-3-methylphenyl)-1,2,4-trimethyl-1H-pyrrole-3-carboxamide N-(4-fluoro-3-methylphenyl)- | 375 |
| 258 | 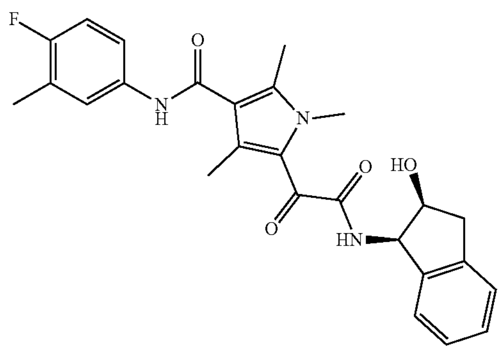 [SMILES: Cc1cc(NC(=O)c2c(C)c(C(=O)C(=O)N[C@@H]3c4ccccc4C[C@@H]3O)n(C)c2C)ccc1F] | 5-(2-(((1R,2S)-2-hydroxy-2,3-dihydro-1H-inden-1-yl)amino)-2-oxoacetyl)-1,2,4-trimethyl-1H-pyrrole-3-carboxamide | 465 |
| 259 | 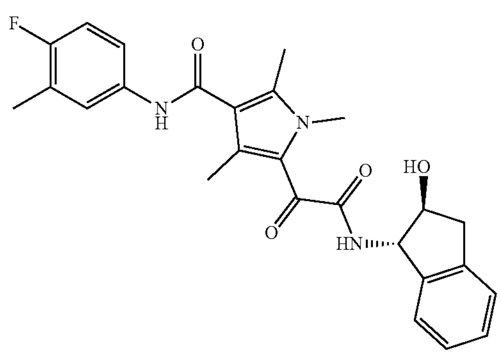 [SMILES: Cc1cc(NC(=O)c2c(C)c(C(=O)C(=O)N[C@H]3c4ccccc4C[C@@H]3O)n(C)c2C)ccc1F] | N-(4-fluoro-3-methylphenyl)-5-(2-(((1S,2S)-2-hydroxy-2,3-dihydro-1H-inden-1-yl)amino)-2-oxoacetyl)-1,2,4-trimethyl-1H-pyrrole-3-carboxamide | 465 |
| 260 | 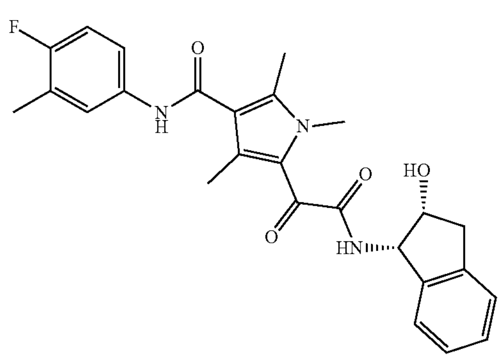 [SMILES: Cc1cc(NC(=O)c2c(C)c(C(=O)C(=O)N[C@H]3c4ccccc4C[C@H]3O)n(C)c2C)ccc1F] | N-(4-fluoro-3-methylphenyl)-5-(2-(((1S,2R)-2-hydroxy-2,3-dihydro-1H-inden-1-yl)amino)-2-oxoacetyl)-1,2,4-trimethyl-1H-pyrrole-3-carboxamide | 465 |

TABLE 1-continued

Exemplary compounds

| Ex. | Structure | Chemical Name | ESI-MS (M + H)+ (m/z) |
|---|---|---|---|
| 261 | 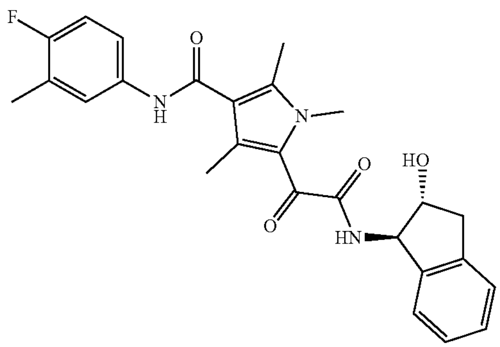 [SMILES: Cc1cc(NC(=O)c2c(C)c(C(=O)C(=O)N[C@@H]3c4ccccc4C[C@H]3O)n(C)c2C)ccc1F] | N-(4-fluoro-3-methylphenyl)-5-(2-(((1R,2R)-2-hydroxy-2,3-dihydro-1H-inden-1-yl)amino)-2-oxoacetyl)-1,2,4-trimethyl-1H-pyrrole-3-carboxamide | 465 |
| 262 | 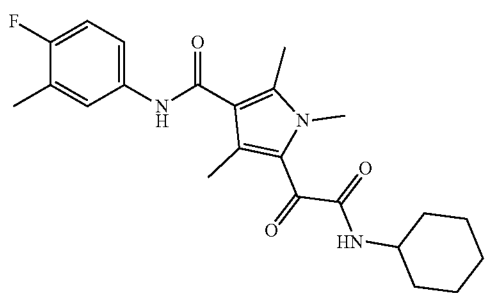 [SMILES: Cc1cc(NC(=O)c2c(C)c(C(=O)C(=O)NC3CCCCC3)n(C)c2C)ccc1F] | 5-(2-(cyclohexylamino)-2-oxoacetyl)-N-(4-fluoro-3-methylphenyl)-1,2,4-trimethyl-1H-pyrrole-3-carboxamide | 414 |
| 263 | 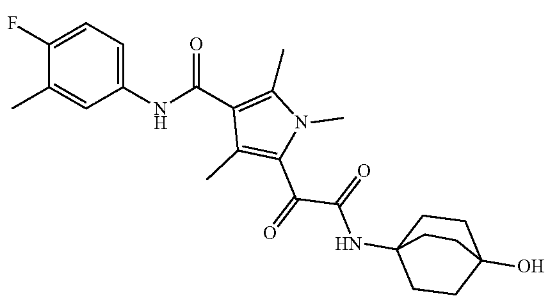 [SMILES: Cc1cc(NC(=O)c2c(C)c(C(=O)C(=O)NC34CCC(O)(CC3)CC4)n(C)c2C)ccc1F] | N-(4-fluoro-3-methylphenyl)-5-(2-((4-hydroxybicyclo[2.2.2]octan-1-yl)amino)-2-oxoacetyl)-1,2,4-trimethyl-1H-pyrrole-3-carboxamide | 457 |
| 264 | 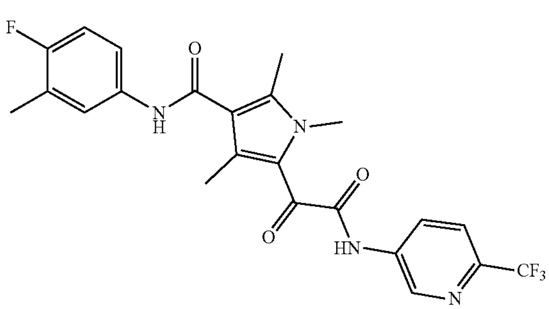 [SMILES: Cc1cc(NC(=O)c2c(C)c(C(=O)C(=O)Nc3ccc(C(F)(F)F)nc3)n(C)c2C)ccc1F] | N-(4-fluoro-3-methylphenyl)-1,2,4-trimethyl-5-(2-oxo-2-((6-(trifluoromethyl)pyridin-3-yl)amino)acetyl)-1H-pyrrole-3-carboxamide | 477 |

TABLE 1-continued

Exemplary compounds

| Ex. | Structure | Chemical Name | ESI-MS (M + H)+ (m/z) |
|---|---|---|---|
| 265 | 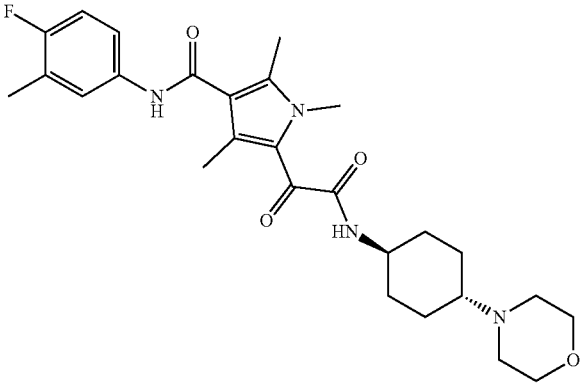 [SMILES: Cc1cc(NC(=O)c2c(C)c(C(=O)C(=O)N[C@H]3CC[C@H](N4CCOCC4)CC3)n(C)c2C)ccc1F] | N-(4-fluoro-3-methylphenyl)-1,2,4-trimethyl-5-(2-(((1s,4s)-4-morpholinocyclohexyl)amino)-2-oxoacety1)-1H-pyrrole-3-carboxamide | 500 |
| 266 | 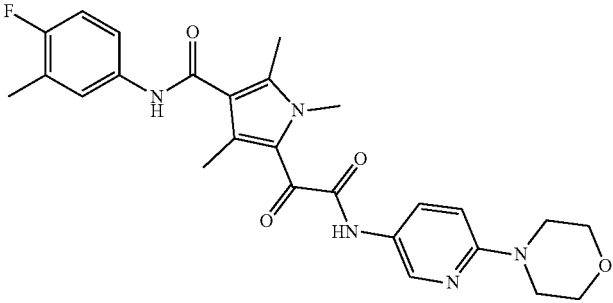 [SMILES: Cc1cc(NC(=O)c2c(C)c(C(=O)C(=O)Nc3ccc(N4CCOCC4)nc3)n(C)c2C)ccc1F] | N-(4-fluoro-3-methylphenyl)-1,2,4-trimethyl-5-(2-((6-morpholinopyridin-3-yl)amino)-2-oxoacetyl)-1H-pyrrole-3-carboxamide | 495 |
| 267 | 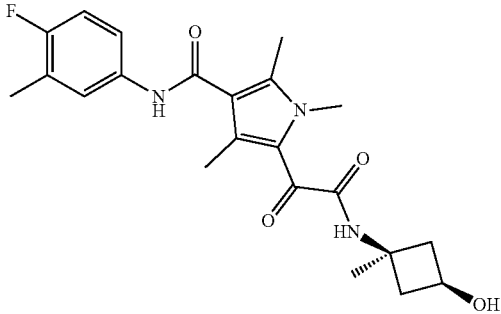 [SMILES: Cc1cc(NC(=O)c2c(C)c(C(=O)C(=O)N[C@]3(C)C[C@H](O)C3)n(C)c2C)ccc1F] | N-(4-fluoro-3-methylphenyl)-5-(2-(((1s,3s)-3-hydroxy-1-methylcyclobutyl)amino)-2-oxoacetyl)-1,2,4-trimethyl-1H-pyrrole-3-carboxamide | 416.2 |
| 268 | 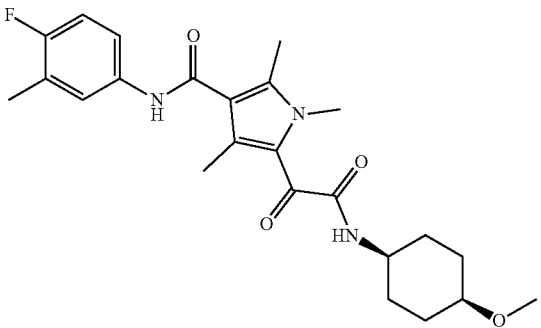 | N-(4-fluoro-3-methylphenyl)-5-(2-(((1s,4s)-4-methoxycyclohexyl)amino)-2-oxoacetyl)-1,2,4-trimethyl-1H-pyrrole-3-carboxamide | 444.2 |

TABLE 1-continued

Exemplary compounds

| Ex. | Structure | Chemical Name | ESI-MS (M + H)+ (m/z) |
|---|---|---|---|
| 269 | 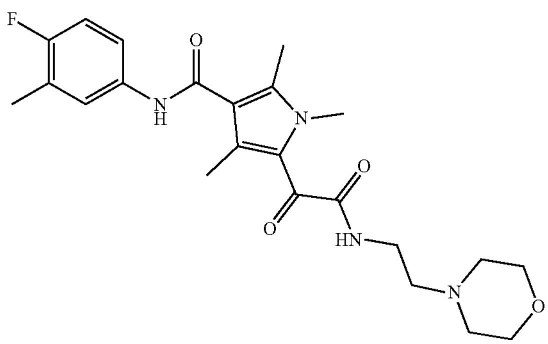 [SMILES: Cc1cc(NC(=O)c2c(C)c(C(=O)C(=O)NCCN3CCOCC3)n(C)c2C)ccc1F] | N-(4-fluoro-3-methylphenyl)-5-(2-(((1r,4r)-4-methoxycyclohexyl)amino)-2-oxoacetyl)-1,2,4-trimethyl-1H-pyrrole-3-carboxamide | 444.2 |
| 270 | 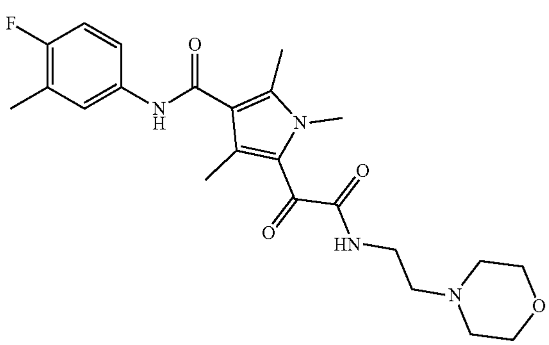 [SMILES: Cc1cc(NC(=O)c2c(C)c(C(=O)C(=O)NCCN3CCOCC3)n(C)c2C)ccc1F] | N-(4-fluoro-3-methylphenyl)-1,2,4-trimethyl-5-(2-((2-morpholinoethyl)amino)-2-oxoacetyl)-1H-pyrrole-3-carboxamide | 445.2 |
| 271 | 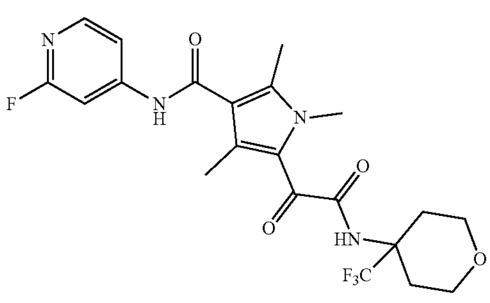 [SMILES: Cc1c(C(=O)Nc2ccnc(F)c2)c(C)n(C)c1C(=O)C(=O)NC1(C(F)(F)F)CCOCC1] | N-(2-fluoropyridin-4-yl)-1,2,4-trimethyl-5-(2-oxo-2-((4-(trifluoromethyl)tetrahydro-2H-pyran-4-yl)amino)acetyl)-1H-pyrrole-3-carboxamide | 471.1 |
| 272 | 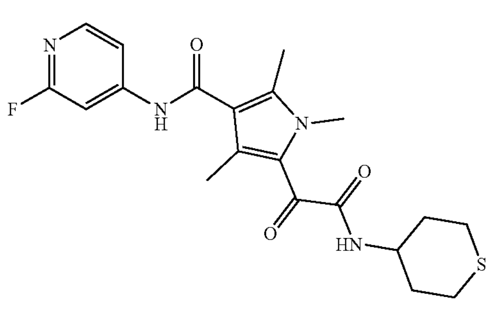 [SMILES: Cc1c(C(=O)Nc2ccnc(F)c2)c(C)n(C)c1C(=O)C(=O)NC1CCSCC1] | N-(2-fluoropyridin-4-yl)-1,2,4-trimethyl-5-(2-oxo-2-((tetrahydro-2H-thiopyran-4-yl)amino)acetyl)-1H-pyrrole-3-carboxamide | 419.1 |

TABLE 1-continued

Exemplary compounds

| Ex. | Structure | Chemical Name | ESI-MS (M + H)+ (m/z) |
|---|---|---|---|
| 273 | 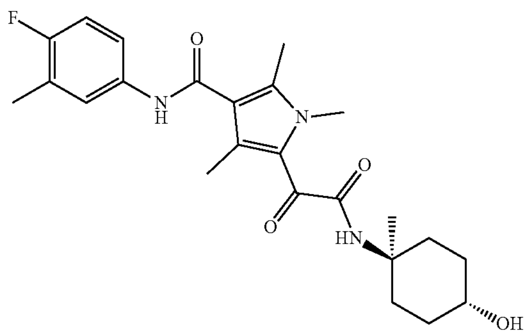 [SMILES: Cc1cc(NC(=O)c2c(C)c(C(=O)C(=O)N[C@]3(C)CC[C@@H](O)CC3)n(C)c2C)ccc1F] | N-(4-fluoro-3-methylphenyl)-5-(2-(((1r,4r)-4-hydroxy-1-methylcyclohexyl)amino)-2-oxoacetyl)-1,2,4-trimethyl-1H-pyrrole-3-carboxamide | 444.2 |
| 274 | 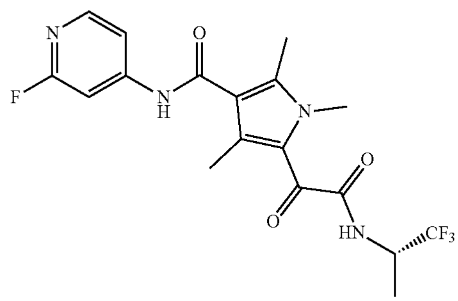 [SMILES: Cc1c(C(=O)Nc2ccnc(F)c2)c(C)n(C)c1C(=O)C(=O)N[C@@H](C)C(F)(F)F] | (S)-N-(2-fluoropyridin-4-yl)-1,2,4-trimethyl-5-(2-oxo-2-((1,1,1-trifluoropropan-2-yl)amino)acetyl)-1H-pyrrole-3-carboxamide | 415.1 |
| 275 | 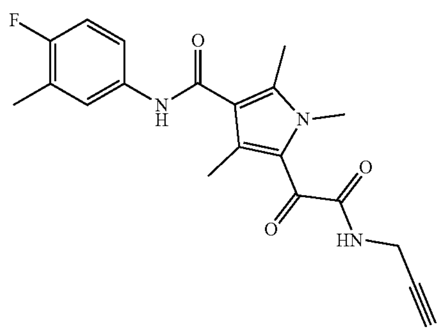 [SMILES: C#CCNC(=O)C(=O)c1c(C)c(C(=O)Nc2ccc(F)c(C)c2)c(C)n1C] | N-(4-fluoro-3-methylphenyl)-1,2,4-trimethyl-5-(2-oxo-2-(prop-2-yn-1-ylamino)acetyl)-1H-pyrrole-3-carboxamide | 370.2 |
| 276 | 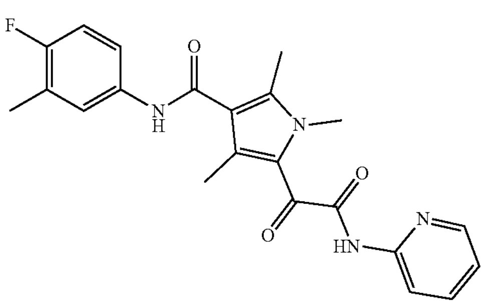 [SMILES: Cc1cc(NC(=O)c2c(C)c(C(=O)C(=O)Nc3ccccn3)n(C)c2C)ccc1F] | N-(4-fluoro-3-methylphenyl)-1,2,4-trimethyl-5-(2-oxo-2-(pyridin-2-ylamino)acetyl)-1H-pyrrole-3-carboxamide | 409 |

TABLE 1-continued

Exemplary compounds

| Ex. | Structure | Chemical Name | ESI-MS (M + H)+ (m/z) |
|---|---|---|---|
| 277 | 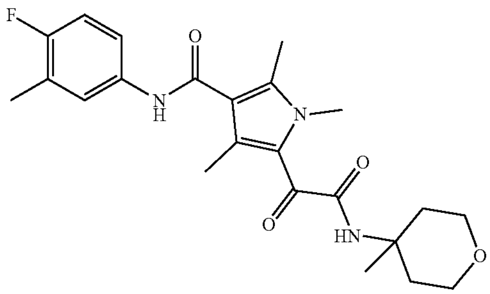 [SMILES: Cc1cc(NC(=O)c2c(C)c(C(=O)C(=O)NC3(C)CCOCC3)n(C)c2C)ccc1F] | N-(4-fluoro-3-methylphenyl)-1,2,4-trimethyl-5-(2-((4-methyltetrahydro-2H-pyran-4-yl)amino)-2-oxoacetyl)-1H-pyrrole-3-carboxamide | 430.2 |
| 278 | 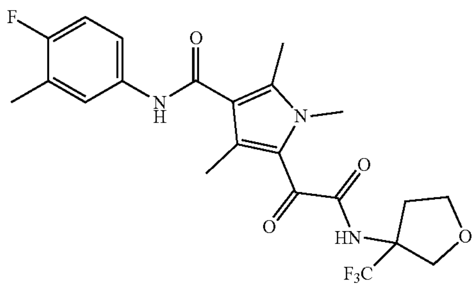 [SMILES: Cc1cc(NC(=O)c2c(C)c(C(=O)C(=O)NC3(C(F)(F)F)CCOC3)n(C)c2C)ccc1F] | N-(4-fluoro-3-methylphenyl)-1,2,4-trimethyl-5-(2-oxo-2-((3-(trifluoromethyl)tetrahydrofuran-3-yl)amino)acetyl)-1H-pyrrole-3-carboxamide | 470.2 |
| 279 | 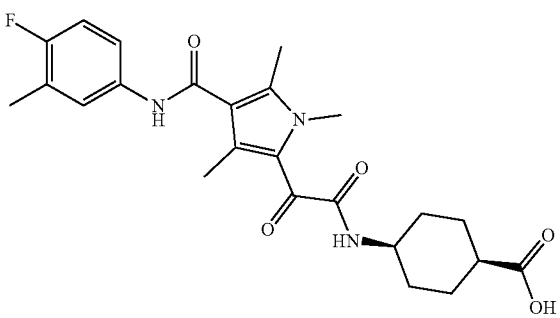 [SMILES: Cc1cc(NC(=O)c2c(C)c(C(=O)C(=O)N[C@H]3CC[C@@H](C(=O)O)CC3)n(C)c2C)ccc1F] | (1s,4s)-4-(2-(4-((4-fluoro-3-methylphenyl)carbamoyl)-1,3,5-trimethyl-1H-pyrrol-2-yl)-2-oxoacetamido)cyclohexane-1-carboxylic acid | 458.2 |
| 280 | 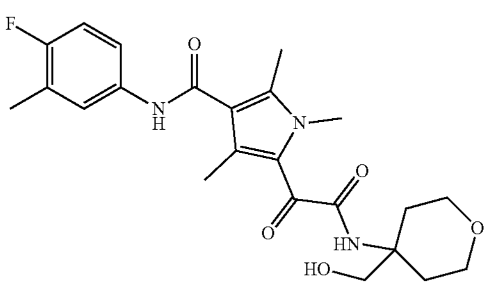 [SMILES: Cc1cc(NC(=O)c2c(C)c(C(=O)C(=O)NC3(CO)CCOCC3)n(C)c2C)ccc1F] | N-(4-fluoro-3-methylphenyl)-5-(2-((4-(hydroxymethyl)tetrahydro-2H-pyran-4-yl)amino)-2-oxoacetyl)-1,2,4-trimethyl-1H-pyrrole-3-carboxamide | 446.1 |
| 281 | 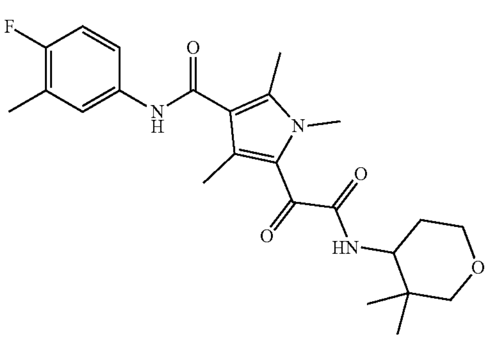 [SMILES: Cc1cc(NC(=O)c2c(C)c(C(=O)C(=O)NC3CCOCC3(C)C)n(C)c2C)ccc1F] | 5-(2-((3,3-dimethyltetrahydro-2H-pyran-4-yl)amino)-2-oxoacetyl)-N-(4-fluoro-3-methylphenyl)-1,2,4-trimethyl-1H-pyrrole-3-carboxamide | 444.2 |

TABLE 1-continued

Exemplary compounds

| Ex. | Structure | Chemical Name | ESI-MS (M + H)+ (m/z) |
|---|---|---|---|
| 282 | 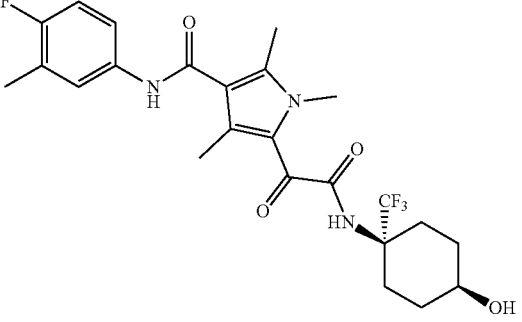 | N-(4-fluoro-3-methylphenyl)-5-(2-(((1s,4s)-4-hydroxy-1-(trifluoromethyl)cyclohexyl)amino)-2-oxoacetyl)-1,2,4-trimethyl-1H-pyrrole-3-carboxamide | 498.2 |
| 283 | 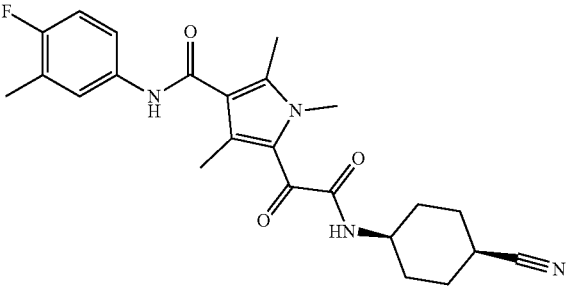 [SMILES: Cc1cc(NC(=O)c2c(C)c(C(=O)C(=O)N[C@H]3CC[C@@H](C#N)CC3)n(C)c2C)ccc1F] | 5-(2-(((1s,4s)-4-cyanocyclohexyl)amino)-2-oxoacetyl)-N-(4-fluoro-3-methylphenyl)-1,2,4-trimethyl-1H-pyrrole-3-carboxamide | 439.2 |
| 284 | 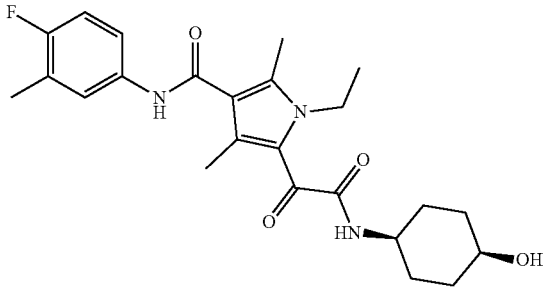 [SMILES: CCn1c(C)c(C(=O)Nc2ccc(F)c(C)c2)c(C)c1C(=O)C(=O)N[C@H]1CC[C@@H](O)CC1] | 1-ethyl-N-(4-fluoro-3-methylphenyl)-5-(2-(((1s,4s)-4-hydroxycyclohexyl)amino)-2-oxoacetyl)-2,4-dimethyl-1H-pyrrole-3-carboxamide | 444.2 |
| 285 | 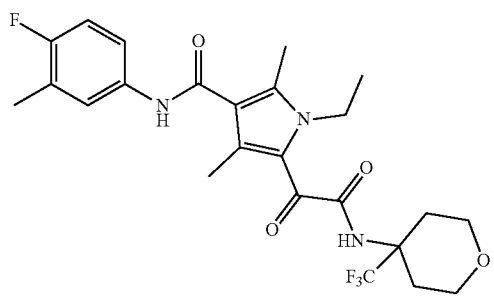 [SMILES: CCn1c(C)c(C(=O)Nc2ccc(F)c(C)c2)c(C)c1C(=O)C(=O)NC1(C(F)(F)F)CCOCC1] | 1-ethyl-N-(4-fluoro-3-methylphenyl)-2,4-dimethyl-5-(2-oxo-2-((4-(trifluoromethyl)tetrahydro-2H-pyran-4-yl)amino)acetyl)-1H-pyrrole-3-carboxamide | 498.2 |

TABLE 1-continued

Exemplary compounds

| Ex. | Structure | Chemical Name | ESI-MS (M + H)+ (m/z) |
|---|---|---|---|
| 286 | 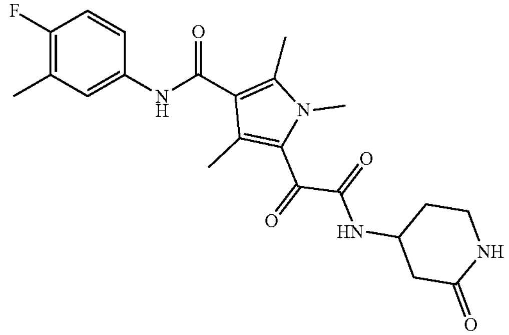 [SMILES: Cc1cc(NC(=O)c2c(C)c(C(=O)C(=O)NC3CCNC(=O)C3)n(C)c2C)ccc1F] | N-(4-fluoro-3-methylphenyl)-1,2,4-trimethyl-5-(2-oxo-2-((2-oxopiperidin-4-yl)amino)acetyl)-1H-pyrrole-3-carboxamide | 429.2 |
| 287 | 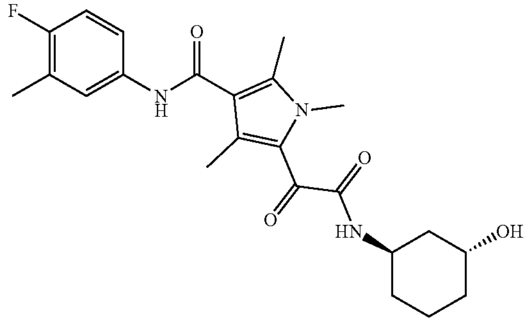 [SMILES: Cc1cc(NC(=O)c2c(C)c(C(=O)C(=O)N[C@@H]3CCC[C@@H](O)C3)n(C)c2C)ccc1F] | N-(4-fluoro-3-methylphenyl)-5-(2-(((1R,3R)-3-hydroxycyclohexyl)amino)-2-oxoacetyl)-1,2,4-trimethyl-1H-pyrrole-3-carboxamide | 430.2 |
| 288 | 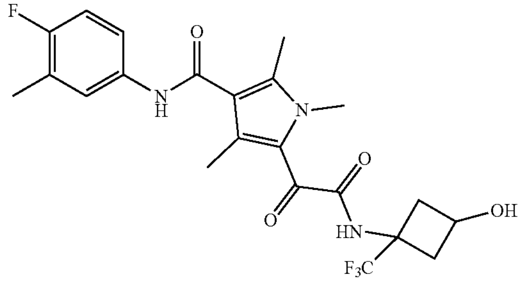 [SMILES: Cc1cc(NC(=O)c2c(C)c(C(=O)C(=O)NC3(C(F)(F)F)CC(O)C3)n(C)c2C)ccc1F] | N-(4-fluoro-3-methylphenyl)-5-(2-((3-hydroxy-1-(trifluoromethyl)cyclobutyl)amino)-2-oxoacetyl)-1,2,4-trimethyl-1H-pyrrole-3-carboxamide | 470.2 |
| 289 | 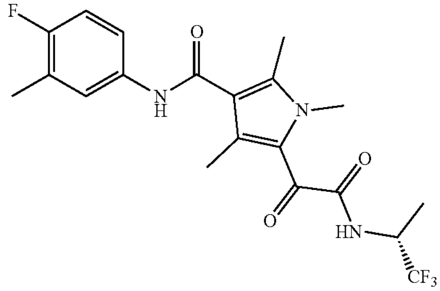 [SMILES: Cc1cc(NC(=O)c2c(C)c(C(=O)C(=O)N[C@H](C)C(F)(F)F)n(C)c2C)ccc1F] | (R)-N-(4-fluoro-3-methylphenyl)-1,2,4-trimethyl-5-(2-oxo-2-((1,1,1-trifluoropropan-2-yl)amino)acetyl)-1H-pyrrole-3-carboxamide | 428.2 |

TABLE 1-continued

Exemplary compounds

| Ex. | Structure | Chemical Name | ESI-MS (M + H)+ (m/z) |
|---|---|---|---|
| 290 | 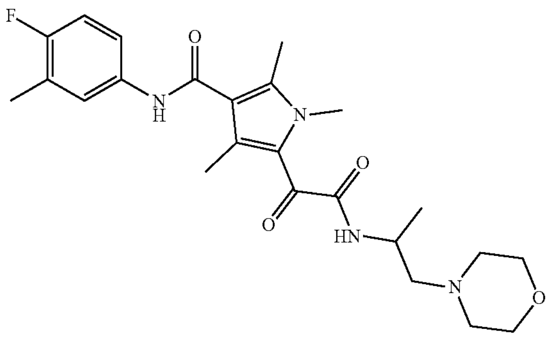 [SMILES: Cc1cc(NC(=O)c2c(C)c(C(=O)C(=O)NC(C)CN3CCOCC3)n(C)c2C)ccc1F] | N-(4-fluoro-3-methylphenyl)-1,2,4-trimethyl-5-(2-((1-morpholinopropan-2-yl)amino)-2-oxoacetyl)-1H-pyrrole-3-carboxamide | 459.3 |
| 291 | 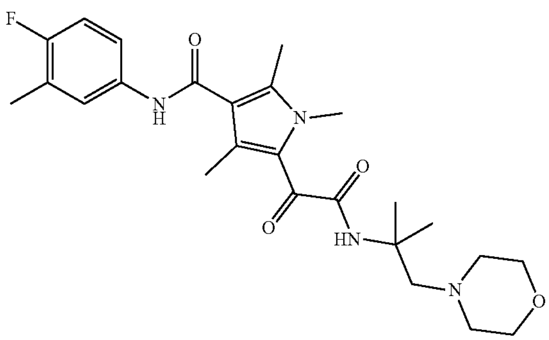 [SMILES: Cc1cc(NC(=O)c2c(C)c(C(=O)C(=O)NC(C)(C)CN3CCOCC3)n(C)c2C)ccc1F] | N-(4-fluoro-3-methylphenyl)-1,2,4-trimethyl-5-(2-((2-methyl-1-morpholinopropan-2-yl)amino)-2-oxoacetyl)-1H-pyrrole-3-carboxamide | 473.3 |
| 292 | 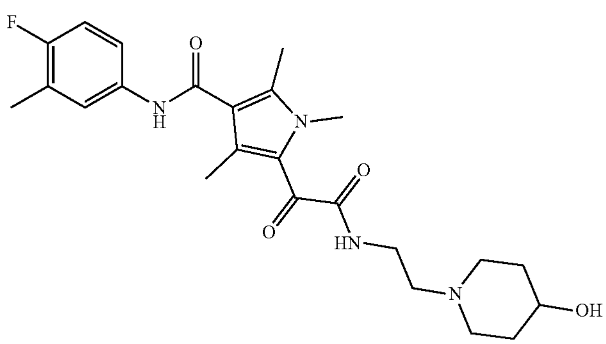 [SMILES: Cc1cc(NC(=O)c2c(C)c(C(=O)C(=O)NCCN3CCC(O)CC3)n(C)c2C)ccc1F] | N-(4-fluoro-3-methylphenyl)-5-(2-((2-(4-hydroxypiperidin-1-yl)ethyl)amino)-2-oxoacetyl)-1,2,4-trimethyl-1H-pyrrole-3-carboxamide | 459.3 |
| 293 | 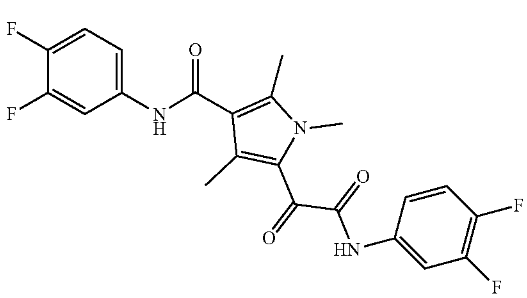 [SMILES: Cc1c(C(=O)Nc2ccc(F)c(F)c2)c(C)n(C)c1C(=O)C(=O)Nc1ccc(F)c(F)c1] | N-(3,4-difluorophenyl)-5-(2-((3,4-difluorophenyl)amino)-2-oxoacetyl)-1,2,4-trimethyl-1H-pyrrole-3-carboxamide | 448.2 |

TABLE 1-continued

Exemplary compounds

| Ex. | Structure | Chemical Name | ESI-MS (M + H)+ (m/z) |
|---|---|---|---|
| 294 | 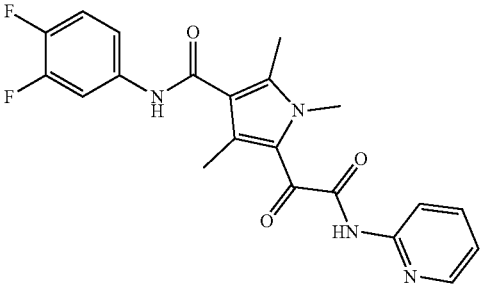 [SMILES: Cc1c(C(=O)Nc2ccc(F)c(F)c2)c(C)n(C)c1C(=O)C(=O)Nc1ccccn1] | N-(3,4-difluorophenyl)-1,2,4-trimethyl-5-(2-oxo-2-(pyridin-2-ylamino)acetyl)-1H-pyrrole-3-carboxamide | 413.2 |
| 295 | 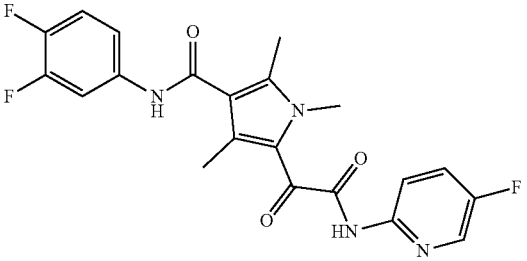 [SMILES: Cc1c(C(=O)Nc2ccc(F)c(F)c2)c(C)n(C)c1C(=O)C(=O)Nc1ccc(F)cn1] | N-(3,4-difluorophenyl)-5-(2-((5-fluoropyridin-2-yl)amino)-2-oxoacetyl)-1,2,4-trimethyl-1H-pyrrole-3-carboxamide | 431.2 |
| 296 | 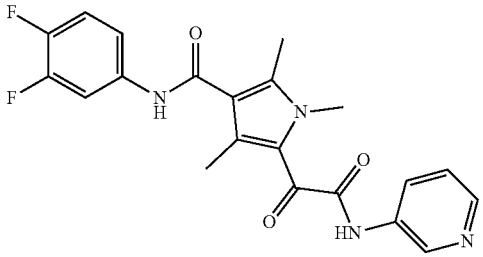 [SMILES: Cc1c(C(=O)Nc2ccc(F)c(F)c2)c(C)n(C)c1C(=O)C(=O)Nc1cccnc1] | N-(3,4-difluorophenyl)-1,2,4-trimethyl-5-(2-oxo-2-(pyridin-3-ylamino)acetyl)-1H-pyrrole-3-carboxamide | 413.2 |
| 297 | 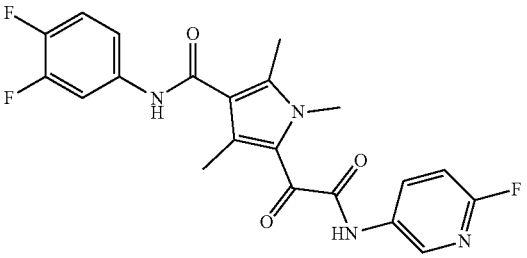 [SMILES: Cc1c(C(=O)Nc2ccc(F)c(F)c2)c(C)n(C)c1C(=O)C(=O)Nc1ccc(F)nc1] | N-(3,4-difluorophenyl)-5-(2-((6-fluoropyridin-3-yl)amino)-2-oxoacetyl)-1,2,4-trimethyl-1H-pyrrole-3-carboxamide | 431.2 |
| 298 | 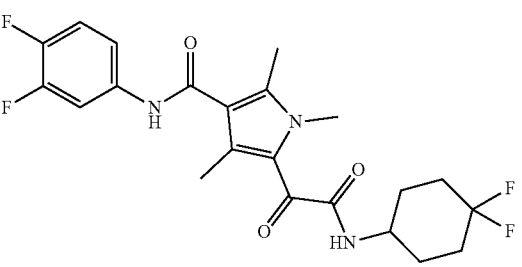 [SMILES: Cc1c(C(=O)Nc2ccc(F)c(F)c2)c(C)n(C)c1C(=O)C(=O)NC1CCC(F)(F)CC1] | 5-(2-((4,4-difluorocyclohexyl)amino)-2-oxoacetyl)-N-(3,4-difluorophenyl)-1,2,4-trimethyl-1H-pyrrole-3-carboxamide | 454.2 |

TABLE 1-continued

Exemplary compounds

| Ex. | Structure | Chemical Name | ESI-MS (M + H)+ (m/z) |
|---|---|---|---|
| 299 | 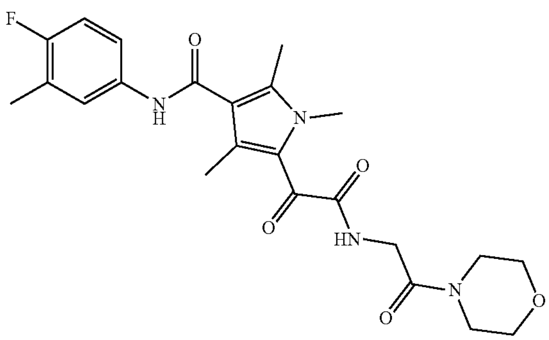 [SMILES: Cc1cc(NC(=O)c2c(C)c(C(=O)C(=O)NCC(=O)N3CCOCC3)n(C)c2C)ccc1F] | N-(4-fluoro-3-methylphenyl)-1,2,4-trimethyl-5-(2-((2-morpholino-2-oxoethyl)amino)-2-oxoacetyl)-1H-pyrrole-3-carboxamide | 459.2 |
| 300 | 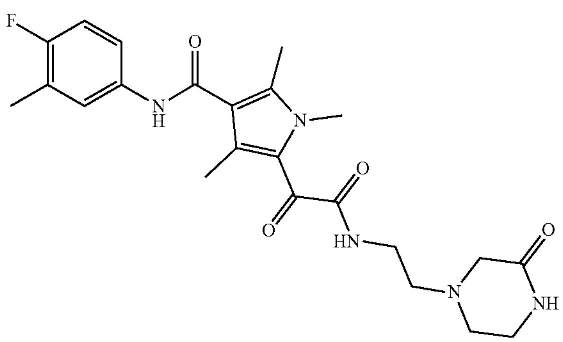 [SMILES: Cc1cc(NC(=O)c2c(C)c(C(=O)C(=O)NCCN3CCNC(=O)C3)n(C)c2C)ccc1F] | N-(4-fluoro-3-methylphenyl)-1,2,4-trimethyl-5-(2-oxo-2-((2-(3-oxopiperazin-1-yl)ethyl)amino)acetyl)-1H-pyrrole-3-carboxamide | 458.2 |
| 301 | 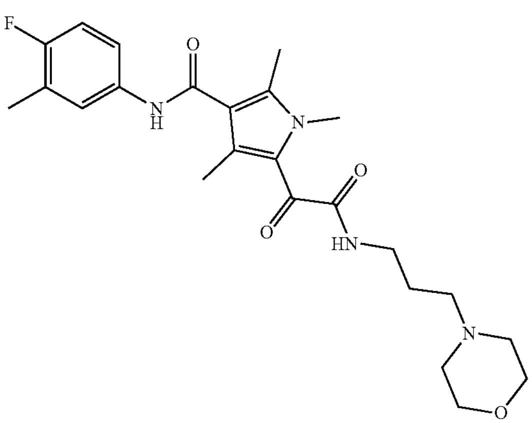 [SMILES: Cc1cc(NC(=O)c2c(C)c(C(=O)C(=O)NCCCN3CCOCC3)n(C)c2C)ccc1F] | N-(4-fluoro-3-methylphenyl)-1,2,4-trimethyl-5-(2-((3-morpholinopropyl)amino)-2-oxoacetyl)-1H-pyrrole-3-carboxamide | 459.3 |
| 302 | 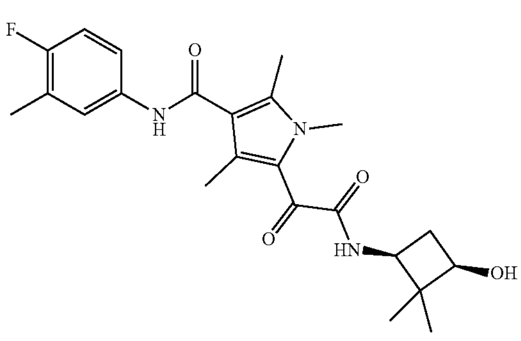 [SMILES: Cc1cc(NC(=O)c2c(C)c(C(=O)C(=O)N[C@H]3C[C@@H](O)C3(C)C)n(C)c2C)ccc1F] | N-(4-fluoro-3-methylphenyl)-5-(2-(((1S,3R)-3-hydroxy-2,2-dimethylcyclobutyl)amino)-2-oxoacetyl)-1,2,4-trimethyl-1H-pyrrole-3-carboxamide | 430.2 |

TABLE 1-continued

Exemplary compounds

| Ex. | Structure | Chemical Name | ESI-MS (M + H)+ (m/z) |
|---|---|---|---|
| 303 | 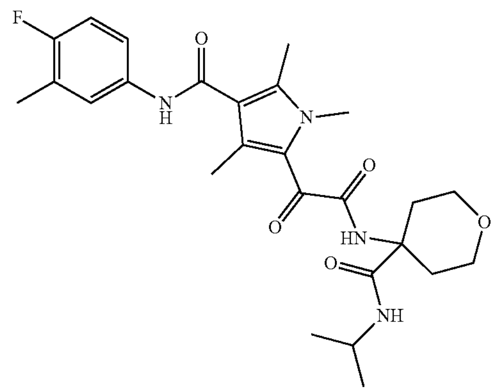 [SMILES: Cc1cc(NC(=O)c2c(C)c(C(=O)C(=O)NC3(C(=O)NC(C)C)CCOCC3)n(C)c2C)ccc1F] | N-(4-fluoro-3-methylphenyl)-5-(2-((4-(isopropylcarbamoyl)tetrahydro-2H-pyran-4-yl)amino)-2-oxoacetyl)-1,2,4-trimethyl-1H-pyrrole-3-carboxamide | 501.3 |
| 304 | 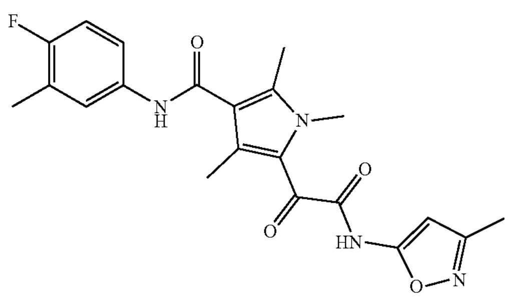 | N-(4-fluoro-3-methylphenyl)-1,2,4-trimethyl-5-(2-((3-methylisoxazol-5-yl)amino)-2-oxoacetyl)-1H-pyrrole-3-carboxamide | 413.2 |
| 305 | 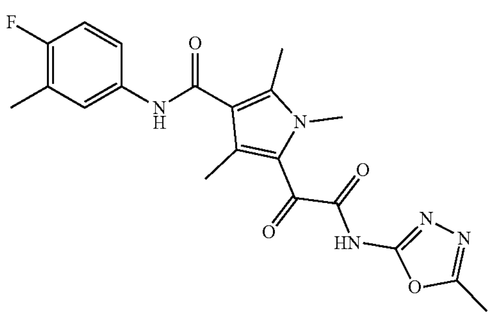 | N-(4-fluoro-3-methylphenyl)-1,2,4-trimethyl-5-(2-((5-methyl-1,3,4-oxadiazol-2-yl)amino)-2-oxoacetyl)-1H-pyrrole-3-carboxamide | 414.2 |
| 306 | 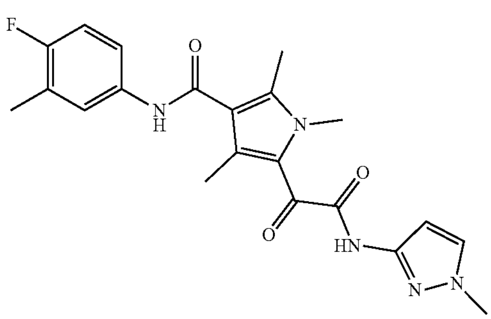 | N-(4-fluoro-3-methylphenyl)-1,2,4-trimethyl-5-(2-(1-methyl-1H-pyrazol-3-yl)amino)-2-oxoacetyl)-1H-pyrrole-3-carboxamide | 412.2 |

TABLE 1-continued

Exemplary compounds

| Ex. | Structure | Chemical Name | ESI-MS (M + H)+ (m/z) |
|---|---|---|---|
| 307 | 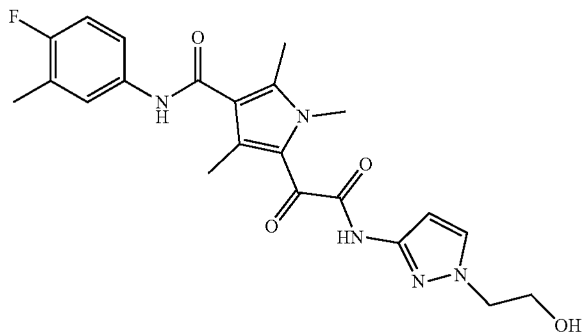 [SMILES: Cc1cc(NC(=O)c2c(C)c(C(=O)C(=O)Nc3ccn(CCO)n3)n(C)c2C)ccc1F] | N-(4-fluoro-3-methylphenyl)-5-(2-((1-(2-hydroxyethyl)-1H-pyrazol-3-yl)amino)-2-oxoacetyl)-1,2,4-trimethyl-1H-pyrrole-3-carboxamide | 442.2 |
| 308 | 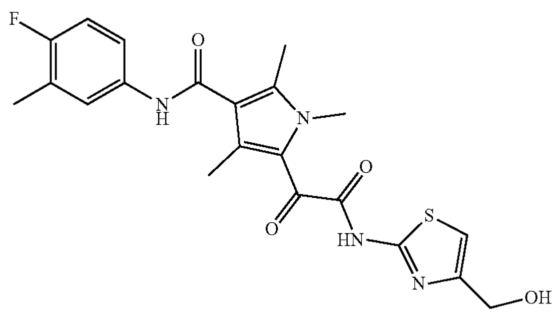 [SMILES: Cc1cc(NC(=O)c2c(C)c(C(=O)C(=O)Nc3nc(CO)cs3)n(C)c2C)ccc1F] | N-(4-fluoro-3-methylphenyl)-5-(2-((4-(hydroxymethyl)thiazol-2-yl)amino)-2-oxoacetyl)-1,2,4-trimethyl-1H-pyrrole-3-carboxamide | 445.2 |
| 309 | 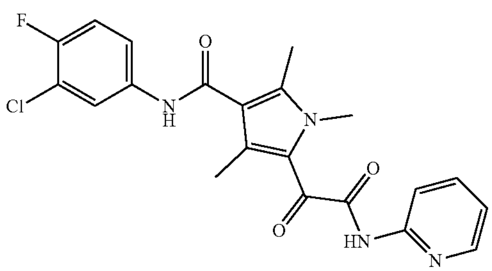 [SMILES: Cc1c(C(=O)Nc2ccc(F)c(Cl)c2)c(C)n(C)c1C(=O)C(=O)Nc1ccccn1] | N-(3-chloro-4-fluorophenyl)-1,2,4-trimethyl-5-(2-oxo-2-(pyridin-2-ylamino)acetyl)-1H-pyrrole-3-carboxamide | 429.2 |
| 310 | 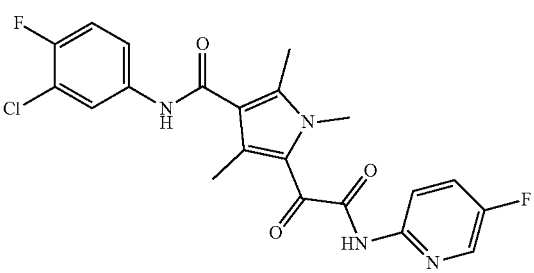 [SMILES: Cc1c(C(=O)Nc2ccc(F)c(Cl)c2)c(C)n(C)c1C(=O)C(=O)Nc1ccc(F)cn1] | N-(3-chloro-4-fluorophenyl)-5-(2-((5-fluoropyridin-2-yl)amino)-2-oxoacetyl)-1,2,4-trimethyl-1H-pyrrole-3-carboxamide | 447.1 |
| 311 | 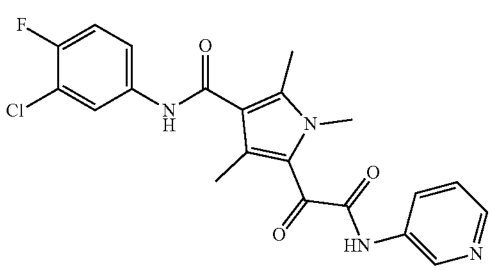 [SMILES: Cc1c(C(=O)Nc2ccc(F)c(Cl)c2)c(C)n(C)c1C(=O)C(=O)Nc1cccnc1] | N-(3-chloro-4-fluorophenyl)-1,2,4-trimethyl-5-(2-oxo-2-(pyridin-3-ylamino)acetyl)-1H-pyrrole-3-carboxamide | 429.1 |

TABLE 1-continued

Exemplary compounds

| Ex. | Structure | Chemical Name | ESI-MS (M + H)+ (m/z) |
|---|---|---|---|
| 312 | 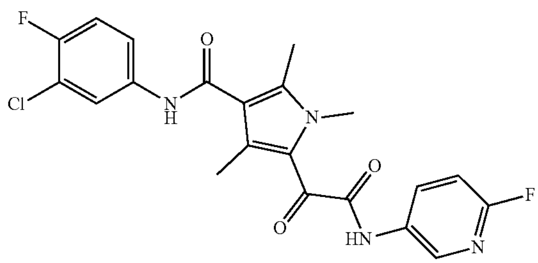 [SMILES: Cc1c(C(=O)Nc2ccc(F)c(Cl)c2)c(C)n(C)c1C(=O)C(=O)Nc1ccc(F)nc1] | N-(3-chloro-4-fluorophenyl)-5-(2-((6-fluoropyridin-3-yl)amino)-2-oxoacetyl)-1,2,4-trimethyl-1H-pyrrole-3-carboxamide | 447.2 |
| 313 | 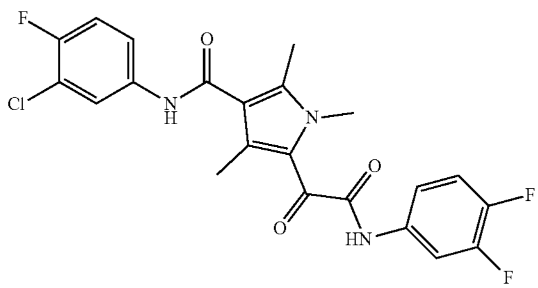 [SMILES: Cc1c(C(=O)Nc2ccc(F)c(Cl)c2)c(C)n(C)c1C(=O)C(=O)Nc1ccc(F)c(F)c1] | N-(3-chloro-4-fluorophenyl)-5-(2-((3,4-difluorophenyl)amino)-2-oxoacetyl)-1,2,4-trimethyl-1H-pyrrole-3-carboxamide | 464.1 |
| 314 | 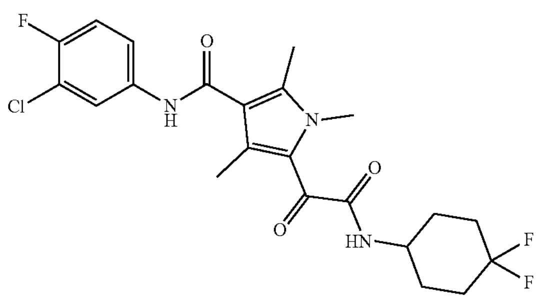 [SMILES: Cc1c(C(=O)Nc2ccc(F)c(Cl)c2)c(C)n(C)c1C(=O)C(=O)NC1CCC(F)(F)CC1] | N-(3-chloro-4-fluorophenyl)-5-(2-((4,4-difluorocyclohexyl)amino)-2-oxoacetyl)-1,2,4-trimethyl-1H-pyrrole-3-carboxamide | 470.2 |
| 315 | 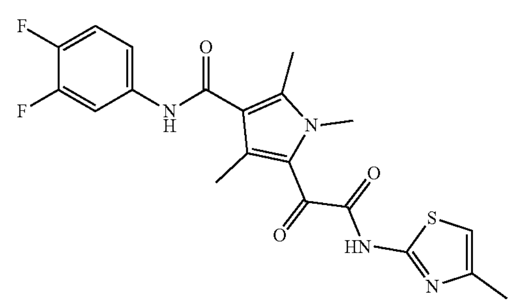 [SMILES: Cc1csc(NC(=O)C(=O)c2c(C)c(C(=O)Nc3ccc(F)c(F)c3)c(C)n2C)n1] | N-(3,4-difluorophenyl)-1,2,4-trimethyl-5-(2-((4-methylthiazol-2-yl)amino)-2-oxoacetyl)-1H-pyrrole-3-carboxamide | 433.1 |
| 316 | 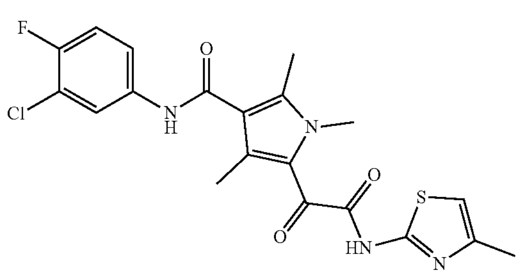 [SMILES: Cc1csc(NC(=O)C(=O)c2c(C)c(C(=O)Nc3ccc(F)c(Cl)c3)c(C)n2C)n1] | N-(3-chloro-4-fluorophenyl)-1,2,4-trimethyl-5-(2-((4-methylthiazol-2-yl)amino)-2-oxoacetyl)-1H-pyrrole-3-carboxamide | 449.1 |

TABLE 1-continued

Exemplary compounds

| Ex. | Structure | Chemical Name | ESI-MS (M + H)+ (m/z) |
|---|---|---|---|
| 317 | 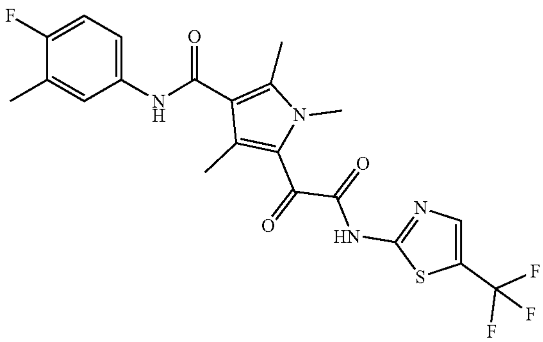 [SMILES: Cc1cc(NC(=O)c2c(C)c(C(=O)C(=O)Nc3ncc(C(F)(F)F)s3)n(C)c2C)ccc1F] | N-(4-fluoro-3-methylphenyl)-1,2,4-trimethyl-5-(2-oxo-2-((5-(trifluoromethyl)thiazol-2-yl)amino)acetyl)-1H-pyrrole-3-carboxamide | 483.2 |
| 318 | 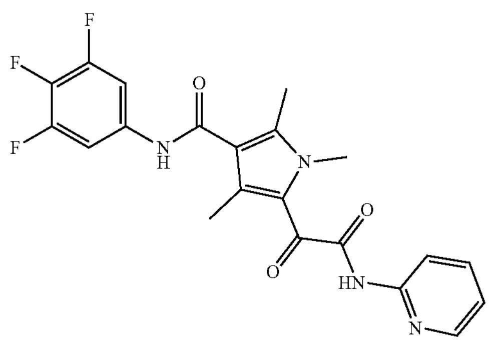 [SMILES: Cc1c(C(=O)Nc2cc(F)c(F)c(F)c2)c(C)n(C)c1C(=O)C(=O)Nc1ccccn1] | 1,2,4-trimethyl-5-(2-oxo-2-(pyridin-2-ylamino)acetyl)-N-(3,4,5-trifluorophenyl)-1H-pyrrole-3-carboxamide | 431.1 |
| 319 | 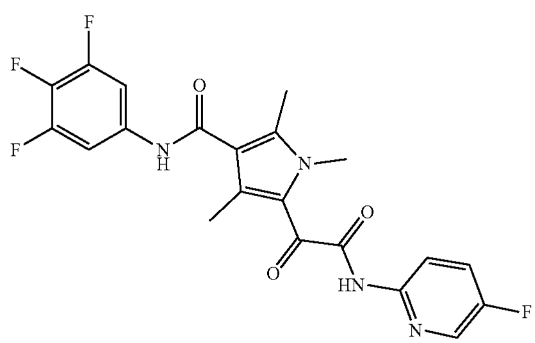 [SMILES: Cc1c(C(=O)Nc2cc(F)c(F)c(F)c2)c(C)n(C)c1C(=O)C(=O)Nc1ccc(F)cn1] | 5-(2-((5-fluoropyridin-2-yl)amino)-2-oxoacetyl)-1,2,4-trimethyl-N-(3,4,5-trifluorophenyl)-1H-pyrrole-3-carboxamide | 449.1 |
| 320 | 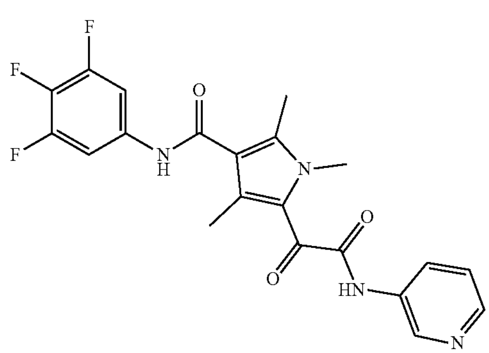 [SMILES: Cc1c(C(=O)Nc2cc(F)c(F)c(F)c2)c(C)n(C)c1C(=O)C(=O)Nc1cccnc1] | 1,2,4-trimethyl-5-(2-oxo-2-(pyridin-3-ylamino)acetyl)-N-(3,4,5-trifluorophenyl)-1H-pyrrole-3-carboxamide | 431.2 |

TABLE 1-continued

Exemplary compounds

| Ex. | Structure | Chemical Name | ESI-MS (M + H)+ (m/z) |
|---|---|---|---|
| 321 | 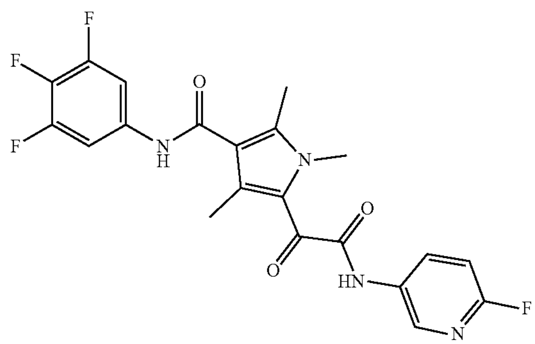 [SMILES: Cc1c(C(=O)Nc2cc(F)c(F)c(F)c2)c(C)n(C)c1C(=O)C(=O)Nc1ccc(F)nc1] | 5-(2-((6-fluoropyridin-3-yl)amino)-2-oxoacetyl)-1,2,4-trimethyl-N-(3,4,5-trifluorophenyl)-1H-pyrrole-3-carboxamide | 449.1 |
| 322 | 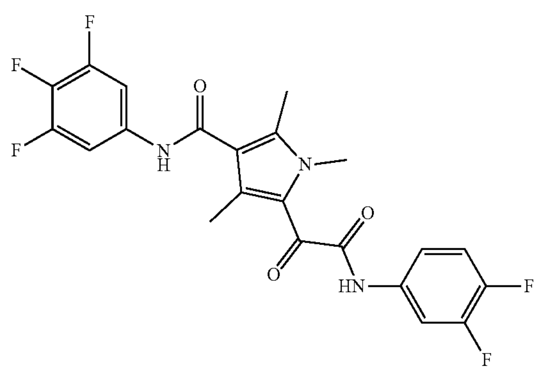 [SMILES: Cc1c(C(=O)Nc2cc(F)c(F)c(F)c2)c(C)n(C)c1C(=O)C(=O)Nc1ccc(F)c(F)c1] | 5-(2-((3,4-difluorophenyl)amino)-2-oxoacetyl)-1,2,4-trimethyl-N-(3,4,5-trifluorophenyl)-1H-pyrrole-3-carboxamide | 466.1 |
| 323 | 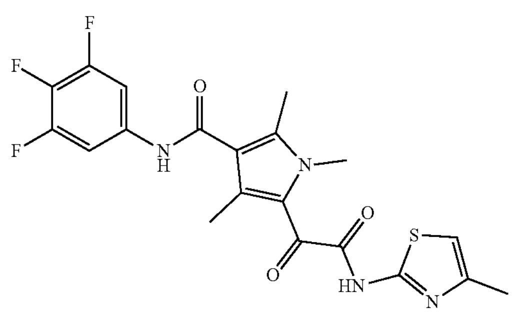 [SMILES: Cc1csc(NC(=O)C(=O)c2c(C)c(C(=O)Nc3cc(F)c(F)c(F)c3)c(C)n2C)n1] | 1,2,4-trimethyl-5-(2-((4-methylthiazol-2-yl)amino)-2-oxoacetyl)-N-(3,4,5-trifluorophenyl)-1H-pyrrole-3-carboxamide | 451.1 |
| 324 | 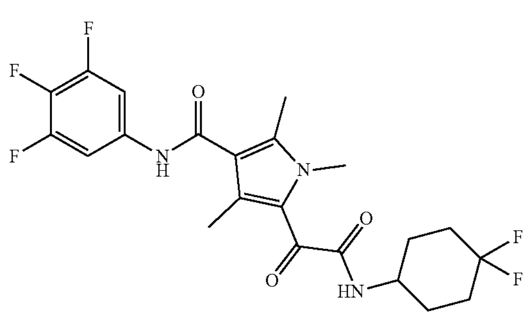 [SMILES: Cc1c(C(=O)Nc2cc(F)c(F)c(F)c2)c(C)n(C)c1C(=O)C(=O)NC1CCC(F)(F)CC1] | 5-(2-((4,4-difluorocyclohexyl)amino)-2-oxoacetyl)-1,2,4-trimethyl-N-(3,4,5-trifluorophenyl)-1H-pyrrole-3-carboxamide | 472.2 |

TABLE 1-continued

Exemplary compounds

| Ex. | Structure | Chemical Name | ESI-MS (M + H)+ (m/z) |
|---|---|---|---|
| 325 | 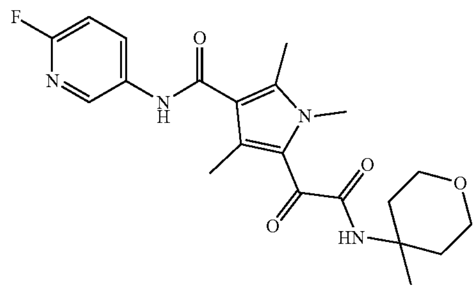 [SMILES: Cc1c(C(=O)Nc2ccc(F)nc2)c(C)n(C)c1C(=O)C(=O)NC1(C)CCOCC1] | N-(6-fluoropyridin-3-yl)-1,2,4-trimethyl-5-(2-((4-methyltetrahydro-2H-pyran-4-yl)amino)-2-oxoacetyl)-1H-pyrrole-3-carboxamide | 417.2 |
| 326 | 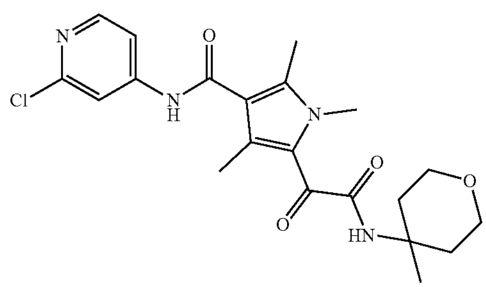 [SMILES: Cc1c(C(=O)Nc2ccnc(Cl)c2)c(C)n(C)c1C(=O)C(=O)NC1(C)CCOCC1] | N-(2-chloropyridin-4-yl)-1,2,4-trimethyl-5-(2-((4-methyltetrahydro-2H-pyran-4-yl)amino)-2-oxoacetyl)-1H-pyrrole-3-carboxamide | 433.2 |
| 327 | 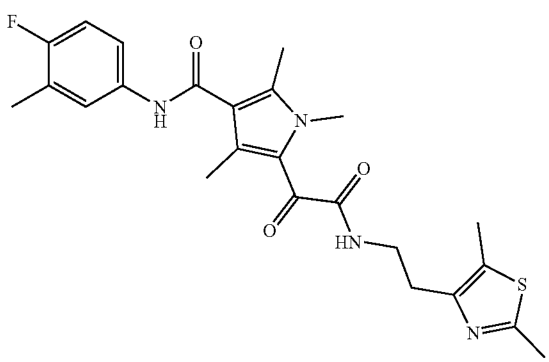 | 5-(2-((2-(2,5-dimethylthiazol-4-yl)ethyl)amino)-2-oxoacetyl)-N-(4-fluoro-3-methylphenyl)-1,2,4-trimethyl-1H-pyrrole-3-carboxamide | 471.2 |
| 328 | 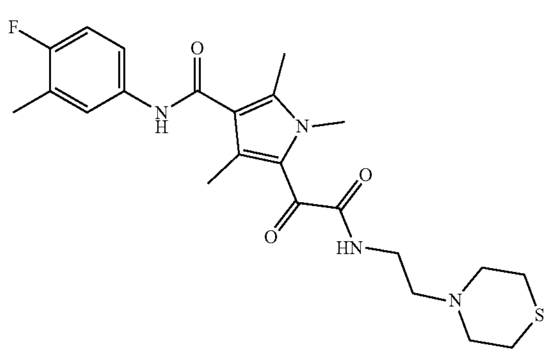 [SMILES: Cc1cc(NC(=O)c2c(C)c(C(=O)C(=O)NCCN3CCSCC3)n(C)c2C)ccc1F] | N-(4-fluoro-3-methylphenyl)-1,2,4-trimethyl-5-(2-oxo-2-((2-thiomorpholinoethyl)amino)acetyl)-1H-pyrrole-3-carboxamide | 461.2 |

TABLE 1-continued

Exemplary compounds

| Ex. | Structure | Chemical Name | ESI-MS (M + H)+ (m/z) |
|---|---|---|---|
| 329 | 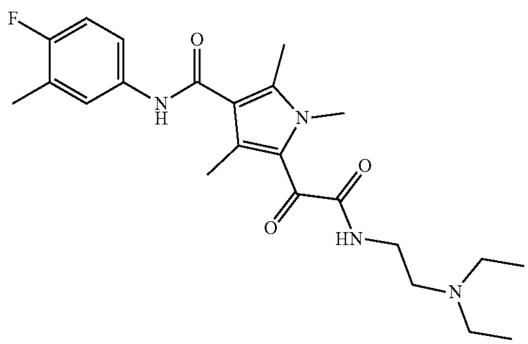 [SMILES: CCN(CC)CCNC(=O)C(=O)c1c(C)c(C(=O)Nc2ccc(F)c(C)c2)c(C)n1C] | 5-(2-((2-(diethylamino)ethyl)amino)-2-oxoacetyl)-N-(4-fluoro-3-methylphenyl)-1,2,4-trimethyl-1H-pyrrole-3-carboxamide | 431.3 |
| 330 | 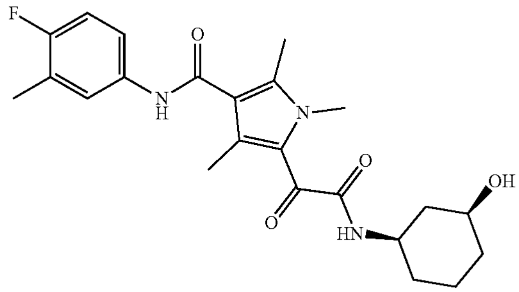 [SMILES: Cc1cc(NC(=O)c2c(C)c(C(=O)C(=O)N[C@@H]3CCC[C@H](O)C3)n(C)c2C)ccc1F] | N-(4-fluoro-3-methylphenyl)-5-(2-(((1R,3S)-3-hydroxycyclohexyl)amino)-2-oxoacetyl)-1,2,4-trimethyl-1H-pyrrole-3-carboxamide | 430.2 |
| 331 | 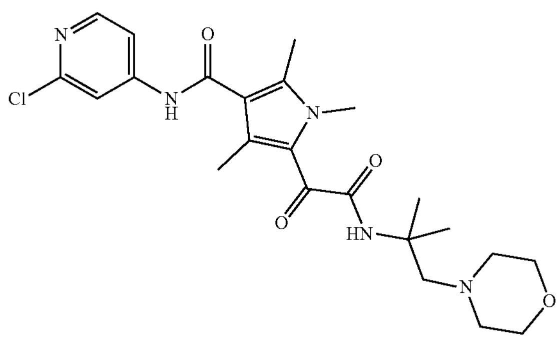 [SMILES: Cc1c(C(=O)Nc2ccnc(Cl)c2)c(C)n(C)c1C(=O)C(=O)NC(C)(C)CN1CCOCC1] | N-(2-chloropyridin-4-yl)-1,2,4-trimethyl-5-(2-((2-methyl-1-morpholinopropan-2-yl)amino)-2-oxoacetyl)-1H-pyrrole-3-carboxamide | 476.2 |
| 332 | 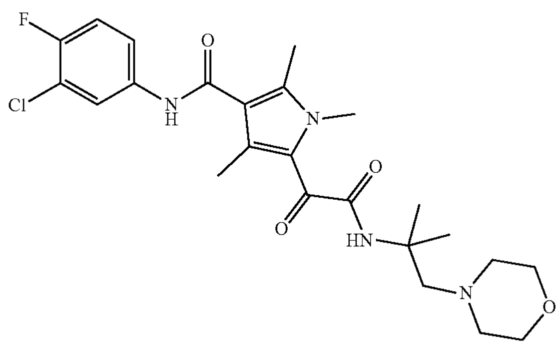 [SMILES: Cc1c(C(=O)Nc2ccc(F)c(Cl)c2)c(C)n(C)c1C(=O)C(=O)NC(C)(C)CN1CCOCC1] | N-(3-chloro-4-fluorophenyl)-1,2,4-trimethyl-5-(2-((2-methyl-1-morpholinopropan-2-yl)amino)-2-oxoacetyl)-1H-pyrrole-3-carboxamide | 493.2 |

TABLE 1-continued

Exemplary compounds

| Ex. | Structure | Chemical Name | ESI-MS (M + H)+ (m/z) |
|---|---|---|---|
| 333 | 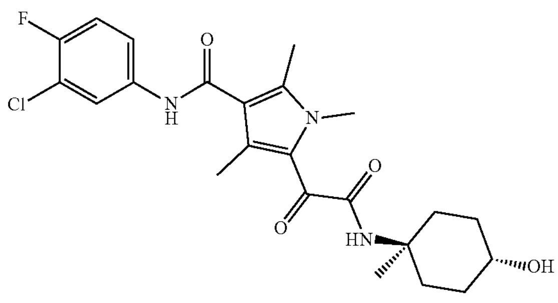 [SMILES: Cc1c(C(=O)Nc2ccc(F)c(Cl)c2)c(C)n(C)c1C(=O)C(=O)N[C@]1(C)CC[C@@H](O)CC1] | N-(3-chloro-4-fluorophenyl)-5-(2-(((1r,4r)-4-hydroxy-1-methylcyclohexyl)amino)-2-oxoacetyl)-1,2,4-trimethyl-1H-pyrrole-3-carboxamide | 464.2 |
| 334 | 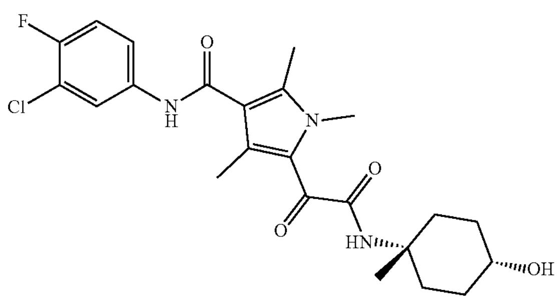 [SMILES: Cc1c(C(=O)Nc2ccc(F)c(Cl)c2)c(C)n(C)c1C(=O)C(=O)N[C@]1(C)CC[C@H](O)CC1] | N-(3-chloro-4-fluorophenyl)-5-(2-(((1s,4s)-4-hydroxy-1-methylcyclohexyl)amino)-2-oxoacetyl)-1,2,4-trimethyl-1H-pyrrole-3-carboxamide | 464.2 |
| 335 | 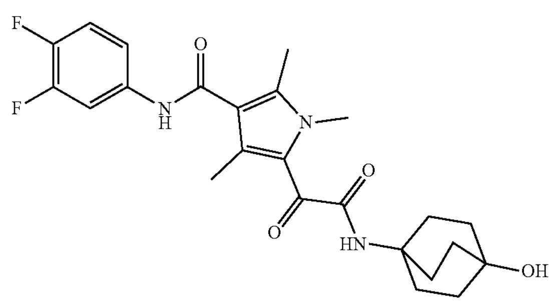 [SMILES: Cc1c(C(=O)Nc2ccc(F)c(F)c2)c(C)n(C)c1C(=O)C(=O)NC12CCC(O)(CC1)CC2] | N-(3,4-difluorophenyl)-5-(2-((4-hydroxybicyclo[2.2.2]octan-1-yl)amino)-2-oxoacetyl)-1,2,4-trimethyl-1H-pyrrole-3-carboxamide | 460.2 |
| 336 | 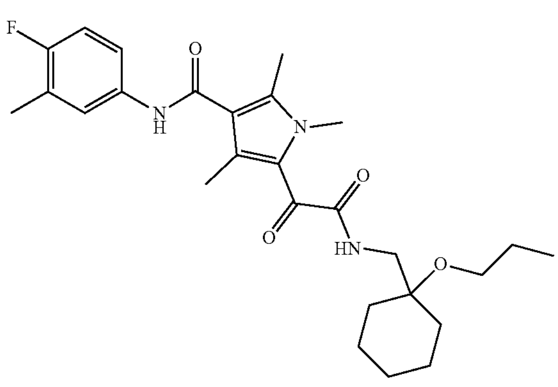 [SMILES: CCCOC1(CNC(=O)C(=O)c2c(C)c(C(=O)Nc3ccc(F)c(C)c3)c(C)n2C)CCCCC1] | N-(4-fluoro-3-methylphenyl)-1,2,4-trimethyl-5-(2-oxo-2-(((1-propoxycyclohexyl)methyl)amino)acetyl)-1H-pyrrole-3-carboxamide | 486.2 |

TABLE 1-continued

Exemplary compounds

| Ex. | Structure | Chemical Name | ESI-MS (M + H)+ (m/z) |
|---|---|---|---|
| 337 | 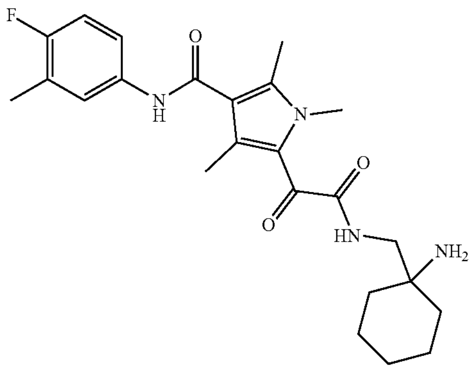 [SMILES: Cc1cc(NC(=O)c2c(C)c(C(=O)C(=O)NCC3(N)CCCCC3)n(C)c2C)ccc1F] | 5-(2-(((1-aminocyclohexyl)methyl)amino)-2-oxoacetyl)-N-(4-fluoro-3-methylphenyl)-1,2,4-trimethyl-1H-pyrrole-3-carboxamide | 443.2 |
| 338 | 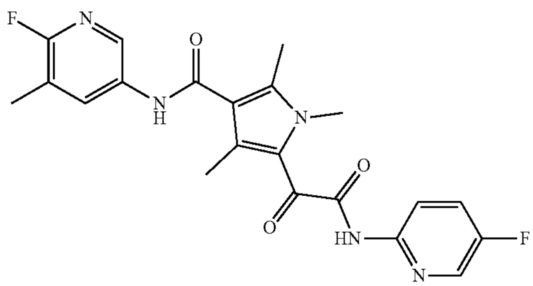 [SMILES: Cc1cc(NC(=O)c2c(C)c(C(=O)C(=O)Nc3ccc(F)cn3)n(C)c2C)cnc1F] | N-(6-fluoro-5-methylpyridin-3-yl)-5-(2-((5-fluoropyridin-2-yl)amino)-2-oxoacetyl)-1,2,4-trimethyl-1H-pyrrole-3-carboxamide | 428.2 |
| 339 | 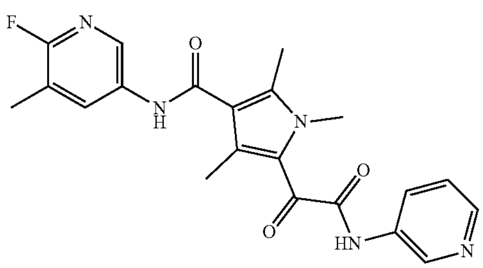 [SMILES: Cc1cc(NC(=O)c2c(C)c(C(=O)C(=O)Nc3cccnc3)n(C)c2C)cnc1F] | N-(6-fluoro-5-methylpyridin-3-yl)-1,2,4-trimethyl-5-(2-oxo-2-(pyridin-3-ylamino)acetyl)-1H-pyrrole-3-carboxamide | 410.2 |
| 340 | 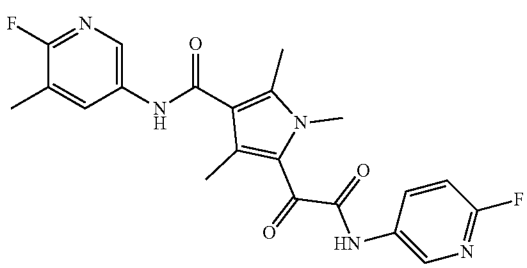 [SMILES: Cc1cc(NC(=O)c2c(C)c(C(=O)C(=O)Nc3ccc(F)nc3)n(C)c2C)cnc1F] | N-(6-fluoro-5-methylpyridin-3-yl)-5-(2-((6-fluoropyridin-3-yl)amino)-2-oxoacetyl)-1,2,4-trimethyl-1H-pyrrole-3-carboxamide | 428.2 |
| 341 | 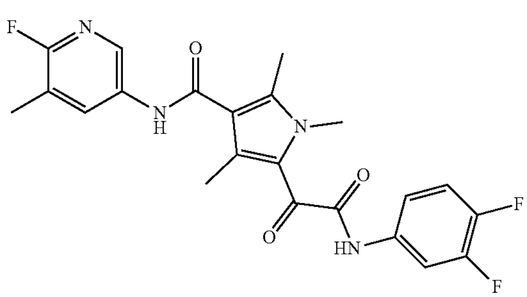 [SMILES: Cc1cc(NC(=O)c2c(C)c(C(=O)C(=O)Nc3ccc(F)c(F)c3)n(C)c2C)cnc1F] | 5-(2-((3,4-difluorophenyl)amino)-2-oxoacetyl)-N-(6-fluoro-5-methylpyridin-3-yl)-1,2,4-trimethyl-1H-pyrrole-3-carboxamide | 445.2 |

TABLE 1-continued

Exemplary compounds

| Ex. | Structure | Chemical Name | ESI-MS (M + H)+ (m/z) |
|---|---|---|---|
| 342 | 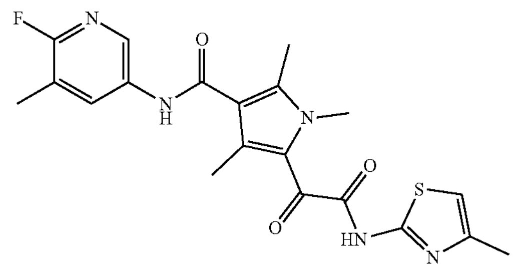 | N-(6-fluoro-5-methylpyridin-3-yl)-1,2,4-trimethyl-5-(2-((4-methylthiazol-2-yl)amino)-2-oxoacetyl)-1H-pyrrole-3-carboxamide | 430.1 |
| 343 | 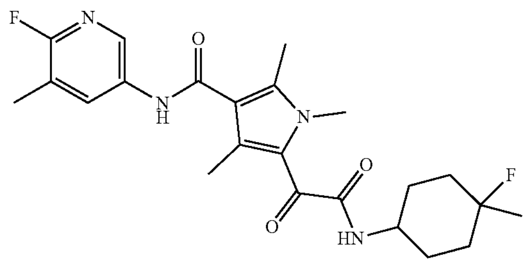 | 5-(2-((4,4-difluorocyclohexyl)amino)-2-oxoacetyl)-N-(6-fluoro-5-methylpyridin-3-yl)-1,2,4-trimethyl-1H-pyrrole-3-carboxamide | 451.2 |
| 344 | 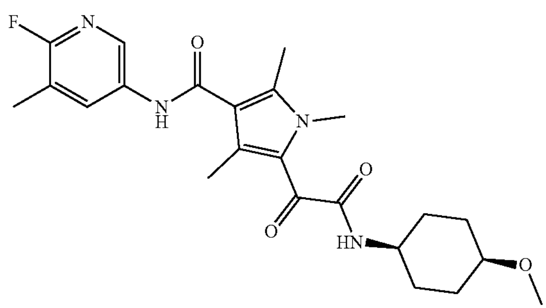 | N-(6-fluoro-5-methylpyridin-3-yl)-5-(2-(((1s,4s)-4-methoxycyclohexyl)amino)-2-oxoacetyl)-1,2,4-trimethyl-1H-pyrrole-3-carboxamide | 445.3 |
| 345 | 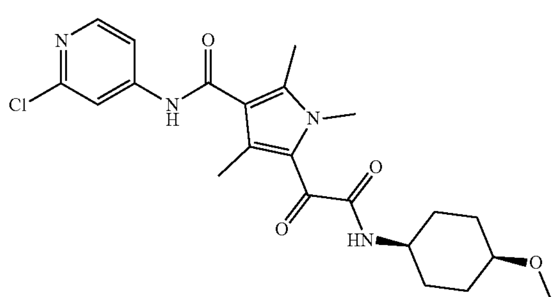 | N-(2-chloropyridin-4-yl)-5-(2-(((1s,4s)-4-methoxycyclohexyl)amino)-2-oxoacetyl)-1,2,4-trimethyl-1H-pyrrole-3-carboxamide | 447.2 |
| 346 | 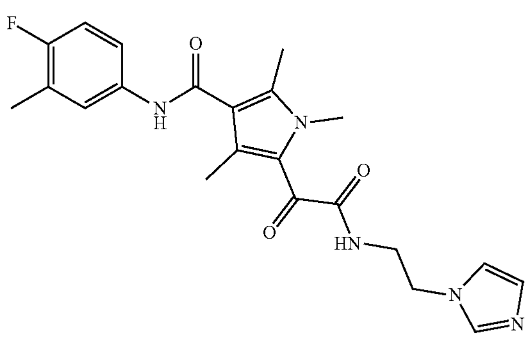 [SMILES: Cc1cc(NC(=O)c2c(C)c(C(=O)C(=O)NCCn3ccnc3)n(C)c2C)ccc1F] | 5-(2-((2-(1H-imidazol-1-yl)ethyl)amino)-2-oxoacetyl)-N-(4-fluoro-3-methylphenyl)-1,2,4-trimethyl-1H-pyrrole-3-carboxamide | 426.2 |

TABLE 1-continued

Exemplary compounds

| Ex. | Structure | Chemical Name | ESI-MS (M + H)+ (m/z) |
|---|---|---|---|
| 347 | 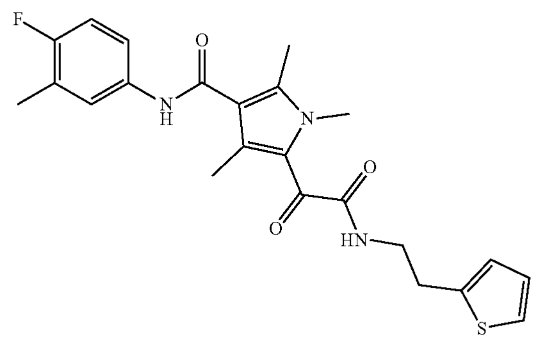 [SMILES: Cc1cc(NC(=O)c2c(C)c(C(=O)C(=O)NCCc3cccs3)n(C)c2C)ccc1F] | N-(4-fluoro-3-methylphenyl)-1,2,4-trimethyl-5-(2-oxo-2-((2-(thiophen-2-yl)ethyl)amino)acetyl)-1H-pyrrole-3-carboxamide | 442.2 |
| 348 | 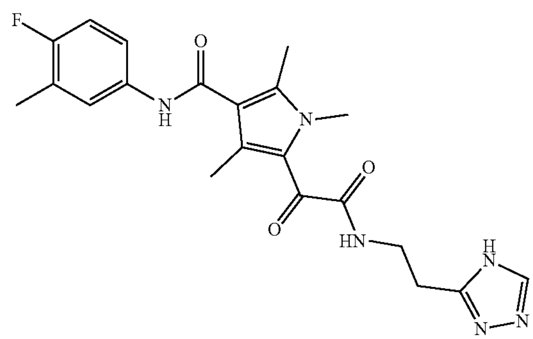 [SMILES: Cc1cc(NC(=O)c2c(C)c(C(=O)C(=O)NCCc3nnc[nH]3)n(C)c2C)ccc1F] | 5-(2-((2-(4H-1,2,4-triazol-3-yl)ethyl)amino)-2-oxoacetyl)-N-(4-fluoro-3-methylphenyl)-1,2,4-trimethyl-1H-pyrrole-3-carboxamide | 427.2 |
| 349 | 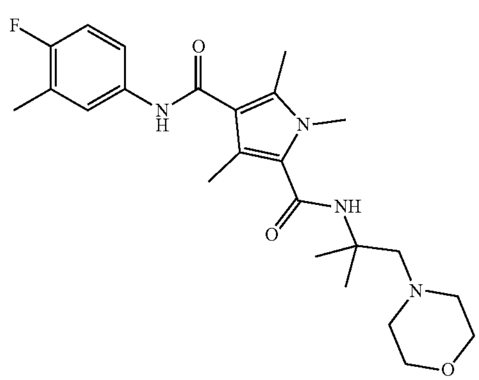 [SMILES: Cc1cc(NC(=O)c2c(C)c(C(=O)NC(C)(C)CN3CCOCC3)n(C)c2C)ccc1F] | N4-(4-fluoro-3-methylphenyl)-1,3,5-trimethyl-N2-(2-methyl-1-morpholinopropan-2-yl)-1H-pyrrole-2,4-dicarboxamide | 445.1 |
| 350 | 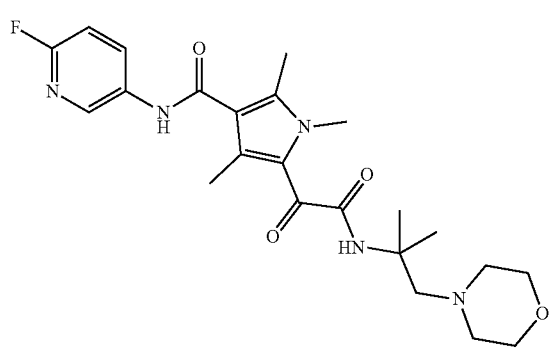 [SMILES: Cc1c(C(=O)Nc2ccc(F)nc2)c(C)n(C)c1C(=O)C(=O)NC(C)(C)CN1CCOCC1] | N-(6-fluoropyridin-3-yl)-1,2,4-trimethyl-5-(2-((2-methyl-1-morpholinopropan-2-yl)amino)-2-oxoacetyl)-1H-pyrrole-3-carboxamide | 460.3 |

TABLE 1-continued

Exemplary compounds

| Ex. | Structure | Chemical Name | ESI-MS (M + H)+ (m/z) |
|---|---|---|---|
| 351 | 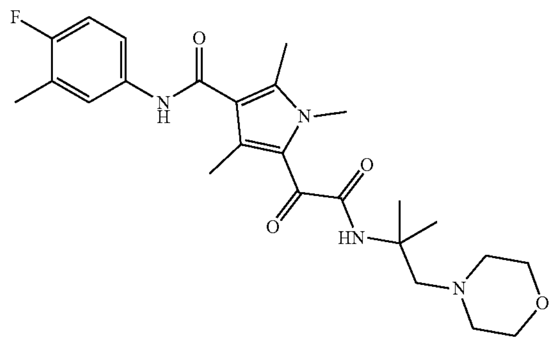 [SMILES: Cc1cc(NC(=O)c2c(C)c(C(=O)C(=O)NC(C)(C)CN3CCOCC3)n(C)c2C)ccc1F] | N-(6-fluoro-5-methylpyridin-3-yl)-1,2,4-trimethyl-5-(2-((2-methyl-1-morpholinopropan-2-yl)amino)-2-oxoacetyl)-1H-pyrrole-3-carboxamide | 474.3 |
| 352 | 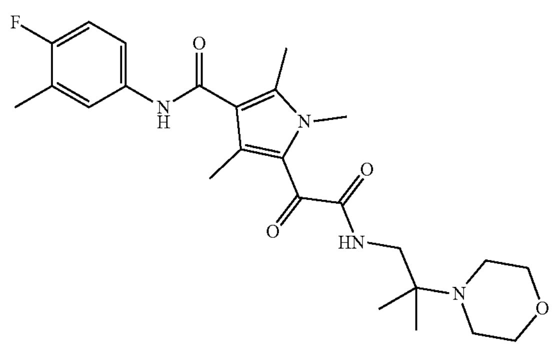 [SMILES: Cc1cc(NC(=O)c2c(C)c(C(=O)C(=O)NCC(C)(C)N3CCOCC3)n(C)c2C)ccc1F] | N-(4-fluoro-3-methylphenyl)-1,2,4-trimethyl-5-(2-((2-methyl-2-morpholinopropyl)amino)-2-oxoacetyl)-1H-pyrrole-3-carboxamide | 473.3 |
| 353 | 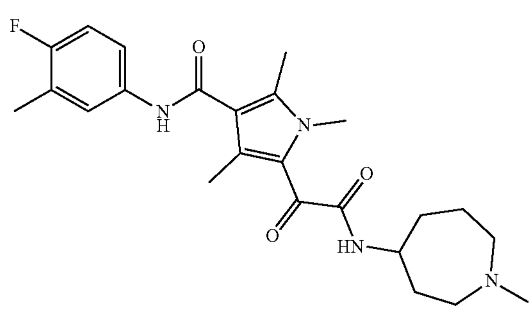 [SMILES: Cc1cc(NC(=O)c2c(C)c(C(=O)C(=O)NC3CCCN(C)CC3)n(C)c2C)ccc1F] | N-(4-fluoro-3-methylphenyl)-1,2,4-trimethyl-5-(2-((1-methylazepan-4-yl)amino)-2-oxoacetyl)-1H-pyrrole-3-carboxamide | 443.2 |
| 354 | 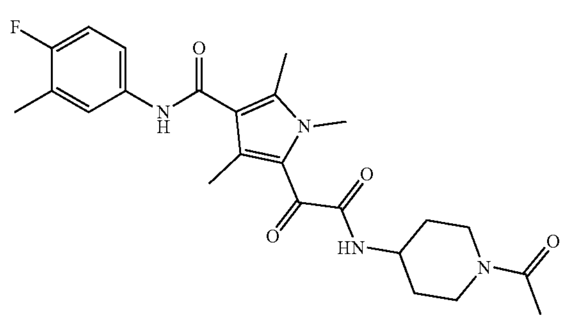 [SMILES: CC(=O)N1CCC(NC(=O)C(=O)c2c(C)c(C(=O)Nc3ccc(F)c(C)c3)c(C)n2C)CC1] | 5-(2-((1-acetylpiperidin-4-yl)amino)-2-oxoacetyl)-N-(4-fluoro-3-methylphenyl)-1,2,4-trimethyl-1H-pyrrole-3-carboxamide | 457.3 |

TABLE 1-continued

Exemplary compounds

| Ex. | Structure | Chemical Name | ESI-MS (M + H)+ (m/z) |
|---|---|---|---|
| 355 | 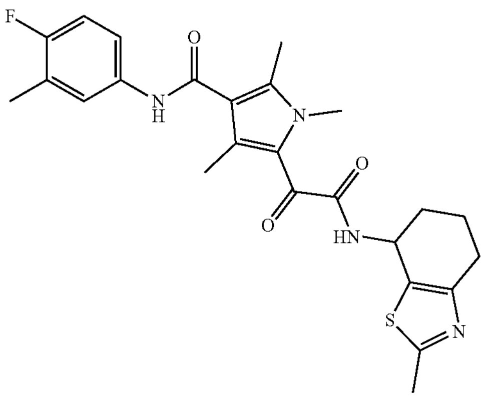 [SMILES: Cc1nc2c(s1)C(NC(=O)C(=O)c1c(C)c(C(=O)Nc3ccc(F)c(C)c3)c(C)n1C)CCC2] | N-(4-fluoro-3-methylphenyl)-1,2,4-trimethyl-5-(2-((2-methyl-4,5,6,7-tetrahydrobenzo[d]thiazol-7-yl)amino)-2-oxoacetyl)-1H-pyrrole-3-carboxamide | 483.2 |
| 356 | 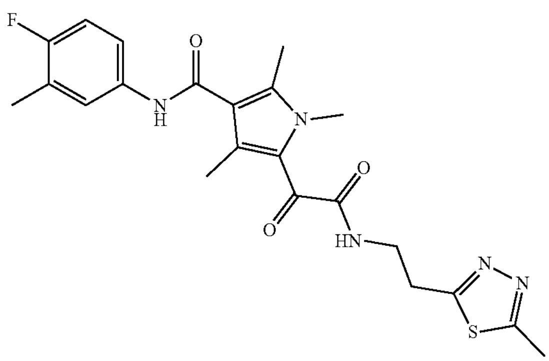 [SMILES: Cc1nnc(CCNC(=O)C(=O)c2c(C)c(C(=O)Nc3ccc(F)c(C)c3)c(C)n2C)s1] | N-(4-fluoro-3-methylphenyl)-1,2,4-trimethyl-5-(2-((2-(5-methyl-1,3,4-thiadiazol-2-yl)ethyl)amino)-2-oxoacetyl)-1H-pyrrole-3-carboxamide | 458.2 |
| 357 | 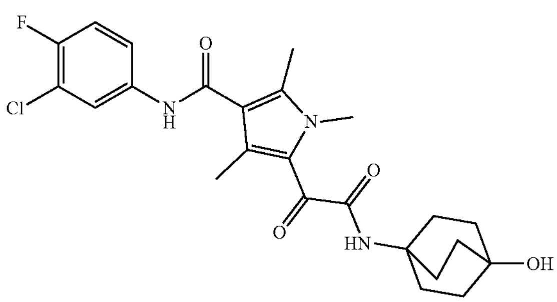 [SMILES: Cc1c(C(=O)Nc2ccc(F)c(Cl)c2)c(C)n(C)c1C(=O)C(=O)NC12CCC(O)(CC1)CC2] | N-(3-chloro-4-fluorophenyl)-5-(2-((4-hydroxybicyclo[2.2.2]octan-1-yl)amino)-2-oxoacetyl)-1,2,4-trimethyl-1H-pyrrole-3-carboxamide | 476.2 |
| 358 | 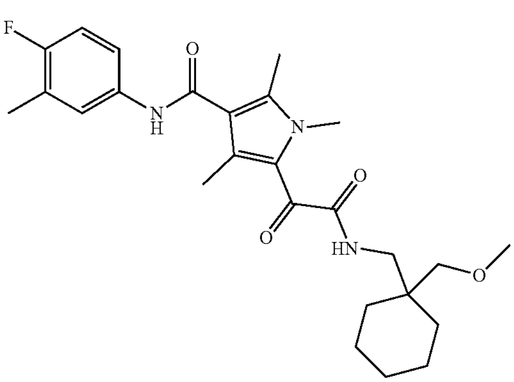 | N-(4-fluoro-3-methylphenyl)-5-(2-(((1-(methoxymethyl)cyclohexyl)methyl)amino)-2-oxoacetyl)-1,2,4-trimethyl-1H-pyrrole-3-carboxamide | 472.2 |

TABLE 1-continued

Exemplary compounds

| Ex. | Structure | Chemical Name | ESI-MS (M + H)+ (m/z) |
|---|---|---|---|
| 359 | 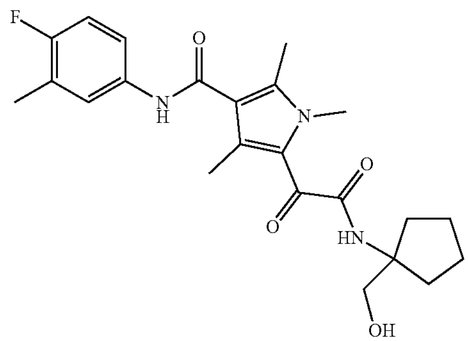 [SMILES: Cc1cc(NC(=O)c2c(C)c(C(=O)C(=O)NC3(CO)CCCC3)n(C)c2C)ccc1F] | N-(4-fluoro-3-methylphenyl)-5-(2-((1-(hydroxymethyl)cyclopentyl)amino)-2-oxoacetyl)-1,2,4-trimethyl-1H-pyrrole-3-carboxamide | 430.2 |
| 360 | 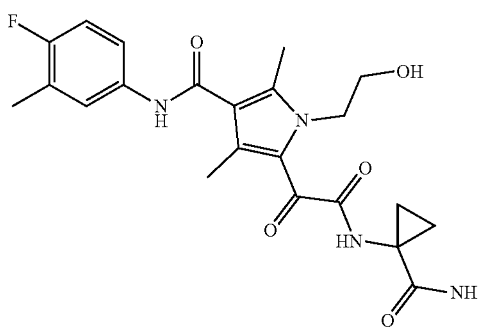 [SMILES: Cc1cc(NC(=O)c2c(C)c(C(=O)C(=O)NC3(C(N)=O)CC3)n(CCO)c2C)ccc1F] | 5-(2-((1-carbamoylcyclopropyl)amino)-2-oxoacetyl)-N-(4-fluoro-3-methylphenyl)-1-(2-hydroxyethyl)-2,4-dimethyl-1H-pyrrole-3-carboxamide | |
| 361 | 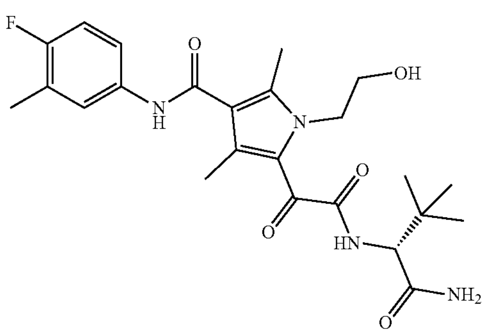 [SMILES: Cc1cc(NC(=O)c2c(C)c(C(=O)C(=O)N[C@@H](C(N)=O)C(C)(C)C)n(CCO)c2C)ccc1F] | (R)-5-(2-((1-amino-3,3-dimethyl-1-oxobutan-2-yl)amino)-2-oxoacetyl)-N-(4-fluoro-3-methylphenyl)-1-(2-hydroxyethyl)-2,4-dimethyl-1H-pyrrole-3-carboxamide | |
| 362 | 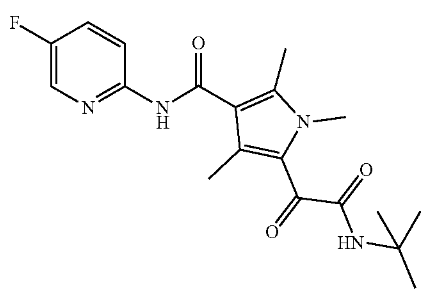 [SMILES: Cc1c(C(=O)Nc2ccc(F)cn2)c(C)n(C)c1C(=O)C(=O)NC(C)(C)C] | 5-(2-(tert-butylamino)-2-oxoacetyl)-N-(5-fluoropyridin-2-yl)-1,2,4-trimethyl-1H-pyrrole-3-carboxamide | |

TABLE 1-continued

Exemplary compounds

| Ex. | Structure | Chemical Name | ESI-MS (M + H)+ (m/z) |
|---|---|---|---|
| 363 | 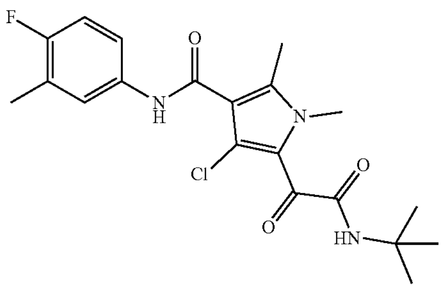 [SMILES: Cc1cc(NC(=O)c2c(Cl)c(C(=O)C(=O)NC(C)(C)C)n(C)c2C)ccc1F] | 5-(2-(tert-butylamino)-2-oxoacetyl)-4-chloro-N-(4-fluoro-3-methylphenyl)-1,2-dimethyl-1H-pyrrole-3-carboxamide | 408.2 |
| 364 | 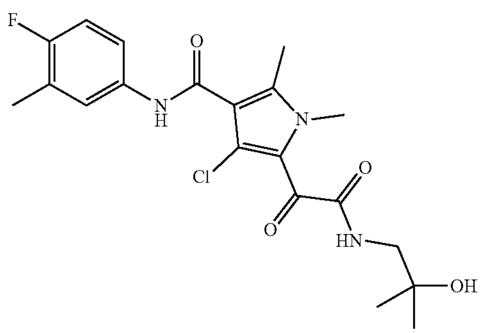 [SMILES: Cc1cc(NC(=O)c2c(Cl)c(C(=O)C(=O)NCC(C)(C)O)n(C)c2C)ccc1F] | 4-chloro-N-(4-fluoro-3-methylphenyl)-5-(2-((2-hydroxy-2-methylpropyl)amino)-2-oxoacetyl)-1,2-dimethyl-1H-pyrrole-3-carboxamide | 422.2 |
| 365 | 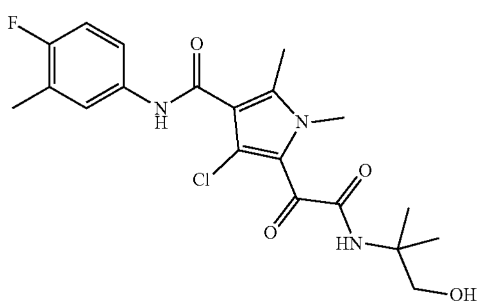 [SMILES: Cc1cc(NC(=O)c2c(Cl)c(C(=O)C(=O)NC(C)(C)CO)n(C)c2C)ccc1F] | 4-chloro-N-(4-fluoro-3-methylphenyl)-5-(2-((1-hydroxy-2-methylpropan-2-yl)amino)-2-oxoacetyl)-1,2-dimethyl-1H-pyrrole-3-carboxamide | 422.1 |
| 366 | 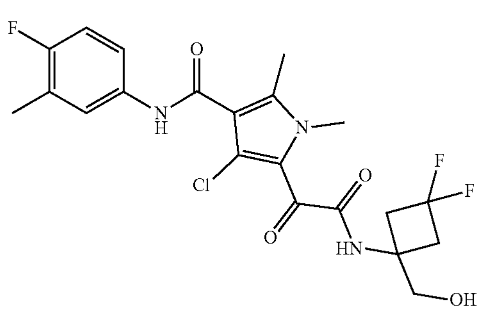 [SMILES: Cc1cc(NC(=O)c2c(Cl)c(C(=O)C(=O)NC3(CO)CC(F)(F)C3)n(C)c2C)ccc1F] | 4-chloro-5-(2-((3,3-difluoro-1-(hydroxymethyl)cyclobutyl)amino)-2-oxoacetyl)-N-(4-fluoro-3-methylphenyl)-1,2-dimethyl-1H-pyrrole-3-carboxamide | 502.1 |

TABLE 1-continued

Exemplary compounds

| Ex. | Structure | Chemical Name | ESI-MS (M + H)+ (m/z) |
|---|---|---|---|
| 367 | 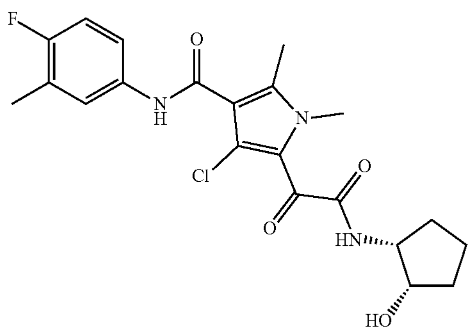 [SMILES: Cc1cc(NC(=O)c2c(Cl)c(C(=O)C(=O)N[C@@H]3CCC[C@@H]3O)n(C)c2C)ccc1F] | 4-chloro-N-(4-fluoro-3-methylphenyl)-5-(2-(((1R,2S)-2-hydroxycyclopentyl)amino)-2-oxoacetyl)-1,2-dimethyl-1H-pyrrole-3-carboxamide | 466.2 |
| 368 | 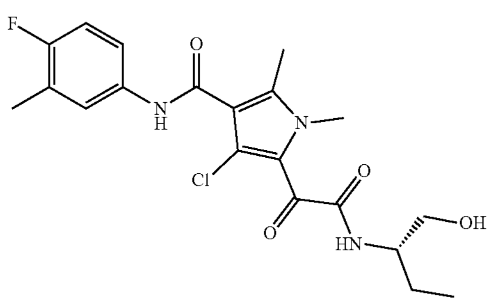 [SMILES: CC[C@@H](CO)NC(=O)C(=O)c1c(Cl)c(C(=O)Nc2ccc(F)c(C)c2)c(C)n1C] | (S)-4-chloro-N-(4-fluoro-3-methylphenyl)-5-(2-((1-hydroxybutan-2-yl)amino)-2-oxoacetyl)-1,2-dimethyl-1H-pyrrole-3-carboxamide | 454.2 |
| 369 | 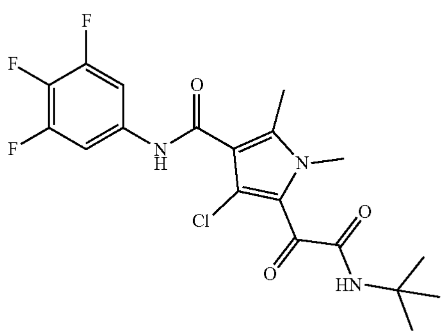 [SMILES: Cc1c(C(=O)Nc2cc(F)c(F)c(F)c2)c(Cl)c(C(=O)C(=O)NC(C)(C)C)n1C] | 5-(2-(tert-butylamino)-2-oxoacetyl)-4-chloro-1,2-dimethyl-N-(3,4,5-trifluorophenyl)-1H-pyrrole-3-carboxamide | 428.1 |
| 370 | 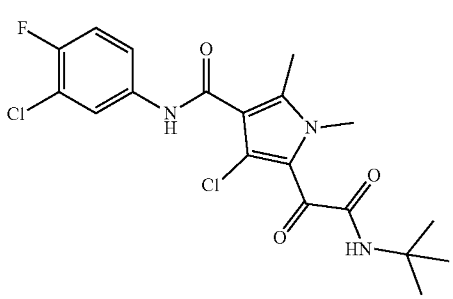 [SMILES: Cc1c(C(=O)Nc2ccc(F)c(Cl)c2)c(Cl)c(C(=O)C(=O)NC(C)(C)C)n1C] | 5-(2-(tert-butylamino)-2-oxoacetyl)-4-chloro-N-(3-chloro-4-fluorophenyl)-1,2-dimethyl-1H-pyrrole-3-carboxamide | 426.1 |

TABLE 1-continued

Exemplary compounds

| Ex. | Structure | Chemical Name | ESI-MS (M + H)+ (m/z) |
|---|---|---|---|
| 371 | 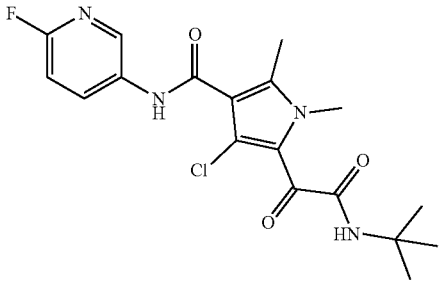 [SMILES: Cc1c(C(=O)Nc2ccc(F)nc2)c(Cl)c(C(=O)C(=O)NC(C)(C)C)n1C] | 5-(2-(tert-butylamino)-2-oxoacetyl)-4-chloro-N-(6-fluoro-5-methylpyridin-3-yl)-1,2-dimethyl-1H-pyrrole-3-carboxamide | 439.2 |
| 372 | 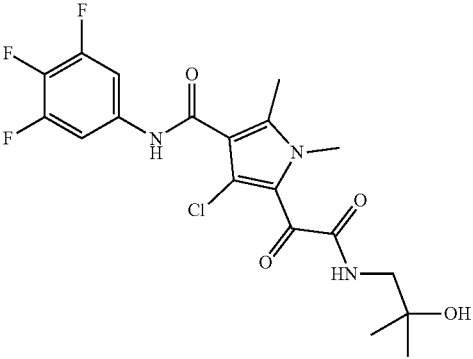 [SMILES: Cc1c(C(=O)Nc2cc(F)c(F)c(F)c2)c(Cl)c(C(=O)C(=O)NCC(C)(C)O)n1C] | 4-chloro-5-(2-((2-hydroxy-2-methylpropyl)amino)-2-oxoacetyl)-1,2-dimethyl-N-(3,4,5-trifluorophenyl)-1H-pyrrole-3-carboxamide | 444.1 |
| 373 | 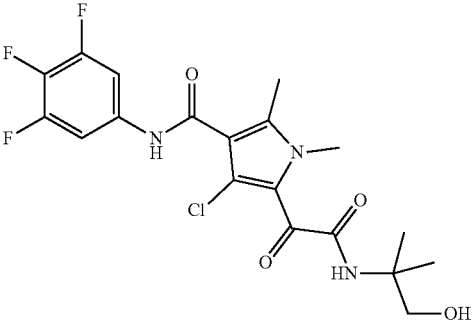 [SMILES: Cc1c(C(=O)Nc2cc(F)c(F)c(F)c2)c(Cl)c(C(=O)C(=O)NC(C)(C)CO)n1C] | 4-chloro-5-(2-((1-hydroxy-2-methylpropan-2-yl)amino)-2-oxoacetyl)-1,2-dimethyl-N-(3,4,5-trifluorophenyl)-1H-pyrrole-3-carboxamide | 444.1 |
| 374 | 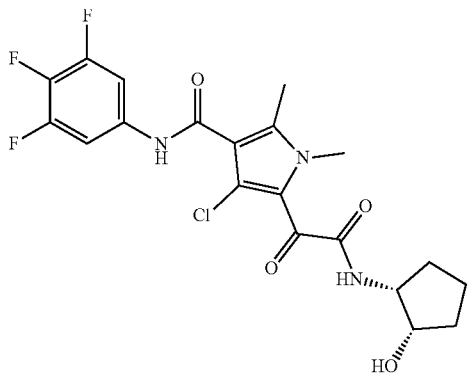 [SMILES: Cc1c(C(=O)Nc2cc(F)c(F)c(F)c2)c(Cl)c(C(=O)C(=O)N[C@@H]2CCC[C@@H]2O)n1C] | 4-chloro-5-(2-(((1R,2S)-2-hydroxycyclopentyl)amino)-2-oxoacetyl)-1,2-dimethyl-N-(3,4,5-trifluorophenyl)-1H-pyrrole-3-carboxamide | 456.1 |

TABLE 1-continued

Exemplary compounds

| Ex. | Structure | Chemical Name | ESI-MS (M + H)+ (m/z) |
|---|---|---|---|
| 375 | 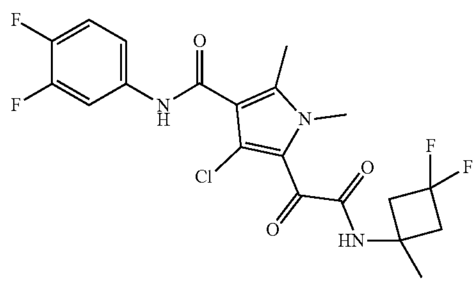 [SMILES: Cc1c(C(=O)Nc2ccc(F)c(F)c2)c(Cl)c(C(=O)C(=O)NC2(C)CC(F)(F)C2)n1C] | 4-chloro-5-(2-((3,3-difluoro-1-methylcyclobutyl)amino)-2-oxoacetyl)-N-(3,4-difluorophenyl)-1,2-dimethyl-1H-pyrrole-3-carboxamide | 458.1 |
| 376 | 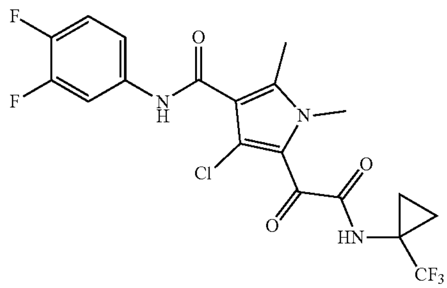 [SMILES: Cc1c(C(=O)Nc2ccc(F)c(F)c2)c(Cl)c(C(=O)C(=O)NC2(C(F)(F)F)CC2)n1C] | 4-chloro-N-(3,4-difluorophenyl)-1,2-dimethyl-5-(2-oxo-2-((1-(trifluoromethyl)cyclopropyl)amino)acetyl)-1H-pyrrole-3-carboxamide | 460.2 |
| 377 | 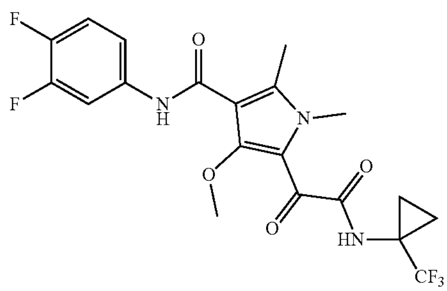 [SMILES: COc1c(C(=O)Nc2ccc(F)c(F)c2)c(C)n(C)c1C(=O)C(=O)NC1(C(F)(F)F)CC1] | N-(3,4-difluorophenyl)-4-methoxy-1,2-dimethyl-5-(2-oxo-2-((1-(trifluoromethyl)cyclopropyl)amino)acetyl)-1H-pyrrole-3-carboxamide | 464.3 |
| 378 | 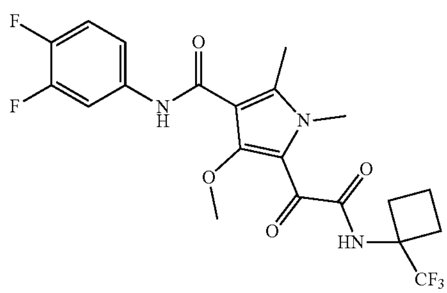 [SMILES: COc1c(C(=O)Nc2ccc(F)c(F)c2)c(C)n(C)c1C(=O)C(=O)NC1(C(F)(F)F)CCC1] | N-(3,4-difluorophenyl)-4-methoxy-1,2-dimethyl-5-(2-oxo-2-((1-(trifluoromethyl)cyclobutyl)amino)acetyl)-1H-pyrrole-3-carboxamide | 474.2 |
| 379 | 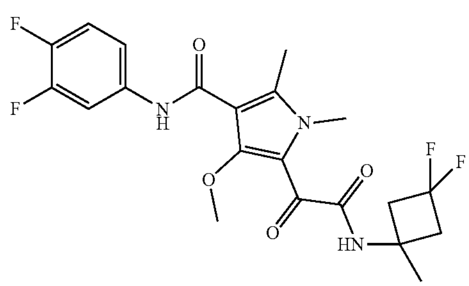 [SMILES: COc1c(C(=O)Nc2ccc(F)c(F)c2)c(C)n(C)c1C(=O)C(=O)NC1(C)CC(F)(F)C1] | 5-(2-((3,3-difluoro-1-methylcyclobutyl)amino)-2-oxoacetyl)-N-(3,4-difluorophenyl)-4-methoxy-1,2-dimethyl-1H-pyrrole-3-carboxamide | 456.2 |

TABLE 1-continued

Exemplary compounds

| Ex. | Structure | Chemical Name | ESI-MS (M + H)+ (m/z) |
| --- | --- | --- | --- |
| 380 | 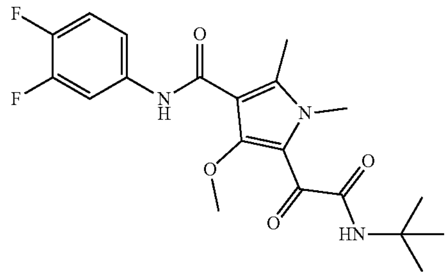 [SMILES: COc1c(C(=O)Nc2ccc(F)c(F)c2)c(C)n(C)c1C(=O)C(=O)NC(C)(C)C] | 5-(2-(tert-butylamino)-2-oxoacetyl)-N-(3,4-difluorophenyl)-4-methoxy-1,2-dimethyl-1H-pyrrole-3-carboxamide | 408.2 |
| 381 | 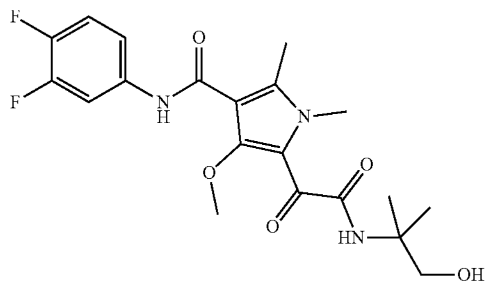 [SMILES: COc1c(C(=O)Nc2ccc(F)c(F)c2)c(C)n(C)c1C(=O)C(=O)NC(C)(C)CO] | N-(3,4-difluorophenyl)-5-(2-(((1-hydroxy-2-methylpropan-2-yl)amino)-2-oxoacetyl)-4-methoxy-1,2-dimethyl-1H-pyrrole-3-carboxamide | 424.2 |
| 382 | 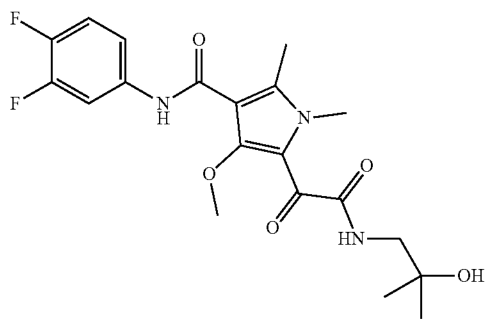 [SMILES: COc1c(C(=O)Nc2ccc(F)c(F)c2)c(C)n(C)c1C(=O)C(=O)NCC(C)(C)O] | N-(3,4-difluorophenyl)-5-(2-((2-hydroxy-2-methylpropyl)amino)-2-oxoacetyl)-4-methoxy-1,2-dimethyl-1H-pyrrole-3-carboxamide | 424.2 |
| 383 | 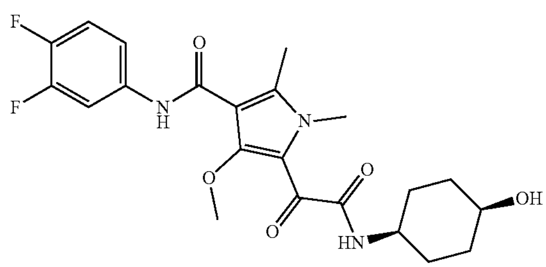 [SMILES: COc1c(C(=O)Nc2ccc(F)c(F)c2)c(C)n(C)c1C(=O)C(=O)N[C@H]1CC[C@@H](O)CC1] | N-(3,4-difluorophenyl)-5-(2-(((1s,4s)-4-hydroxycyclohexyl)amino)-2-oxoacetyl)-4-methoxy-1,2-dimethyl-1H-pyrrole-3-carboxamide | 449.2 |
| 384 | 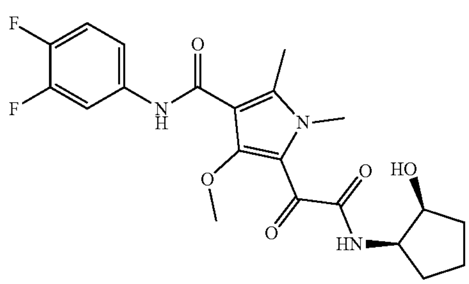 [SMILES: COc1c(C(=O)Nc2ccc(F)c(F)c2)c(C)n(C)c1C(=O)C(=O)N[C@@H]1CCC[C@@H]1O] | N-(3,4-difluorophenyl)-5-(2-(((1R,2S)-2-hydroxycyclopentyl)amino)-2-oxoacetyl)-4-methoxy-1,2-dimethyl-1H-pyrrole-3-carboxamide | 436.2 |

TABLE 1-continued

Exemplary compounds

| Ex. | Structure | Chemical Name | ESI-MS (M + H)+ (m/z) |
|---|---|---|---|
| 385 | 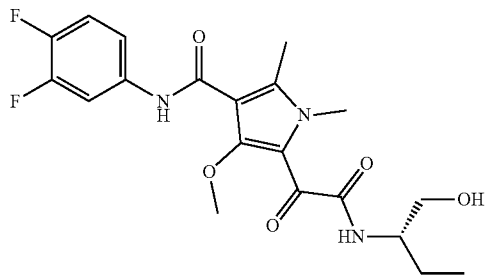 [SMILES: CC[C@@H](CO)NC(=O)C(=O)c1c(OC)c(C(=O)Nc2ccc(F)c(F)c2)c(C)n1C] | (S)-N-(3,4-difluorophenyl)-5-(2-((1-hydroxybutan-2-yl)amino)-2-oxoacetyl)-4-methoxy-1,2-dimethyl-1H-pyrrole-3-carboxamide | 424.2 |
| 386 | 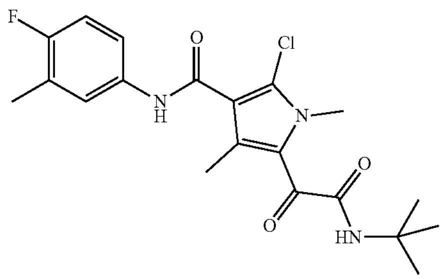 [SMILES: Cc1cc(NC(=O)c2c(C)c(C(=O)C(=O)NC(C)(C)C)n(C)c2Cl)ccc1F] | 5-(2-(tert-butylamino)-2-oxoacetyl)-2-chloro-N-(4-fluoro-3-methylphenyl)-1,4-dimethyl-1H-pyrrole-3-carboxamide | 481.2 |
| 387 | 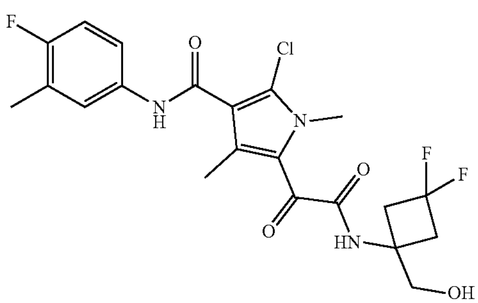 [SMILES: Cc1cc(NC(=O)c2c(C)c(C(=O)C(=O)NC3(CO)CC(F)(F)C3)n(C)c2Cl)ccc1F] | 2-chloro-5-(2-((3,3-difluoro-1-(hydroxymethyl)cyclobutyl)amino)-2-oxoacetyl)-N-(4-fluoro-3-methylphenyl)-1,4-dimethyl-1H-pyrrole-3-carboxamide | 494.1 |
| 388 | 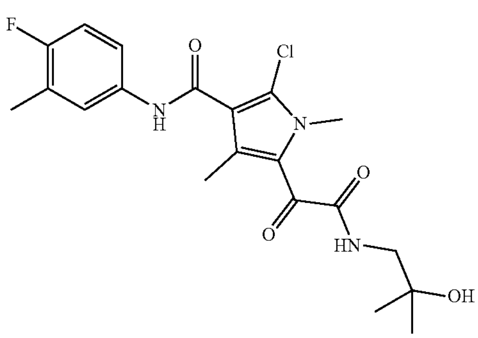 [SMILES: Cc1cc(NC(=O)c2c(C)c(C(=O)C(=O)NCC(C)(C)O)n(C)c2Cl)ccc1F] | 2-chloro-N-(4-fluoro-3-methylphenyl)-5-(2-((2-hydroxy-2-methylpropyl)amino)-2-oxoacetyl)-1,4-dimethyl-1H-pyrrole-3-carboxamide | 447.2 |
| 389 | 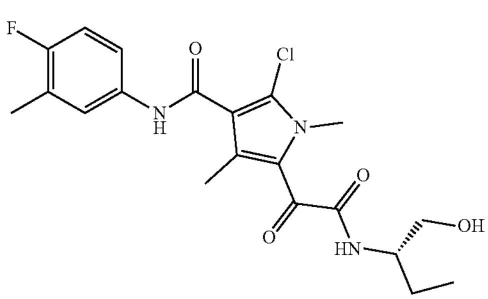 [SMILES: CC[C@@H](CO)NC(=O)C(=O)c1c(C)c(C(=O)Nc2ccc(F)c(C)c2)c(Cl)n1C] | (S)-2-chloro-N-(4-fluoro-3-methylphenyl)-5-(2-((1-hydroxybutan-2-yl)amino)-2-oxoacetyl)-1,4-dimethyl-1H-pyrrole-3-carboxamide | 447.2 |

TABLE 1-continued

Exemplary compounds

| Ex. | Structure | Chemical Name | ESI-MS (M + H)+ (m/z) |
|---|---|---|---|
| 390 | 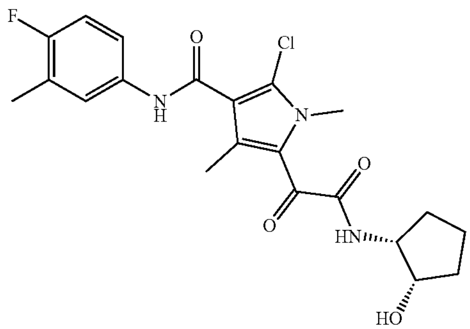 [SMILES: Cc1cc(NC(=O)c2c(C)c(C(=O)C(=O)N[C@@H]3CCC[C@@H]3O)n(C)c2Cl)ccc1F] | 2-chloro-N-(4-fluoro-3-methylphenyl)-5-(2-(((1R,2S)-2-hydroxycyclopentyl)amino)-2-oxoacetyl)-1,4-dimethyl-1H-pyrrole-3-carboxamide | 460.2 |
| 391 | 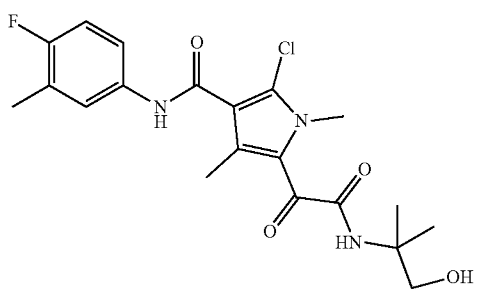 [SMILES: Cc1cc(NC(=O)c2c(C)c(C(=O)C(=O)NC(C)(C)CO)n(C)c2Cl)ccc1F] | 2-chloro-N-(4-fluoro-3-methylphenyl)-5-(2-((1-hydroxy-2-methylpropan-2-yl)amino)-2-oxoacetyl)-1,4-dimethyl-1H-pyrrole-3-carboxamide | 447.2 |
| 392 | 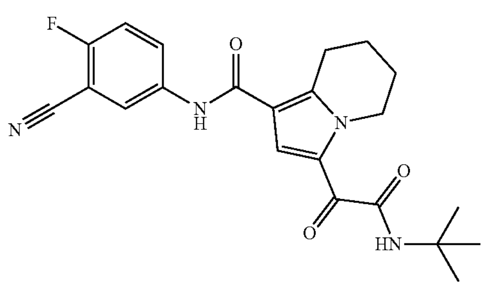 [SMILES: CC(C)(C)NC(=O)C(=O)c1cc(C(=O)Nc2ccc(F)c(C#N)c2)c2n1CCCC2] | 3-(2-(tert-butylamino)-2-oxoacetyl)-N-(3-cyano-4-fluorophenyl)-5,6,7,8-tetrahydroindolizine-1-carboxamide | 411.1 |
| 393 | 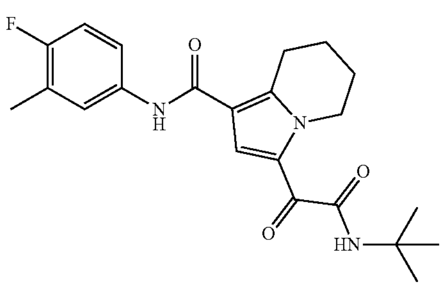 [SMILES: Cc1cc(NC(=O)c2cc(C(=O)C(=O)NC(C)(C)C)n3c2CCCC3)ccc1F] | 3-(2-(tert-butylamino)-2-oxoacetyl)-N-(4-fluoro-3-methylphenyl)-5,6,7,8-tetrahydroindolizine-1-carboxamide | 401.1 |

TABLE 1-continued

Exemplary compounds

| Ex. | Structure | Chemical Name | ESI-MS (M + H)+ (m/z) |
|---|---|---|---|
| 394 | 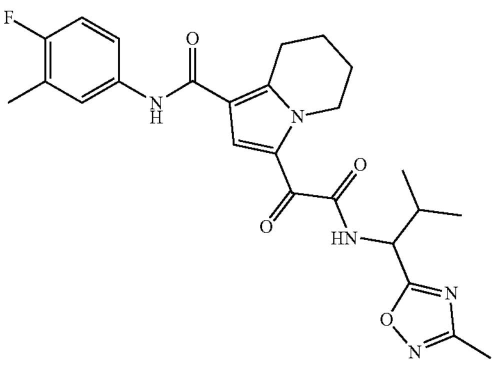 [SMILES: Cc1noc(C(NC(=O)C(=O)c2cc(C(=O)Nc3ccc(F)c(C)c3)c3n2CCCC3)C(C)C)n1] | N-(4-fluoro-3-methylphenyl)-3-(2-((2-methyl-1-(3-methyl-1,2,4-oxadiazol-5-yl)propyl)amino)-2-oxoacetyl)-5,6,7,8-tetrahydroindolizine-1-carboxamide | 482.2 |
| 395 | 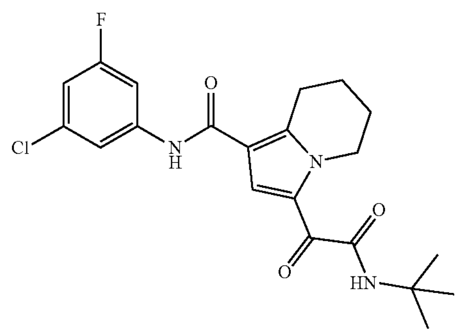 [SMILES: CC(C)(C)NC(=O)C(=O)c1cc(C(=O)Nc2cc(F)cc(Cl)c2)c2n1CCCC2] | 3-(2-(tert-butylamino)-2-oxoacetyl)-N-(3-chloro-5-fluorophenyl)-5,6,7,8-tetrahydroindolizine-1-carboxamide | 418.9 |
| 396 | 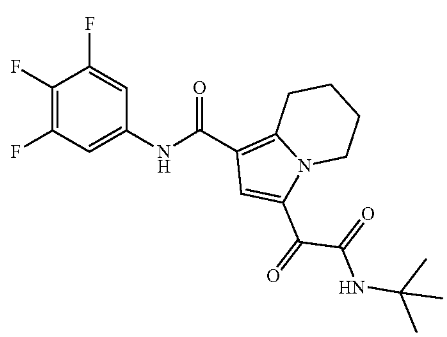 [SMILES: CC(C)(C)NC(=O)C(=O)c1cc(C(=O)Nc2cc(F)c(F)c(F)c2)c2n1CCCC2] | 3-(2-(tert-butylamino)-2-oxoacetyl)-N-(3,4,5-trifluorophenyl)-5,6,7,8-tetrahydroindolizine-1-carboxamide | 421.9 |
| 397 | 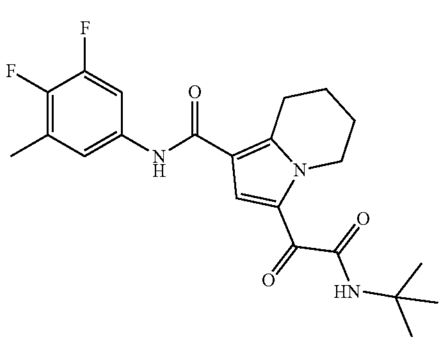 [SMILES: Cc1cc(NC(=O)c2cc(C(=O)C(=O)NC(C)(C)C)n3c2CCCC3)cc(F)c1F] | 3-(2-(tert-butylamino)-2-oxoacetyl)-N-(3,4-difluoro-5-methylphenyl)-5,6,7,8-tetrahydroindolizine-1-carboxamide | 418 |

TABLE 1-continued

Exemplary compounds

| Ex. | Structure | Chemical Name | ESI-MS (M + H)+ (m/z) |
|---|---|---|---|
| 398 | 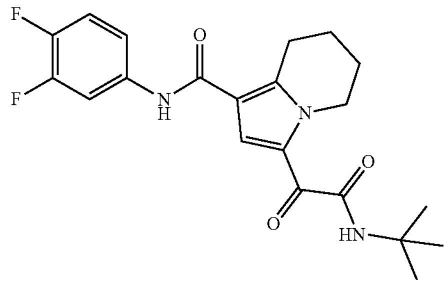 [SMILES: CC(C)(C)NC(=O)C(=O)c1cc(C(=O)Nc2ccc(F)c(F)c2)c2n1CCCC2] | 3-(2-(tert-butylamino)-2-oxoacetyl)-N-(3,4-difluorophenyl)-5,6,7,8-tetrahydroindolizine-1-carboxamide | 403.9 |
| 399 | 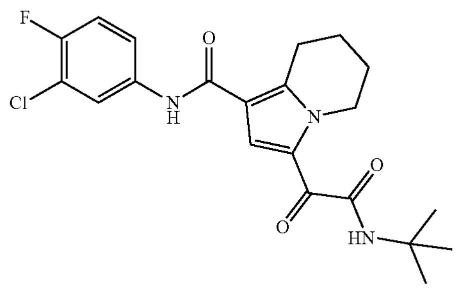 [SMILES: CC(C)(C)NC(=O)C(=O)c1cc(C(=O)Nc2ccc(F)c(Cl)c2)c2n1CCCC2] | 3-(2-(tert-butylamino)-2-oxoacetyl)-N-(3-chloro-4-fluorophenyl)-5,6,7,8-tetrahydroindolizine-1-carboxamide | 419.9 |
| 400 | 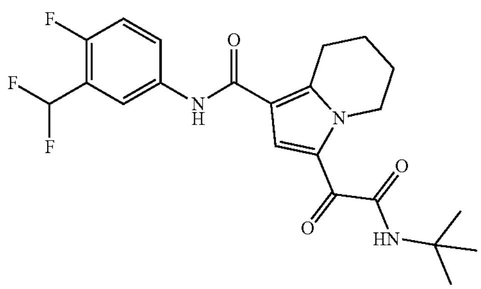 [SMILES: CC(C)(C)NC(=O)C(=O)c1cc(C(=O)Nc2ccc(F)c(C(F)F)c2)c2n1CCCC2] | 3-(2-(tert-butylamino)-2-oxoacetyl)-N-(3-(difluoromethyl)-4-fluorophenyl)-5,6,7,8-tetrahydroindolizine-1-carboxamide | 435.9 |
| 401 | 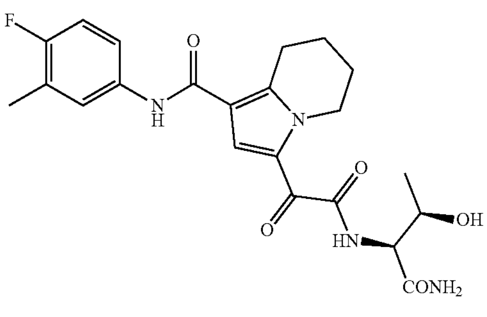 [SMILES: Cc1cc(NC(=O)c2cc(C(=O)C(=O)N[C@H](C(N)=O)[C@@H](C)O)n3c2CCCC3)ccc1F] | 3-(2-(((2S,3R)-1-amino-3-hydroxy-1-oxobutan-2-yl)amino)-2-oxoacetyl)-N-(4-fluoro-3-methylphenyl)-5,6,7,8-tetrahydroindolizine-1-carboxamide | 444.9 |
| 402 | 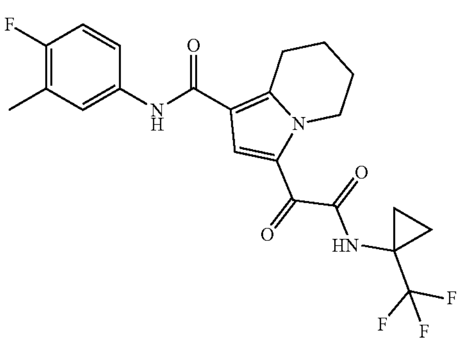 [SMILES: Cc1cc(NC(=O)c2cc(C(=O)C(=O)NC3(C(F)(F)F)CC3)n3c2CCCC3)ccc1F] | N-(4-fluoro-3-methylphenyl)-3-(2-oxo-2-((1-(trifluoromethyl)cyclopropyl)amino)acetyl)-5,6,7,8-tetrahydroindolizine-1-carboxamide | 451.9 |

TABLE 1-continued

Exemplary compounds

| Ex. | Structure | Chemical Name | ESI-MS (M + H)+ (m/z) |
|---|---|---|---|
| 403 | 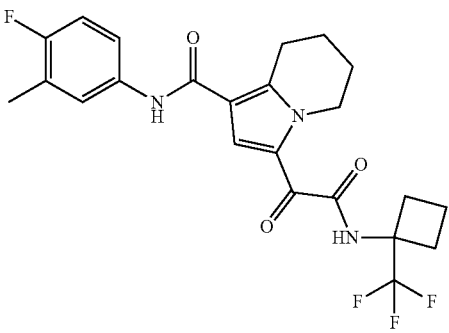 [SMILES: Cc1cc(NC(=O)c2cc(C(=O)C(=O)NC3(C(F)(F)F)CCC3)n3c2CCCC3)ccc1F] | N-(4-fluoro-3-methylphenyl)-3-(2-oxo-2-((1-(trifluoromethyl)cyclobutyl)amino)acetyl)-5,6,7,8-tetrahydroindolizine-1-carboxamide | 465.9 |
| 404 | 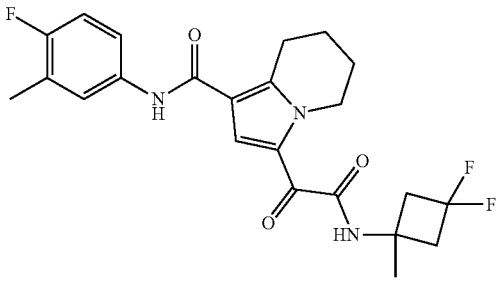 [SMILES: Cc1cc(NC(=O)c2cc(C(=O)C(=O)NC3(C)CC(F)(F)C3)n3c2CCCC3)ccc1F] | 3-(2-((3,3-difluoro-1-methylcyclobutyl)amino)-2-oxoacetyl)-N-(4-fluoro-3-methylphenyl)-5,6,7,8-tetrahydroindolizine-1-carboxamide | 447.9 |
| 405 | 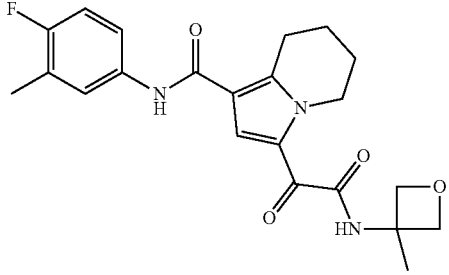 [SMILES: Cc1cc(NC(=O)c2cc(C(=O)C(=O)NC3(C)COC3)n3c2CCCC3)ccc1F] | N-(4-fluoro-3-methylphenyl)-3-(2-((3-methyloxetan-3-yl)amino)-2-oxoacetyl)-5,6,7,8-tetrahydroindolizine-1-carboxamide | 413.9 |
| 406 | 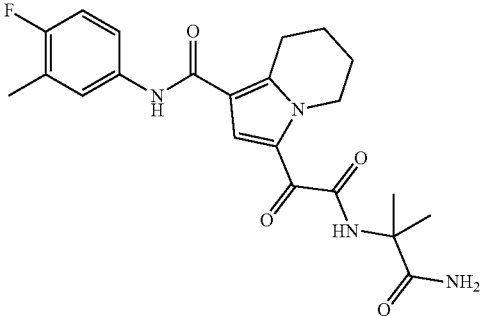 [SMILES: Cc1cc(NC(=O)c2cc(C(=O)C(=O)NC(C)(C)C(N)=O)n3c2CCCC3)ccc1F] | 3-(2-(((1-amino-2-methyl-1-oxopropan-2-yl)amino)-2-oxoacetyl)-N-(4-fluoro-3-methylphenyl)-5,6,7,8-tetrahydroindolizine-1-carboxamide | 429.0 |
| 407 | 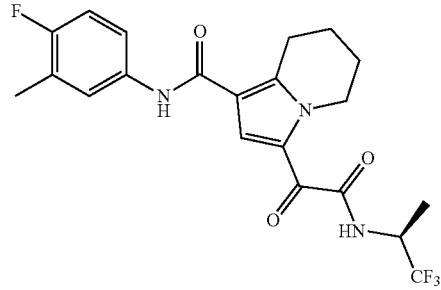 [SMILES: Cc1cc(NC(=O)c2cc(C(=O)C(=O)N[C@@H](C)C(F)(F)F)n3c2CCCC3)ccc1F] | (S)-N-(4-fluoro-3-methylphenyl)-3-(2-oxo-2-((1,1,1-trifluoropropan-2-yl)amino)acetyl)-5,6,7,8-tetrahydroindolizine-1-carboxamide | 439.9 |

TABLE 1-continued

Exemplary compounds

| Ex. | Structure | Chemical Name | ESI-MS (M + H)+ (m/z) |
|---|---|---|---|
| 408 | 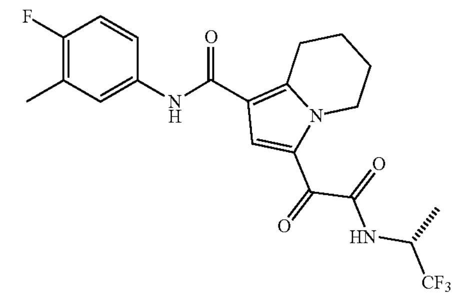 [SMILES: Cc1cc(NC(=O)c2cc(C(=O)C(=O)N[C@H](C)C(F)(F)F)n3c2CCCC3)ccc1F] | (R)-N-(4-fluoro-3-methylphenyl)-3-(2-oxo-2-((1,1,1-trifluoropropan-2-yl)amino)acetyl)-5,6,7,8-tetrahydroindolizine-1-carboxamide | 440.1 |
| 409 | 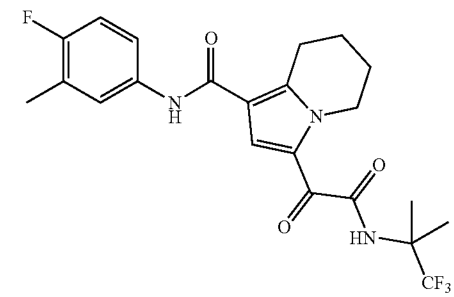 [SMILES: Cc1cc(NC(=O)c2cc(C(=O)C(=O)NC(C)(C)C(F)(F)F)n3c2CCCC3)ccc1F] | N-(4-fluoro-3-methylphenyl)-3-(2-oxo-2-((1,1,1-trifluoro-2-methylpropan-2-yl)amino)acetyl)-5,6,7,8-tetrahydroindolizine-1-carboxamide | 454.1 |
| 410 | 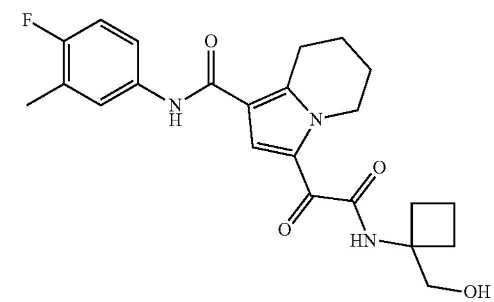 [SMILES: Cc1cc(NC(=O)c2cc(C(=O)C(=O)NC3(CO)CCC3)n3c2CCCC3)ccc1F] | N-(4-fluoro-3-methylphenyl)-3-(2-((1-(hydroxymethyl)cyclobutyl)amino)-2-oxoacetyl)-5,6,7,8-tetrahydroindolizine-1-carboxamide | 427.9 |
| 411 | 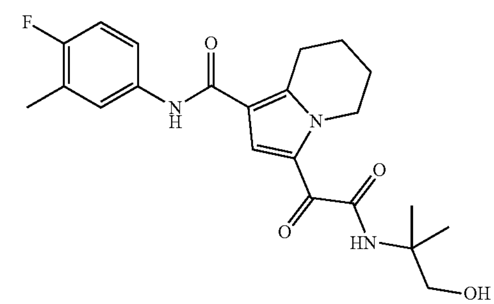 [SMILES: Cc1cc(NC(=O)c2cc(C(=O)C(=O)NC(C)(C)CO)n3c2CCCC3)ccc1F] | N-(4-fluoro-3-methylphenyl)-3-(2-((1-hydroxy-2-methylpropan-2-yl)amino)-2-oxoacetyl)-5,6,7,8-tetrahydroindolizine-1-carboxamide | 416.0 |
| 412 | 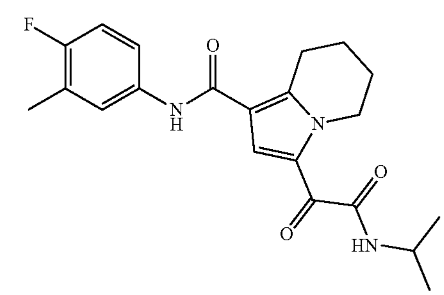 [SMILES: Cc1cc(NC(=O)c2cc(C(=O)C(=O)NC(C)C)n3c2CCCC3)ccc1F] | N-(4-fluoro-3-methylphenyl)-3-(2-(isopropylamino)-2-oxoacetyl)-5,6,7,8-tetrahydroindolizine-1-carboxamide | 386.1 |

TABLE 1-continued

Exemplary compounds

| Ex. | Structure | Chemical Name | ESI-MS (M + H)+ (m/z) |
|---|---|---|---|
| 413 | 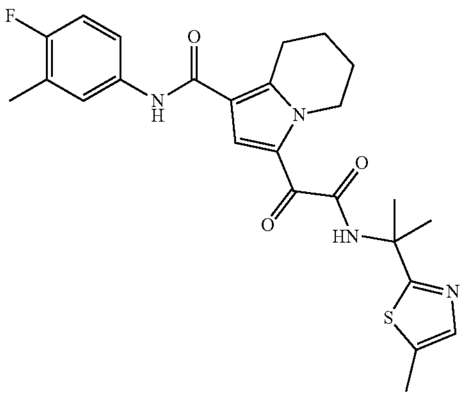 [SMILES: Cc1cnc(C(C)(C)NC(=O)C(=O)c2cc(C(=O)Nc3ccc(F)c(C)c3)c3n2CCCC3)s1] | N-(4-fluoro-3-methylphenyl)-3-(2-((2-(5-methylthiazol-2-yl)propan-2-yl)amino)-2-oxoacetyl)-5,6,7,8-tetrahydroindolizine-1-carboxamide | 483.2 |
| 414 | 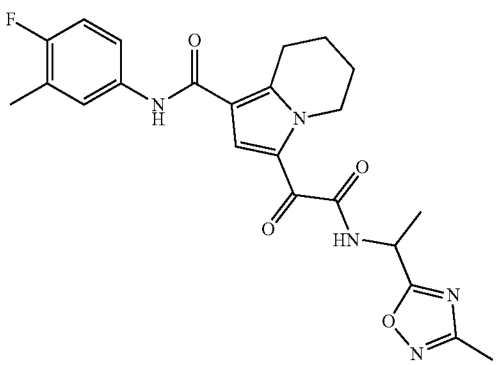 | N-(4-fluoro-3-methylphenyl)-3-(2-((1-(3-methyl-1,2,4-oxadiazol-5-yl)ethyl)amino)-2-oxoacetyl)-5,6,7,8-tetrahydroindolizine-1-carboxamide | 453.2 |
| 415 | 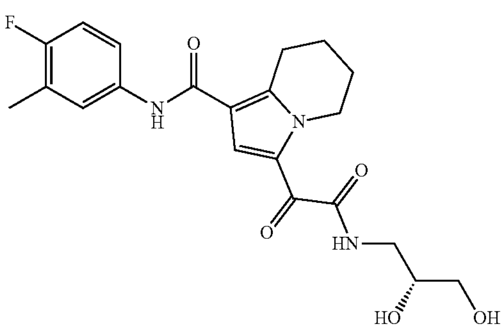 [SMILES: Cc1cc(NC(=O)c2cc(C(=O)C(=O)NC[C@@H](O)CO)n3c2CCCC3)ccc1F] | (R)-3-(2-((2,3-dihydroxypropyl)amino)-2-oxoacetyl)-N-(4-fluoro-3-methylphenyl)-5,6,7,8-tetrahydroindolizine-1-carboxamide | 418.1 |
| 416 | 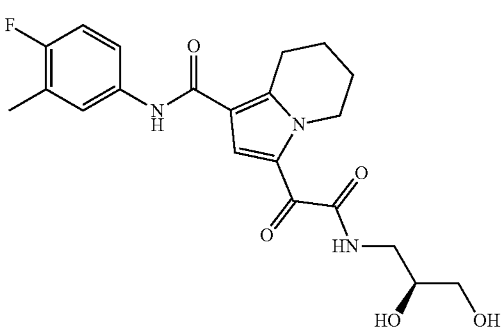 [SMILES: Cc1cc(NC(=O)c2cc(C(=O)C(=O)NC[C@H](O)CO)n3c2CCCC3)ccc1F] | (S)-3-(2-((2,3-dihydroxypropyl)amino)-2-oxoacetyl)-N-(4-fluoro-3-methylphenyl)-5,6,7,8-tetrahydroindolizine-1-carboxamide | 418.1 |

TABLE 1-continued

Exemplary compounds

| Ex. | Structure | Chemical Name | ESI-MS (M + H)+ (m/z) |
|---|---|---|---|
| 417 | 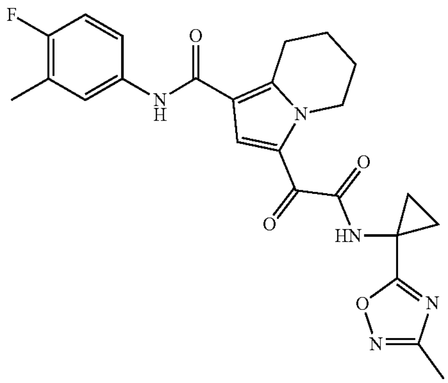 | 3-(2-(((2S,3S)-1,3-dihydroxybutan-2-yl)amino)-2-oxoacetyl)-N-(4-fluoro-3-methylphenyl)-5,6,7,8-tetrahydroindolizine-1-carboxamide | 432.1 |
| 418 | 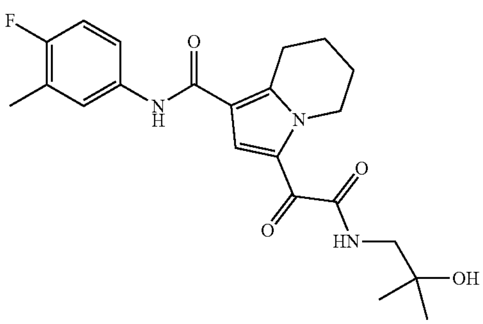 [SMILES: Cc1cc(NC(=O)c2cc(C(=O)C(=O)NCC(C)(C)O)n3c2CCCC3)ccc1F] | N-(4-fluoro-3-methylphenyl)-3-(2-((1-(3-methyl-1,2,4-oxadiazol-5-yl)cyclopropyl)amino)-2-oxoacetyl)-5,6,7,8-tetrahydroindolizine-1-carboxamide | 466.1 |
| 419 | 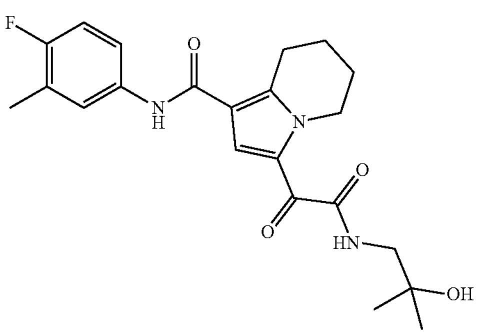 [SMILES: Cc1cc(NC(=O)c2cc(C(=O)C(=O)NCC(C)(C)O)n3c2CCCC3)ccc1F] | N-(4-fluoro-3-methylphenyl)-3-(2-((2-hydroxy-2-methylpropyl)amino)-2-oxoacetyl)-5,6,7,8-tetrahydroindolizine-1-carboxamide | 416.1 |
| 420 | 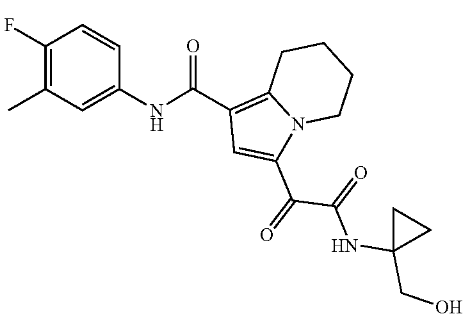 [SMILES: Cc1cc(NC(=O)c2cc(C(=O)C(=O)NC3(CO)CC3)n3c2CCCC3)ccc1F] | N-(4-fluoro-3-methylphenyl)-3-(2-((1-(hydroxymethyl)cyclopropyl)amino)-2-oxoacetyl)-5,6,7,8-tetrahydroindolizine-1-carboxamide | 414.1 |

TABLE 1-continued

Exemplary compounds

| Ex. | Structure | Chemical Name | ESI-MS (M + H)+ (m/z) |
|---|---|---|---|
| 421 | 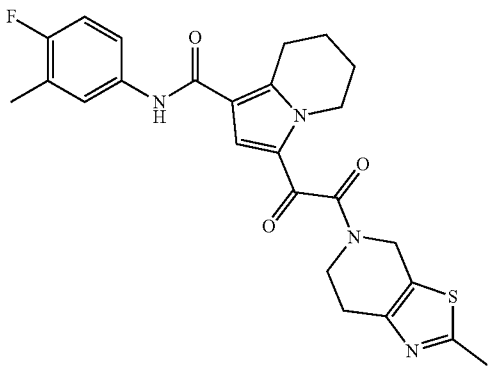 | 3-(2-(2-amino-6,7-dihydrothiazolo[5,4-c]pyridin-5(4H)-yl)-2-oxoacetyl)-N-(4-fluoro-3-methylphenyl)-5,6,7,8-tetrahydroindolizine-1-carboxamide | 482.1 |
| 422 | 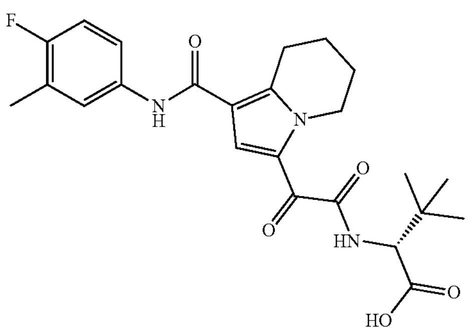 [SMILES: Cc1cc(NC(=O)c2cc(C(=O)C(=O)N[C@@H](C(=O)O)C(C)(C)C)n3c2CCCC3)ccc1F] | (R)-2-(2-(1-((4-fluoro-3-methylphenyl)carbamoyl)-5,6,7,8-tetrahydroindolizin-3-yl)-2-oxoacetamido)-3,3-dimethylbutanoic acid | 458.1 |
| 423 | 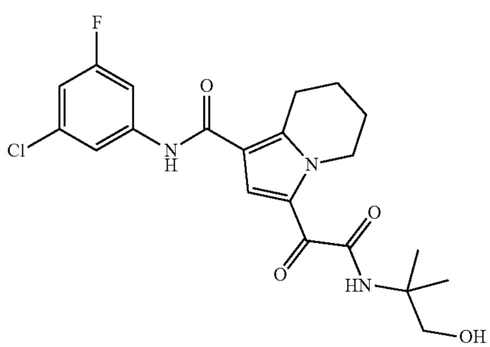 [SMILES: CC(C)(CO)NC(=O)C(=O)c1cc(C(=O)Nc2cc(F)cc(Cl)c2)c2n1CCCC2] | N-(3-chloro-5-fluorophenyl)-3-(2-((1-hydroxy-2-methylpropan-2-yl)amino)-2-oxoacetyl)-5,6,7,8-tetrahydroindolizine-1-carboxamide | 436.0 |
| 424 | 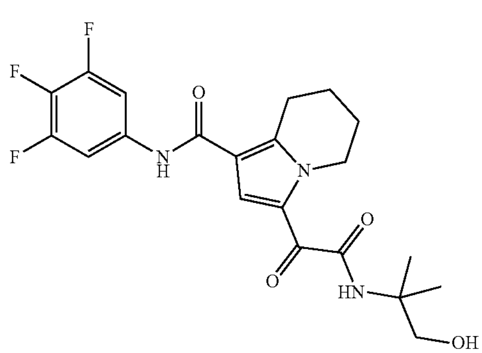 [SMILES: CC(C)(CO)NC(=O)C(=O)c1cc(C(=O)Nc2cc(F)c(F)c(F)c2)c2n1CCCC2] | 3-(2-((1-hydroxy-2-methylpropan-2-yl)amino)-2-oxoacetyl)-N-(3,4,5-trifluorophenyl)-5,6,7,8-tetrahydroindolizine-1-carboxamide | 438.1 |

TABLE 1-continued

Exemplary compounds

| Ex. | Structure | Chemical Name | ESI-MS (M + H)+ (m/z) |
|---|---|---|---|
| 425 | 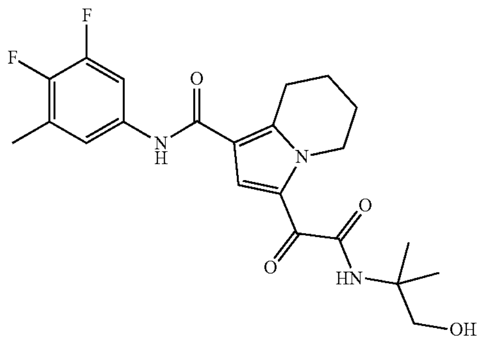 [SMILES: Cc1cc(NC(=O)c2cc(C(=O)C(=O)NC(C)(C)CO)n3c2CCCC3)cc(F)c1F] | N-(3,4-difluoro-5-methylphenyl)-3-(2-((1-hydroxy-2-methylpropan-2-yl)amino)-2-oxoacetyl)-5,6,7,8-tetrahydroindolizine-1-carboxamide | 434.2 |
| 426 | 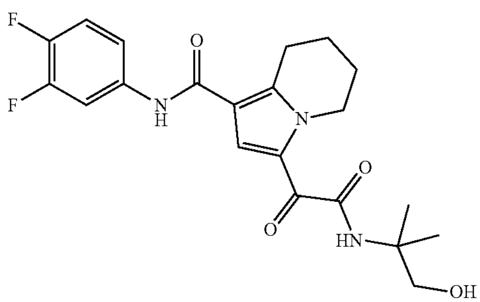 [SMILES: CC(C)(CO)NC(=O)C(=O)c1cc(C(=O)Nc2ccc(F)c(F)c2)c2n1CCCC2] | N-(3,4-difluorophenyl)-3-(2-((1-hydroxy-2-methylpropan-2-yl)amino)-2-oxoacetyl)-5,6,7,8-tetrahydroindolizine-1-carboxamide | 420.1 |
| 427 | 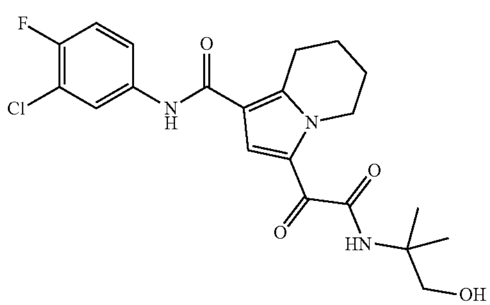 [SMILES: CC(C)(CO)NC(=O)C(=O)c1cc(C(=O)Nc2ccc(F)c(Cl)c2)c2n1CCCC2] | N-(3-chloro-4-fluorophenyl)-3-(2-((1-hydroxy-2-methylpropan-2-yl)amino)-2-oxoacetyl)-5,6,7,8-tetrahydroindolizine-1-carboxamide | 435.8 |
| 428 | 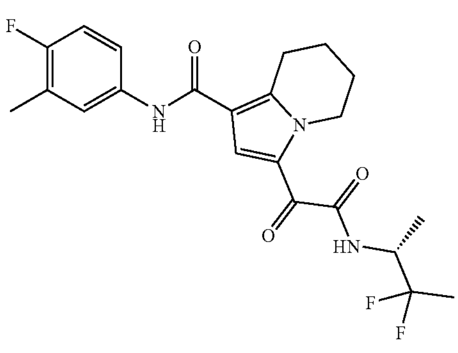 [SMILES: Cc1cc(NC(=O)c2cc(C(=O)C(=O)N[C@H](C)C(C)(F)F)n3c2CCCC3)ccc1F] | (R)-3-(2-((3,3-difluorobutan-2-yl)amino)-2-oxoacetyl)-N-(4-fluoro-3-methylphenyl)-5,6,7,8-tetrahydroindolizine-1-carboxamide | 436.1 |

TABLE 1-continued

Exemplary compounds

| Ex. | Structure | Chemical Name | ESI-MS (M + H)+ (m/z) |
|---|---|---|---|
| 429 | 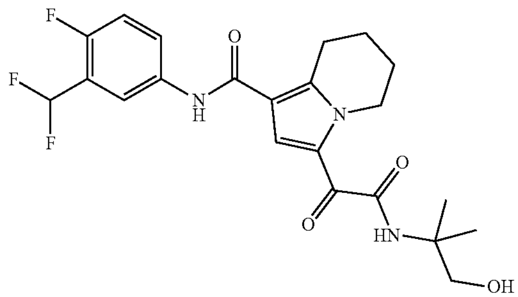 [SMILES: CC(C)(CO)NC(=O)C(=O)c1cc(C(=O)Nc2ccc(F)c(C(F)F)c2)c2n1CCCC2] | N-(3-(difluoromethyl)-4-fluorophenyl)-3-(2-((1-hydroxy-2-methylpropan-2-yl)amino)-2-oxoacetyl)-5,6,7,8-tetrahydroindolizine-1-carboxamide | 452.0 |
| 430 | 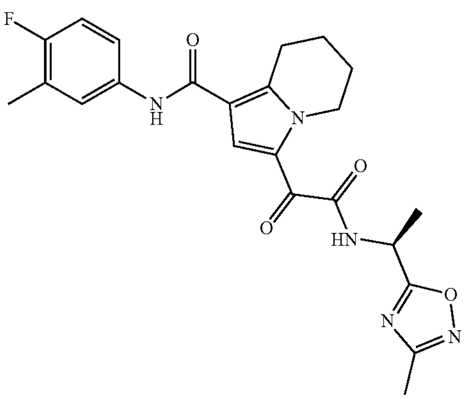 [SMILES: Cc1noc([C@H](C)NC(=O)C(=O)c2cc(C(=O)Nc3ccc(F)c(C)c3)c3n2CCCC3)n1] | (S)-N-(4-fluoro-3-methylphenyl)-3-(2-((1-(3-methyl-1,2,4-oxadiazol-5-yl)ethyl)amino)-2-oxoacetyl)-5,6,7,8-tetrahydroindolizine-1-carboxamide | 454.1 |
| 431 | 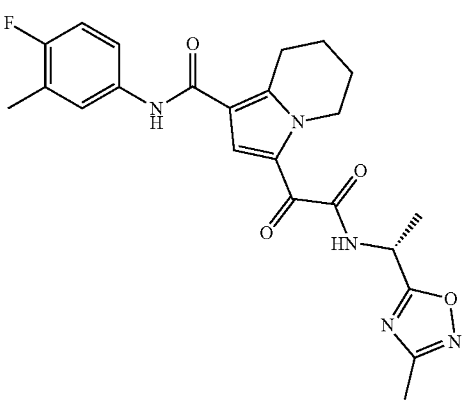 [SMILES: Cc1noc([C@@H](C)NC(=O)C(=O)c2cc(C(=O)Nc3ccc(F)c(C)c3)c3n2CCCC3)n1] | (R)-N-(4-fluoro-3-methylphenyl)-3-(2-((1-(3-methyl-1,2,4-oxadiazol-5-yl)ethyl)amino)-2-oxoacetyl)-5,6,7,8-tetrahydroindolizine-1-carboxamide | 454.1 |
| 432 | 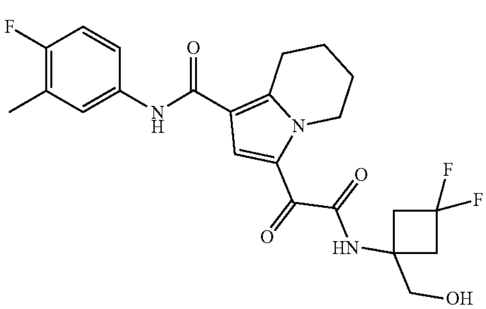 [SMILES: Cc1cc(NC(=O)c2cc(C(=O)C(=O)NC3(CO)CC(F)(F)C3)n3c2CCCC3)ccc1F] | 3-(2-((3,3-difluoro-1-(hydroxymethyl)cyclobutyl)amino)-2-oxoacetyl)-N-(4-fluoro-3-methylphenyl)-5,6,7,8-tetrahydroindolizine-1-carboxamide | 464.0 |

TABLE 1-continued

Exemplary compounds

| Ex. | Structure | Chemical Name | ESI-MS (M + H)+ (m/z) |
| --- | --- | --- | --- |
| 433 | 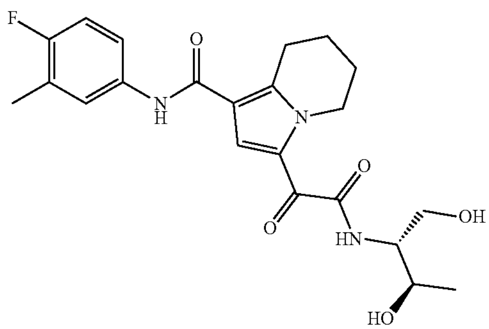 [SMILES: Cc1cc(NC(=O)c2cc(C(=O)C(=O)N[C@H](CO)[C@@H](C)O)n3c2CCCC3)ccc1F] | 3-(2-(((2R,3R)-1,3-dihydroxybutan-2-yl)amino)-2-oxoacetyl)-N-(4-fluoro-3-methylphenyl)-5,6,7,8-tetrahydroindolizine-1-carboxamide | 432.1 |
| 434 | 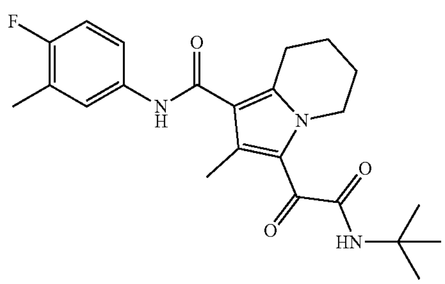 [SMILES: Cc1cc(NC(=O)c2c(C)c(C(=O)C(=O)NC(C)(C)C)n3c2CCCC3)ccc1F] | 3-(2-(tert-butylamino)-2-oxoacetyl)-N-(4-fluoro-3-methylphenyl)-2-methyl-5,6,7,8-tetrahydroindolizine-1-carboxamide | 414.1 |
| 435 | 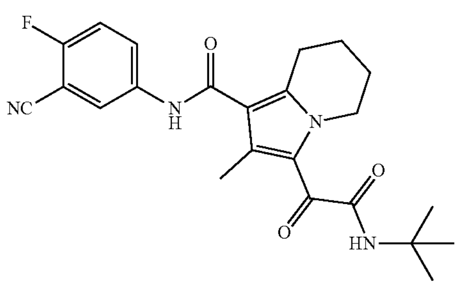 [SMILES: Cc1c(C(=O)Nc2ccc(F)c(C#N)c2)c2n(c1C(=O)C(=O)NC(C)(C)C)CCCC2] | 3-(2-(tert-butylamino)-2-oxoacetyl)-N-(3-cyano-4-fluorophenyl)-2-methyl-5,6,7,8-tetrahydroindolizine-1-carboxamide | 425.1 |
| 436 | 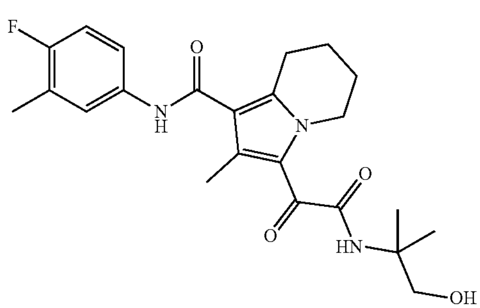 [SMILES: Cc1cc(NC(=O)c2c(C)c(C(=O)C(=O)NC(C)(C)CO)n3c2CCCC3)ccc1F] | N-(4-fluoro-3-methylphenyl)-3-(2-((1-hydroxy-2-methylpropan-2-yl)amino)-2-oxoacetyl)-2-methyl-5,6,7,8-tetrahydroindolizine-1-carboxamide | 430.1 |

TABLE 1-continued

Exemplary compounds

| Ex. | Structure | Chemical Name | ESI-MS (M + H)+ (m/z) |
|---|---|---|---|
| 437 | 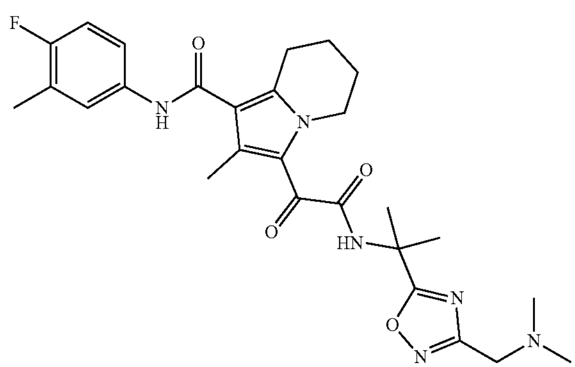 [SMILES: Cc1cc(NC(=O)c2c(C)c(C(=O)C(=O)NC(C)(C)c3nc(CN(C)C)no3)n3c2CCCC3)ccc1F] | 3-(2-((2-(3-((dimethylamino)methyl)-1,2,4-oxadiazol-5-yl)propan-2-yl)amino)-2-oxoacetyl)-N-(4-fluoro-3-methylphenyl)-2-methyl-5,6,7,8-tetrahydroindolizine-1-carboxamide | 525.2 |
| 438 | 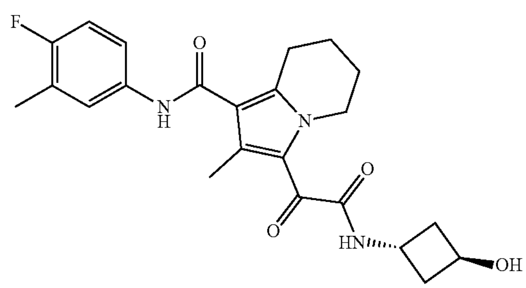 [SMILES: Cc1cc(NC(=O)c2c(C)c(C(=O)C(=O)N[C@H]3C[C@H](O)C3)n3c2CCCC3)ccc1F] | N-(4-fluoro-3-methylphenyl)-3-(2-(((1r,3r)-3-hydroxycyclobutyl)amino)-2-oxoacetyl)-2-methyl-5,6,7,8-tetrahydroindolizine-1-carboxamide | 428.1 |
| 439 | 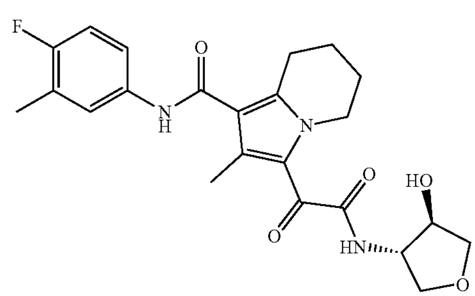 [SMILES: Cc1cc(NC(=O)c2c(C)c(C(=O)C(=O)N[C@H]3COC[C@@H]3O)n3c2CCCC3)ccc1F] | N-(4-fluoro-3-methylphenyl)-3-(2-(((3S,4R)-4-hydroxytetrahydrofuran-3-yl)amino)-2-oxoacetyl)-2-methyl-5,6,7,8-tetrahydroindolizine-1-carboxamide | 441.1 |
| 440 | 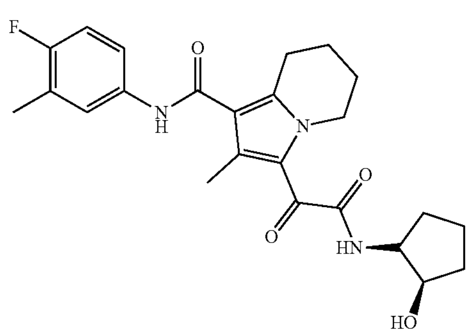 | N-(4-fluoro-3-methylphenyl)-3-(2-(((1S,2R)-2-hydroxycyclopentyl)amino)-2-oxoacetyl)-2-methyl-5,6,7,8-tetrahydroindolizine-1-carboxamide | 442.1 |

TABLE 1-continued

Exemplary compounds

| Ex. | Structure | Chemical Name | ESI-MS (M + H)+ (m/z) |
|---|---|---|---|
| 441 | 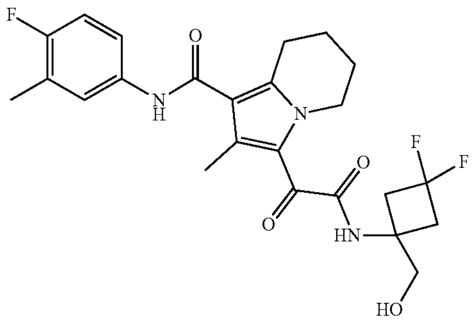 [SMILES: Cc1cc(NC(=O)c2c(C)c(C(=O)C(=O)NC3(CO)CC(F)(F)C3)n3c2CCCC3)ccc1F] | 3-(2-((3,3-difluoro-1-(hydroxymethyl)cyclobutyl)amino)-2-oxoacetyl)-N-(4-fluoro-3-methylphenyl)-2-methyl-5,6,7,8-tetrahydroindolizine-1-carboxamide | 478.1 |
| 442 | 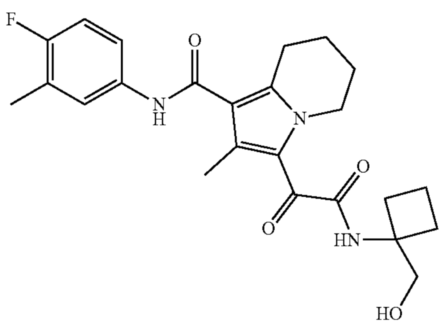 [SMILES: Cc1cc(NC(=O)c2c(C)c(C(=O)C(=O)NC3(CO)CCC3)n3c2CCCC3)ccc1F] | N-(4-fluoro-3-methylphenyl)-3-(2-((1-(hydroxymethyl)cyclobutyl)amino)-2-oxoacetyl)-2-methyl-5,6,7,8-tetrahydroindolizine-1-carboxamide | 442.1 |
| 443 | 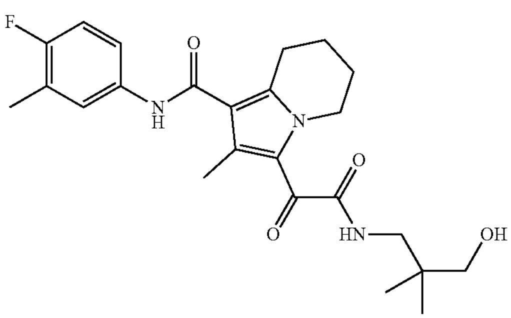 [SMILES: Cc1cc(NC(=O)c2c(C)c(C(=O)C(=O)NCC(C)(C)CO)n3c2CCCC3)ccc1F] | N-(4-fluoro-3-methylphenyl)-3-(2-((3-hydroxy-2,2-dimethylpropyl)amino)-2-oxoacetyl)-2-methyl-5,6,7,8-tetrahydroindolizine-1-carboxamide | 444.1 |
| 444 | 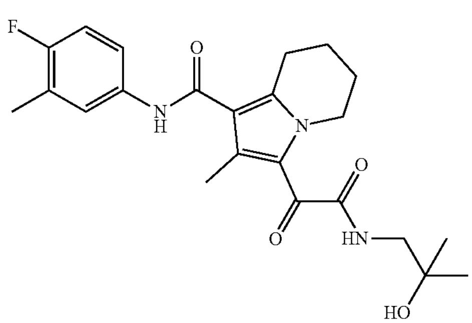 | N-(4-fluoro-3-methylphenyl)-3-(2-((2-hydroxy-2-methylpropyl)amino)-2-oxoacetyl)-2-methyl-5,6,7,8-tetrahydroindolizine-1-carboxamide | 430.1 |

TABLE 1-continued

Exemplary compounds

| Ex. | Structure | Chemical Name | ESI-MS (M + H)+ (m/z) |
|---|---|---|---|
| 445 | 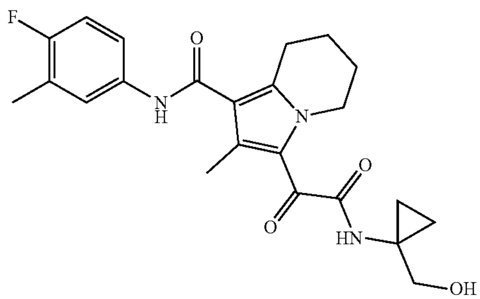 [SMILES: Cc1cc(NC(=O)c2c(C)c(C(=O)C(=O)NC3(CO)CC3)n3c2CCCC3)ccc1F] | N-(4-fluoro-3-methylphenyl)-3-(2-((1-(hydroxymethyl)cyclopropyl)amino)-2-oxoacetyl)-2-methyl-5,6,7,8-tetrahydroindolizine-1-carboxamide | 428.1 |
| 446 | 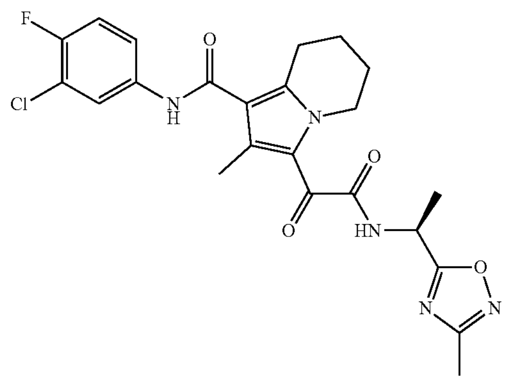 [SMILES: Cc1noc([C@H](C)NC(=O)C(=O)c2c(C)c(C(=O)Nc3ccc(F)c(Cl)c3)c3n2CCCC3)n1] | (S)-N-(3-chloro-4-fluorophenyl)-2-methyl-3-(2-(((1-(3-methyl-1,2,4-oxadiazol-5-yl)ethyl)amino)-2-oxoacetyl)-5,6,7,8-tetrahydroindolizine-1-carboxamide | 488.0 |
| 447 | 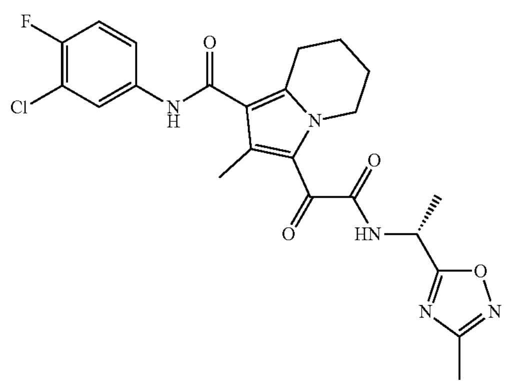 [SMILES: Cc1noc([C@@H](C)NC(=O)C(=O)c2c(C)c(C(=O)Nc3ccc(F)c(Cl)c3)c3n2CCCC3)n1] | (R)-N-(3-chloro-4-fluorophenyl)-2-methyl-3-(2-(((1-(3-methyl-1,2,4-oxadiazol-5-yl)ethyl)amino)-2-oxoacetyl)-5,6,7,8-tetrahydroindolizine-1-carboxamide | 488.0 |
| 448 | 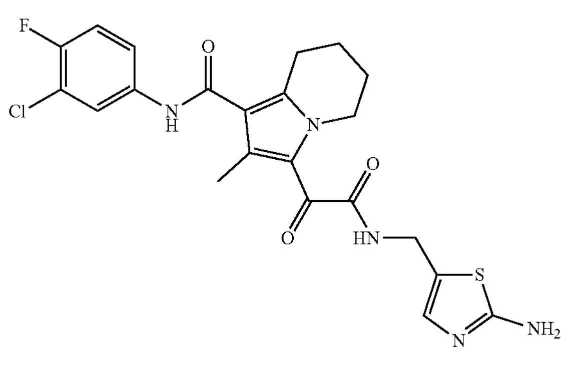 [SMILES: Cc1c(C(=O)Nc2ccc(F)c(Cl)c2)c2n(c1C(=O)C(=O)NCc1cnc(N)s1)CCCC2] | 3-(2-(((2-aminothiazol-5-yl)methyl)amino)-2-oxoacetyl)-N-(3-chloro-4-fluorophenyl)-2-methyl-5,6,7,8-tetrahydroindolizine-1-carboxamide | 490.0 |

TABLE 1-continued

Exemplary compounds

| Ex. | Structure | Chemical Name | ESI-MS (M + H)+ (m/z) |
|---|---|---|---|
| 449 | 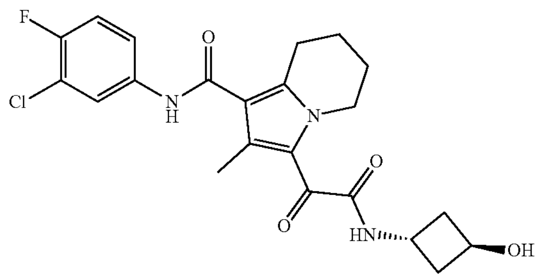 [SMILES: Cc1c(C(=O)Nc2ccc(F)c(Cl)c2)c2n(c1C(=O)C(=O)N[C@H]1C[C@H](O)C1)CCCC2] | N-(3-chloro-4-fluorophenyl)-3-(2-(((1r,3r)-3-hydroxycyclobutyl)amino)-2-oxoacetyl)-2-methyl-5,6,7,8-tetrahydroindolizine-1-carboxamide | 448.1 |
| 450 | 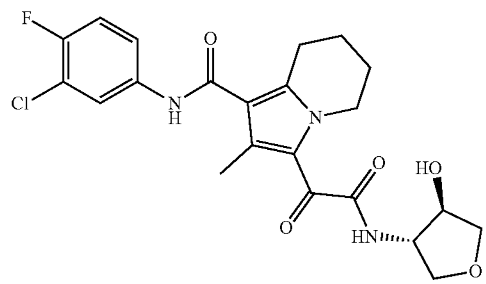 [SMILES: Cc1c(C(=O)Nc2ccc(F)c(Cl)c2)c2n(c1C(=O)C(=O)N[C@H]1COC[C@@H]1O)CCCC2] | N-(3-chloro-4-fluorophenyl)-3-(2-(((3S,4R)-4-hydroxytetrahydrofuran-3-yl)amino)-2-oxoacetyl)-2-methyl-5,6,7,8-tetrahydroindolizine-1-carboxamide | 464.1 |
| 451 | 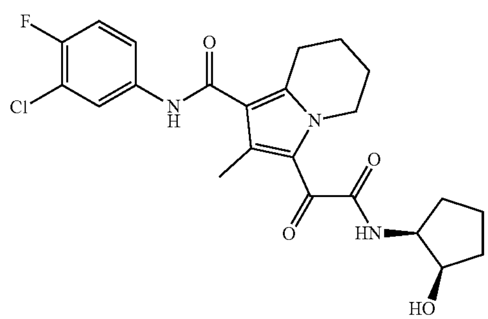 [SMILES: Cc1c(C(=O)Nc2ccc(F)c(Cl)c2)c2n(c1C(=O)C(=O)N[C@H]1CCC[C@H]1O)CCCC2] | N-(3-chloro-4-fluorophenyl)-3-(2-(((1S,2R)-2-hydroxycyclopentyl)amino)-2-oxoacetyl)-2-methyl-5,6,7,8-tetrahydroindolizine-1-carboxamide | 462.1 |
| 452 | 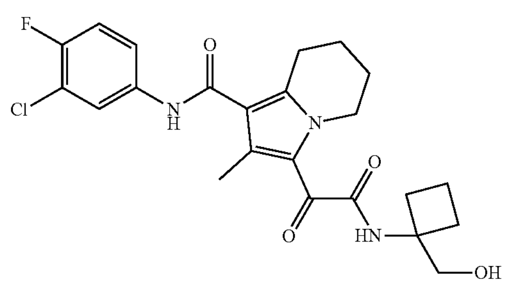 [SMILES: Cc1c(C(=O)Nc2ccc(F)c(Cl)c2)c2n(c1C(=O)C(=O)NC1(CO)CCC1)CCCC2] | N-(3-chloro-4-fluorophenyl)-3-(2-((1-(hydroxymethyl)cyclobutyl)amino)-2-oxoacetyl)-2-methyl-5,6,7,8-tetrahydroindolizine-1-carboxamide | 462.1 |
| 453 | 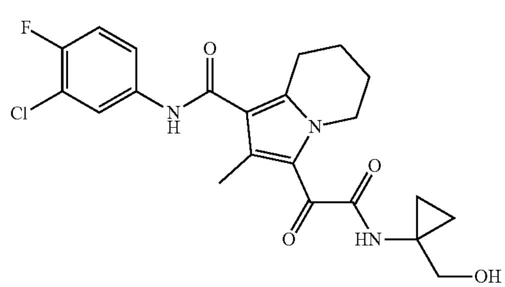 [SMILES: Cc1c(C(=O)Nc2ccc(F)c(Cl)c2)c2n(c1C(=O)C(=O)NC1(CO)CC1)CCCC2] | N-(3-chloro-4-fluorophenyl)-3-(2-((1-(hydroxymethyl)cyclopropyl)amino)-2-oxoacetyl)-2-methyl-5,6,7,8-tetrahydroindolizine-1-carboxamide | 448.0 |

TABLE 1-continued

Exemplary compounds

| Ex. | Structure | Chemical Name | ESI-MS (M + H)+ (m/z) |
|---|---|---|---|
| 454 | 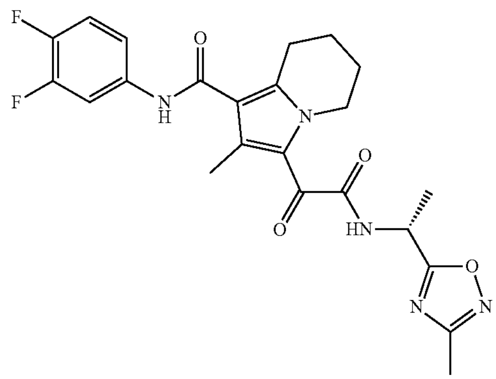 [SMILES: Cc1noc([C@@H](C)NC(=O)C(=O)c2c(C)c(C(=O)Nc3ccc(F)c(F)c3)c3n2CCCC3)n1] | (R)-N-(3,4-difluorophenyl)-2-methyl-3-(2-((1-(3-methyl-1,2,4-oxadiazol-5-yl)ethyl)amino)-2-oxoacetyl)-5,6,7,8-tetrahydroindolizine-1-carboxamide | 472.1 |
| 455 | 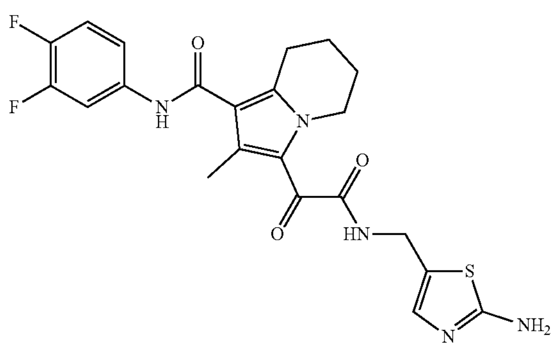 [SMILES: Cc1c(C(=O)Nc2ccc(F)c(F)c2)c2n(c1C(=O)C(=O)NCc1cnc(N)s1)CCCC2] | 3-(2-(((2-aminothiazol-5-yl)methyl)amino)-2-oxoacetyl)-N-(3,4-difluorophenyl)-2-methyl-5,6,7,8-tetrahydroindolizine-1-carboxamide | 474.1 |
| 456 | 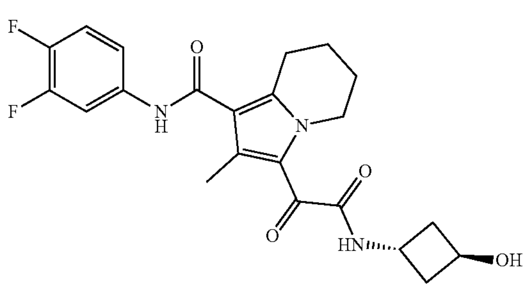 | N-(3,4-difluorophenyl)-3-(2-(((1r,3r)-3-hydroxycyclobutyl)amino)-2-oxoacetyl)-2-methyl-5,6,7,8-tetrahydroindolizine-1-carboxamide | 432.1 |
| 457 | 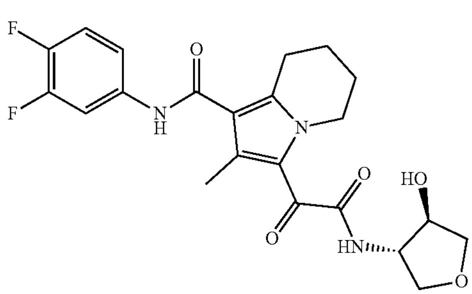 [SMILES: Cc1c(C(=O)Nc2ccc(F)c(F)c2)c2n(c1C(=O)C(=O)N[C@H]1COC[C@@H]1O)CCCC2] | N-(3,4-difluorophenyl)-3-(2-(((3S,4R)-4-hydroxytetrahydrofuran-3-yl)amino)-2-oxoacetyl)-2-methyl-5,6,7,8-tetrahydroindolizine-1-carboxamide | 448.1 |

TABLE 1-continued

Exemplary compounds

| Ex. | Structure | Chemical Name | ESI-MS (M + H)+ (m/z) |
|---|---|---|---|
| 458 | 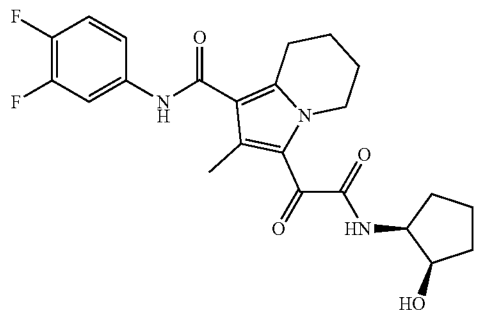 [SMILES: Cc1c(C(=O)Nc2ccc(F)c(F)c2)c2n(c1C(=O)C(=O)N[C@H]1CCC[C@H]1O)CCCC2] | N-(3,4-difluorophenyl)-3-(2-(((1S,2R)-2-hydroxycyclopentyl)amino)-2-oxoacetyl)-2-methyl-5,6,7,8-tetrahydroindolizine-1-carboxamide | 446.1 |
| 459 | 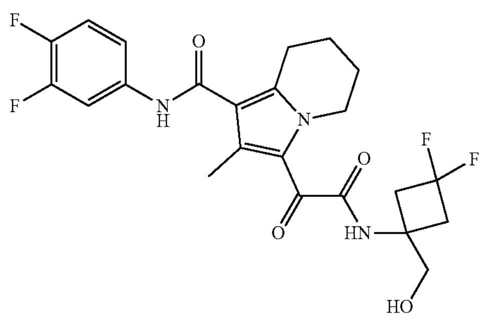 [SMILES: Cc1c(C(=O)Nc2ccc(F)c(F)c2)c2n(c1C(=O)C(=O)NC1(CO)CC(F)(F)C1)CCCC2] | 3-(2-((3,3-difluoro-1-(hydroxymethyl)cyclobutyl)amino)-2-oxoacetyl)-N-(3,4-difluorophenyl)-2-methyl-5,6,7,8-tetrahydroindolizine-1-carboxamide | 482.1 |
| 460 | 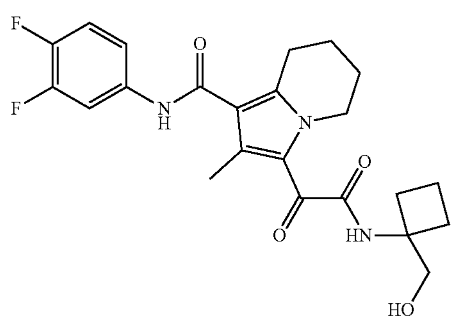 [SMILES: Cc1c(C(=O)Nc2ccc(F)c(F)c2)c2n(c1C(=O)C(=O)NC1(CO)CCC1)CCCC2] | N-(3,4-difluorophenyl)-3-(2-((1-(hydroxymethyl)cyclobutyl)amino)-2-oxoacetyl)-2-methyl-5,6,7,8-tetrahydroindolizine-1-carboxamide | 446.1 |
| 461 | 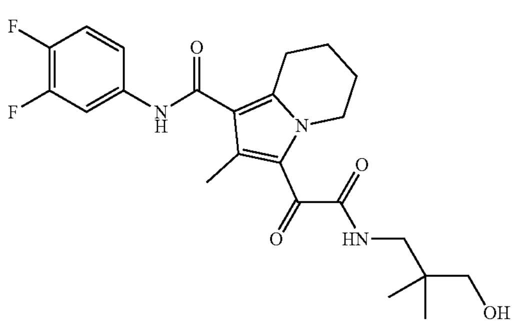 [SMILES: Cc1c(C(=O)Nc2ccc(F)c(F)c2)c2n(c1C(=O)C(=O)NCC(C)(C)CO)CCCC2] | N-(3,4-difluorophenyl)-3-(2-((3-hydroxy-2,2-dimethylpropyl)amino)-2-oxoacetyl)-2-methyl-5,6,7,8-tetrahydroindolizine-1-carboxamide | 448.1 |

TABLE 1-continued

Exemplary compounds

| Ex. | Structure | Chemical Name | ESI-MS (M + H)+ (m/z) |
|---|---|---|---|
| 462 | 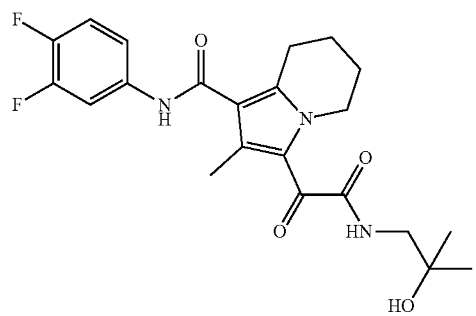 [SMILES: Cc1c(C(=O)Nc2ccc(F)c(F)c2)c2n(c1C(=O)C(=O)NCC(C)(C)O)CCCC2] | N-(3,4-difluorophenyl)-3-(2-((2-hydroxy-2-methylpropyl)amino)-2-oxoacetyl)-2-methyl-5,6,7,8-tetrahydroindolizine-1-carboxamide | 434.2 |
| 463 | 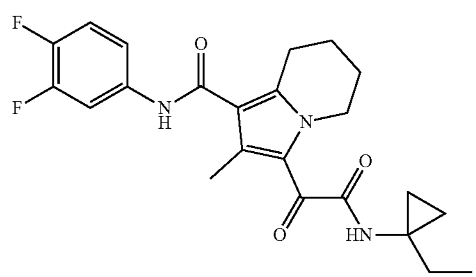 [SMILES: CCC1(NC(=O)C(=O)c2c(C)c(C(=O)Nc3ccc(F)c(F)c3)c3n2CCCC3)CC1] | N-(3,4-difluorophenyl)-3-(2-((1-(hydroxymethyl)cyclopropyl)amino)-2-oxoacetyl)-2-methyl-5,6,7,8-tetrahydroindolizine-1-carboxamide | 432.1 |
| 464 | 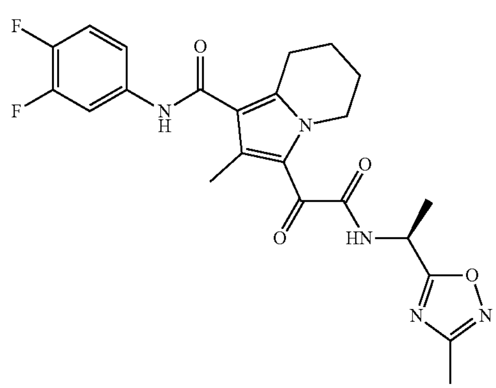 [SMILES: Cc1noc([C@H](C)NC(=O)C(=O)c2c(C)c(C(=O)Nc3ccc(F)c(F)c3)c3n2CCCC3)n1] | (S)-N-(3,4-difluorophenyl)-2-methyl-3-(2-((1-(3-methyl-1,2,4-oxadiazol-5-yl)ethyl)amino)-2-oxoacetyl)-5,6,7,8-tetrahydroindolizine-1-carboxamide | 472.1 |
| 465 | 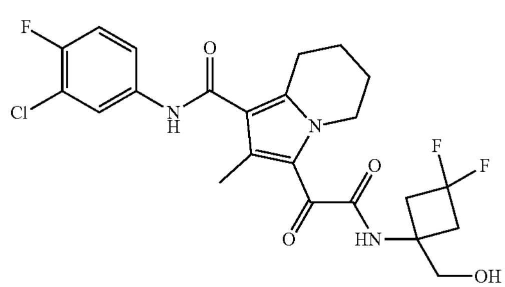 [SMILES: Cc1c(C(=O)Nc2ccc(F)c(Cl)c2)c2n(c1C(=O)C(=O)NC1(CO)CC(F)(F)C1)CCCC2] | N-(3-chloro-4-fluorophenyl)-3-(2-((3,3-difluoro-1-(hydroxymethyl)cyclobutyl)amino)-2-oxoacetyl)-2-methyl-5,6,7,8-tetrahydroindolizine-1-carboxamide | 498.1 |

TABLE 1-continued

Exemplary compounds

| Ex. | Structure | Chemical Name | ESI-MS (M + H)+ (m/z) |
|---|---|---|---|
| 466 | 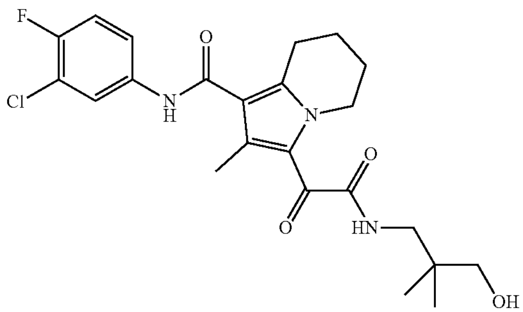 [SMILES: Cc1c(C(=O)Nc2ccc(F)c(Cl)c2)c2n(c1C(=O)C(=O)NCC(C)(C)CO)CCCC2] | N-(3-chloro-4-fluorophenyl)-3-(2-((3-hydroxy-2,2-dimethylpropyl)amino)-2-oxoacetyl)-2-methyl-5,6,7,8-tetrahydroindolizine-1-carboxamide | 464.1 |
| 467 | 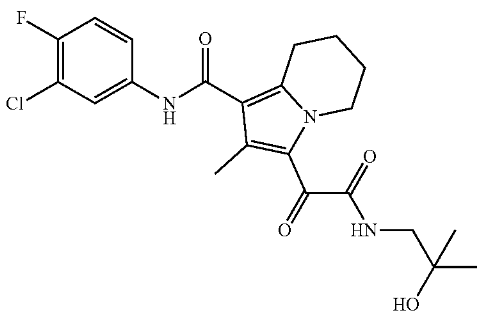 [SMILES: Cc1c(C(=O)Nc2ccc(F)c(Cl)c2)c2n(c1C(=O)C(=O)NCC(C)(C)O)CCCC2] | N-(3-chloro-4-fluorophenyl)-3-(2-((2-hydroxy-2-methylpropyl)amino)-2-oxoacetyl)-2-methyl-5,6,7,8-tetrahydroindolizine-1-carboxamide | 450.1 |
| 468 | 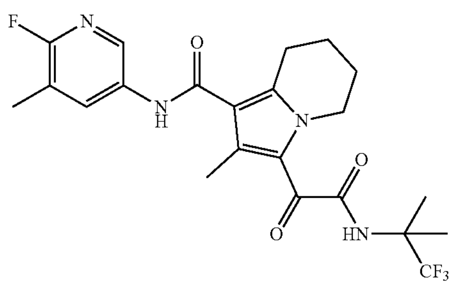 [SMILES: Cc1cc(NC(=O)c2c(C)c(C(=O)C(=O)NC(C)(C)C(F)(F)F)n3c2CCCC3)cnc1F] | N-(6-fluoro-5-methylpyridin-3-yl)-2-methyl-3-(2-oxo-2-(((1,1,1-trifluoro-2-methylpropan-2-yl)amino)acetyl)-5,6,7,8-tetrahydroindolizine-1-carboxamide | 469.2 |
| 469 | 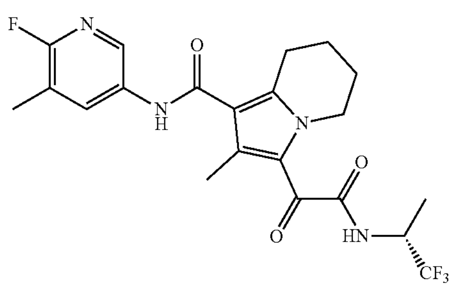 [SMILES: Cc1cc(NC(=O)c2c(C)c(C(=O)C(=O)N[C@H](C)C(F)(F)F)n3c2CCCC3)cnc1F] | (R)-N-(6-fluoro-5-methylpyridin-3-yl)-2-methyl-3-(2-oxo-2-((1,1,1-trifluoropropan-2-yl)amino)acetyl)-5,6,7,8-tetrahydroindolizine-1-carboxamide | 455.2 |
| 470 | 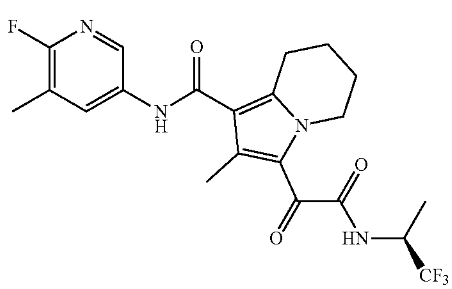 [SMILES: Cc1cc(NC(=O)c2c(C)c(C(=O)C(=O)N[C@@H](C)C(F)(F)F)n3c2CCCC3)cnc1F] | (S)-N-(6-fluoro-5-methylpyridin-3-yl)-2-methyl-3-(2-oxo-2-((1,1,1-trifluoropropan-2-yl)amino)acetyl)-5,6,7,8-tetrahydroindolizine-1-carboxamide | 455.2 |

| Ex. | Structure | Chemical Name | ESI-MS (M + H)+ (m/z) |
|---|---|---|---|
| 471 | 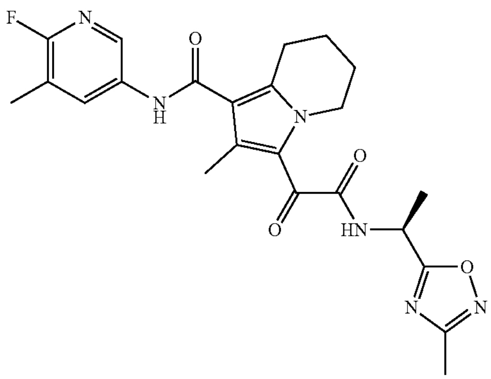 [SMILES: Cc1noc([C@H](C)NC(=O)C(=O)c2c(C)c(C(=O)Nc3cnc(F)c(C)c3)c3n2CCCC3)n1] | (S)-N-(6-fluoro-5-methylpyridin-3-yl)-2-methyl-3-(2-((1-(3-methyl-1,2,4-oxadiazol-5-yl)ethyl)amino)-2-oxoacetyl)-5,6,7,8-tetrahydroindolizine-1-carboxamide | 469.2 |
| 472 | 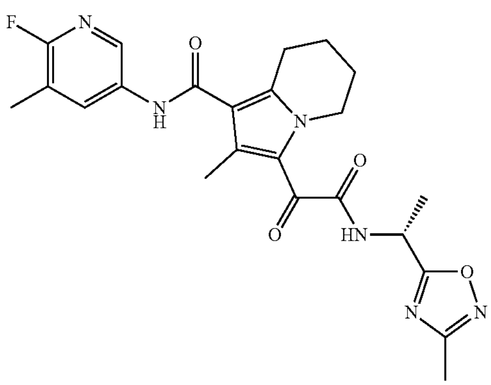 | (R)-N-(6-fluoro-5-methylpyridin-3-yl)-2-methyl-3-(2-((1-(3-methyl-1,2,4-oxadiazol-5-yl)ethyl)amino)-2-oxoacetyl)-5,6,7,8-tetrahydroindolizine-1-carboxamide | 469.2 |
| 473 | 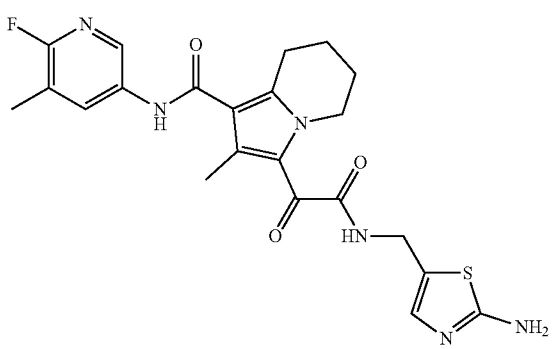 [SMILES: Cc1cc(NC(=O)c2c(C)c(C(=O)C(=O)NCc3cnc(N)s3)n3c2CCCC3)cnc1F] | 3-(2-(((2-aminothiazol-5-yl)methyl)amino)-2-oxoacetyl)-N-(6-fluoro-5-methylpyridin-3-yl)-2-methyl-5,6,7,8-tetrahydroindolizine-1-carboxamide | 471.1 |
| 474 | 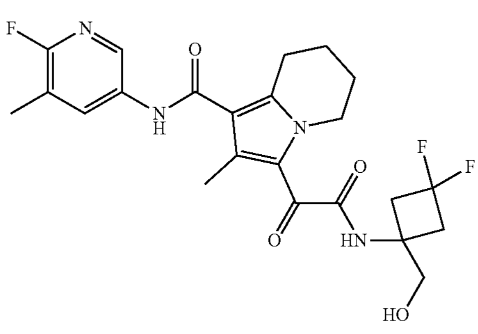 [SMILES: Cc1cc(NC(=O)c2c(C)c(C(=O)C(=O)NC3(CO)CC(F)(F)C3)n3c2CCCC3)cnc1F] | 3-(2-((3,3-difluoro-1-(hydroxymethyl)cyclobutyl)amino)-2-oxoacetyl)-N-(6-fluoro-5-methylpyridin-3-yl)-2-methyl-5,6,7,8-tetrahydroindolizine-1-carboxamide | 478.8 |

TABLE 1-continued

Exemplary compounds

| Ex. | Structure | Chemical Name | ESI-MS (M + H)+ (m/z) |
|---|---|---|---|
| 475 | 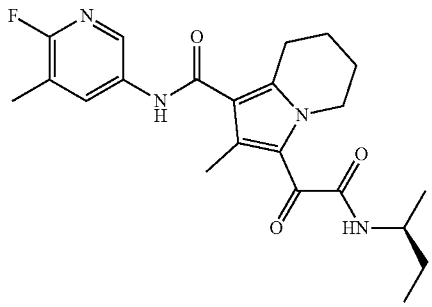 [SMILES: CC[C@H](C)NC(=O)C(=O)c1c(C)c(C(=O)Nc2cnc(F)c(C)c2)c2n1CCCC2] | (S)-3-(2-(sec-butylamino)-2-oxoacetyl)-N-(6-fluoro-5-methylpyridin-3-yl)-2-methyl-5,6,7,8-tetrahydroindolizine-1-carboxamide | 415.3 |
| 476 | 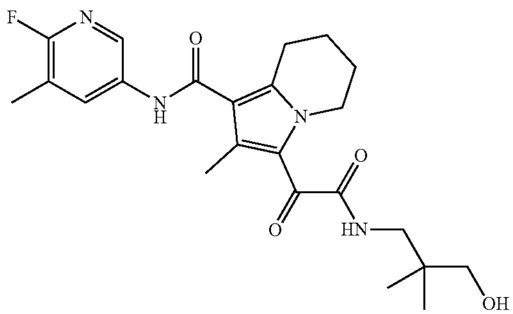 [SMILES: Cc1cc(NC(=O)c2c(C)c(C(=O)C(=O)NCC(C)(C)CO)n3c2CCCC3)cnc1F] | N-(6-fluoro-5-methylpyridin-3-yl)-3-(2-((3-hydroxy-2,2-dimethylpropyl)amino)-2-oxoacetyl)-2-methyl-5,6,7,8-tetrahydroindolizine-1-carboxamide | 445.2 |
| 477 | 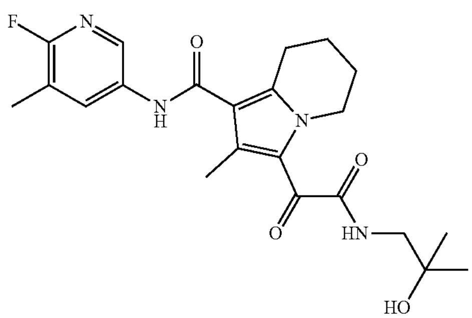 [SMILES: Cc1cc(NC(=O)c2c(C)c(C(=O)C(=O)NCC(C)(C)O)n3c2CCCC3)cnc1F] | N-(6-fluoro-5-methylpyridin-3-yl)-3-(2-((2-hydroxy-2-methylpropyl)amino)-2-oxoacetyl)-2-methyl-5,6,7,8-tetrahydroindolizine-1-carboxamide | 431.1 |
| 478 | 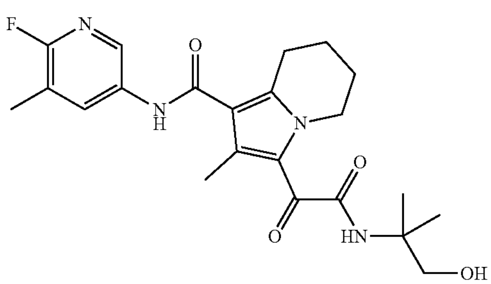 [SMILES: Cc1cc(NC(=O)c2c(C)c(C(=O)C(=O)NC(C)(C)CO)n3c2CCCC3)cnc1F] | N-(6-fluoro-5-methylpyridin-3-yl)-3-(2-((1-hydroxy-2-methylpropan-2-yl)amino)-2-oxoacetyl)-2-methyl-5,6,7,8-tetrahydroindolizine-1-carboxamide | 430.9 |
| 479 | 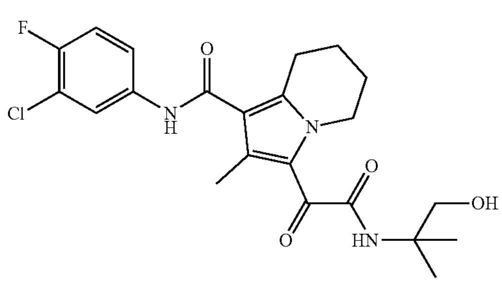 [SMILES: Cc1c(C(=O)Nc2ccc(F)c(Cl)c2)c2n(c1C(=O)C(=O)NC(C)(C)CO)CCCC2] | N-(3-chloro-4-fluorophenyl)-3-(2-((1-hydroxy-2-methylpropan-2-yl)amino)-2-oxoacetyl)-2-methyl-5,6,7,8-tetrahydroindolizine-1-carboxamide | |

TABLE 1-continued

Exemplary compounds

| Ex. | Structure | Chemical Name | ESI-MS (M + H)+ (m/z) |
|---|---|---|---|
| 480 | 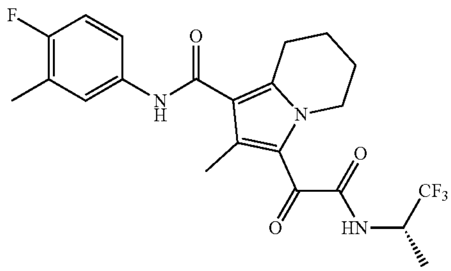 [SMILES: Cc1cc(NC(=O)c2c(C)c(C(=O)C(=O)N[C@@H](C)C(F)(F)F)n3c2CCCC3)ccc1F] | (S)-N-(4-fluoro-3-methylphenyl)-2-methyl-3-(2-oxo-2-((1,1,1-trifluoropropan-2-yl)amino)acetyl)-5,6,7,8-tetrahydroindolizine-1-carboxamide | |
| 481 | 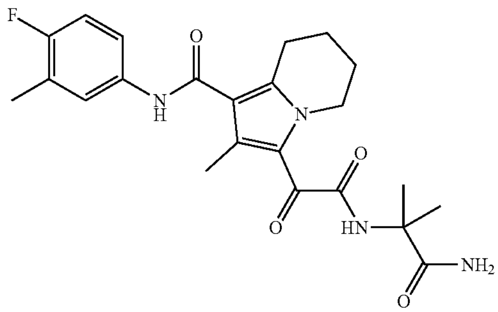 [SMILES: Cc1cc(NC(=O)c2c(C)c(C(=O)C(=O)NC(C)(C)C(N)=O)n3c2CCCC3)ccc1F] | 3-(2-((1-amino-2-methyl-1-oxopropan-2-yl)amino)-2-oxoacetyl)-N-(4-fluoro-3-methylphenyl)-2-methyl-5,6,7,8-tetrahydroindolizine-1-carboxamide | |
| 482 | 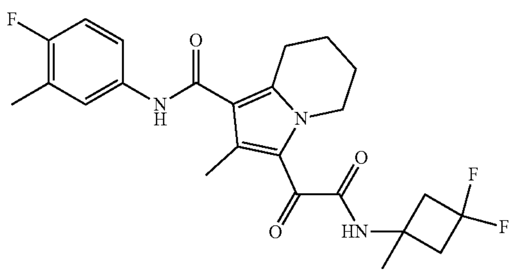 [SMILES: Cc1cc(NC(=O)c2c(C)c(C(=O)C(=O)NC3(C)CC(F)(F)C3)n3c2CCCC3)ccc1F] | 3-(2-((3,3-difluoro-1-methylcyclobutyl)amino)-2-oxoacetyl)-N-(4-fluoro-3-methylphenyl)-2-methyl-5,6,7,8-tetrahydroindolizine-1-carboxamide | |
| 483 | 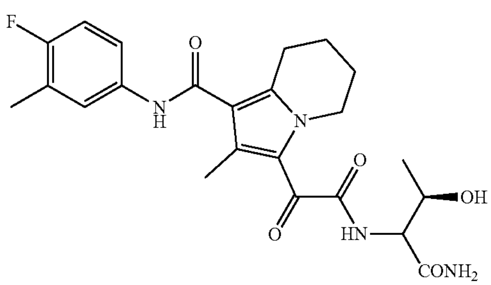 [SMILES: Cc1cc(NC(=O)c2c(C)c(C(=O)C(=O)NC(C(N)=O)[C@@H](C)O)n3c2CCCC3)ccc1F] | 3-(2-(((2S,3R)-1-amino-3-hydroxy-1-oxobutan-2-yl)amino)-2-oxoacetyl)-N-(4-fluoro-3-methylphenyl)-2-methyl-5,6,7,8-tetrahydroindolizine-1-carboxamide | |
| 484 | 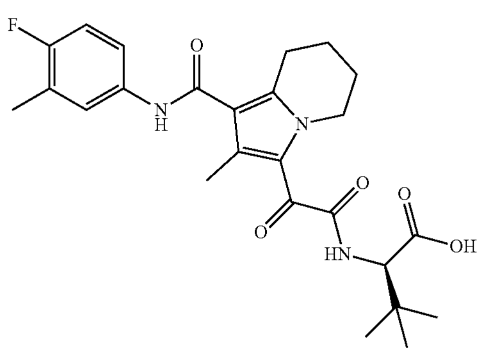 [SMILES: Cc1cc(NC(=O)c2c(C)c(C(=O)C(=O)N[C@@H](C(=O)O)C(C)(C)C)n3c2CCCC3)ccc1F] | (R)-2-(2-(1-((4-fluoro-3-methylphenyl)carbamoyl)-2-methyl-5,6,7,8-tetrahydroindolizin-3-yl)-2-oxoacetamido)-3,3-dimethylbutanoic acid | |

TABLE 1-continued

Exemplary compounds

| Ex. | Structure | Chemical Name | ESI-MS (M + H)+ (m/z) |
|---|---|---|---|
| 485 | 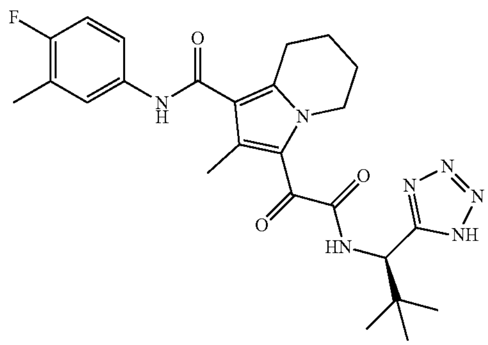 [SMILES: Cc1cc(NC(=O)c2c(C)c(C(=O)C(=O)N[C@@H](c3nnn[nH]3)C(C)(C)C)n3c2CCCC3)ccc1F] | (R)-3-(2-((2,2-dimethyl-1-(1H-tetrazol-5-yl)propyl)amino)-2-oxoacetyl)-N-(4-fluoro-3-methylphenyl)-2-methyl-5,6,7,8-tetrahydroindolizine-1-carboxamide | |
| 486 | 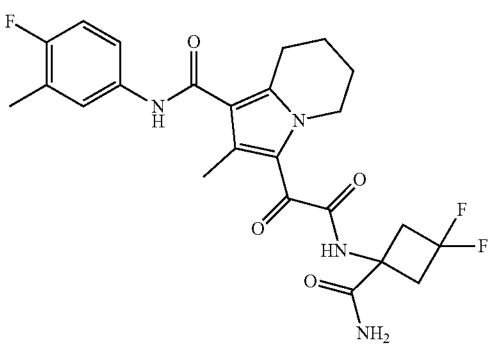 [SMILES: Cc1cc(NC(=O)c2c(C)c(C(=O)C(=O)NC3(C(N)=O)CC(F)(F)C3)n3c2CCCC3)ccc1F] | 3-(2-((1-carbamoyl-3,3-difluorocyclobutyl)amino)-2-oxoacetyl)-N-(4-fluoro-3-methylphenyl)-2-methyl-5,6,7,8-tetrahydroindolizine-1-carboxamide | |
| 487 | 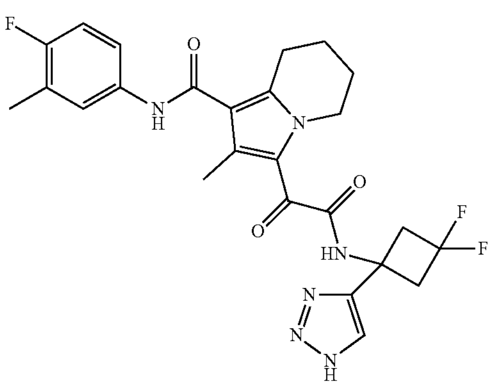 [SMILES: Cc1cc(NC(=O)c2c(C)c(C(=O)C(=O)NC3(c4c[nH]nn4)CC(F)(F)C3)n3c2CCCC3)ccc1F] | 3-(2-((3,3-difluoro-1-(1H-1,2,3-triazol-4-yl)cyclobutyl)amino)-2-oxoacetyl)-N-(4-fluoro-3-methylphenyl)-2-methyl-5,6,7,8-tetrahydroindolizine-1-carboxamide | |
| 488 | 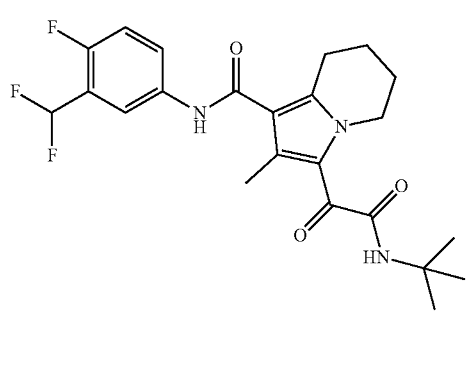 [SMILES: Cc1c(C(=O)Nc2ccc(F)c(C(F)F)c2)c2n(c1C(=O)C(=O)NC(C)(C)C)CCCC2] | 3-(2-(tert-butylamino)-2-oxoacetyl)-N-(3-(difluoromethyl)-4-fluorophenyl)-2-methyl-5,6,7,8-tetrahydroindolizine-1-carboxamide | |

TABLE 1-continued

Exemplary compounds

| Ex. | Structure | Chemical Name | ESI-MS (M + H)+ (m/z) |
|---|---|---|---|
| 489 | 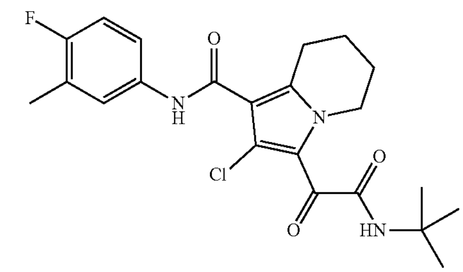 [SMILES: Cc1cc(NC(=O)c2c(Cl)c(C(=O)C(=O)NC(C)(C)C)n3c2CCCC3)ccc1F] | 3-(2-(tert-butylamino)-2-oxoacetyl)-2-chloro-N-(4-fluoro-3-methylphenyl)-5,6,7,8-tetrahydroindolizine-1-carboxamide | 433.7 |
| 490 | 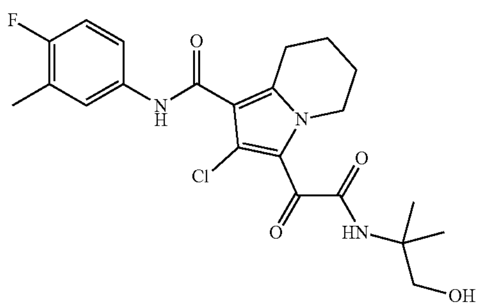 [SMILES: Cc1cc(NC(=O)c2c(Cl)c(C(=O)C(=O)NC(C)(C)CO)n3c2CCCC3)ccc1F] | 2-chloro-N-(4-fluoro-3-methylphenyl)-3-(2-((1-hydroxy-2-methylpropan-2-yl)amino)-2-oxoacetyl)-5,6,7,8-tetrahydroindolizine-1-carboxamide | 450.1 |
| 491 | 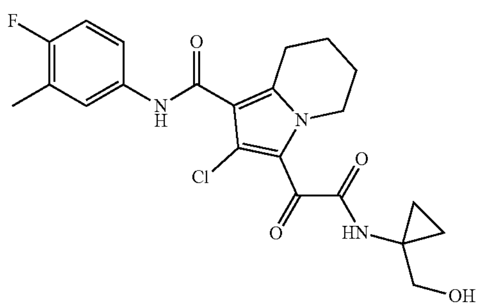 [SMILES: Cc1cc(NC(=O)c2c(Cl)c(C(=O)C(=O)NC3(CO)CC3)n3c2CCCC3)ccc1F] | 2-chloro-N-(4-fluoro-3-methylphenyl)-3-(2-((1-(hydroxymethyl)cyclopropyl)amino)-2-oxoacetyl)-5,6,7,8-tetrahydroindolizine-1-carboxamide | 448.0 |
| 492 | 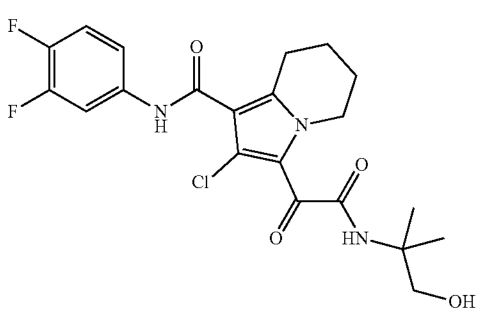 [SMILES: CC(C)(CO)NC(=O)C(=O)c1c(Cl)c(C(=O)Nc2ccc(F)c(F)c2)c2n1CCCC2] | 2-chloro-N-(3,4-difluorophenyl)-3-(2-((1-hydroxy-2-methylpropan-2-yl)amino)-2-oxoacetyl)-5,6,7,8-tetrahydroindolizine-1-carboxamide | 454.1 |

TABLE 1-continued

Exemplary compounds

| Ex. | Structure | Chemical Name | ESI-MS (M + H)+ (m/z) |
|---|---|---|---|
| 493 | 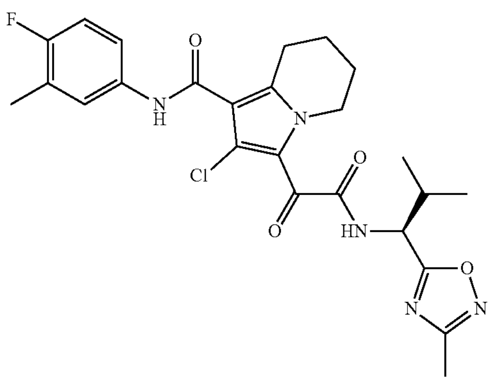 [SMILES: Cc1noc([C@@H](NC(=O)C(=O)c2c(Cl)c(C(=O)Nc3ccc(F)c(C)c3)c3n2CCCC3)C(C)C)n1] | (S)-2-chloro-N-(4-fluoro-3-methylphenyl)-3-(2-((2-methyl-1-(3-methyl-1,2,4-oxadiazol-5-yl)propyl)amino)-2-oxoacetyl)-5,6,7,8-tetrahydroindolizine-1-carboxamide | 516.1 |
| 494 | 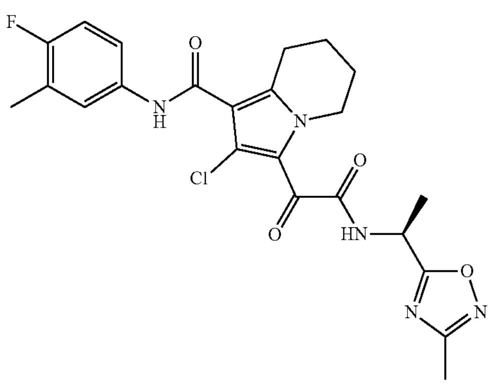 [SMILES: Cc1noc([C@H](C)NC(=O)C(=O)c2c(Cl)c(C(=O)Nc3ccc(F)c(C)c3)c3n2CCCC3)n1] | (S)-2-chloro-N-(4-fluoro-3-methylphenyl)-3-(2-((1-(3-methyl-1,2,4-oxadiazol-5-yl)ethyl)amino)-2-oxoacetyl)-5,6,7,8-tetrahydroindolizine-1-carboxamide | 448.1 |
| 495 | 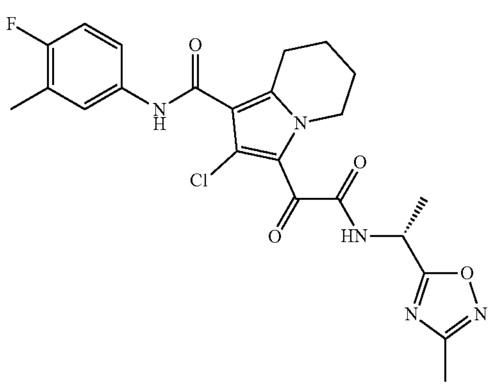 | (R)-2-chloro-N-(4-fluoro-3-methylphenyl)-3-(2-((1-(3-methyl-1,2,4-oxadiazol-5-yl)ethyl)amino)-2-oxoacetyl)-5,6,7,8-tetrahydroindolizine-1-carboxamide | 448.1 |
| 496 | 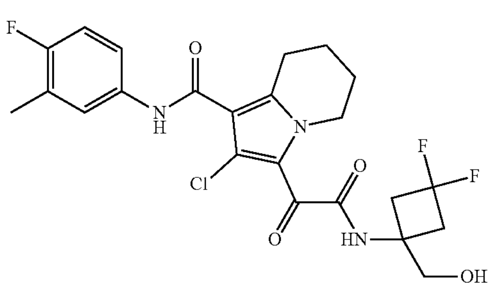 [SMILES: Cc1cc(NC(=O)c2c(Cl)c(C(=O)C(=O)NC3(CO)CC(F)(F)C3)n3c2CCCC3)ccc1F] | 2-chloro-3-(2-((3,3-difluoro-1-(hydroxymethyl)cyclobutyl)amino)-2-oxoacetyl)-N-(4-fluoro-3-methylphenyl)-5,6,7,8-tetrahydroindolizine-1-carboxamide | 498.1 |

TABLE 1-continued

Exemplary compounds

| Ex. | Structure | Chemical Name | ESI-MS (M + H)+ (m/z) |
|---|---|---|---|
| 497 | 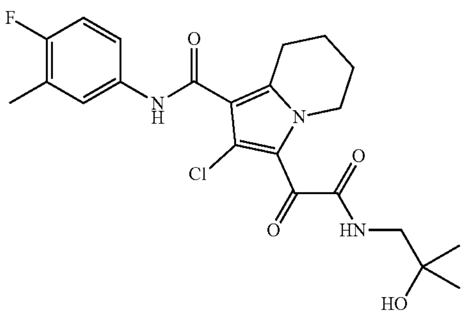 [SMILES: Cc1cc(NC(=O)c2c(Cl)c(C(=O)C(=O)NCC(C)(C)O)n3c2CCCC3)ccc1F] | 2-chloro-N-(4-fluoro-3-methylphenyl)-3-(2-((2-hydroxy-2-methylpropyl)amino)-2-oxoacetyl)-5,6,7,8-tetrahydroindolizine-1-carboxamide | 450.0 |
| 498 | 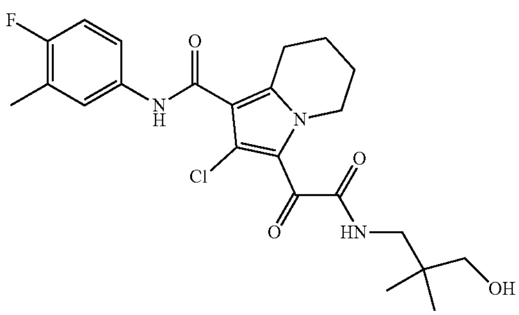 [SMILES: Cc1cc(NC(=O)c2c(Cl)c(C(=O)C(=O)NCC(C)(C)CO)n3c2CCCC3)ccc1F] | 2-chloro-N-(4-fluoro-3-methylphenyl)-3-(2-((3-hydroxy-2,2-dimethylpropyl)amino)-2-oxoacetyl)-5,6,7,8-tetrahydroindolizine-1-carboxamide | 464.0 |
| 499 | 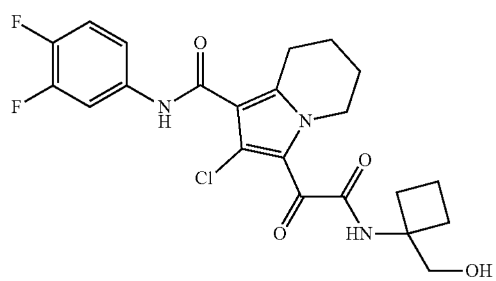 | 2-chloro-N-(3,4-difluorophenyl)-3-(2-((1-(hydroxymethyl)cyclobutyl)amino)-2-oxoacetyl)-5,6,7,8-tetrahydroindolizine-1-carboxamide | 466.1 |
| 500 | 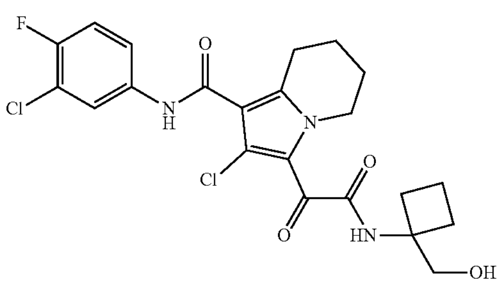 | 2-chloro-N-(3-chloro-4-fluorophenyl)-3-(2-((1-(hydroxymethyl)cyclobutyl)amino)-2-oxoacetyl)-5,6,7,8-tetrahydroindolizine-1-carboxamide | 482.0 |
| 501 | 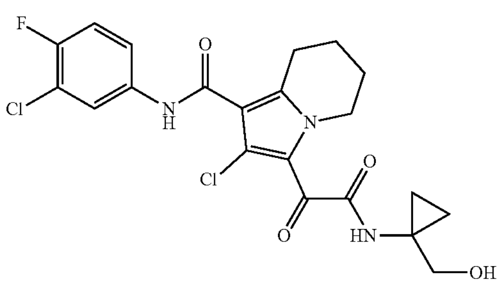 [SMILES: O=C(NC1(CO)CC1)C(=O)c1c(Cl)c(C(=O)Nc2ccc(F)c(Cl)c2)c2n1CCCC2] | 2-chloro-N-(3-chloro-4-fluorophenyl)-3-(2-((1-(hydroxymethyl)cyclopropyl)amino)-2-oxoacetyl)-5,6,7,8-tetrahydroindolizine-1-carboxamide | 468.0 |

TABLE 1-continued

Exemplary compounds

| Ex. | Structure | Chemical Name | ESI-MS (M + H)+ (m/z) |
|---|---|---|---|
| 502 | 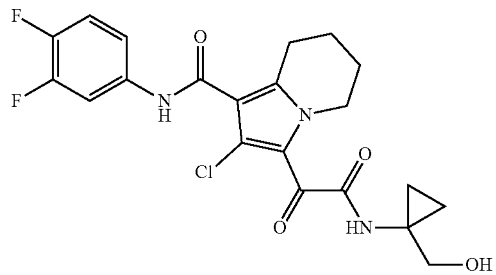 [SMILES: O=C(NC1(CO)CC1)C(=O)c1c(Cl)c(C(=O)Nc2ccc(F)c(F)c2)c2n1CCCC2] | 2-chloro-N-(3,4-difluorophenyl)-3-(2-((1-(hydroxymethyl)cyclopropyl)amino)-2-oxoacetyl)-5,6,7,8-tetrahydroindolizine-1-carboxamide | 452.0 |
| 503 | 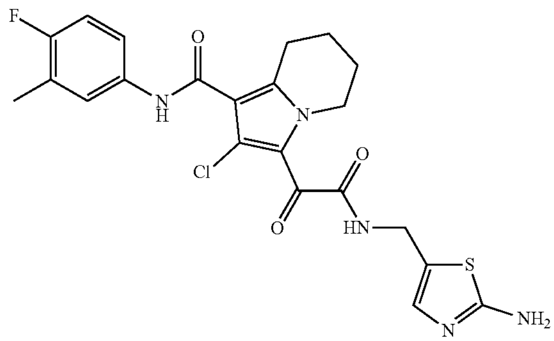 [SMILES: Cc1cc(NC(=O)c2c(Cl)c(C(=O)C(=O)NCc3cnc(N)s3)n3c2CCCC3)ccc1F] | 3-(2-(((2-aminothiazol-5-yl)methyl)amino)-2-oxoacetyl)-2-chloro-N-(4-fluoro-3-methylphenyl)-5,6,7,8-tetrahydroindolizine-1-carboxamide | 490.0 |
| 504 | 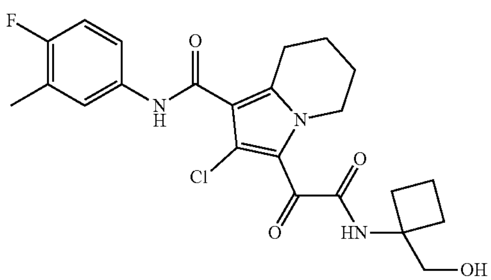 [SMILES: Cc1cc(NC(=O)c2c(Cl)c(C(=O)C(=O)NC3(CO)CCC3)n3c2CCCC3)ccc1F] | 2-chloro-N-(4-fluoro-3-methylphenyl)-3-(2-((1-(hydroxymethyl)cyclobutyl)amino)-2-oxoacetyl)-5,6,7,8-tetrahydroindolizine-1-carboxamide | 462.0 |
| 505 | 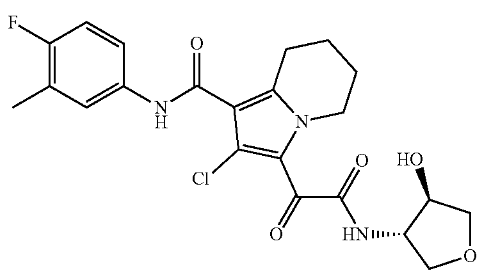 [SMILES: Cc1cc(NC(=O)c2c(Cl)c(C(=O)C(=O)N[C@H]3COC[C@@H]3O)n3c2CCCC3)ccc1F] | 2-chloro-N-(4-fluoro-3-methylphenyl)-3-(2-(((3S,4R)-4-hydroxytetrahydrofuran-3-yl)amino)-2-oxoacetyl)-5,6,7,8-tetrahydroindolizine-1-carboxamide | 464.0 |
| 506 | 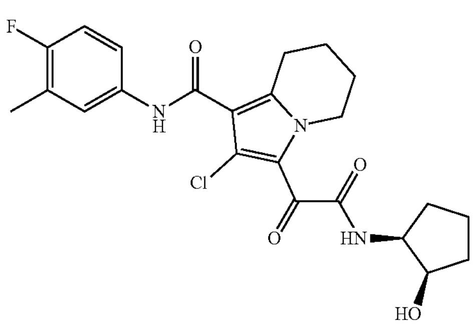 [SMILES: Cc1cc(NC(=O)c2c(Cl)c(C(=O)C(=O)N[C@H]3CCC[C@H]3O)n3c2CCCC3)ccc1F] | 2-chloro-N-(4-fluoro-3-methylphenyl)-3-(2-(((1S,2R)-2-hydroxycyclopentyl)amino)-2-oxoacetyl)-5,6,7,8-tetrahydroindolizine-1-carboxamide | 462.0 |

TABLE 1-continued

Exemplary compounds

| Ex. | Structure | Chemical Name | ESI-MS (M + H)+ (m/z) |
|---|---|---|---|
| 507 | 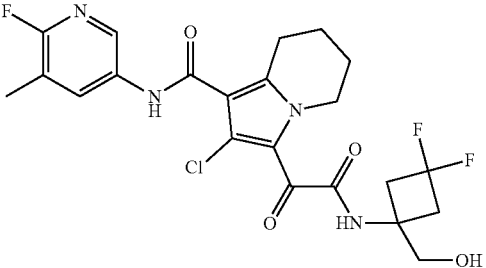 [SMILES: Cc1cc(NC(=O)c2c(Cl)c(C(=O)C(=O)NC3(CO)CC(F)(F)C3)n3c2CCCC3)cnc1F] | 2-chloro-3-(2-((3,3-difluoro-1-(hydroxymethyl)cyclobutyl)amino)-2-oxoacetyl)-N-(6-fluoro-5-methylpyridin-3-yl)-5,6,7,8-tetrahydroindolizine-1-carboxamide | 498.1 |
| 508 | 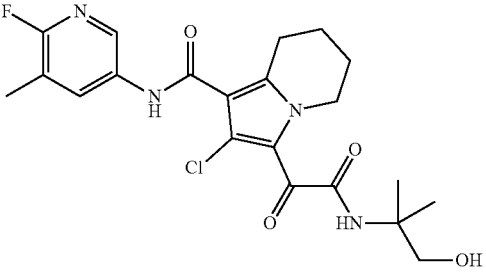 [SMILES: Cc1cc(NC(=O)c2c(Cl)c(C(=O)C(=O)NC(C)(C)CO)n3c2CCCC3)cnc1F] | 2-chloro-N-(6-fluoro-5-methylpyridin-3-yl)-3-(2-((1-hydroxy-2-methylpropan-2-yl)amino)-2-oxoacetyl)-5,6,7,8-tetrahydroindolizine-1-carboxamide | 451.1 |
| 509 | 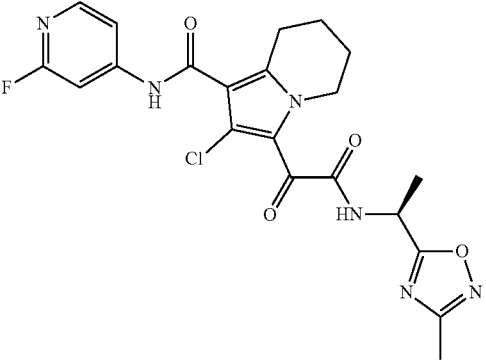 [SMILES: Cc1noc([C@H](C)NC(=O)C(=O)c2c(Cl)c(C(=O)Nc3ccnc(F)c3)c3n2CCCC3)n1] | (S)-2-chloro-N-(2-fluoropyridin-4-yl)-3-(2-((1-(3-methyl-1,2,4-oxadiazol-5-yl)ethyl)amino)-2-oxoacetyl)-5,6,7,8-tetrahydroindolizine-1-carboxamide | 475.1 |
| 510 | 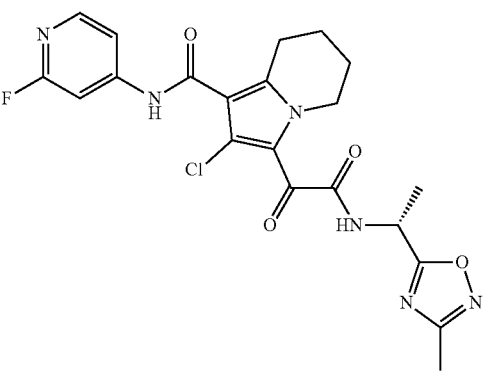 [SMILES: Cc1noc([C@@H](C)NC(=O)C(=O)c2c(Cl)c(C(=O)Nc3ccnc(F)c3)c3n2CCCC3)n1] | (R)-2-chloro-N-(2-fluoropyridin-4-yl)-3-(2-((1-(3-methyl-1,2,4-oxadiazol-5-yl)ethyl)amino)-2-oxoacetyl)-5,6,7,8-tetrahydroindolizine-1-carboxamide | 475.0 |

TABLE 1-continued

Exemplary compounds

| Ex. | Structure | Chemical Name | ESI-MS (M + H)+ (m/z) |
|---|---|---|---|
| 511 | 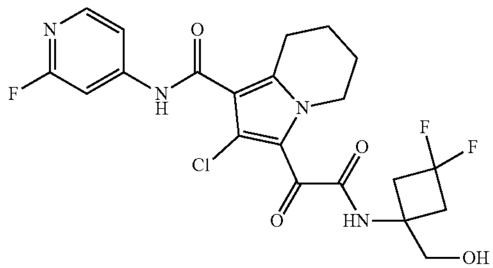 [SMILES: O=C(NC1(CO)CC(F)(F)C1)C(=O)c1c(Cl)c(C(=O)Nc2ccnc(F)c2)c2n1CCCC2] | 2-chloro-3-(2-((3,3-difluoro-1-(hydroxymethyl)cyclobutyl)amino)-2-oxoacetyl)-N-(2-fluoropyridin-4-yl)-5,6,7,8-tetrahydroindolizine-1-carboxamide | 485.0 |
| 512 | 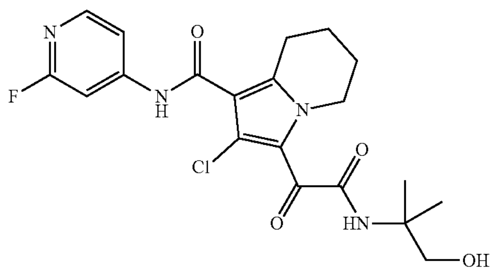 [SMILES: CC(C)(CO)NC(=O)C(=O)c1c(Cl)c(C(=O)Nc2ccnc(F)c2)c2n1CCCC2] | 2-chloro-N-(2-fluoropyridin-4-yl)-3-(2-((1-hydroxy-2-methylpropan-2-yl)amino)-2-oxoacetyl)-5,6,7,8-tetrahydroindolizine-1-carboxamide | 437.1 |
| 513 | 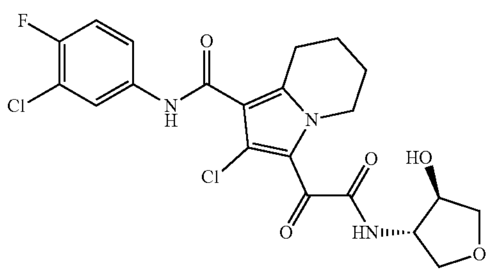 [SMILES: O=C(N[C@H]1COC[C@@H]1O)C(=O)c1c(Cl)c(C(=O)Nc2ccc(F)c(Cl)c2)c2n1CCCC2] | 2-chloro-N-(3-chloro-4-fluorophenyl)-3-(2-(((3S,4R)-4-hydroxytetrahydrofuran-3-yl)amino)-2-oxoacetyl)-5,6,7,8-tetrahydroindolizine-1-carboxamide | 484.0 |
| 514 | 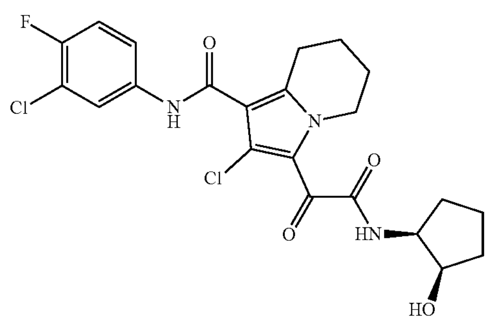 | 2-chloro-N-(3-chloro-4-fluorophenyl)-3-(2-(((1S,2R)-2-hydroxycyclopentyl)amino)-2-oxoacetyl)-5,6,7,8-tetrahydroindolizine-1-carboxamide | 482.0 |
| 515 | 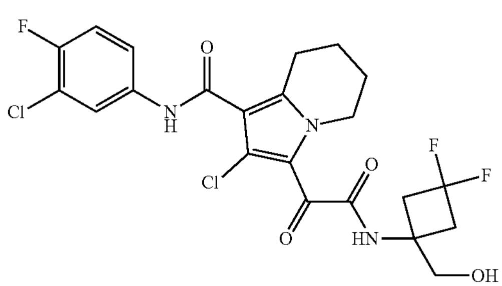 [SMILES: O=C(NC1(CO)CC(F)(F)C1)C(=O)c1c(Cl)c(C(=O)Nc2ccc(F)c(Cl)c2)c2n1CCCC2] | 2-chloro-N-(3-chloro-4-fluorophenyl)-3-(2-((3,3-difluoro-1-(hydroxymethyl)cyclobutyl)amino)-2-oxoacetyl)-5,6,7,8-tetrahydroindolizine-1-carboxamide | 518.0 |

| Ex. | Structure | Chemical Name | ESI-MS (M + H)+ (m/z) |
|---|---|---|---|
| 516 | 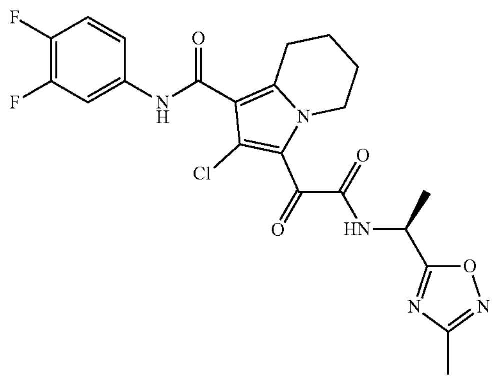 | (S)-2-chloro-N-(3,4-difluorophenyl)-3-(2-((1-(3-methyl-1,2,4-oxadiazol-5-yl)ethyl)amino)-2-oxoacetyl)-5,6,7,8-tetrahydroindolizine-1-carboxamide | 492.1 |
| 517 | 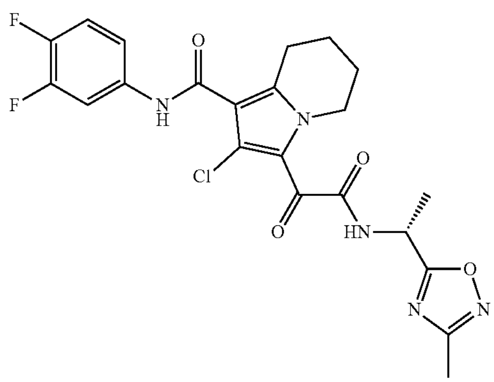 | (R)-2-chloro-N-(3,4-difluorophenyl)-3-(2-((1-(3-methyl-1,2,4-oxadiazol-5-yl)ethyl)amino)-2-oxoacetyl)-5,6,7,8-tetrahydroindolizine-1-carboxamide | 492.1 |
| 518 | 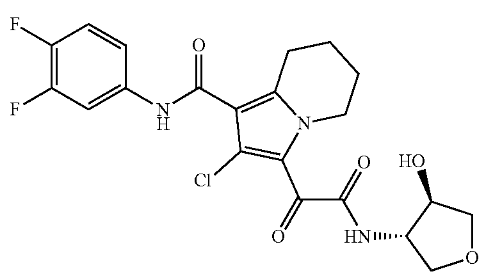 | 2-chloro-N-(3,4-difluorophenyl)-3-(2-(((3S,4R)-4-hydroxytetrahydrofuran-3-yl)amino)-2-oxoacetyl)-5,6,7,8-tetrahydroindolizine-1-carboxamide | 468.0 |
| 519 | 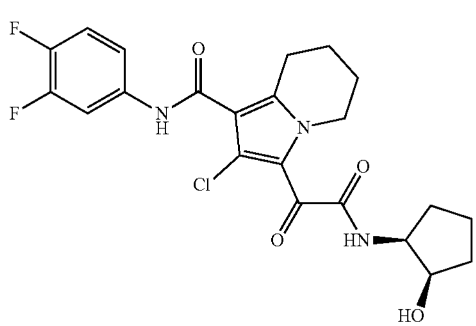 [SMILES: O=C(N[C@H]1CCC[C@H]1O)C(=O)c1c(Cl)c(C(=O)Nc2ccc(F)c(F)c2)c2n1CCCC2] | 2-chloro-N-(3,4-difluorophenyl)-3-(2-(((1S,2R)-2-hydroxycyclopentyl)amino)-2-oxoacetyl)-5,6,7,8-tetrahydroindolizine-1-carboxamide | 466.1 |

TABLE 1-continued

Exemplary compounds

| Ex. | Structure | Chemical Name | ESI-MS (M + H)+ (m/z) |
|---|---|---|---|
| 520 | 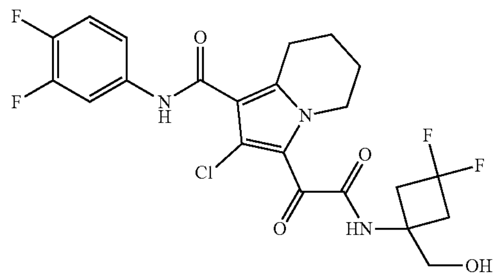 [SMILES: O=C(NC1(CO)CC(F)(F)C1)C(=O)c1c(Cl)c(C(=O)Nc2ccc(F)c(F)c2)c2n1CCCC2] | 2-chloro-3-(2-((3,3-difluoro-1-(hydroxymethyl)cyclobutyl)amino)-2-oxoacetyl)-N-(3,4-difluorophenyl)-5,6,7,8-tetrahydroindolizine-1-carboxamide | 502.0 |
| 521 | 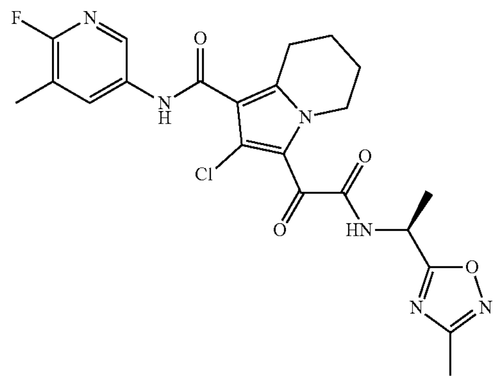 [SMILES: Cc1noc([C@H](C)NC(=O)C(=O)c2c(Cl)c(C(=O)Nc3cnc(F)c(C)c3)c3n2CCCC3)n1] | (S)-2-chloro-N-(6-fluoro-5-methylpyridin-3-yl)-3-(2-((1-(3-methyl-1,2,4-oxadiazol-5-yl)ethyl)amino)-2-oxoacetyl)-5,6,7,8-tetrahydroindolizine-1-carboxamide | 489.1 |
| 522 | 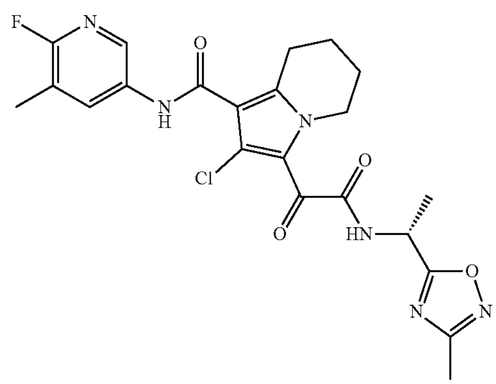 [SMILES: Cc1noc([C@@H](C)NC(=O)C(=O)c2c(Cl)c(C(=O)Nc3cnc(F)c(C)c3)c3n2CCCC3)n1] | (R)-2-chloro-N-(6-fluoro-5-methylpyridin-3-yl)-3-(2-((1-(3-methyl-1,2,4-oxadiazol-5-yl)ethyl)amino)-2-oxoacetyl)-5,6,7,8-tetrahydroindolizine-1-carboxamide | 489.1 |
| 523 | 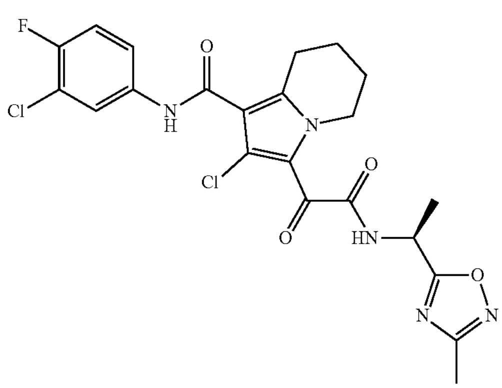 [SMILES: Cc1noc([C@H](C)NC(=O)C(=O)c2c(Cl)c(C(=O)Nc3ccc(F)c(Cl)c3)c3n2CCCC3)n1] | (S)-2-chloro-N-(3-chloro-4-fluorophenyl)-3-(2-((1-(3-methyl-1,2,4-oxadiazol-5-yl)ethyl)amino)-2-oxoacetyl)-5,6,7,8-tetrahydroindolizine-1-carboxamide | 508.0 |

TABLE 1-continued

Exemplary compounds

| Ex. | Structure | Chemical Name | ESI-MS (M + H)+ (m/z) |
|---|---|---|---|
| 524 | 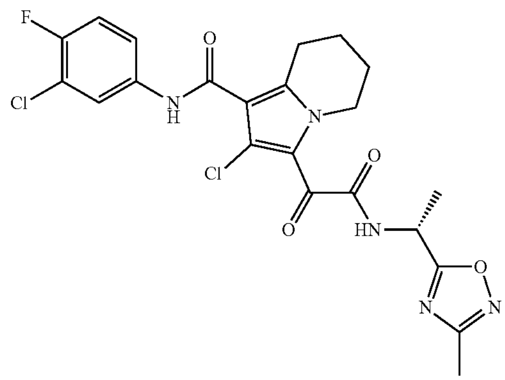 [SMILES: Cc1noc([C@@H](C)NC(=O)C(=O)c2c(Cl)c(C(=O)Nc3ccc(F)c(Cl)c3)c3n2CCCC3)n1] | (R)-2-chloro-N-(3-chloro-4-fluorophenyl)-3-(2-((1-(3-methyl-1,2,4-oxadiazol-5-yl)ethyl)amino)-2-oxoacetyl)-5,6,7,8-tetrahydroindolizine-1-carboxamide | 508.0 |
| 525 | 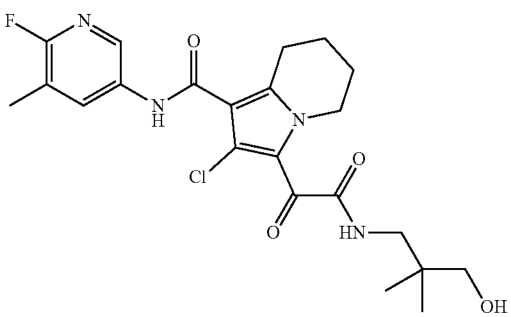 [SMILES: Cc1cc(NC(=O)c2c(Cl)c(C(=O)C(=O)NCC(C)(C)CO)n3c2CCCC3)cnc1F] | 2-chloro-N-(6-fluoro-5-methylpyridin-3-yl)-3-(2-((3-hydroxy-2,2-dimethylpropyl)amino)-2-oxoacetyl)-5,6,7,8-tetrahydroindolizine-1-carboxamide | 465.1 |
| 526 | 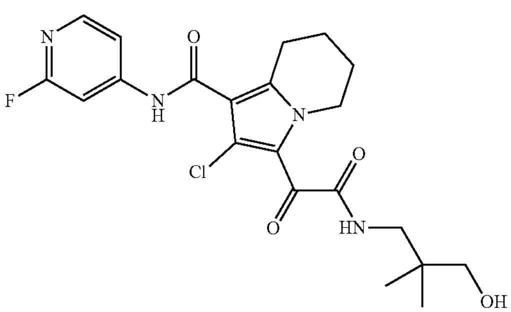 [SMILES: CC(C)(CO)CNC(=O)C(=O)c1c(Cl)c(C(=O)Nc2ccnc(F)c2)c2n1CCCC2] | 2-chloro-N-(2-fluoropyridin-4-yl)-3-(2-((3-hydroxy-2,2-dimethylpropyl)amino)-2-oxoacetyl)-5,6,7,8-tetrahydroindolizine-1-carboxamide | 451.1 |
| 527 | 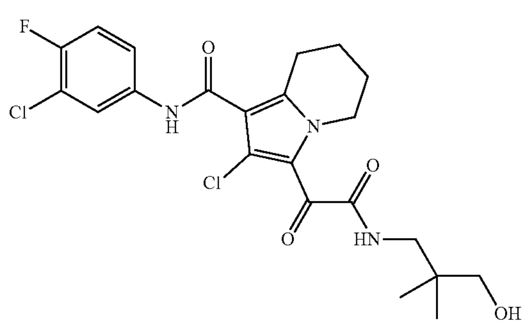 [SMILES: CC(C)(CO)CNC(=O)C(=O)c1c(Cl)c(C(=O)Nc2ccc(F)c(Cl)c2)c2n1CCCC2] | 2-chloro-N-(3-chloro-4-fluorophenyl)-3-(2-((3-hydroxy-2,2-dimethylpropyl)amino)-2-oxoacetyl)-5,6,7,8-tetrahydroindolizine-1-carboxamide | 484.1 |

TABLE 1-continued

Exemplary compounds

| Ex. | Structure | Chemical Name | ESI-MS (M + H)+ (m/z) |
|---|---|---|---|
| 528 | 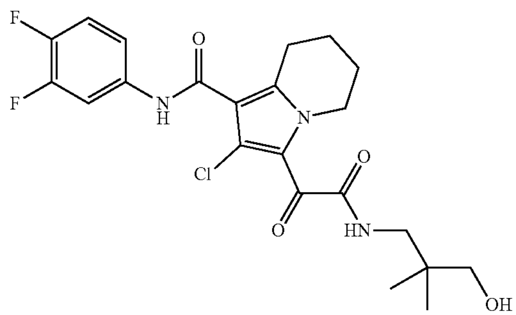 [SMILES: CC(C)(CO)CNC(=O)C(=O)c1c(Cl)c(C(=O)Nc2ccc(F)c(F)c2)c2n1CCCC2] | 2-chloro-N-(3,4-difluorophenyl)-3-(2-((3-hydroxy-2,2-dimethylpropyl)amino)-2-oxoacetyl)-5,6,7,8-tetrahydroindolizine-1-carboxamide | 468.1 |
| 529 | 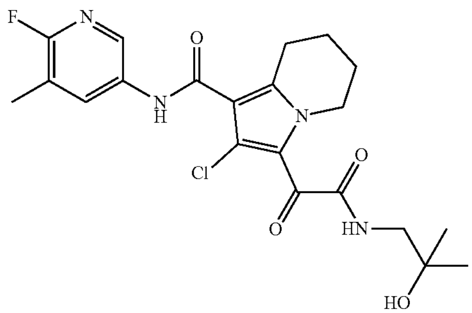 [SMILES: Cc1cc(NC(=O)c2c(Cl)c(C(=O)C(=O)NCC(C)(C)O)n3c2CCCC3)cnc1F] | 2-chloro-N-(6-fluoro-5-methylpyridin-3-yl)-3-(2-((2-hydroxy-2-methylpropyl)amino)-2-oxoacetyl)-5,6,7,8-tetrahydroindolizine-1-carboxamide | 451.1 |
| 530 | 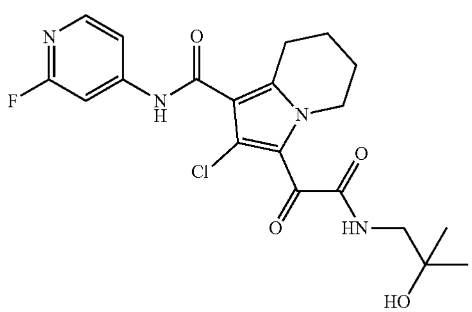 [SMILES: CC(C)(O)CNC(=O)C(=O)c1c(Cl)c(C(=O)Nc2ccnc(F)c2)c2n1CCCC2] | 2-chloro-N-(2-fluoropyridin-4-yl)-3-(2-((2-hydroxy-2-methylpropyl)amino)-2-oxoacetyl)-5,6,7,8-tetrahydroindolizine-1-carboxamide | 437.1 |
| 531 | 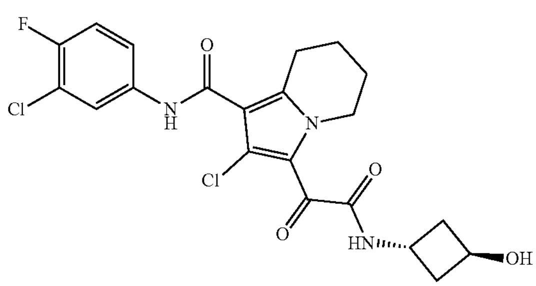 [SMILES: O=C(N[C@H]1C[C@H](O)C1)C(=O)c1c(Cl)c(C(=O)Nc2ccc(F)c(Cl)c2)c2n1CCCC2] | 2-chloro-N-(3-chloro-4-fluorophenyl)-3-(2-(((1r,3r)-3-hydroxycyclobutyl)amino)-2-oxoacetyl)-5,6,7,8-tetrahydroindolizine-1-carboxamide | 468.1 |
| 532 | 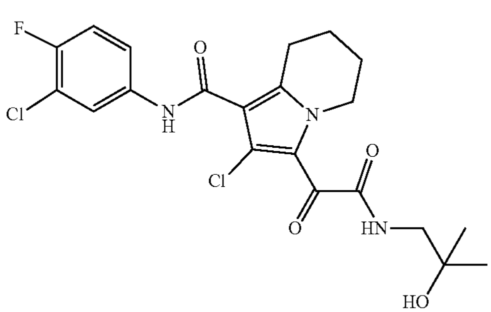 [SMILES: CC(C)(O)CNC(=O)C(=O)c1c(Cl)c(C(=O)Nc2ccc(F)c(Cl)c2)c2n1CCCC2] | 2-chloro-N-(3-chloro-4-fluorophenyl)-3-(2-((2-hydroxy-2-methylpropyl)amino)-2-oxoacetyl)-5,6,7,8-tetrahydroindolizine-1-carboxamide | 470.0 |

TABLE 1-continued

Exemplary compounds

| Ex. | Structure | Chemical Name | ESI-MS (M + H)+ (m/z) |
|---|---|---|---|
| 533 | 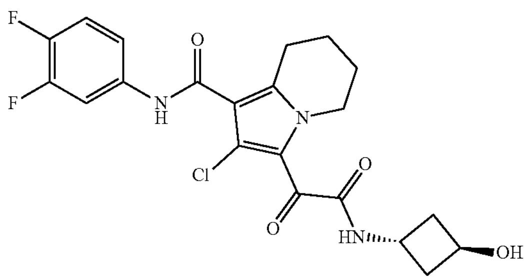 [SMILES: O=C(N[C@H]1C[C@H](O)C1)C(=O)c1c(Cl)c(C(=O)Nc2ccc(F)c(F)c2)c2n1CCCC2] | 2-chloro-N-(3,4-difluorophenyl)-3-(2-(((1r,3r)-3-hydroxycyclobutyl)amino)-2-oxoacetyl)-5,6,7,8-tetrahydroindolizine-1-carboxamide | 452.1 |
| 534 | 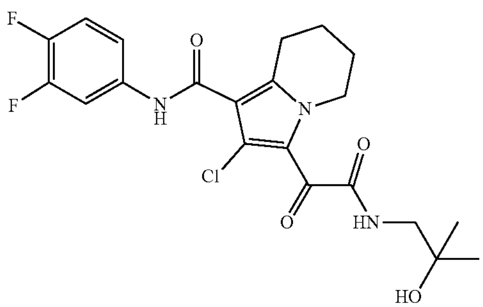 [SMILES: CC(C)(O)CNC(=O)C(=O)c1c(Cl)c(C(=O)Nc2ccc(F)c(F)c2)c2n1CCCC2] | 2-chloro-N-(3,4-difluorophenyl)-3-(2-((2-hydroxy-2-methylpropyl)amino)-2-oxoacetyl)-5,6,7,8-tetrahydroindolizine-1-carboxamide | 454.1 |
| 535 | 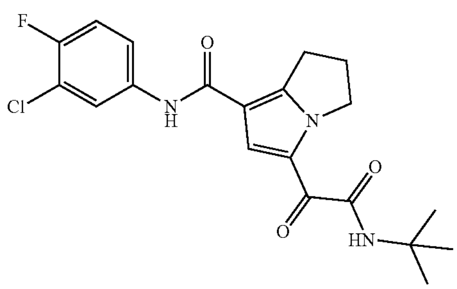 [SMILES: CC(C)(C)NC(=O)C(=O)c1cc(C(=O)Nc2ccc(F)c(Cl)c2)c2n1CCC2] | 5-(2-(tert-butylamino)-2-oxoacetyl)-N-(3-chloro-4-fluorophenyl)-2,3-dihydro-1H-pyrrolizine-7-carboxamide | 406.1 |
| 536 | 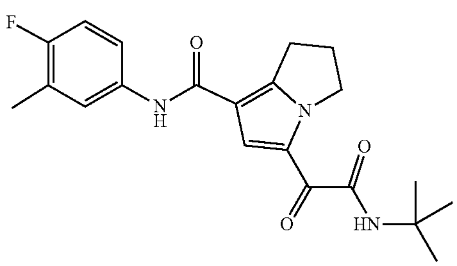 [SMILES: Cc1cc(NC(=O)c2cc(C(=O)C(=O)NC(C)(C)C)n3c2CCC3)ccc1F] | 5-(2-(tert-butylamino)-2-oxoacetyl)-N-(4-fluoro-3-methylphenyl)-2,3-dihydro-1H-pyrrolizine-7-carboxamide | 386.2 |
| 537 | 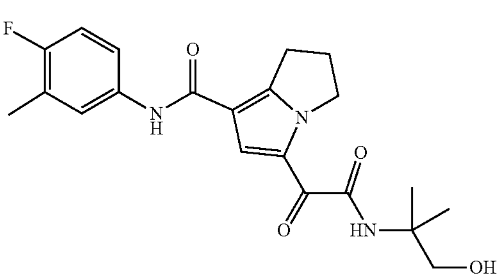 [SMILES: Cc1cc(NC(=O)c2cc(C(=O)C(=O)NC(C)(C)CO)n3c2CCC3)ccc1F] | N-(4-fluoro-3-methylphenyl)-5-(2-((1-hydroxy-2-methylpropan-2-yl)amino)-2-oxoacetyl)-2,3-dihydro-1H-pyrrolizine-7-carboxamide | 401.9 |

TABLE 1-continued

Exemplary compounds

| Ex. | Structure | Chemical Name | ESI-MS (M + H)+ (m/z) |
|---|---|---|---|
| 538 | 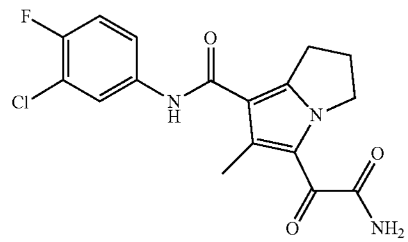 [SMILES: Cc1c(C(=O)Nc2ccc(F)c(Cl)c2)c2n(c1C(=O)C(N)=O)CCC2] | 5-(2-amino-2-oxoacetyl)-N-(3-chloro-4-fluorophenyl)-6-methyl-2,3-dihydro-1H-pyrrolizine-7-carboxamide | |
| 539 | 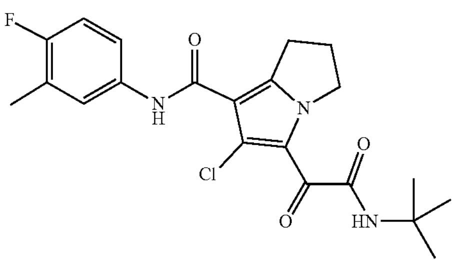 [SMILES: Cc1cc(NC(=O)c2c(Cl)c(C(=O)C(=O)NC(C)(C)C)n3c2CCC3)ccc1F] | 5-(2-(tert-butylamino)-2-oxoacetyl)-6-chloro-N-(4-fluoro-3-methylphenyl)-2,3-dihydro-1H-pyrrolizine-7-carboxamide | 420.2 |
| 540 | 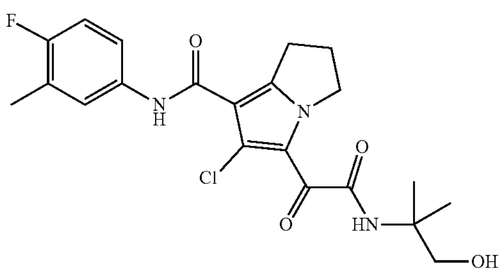 [SMILES: Cc1cc(NC(=O)c2c(Cl)c(C(=O)C(=O)NC(C)(C)CO)n3c2CCC3)ccc1F] | 6-chloro-N-(4-fluoro-3-methylphenyl)- 5-(2-((1-hydroxy-2-methylpropan-2-yl)amino)-2-oxoacetyl)-2,3-dihydro-1H-pyrrolizine-7-carboxamide | 436.0 |
| 541 | 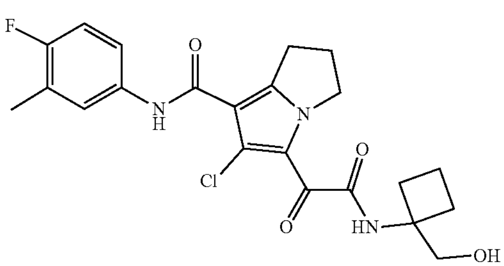 [SMILES: Cc1cc(NC(=O)c2c(Cl)c(C(=O)C(=O)NC3(CO)CCC3)n3c2CCC3)ccc1F] | 6-chloro-N-(4-fluoro-3-methylphenyl)-5-(2-((1-(hydroxymethyl)cyclobutyl)amino)-2-oxoacetyl)-2,3-dihydro-1H-pyrrolizine-7-carboxamide | 448.1 |
| 542 | 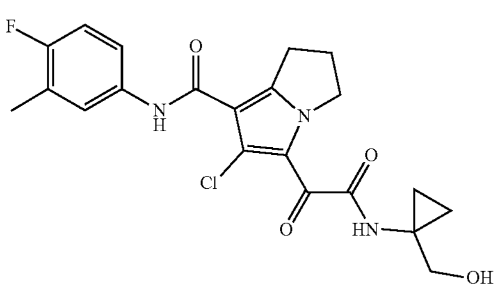 [SMILES: Cc1cc(NC(=O)c2c(Cl)c(C(=O)C(=O)NC3(CO)CC3)n3c2CCC3)ccc1F] | 6-chloro-N-(4-fluoro-3-methylphenyl)-5-(2-((1-(hydroxymethyl)cyclopropyl)amino)-2-oxoacetyl)-2,3-dihydro-1H-pyrrolizine-7-carboxamide | 434.1 |

TABLE 1-continued

Exemplary compounds

| Ex. | Structure | Chemical Name | ESI-MS (M + H)+ (m/z) |
|---|---|---|---|
| 543 | 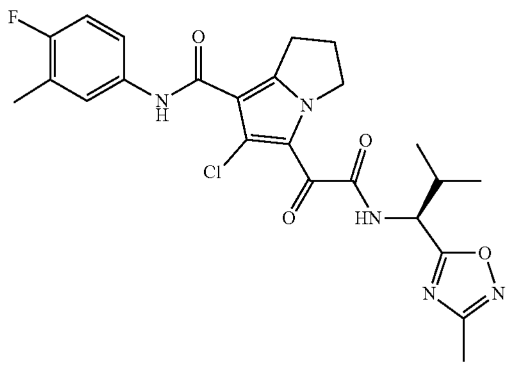 [SMILES: Cc1noc([C@@H](NC(=O)C(=O)c2c(Cl)c(C(=O)Nc3ccc(F)c(C)c3)c3n2CCC3)C(C)C)n1] | (S)-6-chloro-N-(4-fluoro-3-methylphenyl)-5-(2-((2-methyl-1-(3-methyl-1,2,4-oxadiazol-5-yl)propyl)amino)-2-oxoacetyl)-2,3-dihydro-1H-pyrrolizine-7-carboxamide | 502.0 |
| 544 | 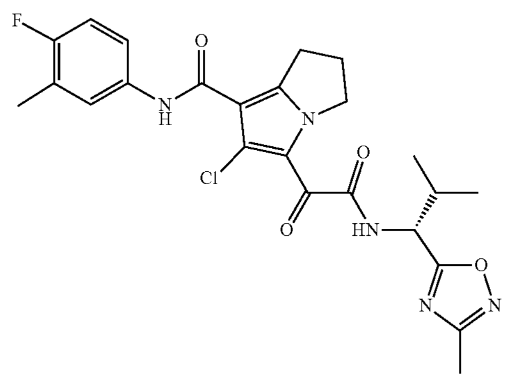 [SMILES: Cc1noc([C@H](NC(=O)C(=O)c2c(Cl)c(C(=O)Nc3ccc(F)c(C)c3)c3n2CCC3)C(C)C)n1] | (R)-6-chloro-N-(4-fluoro-3-methylphenyl)-5-(2-((2-methyl-1-(3-methyl-1,2,4-oxadiazol-5-yl)propyl)amino)-2-oxoacetyl)-2,3-dihydro-1H-pyrrolizine-7-carboxamide | 502.0 |
| 545 | 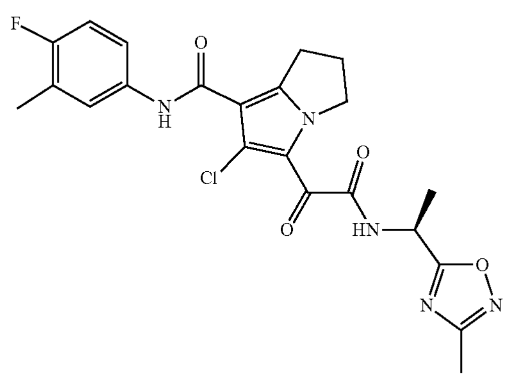 [SMILES: Cc1noc([C@H](C)NC(=O)C(=O)c2c(Cl)c(C(=O)Nc3ccc(F)c(C)c3)c3n2CCC3)n1] | (S)-6-chloro-N-(4-fluoro-3-methylphenyl)-5-(2-((1-(3-methyl-1,2,4-oxadiazol-5-yl)ethyl)amino)-2-oxoacetyl)-2,3-dihydro-1H-pyrrolizine-7-carboxamide | 474.0 |
| 546 | 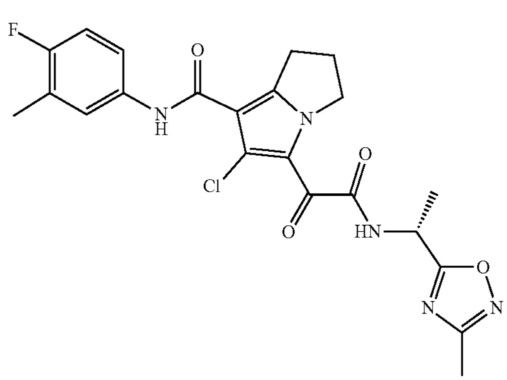 [SMILES: Cc1noc([C@@H](C)NC(=O)C(=O)c2c(Cl)c(C(=O)Nc3ccc(F)c(C)c3)c3n2CCC3)n1] | (R)-6-chloro-N-(4-fluoro-3-methylphenyl)-5-(2-((1-(3-methyl-1,2,4-oxadiazol-5-yl)ethyl)amino)-2-oxoacetyl)-2,3-dihydro-1H-pyrrolizine-7-carboxamide | 474.0 |

TABLE 1-continued

Exemplary compounds

| Ex. | Structure | Chemical Name | ESI-MS (M + H)+ (m/z) |
|---|---|---|---|
| 547 | 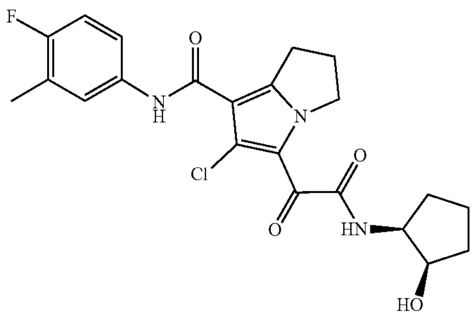 [SMILES: Cc1cc(NC(=O)c2c(Cl)c(C(=O)C(=O)N[C@H]3CCC[C@H]3O)n3c2CCC3)ccc1F] | 6-chloro-N-(4-fluoro-3-methylphenyl)-5-(2-(((1S,2R)-2-hydroxycyclopentyl)amino)-2-oxoacetyl)-2,3-dihydro-1H-pyrrolizine-7-carboxamide | 448.1 |
| 548 | 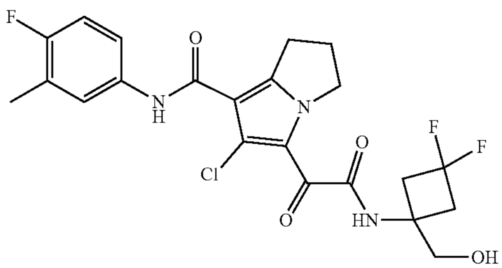 [SMILES: Cc1cc(NC(=O)c2c(Cl)c(C(=O)C(=O)NC3(CO)CC(F)(F)C3)n3c2CCC3)ccc1F] | 6-chloro-5-(2-((3,3-difluoro-1-(hydroxymethyl)cyclobutyl)amino)-2-oxoacetyl)-N-(4-fluoro-3-methylphenyl)-2,3-dihydro-1H-pyrrolizine-7-carboxamide | 484.0 |
| 549 | 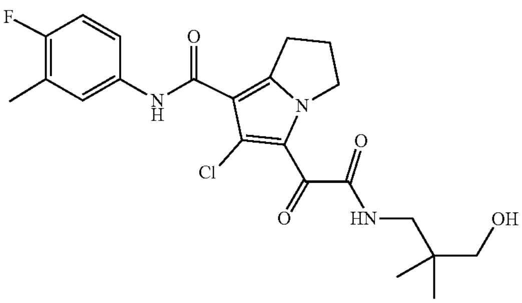 [SMILES: Cc1cc(NC(=O)c2c(Cl)c(C(=O)C(=O)NCC(C)(C)CO)n3c2CCC3)ccc1F] | 6-chloro-N-(4-fluoro-3-methylphenyl)-5-(2-((3-hydroxy-2,2-dimethylpropyl)amino)-2-oxoacetyl)-2,3-dihydro-1H-pyrrolizine-7-carboxamide | 450.0 |
| 550 | 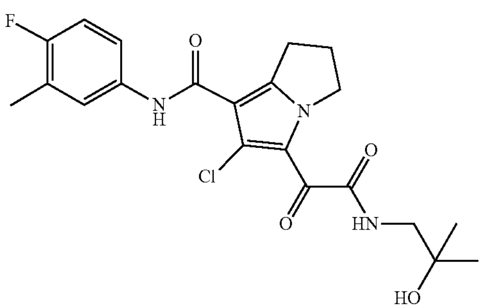 [SMILES: Cc1cc(NC(=O)c2c(Cl)c(C(=O)C(=O)NCC(C)(C)O)n3c2CCC3)ccc1F] | 6-chloro-N-(4-fluoro-3-methylphenyl)-5-(2-((2-hydroxy-2-methylpropyl)amino)-2-oxoacetyl)-2,3-dihydro-1H-pyrrolizine-7-carboxamide | 436.1 |
| 551 | 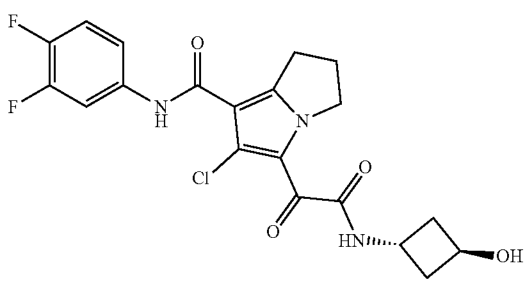 [SMILES: O=C(N[C@H]1C[C@H](O)C1)C(=O)c1c(Cl)c(C(=O)Nc2ccc(F)c(F)c2)c2n1CCC2] | 6-chloro-N-(3,4-difluorophenyl)-5-(2-(((1r,3r)-3-hydroxycyclobutyl)amino)-2-oxoacetyl)-2,3-dihydro-1H-pyrrolizine-7-carboxamide | 437.9 |

TABLE 1-continued

Exemplary compounds

| Ex. | Structure | Chemical Name | ESI-MS (M + H)+ (m/z) |
|---|---|---|---|
| 552 | 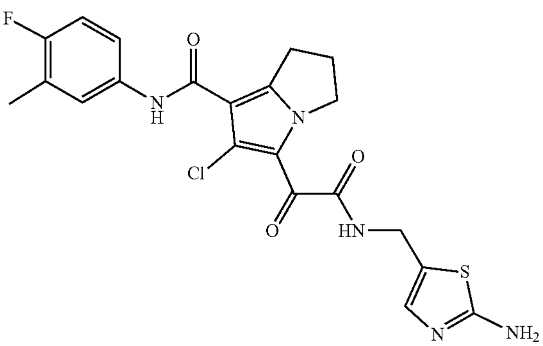 [SMILES: Cc1cc(NC(=O)c2c(Cl)c(C(=O)C(=O)NCc3cnc(N)s3)n3c2CCC3)ccc1F] | 5-(2-(((2-aminothiazol-5-yl)methyl)amino)-2-oxoacetyl)-6-chloro-N-(4-fluoro-3-methylphenyl)-2,3-dihydro-1H-pyrrolizine-7-carboxamide | 476.0 |
| 553 | 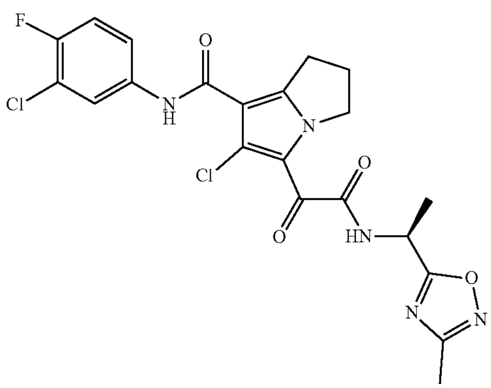 [SMILES: Cc1noc([C@H](C)NC(=O)C(=O)c2c(Cl)c(C(=O)Nc3ccc(F)c(Cl)c3)c3n2CCC3)n1] | (S)-6-chloro-N-(3-chloro-4-fluorophenyl)-5-(2-((1-(3-methyl-1,2,4-oxadiazol-5-yl)ethyl)amino)-2-oxoacetyl)-2,3-dihydro-1H-pyrrolizine-7-carboxamide | 494.0 |
| 554 | 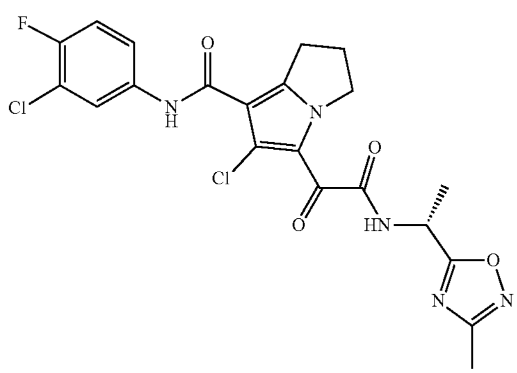 [SMILES: Cc1noc([C@@H](C)NC(=O)C(=O)c2c(Cl)c(C(=O)Nc3ccc(F)c(Cl)c3)c3n2CCC3)n1] | (R)-6-chloro-N-(3-chloro-4-fluorophenyl)-5-(2-((1-(3-methyl-1,2,4-oxadiazol-5-yl)ethyl)amino)-2-oxoacetyl)-2,3-dihydro-1H-pyrrolizine-7-carboxamide | 494.0 |
| 555 | 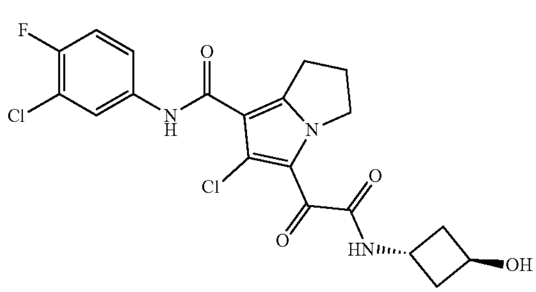 [SMILES: O=C(N[C@H]1C[C@H](O)C1)C(=O)c1c(Cl)c(C(=O)Nc2ccc(F)c(Cl)c2)c2n1CCC2] | 6-chloro-N-(3-chloro-4-fluorophenyl)-5-(2-(((1r,3r)-3-hydroxycyclobutyl)amino)-2-oxoacetyl)-2,3-dihydro-1H-pyrrolizine-7-carboxamide | 454.1 |

TABLE 1-continued

Exemplary compounds

| Ex. | Structure | Chemical Name | ESI-MS (M + H)+ (m/z) |
|---|---|---|---|
| 556 | 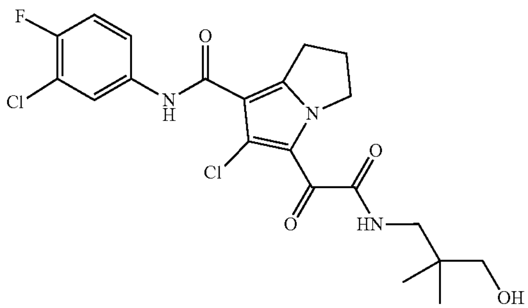 [SMILES: CC(C)(CO)CNC(=O)C(=O)c1c(Cl)c(C(=O)Nc2ccc(F)c(Cl)c2)c2n1CCC2] | 6-chloro-N-(3-chloro-4-fluorophenyl)-5-(2-((3-hydroxy-2,2-dimethylpropyl)amino)-2-oxoacetyl)-2,3-dihydro-1H-pyrrolizine-7-carboxamide | 470.0 |
| 557 | 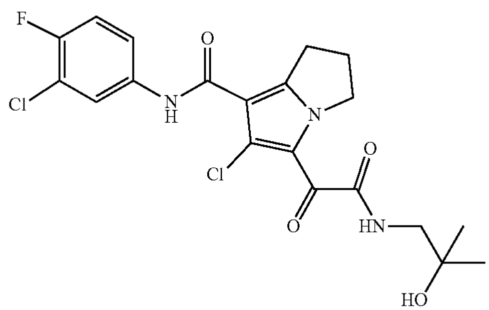 [SMILES: CC(C)(O)CNC(=O)C(=O)c1c(Cl)c(C(=O)Nc2ccc(F)c(Cl)c2)c2n1CCC2] | 6-chloro-N-(3-chloro-4-fluorophenyl)-5-(2-((2-hydroxy-2-methylpropyl)amino)-2-oxoacetyl)-2,3-dihydro-1H-pyrrolizine-7-carboxamide | 456.0 |
| 558 | 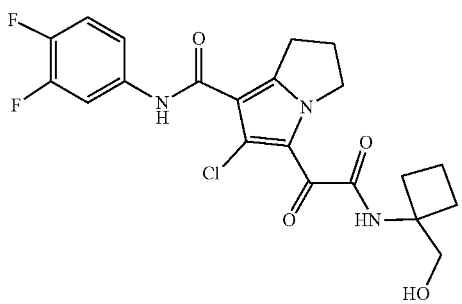 [SMILES: O=C(NC1(CO)CCC1)C(=O)c1c(Cl)c(C(=O)Nc2ccc(F)c(F)c2)c2n1CCC2] | 6-chloro-N-(3,4-difluorophenyl)-5-(2-((1-(hydroxymethyl)cyclobutyl)amino)-2-oxoacetyl)-2,3-dihydro-1H-pyrrolizine-7-carboxamide | 452.0 |
| 559 | 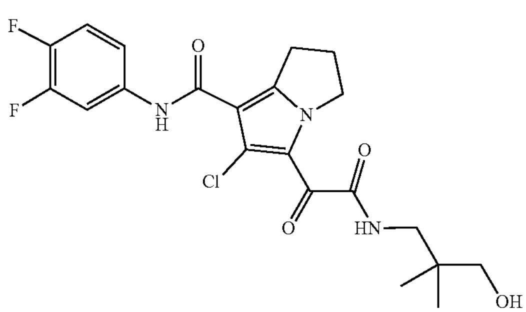 [SMILES: CC(C)(CO)CNC(=O)C(=O)c1c(Cl)c(C(=O)Nc2ccc(F)c(F)c2)c2n1CCC2] | 6-chloro-N-(3,4-difluorophenyl)-5-(2-((3-hydroxy-2,2-dimethylpropyl)amino)-2-oxoacetyl)-2,3-dihydro-1H-pyrrolizine-7-carboxamide | 454.0 |
| 560 | 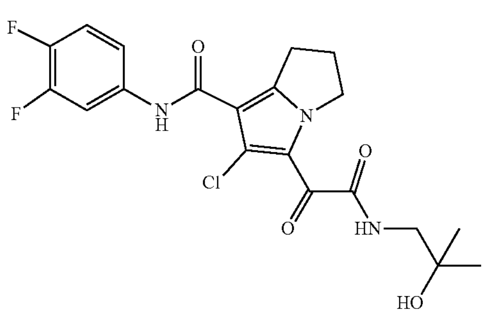 [SMILES: CC(C)(O)CNC(=O)C(=O)c1c(Cl)c(C(=O)Nc2ccc(F)c(F)c2)c2n1CCC2] | 6-chloro-N-(3,4-difluorophenyl)-5-(2-((2-hydroxy-2-methylpropyl)amino)-2-oxoacetyl)-2,3-dihydro-1H-pyrrolizine-7-carboxamide | 440.1 |

TABLE 1-continued

Exemplary compounds

| Ex. | Structure | Chemical Name | ESI-MS (M + H)+ (m/z) |
|---|---|---|---|
| 561 | 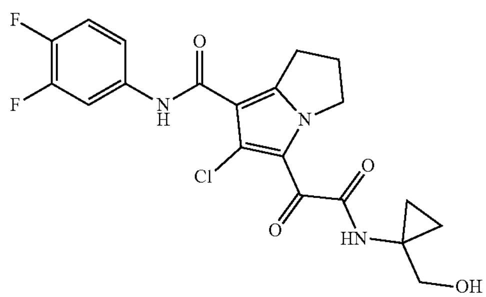 [SMILES: O=C(NC1(CO)CC1)C(=O)c1c(Cl)c(C(=O)Nc2ccc(F)c(F)c2)c2n1CCC2] | 6-chloro-N-(3,4-difluorophenyl)-5-(2-((1-(hydroxymethyl)cyclopropyl)amino)-2-oxoacetyl)-2,3-dihydro-1H-pyrrolizine-7-carboxamide | 438.1 |
| 562 | 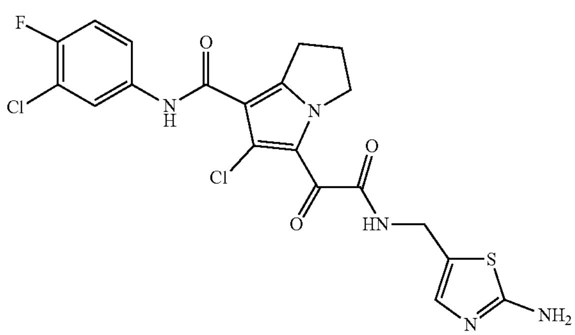 [SMILES: Nc1ncc(CNC(=O)C(=O)c2c(Cl)c(C(=O)Nc3ccc(F)c(Cl)c3)c3n2CCC3)s1] | 5-(2-(((2-aminothiazol-5-yl)methyl)amino)-2-oxoacetyl)-6-chloro-N-(3-chloro-4-fluorophenyl)-2,3-dihydro-1H-pyrrolizine-7-carboxamide | 495.9 |
| 563 | 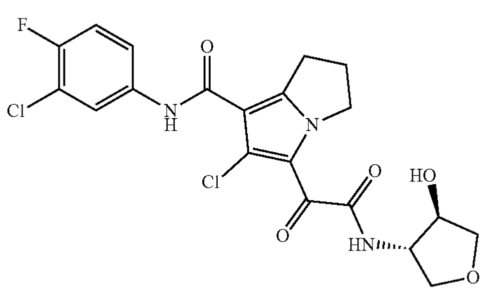 [SMILES: O=C(N[C@H]1COC[C@@H]1O)C(=O)c1c(Cl)c(C(=O)Nc2ccc(F)c(Cl)c2)c2n1CCC2] | 6-chloro-N-(3-chloro-4-fluorophenyl)-5-(2-(((3S,4R)-4-hydroxytetrahydrofuran-3-yl)amino)-2-oxoacetyl)-2,3-dihydro-1H-pyrrolizine-7-carboxamide | 470.0 |
| 564 | 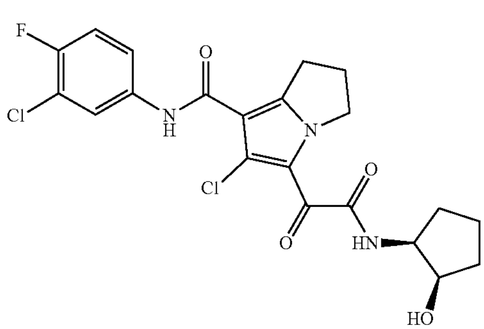 [SMILES: O=C(N[C@H]1CCC[C@H]1O)C(=O)c1c(Cl)c(C(=O)Nc2ccc(F)c(Cl)c2)c2n1CCC2] | 6-chloro-N-(3-chloro-4-fluorophenyl)-5-(2-(((1S,2R)-2-hydroxycyclopentyl)amino)-2-oxoacetyl)-2,3-dihydro-1H-pyrrolizine-7-carboxamide | 468.0 |

TABLE 1-continued

Exemplary compounds

| Ex. | Structure | Chemical Name | ESI-MS (M + H)+ (m/z) |
|---|---|---|---|
| 565 | 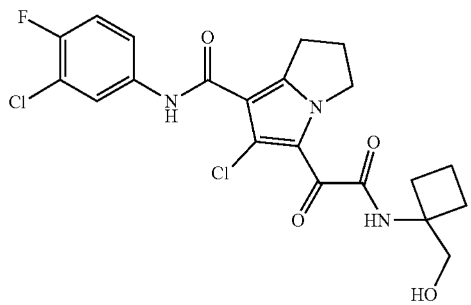 [SMILES: O=C(NC1(CO)CCC1)C(=O)c1c(Cl)c(C(=O)Nc2ccc(F)c(Cl)c2)c2n1CCC2] | 6-chloro-N-(3-chloro-4-fluorophenyl)-5-(2-((1-(hydroxymethyl)cyclobutyl)amino)-2-oxoacetyl)-2,3-dihydro-1H-pyrrolizine-7-carboxamide | 468.0 |
| 566 | 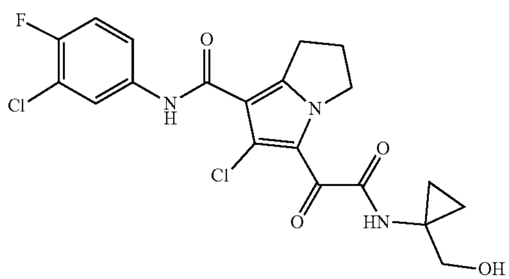 [SMILES: O=C(NC1(CO)CC1)C(=O)c1c(Cl)c(C(=O)Nc2ccc(F)c(Cl)c2)c2n1CCC2] | 6-chloro-N-(3-chloro-4-fluorophenyl)-5 -(2-((1-(hydroxymethyl)cyclopropyl)amino)-2-oxoacetyl)-2,3-dihydro-1H-pyrrolizine-7-carboxamide | 454.0 |
| 567 | 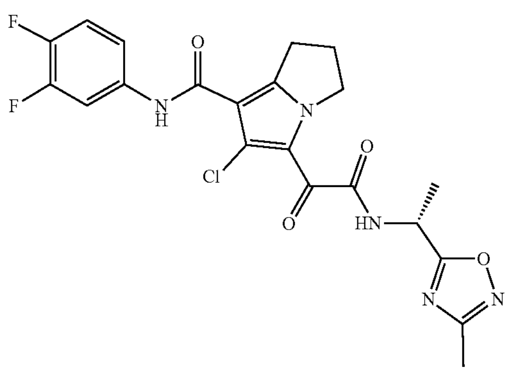 [SMILES: Cc1noc([C@@H](C)NC(=O)C(=O)c2c(Cl)c(C(=O)Nc3ccc(F)c(F)c3)c3n2CCC3)n1] | (R)-6-chloro-N-(3,4-difluorophenyl)-5-(2-((1-(3-methyl-1,2,4-oxadiazol-5-yl)ethyl)amino)-2-oxoacetyl)-2,3-dihydro-1H-pyrrolizine-7-carboxamide | 478.1 |
| 568 | 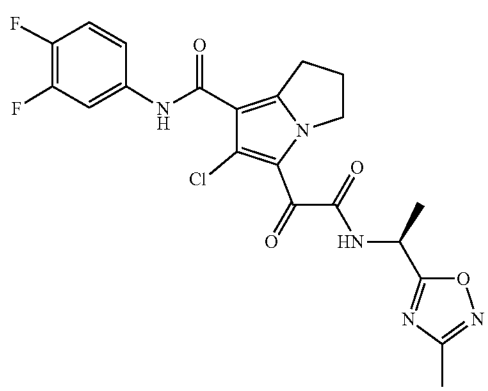 [SMILES: Cc1noc([C@H](C)NC(=O)C(=O)c2c(Cl)c(C(=O)Nc3ccc(F)c(F)c3)c3n2CCC3)n1] | (S)-6-chloro-N-(3,4-difluorophenyl)-5-(2-((1-(3-methyl-1,2,4-oxadiazol-5-yl)ethyl)amino)-2-oxoacetyl)-2,3-dihydro-1H-pyrrolizine-7-carboxamide | 478.0 |

TABLE 1-continued

Exemplary compounds

| Ex. | Structure | Chemical Name | ESI-MS (M + H)+ (m/z) |
|---|---|---|---|
| 569 | 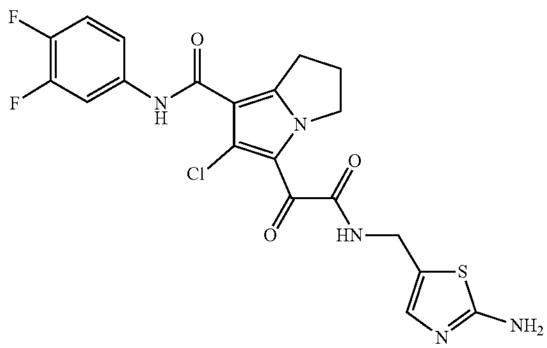 [SMILES: Nc1ncc(CNC(=O)C(=O)c2c(Cl)c(C(=O)Nc3ccc(F)c(F)c3)c3n2CCC3)s1] | 5-(2-(((2-aminothiazol-5-yl)methyl)amino)-2-oxoacetyl)-6-chloro-N-(3,4-difluorophenyl)-2,3-dihydro-1H-pyrrolizine-7-carboxamide | 480.1 |
| 570 | 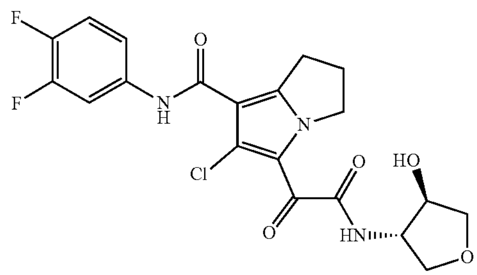 [SMILES: O=C(N[C@H]1COC[C@@H]1O)C(=O)c1c(Cl)c(C(=O)Nc2ccc(F)c(F)c2)c2n1CCC2] | 6-chloro-N-(3,4-difluorophenyl)-5-(2-(((3S,4R)-4-hydroxytetrahydrofuran-3-yl)amino)-2-oxoacetyl)-2,3-dihydro-1H-pyrrolizine-7-carboxamide | 454.1 |
| 571 | 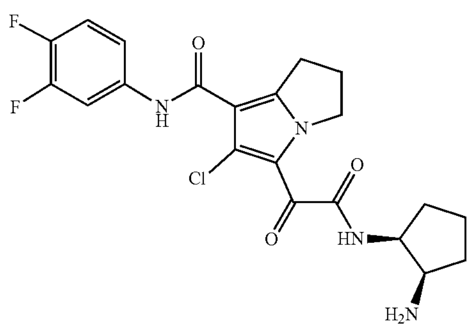 [SMILES: N[C@@H]1CCC[C@@H]1NC(=O)C(=O)c1c(Cl)c(C(=O)Nc2ccc(F)c(F)c2)c2n1CCC2] | 6-chloro-N-(3,4-difluorophenyl)-5-(2-(((1S,2R)-2-hydroxycyclopentyl)amino)-2-oxoacetyl)-2,3-dihydro-1H-pyrrolizine-7-carboxamide | 452.0 |
| 572 | 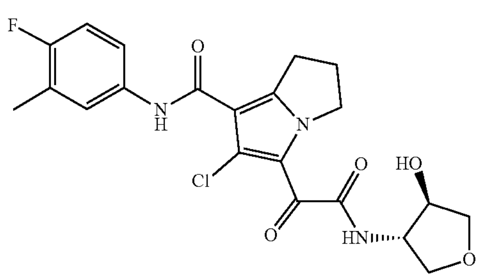 [SMILES: Cc1cc(NC(=O)c2c(Cl)c(C(=O)C(=O)N[C@H]3COC[C@@H]3O)n3c2CCC3)ccc1F] | 6-chloro-N-(4-fluoro-3-methylphenyl)-5-(2-(((3S,4R)-4-hydroxytetrahydrofuran-3-yl)amino)-2-oxoacetyl)-2,3-dihydro-1H-pyrrolizine-7-carboxamide | 450.0 |
| 573 | 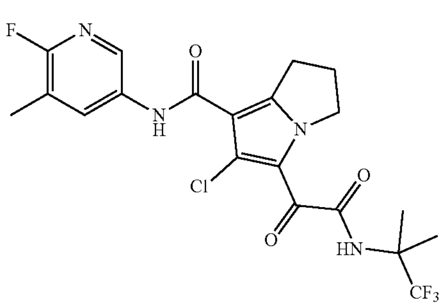 [SMILES: Cc1cc(NC(=O)c2c(Cl)c(C(=O)C(=O)NC(C)(C)C(F)(F)F)n3c2CCC3)cnc1F] | 6-chloro-N-(6-fluoro-5-methylpyridin-3-yl)-5-(2-oxo-2-((1,1,1-trifluoro-2-methylpropan-2-yl)amino)acetyl)-2,3-dihydro-1H-pyrrolizine-7-carboxamide | 475.0 |

TABLE 1-continued

Exemplary compounds

| Ex. | Structure | Chemical Name | ESI-MS (M + H)+ (m/z) |
|---|---|---|---|
| 574 | 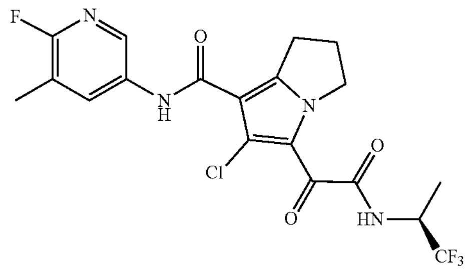 [SMILES: Cc1cc(NC(=O)c2c(Cl)c(C(=O)C(=O)N[C@@H](C)C(F)(F)F)n3c2CCC3)cnc1F] | (S)-6-chloro-N-(6-fluoro-5-methylpyridin-3-yl)-5-(2-oxo-2-((1,1,1-trifluoropropan-2-yl)amino)acetyl)-2,3-dihydro-1H-pyrrolizine-7-carboxamide | 461.1 |
| 575 | 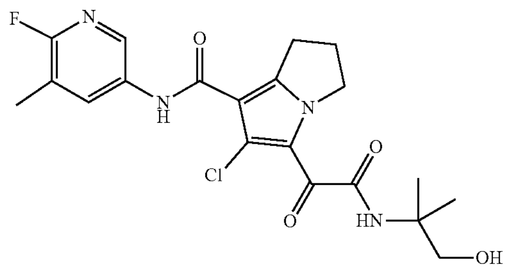 [SMILES: Cc1cc(NC(=O)c2c(Cl)c(C(=O)C(=O)NC(C)(C)CO)n3c2CCC3)cnc1F] | 6-chloro-N-(6-fluoro-5-methylpyridin-3-yl)-5-(2-((1-hydroxy-2-methylpropan-2-yl)amino)-2-oxoacetyl)-2,3-dihydro-1H-pyrrolizine-7-carboxamide | 437.1 |
| 576 | 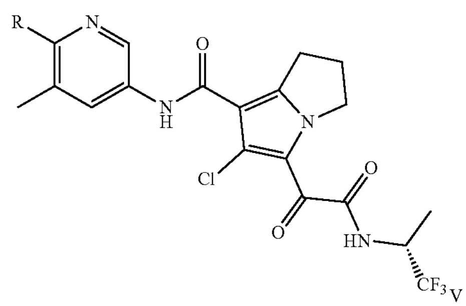 | (R)-6-chloro-N-(6-fluoro-5-methylpyridin-3-yl)-5-(2-oxo-2-((1,1,1-trifluoropropan-2-yl)amino)acetyl)-2,3-dihydro-1H-pyrrolizine-7-carboxamide | 461.0 |
| 577 | 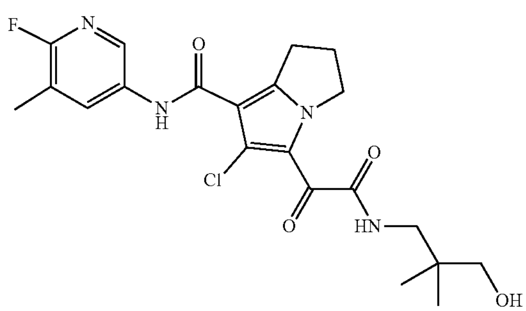 [SMILES: Cc1cc(NC(=O)c2c(Cl)c(C(=O)C(=O)NCC(C)(C)CO)n3c2CCC3)cnc1F] | 6-chloro-N-(6-fluoro-5-methylpyridin-3-yl)-5-(2-((3-hydroxy-2,2-dimethylpropyl)amino)-2-oxoacetyl)-2,3-dihydro-1H-pyrrolizine-7-carboxamide | 451.1 |
| 578 | 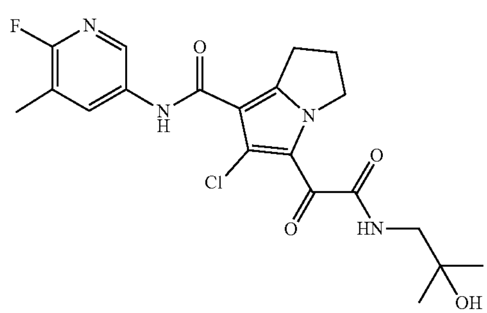 [SMILES: Cc1cc(NC(=O)c2c(Cl)c(C(=O)C(=O)NCC(C)(C)O)n3c2CCC3)cnc1F] | 6-chloro-N-(6-fluoro-5-methylpyridin-3-yl)-5-(2-((2-hydroxy-2-methylpropyl)amino)-2-oxoacetyl)-2,3-dihydro-1H-pyrrolizine-7-carboxamide | 437.1 |

TABLE 1-continued

Exemplary compounds

| Ex. | Structure | Chemical Name | ESI-MS (M + H)+ (m/z) |
|---|---|---|---|
| 579 | 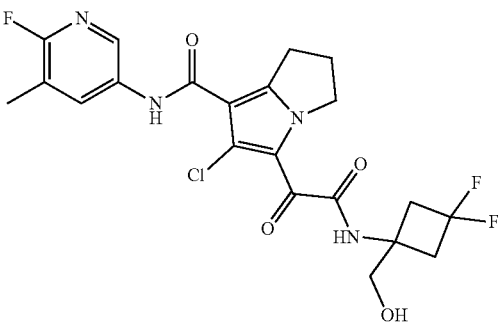 [SMILES: Cc1cc(NC(=O)c2c(Cl)c(C(=O)C(=O)NC3(CO)CC(F)(F)C3)n3c2CCC3)cnc1F] | 6-chloro-5-(2-((3,3-difluoro-1-(hydroxymethyl)cyclobutyl)amino)-2-oxoacetyl)-N-(6-fluoro-5-methylpyridin-3-yl)-2,3-dihydro-1H-pyrrolizine-7-carboxamide | 485.1 |
| 580 | 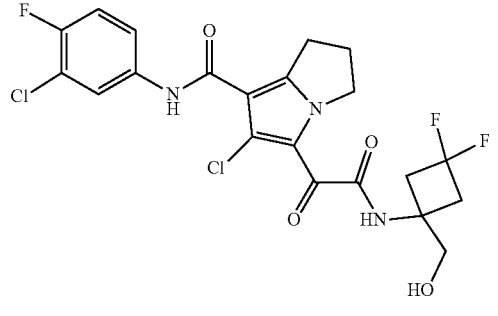 [SMILES: O=C(NC1(CO)CC(F)(F)C1)C(=O)c1c(Cl)c(C(=O)Nc2ccc(F)c(Cl)c2)c2n1CCC2] | 6-chloro-N-(3-chloro-4-fluorophenyl)-5-(2-((3,3-difluoro-1-(hydroxymethyl)cyclobutyl)amino)-2-oxoacetyl)-2,3-dihydro-1H-pyrrolizine-7-carboxamide | 504.0 |
| 581 | 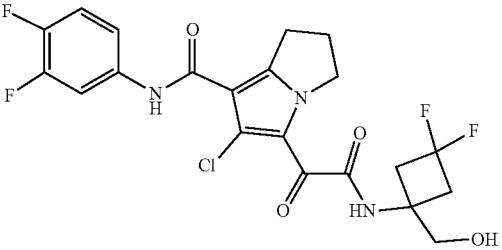 [SMILES: O=C(NC1(CO)CC(F)(F)C1)C(=O)c1c(Cl)c(C(=O)Nc2ccc(F)c(F)c2)c2n1CCC2] | 6-chloro-5-(2-((3,3-difluoro-1-(hydroxymethyl)cyclobutyl)amino)-2-oxoacetyl)-N-(3,4-difluorophenyl)-2,3-dihydro-1H-pyrrolizine-7-carboxamide | 488.0 |
| 582 | 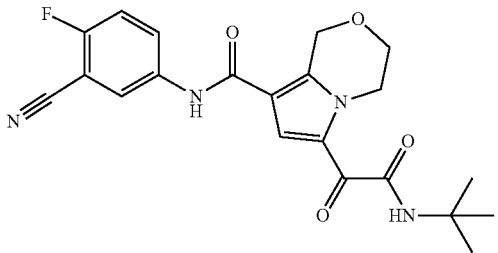 [SMILES: CC(C)(C)NC(=O)C(=O)c1cc(C(=O)Nc2ccc(F)c(C#N)c2)c2n1CCOC2] | 6-(2-(tert-butylamino)-2-oxoacetyl)-N-(3-cyano-4-fluorophenyl)-3,4-dihydro-1H-pyrrolo[2,1-c][1,4]oxazine-8-carboxamide | 412.8 |
| 583 | 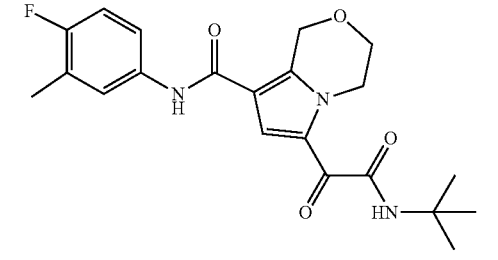 [SMILES: Cc1cc(NC(=O)c2cc(C(=O)C(=O)NC(C)(C)C)n3c2COCC3)ccc1F] | 6-(2-(tert-butylamino)-2-oxoacetyl)-N-(4-fluoro-3-methylphenyl)-3,4-dihydro-1H-pyrrolo[2,1-c][1,4]oxazine-8-carboxamide | 401.9 |

TABLE 1-continued

Exemplary compounds

| Ex. | Structure | Chemical Name | ESI-MS (M + H)+ (m/z) |
|---|---|---|---|
| 584 | 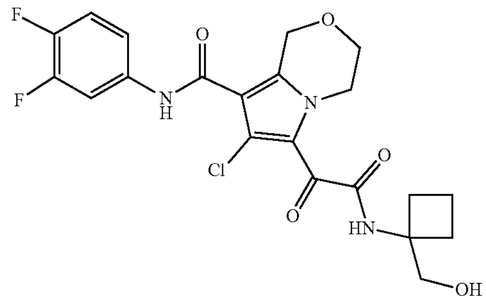 [SMILES: O=C(NC1(CO)CCC1)C(=O)c1c(Cl)c(C(=O)Nc2ccc(F)c(F)c2)c2n1CCOC2] | 7-chloro-N-(3,4-difluorophenyl)-6-(2-((1-(hydroxymethyl)cyclobutyl)amino)-2-oxoacetyl)-3,4-dihydro-1H-pyrrolo[2,1-c][1,4]oxazine-8-carboxamide | 468.0 |
| 585 | 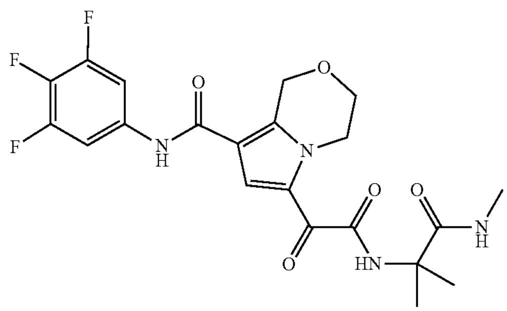 [SMILES: CNC(=O)C(C)(C)NC(=O)C(=O)c1cc(C(=O)Nc2cc(F)c(F)c(F)c2)c2n1CCOC2] | 6-(2-((2-methyl-1-(methylamino)-1-oxopropan-2-yl)amino)-2-oxoacetyl)-N-(3,4,5-trifluorophenyl)-3,4-dihydro-1H-pyrrolo[2,1-c][1,4]oxazine-8-carboxamide | |
| 586 | 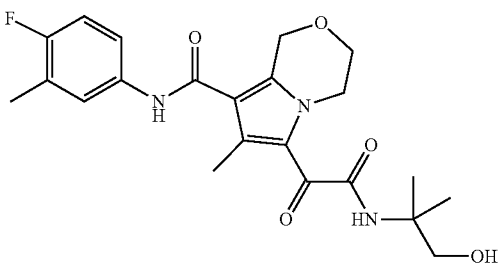 [SMILES: Cc1cc(NC(=O)c2c(C)c(C(=O)C(=O)NC(C)(C)CO)n3c2COCC3)ccc1F] | N-(4-fluoro-3-methylphenyl)-6-(2-((1-hydroxy-2-methylpropan-2-yl)amino)-2-oxoacetyl)-7-methyl-3,4-dihydro-1H-pyrrolo[2,1-c][1,4]oxazine-8-carboxamide | |
| 587 | 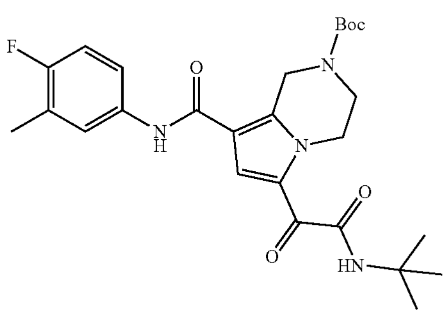 [SMILES: Cc1cc(NC(=O)c2cc(C(=O)C(=O)NC(C)(C)C)n3c2CN(C(=O)OC(C)(C)C)CC3)ccc1F] | tert-butyl 6-(2-(tert-butylamino)-2-oxoacetyl)-8-((4-fluoro-3-methylphenyl)carbamoyl)-3,4-dihydropyrrolo[1,2-a]pyrazine-2(1H)-carboxylate | 501.0 |
| 588 | 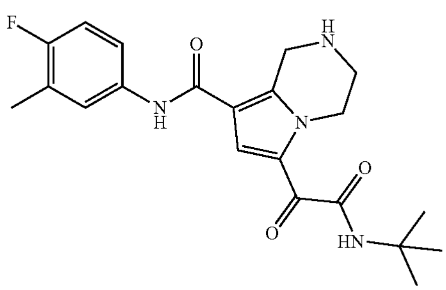 [SMILES: Cc1cc(NC(=O)c2cc(C(=O)C(=O)NC(C)(C)C)n3c2CNCC3)ccc1F] | 6-(2-(tert-butylamino)-2-oxoacetyl)-N-(4-fluoro-3-methylphenyl)-1,2,3,4-tetrahydropyrrolo[1,2-a]pyrazine-8-carboxamide | 401.0 |

TABLE 1-continued

Exemplary compounds

| Ex. | Structure | Chemical Name | ESI-MS (M + H)+ (m/z) |
|---|---|---|---|
| 589 | 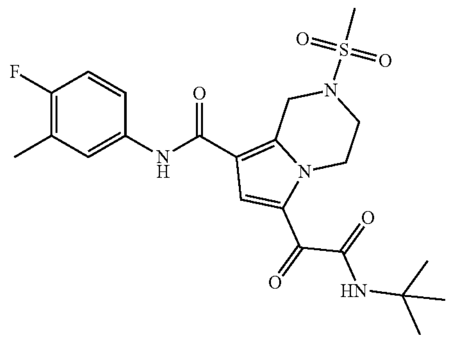 [SMILES: Cc1cc(NC(=O)c2cc(C(=O)C(=O)NC(C)(C)C)n3c2CN(S(C)(=O)=O)CC3)ccc1F] | 6-(2-(tert-butylamino)-2-oxoacetyl)-N-(4-fluoro-3-methylphenyl)-2-(methylsulfonyl)-1,2,3,4-tetrahydropyrrolo[1,2-a]pyrazine-8-carboxamide | 479.0 |
| 590 | 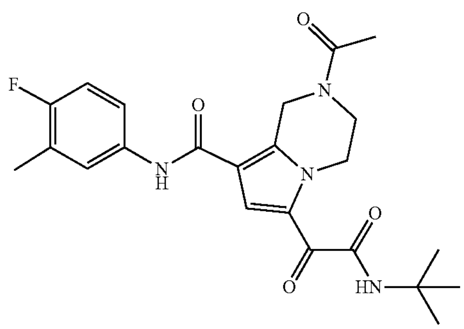 [SMILES: CC(=O)N1CCn2c(C(=O)C(=O)NC(C)(C)C)cc(C(=O)Nc3ccc(F)c(C)c3)c2C1] | 2-acetyl-6-(2-(tert-butylamino)-2-oxoacetyl)-N-(4-fluoro-3-methylphenyl)-1,2,3,4-tetrahydropyrrolo[1,2-a]pyrazine-8-carboxamide | 443.0 |
| 591 | 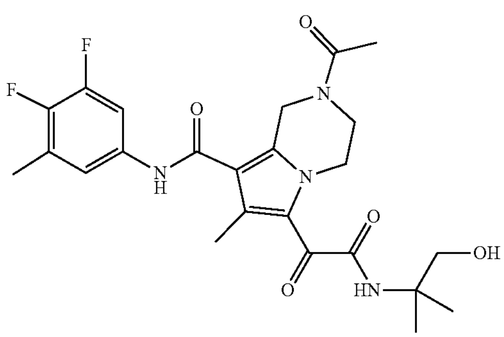 [SMILES: CC(=O)N1CCn2c(c(C(=O)Nc3cc(C)c(F)c(F)c3)c(C)c2C(=O)C(=O)NC(C)(C)CO)C1] | 2-acetyl-N-(3,4-difluoro-5-methylphenyl)-6-(2-((1-hydroxy-2-methylpropan-2-yl)amino)-2-oxoacetyl)-7-methyl-1,2,3,4-tetrahydropyrrolo[1,2-a]pyrazine-8-carboxamide | |
| 592 | 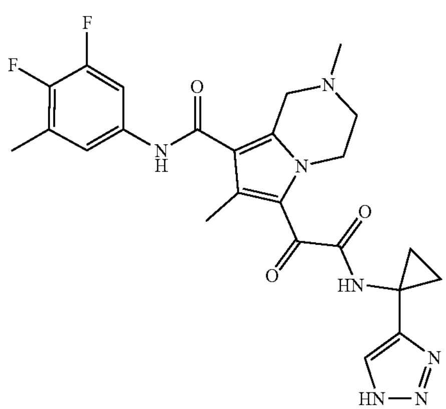 [SMILES: Cc1cc(NC(=O)c2c(C)c(C(=O)C(=O)NC3(c4c[nH]nn4)CC3)n3c2CN(C)CC3)cc(F)c1F] | 6-(2-((1-(1H-1,2,3-triazol-4-yl)cyclopropyl)amino)-2-oxoacetyl)-N-(3,4-difluoro-5-methylphenyl)-2,7-dimethyl-1,2,3,4-tetrahydropyrrolo[1,2-a]pyrazine-8-carboxamide | |

TABLE 1-continued

Exemplary compounds

| Ex. | Structure | Chemical Name | ESI-MS (M + H)+ (m/z) |
|---|---|---|---|
| 593 | 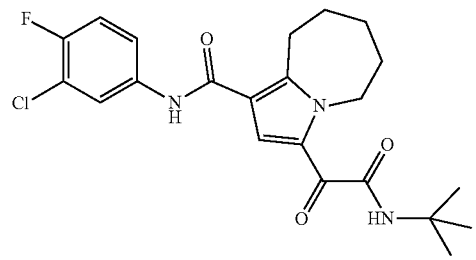 [SMILES: CC(C)(C)NC(=O)C(=O)c1cc(C(=O)Nc2ccc(F)c(Cl)c2)c2n1CCCCC2] | 3-(2-(tert-butylamino)-2-oxoacetyl)-N-(3-chloro-4-fluorophenyl)-6,7,8,9-tetrahydro-5H-pyrrolo[1,2-a]azepine-1-carboxamide | |
| 594 | 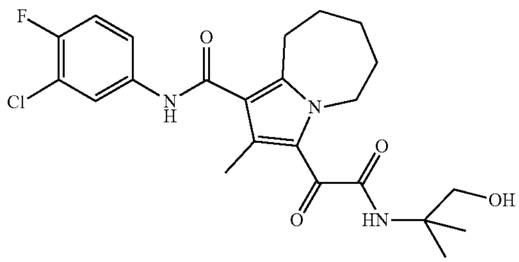 [SMILES: Cc1c(C(=O)Nc2ccc(F)c(Cl)c2)c2n(c1C(=O)C(=O)NC(C)(C)CO)CCCCC2] | N-(3-chloro-4-fluorophenyl)-3-(2-((1-hydroxy-2-methylpropan-2-yl)amino)-2-oxoacetyl)-2-methyl-6,7,8,9-tetrahydro-5H-pyrrolo[1,2-a]azepine-1-carboxamide | |
| 595 | 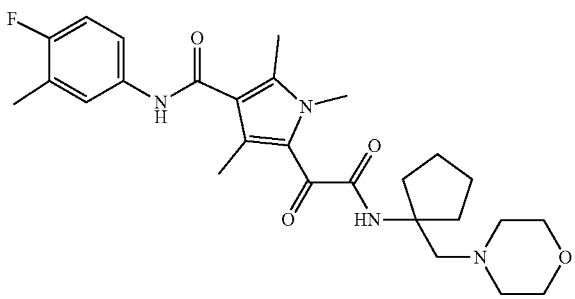 [SMILES: Cc1cc(NC(=O)c2c(C)c(C(=O)C(=O)NC3(CN4CCOCC4)CCCC3)n(C)c2C)ccc1F] | N-(4-fluoro-3-methylphenyl)-1,2,4-trimethyl-5-(2-((1-(morpholinomethyl)cyclopentyl)amino)-2-oxoacetyl)-1H-pyrrole-3-carboxamide | 499.3 |
| 596 | 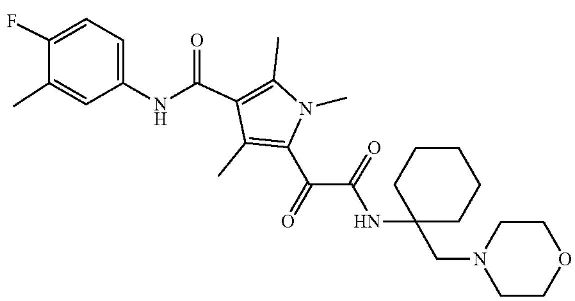 [SMILES: Cc1cc(NC(=O)c2c(C)c(C(=O)C(=O)NC3(CN4CCOCC4)CCCCC3)n(C)c2C)ccc1F] | N-(4-fluoro-3-methylphenyl)-1,2,4-trimethyl-5-(2-((1-(morpholinomethyl)cyclohexyl)amino)-2-oxoacetyl)-1H-pyrrole-3-carboxamide | 513.3 |
| 597 | 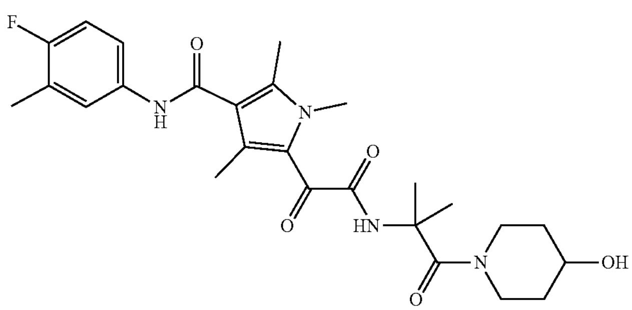 [SMILES: Cc1cc(NC(=O)c2c(C)c(C(=O)C(=O)NC(C)(C)C(=O)N3CCC(O)CC3)n(C)c2C)ccc1F] | N-(4-fluoro-3-methylphenyl)-5-(2-((1-(4-hydroxypiperidin-1-yl)-2-methyl-1-oxopropan-2-yl)amino)-2-oxoacetyl)-1,2,4-trimethyl-1H-pyrrole-3-carboxamide | 501.3 |

TABLE 1-continued

Exemplary compounds

| Ex. | Structure | Chemical Name | ESI-MS (M + H)+ (m/z) |
|---|---|---|---|
| 598 | 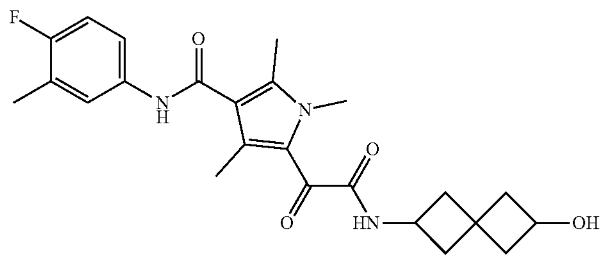 [SMILES: Cc1cc(NC(=O)c2c(C)c(C(=O)C(=O)NC3CC4(CC(O)C4)C3)n(C)c2C)ccc1F] | N-(4-fluoro-3-methylphenyl)-5-(2-((6-hydroxyspiro[3.3]heptan-2-yl)amino)-2-oxoacetyl)-1,2,4-trimethyl-1H-pyrrole-3-carboxamide | 442.2 |
| 599 | 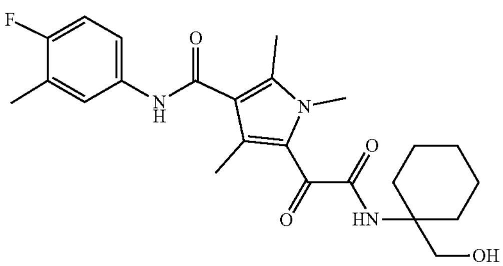 [SMILES: Cc1cc(NC(=O)c2c(C)c(C(=O)C(=O)NC3(CO)CCCCC3)n(C)c2C)ccc1F] | N-(4-fluoro-3-methylphenyl)-5-(2-((1-(hydroxymethyl)cyclohexyl)amino)-2-oxoacetyl)-1,2,4-trimethyl-1H-pyrrole-3-carboxamide | 441.1 |
| 600 | 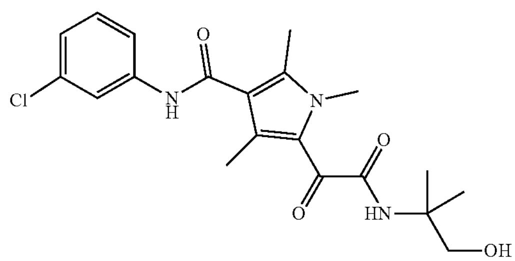 [SMILES: Cc1c(C(=O)Nc2cccc(Cl)c2)c(C)n(C)c1C(=O)C(=O)NC(C)(C)CO] | N-(3-chlorophenyl)-5-(2-((1-hydroxy-2-methylpropan-2-yl)amino)-2-oxoacetyl)-1,2,4-trimethyl-1H-pyrrole-3-carboxamide | 406.2 |
| 601 | 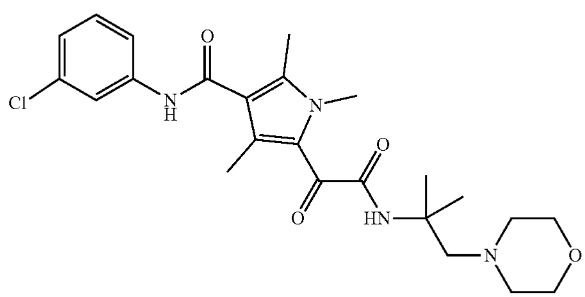 [SMILES: Cc1c(C(=O)Nc2cccc(Cl)c2)c(C)n(C)c1C(=O)C(=O)NC(C)(C)CN1CCOCC1] | N-(3-chlorophenyl)-1,2,4-trimethyl-5-(2-((2-methyl-1-morpholinopropan-2-yl)amino)-2-oxoacetyl)-1H-pyrrole-3-carboxamide | 475.2 |
| 602 | 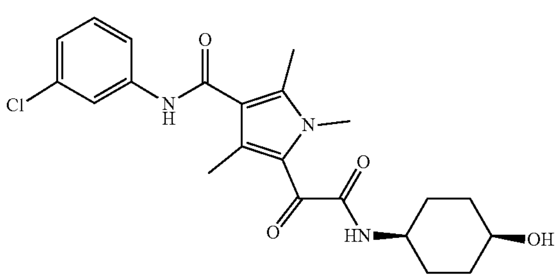 [SMILES: Cc1c(C(=O)Nc2cccc(Cl)c2)c(C)n(C)c1C(=O)C(=O)N[C@H]1CC[C@@H](O)CC1] | N-(3-chlorophenyl)-5-(2-(((1s,4s)-4-hydroxycyclohexyl)amino)-2-oxoacetyl)-1,2,4-trimethyl-1H-pyrrole-3-carboxamide | 432.2 |

TABLE 1-continued

Exemplary compounds

| Ex. | Structure | Chemical Name | ESI-MS (M + H)+ (m/z) |
|---|---|---|---|
| 603 | 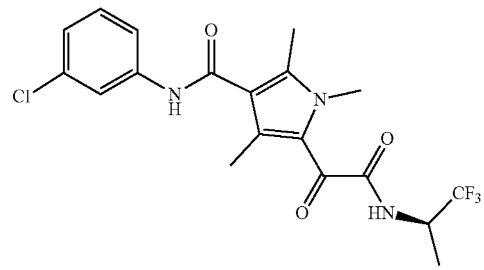 [SMILES: Cc1c(C(=O)Nc2cccc(Cl)c2)c(C)n(C)c1C(=O)C(=O)N[C@H](C)C(F)(F)F] | (R)-N-(3-chlorophenyl)-1,2,4-trimethyl-5-(2-oxo-2-((1,1,1-trifluoropropan-2-yl)amino)acetyl)-1H-pyrrole-3-carboxamide | 430.1 |
| 604 | 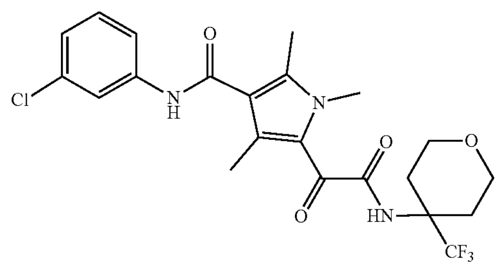 [SMILES: Cc1c(C(=O)Nc2cccc(Cl)c2)c(C)n(C)c1C(=O)C(=O)NC1(C(F)(F)F)CCOCC1] | N-(3-chlorophenyl)-1,2,4-trimethyl-5-(2-oxo-2-((4-(trifluoromethyl)tetrahydro-2H-pyran-4-yl)amino)acetyl)-1H-pyrrole-3-carboxamide | 486.1 |
| 605 | 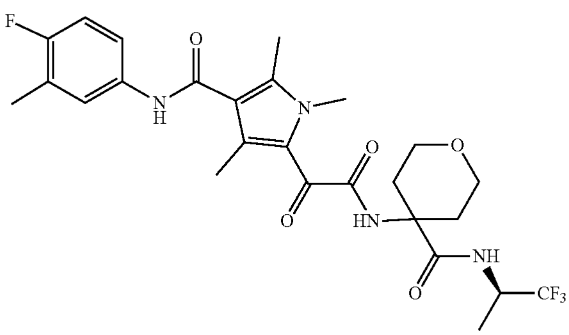 [SMILES: Cc1cc(NC(=O)c2c(C)c(C(=O)C(=O)NC3(C(=O)N[C@H](C)C(F)(F)F)CCOCC3)n(C)c2C)ccc1F] | (R)-N-(4-fluoro-3-methylphenyl)-1,2,4-trimethyl-5-(2-oxo-2-((4-((1,1,1-trifluoropropan-2-yl)carbamoyl)tetrahydro-2H-pyran-4-yl)amino)acetyl)-1H-pyrrole-3-carboxamide | 555.1 |
| 606 | 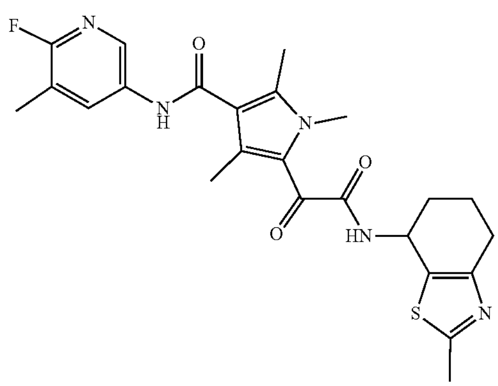 [SMILES: Cc1nc2c(s1)C(NC(=O)C(=O)c1c(C)c(C(=O)Nc3cnc(F)c(C)c3)c(C)n1C)CCC2] | N-(6-fluoro-5-methylpyridin-3-yl)-1,2,4-trimethyl-5-(2-((2-methyl-4,5,6,7-tetrahydrobenzo[d]thiazol-7-yl)amino)-2-oxoacetyl)-1H-pyrrole-3-carboxamide | 484.2 |

TABLE 1-continued

Exemplary compounds

| Ex. | Structure | Chemical Name | ESI-MS (M + H)+ (m/z) |
|---|---|---|---|
| 607 | 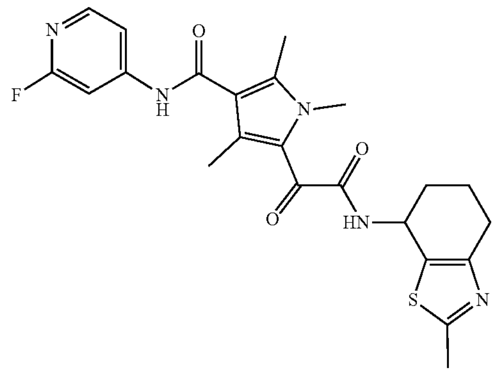 [SMILES: Cc1nc2c(s1)C(NC(=O)C(=O)c1c(C)c(C(=O)Nc3ccnc(F)c3)c(C)n1C)CCC2] | N-(2-fluoropyridin-4-yl)-1,2,4-trimethyl-5-(2-((2-methyl-4,5,6,7-tetrahydrobenzo[d]thiazol-7-yl)amino)-2-oxoacetyl)-1H-pyrrole-3-carboxamide | 470.2 |
| 608 | 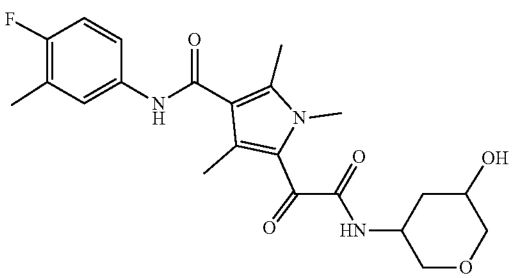 [SMILES: Cc1cc(NC(=O)c2c(C)c(C(=O)C(=O)NC3COCC(O)C3)n(C)c2C)ccc1F] | N-(4-fluoro-3-methylphenyl)-5-(2-((5-hydroxytetrahydro-2H-pyran-3-yl)amino)-2-oxoacetyl)-1,2,4-trimethyl-1H-pyrrole-3-carboxamide | 432.2 |
| 609 | 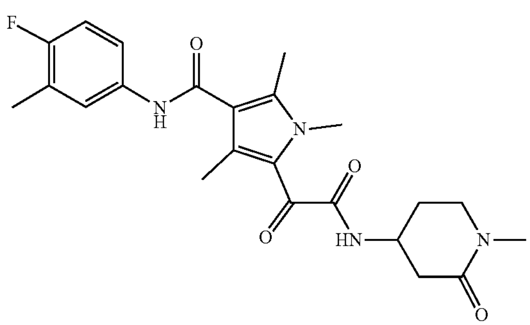 [SMILES: Cc1cc(NC(=O)c2c(C)c(C(=O)C(=O)NC3CCN(C)C(=O)C3)n(C)c2C)ccc1F] | N-(4-fluoro-3-methylphenyl)-1,2,4-trimethyl-5-(2-((1-methyl-2-oxopiperidin-4-yl)amino)-2-oxoacetyl)-1H-pyrrole-3-carboxamide | 443.2 |
| 610 | 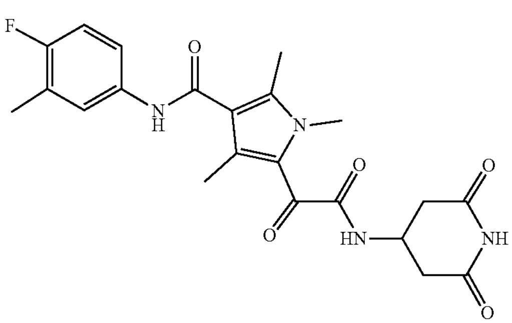 [SMILES: Cc1cc(NC(=O)c2c(C)c(C(=O)C(=O)NC3CC(=O)NC(=O)C3)n(C)c2C)ccc1F] | 5-(2-((2,6-dioxopiperidin-4-yl)amino)-2-oxoacetyl)-N-(4-fluoro-3-methylphenyl)-1,2,4-trimethyl-1H-pyrrole-3-carboxamide | 443.2 |

TABLE 1-continued

Exemplary compounds

| Ex. | Structure | Chemical Name | ESI-MS (M + H)+ (m/z) |
|---|---|---|---|
| 611 | 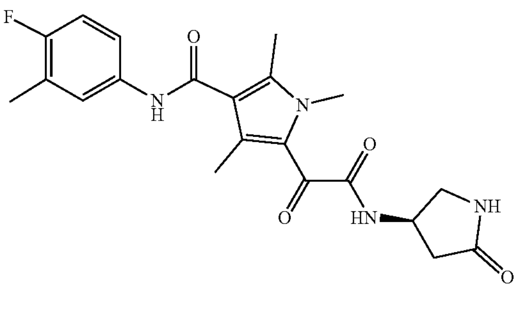 [SMILES: Cc1cc(NC(=O)c2c(C)c(C(=O)C(=O)N[C@H]3CNC(=O)C3)n(C)c2C)ccc1F] | (R)-N-(4-fluoro-3-methylphenyl)-1,2,4-trimethyl-5-(2-oxo-2-((5-oxopyrrolidin-3-yl)amino)acetyl)-1H-pyrrole-3-carboxamide | 415.2 |
| 612 | 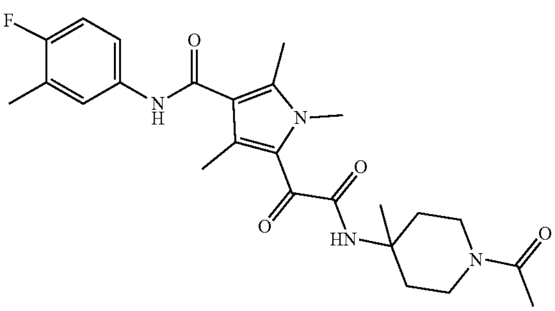 [SMILES: CC(=O)N1CCC(C)(NC(=O)C(=O)c2c(C)c(C(=O)Nc3ccc(F)c(C)c3)c(C)n2C)CC1] | 5-(2-((1-acetyl-4-methylpiperidin-4-yl)amino)-2-oxoacetyl)-N-(4-fluoro-3-methylphenyl)-1,2,4-trimethyl-1H-pyrrole-3-carboxamide | 471.2 |
| 613 | 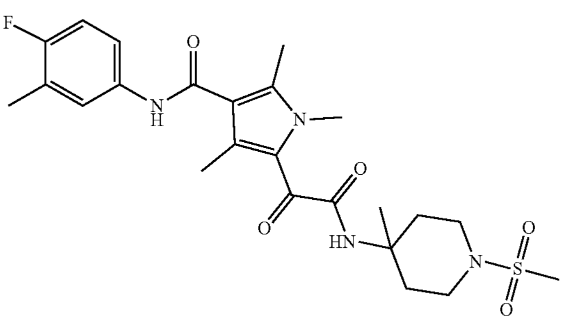 [SMILES: Cc1cc(NC(=O)c2c(C)c(C(=O)C(=O)NC3(C)CCN(S(C)(=O)=O)CC3)n(C)c2C)ccc1F] | N-(4-fluoro-3-methylphenyl)-1,2,4-trimethyl-5-(2-((4-methyl-1-(methylsulfonyl)piperidin-4-yl)amino)-2-oxoacetyl)-1H-pyrrole-3-carboxamide | 507.2 |
| 614 | 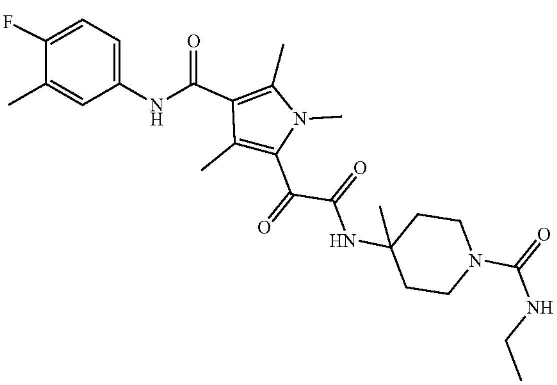 [SMILES: CCNC(=O)N1CCC(C)(NC(=O)C(=O)c2c(C)c(C(=O)Nc3ccc(F)c(C)c3)c(C)n2C)CC1] | N-ethyl-4-(2-(4-((4-fluoro-3-methylphenyl)carbamoyl)-1,3,5-trimethyl-1H-pyrrol-2-yl)-2-oxoacetamido)-4-methylpiperidine-1-carboxamide | 500.3 |

TABLE 1-continued

Exemplary compounds

| Ex. | Structure | Chemical Name | ESI-MS (M + H)+ (m/z) |
|---|---|---|---|
| 615 | 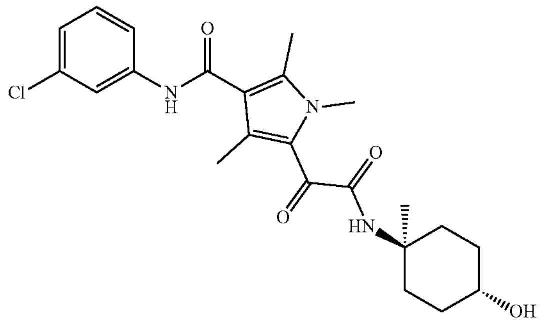 [SMILES: Cc1c(C(=O)Nc2cccc(Cl)c2)c(C)n(C)c1C(=O)C(=O)N[C@]1(C)CC[C@@H](O)CC1] | N-(3-chlorophenyl)-5-(2-(((1r,4r)-4-hydroxy-1-methylcyclohexyl)amino)-2-oxoacetyl)-1,2,4-trimethyl-1H-pyrrole-3-carboxamide | 446.2 |
| 616 | 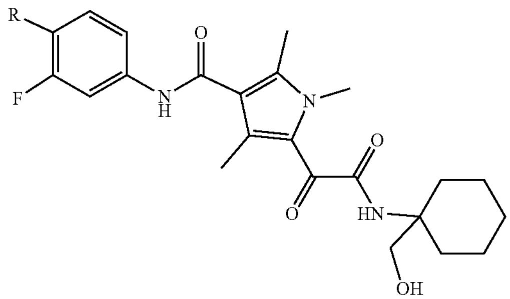 | N-(3,4-difluorophenyl)-5-(2-(((1-(hydroxymethyl)cyclohexyl)amino)-2-oxoacetyl)-1,2,4-trimethyl-1H-pyrrole-3-carboxamide | 448.2 |
| 617 | 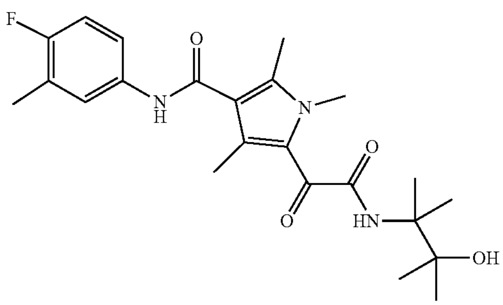 [SMILES: Cc1cc(NC(=O)c2c(C)c(C(=O)C(=O)NC(C)(C)C(C)(C)O)n(C)c2C)ccc1F] | N-(4-fluoro-3-methylphenyl)-5-(2-((3-hydroxy-2,3-dimethylbutan-2-yl)amino)-2-oxoacetyl)-1,2,4-trimethyl-1H-pyrrole-3-carboxamide | 432.2 |
| 618 | 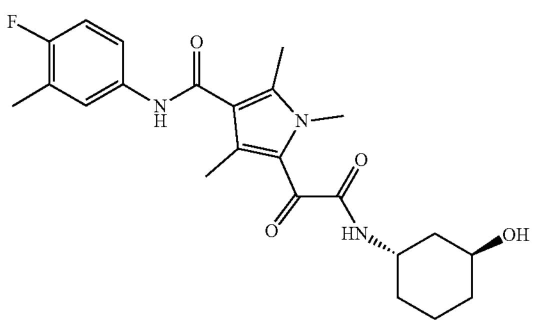 [SMILES: Cc1cc(NC(=O)c2c(C)c(C(=O)C(=O)N[C@H]3CCC[C@H](O)C3)n(C)c2C)ccc1F] | N-(4-fluoro-3-methylphenyl)-5-(2-((((1S,3S)-3-hydroxycyclohexyl)amino)-2-oxoacetyl)-1,2,4-trimethyl-1H-pyrrole-3-carboxamide | 430.2 |
| 619 | 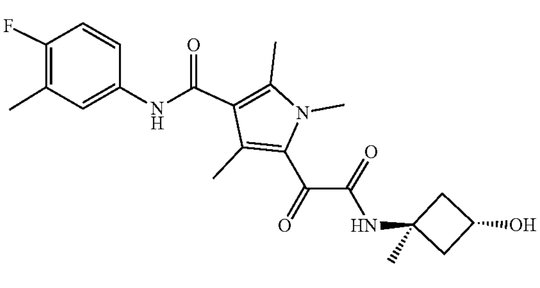 [SMILES: Cc1cc(NC(=O)c2c(C)c(C(=O)C(=O)N[C@]3(C)C[C@@H](O)C3)n(C)c2C)ccc1F] | N-(4-fluoro-3-methylphenyl)-5-(2-(((1r,3r)-3-hydroxy-1-methylcyclobutyl)amino)-2-oxoacetyl)-1,2,4-trimethyl-1H-pyrrole-3-carboxamide | 416.2 |

TABLE 1-continued

Exemplary compounds

| Ex. | Structure | Chemical Name | ESI-MS (M + H)+ (m/z) |
|---|---|---|---|
| 620 | 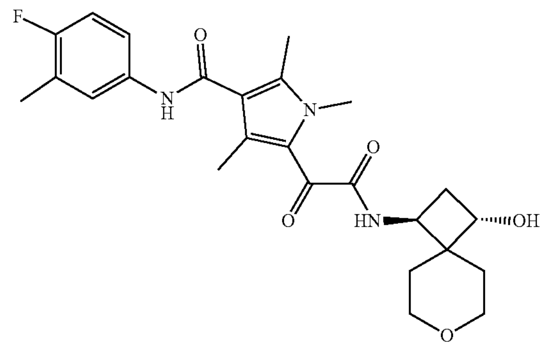 [SMILES: Cc1cc(NC(=O)c2c(C)c(C(=O)C(=O)N[C@H]3C[C@H](O)C34CCOCC4)n(C)c2C)ccc1F] | N-(4-fluoro-3-methylphenyl)-5-(2-(((1S,3S)-3-hydroxy-7-oxaspiro[3.5]nonan-1-yl)amino)-2-oxoacetyl)-1,2,4-trimethyl-1H-pyrrole-3-carboxamide | 472.2 |
| 621 | 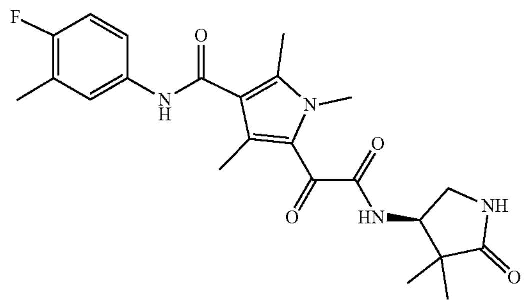 [SMILES: Cc1cc(NC(=O)c2c(C)c(C(=O)C(=O)N[C@H]3CNC(=O)C3(C)C)n(C)c2C)ccc1F] | (R)-5-(2-((4,4-dimethyl-5-oxopyrrolidin-3-yl)amino)-2-oxoacetyl)-N-(4-fluoro-3-methylphenyl)-1,2,4-trimethyl-1H-pyrrole-3-carboxamide | 443.2 |
| 622 | 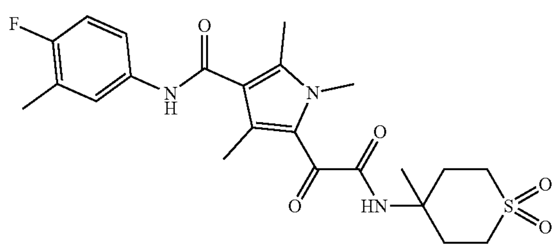 [SMILES: Cc1cc(NC(=O)c2c(C)c(C(=O)C(=O)NC3(C)CCS(=O)(=O)CC3)n(C)c2C)ccc1F] | N-(4-fluoro-3-methylphenyl)-1,2,4-trimethyl-5-(2-((4-methyl-1,1-dioxidotetrahydro-2H-thiopyran-4-yl)amino)-2-oxoacetyl)-1H-pyrrole-3-carboxamide | 478.2 |
| 623 | 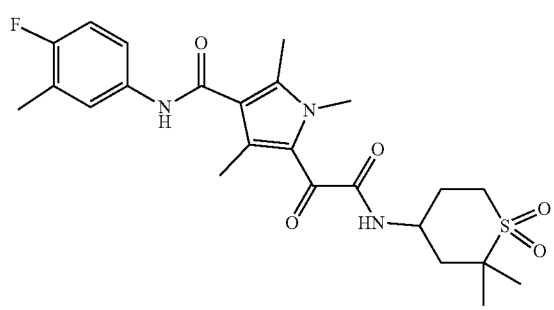 [SMILES: Cc1cc(NC(=O)c2c(C)c(C(=O)C(=O)NC3CCS(=O)(=O)C(C)(C)C3)n(C)c2C)ccc1F] | 5-(2-((2,2-dimethyl-1,1-dioxidotetrahydro-2H-thiopyran-4-yl)amino)-2-oxoacetyl)-N-(4-fluoro-3-methylphenyl)-1,2,4-trimethyl-1H-pyrrole-3-carboxamide | 492.2 |
| 624 | 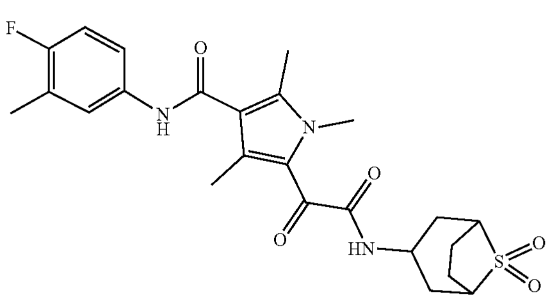 [SMILES: Cc1cc(NC(=O)c2c(C)c(C(=O)C(=O)NC3CC4CCC(C3)S4(=O)=O)n(C)c2C)ccc1F] | 5-(2-((8,8-dioxido-8-thiabicyclo[3.2.1]octan-3-yl)amino)-2-oxoacetyl)-N-(4-fluoro-3-methylphenyl)-1,2,4-trimethyl-1H-pyrrole-3-carboxamide | 490.2 |

TABLE 1-continued

Exemplary compounds

| Ex. | Structure | Chemical Name | ESI-MS (M + H)+ (m/z) |
|---|---|---|---|
| 625 | 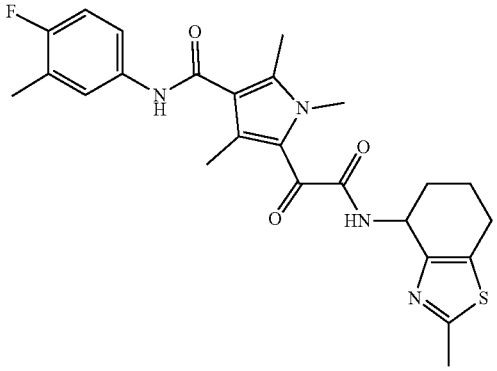 [SMILES: Cc1nc2c(s1)CCCC2NC(=O)C(=O)c1c(C)c(C(=O)Nc2ccc(F)c(C)c2)c(C)n1C] | N-(4-fluoro-3-methylphenyl)-1,2,4-trimethyl-5-(2-((2-methyl-4,5,6,7-tetrahydrobenzo[d]thiazol-4-yl)amino)-2-oxoacetyl)-1H-pyrrole-3-carboxamide | 483.2 |
| 626 | 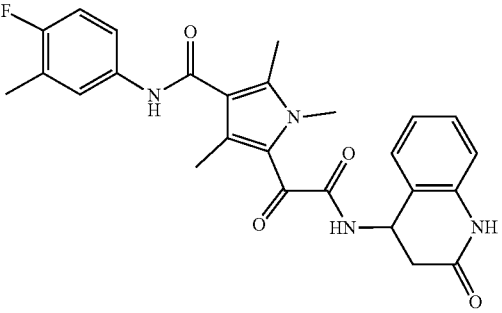 [SMILES: Cc1cc(NC(=O)c2c(C)c(C(=O)C(=O)NC3CC(=O)Nc4ccccc43)n(C)c2C)ccc1F] | N-(4-fluoro-3-methylphenyl)-1,2,4-trimethyl-5-(2-oxo-2-((2-oxo-1,2,3,4-tetrahydroquinolin-4-yl)amino)acetyl)-1H-pyrrole-3-carboxamide | 477.2 |
| 627 | 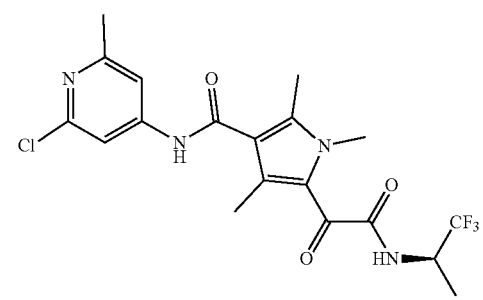 [SMILES: Cc1cc(NC(=O)c2c(C)c(C(=O)C(=O)N[C@H](C)C(F)(F)F)n(C)c2C)cc(Cl)n1] | (R)-N-(2-chloro-6-methylpyridin-4-yl)-1,2,4-trimethyl-5-(2-oxo-2-((1,1,1-trifluoropropan-2-yl)amino)acetyl)-1H-pyrrole-3-carboxamide | 445.1 |
| 628 | 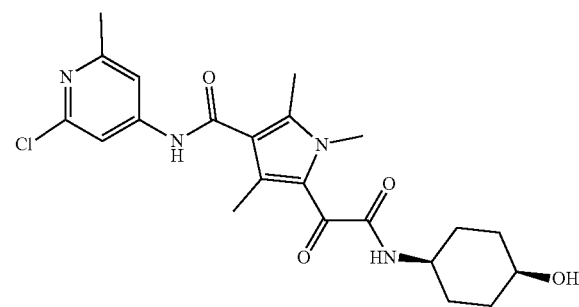 [SMILES: Cc1cc(NC(=O)c2c(C)c(C(=O)C(=O)N[C@H]3CC[C@@H](O)CC3)n(C)c2C)cc(Cl)n1] | N-(2-chloro-6-methylpyridin-4-yl)-5-(2-(((1s,4s)-4-hydroxycyclohexyl)amino)-2-oxoacetyl)-1,2,4-trimethyl-1H-pyrrole-3-carboxamide | 447.2 |

TABLE 1-continued

Exemplary compounds

| Ex. | Structure | Chemical Name | ESI-MS (M + H)+ (m/z) |
|---|---|---|---|
| 629 | 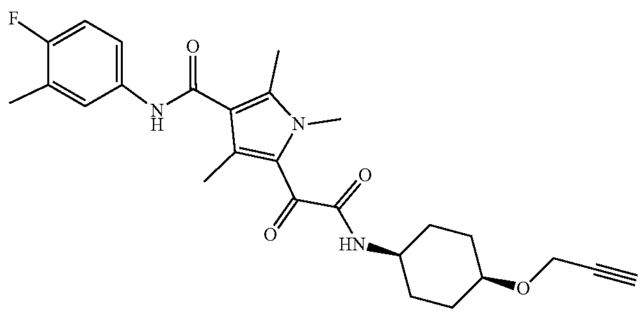 [SMILES: C#CCO[C@H]1CC[C@@H](NC(=O)C(=O)c2c(C)c(C(=O)Nc3ccc(F)c(C)c3)c(C)n2C)CC1] | N-(4-fluoro-3-methylphenyl)-1,2,4-trimethyl-5-(2-oxo-2-(((1s,4s)-4-(prop-2-yn-1-yloxy)cyclohexyl)amino)acetyl)-1H-pyrrole-3-carboxamide | 468.3 |
| 630 | 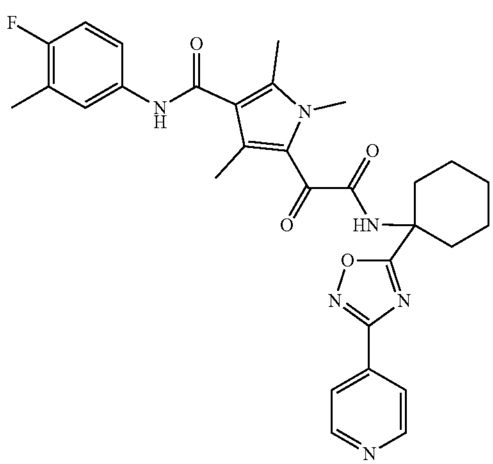 [SMILES: Cc1cc(NC(=O)c2c(C)c(C(=O)C(=O)NC3(c4nc(-c5ccncc5)no4)CCCCC3)n(C)c2C)ccc1F] | N-(4-fluoro-3-methylphenyl)-1,2,4-trimethyl-5-(2-oxo-2-((1-(3-(pyridin-4-yl)-1,2,4-oxadiazol-5-yl)cyclohexyl)amino)acetyl)-1H-pyrrole-3-carboxamide | 559.2 |
| 631 | 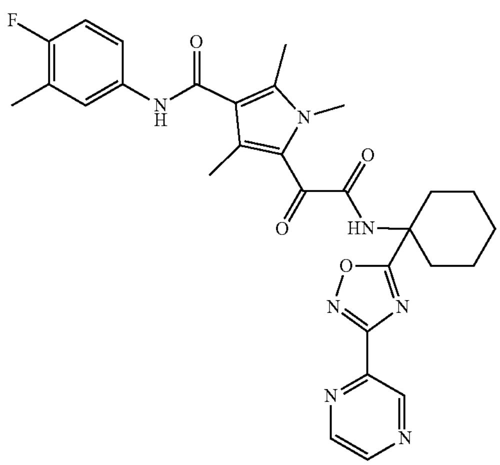 [SMILES: Cc1cc(NC(=O)c2c(C)c(C(=O)C(=O)NC3(c4nc(-c5cnccn5)no4)CCCCC3)n(C)c2C)ccc1F] | N-(4-fluoro-3-methylphenyl)-1,2,4-trimethyl-5-(2-oxo-2-((1-(3-(pyrazin-2-yl)-1,2,4-oxadiazol-5-yl)cyclohexyl)amino)acetyl)-1H-pyrrole-3-carboxamide | 560.1 |

TABLE 1-continued

Exemplary compounds

| Ex. | Structure | Chemical Name | ESI-MS (M + H)+ (m/z) |
|---|---|---|---|
| 632 | 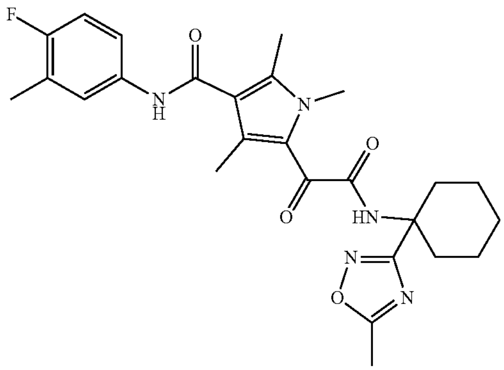 [SMILES: Cc1nc(C2(NC(=O)C(=O)c3c(C)c(C(=O)Nc4ccc(F)c(C)c4)c(C)n3C)CCCCC2)no1] | N-(4-fluoro-3-methylphenyl)-1,2,4-trimethyl-5-(2-((1-(5-methyl-1,2,4-oxadiazol-3-yl)cyclohexyl)amino)-2-oxoacetyl)-1H-pyrrole-3-carboxamide | 496.2 |
| 633 | 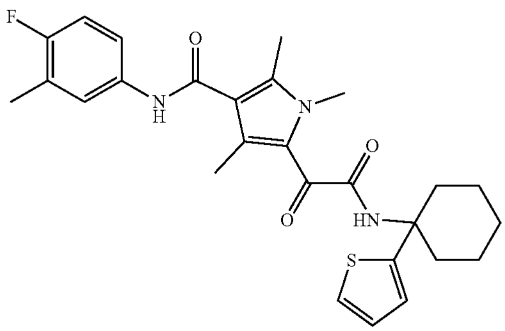 [SMILES: Cc1cc(NC(=O)c2c(C)c(C(=O)C(=O)NC3(c4cccs4)CCCCC3)n(C)c2C)ccc1F] | N-(4-fluoro-3-methylphenyl)-1,2,4-trimethyl-5-(2-oxo-2-((1-(thiophen-2-yl)cyclohexyl)amino)acetyl)-1H-pyrrole-3-carboxamide | 496.2 |
| 634 | 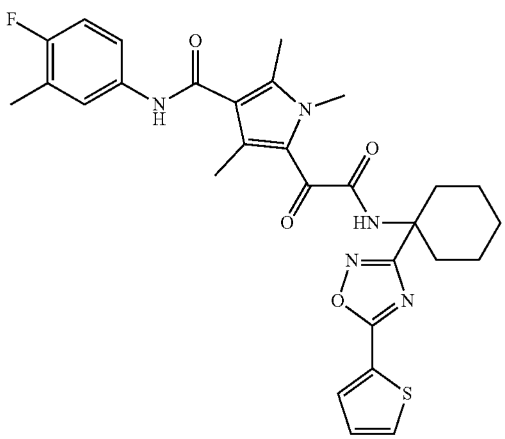 [SMILES: Cc1cc(NC(=O)c2c(C)c(C(=O)C(=O)NC3(c4noc(-c5cccs5)n4)CCCCC3)n(C)c2C)ccc1F] | N-(4-fluoro-3-methylphenyl)-1,2,4-trimethyl-5-(2-oxo-2-((1-(5-(thiophen-2-yl)-1,2,4-oxadiazol-3-yl)cyclohexyl)amino)acetyl)-1H-pyrrole-3-carboxamide | 564.2 |
| 635 | 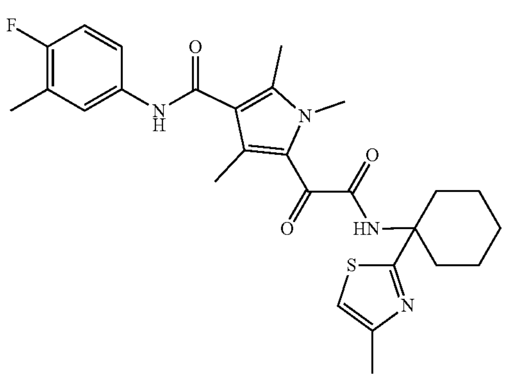 [SMILES: Cc1csc(C2(NC(=O)C(=O)c3c(C)c(C(=O)Nc4ccc(F)c(C)c4)c(C)n3C)CCCCC2)n1] | N-(4-fluoro-3-methylphenyl)-1,2,4-trimethyl-5-(2-((1-(4-methylthiazol-2-yl)cyclopentyl)amino)-2-oxoacetyl)-1H-pyrrole-3-carboxamide | 497.2 |

TABLE 1-continued

Exemplary compounds

| Ex. | Structure | Chemical Name | ESI-MS (M + H)+ (m/z) |
|---|---|---|---|
| 636 | 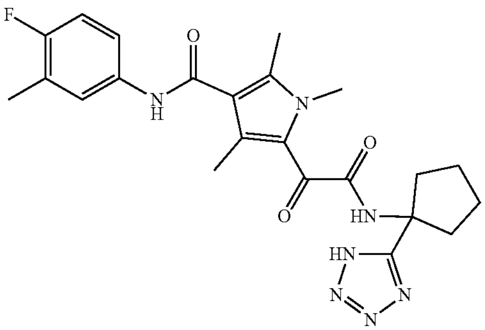 [SMILES: Cc1cc(NC(=O)c2c(C)c(C(=O)C(=O)NC3(c4nnn[nH]4)CCCC3)n(C)c2C)ccc1F] | 5-(2-((1-(1H-tetrazol-5-yl)cyclopentyl)amino)-2-oxoacetyl)-N-(4-fluoro-3-methylphenyl)-1,2,4-trimethyl-1H-pyrrole-3-carboxamide | 468.2 |
| 637 | 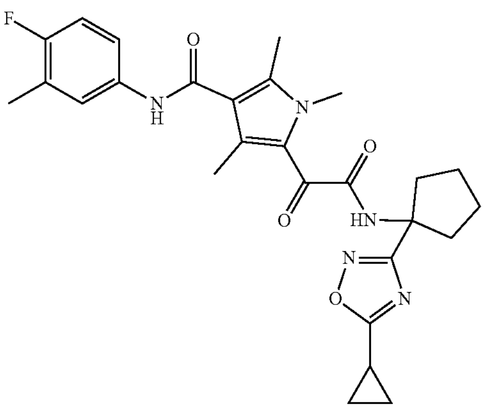 [SMILES: Cc1cc(NC(=O)c2c(C)c(C(=O)C(=O)NC3(c4noc(C5CC5)n4)CCCC3)n(C)c2C)ccc1F] | 5-(2-((1-(5-cyclopropyl-1,2,4-oxadiazol-3-yl)cyclopentyl)amino)-2-oxoacetyl)-N-(4-fluoro-3-methylphenyl)-1,2,4-trimethyl-1H-pyrrole-3-carboxamide | 508.1 |
| 638 | 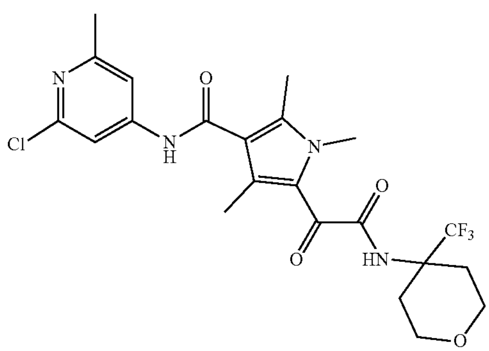 [SMILES: Cc1cc(NC(=O)c2c(C)c(C(=O)C(=O)NC3(C(F)(F)F)CCOCC3)n(C)c2C)cc(Cl)n1] | N-(2-chloro-6-methylpyridin-4-yl)-1,2,4-trimethyl-5-(2-oxo-2-((4-(trifluoromethyl)tetrahydro-2H-pyran-4-yl)amino)acetyl)-1H-pyrrole-3-carboxamide | 501.2 |
| 639 | 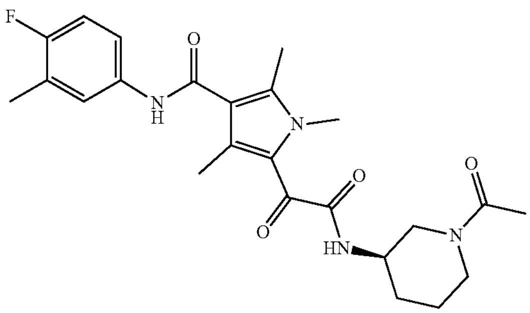 [SMILES: CC(=O)N1CCC[C@@H](NC(=O)C(=O)c2c(C)c(C(=O)Nc3ccc(F)c(C)c3)c(C)n2C)C1] | (R)-5-(2-((1-acetylpiperidin-3-yl)amino)-2-oxoacetyl)-N-(4-fluoro-3-methylphenyl)-1,2,4-trimethyl-1H-pyrrole-3-carboxamide | 457.2 |

TABLE 1-continued

Exemplary compounds

| Ex. | Structure | Chemical Name | ESI-MS (M + H)+ (m/z) |
|---|---|---|---|
| 640 | 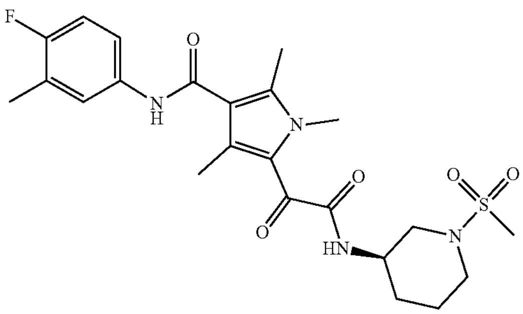 | (R)-N-(4-fluoro-3-methylphenyl)-1,2,4-trimethyl-5-(2-((1-(methylsulfonyl)piperidin-3-yl)amino)-2-oxoacetyl)-1H-pyrrole-3-carboxamide | 493.2 |
| 641 | 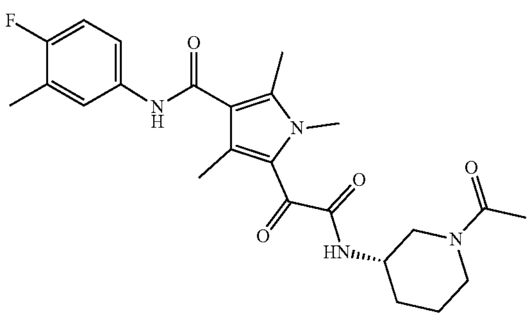 [SMILES: CC(=O)N1CCC[C@H](NC(=O)C(=O)c2c(C)c(C(=O)Nc3ccc(F)c(C)c3)c(C)n2C)C1] | (S)-5-(2-((1-acetylpiperidin-3-yl)amino)-2-oxoacetyl)-N-(4-fluoro-3-methylphenyl)-1,2,4-trimethyl-1H-pyrrole-3-carboxamide | 457.2 |
| 642 | 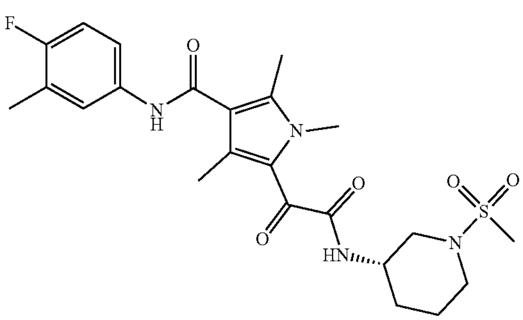 | (S)-N-(4-fluoro-3-methylphenyl)-1,2,4-trimethyl-5-(2-((1-(methylsulfonyl)piperidin-3-yl)amino)-2-oxoacetyl)-1H-pyrrole-3-carboxamide | 493.2 |
| 643 | 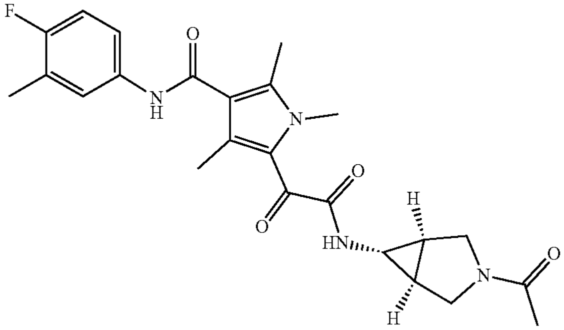 [SMILES: CC(=O)N1C[C@@H]2[C@H](C1)[C@H]2NC(=O)C(=O)c1c(C)c(C(=O)Nc2ccc(F)c(C)c2)c(C)n1C] | 5-(2-(((1R,5S,6s)-3-acetyl-3-azabicyclo[3.1.0]hexan-6-yl)amino)-2-oxoacetyl)-N-(4-fluoro-3-methylphenyl)-1,2,4-trimethyl-1H-pyrrole-3-carboxamide | 155.2 |

TABLE 1-continued

Exemplary compounds

| Ex. | Structure | Chemical Name | ESI-MS (M + H)+ (m/z) |
|---|---|---|---|
| 644 | 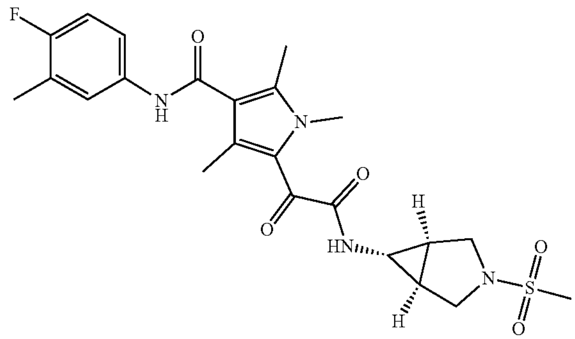 | N-(4-fluoro-3-methylphenyl)-1,2,4-trimethyl-5-(2-(((1R,5S,6s)-3-(methylsulfonyl)-3-azabicyclo[3.1.0]hexan-6-yl)amino)-2-oxoacetyl)-1H-pyrrole-3-carboxamide | 491.2 |
| 645 | 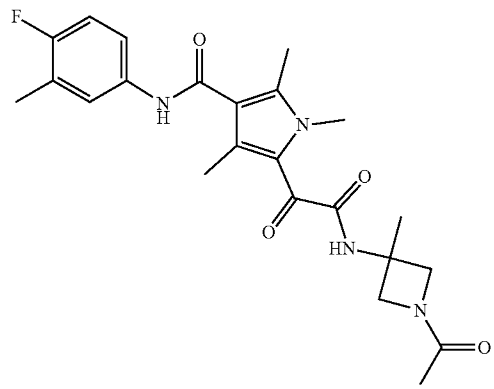 [SMILES: CC(=O)N1CC(C)(NC(=O)C(=O)c2c(C)c(C(=O)Nc3ccc(F)c(C)c3)c(C)n2C)C1] | 5-(2-((1-acetyl-3-methylazetidin-3-yl)amino)-2-oxoacetyl)-N-(4-fluoro-3-methylphenyl)-1,2,4-trimethyl-1H-pyrrole-3-carboxamide | 443.2 |
| 646 | 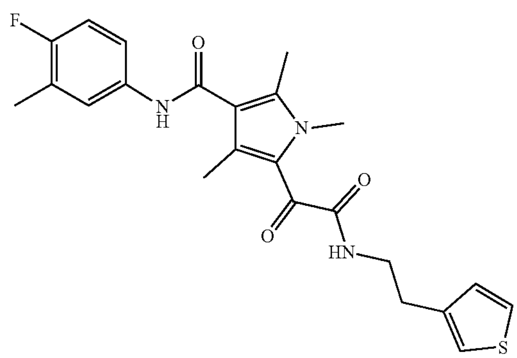 [SMILES: Cc1cc(NC(=O)c2c(C)c(C(=O)C(=O)NCCc3ccsc3)n(C)c2C)ccc1F] | N-(4-fluoro-3-methylphenyl)-1,2,4-trimethyl-5-(2-oxo-2-((2-(thiophen-3-yl)ethyl)amino)acetyl)-1H-pyrrole-3-carboxamide | 442.2 |
| 647 | 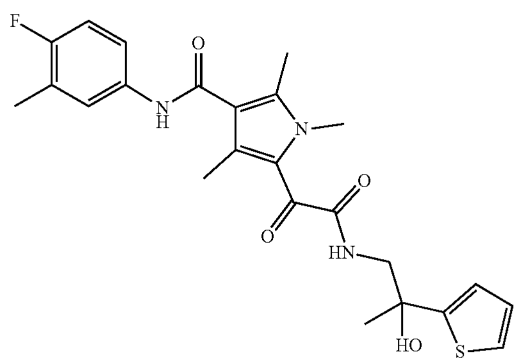 [SMILES: Cc1cc(NC(=O)c2c(C)c(C(=O)C(=O)NCC(C)(O)c3cccs3)n(C)c2C)ccc1F] | N-(4-fluoro-3-methylphenyl)-5-(2-((2-hydroxy-2-(thiophen-2-yl)propyl)amino)-2-oxoacetyl)-1,2,4-trimethyl-1H-pyrrole-3-carboxamide | 472.2 |

TABLE 1-continued

Exemplary compounds

| Ex. | Structure | Chemical Name | ESI-MS (M + H)+ (m/z) |
|---|---|---|---|
| 648 | 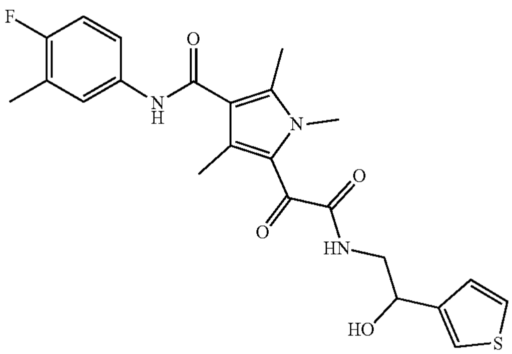 [SMILES: Cc1cc(NC(=O)c2c(C)c(C(=O)C(=O)NCC(O)c3ccsc3)n(C)c2C)ccc1F] | N-(4-fluoro-3-methylphenyl)-5-(2-((2-hydroxy-2-(thiophen-3-yl)ethyl)amino)-2-oxoacetyl)-1,2,4-trimethyl-1H-pyrrole-3-carboxamide | 458.2 |
| 649 | 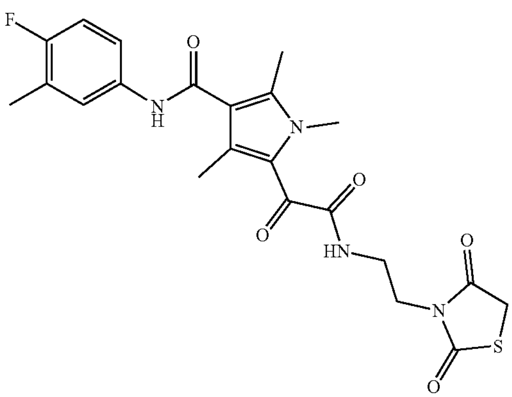 [SMILES: Cc1cc(NC(=O)c2c(C)c(C(=O)C(=O)NCCN3C(=O)CSC3=O)n(C)c2C)ccc1F] | 5-(2-((2-(2,4-dioxothiazolidin-3-yl)ethyl)amino)-2-oxoacetyl)-N-(4-fluoro-3-methylphenyl)-1,2,4-trimethyl-1H-pyrrole-3-carboxamide | 475.1 |
| 650 | 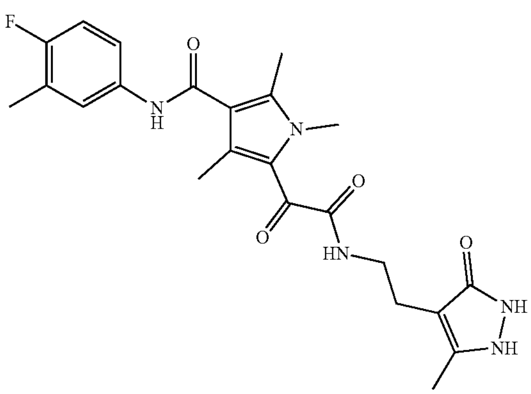 [SMILES: Cc1cc(NC(=O)c2c(C)c(C(=O)C(=O)NCCc3c(C)[nH][nH]c3=O)n(C)c2C)ccc1F] | N-(4-fluoro-3-methylphenyl)-1,2,4-trimethyl-5-(2-((2-(5-methyl-3-oxo-2,3-dihydro-1H-pyrazol-4-yl)ethyl)amino)-2-oxoacetyl)-1H-pyrrole-3-carboxamide | 456.2 |
| 651 | 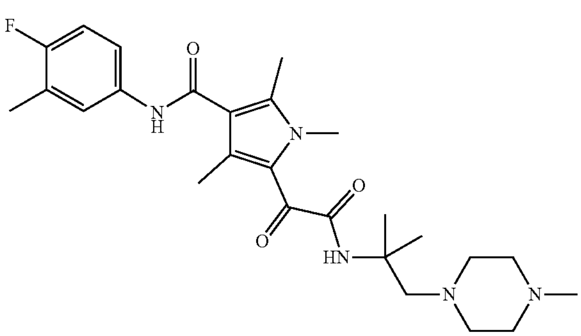 | N-(4-fluoro-3-methylphenyl)-1,2,4-trimethyl-5-(2-((2-methyl-1-(4-methylpiperazin-1-yl)propan-2-yl)amino)-2-oxoacetyl)-1H-pyrrole-3-carboxamide | 486.3 |

TABLE 1-continued

Exemplary compounds

| Ex. | Structure | Chemical Name | ESI-MS (M + H)+ (m/z) |
|---|---|---|---|
| 652 | 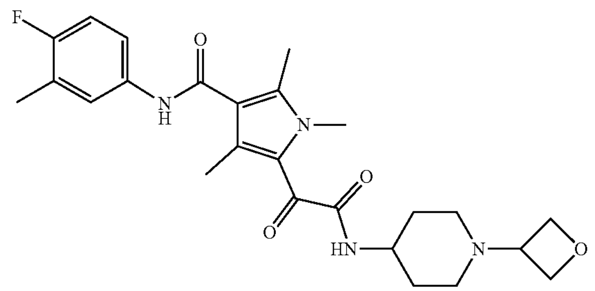 [SMILES: Cc1cc(NC(=O)c2c(C)c(C(=O)C(=O)NC3CCN(C4COC4)CC3)n(C)c2C)ccc1F] | N-(4-fluoro-3-methylphenyl)-1,2,4-trimethyl-5-(2-((1-(oxetan-3-yl)piperidin-4-yl)amino)-2-oxoacetyl)-1H-pyrrole-3-carboxamide | 471.3 |
| 653 | 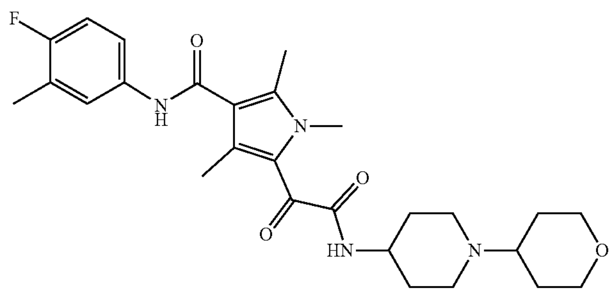 | N-(4-fluoro-3-methylphenyl)-1.2.4-trimethyl-5-(2-oxo-2-((1-(tetrahydro-2H-pyran-4-yl)piperidin-4-yl)amino)acetyl)-1H-pyrrole-3-carboxamide | 499.3 |
| 654 | 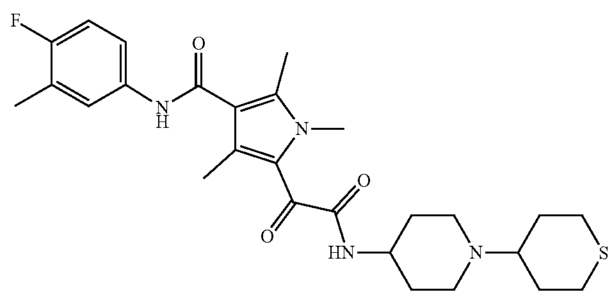 [SMILES: Cc1cc(NC(=O)c2c(C)c(C(=O)C(=O)NC3CCN(C4CCOCC4)CC3)n(C)c2C)ccc1F] | N-(4-fluoro-3-methylphenyl)-1,2,4-trimethyl-5-(2-oxo-2-((1-(tetrahydro-2H-thiopyran-4-yl)piperidin-4-yl)amino)acetyl)-1H-pyrrole-3-carboxamide | 515.3 |
| 655 | 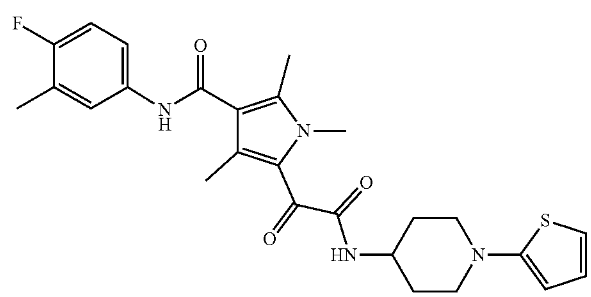 [SMILES: Cc1cc(NC(=O)c2c(C)c(C(=O)C(=O)NC3CCN(c4cccs4)CC3)n(C)c2C)ccc1F] | N-(4-fluoro-3-methylphenyl)-1,2,4-trimethyl-5-(2-oxo-2-((1-(thiophen-2-yl)piperidin-4-yl)amino)acetyl)-1H-pyrrole-3-carboxamide | 497.3 |
| 656 | 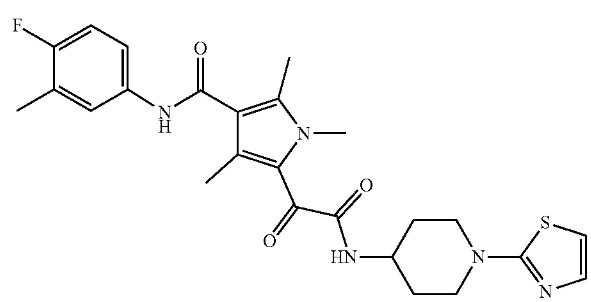 [SMILES: Cc1cc(NC(=O)c2c(C)c(C(=O)C(=O)NC3CCN(c4nccs4)CC3)n(C)c2C)ccc1F] | N-(4-fluoro-3-methylphenyl)-1,2,4-trimethyl-5-(2-oxo-2-((1-(thiazol-2-yl)piperidin-4-yl)amino)acetyl)-1H-pyrrole-3-carboxamide | 498.2 |

TABLE 1-continued

Exemplary compounds

| Ex. | Structure | Chemical Name | ESI-MS (M + H)+ (m/z) |
|---|---|---|---|
| 657 | 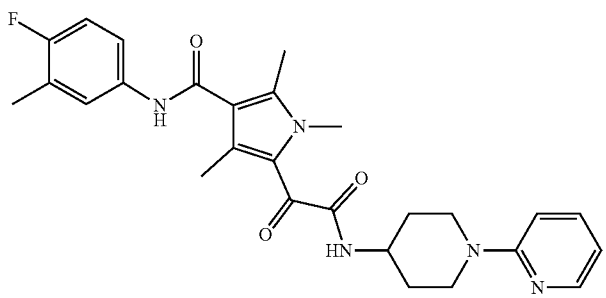 [SMILES: Cc1cc(NC(=O)c2c(C)c(C(=O)C(=O)NC3CCN(c4ccccn4)CC3)n(C)c2C)ccc1F] | N-(4-fluoro-3-methylphenyl)-1,2,4-trimethyl-5-(2-oxo-2-((1-(pyridin-2-yl)piperidin-4-yl)amino)acetyl)-1H-pyrrole-3-carboxamide | 492.3 |
| 658 | 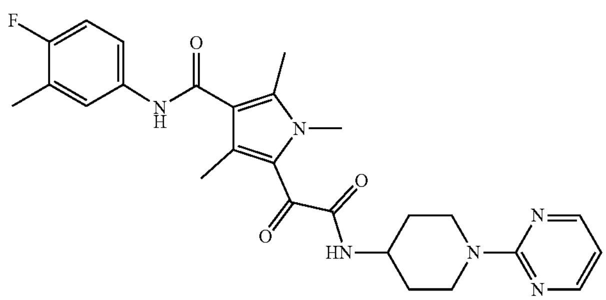 [SMILES: Cc1cc(NC(=O)c2c(C)c(C(=O)C(=O)NC3CCN(c4ncccn4)CC3)n(C)c2C)ccc1F] | N-(4-fluoro-3-methylphenyl)-1,2,4-trimethyl-5-(2-oxo-2-((1-(pyrimidin-2-yl)piperidin-4-yl)amino)acetyl)-1H-pyrrole-3-carboxamide | 493.3 |
| 659 | 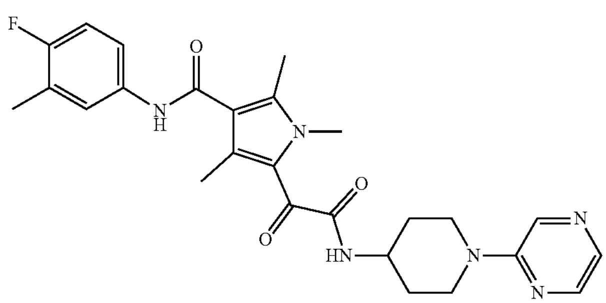 [SMILES: Cc1cc(NC(=O)c2c(C)c(C(=O)C(=O)NC3CCN(c4cnccn4)CC3)n(C)c2C)ccc1F] | N-(4-fluoro-3-methylphenyl)-1,2,4-trimethyl-5-(2-oxo-2-((1-(pyrazin-2-yl)piperidin-4-yl)amino)acetyl)-1H-pyrrole-3-carboxamide | 493.3 |
| 660 | 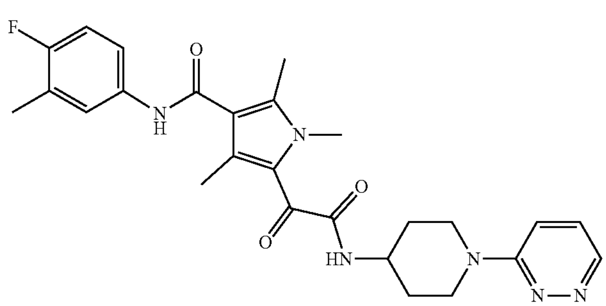 [SMILES: Cc1cc(NC(=O)c2c(C)c(C(=O)C(=O)NC3CCN(c4cccnn4)CC3)n(C)c2C)ccc1F] | N-(4-fluoro-3-methylphenyl)-1,2,4-trimethyl-5-(2-oxo-2-((1-(pyridazin-3-yl)piperidin-4-yl)amino)acetyl)-1H-pyrrole-3-carboxamide | 493.3 |

TABLE 1-continued

Exemplary compounds

| Ex. | Structure | Chemical Name | ESI-MS (M + H)+ (m/z) |
|---|---|---|---|
| 661 | 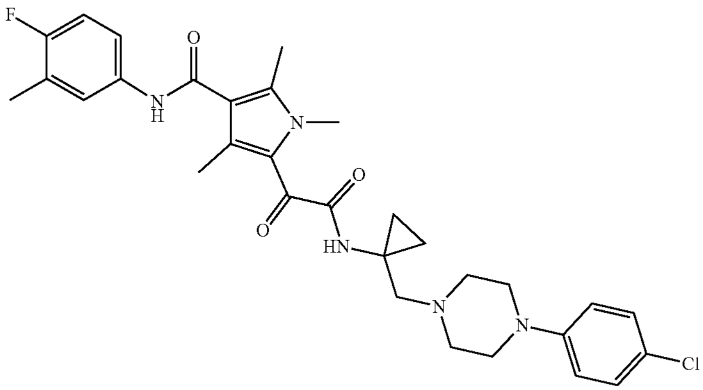 [SMILES: Cc1cc(NC(=O)c2c(C)c(C(=O)C(=O)NC3(CN4CCN(c5ccc(Cl)cc5)CC4)CC3)n(C)c2C)ccc1F] | 5-(2-((1-(((4-(4-chlorophenyl)piperazin-1-yl)methyl)cyclopropyl)amino)-2-oxoacetyl)-N-(4-fluoro-3-methylphenyl)-1,2,4-trimethyl-1H-pyrrole-3-carboxamide | 580.3 |
| 662 | 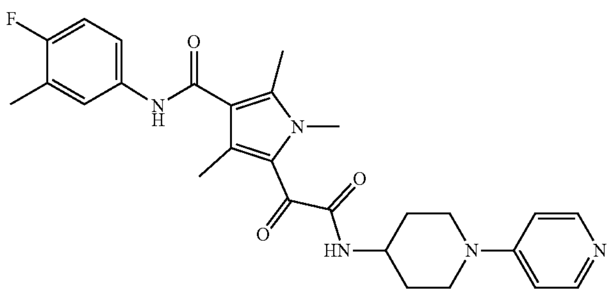 [SMILES: Cc1cc(NC(=O)c2c(C)c(C(=O)C(=O)NC3CCN(c4ccncc4)CC3)n(C)c2C)ccc1F] | N-(4-fluoro-3-methylphenyl)-1,2,4-trimethyl-5-(2-oxo-2-((1-(pyridin-4-yl)piperidin-4-yl)amino)acetyl)-1H-pyrrole-3-carboxamide | 492.3 |
| 663 | 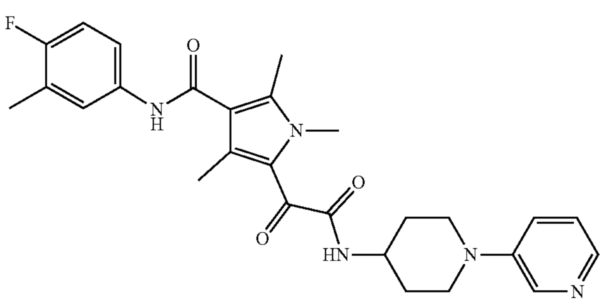 [SMILES: Cc1cc(NC(=O)c2c(C)c(C(=O)C(=O)NC3CCN(c4cccnc4)CC3)n(C)c2C)ccc1F] | N-(4-fluoro-3-methylphenyl)-1,2,4-trimethyl-5-(2-oxo-2-((1-(pyridin-3-yl)piperidin-4-yl)amino)acetyl)-1H-pyrrole-3-carboxamide | 492.3 |
| 664 | 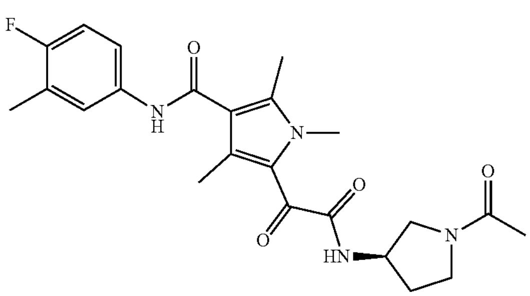 [SMILES: CC(=O)N1CC[C@@H](NC(=O)C(=O)c2c(C)c(C(=O)Nc3ccc(F)c(C)c3)c(C)n2C)C1] | (R)-5-(2-((1-acetylpyrrolidin-3-yl)amino)-2-oxoacetyl)-N-(4-fluoro-3-methylphenyl)-1,2,4-trimethyl-1H-pyrrole-3-carboxamide | 443.2 |

TABLE 1-continued

Exemplary compounds

| Ex. | Structure | Chemical Name | ESI-MS (M + H)+ (m/z) |
|---|---|---|---|
| 665 | 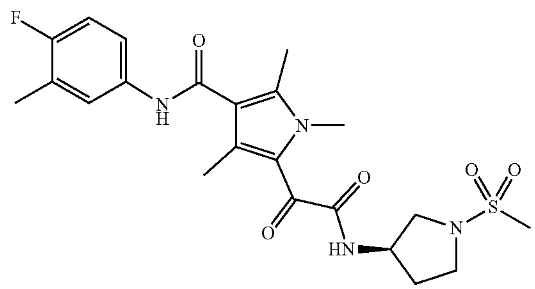 | (R)-N-(4-fluoro-3-methylphenyl)-1,2,4-trimethyl-5-(2-((1-(methylsulfonyl)pyrrolidin-3-yl)amino)-2-oxoacetyl)-1H-pyrrole-3-carboxamide | 479.2 |
| 666 | 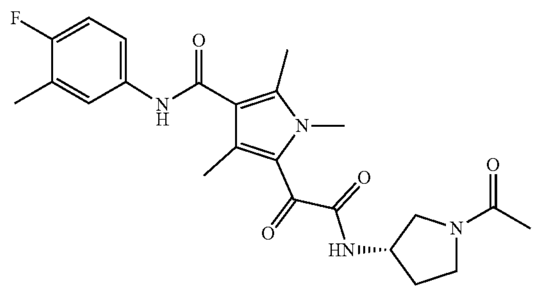 [SMILES: CC(=O)N1CC[C@H](NC(=O)C(=O)c2c(C)c(C(=O)Nc3ccc(F)c(C)c3)c(C)n2C)C1] | (S)-5-(2-((1-acetylpyrrolidin-3-yl)amino)-2-oxoacetyl)-N-(4-fluoro-3-methylphenyl)-1,2,4-trimethyl-1H-pyrrole-3-carboxamide | 443.2 |
| 667 | 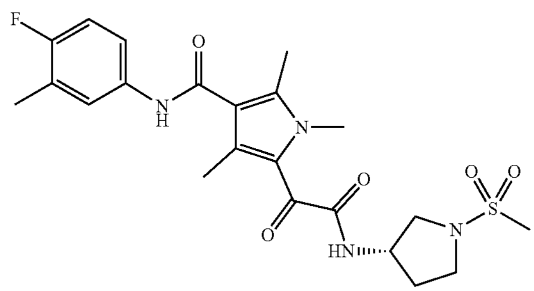 | (S)-N-(4-fluoro-3-methylphenyl)-1,2,4-trimethyl-5-(2-((1-(methylsulfonyl)pyrrolidin-3-yl)amino)-2-oxoacetyl)-1H-pyrrole-3-carboxamide | 479.2 |
| 668 | 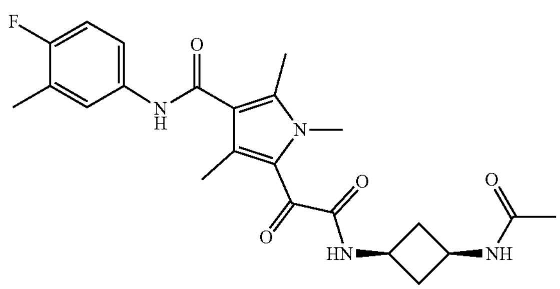 [SMILES: CC(=O)N[C@H]1C[C@@H](NC(=O)C(=O)c2c(C)c(C(=O)Nc3ccc(F)c(C)c3)c(C)n2C)C1] | 5-(2-(((1s,3s)-3-acetamidocyclobutyl)amino)-2-oxoacetyl)-N-(4-fluoro-3-methylphenyl)-1,2,4-trimethyl-1H-pyrrole-3-carboxamide | 443.2 |
| 669 | 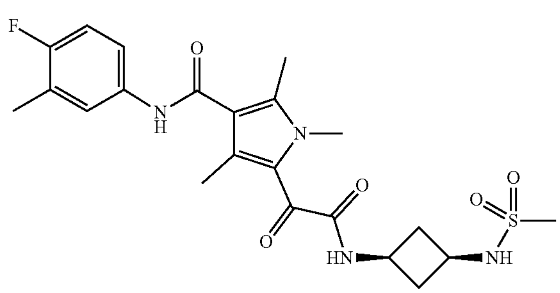 | N-(4-fluoro-3-methylphenyl)-1,2,4-trimethyl-5-(2-(((1s,3s)-3-(methylsulfonamido)cyclobutyl)amino)-2-oxoacetyl)-1H-pyrrole-3-carboxamide | 479.2 |

TABLE 1-continued

Exemplary compounds

| Ex. | Structure | Chemical Name | ESI-MS (M + H)+ (m/z) |
|---|---|---|---|
| 670 | 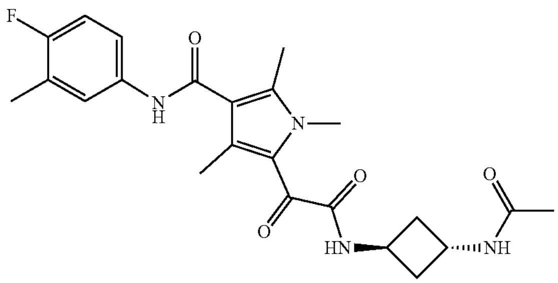 [SMILES: CC(=O)N[C@H]1C[C@H](NC(=O)C(=O)c2c(C)c(C(=O)Nc3ccc(F)c(C)c3)c(C)n2C)C1] | 5-(2-(((1r,3r)-3-acetamidocyclobutyl)amino)-2-oxoacetyl)-N-(4-fluoro-3-methylphenyl)-1,2,4-trimethyl-1H-pyrrole-3-carboxamide | 443.2 |
| 671 | 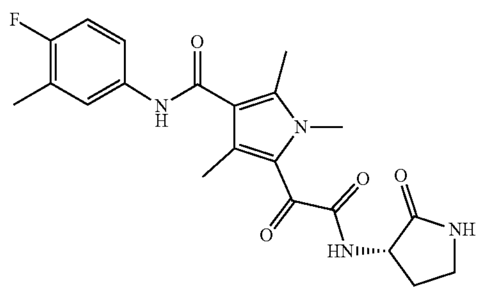 [SMILES: Cc1cc(NC(=O)c2c(C)c(C(=O)C(=O)N[C@H]3CCNC3=O)n(C)c2C)ccc1F] | (S)-N-(4-fluoro-3-methylphenyl)-1,2,4-trimethyl-5-(2-oxo-2-((2-oxopyrrolidin-3-yl)amino)acetyl)-1H-pyrrole-3-carboxamide | 415.2 |
| 672 | 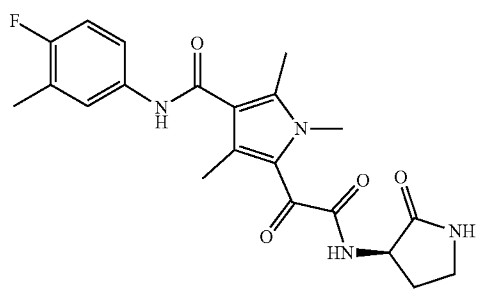 [SMILES: Cc1cc(NC(=O)c2c(C)c(C(=O)C(=O)N[C@@H]3CCNC3=O)n(C)c2C)ccc1F] | (R)-N-(4-fluoro-3-methylphenyl)-1,2,4-trimethyl-5-(2-oxo-2-((2-oxopyrrolidin-3-yl)amino)acetyl)-1H-pyrrole-3-carboxamide | 415.2 |
| 673 | 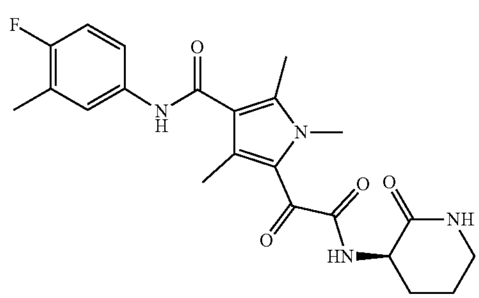 [SMILES: Cc1cc(NC(=O)c2c(C)c(C(=O)C(=O)N[C@@H]3CCCNC3=O)n(C)c2C)ccc1F] | (R)-N-(4-fluoro-3-methylphenyl)-1,2,4-trimethyl-5-(2-oxo-2-((2-oxopiperidin-3-yl)amino)acetyl)-1H-pyrrole-3-carboxamide | 429.2 |
| 674 | 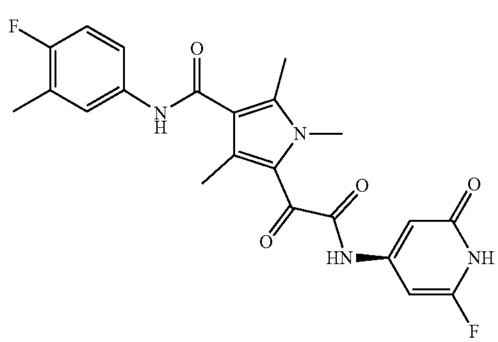 | 5-(2-((6-fluoro-2-oxo-1,2-dihydropyridin-4-yl)amino)-2-oxoacetyl)-N-(4-fluoro-3-methylphenyl)-1,2,4-trimethyl-1H-pyrrole-3-carboxamide | 443.2 |

TABLE 1-continued

Exemplary compounds

| Ex. | Structure | Chemical Name | ESI-MS (M + H)+ (m/z) |
|---|---|---|---|
| 675 | 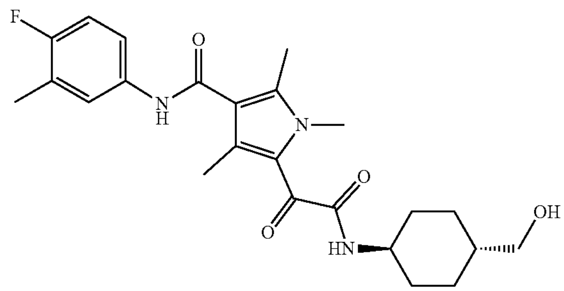 [SMILES: Cc1cc(NC(=O)c2c(C)c(C(=O)C(=O)N[C@H]3CC[C@H](CO)CC3)n(C)c2C)ccc1F] | N-(4-fluoro-3-methylphenyl)-5-(2-(((1r,4r)-4-(hydroxymethyl)cyclohexyl)amino)-2-oxoacetyl)-1,2,4-trimethyl-1H-pyrrole-3-carboxamide | 444.2 |
| 676 | 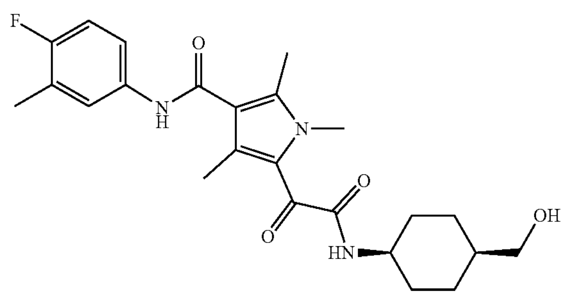 [SMILES: Cc1cc(NC(=O)c2c(C)c(C(=O)C(=O)N[C@H]3CC[C@@H](CO)CC3)n(C)c2C)ccc1F] | N-(4-fluoro-3-methylphenyl)-5-(2-(((1s,4s)-4-(hydroxymethyl)cyclohexyl)amino)-2-oxoacetyl)-1,2,4-trimethyl-1H-pyrrole-3-carboxamide | 444.2 |
| 677 | 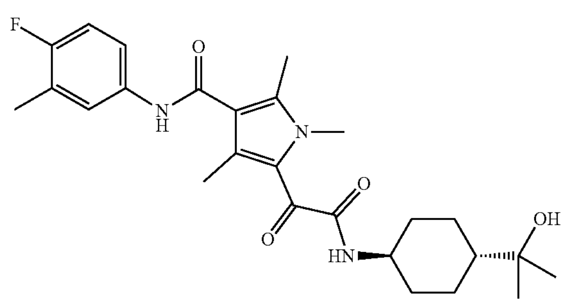 [SMILES: Cc1cc(NC(=O)c2c(C)c(C(=O)C(=O)N[C@H]3CC[C@H](C(C)(C)O)CC3)n(C)c2C)ccc1F] | N-(4-fluoro-3-methylphenyl)-5-(2-(((1r,4r)-4-(2-hydroxypropan-2-yl)cyclohexyl)amino)-2-oxoacetyl)-1,2,4-trimethyl-1H-pyrrole-3-carboxamide | 472.2 |
| 678 | 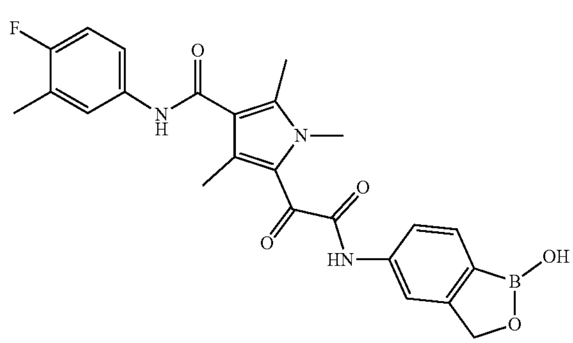 [SMILES: Cc1cc(NC(=O)c2c(C)c(C(=O)C(=O)Nc3ccc4c(c3)COB4O)n(C)c2C)ccc1F] | N-(4-fluoro-3-methylphenyl)-5-(2-(((1-hydroxy-1,3-dihydrobenzo[c][1,2]oxaborol-5-yl)amino)-2-oxoacetyl)-1,2,4-trimethyl-1H-pyrrole-3-carboxamide | 464.2 |

TABLE 1-continued

Exemplary compounds

| Ex. | Structure | Chemical Name | ESI-MS (M + H)+ (m/z) |
|---|---|---|---|
| 679 | 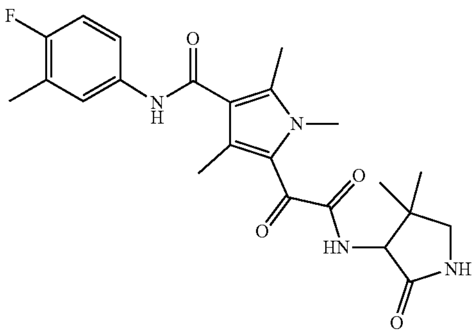 [SMILES: Cc1cc(NC(=O)c2c(C)c(C(=O)C(=O)NC3C(=O)NCC3(C)C)n(C)c2C)ccc1F] | 5-(2-((4,4-dimethyl-2-oxopyrrolidin-3-yl)amino)-2-oxoacetyl)-N-(4-fluoro-3-methylphenyl)-1,2,4-trimethyl-1H-pyrrole-3-carboxamide | 443.2 |
| 680 | 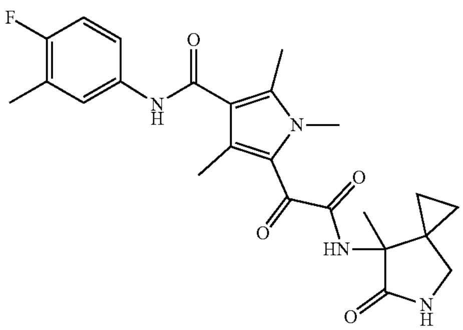 [SMILES: Cc1cc(NC(=O)c2c(C)c(C(=O)C(=O)NC3(C)C(=O)NCC34CC4)n(C)c2C)ccc1F] | N-(4-fluoro-3-methylphenyl)-1,2,4-trimethyl-5-(2-((7-methyl-6-oxo-5-azaspiro[2.4]heptan-7-yl)amino)-2-oxoacetyl)-1H-pyrrole-3-carboxamide | 455.2 |
| 681 | 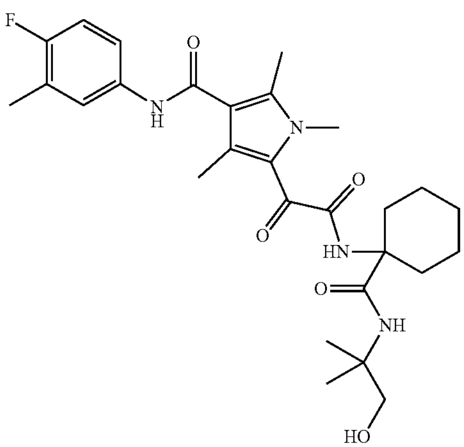 [SMILES: Cc1cc(NC(=O)c2c(C)c(C(=O)C(=O)NC3(C(=O)NC(C)(C)CO)CCCCC3)n(C)c2C)ccc1F] | N-(4-fluoro-3-methylphenyl)-5-(2-((4-((1-hydroxy-2-methylpropan-2-yl)carbamoyl)tetrahydro-2H-pyran-4-yl)amino)-2-oxoacetyl)-1,2,4-trimethyl-1H-pyrrole-3-carboxamide | 531.3 |
| 682 | 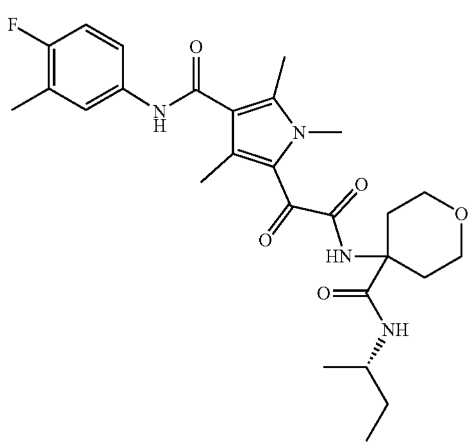 [SMILES: CC[C@H](C)NC(=O)C1(NC(=O)C(=O)c2c(C)c(C(=O)Nc3ccc(F)c(C)c3)c(C)n2C)CCOCC1] | (S)-5-(2-((4-(sec-butylcarbamoyl)tetrahydro-2H-pyran-4-yl)amino)-2-oxoacetyl)-N-(4-fluoro-3-methylphenyl)-1,2,4-trimethyl-1H-pyrrole-3-carboxamide | 515.3 |

TABLE 1-continued

Exemplary compounds

| Ex. | Structure | Chemical Name | ESI-MS (M + H)+ (m/z) |
|---|---|---|---|
| 683 | 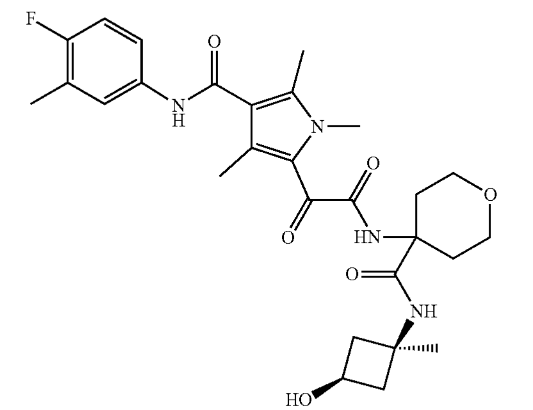 [SMILES: Cc1cc(NC(=O)c2c(C)c(C(=O)C(=O)NC3(C(=O)N[C@]4(C)C[C@H](O)C4)CCOCC3)n(C)c2C)ccc1F] | N-(4-fluoro-3-methylphenyl)-5-(2-((4-(((1s,3s)-3-hydroxy-1-methylcyclobutyl)carbamoyl)tetrahydro-2H-pyran-4-yl)amino)-2-oxoacetyl)-1,2,4-trimethyl-1H-pyrrole-3-carboxamide | 543.3 |
| 684 | 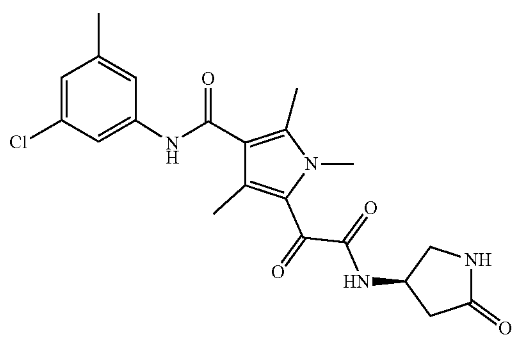 [SMILES: Cc1cc(Cl)cc(NC(=O)c2c(C)c(C(=O)C(=O)N[C@H]3CNC(=O)C3)n(C)c2C)c1] | (R)-N-(3-chloro-5-methylphenyl)-1,2,4-trimethyl-5-(2-oxo-2-((5-oxopyrrolidin-3-yl)amino)acetyl)-1H-pyrrole-3-carboxamide | 431.2 |
| 685 | 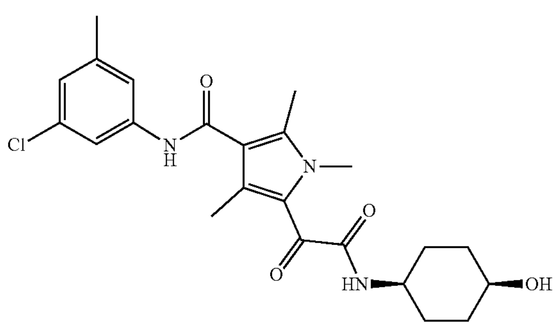 [SMILES: Cc1cc(Cl)cc(NC(=O)c2c(C)c(C(=O)C(=O)N[C@H]3CC[C@@H](O)CC3)n(C)c2C)c1] | N-(3-chloro-5-methylphenyl)-5-(2-(((1s,4s)-4-hydroxycyclohexyl)amino)-2-oxoacetyl)-1,2,4-trimethyl-1H-pyrrole-3-carboxamide | 446.2 |
| 686 | 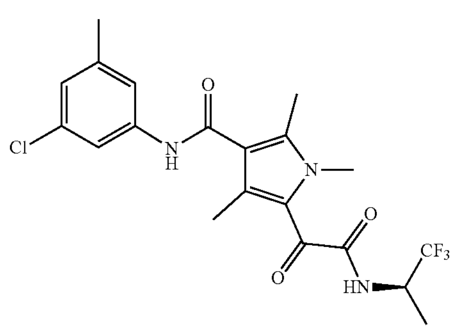 [SMILES: Cc1cc(Cl)cc(NC(=O)c2c(C)c(C(=O)C(=O)N[C@H](C)C(F)(F)F)n(C)c2C)c1] | (R)-N-(3-chloro-5-methylphenyl)-1,2,4-trimethyl-5-(2-oxo-2-((1,1,1-trifluoropropan-2-yl)amino)acetyl)-1H-pyrrole-3-carboxamide | 444.1 |

TABLE 1-continued

Exemplary compounds

| Ex. | Structure | Chemical Name | ESI-MS (M + H)+ (m/z) |
|---|---|---|---|
| 687 | 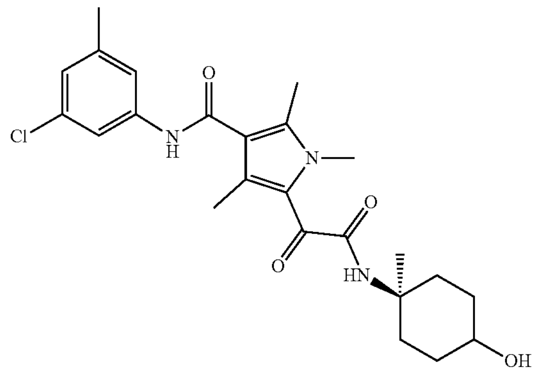 | N-(3-chloro-5-methylphenyl)-5-(2-(((1r,4r)-4-hydroxy-1-methylcyclohexyl)amino)-2-oxoacetyl)-1,2,4-trimethyl-1H-pyrrole-3-carboxamide | 460.2 |
| 688 | 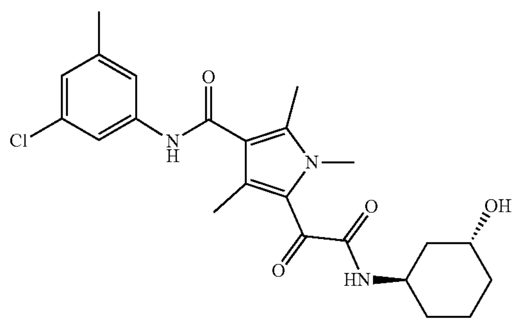 [SMILES: Cc1cc(Cl)cc(NC(=O)c2c(C)c(C(=O)C(=O)N[C@@H]3CCC[C@@H](O)C3)n(C)c2C)c1] | N-(3-chloro-5-methylphenyl)-5-(2-(((1R,3R)-3-hydroxycyclohexyl)amino)-2-oxoacetyl)-1,2,4-trimethyl-1H-pyrrole-3-carboxamide | 446.2 |
| 689 | 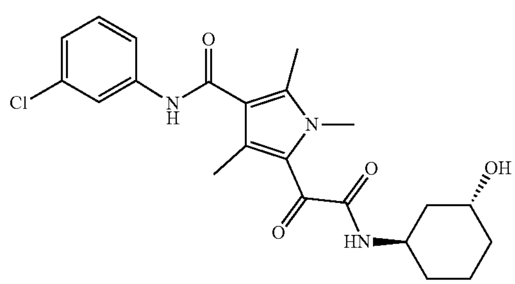 [SMILES: Cc1c(C(=O)Nc2cccc(Cl)c2)c(C)n(C)c1C(=O)C(=O)N[C@@H]1CCC[C@@H](O)C1] | N-(3-chlorophenyl)-5-(2-(((1R,3R)-3-hydroxycyclohexyl)amino)-2-oxoacetyl)-1,2,4-trimethyl-1H-pyrrole-3-carboxamide | 432.2 |
| 690 | 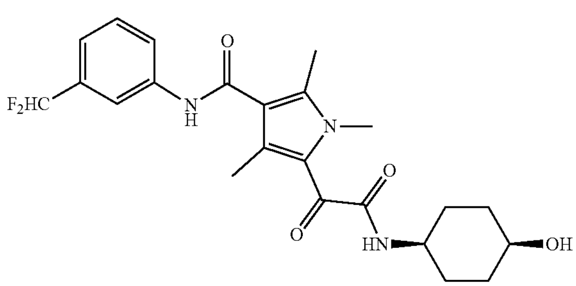 [SMILES: Cc1c(C(=O)Nc2cccc(C(F)F)c2)c(C)n(C)c1C(=O)C(=O)N[C@H]1CC[C@@H](O)CC1] | N-(3-(difluoromethyl)phenyl)-5-(2-(((1s,4s)-4-hydroxycyclohexyl)amino)-2-oxoacetyl)-1,2,4-trimethyl-1H-pyrrole-3-carboxamide | 448.2 |

TABLE 1-continued

Exemplary compounds

| Ex. | Structure | Chemical Name | ESI-MS (M + H)+ (m/z) |
|---|---|---|---|
| 691 | 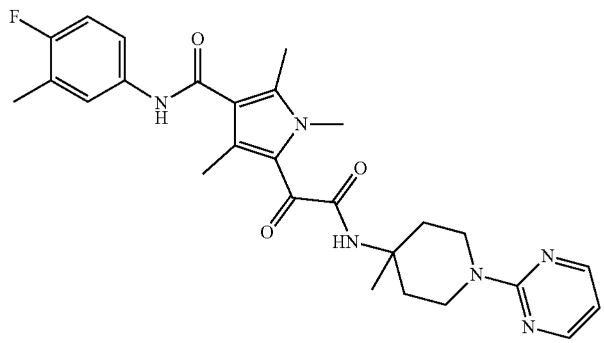 [SMILES: Cc1cc(NC(=O)c2c(C)c(C(=O)C(=O)NC3(C)CCN(c4ncccn4)CC3)n(C)c2C)ccc1F] | N-(4-fluoro-3-methylphenyl)-1,2,4-trimethyl-5-(2-((4-methyl-1-(pyrimidin-2-yl)piperidin-4-yl)amino)-2-oxoacetyl)-1H-pyrrole-3-carboxamide | 507.3 |
| 692 | 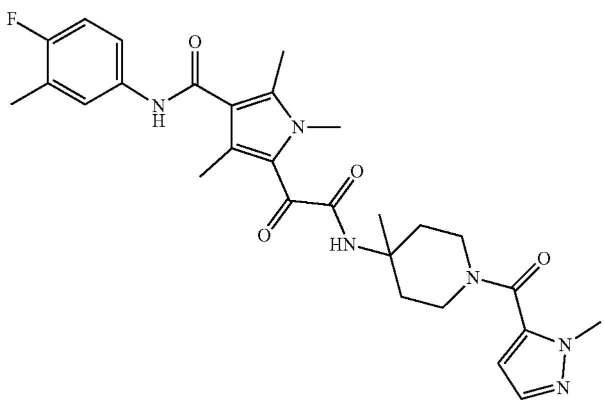 | N-(4-fluoro-3-methylphenyl)-1,2,4-trimethyl-5-(2-((4-methyl-1-(1-methyl-1H-pyrazole-5-carbonyl)piperidin-4-yl)amino)-2-oxoacetyl)-1H-pyrrole-3-carboxamide | 537.2 |
| 693 | 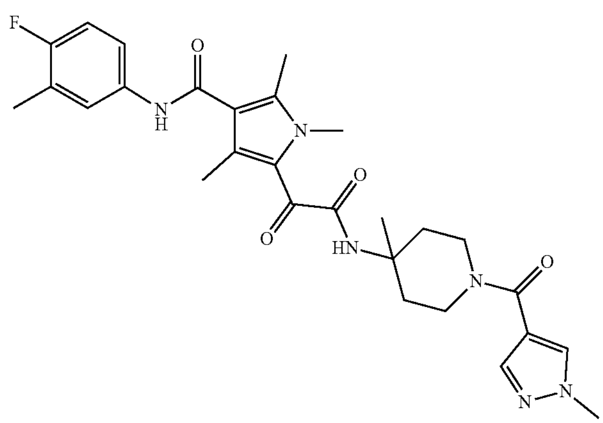 | N-(4-fluoro-3-methylphenyl)-1,2,4-trimethyl-5-(2-((4-methyl-1-(1-methyl-1H-pyrazole-4-carbonyl)piperidin-4-yl)amino)-2-oxoacetyl)-1H-pyrrole-3-carboxamide | 537.2 |
| 694 | 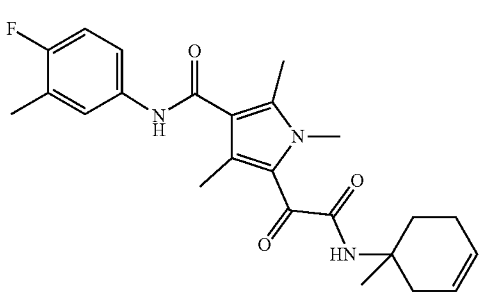 [SMILES: Cc1cc(NC(=O)c2c(C)c(C(=O)C(=O)NC3(C)CC=CCC3)n(C)c2C)ccc1F] | N-(4-fluoro-3-methylphenyl)-1,2,4-trimethyl-5-(2-((1-methylcyclohex-3-en-1-yl)amino)-2-oxoacetyl)-1H-pyrrole-3-carboxamide | 426.2 |

TABLE 1-continued

Exemplary compounds

| Ex. | Structure | Chemical Name | ESI-MS (M + H)+ (m/z) |
|---|---|---|---|
| 695 | 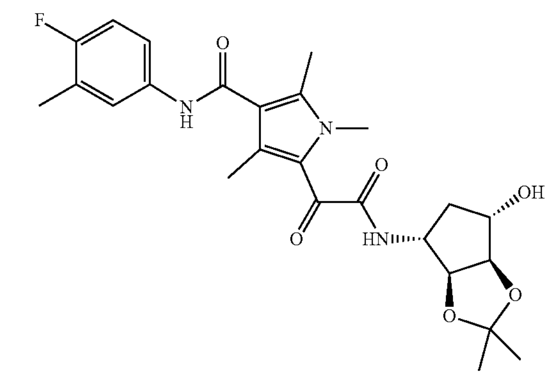 [SMILES: Cc1cc(NC(=O)c2c(C)c(C(=O)C(=O)N[C@@H]3C[C@H](O)[C@H]4OC(C)(C)O[C@H]43)n(C)c2C)ccc1F] | N-(4-fluoro-3-methylphenyl)-5-(2-(((3aS,4R,6S,6aR)-6-hydroxy-2,2-dimethyltetrahydro-4H-cyclopenta[d][1,3]dioxol-4-yl)amino)-2-oxoacetyl)-1,2,4-trimethyl-1H-pyrrole-3-carboxamide | 488.2 |
| 696 | 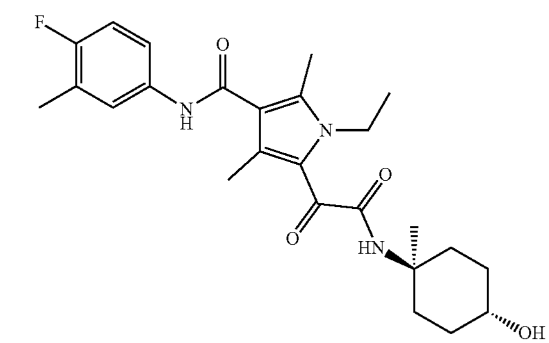 [SMILES: CCn1c(C)c(C(=O)Nc2ccc(F)c(C)c2)c(C)c1C(=O)C(=O)N[C@]1(C)CC[C@@H](O)CC1] | 1-ethyl-N-(4-fluoro-3-methylphenyl)-5-(2-(((1r,4r)-4-hydroxy-1-methylcyclohexyl)amino)-2-oxoacetyl)-2,4-dimethyl-1H-pyrrole-3-carboxamide | 458.3 |
| 697 | 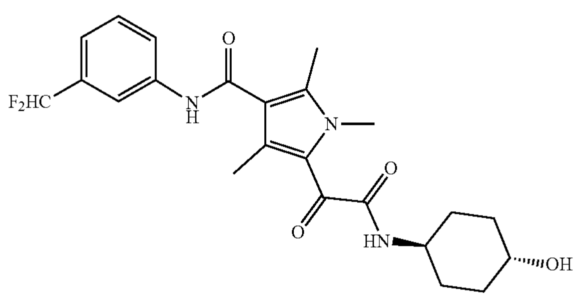 [SMILES: Cc1c(C(=O)Nc2cccc(C(F)F)c2)c(C)n(C)c1C(=O)C(=O)N[C@H]1CC[C@H](O)CC1] | N-(3-(difluoromethyl)phenyl)-5-(2-(((1r,4r)-4-hydroxycyclohexyl)amino)-2-oxoacetyl)-1,2,4-trimethyl-1H-pyrrole-3-carboxamide | 448.2 |
| 698 | 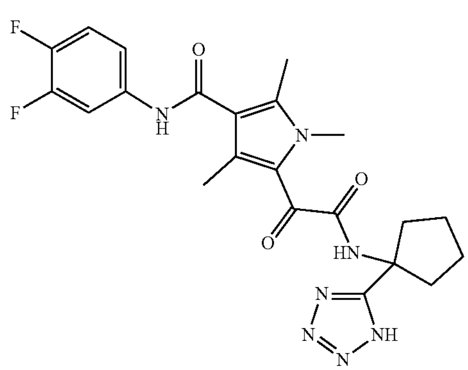 [SMILES: Cc1c(C(=O)Nc2ccc(F)c(F)c2)c(C)n(C)c1C(=O)C(=O)NC1(c2nnn[nH]2)CCCC1] | 5-(2-((1-(1H-tetrazol-5-yl)cyclopentyl)amino)-2-oxoacetyl)-N-(3,4-difluorophenyl)-1,2,4-trimethyl-1H-pyrrole-3-carboxamide | 472.1 |

TABLE 1-continued

Exemplary compounds

| Ex. | Structure | Chemical Name | ESI-MS (M + H)+ (m/z) |
|---|---|---|---|
| 699 | 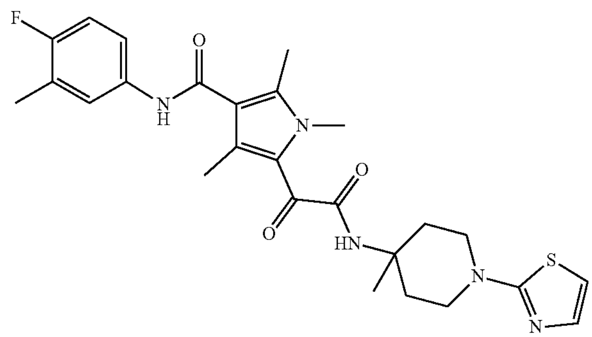 [SMILES: Cc1cc(NC(=O)c2c(C)c(C(=O)C(=O)NC3(C)CCN(c4nccs4)CC3)n(C)c2C)ccc1F] | N-(4-fluoro-3-methylphenyl)-1,2,4-trimethyl-5-(2-((4-methyl-1-(thiazol-2-yl)piperidin-4-yl)amino)-2-oxoacetyl)-1H-pyrrole-3-carboxamide | 512.3 |
| 700 | 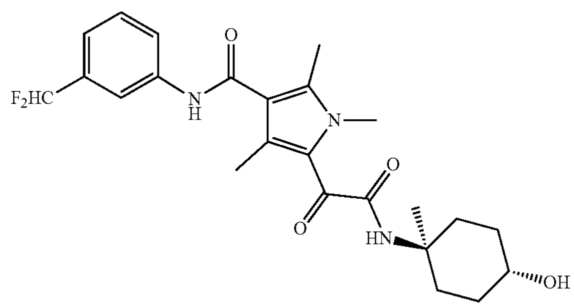 [SMILES: Cc1c(C(=O)Nc2cccc(C(F)F)c2)c(C)n(C)c1C(=O)C(=O)N[C@]1(C)CC[C@@H](O)CC1] | N-(3-(difluoromethyl)phenyl)-5-(2-(((1r,4r)-4-hydroxy-1-methylcyclohexyl)amino)-2-oxoacetyl)-1,2,4-trimethyl-1H-pyrrole-3-carboxamide | 462.2 |
| 701 | 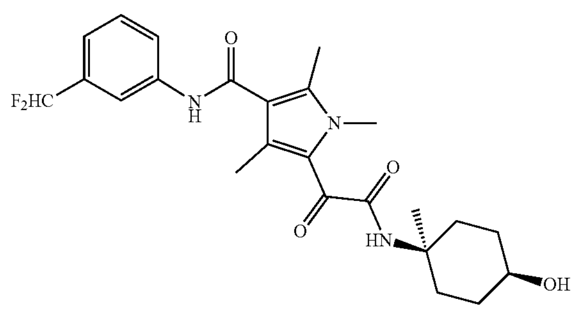 [SMILES: Cc1c(C(=O)Nc2cccc(C(F)F)c2)c(C)n(C)c1C(=O)C(=O)N[C@]1(C)CC[C@H](O)CC1] | N-(3-(difluoromethyl)phenyl)-5-(2-(((1s,4s)-4-hydroxy-1-methylcyclohexyl)amino)-2-oxoacetyl)-1,2,4-trimethyl-1H-pyrrole-3-carboxamide | 462.2 |
| 702 | 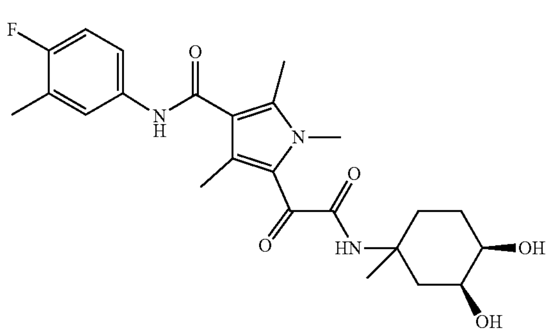 [SMILES: Cc1cc(NC(=O)c2c(C)c(C(=O)C(=O)NC3(C)CC[C@@H](O)[C@@H](O)C3)n(C)c2C)ccc1F] | 5-(2-(((3S,4R)-3,4-dihydroxy-1-methylcyclohexyl)amino)-2-oxoacetyl)-N-(4-fluoro-3-methylphenyl)-1,2,4-trimethyl-1H-pyrrole-3-carboxamide | 460.2 |

TABLE 1-continued

Exemplary compounds

| Ex. | Structure | Chemical Name | ESI-MS (M + H)+ (m/z) |
|---|---|---|---|
| 703 | 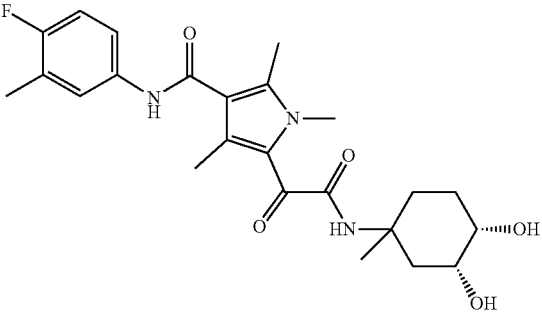 [SMILES: Cc1cc(NC(=O)c2c(C)c(C(=O)C(=O)NC3(C)CC[C@H](O)[C@H](O)C3)n(C)c2C)ccc1F] | 5-(2-(((3R,4S)-3,4-dihydroxy-1-methylcyclohexyl)amino)-2-oxoacetyl)-N-(4-fluoro-3-methylphenyl)-1,2,4-trimethyl-1H-pyrrole-3-carboxamide | 460.2 |
| 704 | 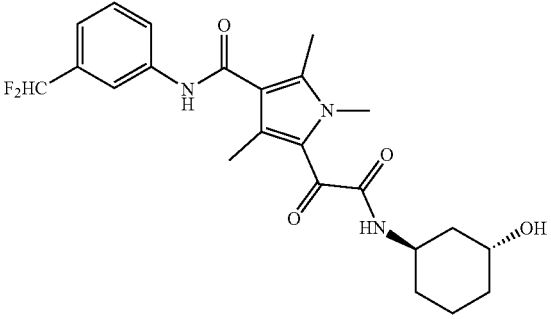 [SMILES: Cc1c(C(=O)Nc2cccc(C(F)F)c2)c(C)n(C)c1C(=O)C(=O)N[C@@H]1CCC[C@@H](O)C1] | N-(3-(difluoromethyl)phenyl)-5-(2-(((1R,3R)-3-hydroxycyclohexyl)amino)-2-oxoacetyl)-1,2,4-trimethyl-1H-pyrrole-3-carboxamide | 448.2 |
| 705 | 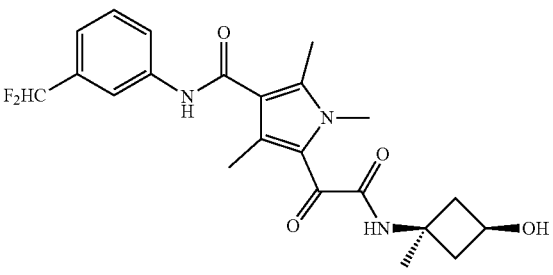 [SMILES: Cc1c(C(=O)Nc2cccc(C(F)F)c2)c(C)n(C)c1C(=O)C(=O)N[C@]1(C)C[C@H](O)C1] | N-(3-(difluoromethyl)phenyl)-5-(2-(((1s,3s)-3-hydroxy-1-methylcyclobutyl)amino)-2-oxoacetyl)-1,2,4-trimethyl-1H-pyrrole-3-carboxamide | 434.2 |
| 706 | 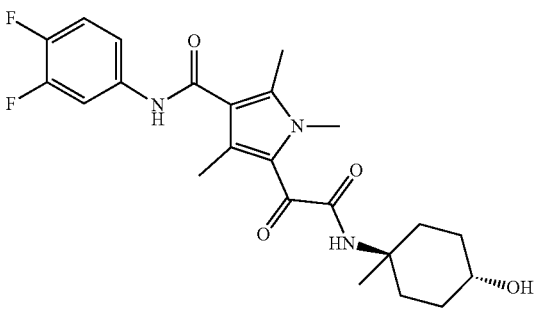 [SMILES: Cc1c(C(=O)Nc2ccc(F)c(F)c2)c(C)n(C)c1C(=O)C(=O)N[C@]1(C)CC[C@@H](O)CC1] | N-(3,4-difluorophenyl)-5-(2-(((1r,4r)-4-hydroxy-1-methylcyclohexyl)amino)-2-oxoacetyl)-1,2,4-trimethyl-1H-pyrrole-3-carboxamide | 448.2 |

TABLE 1-continued

Exemplary compounds

| Ex. | Structure | Chemical Name | ESI-MS (M + H)+ (m/z) |
|---|---|---|---|
| 707 | 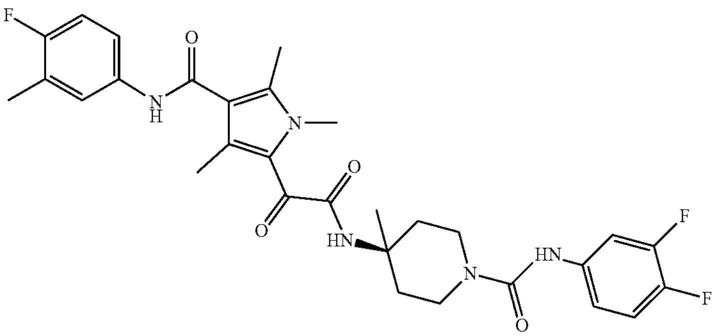 | N-(3,4-difluorophenyl)-4-(2-(4-((4-fluoro-3-methylphenyl)carbamoyl)-1,3,5-trimethyl-1H-pyrrol-2-yl)-2-oxoacetamido)-4-methylpiperidine-1-carboxamide | 584.2 |
| 708 | 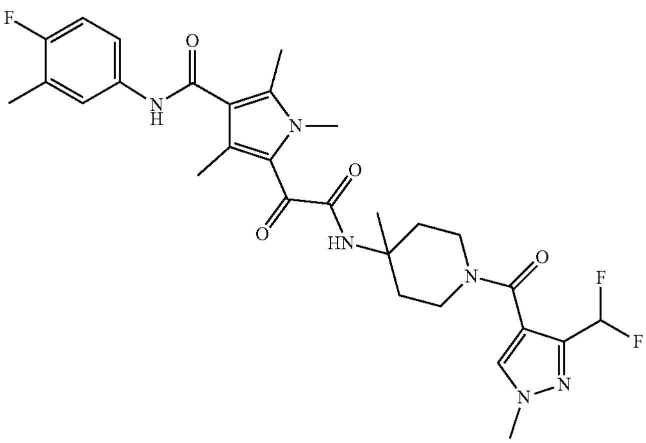 [SMILES: Cc1cc(NC(=O)c2c(C)c(C(=O)C(=O)NC3(C)CCN(C(=O)c4cn(C)nc4C(F)F)CC3)n(C)c2C)ccc1F] | 5-(2-((1-(3-(difluoromethyl)-1-methyl-1H-pyrazole-4-carbonyl)-4-methylpiperidin-4-yl)amino)-2-oxoacetyl)-N-(4-fluoro-3-methylphenyl)-1,2,4-trimethyl-1H-pyrrole-3-carboxamide | 587.3 |
| 709 | 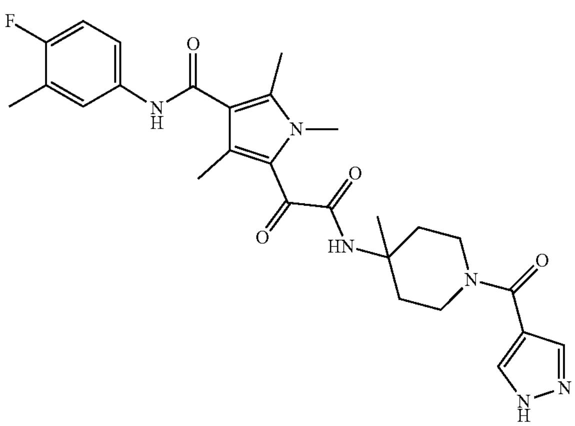 [SMILES: Cc1cc(NC(=O)c2c(C)c(C(=O)C(=O)NC3(C)CCN(C(=O)c4cn[nH]c4)CC3)n(C)c2C)ccc1F] | N-(4-fluoro-3-methylphenyl)-1,2,4-trimethyl-5-(2-((4-methyl-1-(1H-pyrazole-4-carbonyl)piperidin-4-yl)amino)-2-oxoacetyl)-1H-pyrrole-3-carboxamide | 523.2 |
| 710 | 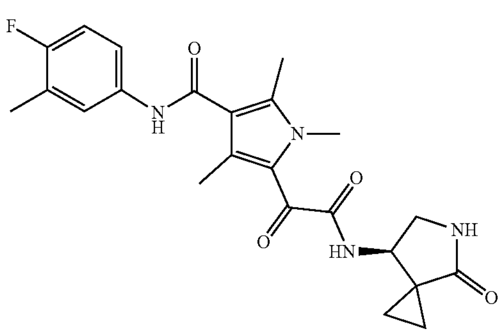 [SMILES: Cc1cc(NC(=O)c2c(C)c(C(=O)C(=O)N[C@H]3CNC(=O)C34CC4)n(C)c2C)ccc1F] | (R)-N-(4-fluoro-3-methylphenyl)-1,2,4-trimethyl-5-(2-oxo-2-((4-oxo-5-azaspiro[2.4]heptan-7-yl)amino)acetyl)-1H-pyrrole-3-carboxamide | 441.2 |

TABLE 1-continued

Exemplary compounds

| Ex. | Structure | Chemical Name | ESI-MS (M + H)+ (m/z) |
|---|---|---|---|
| 711 | 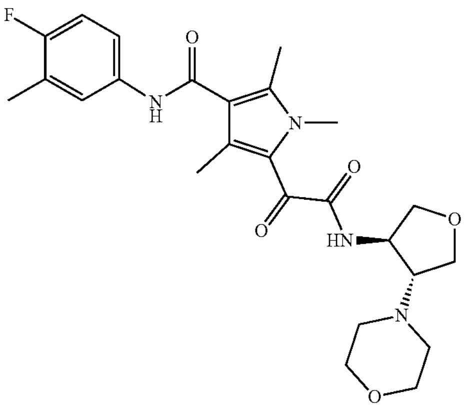 [SMILES: Cc1cc(NC(=O)c2c(C)c(C(=O)C(=O)N[C@H]3COC[C@@H]3N3CCOCC3)n(C)c2C)ccc1F] | N-(4-fluoro-3-methylphenyl)-1,2,4-trimethyl-5-(2-(((3R,4R)-4-morpholinotetrahydrofuran-3-yl)amino)-2-oxoacetyl)-1H-pyrrole-3-carboxamide | 487.2 |
| 712 | 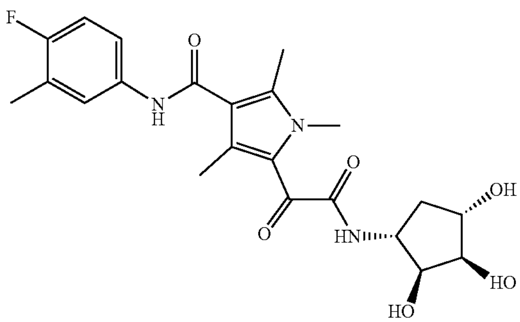 [SMILES: Cc1cc(NC(=O)c2c(C)c(C(=O)C(=O)N[C@@H]3C[C@H](O)[C@@H](O)[C@H]3O)n(C)c2C)ccc1F] | N-(4-fluoro-3-methylphenyl)-1,2,4-trimethyl-5-(2-oxo-2-(((1R,2S,3R,4S)-2,3,4-trihydroxycyclopentyl)amino)acetyl)-1H-pyrrole-3-carboxamide | 448.2 |
| 713 | 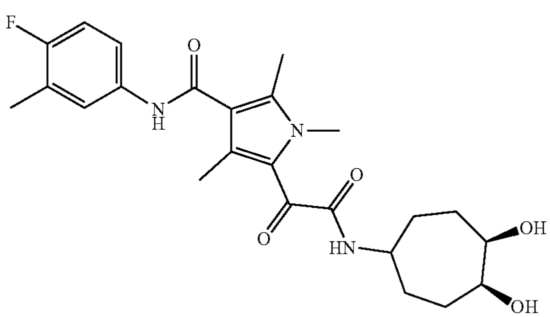 [SMILES: Cc1cc(NC(=O)c2c(C)c(C(=O)C(=O)NC3CC[C@@H](O)[C@@H](O)CC3)n(C)c2C)ccc1F] | 5-(2-(((4R,5S)-4,5-dihydroxycycloheptyl)amino)-2-oxoacetyl)-N-(4-fluoro-3-methylphenyl)-1,2,4-trimethyl-1H-pyrrole-3-carboxamide | 460.2 |
| 714 | 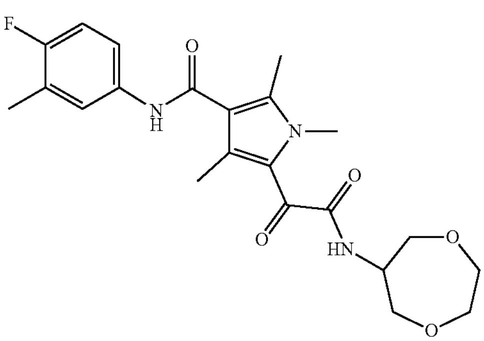 [SMILES: Cc1cc(NC(=O)c2c(C)c(C(=O)C(=O)NC3COCCOC3)n(C)c2C)ccc1F] | 5-(2-((1,4-dioxepan-6-yl)amino)-2-oxoacetyl)-N-(4-fluoro-3-methylphenyl)-1,2,4-trimethyl-1H-pyrrole-3-carboxamide | 432.1 |

TABLE 1-continued

Exemplary compounds

| Ex. | Structure | Chemical Name | ESI-MS (M + H)+ (m/z) |
|---|---|---|---|
| 715 | 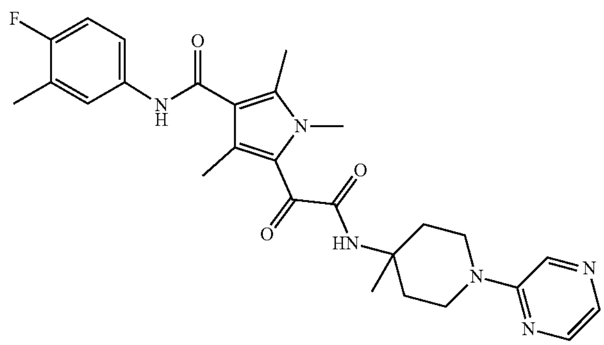 [SMILES: Cc1cc(NC(=O)c2c(C)c(C(=O)C(=O)NC3(C)CCN(c4cnccn4)CC3)n(C)c2C)ccc1F] | N-(4-fluoro-3-methylphenyl)-1,2,4-trimethyl-5-(2-((4-methyl-1-(pyrazin-2-yl)piperidin-4-yl)amino)-2-oxoacetyl)-1H-pyrrole-3-carboxamide | 507.3 |
| 716 | 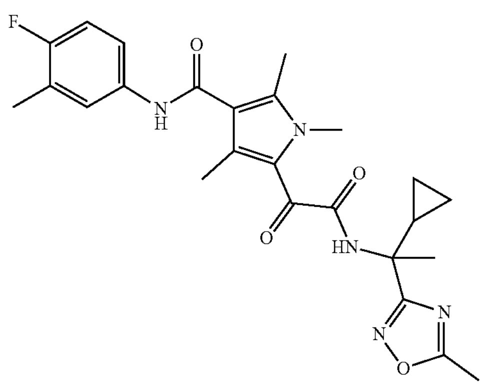 | 5-(2-((1-cyclopropyl-1-(5-methyl-1,2,4-oxadiazol-3-yl)ethyl)amino)-2-oxoacetyl)-N-(4-fluoro-3-methylphenyl)-1,2,4-trimethyl-1H-pyrrole-3-carboxamide | 482.2 |
| 717 | 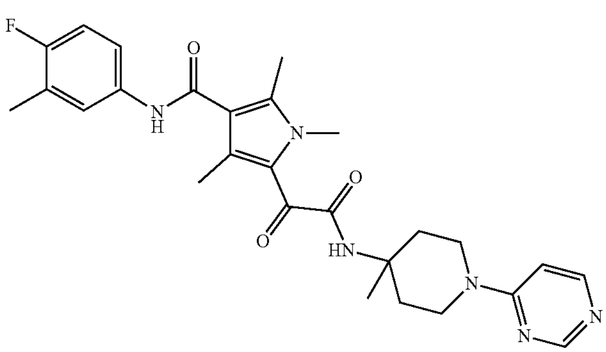 [SMILES: Cc1cc(NC(=O)c2c(C)c(C(=O)C(=O)NC3(C)CCN(c4ccncn4)CC3)n(C)c2C)ccc1F] | N-(4-fluoro-3-methylphenyl)-1,2,4-trimethyl-5-(2-((4-methyl-1-(pyrimidin-4-yl)piperidin-4-yl)amino)-2-oxoacetyl)-1H-pyrrole-3-carboxamide | 507.3 |
| 718 | 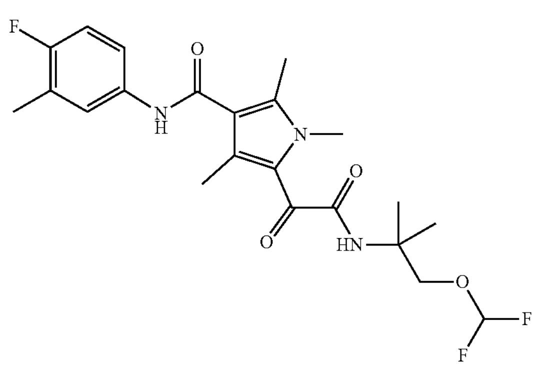 [SMILES: Cc1cc(NC(=O)c2c(C)c(C(=O)C(=O)NC(C)(C)COC(F)F)n(C)c2C)ccc1F] | 5-(2-((1-(difluoromethoxy)-2-methylpropan-2-yl)amino)-2-oxoacetyl)-N-(4-fluoro-3-methylphenyl)-1,2,4-trimethyl-1H-pyrrole-3-carboxamide | 454.2 |

TABLE 1-continued

Exemplary compounds

| Ex. | Structure | Chemical Name | ESI-MS (M + H)+ (m/z) |
|---|---|---|---|
| 719 | 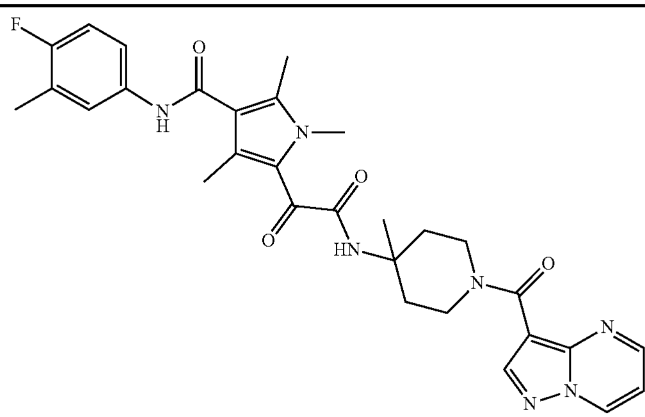 | N-(4-fluoro-3-methylphenyl)-1,2,4-trimethyl-5-(2-((4-methyl-1-(pyrazolo[1,5-a]pyrimidine-3-carbonyl)piperidin-4-yl)amino)-2-oxoacetyl)-1H-pyrrole-3-carboxamide | 574.3 |
| 720 | 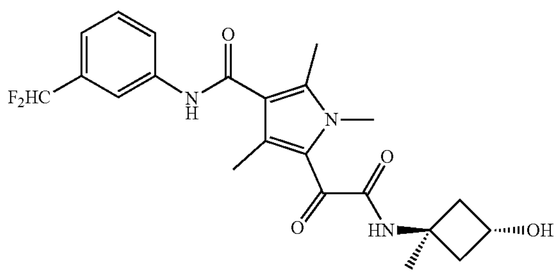 [SMILES: Cc1c(C(=O)Nc2cccc(C(F)F)c2)c(C)n(C)c1C(=O)C(=O)N[C@]1(C)C[C@@H](O)C1] | N-(3-(difluoromethyl)phenyl)-5-(2-(((1r,3r)-3-hydroxy-1-methylcyclobutyl)amino)-2-oxoacetyl)-1,2,4-trimethyl-1H-pyrrole-3-carboxamide | 434.2 |
| 721 | 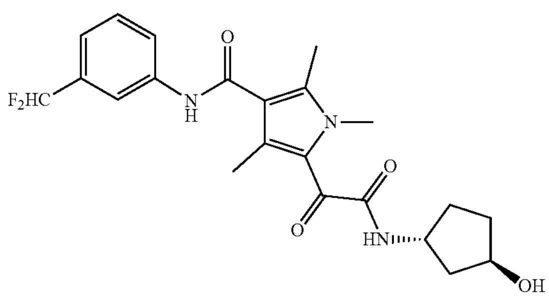 [SMILES: Cc1c(C(=O)Nc2cccc(C(F)F)c2)c(C)n(C)c1C(=O)C(=O)N[C@@H]1CC[C@@H](O)C1] | N-(3-(difluoromethyl)phenyl)-5-(2-(((1R,3R)-3-hydroxycyclopentyl)amino)-2-oxoacetyl)-1,2,4-trimethyl-1H-pyrrole-3-carboxamide | 434.2 |
| 722 | 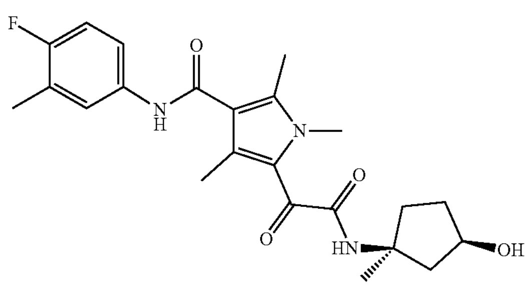 [SMILES: Cc1cc(NC(=O)c2c(C)c(C(=O)C(=O)N[C@@]3(C)CC[C@@H](O)C3)n(C)c2C)ccc1F] | N-(4-fluoro-3-methylphenyl)-5-(2-(((1S,3R)-3-hydroxy-1-methylcyclopentyl)amino)-2-oxoacetyl)-1,2,4-trimethyl-1H-pyrrole-3-carboxamide | 430.2 |
| 723 | 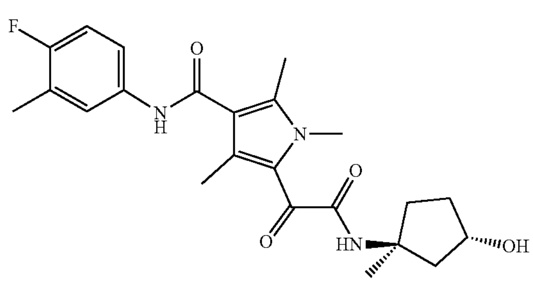 [SMILES: Cc1cc(NC(=O)c2c(C)c(C(=O)C(=O)N[C@@]3(C)CC[C@H](O)C3)n(C)c2C)ccc1F] | N-(4-fluoro-3-methylphenyl)-5-(2-(((1S,3S)-3-hydroxy-1-methylcyclopentyl)amino)-2-oxoacetyl)-1,2,4-trimethyl-1H-pyrrole-3-carboxamide | 430.2 |

TABLE 1-continued

Exemplary compounds

| Ex. | Structure | Chemical Name | ESI-MS (M + H)+ (m/z) |
|---|---|---|---|
| 724 | 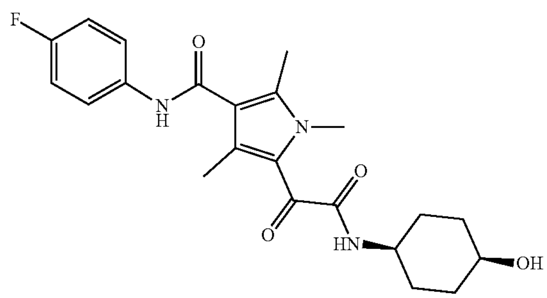 [SMILES: Cc1c(C(=O)Nc2ccc(F)cc2)c(C)n(C)c1C(=O)C(=O)N[C@H]1CC[C@@H](O)CC1] | N-(4-fluorophenyl)-5-(2-(((1s,4s)-4-hydroxycyclohexyl)amino)-2-oxoacetyl)-1,2,4-trimethyl-1H-pyrrole-3-carboxamide | 416.2 |
| 725 | 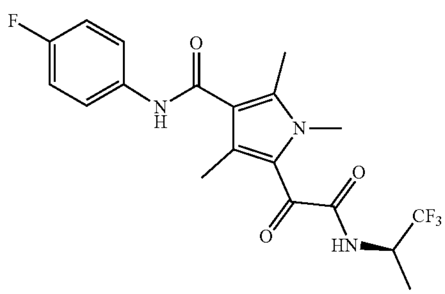 [SMILES: Cc1c(C(=O)Nc2ccc(F)cc2)c(C)n(C)c1C(=O)C(=O)N[C@H](C)C(F)(F)F] | (R)-N-(4-fluorophenyl)-1,2,4-trimethyl-5-(2-oxo-2-((1,1,1-trifluoropropan-2-yl)amino)acetyl)-1H-pyrrole-3-carboxamide | 414.2 |
| 726 | 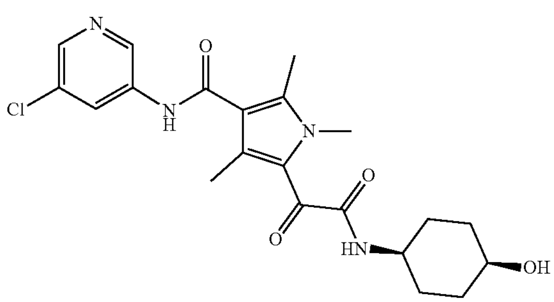 [SMILES: Cc1c(C(=O)Nc2cncc(Cl)c2)c(C)n(C)c1C(=O)C(=O)N[C@H]1CC[C@@H](O)CC1] | N-(5-chloropyridin-3-yl)-5-(2-(((1s,4s)-4-hydroxycyclohexyl)amino)-2-oxoacetyl)-1,2,4-trimethyl-1H-pyrrole-3-carboxamide | 433.2 |
| 727 | 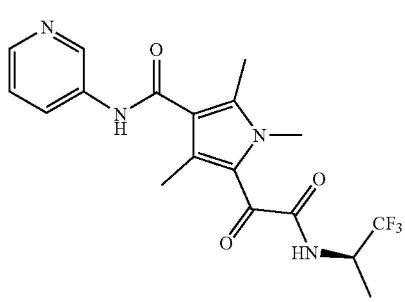 [SMILES: Cc1c(C(=O)Nc2cccnc2)c(C)n(C)c1C(=O)C(=O)N[C@H](C)C(F)(F)F] | (R)-N-(5-chloropyridin-3-yl)-1,2,4-trimethyl-5-(2-oxo-2-((1,1,1-trifluoropropan-2-yl)amino)acetyl)-1H-pyrrole-3-carboxamide | 431.1 |

TABLE 1-continued

Exemplary compounds

| Ex. | Structure | Chemical Name | ESI-MS (M + H)+ (m/z) |
|---|---|---|---|
| 728 | 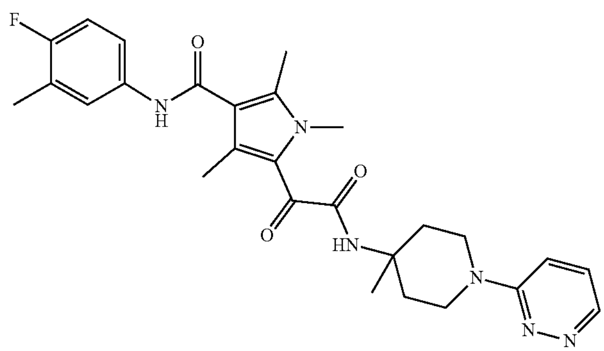 [SMILES: Cc1cc(NC(=O)c2c(C)c(C(=O)C(=O)NC3(C)CCN(c4cccnn4)CC3)n(C)c2C)ccc1F] | N-(4-fluoro-3-methylphenyl)-1,2,4-trimethyl-5-(2-((4-methyl-1-(pyridazin-3-yl)piperidin-4-yl)amino)-2-oxoacetyl)-1H-pyrrole-3-carboxamide | 507.3 |
| 729 | 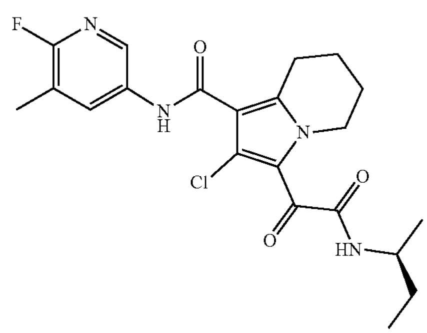 [SMILES: CC[C@H](C)NC(=O)C(=O)c1c(Cl)c(C(=O)Nc2cnc(F)c(C)c2)c2n1CCCC2] | (S)-3-(2-(sec-butylamino)-2-oxoacetyl)-2-chloro-N-(6-fluoro-5-methylpyridin-3-yl)-5,6,7,8-tetrahydroindolizine-1-carboxamide | 435.1 |
| 730 | 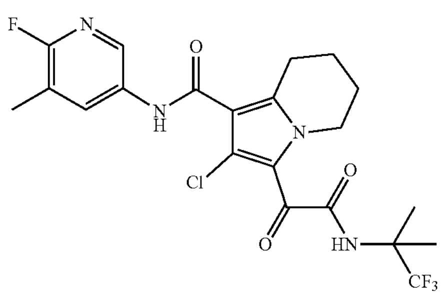 [SMILES: Cc1cc(NC(=O)c2c(Cl)c(C(=O)C(=O)NC(C)(C)C(F)(F)F)n3c2CCCC3)cnc1F] | 2-chloro-N-(6-fluoro-5-methylpyridin-3-yl)-3-(2-oxo-2-((1,1,1-trifluoro-2-methylpropan-2-yl)amino)acetyl)-5,6,7,8-tetrahydroindolizine-1-carboxamide | 489.0 |
| 731 | 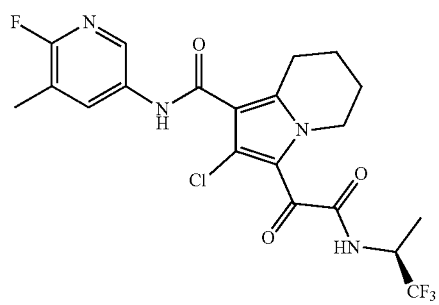 [SMILES: Cc1cc(NC(=O)c2c(Cl)c(C(=O)C(=O)N[C@@H](C)C(F)(F)F)n3c2CCCC3)cnc1F] | (S)-2-chloro-N-(6-fluoro-5-methylpyridin-3-yl)-3-(2-oxo-2-((1,1,1-trifluoropropan-2-yl)amino)acetyl)-5,6,7,8-tetrahydroindolizine-1-carboxamide | 475.1 |

TABLE 1-continued

Exemplary compounds

| Ex. | Structure | Chemical Name | ESI-MS (M + H)+ (m/z) |
|---|---|---|---|
| 732 | 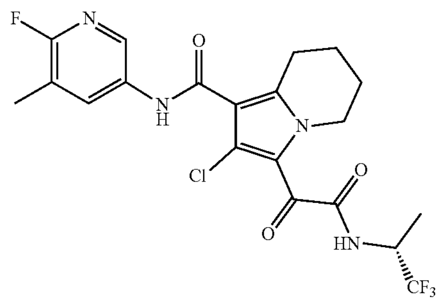 [SMILES: Cc1cc(NC(=O)c2c(Cl)c(C(=O)C(=O)N[C@H](C)C(F)(F)F)n3c2CCCC3)cnc1F] | (R)-2-chloro-N-(6-fluoro-5-methylpyridin-3-yl)-3-(2-oxo-2-((1,1,1-trifluoropropan-2-yl)amino)acetyl)-5,6,7,8-tetrahydroindolizine-1-carboxamide | 475.1 |
| 733 | 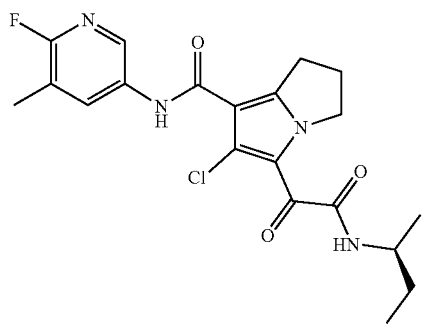 [SMILES: CC[C@H](C)NC(=O)C(=O)c1c(Cl)c(C(=O)Nc2cnc(F)c(C)c2)c2n1CCC2] | (S)-5-(2-(sec-butylamino)-2-oxoacetyl)-6-chloro-N-(6-fluoro-5-methylpyridin-3-yl)-2,3-dihydro-1H-pyrrolizine-7-carboxamide | 421.0 |
| 734 | 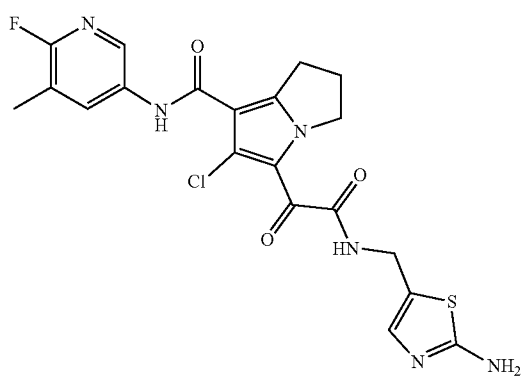 [SMILES: Cc1cc(NC(=O)c2c(Cl)c(C(=O)C(=O)NCc3cnc(N)s3)n3c2CCC3)cnc1F] | 5-(2-(((2-aminothiazol-5-yl)methyl)amino)-2-oxoacetyl)-6-chloro-N-(6-fluoro-5-methylpyridin-3-yl)-2,3-dihydro-1H-pyrrolizine-7-carboxamide | 477.0 |
| 735 | 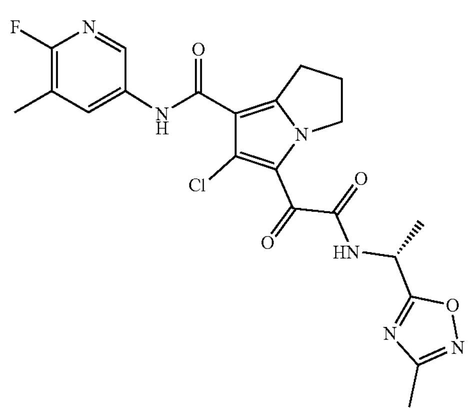 [SMILES: Cc1noc([C@@H](C)NC(=O)C(=O)c2c(Cl)c(C(=O)Nc3cnc(F)c(C)c3)c3n2CCC3)n1] | (R)-6-chloro-N-(6-fluoro-5-methylpyridin-3-yl)-5-(2-((1-(3-methyl-1,2,4-oxadiazol-5-yl)ethyl)amino)-2-oxoacetyl)-2,3-dihydro-1H-pyrrolizine-7-carboxamide | 475.1 |

TABLE 1-continued

Exemplary compounds

| Ex. | Structure | Chemical Name | ESI-MS (M + H)+ (m/z) |
|---|---|---|---|
| 736 | 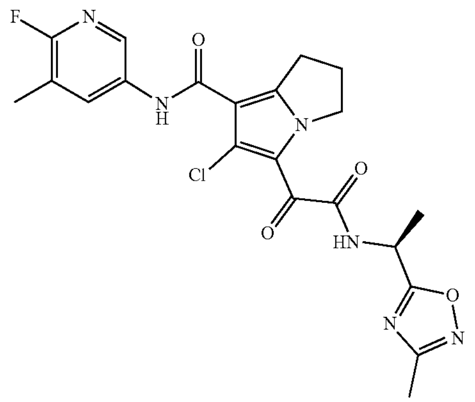 [SMILES: Cc1noc([C@H](C)NC(=O)C(=O)c2c(Cl)c(C(=O)Nc3cnc(F)c(C)c3)c3n2CCC3)n1] | (S)-6-chloro-N-(6-fluoro-5-methylpyridin-3-yl)-5-(2-((1-(3-methyl-1,2,4-oxadiazol-5-yl)ethyl)amino)-2-oxoacetyl)-2,3-dihydro-1H-pyrrolizine-7-carboxamide | 475.1 |
| 737 | 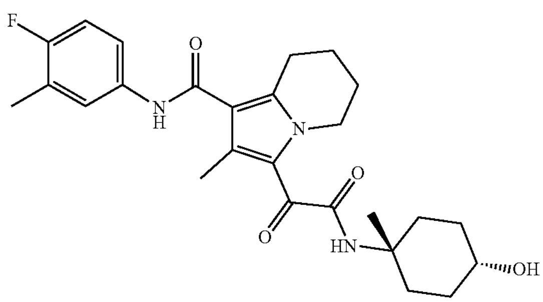 [SMILES: Cc1cc(NC(=O)c2c(C)c(C(=O)C(=O)N[C@]3(C)CC[C@H](O)CC3)n3c2CCCC3)ccc1F] | N-(4-fluoro-3-methylphenyl)-3-(2-(((1s,4s)-4-hydroxy-1-methylcyclohexyl)amino)-2-oxoacetyl)-2-methyl-5,6,7,8-tetrahydroindolizine-1-carboxamide | 470.2 |
| 738 | 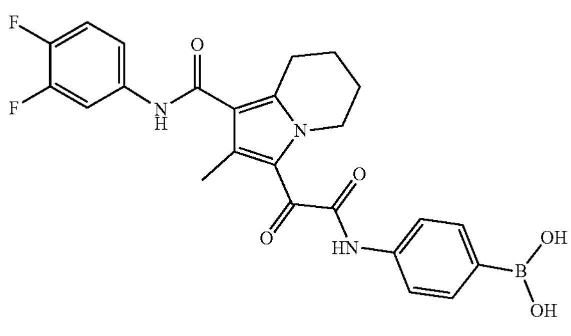 [SMILES: Cc1c(C(=O)Nc2ccc(F)c(F)c2)c2n(c1C(=O)C(=O)Nc1ccc(B(O)O)cc1)CCCC2] | (4-(2-(1-((3,4-difluorophenyl)carbamoyl)-2-methyl-5,6,7,8-tetrahydroindolizin-3-yl)-2-oxoacetamido)phenyl)boronic acid | 482.1 |
| 739 | 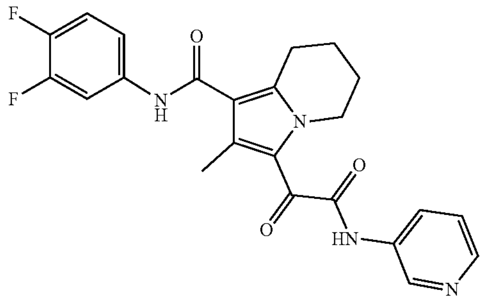 [SMILES: Cc1c(C(=O)Nc2ccc(F)c(F)c2)c2n(c1C(=O)C(=O)Nc1cccnc1)CCCC2] | N-(4-fluoro-3-methylphenyl)-2-methyl-3-(2-oxo-2-(pyridin-3-ylamino)acetyl)-5,6,7,8-tetrahydroindolizine-1-carboxamide | 435.1 |

TABLE 1-continued

Exemplary compounds

| Ex. | Structure | Chemical Name | ESI-MS (M + H)+ (m/z) |
|---|---|---|---|
| 740 | 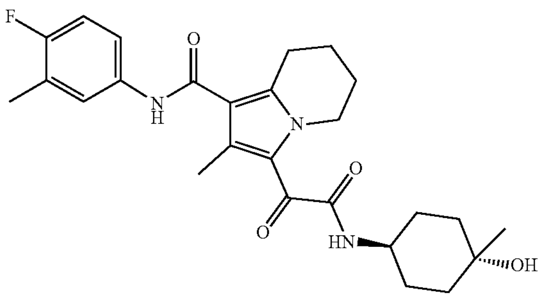 [SMILES: Cc1cc(NC(=O)c2c(C)c(C(=O)C(=O)N[C@H]3CC[C@](C)(O)CC3)n3c2CCCC3)ccc1F] | N-(4-fluoro-3-methylphenyl)-3-(2-(((1r,4r)-4-hydroxy-4-methylcyclohexyl)amino)-2-oxoacetyl)-2-methyl-5,6,7,8-tetrahydroindolizine-1-carboxamide | 470.2 |
| 741 | 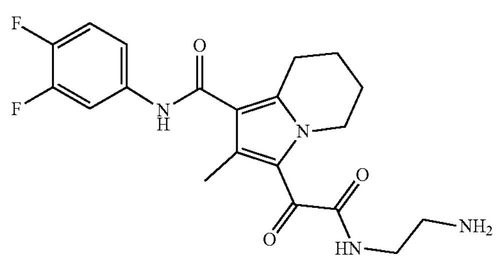 [SMILES: Cc1c(C(=O)Nc2ccc(F)c(F)c2)c2n(c1C(=O)C(=O)NCCN)CCCC2] | 3-(2-((2-aminoethyl)amino)-2-oxoacetyl)-N-(3,4-difluorophenyl)-2-methyl-5,6,7,8-tetrahydroindolizine-1-carboxamide | 405.1 |
| 742 | 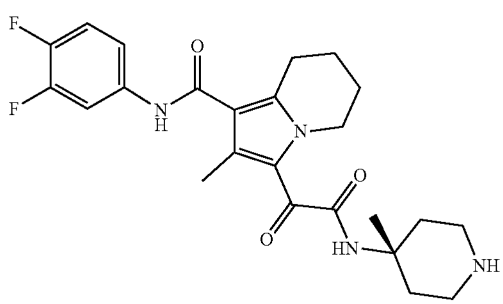 | N-(3,4-difluorophenyl)-2-methyl-3-(2-((4-methylpiperidin-4-yl)amino)-2-oxoacetyl)-5,6,7,8-tetrahydroindolizine-1-carboxamide | 459.2 |
| 743 | 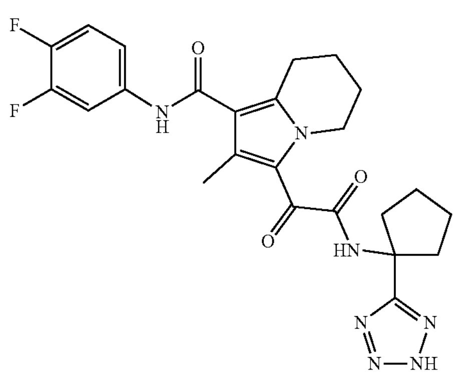 [SMILES: Cc1c(C(=O)Nc2ccc(F)c(F)c2)c2n(c1C(=O)C(=O)NC1(c3nn[nH]n3)CCCC1)CCCC2] | 3-(2-((1-(2H-tetrazol-5-yl)cyclopentyl)amino)-2-oxoacetyl)-N-(3,4-difluorophenyl)-2-methyl-5,6,7,8-tetrahydroindolizine-1-carboxamide | 498.2 |

TABLE 1-continued

Exemplary compounds

| Ex. | Structure | Chemical Name | ESI-MS (M + H)+ (m/z) |
|---|---|---|---|
| 744 | 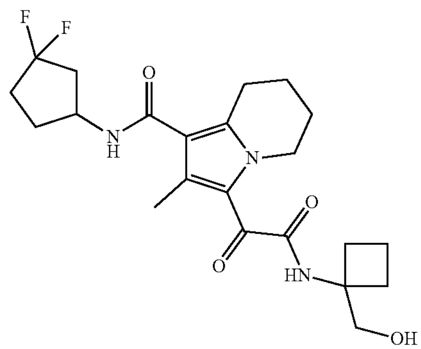 [SMILES: Cc1c(C(=O)NC2CCC(F)(F)C2)c2n(c1C(=O)C(=O)NC1(CO)CCC1)CCCC2] | N-(3,3-difluorocyclopentyl)-3-(2-((1-(hydroxymethyl)cyclobutyl)amino)-2-oxoacetyl)-2-methyl-5,6,7,8-tetrahydroindolizine-1-carboxamide | 438.3 |
| 745 | 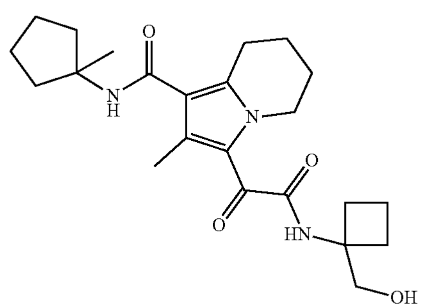 [SMILES: Cc1c(C(=O)NC2(C)CCCC2)c2n(c1C(=O)C(=O)NC1(CO)CCC1)CCCC2] | 3-(2-((1-(hydroxymethyl)cyclobutyl)amino)-2-oxoacetyl)-2-methyl-N-(1-methylcyclopentyl)-5,6,7,8-tetrahydroindolizine-1-carboxamide | 416.3 |
| 746 | 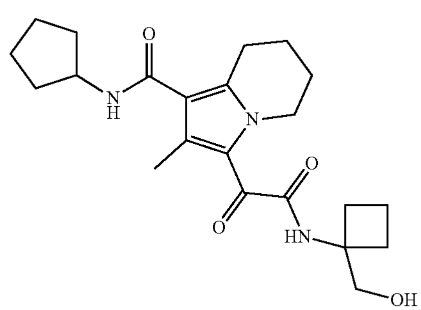 [SMILES: Cc1c(C(=O)NC2CCCC2)c2n(c1C(=O)C(=O)NC1(CO)CCC1)CCCC2] | N-cyclopentyl-3-(2-((1-(hydroxymethyl)cyclobutyl)amino)-2-oxoacetyl)-2-methyl-5,6,7,8-tetrahydroindolizine-1-carboxamide | 402.3 |
| 748 | 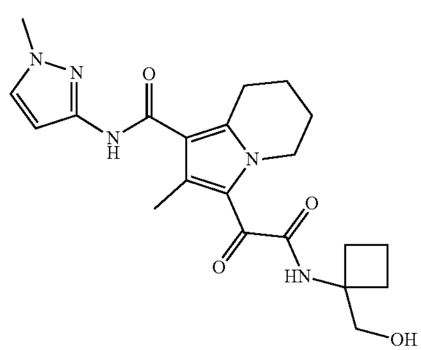 [SMILES: Cc1c(C(=O)Nc2ccn(C)n2)c2n(c1C(=O)C(=O)NC1(CO)CCC1)CCCC2] | 3-(2-((1-(hydroxymethyl)cyclobutyl)amino)-2-oxoacetyl)-2-methyl-N-(1-methyl-1H-pyrazol-3-yl)-5,6,7,8-tetrahydroindolizine-1-carboxamide | 414.2 |

TABLE 1-continued

Exemplary compounds

| Ex. | Structure | Chemical Name | ESI-MS (M + H)+ (m/z) |
|---|---|---|---|
| 749 | 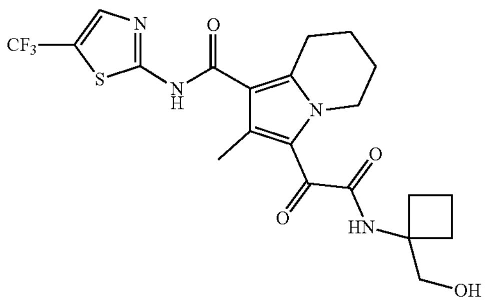 [SMILES: Cc1c(C(=O)Nc2ncc(C(F)(F)F)s2)c2n(c1C(=O)C(=O)NC1(CO)CCC1)CCCC2] | 3-(2-((1-(hydroxymethyl)cyclobutyl)amino)-2-oxoacetyl)-2-methyl-N-(5-(trifluoromethyl)thiazol-2-yl)-5,6,7,8-tetrahydroindolizine-1-carboxamide | 485.1 |
| 750 | 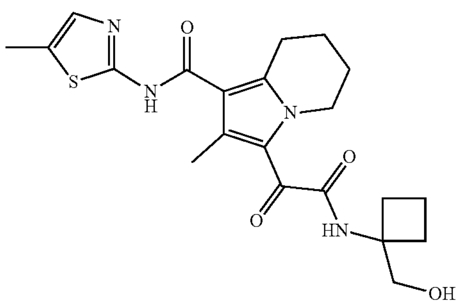 [SMILES: Cc1cnc(NC(=O)c2c(C)c(C(=O)C(=O)NC3(CO)CCC3)n3c2CCCC3)s1] | 3-(2-((1-(hydroxymethyl)cyclobutyl)amino)-2-oxoacetyl)-2-methyl-N-(5-methylthiazol-2-yl)-5,6,7,8-tetrahydroindolizine-1-carboxamide | 431.2 |
| 751 | 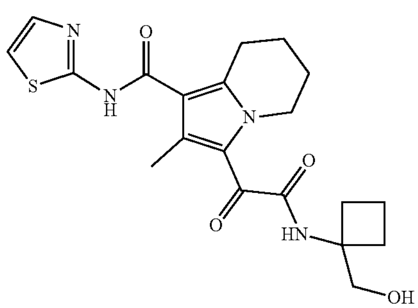 [SMILES: Cc1c(C(=O)Nc2nccs2)c2n(c1C(=O)C(=O)NC1(CO)CCC1)CCCC2] | 3-(2-((1-(hydroxymethyl)cyclobutyl)amino)-2-oxoacetyl)-2-methyl-N-(thiazol-2-yl)-5,6,7,8-tetrahydroindolizine-1-carboxamide | 417.2 |
| 752 | 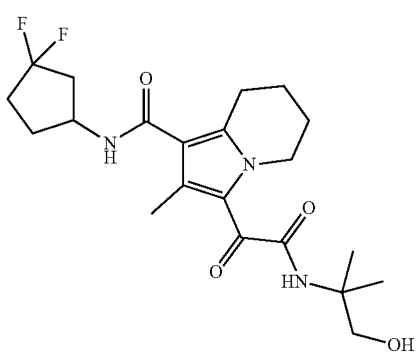 [SMILES: Cc1c(C(=O)NC2CCC(F)(F)C2)c2n(c1C(=O)C(=O)NC(C)(C)CO)CCCC2] | N-(3,3-difluorocyclopentyl)-3-(2-((1-hydroxy-2-methylpropan-2-yl)amino)-2-oxoacetyl)-2-methyl-5,6,7,8-tetrahydroindolizine-1-carboxamide | 426.2 |

TABLE 1-continued

Exemplary compounds

| Ex. | Structure | Chemical Name | ESI-MS (M + H)+ (m/z) |
|---|---|---|---|
| 753 | 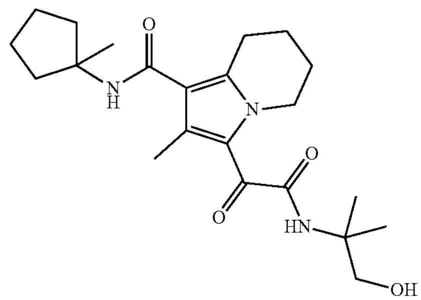 [SMILES: Cc1c(C(=O)NC2(C)CCCC2)c2n(c1C(=O)C(=O)NC(C)(C)CO)CCCC2] | 3-(2-((1-hydroxy-2-methylpropan-2-yl)amino)-2-oxoacetyl)-2-methyl-N-(1-methylcyclopentyl)-5,6,7,8-tetrahydroindolizine-1-carboxamide | 404.3 |
| 754 | 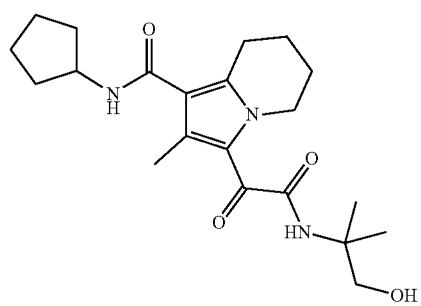 [SMILES: Cc1c(C(=O)NC2CCCC2)c2n(c1C(=O)C(=O)NC(C)(C)CO)CCCC2] | N-cyclopentyl-3-(2-((1-hydroxy-2-methylpropan-2-yl)amino)-2-oxoacetyl)-2-methyl-5,6,7,8-tetrahydroindolizine-1-carboxamide | 390.2 |
| 756 | 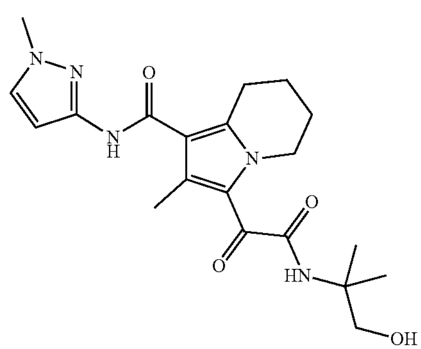 [SMILES: Cc1c(C(=O)Nc2ccn(C)n2)c2n(c1C(=O)C(=O)NC(C)(C)CO)CCCC2] | 3-(2-((1-hydroxy-2-methylpropan-2-yl)amino)-2-oxoacetyl)-2-methyl-N-(1-methyl-1H-pyrazol-3-yl)-5,6,7,8-tetrahydroindolizine-1-carboxamide | 402.2 |
| 757 | 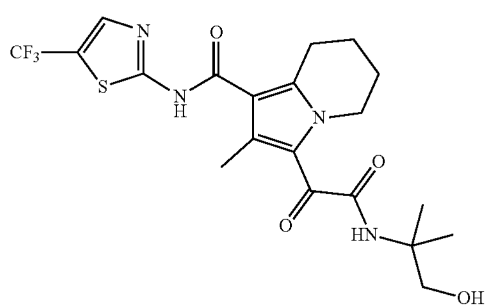 [SMILES: Cc1c(C(=O)Nc2ncc(C(F)(F)F)s2)c2n(c1C(=O)C(=O)NC(C)(C)CO)CCCC2] | 3-(2-((1-hydroxy-2-methylpropan-2-yl)amino)-2-oxoacetyl)-2-methyl-N-(5-(trifluoromethyl)thiazol-2-yl)-5,6,7,8-tetrahydroindolizine-1-carboxamide | 473.2 |

TABLE 1-continued

Exemplary compounds

| Ex. | Structure | Chemical Name | ESI-MS (M + H)+ (m/z) |
|---|---|---|---|
| 758 | 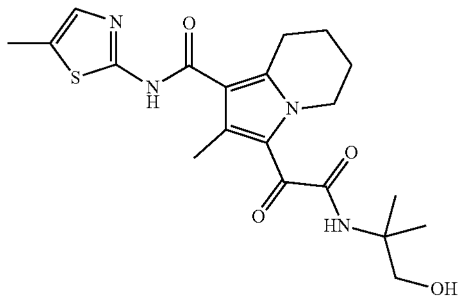 [SMILES: Cc1cnc(NC(=O)c2c(C)c(C(=O)C(=O)NC(C)(C)CO)n3c2CCCC3)s1] | 3-(2-((1-hydroxy-2-methylpropan-2-yl)amino)-2-oxoacetyl)-2-methyl-N-(5-methylthiazol-2-yl)-5,6,7,8-tetrahydroindolizine-1-carboxamide | 419.2 |
| 759 | 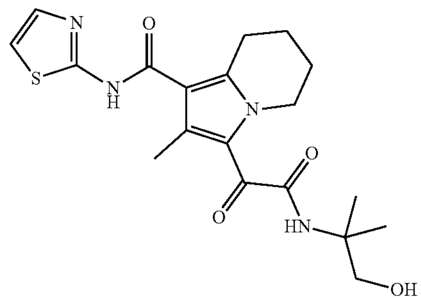 [SMILES: Cc1c(C(=O)Nc2nccs2)c2n(c1C(=O)C(=O)NC(C)(C)CO)CCCC2] | 3-(2-((1-hydroxy-2-methylpropan-2-yl)amino)-2-oxoacetyl)-2-methyl-N-(thiazol-2-yl)-5,6,7,8-tetrahydroindolizine-1-carboxamide | 405.1 |

Further Forms of Compounds Disclosed Herein

Isomers/Stereoisomers

In some embodiments, the compounds described herein exist as geometric isomers. In some embodiments, the compounds described herein possess one or more double bonds. The compounds presented herein include all cis, trans, syn, anti, entgegen (E), and zusammen (Z) isomers as well as the corresponding mixtures thereof. In some situations, the compounds described herein possess one or more chiral centers and each center exists in the R configuration, or S configuration. The compounds described herein include all diastereomeric, enantiomeric, and epimeric forms as well as the corresponding mixtures thereof. In additional embodiments of the compounds and methods provided herein, mixtures of enantiomers and/or diastereoisomers, resulting from a single preparative step, combination, or interconversion are useful for the applications described herein. In some embodiments, the compounds described herein are prepared as their individual stereoisomers by reacting a racemic mixture of the compound with an optically active resolving agent to form a pair of diastereoisomeric compounds, separating the diastereomers and recovering the optically pure enantiomers. In some embodiments, dissociable complexes are preferred. In some embodiments, the diastereomers have distinct physical properties (e.g., melting points, boiling points, solubilities, reactivity, etc.) and are separated by taking advantage of these dissimilarities. In some embodiments, the diastereomers are separated by chiral chromatography, or preferably, by separation/resolution techniques based upon differences in solubility. In some embodiments, the optically pure enantiomer is then recovered, along with the resolving agent, by any practical means that would not result in racemization.

Labeled Compounds

In some embodiments, the compounds described herein exist in their isotopically-labeled forms. In some embodiments, the methods disclosed herein include methods of treating diseases by administering such isotopically-labeled compounds. In some embodiments, the methods disclosed herein include methods of treating diseases by administering such isotopically-labeled compounds as pharmaceutical compositions. Thus, in some embodiments, the compounds disclosed herein include isotopically-labeled compounds, which are identical to those recited herein, but for the fact that one or more atoms are replaced by an atom having an atomic mass or mass number different from the atomic mass or mass number usually found in nature. Examples of isotopes that can be incorporated into compounds disclosed herein include isotopes of hydrogen, carbon, nitrogen, oxygen, phosphorous, sulfur, fluorine and chloride, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. Compounds described herein, and the pharmaceutically acceptable salts, solvates, or stereoisomers thereof which contain the aforementioned isotopes and/or other isotopes of other atoms are within the scope of this invention. Certain isotopically-labeled compounds, for example those into which radioactive isotopes such as $^{3}H$ and $^{14}C$ are incorporated, are useful in drug and/or substrate tissue distribution assays. Tritiated, i.e., $^{3}H$ and carbon-14, i.e., $^{14}C$, isotopes are particularly preferred for their ease of preparation and detectability. Further, substitution with heavy isotopes such as deuterium, i.e., $^{2}H$, produces certain therapeutic advantages resulting from greater metabolic stability, for example increased in vivo half-life or reduced dosage requirements.

In some embodiments, the compounds described herein are labeled by other means, including, but not limited to, the use of chromophores or fluorescent moieties, bioluminescent labels, or chemiluminescent labels.

Pharmaceutically Acceptable Salts

In some embodiments, the compounds described herein exist as their pharmaceutically acceptable salts. In some embodiments, the methods disclosed herein include methods of treating diseases by administering such pharmaceutically acceptable salts. In some embodiments, the methods disclosed herein include methods of treating diseases by administering such pharmaceutically acceptable salts as pharmaceutical compositions.

In some embodiments, the compounds described herein possess acidic or basic groups and therefore react with any of a number of inorganic or organic bases, and inorganic and organic acids, to form a pharmaceutically acceptable salt. In some embodiments, these salts are prepared in situ during the final isolation and purification of the compounds disclosed herein, or a solvate, or stereoisomer thereof, or by separately reacting a purified compound in its free form with a suitable acid or base, and isolating the salt thus formed.

Examples of pharmaceutically acceptable salts include those salts prepared by reaction of the compounds described herein with a mineral, organic acid or inorganic base, such salts including, acetate, acrylate, adipate, alginate, aspartate, benzoate, benzenesulfonate, bisulfate, bisulfite, bromide, butyrate, butyn-1,4-dioate, camphorate, camphorsulfonate, caproate, caprylate, chlorobenzoate, chloride, citrate, cyclopentanepropionate, decanoate, digluconate, dihydrogenphosphate, dinitrobenzoate, dodecylsulfate, ethanesulfonate, formate, fumarate, glucoheptanoate, glycerophosphate, glycolate, hemisulfate, heptanoate, hexanoate, hexyne-1,6-dioate, hydroxybenzoate, γ-hydroxybutyrate, hydrochloride, hydrobromide, hydroiodide, 2-hydroxyethanesulfonate, iodide, isobutyrate, lactate, maleate, malonate, methanesulfonate, mandelate metaphosphate, methanesulfonate, methoxybenzoate, methylbenzoate, monohydrogenphosphate, 1-napthalenesulfonate, 2-napthalenesulfonate, nicotinate, nitrate, palmoate, pectinate, persulfate, 3-phenylpropionate, phosphate, picrate, pivalate, propionate, pyrosulfate, pyrophosphate, propiolate, phthalate, phenylacetate, phenylbutyrate, propanesulfonate, salicylate, succinate, sulfate, sulfite, succinate, suberate, sebacate, sulfonate, tartrate, thiocyanate, tosylateundeconate and xylenesulfonate.

Further, the compounds described herein can be prepared as pharmaceutically acceptable salts formed by reacting the free base form of the compound with a pharmaceutically acceptable inorganic or organic acid, including, but not limited to, inorganic acids such as hydrochloric acid, hydrobromic acid, sulfuric acid, nitric acid, phosphoric acid metaphosphoric acid, and the like; and organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, p-toluenesulfonic acid, tartaric acid, trifluoroacetic acid, citric acid, benzoic acid, 3-(4-hydroxybenzoyl)benzoic acid, cinnamic acid, mandelic acid, arylsulfonic acid, methanesulfonic acid, ethanesulfonic acid, 1,2-ethanedisulfonic acid, 2-hydroxyethanesulfonic acid, benzenesulfonic acid, 2-naphthalenesulfonic acid, 4-methylbicyclo-[2.2.2]oct-2-ene-1-carboxylic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid and muconic acid. In some embodiments, other acids, such as oxalic, while not in themselves pharmaceutically acceptable, are employed in the preparation of salts useful as intermediates in obtaining the compounds disclosed herein, solvate, or stereoisomer thereof and their pharmaceutically acceptable acid addition salts.

In some embodiments, those compounds described herein which comprise a free acid group react with a suitable base, such as the hydroxide, carbonate, bicarbonate, sulfate, of a pharmaceutically acceptable metal cation, with ammonia, or with a pharmaceutically acceptable organic primary, secondary, tertiary, or quaternary amine. Representative salts include the alkali or alkaline earth salts, like lithium, sodium, potassium, calcium, and magnesium, and aluminum salts and the like. Illustrative examples of bases include sodium hydroxide, potassium hydroxide, choline hydroxide, sodium carbonate, $N^+$ $(C_{1-4}$ alkyl$)_4$, and the like.

Representative organic amines useful for the formation of base addition salts include ethylamine, diethylamine, ethylenediamine, ethanolamine, diethanolamine, piperazine and the like. It should be understood that the compounds described herein also include the quaternization of any basic nitrogen-containing groups they contain. In some embodiments, water or oil-soluble or dispersible products are obtained by such quaternization.

Solvates

In some embodiments, the compounds described herein exist as solvates. The invention provides for methods of treating diseases by administering such solvates. The invention further provides for methods of treating diseases by administering such solvates as pharmaceutical compositions.

Solvates contain either stoichiometric or non-stoichiometric amounts of a solvent, and, in some embodiments, are formed during the process of crystallization with pharmaceutically acceptable solvents such as water, ethanol, and the like. Hydrates are formed when the solvent is water, or alcoholates are formed when the solvent is alcohol. Solvates of the compounds described herein can be conveniently prepared or formed during the processes described herein. By way of example only, hydrates of the compounds described herein can be conveniently prepared by recrystallization from an aqueous/organic solvent mixture, using organic solvents including, but not limited to, dioxane, tetrahydrofuran or methanol. In addition, the compounds provided herein can exist in unsolvated as well as solvated forms. In general, the solvated forms are considered equivalent to the unsolvated forms for the purposes of the compounds and methods provided herein.

Tautomers

In some situations, compounds exist as tautomers. The compounds described herein include all possible tautomers within the formulas described herein. Tautomers are compounds that are interconvertible by migration of a hydrogen atom, accompanied by a switch of a single bond and adjacent double bond. In bonding arrangements where tautomerization is possible, a chemical equilibrium of the tautomers will exist. All tautomeric forms of the compounds disclosed herein are contemplated. The exact ratio of the tautomers depends on several factors, including temperature, solvent, and pH.

Preparation of Compounds

Example 1: Synthesis of 5-(2-(tert-butylamino)-2-oxoacetyl)-N-(4-fluoro-3-methylphenyl)-1-methyl-1H-pyrrole-3-carboxamide

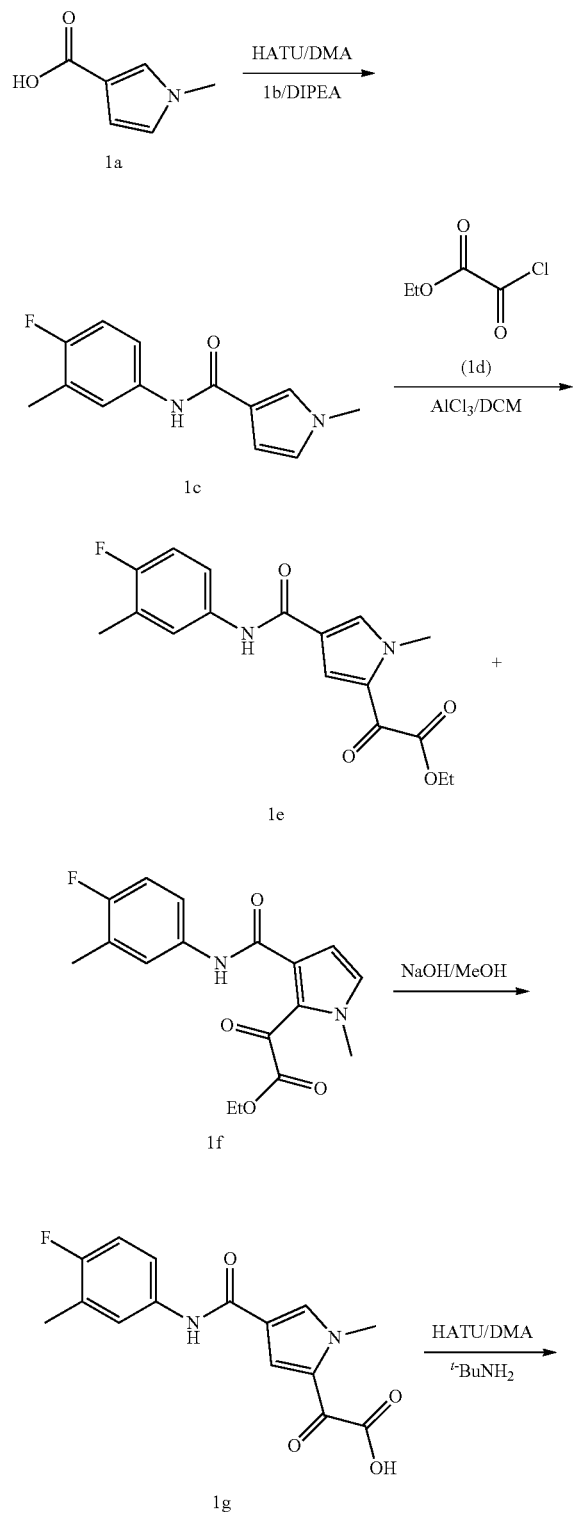

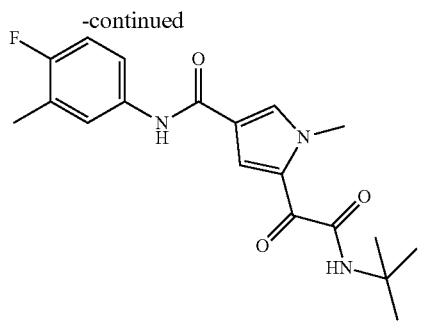

Step 1: Synthesis of N-(4-fluoro-3-methylphenyl)-1-methyl-1H-pyrrole-3-carboxamide (1c)

HATU (3.4 g, 8.8 mmol) was added to a solution of 1-methyl-1H-pyrrole-3-carboxylic acid (1a, 1 g, 8 mmol) in DMA (15 mL) at rt. After 30 min, 4-fluoro-3-methylaniline (1b, 1 g, 8 mmol) and DIPEA (1 g, 8 mmol) in DMA (5 mL) were added dropwise. The resulting mixture was stirred at rt for 20 hrs. The reaction mixture was diluted with EtOAc, washed with aqueous HCl (0.5 N, 20 mL) and brine. The organic layer was dried over $Na_2SO_4$, filtered, concentrated in vacuo, and purified by flash chromatography on silica gel (EtOAc/Hexanes 0~100%) to afford the product as white solid (0.9 g). ESI-MS, m/z 233 (MH)+.

Step 2: Synthesis of ethyl 2-(4-((4-fluoro-3-methylphenyl)carbamoyl)-1-methyl-1H-pyrrol-2-yl)-2-oxoacetate (1e)

Ethyl 2-chloro-2-oxoacetate (1d, 0.6 g, 4.4 mmol) was added to a solution of 1c (0.5 g, 2.2 mmol) in DCM (10 mL) at 0° C. under argon. After 20 min, $AlCl_3$ (0.6 g, 4.4 mmol) was added in portions, and the mixture was warmed to rt for 4 hrs. The reaction mixture was poured over ice-water, and extracted with DCM (2×30 mL). The combined extracts were washed with water, saturated $NaHCO_3$, brine and concentrated under vacuum to give crude product 1e. ESI-MS, m/z 333 (MH)+.

Step 3: Synthesis of 2-(4-((4-fluoro-3-methylphenyl)carbamoyl)-1-methyl-1H-pyrrol-2-yl)-2-oxoacetic acid (1g)

NaOH (2 N, 3 mL) was added to a solution of the crude product 1e in EtOH (6 mL) at 0° C. The mixture was warmed to rt for 2 hrs, then, cooled with ice-water and carefully neutralized with aqueous HCl (0.5 N) to pH ~2. The resulting mixture was concentrated under vacuum to remove MeOH, then, lyophilized to afford crude product 1g as white solid: ESI-MS, m/z 305 (MH)+.

Step 4: Synthesis of 5-(2-(tert-butylamino)-2-oxoacetyl)-N-(4-fluoro-3-methylphenyl)-1-methyl-1H-pyrrole-3-carboxamide (1)

HATU (90 mg, 0.24 mmol) was added to a solution of 1g (60 mg, 0.19) in DMA (0.75 mL) at 0° C. After 20 min, tert-butylamine (20 mg, 0.28) and DIPEA (50 mg, 0.38 mmol) in DMA (0.4 mL) were added. The reaction mixture was stirred at rt for 20 hrs. The reaction mixture was quenched with aqueous TFA (4%, 0.4 mL), then, extracted with EtOAc (10 mL). The organic layer was washed with water and brine, concentrated in vacuo, then, purified by reverse phase chromatography eluted with ACN and water, and dried using lyophilization to afford the title product as white solid. ESI-MS, m/z 360 (MH)$^+$.

Example 2: Synthesis of 5-(2-(tert-butylamino)-2-oxoacetyl)-N-(4-fluoro-3-methylphenyl)-1,2,4-trimethyl-1H-pyrrole-3-carboxamide

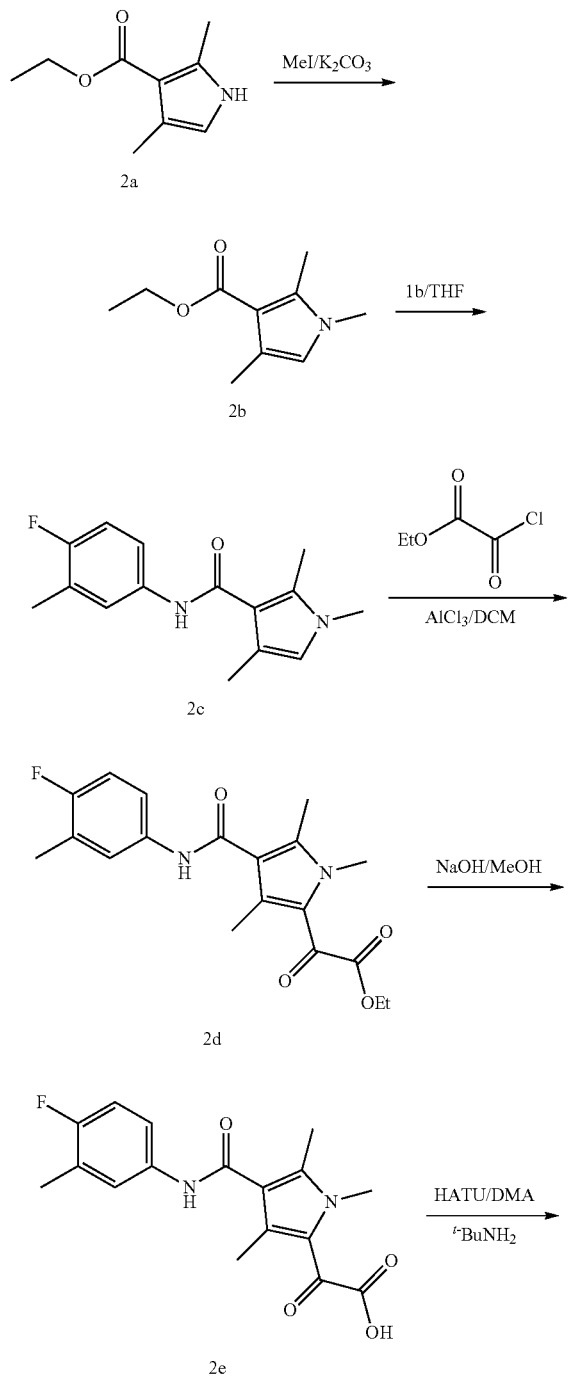

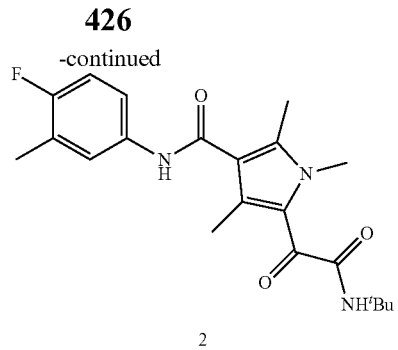

Step 1: Synthesis of ethyl 1,2,4-trimethyl-1H-pyrrole-3-carboxylate (2b)

MeI (0.75 g, 5.3 mmol) was added to a mixture of 2a (0.5 g, 3.2 mmol) and K$_2$CO$_3$ (1 g, 7.2 mmol) in DMA (15 mL) at 0° C. The reaction mixture was warmed to rt for 40 hrs. The reaction mixture was diluted with the addition of water, and extracted with EtOAc (2×10 mL). The combined extracts were washed with water and brine, concentrated in vacuo, then, purified by flash chromatography on silica gel (EtOAc/Hexanes 0~100%) to afford 2b as white solid (0.3 g). ESI-MS, m/z 182 (MH)$^+$.

Step 2: Synthesis of N-(4-fluoro-3-methylphenyl)-1,2,4-trimethyl-1H-pyrrole-3-carboxamide (2c)

LiHMDS (1 N in THF, 4 mL) was added to a solution of 2b (0.3 g, 1.7 mmol) and 1b (0.3 g, 2.4 mmol) in THF (10 mL) at 0° C. under argon. After 1 h, the reaction was quenched with saturated aqueous NH$_4$C$_1$ and extracted with EtOAc. The organic layer was washed with brine and concentrated in vacuo. The residue was purified by flash chromatography on silica gel (EtOAc/Hexanes 0~100%) to afford 3b as white solid (0.35 g). ESI-MS, m/z 261 (MH)$^+$.

Step 3: Synthesis of ethyl 2-(4-((4-fluoro-3-methylphenyl)carbamoyl)-1,3,5-trimethyl-1H-pyrrol-2-yl)-2-oxoacetate (2d)

The title compound was prepared following the procedures described in Example 1, Steps 2, using 2c. The final product was purified by flash chromatography on silica gel (EtOAc/Hexanes 0~100%) to afford 2d as white solid (0.32 g). ESI-MS, m/z 361 (MH)$^+$.

Step 4: Synthesis of 2-(4-((4-fluoro-3-methylphenyl)carbamoyl)-1,3,5-trimethyl-1H-pyrrol-2-yl)-2-oxoacetic acid (2e)

The title compound was prepared following the procedures described in Example 1, Steps 3, using 2d instead of 1d. The crude product was dried using lyophilization as white solid, which was used without further purification. ESI-MS, m/z 333 (MH)$^+$.

Step 5: Synthesis of 5-(2-(tert-butylamino)-2-oxoacetyl)-N-(4-fluoro-3-methylphenyl)-1,2,4-trimethyl-1H-pyrrole-3-carboxamide The title compounds were prepared following the procedure described in Example 1, Step 4, using 2e. The final product was purified by reverse phase chromatography eluted with ACN and water and dried using lyophilization to afford the title products as white solids. ESI-MS, m/z 388 (MH)$^+$.

Example 3: Synthesis of 5-(2-(tert-butylamino)-2-oxoacetyl)-N-(3-chloro-4-fluorophenyl)-2,4-dimethyl-1H-pyrrole-3-carboxamide

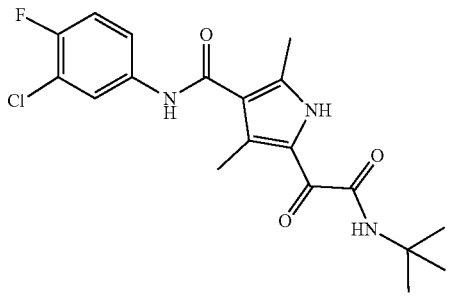 [SMILES: Cc1[nH]c(C(=O)C(=O)NC(C)(C)C)c(C)c1C(=O)Nc1ccc(F)c(Cl)c1]

The title compound was prepared from compound 2a following the procedure described in Example 2, Step 2 through Step 5, using 4-fluoro-3-chloroaniline instead of 4-fluoro-3-methylaniline. The final product was purified by reverse phase chromatography eluted with ACN and water and dried using lyophilization to afford the title product as white solid. ESI-MS, m/z 394 (MH)+.

Example 4: Synthesis of 5-(2-(tert-butylamino)-2-oxoacetyl)-N-(3,4-difluorophenyl)-1,2,4-trimethyl-1H-pyrrole-3-carboxamide

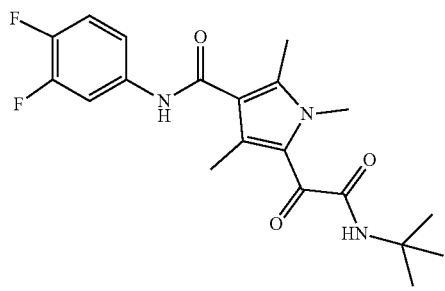 [SMILES: Cc1c(C(=O)Nc2ccc(F)c(F)c2)c(C)n(C)c1C(=O)C(=O)NC(C)(C)C]

The title compound was prepared following the procedure described in Example 2, Step 2 through Step 5, using 3,4-difluoroaniline instead of 4-fluoro-3-methylaniline. The final product was purified by reverse phase chromatography eluted with ACN and water and dried using lyophilization to afford the title product as a white solids. ESI-MS, m/z 392 (MH)+.

Example 5: Synthesis of 5-(2-(tert-butylamino)-2-oxoacetyl)-N-(6-fluoropyridin-3-yl)-1,2,4-trimethyl-1H-pyrrole-3-carboxamide

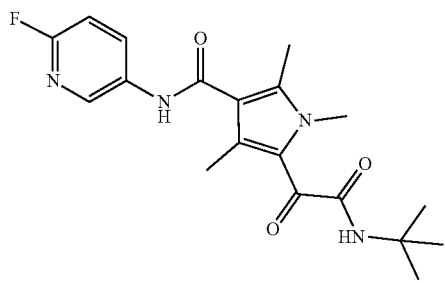 [SMILES: Cc1c(C(=O)Nc2ccc(F)nc2)c(C)n(C)c1C(=O)C(=O)NC(C)(C)C]

The title compounds were prepared following the procedure described in Example 2, Step 2 through Step 5, using 6-fluoropyridin-3-amine instead of 4-fluoro-3-methylaniline. The final product was purified by reverse phase chromatography eluted with ACN and water and dried using lyophilization to afford the title products as white solids. ESI-MS, m/z 375 (MH)+.

Example 6: Synthesis of 5-(2-((1-fluoro-2-methylpropan-2-yl)amino)-2-oxoacetyl)-N-(4-fluoro-3-methylphenyl)-1,2,4-trimethyl-1H-pyrrole-3-carboxamide

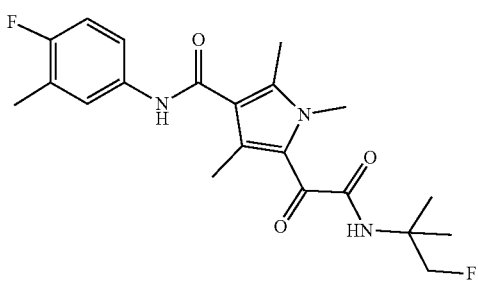 [SMILES: Cc1cc(NC(=O)c2c(C)c(C(=O)C(=O)NC(C)(C)CF)n(C)c2C)ccc1F]

The title compounds were prepared following the procedure described in Example 2, Step 5, using 1-fluoro-2-methylpropan-2-amine. The final product was purified by reverse phase chromatography eluted with ACN and water and dried using lyophilization to afford the title products as white solids. ESI-MS, m/z 406 (MH)+.

Example 7: Synthesis of N-(4-fluoro-3-methylphenyl)-5-(2-((1-(hydroxymethyl)cyclopropyl)amino)-2-oxoacetyl)-1,2,4-trimethyl-1H-pyrrole-3-carboxamide

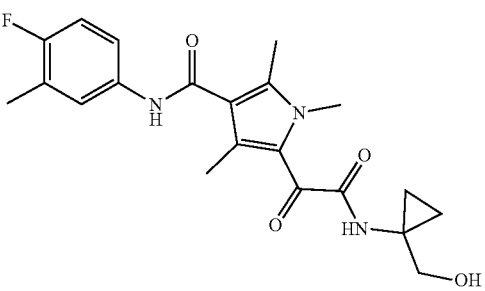 [SMILES: Cc1cc(NC(=O)c2c(C)c(C(=O)C(=O)NC3(CO)CC3)n(C)c2C)ccc1F]

The title compounds were prepared following the procedure described in Example 2, Step 5, using (1-aminocyclopropyl)methanol. The final product was purified by reverse phase chromatography eluted with ACN and water and dried using lyophilization to afford the title products as white solids. ESI-MS, m/z 402 (MH)+.

Example 8: Synthesis of N-(4-fluoro-3-methylphenyl)-5-(2-((1-hydroxy-2-methylpropan-2-yl)amino)-2-oxoacetyl)-1,2,4-trimethyl-1H-pyrrole-3-carboxamide

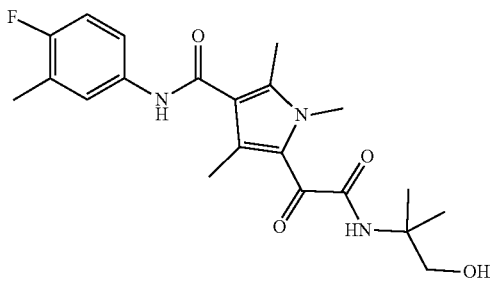 [SMILES: Cc1cc(NC(=O)c2c(C)c(C(=O)C(=O)NC(C)(C)CO)n(C)c2C)ccc1F]

The title compounds were prepared following the procedure described in Example 2, Step 5, using 2-amino-2-methylpropan-1-ol. The final product was purified by reverse phase chromatography eluted with ACN and water and dried using lyophilization to afford the title products as white solids. $^1$H NMR (400 MHz, CD$_3$OD) δ 8.2 (s, 1H), 7.42-7.49 (m, 2H), 6.99 (dd, 1H, J=8.7, 9.3 Hz), 3.81 (s, 3H), 3.64 (s, 2H), 2.36-2.38 (m, 611), 2.26 (s, 3H), 1.38 (s, 6H). ESI-MS, m/z 404 (MH)$^+$. EXAMPLE 9: Synthesis of N-(4-fluoro-3-methylphenyl)-1,2,4-trimethyl-5-(2-oxo-2-((1,1,1-trifluoro-2-methylpropan-2-yl)amino)acetyl)-1H-pyrrole-3-carboxamide.

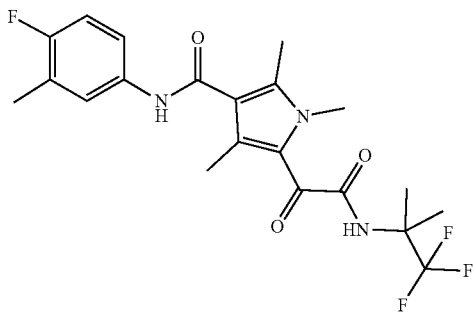 [SMILES: Cc1cc(NC(=O)c2c(C)c(C(=O)C(=O)NC(C)(C)C(F)(F)F)n(C)c2C)ccc1F]

The title compounds were prepared following the procedure described in Example 2, Step 5, using 1,1,1-trifluoro-2-methylpropan-2-amine. The final product was purified by reverse phase chromatography eluted with ACN and water and dried using lyophilization to afford the title products as white solids. ESI-MS, m/z 442 (MH)$^+$.

Example 10: Synthesis of N-(4-fluoro-3-methylphenyl)-1,2,4-trimethyl-5-(2-oxo-2-((1,1,1-trifluoropropan-2-yl)amino)acetyl)-1H-pyrrole-3-carboxamide

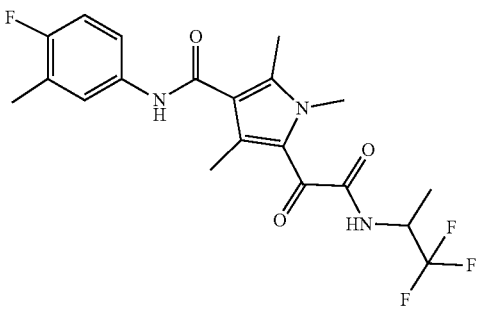 [SMILES: Cc1cc(NC(=O)c2c(C)c(C(=O)C(=O)NC(C)C(F)(F)F)n(C)c2C)ccc1F]

The title compounds were prepared following the procedure described in Example 2, Step 5, using 1,1,1-trifluoropropan-2-amine. The final product was purified by reverse phase chromatography eluted with ACN and water and dried using lyophilization to afford the title products as white solids. ESI-MS, m/z 428 (MH)$^+$.

Example 11: Synthesis of N-(4-fluoro-3-methylphenyl)-5-(2-((4-hydroxy-2-methylbutan-2-yl)amino)-2-oxoacetyl)-1,2,4-trimethyl-1H-pyrrole-3-carboxamide

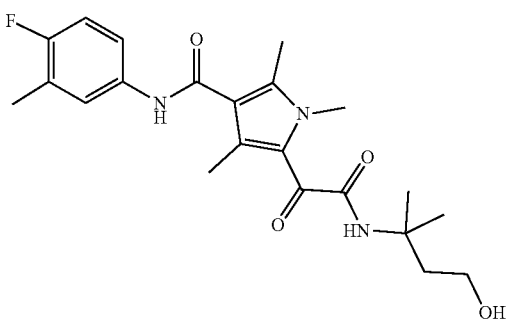 [SMILES: Cc1cc(NC(=O)c2c(C)c(C(=O)C(=O)NC(C)(C)CCO)n(C)c2C)ccc1F]

The title compounds were prepared following the procedure described in Example 2, Step 5, using 3-amino-3-methylbutan-1-ol. The final product was purified by reverse phase chromatography eluted with ACN and water and dried using lyophilization to afford the title products as white solids. ESI-MS, m/z 418 (MH)$^+$.

Example 12: Synthesis of N-(4-fluoro-3-methylphenyl)-5-(2-((1-(hydroxymethyl)cyclobutyl)amino)-2-oxoacetyl)-1,2,4-trimethyl-1H-pyrrole-3-carboxamide

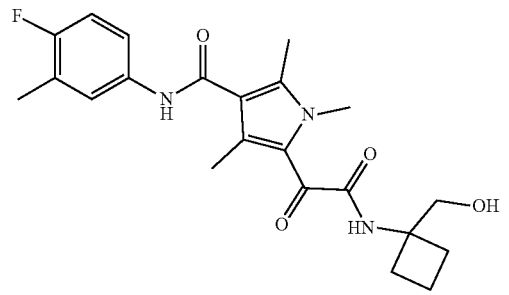 [SMILES: Cc1cc(NC(=O)c2c(C)c(C(=O)C(=O)NC3(CO)CCC3)n(C)c2C)ccc1F]

The title compounds were prepared following the procedure described in Example 2, Step 5, using (1-aminocyclobutyl)methanol. The final product was purified by reverse phase chromatography eluted with ACN and water and dried using lyophilization to afford the title products as white solids. ESI-MS, m/z 416 (MH)$^+$.

Example 13: Synthesis of N-(4-fluoro-3-methylphenyl)-5-(2-((3-(hydroxymethyl)tetrahydrofuran-3-yl)amino)-2-oxoacetyl)-1,2,4-trimethyl-1H-pyrrole-3-carboxamide

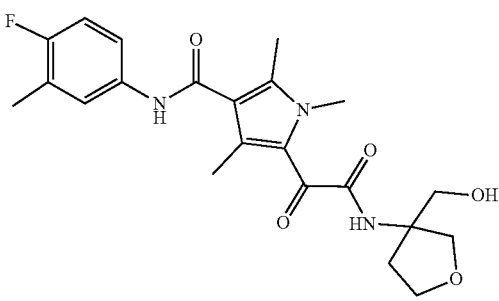 [SMILES: Cc1cc(NC(=O)c2c(C)c(C(=O)C(=O)NC3(CO)CCOC3)n(C)c2C)ccc1F]

The title compound was prepared following the procedure described in Example 2, Step 5, using (3-aminotetrahydrofuran-3-yl)methanol. The final product was purified by reverse phase chromatography eluted with ACN and water and dried using lyophilization to afford the title products as white solids. ESI-MS, m/z 432 (MH)⁺.

Example 14: Synthesis of 5-(2-(((3s,5s,7s)-adamantan-1-yl)amino)-2-oxoacetyl)-N-(4-fluoro-3-methylphenyl)-1,2,4-trimethyl-1H-pyrrole-3-carboxamide

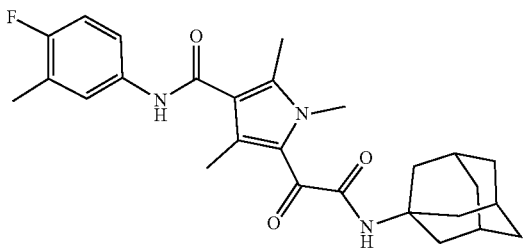 [SMILES: Cc1cc(NC(=O)c2c(C)c(C(=O)C(=O)NC34CC5CC(CC(C5)C3)C4)n(C)c2C)ccc1F]

The title compounds were prepared following the procedure described in Example 2, Step 5, using 1-adamantylamine. The final product was purified by reverse phase chromatography eluted with ACN and water and dried using lyophilization to afford the title products as white solids. ESI-MS, m/z 466 (MH)⁺.

Example 15: Synthesis of N-(4-fluoro-3-methylphenyl)-5-(2-(((1r,3s,5R,7S)-3-hydroxyadamantan-1-yl)amino)-2-oxoacetyl)-1,2,4-trimethyl-1H-pyrrole-3-carboxamide

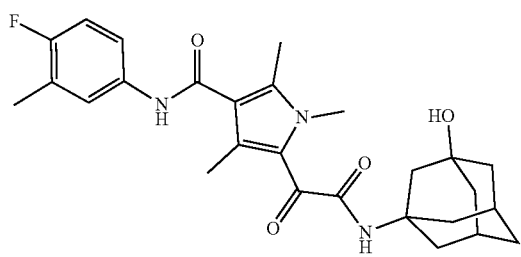 [SMILES: Cc1cc(NC(=O)c2c(C)c(C(=O)C(=O)NC34CC5CC(CC(O)(C5)C3)C4)n(C)c2C)ccc1F]

The title compounds were prepared following the procedure described in Example 2, Step 5, using 3-aminoadamantan-1-ol. The final product was purified by reverse phase chromatography eluted with ACN and water and dried using lyophilization to afford the title products as white solids. ESI-MS, m/z 482 (MH)⁺.

Example 16: Synthesis of N-(6-fluoropyridin-3-yl)-5-(2-(((1r,3s,5R,7S)-3-hydroxyadamantan-1-yl)amino)-2-oxoacetyl)-1,2,4-trimethyl-1H-pyrrole-3-carboxamide

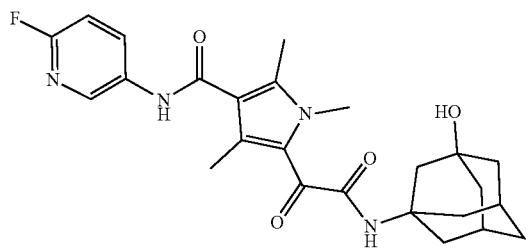 [SMILES: Cc1c(C(=O)Nc2ccc(F)nc2)c(C)n(C)c1C(=O)C(=O)NC12CC3CC(CC(O)(C3)C1)C2]

The title compounds were prepared following the procedure described in Example 5, using 3-aminoadamantan-1-ol instead of tert-butylamine. The final product was purified by reverse phase chromatography eluted with ACN and water and dried using lyophilization to afford the title products as white solids. ESI-MS, m/z 469 (MH)⁺.

Example 17: Synthesis of 5-(2-(((1r,3r)-adamantan-2-yl)amino)-2-oxoacetyl)-N-(4-fluoro-3-methylphenyl)-1,2,4-trimethyl-1H-pyrrole-3-carboxamide

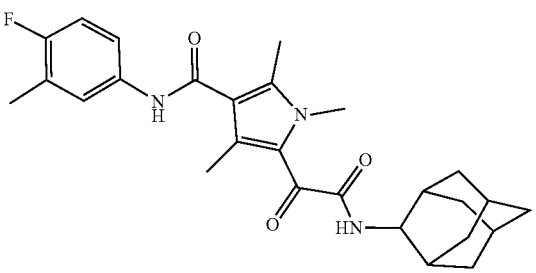 [SMILES: Cc1cc(NC(=O)c2c(C)c(C(=O)C(=O)NC3C4CC5CC(C4)CC3C5)n(C)c2C)ccc1F]

The title compounds were prepared following the procedure described in Example 2, Step 5, using 2-adamantylamine. The final product was purified by reverse phase chromatography eluted with ACN and water and dried using lyophilization to afford the title products as white solids. ESI-MS, m/z 466 (MH)⁺.

Example 18: Synthesis of N-(4-fluoro-3-methylphenyl)-5-(2-(((2R,3as,5S,6as)-hexahydro-2,5-methanopentalen-3a(1H)-yl)amino)-2-oxoacetyl)-1,2,4-trimethyl-1H-pyrrole-3-carboxamide

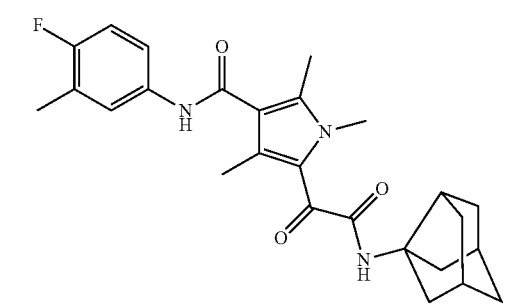 [SMILES: Cc1cc(NC(=O)c2c(C)c(C(=O)C(=O)NC34CC5CC(CC3C5)C4)n(C)c2C)ccc1F]

The title compounds were prepared following the procedure described in Example 2, Step 5, using 3-noradamantanamine. The final product was purified by reverse phase chromatography eluted with ACN and water and dried using lyophilization to afford the title products as white solids. ESI-MS, m/z 452 (MH)+.

Example 19: Synthesis of N-(6-fluoropyridin-3-yl)-5-(2-(((2R,3as,5S,6as)-hexahydro-2,5-methanopentalen-3a (1H)-yl)amino)-2-oxoacetyl)-1,2,4-trimethyl-1H-pyrrole-3-carboxamide

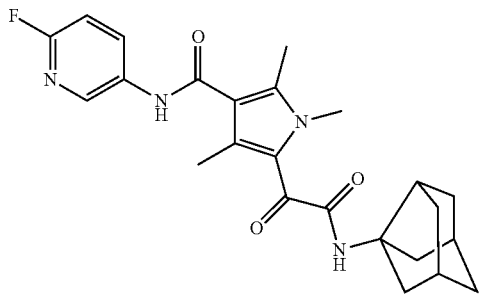 [SMILES: Cc1c(C(=O)Nc2ccc(F)nc2)c(C)n(C)c1C(=O)C(=O)NC12CC3CC(CC1C3)C2]

The title compounds were prepared following the procedure described in Example 5, using 3-noradamantanamine instead of tert-butylamine. The final product was purified by reverse phase chromatography eluted with ACN and water and dried using lyophilization to afford the title products as white solids. ESI-MS, m/z 439 (MH)+.

Example 20: Synthesis of 5-(2-((2-amino-4,5,6,7-tetrahydrobenzo[d]thiazol-6-yl)amino)-2-oxoacetyl)-N-(4-fluoro-3-methylphenyl)-1,2,4-trimethyl-1H-pyrrole-3-carboxamide

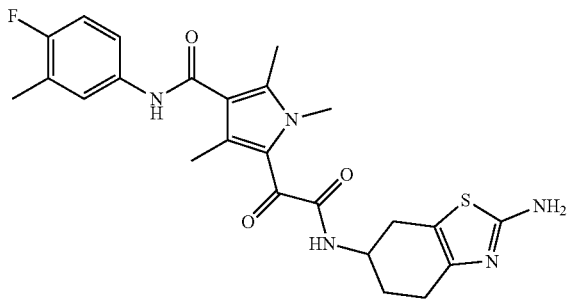 [SMILES: Cc1cc(NC(=O)c2c(C)c(C(=O)C(=O)NC3CCc4nc(N)sc4C3)n(C)c2C)ccc1F]

The title compounds were prepared following the procedure described in Example 2, Step 5, using 4,5,6,7-tetrahydrobenzo[d]thiazole-2,6-diamine. The final product was purified by reverse phase chromatography eluted with ACN and water and dried using lyophilization to afford the title products as white solids. ESI-MS, m/z 484 (MH)+.

Example 21: Synthesis of 5-(2-(tert-butoxyamino)-2-oxoacetyl)-N-(3-chloro-4-fluorophenyl)-1-methyl-1H-pyrrole-3-carboxamide

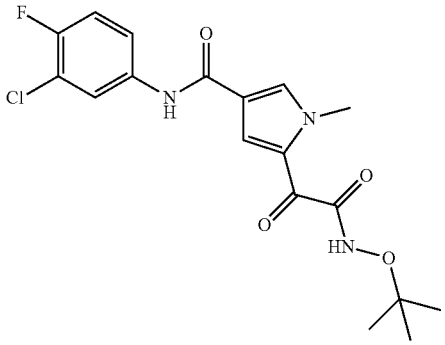 [SMILES: Cn1cc(C(=O)Nc2ccc(F)c(Cl)c2)cc1C(=O)C(=O)NOC(C)(C)C]

The title compound was prepared following the procedure described in Example 1, 4-fluoro-3-chloroaniline instead of 4-fluoro-3-methylaniline in Step 1, and using O-(tert-butyl)hydroxylamine instead of t-butylamine in Step 5. The final product was purified by reverse phase chromatography eluted with ACN and water and dried using lyophilization to afford the title products as white solids. ESI-MS, m/z 396 (MH)+.

Example 22: Synthesis of tert-butyl 2-(2-(4-((4-fluoro-3-methylphenyl)carbamoyl)-1,3,5-trimethyl-1H-pyrrol-2-yl)-2-oxoacetamido)-2-methylpropanoate

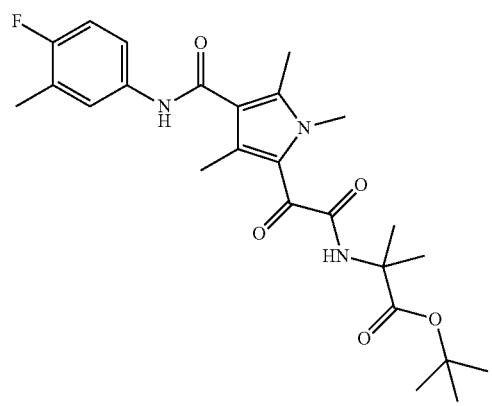 [SMILES: Cc1cc(NC(=O)c2c(C)c(C(=O)C(=O)NC(C)(C)C(=O)OC(C)(C)C)n(C)c2C)ccc1F]

The title compound was prepared following the procedure described in Example 2, Step 5, using tert-butyl 2-amino-2-methylpropanoate. The final product was purified by reverse phase chromatography eluted with ACN and water and dried using lyophilization to afford the title products as white solids. ESI-MS, m/z 474 (MH)+.

435

Example 27: Synthesis of methyl (2-(4-((4-fluoro-3-methylphenyl)carbamoyl)-1,3,5-trimethyl-1H-pyrrol-2-yl)-2-oxoacetyl)-L-threoninate

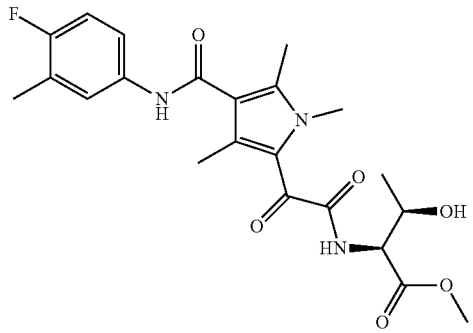 [SMILES: COC(=O)[C@@H](NC(=O)C(=O)c1c(C)c(C(=O)Nc2ccc(F)c(C)c2)c(C)n1C)[C@@H](C)O]

DIPEA (0.229 g, 1.77 mmol) was added to a mixture of 2e (0.195 g, 0.59 mmol), L-Threonine methyl ester hydrochloride (0.11 g, 0.65 mmol) and HATU (0.269 g, 0.71 mmol) in DMF (3 mL) at ambient temperature. After 16 h, the reaction mixture was diluted into aqueous HCl (1 N, 20 mL) and extracted with EtOAc (3×15 mL). The combined extracts were washed with aqueous HCl (1 N, 10 mL), aqueous NH$_4$Cl (saturated, 10 mL) and brine (10 mL). The organic layer was dried over Na$_2$SO$_4$ (s), filtered, concentrated in vacuo, then, purified by flash chromatography on silica gel (EtOAc/Hexanes 0~100%) to afford the title product as white solid (0.223 g). ESI-MS, m/z 448.2 (HM)$^+$.

Example 29: Synthesis of 2-(2-(4-((4-fluoro-3-methylphenyl)carbamoyl)-1,3,5-trimethyl-1H-pyrrol-2-yl)-2-oxoacetamido)-2-methylpropanoic acid

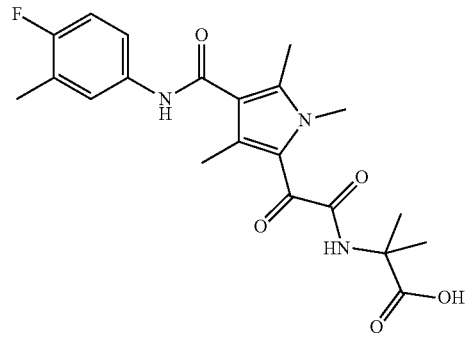 [SMILES: Cc1cc(NC(=O)c2c(C)c(C(=O)C(=O)NC(C)(C)C(=O)O)n(C)c2C)ccc1F]

TFA (0.4 mL) was added to a solution of Example 22 (15 mg) in DCM (1 mL) at 0° C. After 2 hrs at 0° C., the reaction mixture was warmed to rt for 1 hr. The solvent was removed and the residue was purified by reverse phase chromatography eluted with ACN and water and dried using lyophilization to afford the title products as white solids. ESI-MS, m/z 418 (MH)$^+$.

436

Example 34: Synthesis of (2-(4-((4-fluoro-3-methylphenyl)carbamoyl)-1,3,5-trimethyl-1H-pyrrol-2-yl)-2-oxoacetyl)-L-threonine

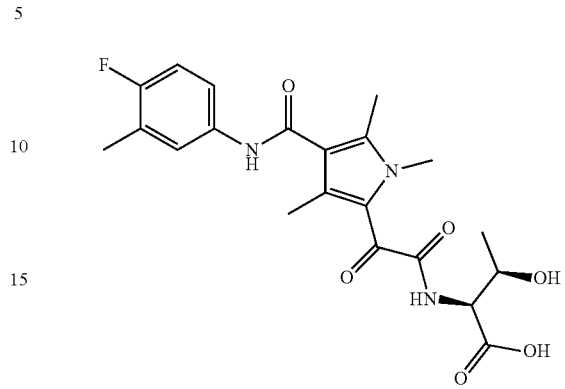

NaOH (1 N, 0.5 mL) was added to a solution of Example 27 (0.093 g, 0.208 mmol) in MeOH (5 mL) at ambient temperature. After 2 h the reaction mixture was carefully neutralized with aqueous HCl (1 N) to pH ~2. The resulting mixture was concentrated under vacuum to remove MeOH, then, purified by reverse phase chromatography eluted with ACN and water, and dried using lyophilization to afford the title product as pale yellow solid: ESI-MS, m/z 434.2 (MH)$^+$.

Example 36: Synthesis of 5-(2-((1-amino-2-methyl-1-oxopropan-2-yl)amino)-2-oxoacetyl)-N-(4-fluoro-3-methylphenyl)-1,2,4-trimethyl-1H-pyrrole-3-carboxamide

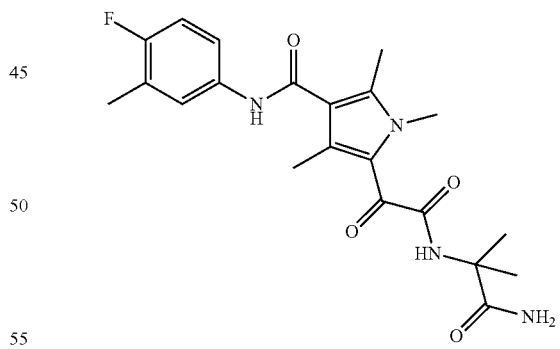

The title compounds were prepared following the procedure described in Example 2, Step 5, using 2-amino-2-methylpropanamide. The final product was purified by reverse phase chromatography eluted with ACN and water and dried using lyophilization to afford the title products as white solids. ESI-MS, m/z 417 (MH)$^+$.

Example 37: Synthesis of 5-(2-((1-carbamoylcyclopropyl)amino)-2-oxoacetyl)-N-(4-fluoro-3-methylphenyl)-1,2,4-trimethyl-1H-pyrrole-3-carboxamide

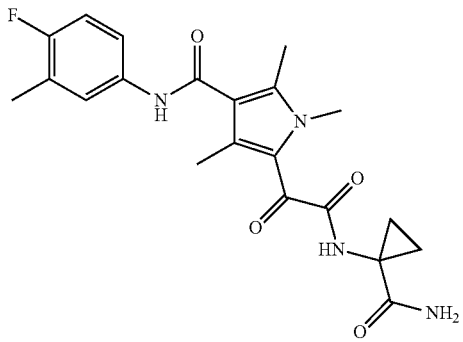 [SMILES: Cc1cc(NC(=O)c2c(C)c(C(=O)C(=O)NC3(C(N)=O)CC3)n(C)c2C)ccc1F]

The title compounds were prepared following the procedure described in Example 2, Step 5, using 1-aminocyclopropane-1-carboxamide. The final product was purified by reverse phase chromatography eluted with ACN and water and dried using lyophilization to afford the title products as white solids. ESI-MS, m/z 415 (MH)+.

Example 38: Synthesis of 5-(2-((1-carbamoylcyclopentyl)amino)-2-oxoacetyl)-N-(4-fluoro-3-methylphenyl)-1,2,4-trimethyl-1H-pyrrole-3-carboxamide

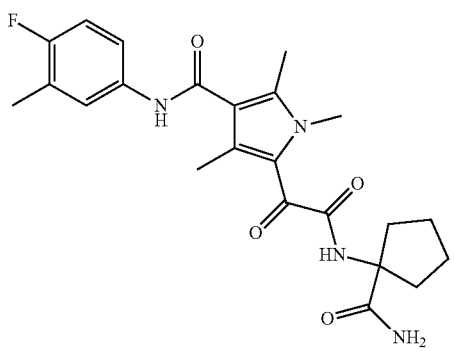 [SMILES: Cc1cc(NC(=O)c2c(C)c(C(=O)C(=O)NC3(C(N)=O)CCCC3)n(C)c2C)ccc1F]

The title compounds were prepared following the procedure described in Example 2, Step 5, using 1-aminocyclopentane-1-carboxamide. The final product was purified by reverse phase chromatography eluted with ACN and water and dried using lyophilization to afford the title products as white solids. ESI-MS, m/z 443 (MH)+.

Example 42: 5-(2-(((2S,3R)-1-amino-3-hydroxy-1-oxobutan-2-yl)amino)-2-oxoacetyl)-N-(4-fluoro-3-methylphenyl)-1,2,4-trimethyl-1H-pyrrole-3-carboxamide

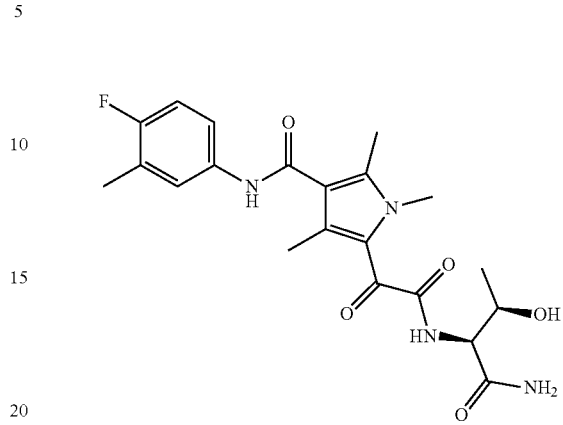

DIPEA (0.25 g, 1.93 mmol) and DMAP (0.02 g, 0.16 mmol) were added to a mixture of 34 (0.7 g, 0.16 mmol), NH$_4$Cl (0.043 g, 0.81 mmol) and HATU (0.184 g, 0.48 mmol) in DMF (3 mL) at ambient temperature. After 16 h, the reaction mixture was diluted into aqueous HCl (1 N, 20 mL) and extracted with EtOAc (3×15 mL). The combined extracts were washed with aqueous HCl (1 N, 10 mL), aqueous NH$_4$Cl (saturated, 10 mL) and brine (10 mL). The organic layer was dried over Na$_2$SO$_4$ (s), filtered, concentrated in vacuo. The final product was purified by reverse phase chromatography eluted with ACN and water and dried using lyophilization to afford the title products as white solids. ESI-MS, m/z 433.2 (MH)+.

Example 43: Synthesis of 5-(2-(((1r,3r,5r,7r)-2-carbamoyladamantan-2-yl)amino)-2-oxoacetyl)-N-(4-fluoro-3-methylphenyl)-1,2,4-trimethyl-1H-pyrrole-3-carboxamide

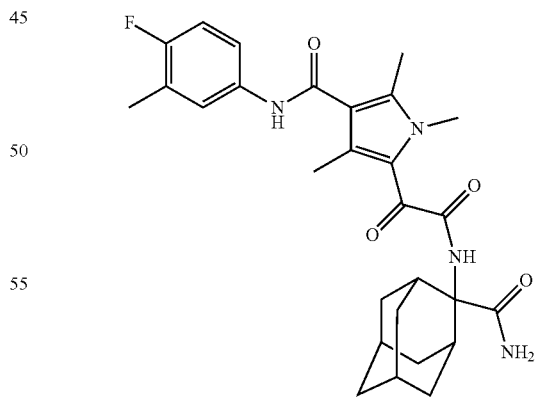

The title compounds were prepared following the procedure described in Example 2, Step 5, using 2-aminoadamantane-2-carboxamide. The final product was purified by reverse phase chromatography eluted with ACN and water and dried using lyophilization to afford the title products as white solids. ESI-MS, m/z 509 (MH)+.

Example 47: Synthesis of N-(4-fluoro-3-methylphenyl)-5-(2-(4-hydroxypiperidin-1-yl)-2-oxoacetyl)-1,2,4-trimethyl-1H-pyrrole-3-carboxamide

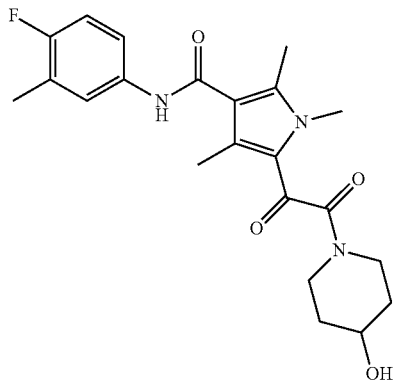 [SMILES: Cc1cc(NC(=O)c2c(C)c(C(=O)C(=O)N3CCC(O)CC3)n(C)c2C)ccc1F]

The title compounds were prepared following the procedure described in Example 2, Step 5, using piperidin-4-ol. The final product was purified by reverse phase chromatography eluted with ACN and water and dried using lyophilization to afford the title products as white solids. ESI-MS, m/z 416 (MH)+.

Example 48: Synthesis of N-(4-fluoro-3-methylphenyl)-5-(2-((1R,3s,5S)-3-hydroxy-8-azabicyclo[3.2.1]octan-8-yl)-2-oxoacetyl)-1,2,4-trimethyl-1H-pyrrole-3-carboxamide

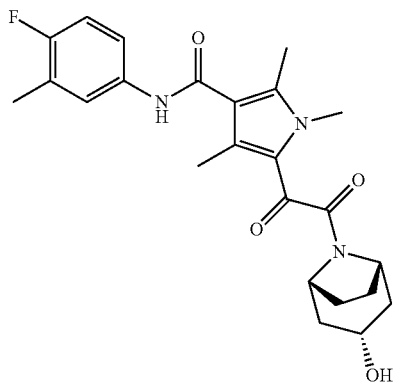 [SMILES: Cc1cc(NC(=O)c2c(C)c(C(=O)C(=O)N3[C@@H]4CC[C@H]3C[C@H](O)C4)n(C)c2C)ccc1F]

The title compounds were prepared following the procedure described in Example 2, Step 5, using (1R,3s,5S)-8-azabicyclo[3.2.1]octan-3-ol. The final product was purified by reverse phase chromatography eluted with ACN and water and dried using lyophilization to afford the title products as white solids. ESI-MS, m/z 442 (MH)+.

Example 49: Synthesis of 5-(2-(2-amino-6,7-dihydrothiazolo[5,4-c]pyridin-5(4H)-yl)-2-oxoacetyl)-N-(4-fluoro-3-methylphenyl)-1,2,4-trimethyl-1H-pyrrole-3-carboxamide

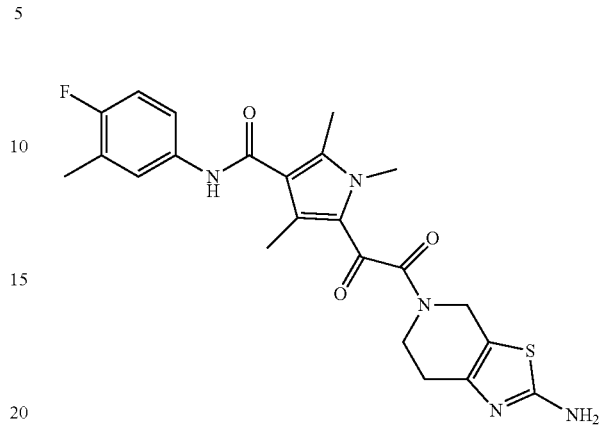

The title compounds were prepared following the procedure described in Example 2, Step 5, using 4,5,6,7-tetrahydrothiazolo[5,4-c]pyridin-2-amine. The final product was purified by reverse phase chromatography eluted with ACN and water and dried using lyophilization to afford the title products as white solids. ESI-MS, m/z 434 (MH)+.

Example 50: N-(4-fluoro-3-methylphenyl)-5-(2-((1-hydroxy-2-methylpropan-2-yl)amino)-2-oxoacetyl)-1-(2-hydroxyethyl)-2,4-dimethyl-1H-pyrrole-3-carboxamide

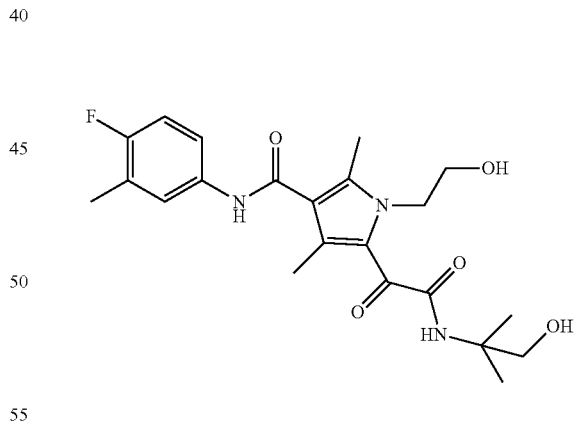

The title compounds were prepared following the procedure described in Example 71, Step 5, using 2-amino-2-methylpropan-1-ol. The final product was purified by reverse phase chromatography eluted with ACN and water and dried using lyophilization to afford the title products as white solids. ESI-MS, m/z 434 (MH)+.

Example 53: Synthesis of N-(4-fluoro-3-methylphenyl)-5-(2-(4-hydroxy-3,3-dimethylpiperidin-1-yl)-2-oxoacetyl)-1,2,4-trimethyl-1H-pyrrole-3-carboxamide

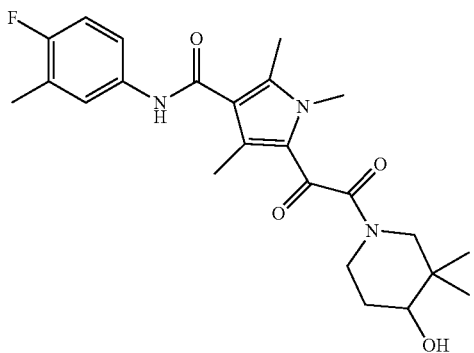 [SMILES: Cc1cc(NC(=O)c2c(C)c(C(=O)C(=O)N3CCC(O)C(C)(C)C3)n(C)c2C)ccc1F]

The title compounds were prepared following the procedure described in Example 2, Step 5, using 3,3-dimethylpiperidin-4-ol. The final product was purified by reverse phase chromatography eluted with ACN and water and dried using lyophilization to afford the title products as white solids. ESI-MS, m/z 444.2 (MH)+.

Example 59: N-(4-fluoro-3-methylphenyl)-5-(2-(((1s,3R,4s,5S,7s)-4-hydroxyadamantan-1-yl)amino)-2-oxoacetyl)-1,2,4-trimethyl-1H-pyrrole-3-carboxamide

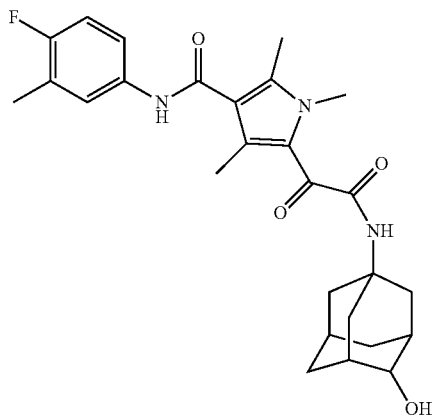 [SMILES: Cc1cc(NC(=O)c2c(C)c(C(=O)C(=O)NC34CC5CC(C3)C(O)C(C5)C4)n(C)c2C)ccc1F]

The title compounds were prepared following the procedure described in Example 2, Step 5, using 5-aminoadamantan-2-ol. The final product was purified by reverse phase chromatography eluted with ACN and water and dried using lyophilization to afford the title products as white solids. ESI-MS, m/z 482 (MH)+.

Example 63: Synthesis of (R)-5-(2-((3,3-dimethylbutan-2-yl)amino)-2-oxoacetyl)-N-(4-fluoro-3-methylphenyl)-1,2,4-trimethyl-1H-pyrrole-3-carboxamide

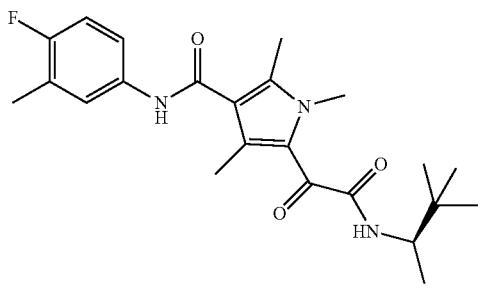 [SMILES: Cc1cc(NC(=O)c2c(C)c(C(=O)C(=O)N[C@H](C)C(C)(C)C)n(C)c2C)ccc1F]

The title compounds were prepared following the procedure described in Example 2, Step 5, using (R)-(−)-3,3-dimethyl-2-butylamine. The final product was purified by reverse phase chromatography eluted with ACN and water and dried using lyophilization to afford the title products as white solids. ESI-MS, m/z 416.2 (MH)+.

Example 64: Synthesis of N-(4-fluoro-3-methylphenyl)-1,2,4-trimethyl-5-(2-(neopentylamino)-2-oxoacetyl)-1H-pyrrole-3-carboxamide

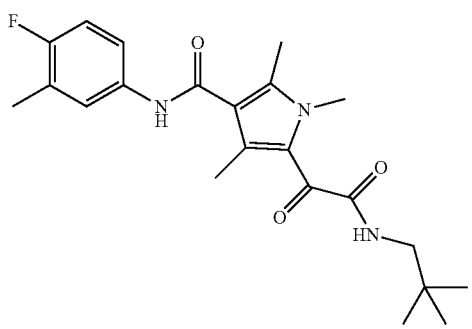 [SMILES: Cc1cc(NC(=O)c2c(C)c(C(=O)C(=O)NCC(C)(C)C)n(C)c2C)ccc1F]

The title compounds were prepared following the procedure described in Example 2, Step 5, using 2,2-dimethylpropan-1-amine. The final product was purified by reverse phase chromatography eluted with ACN and water and dried using lyophilization to afford the title products as white solids. ESI-MS, m/z 402.2 (MH)+.

Example 65: Synthesis of N-(4-fluoro-3-methylphenyl)-5-(2-((3-hydroxy-2,2-dimethylpropyl)amino)-2-oxoacetyl)-1,2,4-trimethyl-1H-pyrrole-3-carboxamide

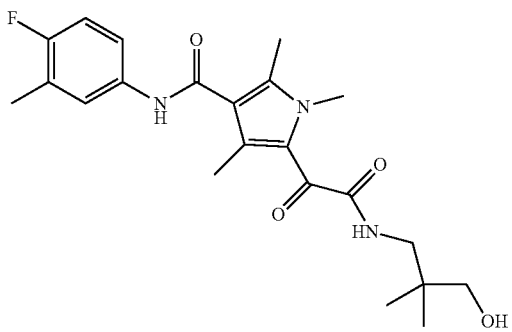 [SMILES: Cc1cc(NC(=O)c2c(C)c(C(=O)C(=O)NCC(C)(C)CO)n(C)c2C)ccc1F]

The title compounds were prepared following the procedure described in Example 2, Step 5, using 3-amino-2,2-dimethylpropan-1-ol. The final product was purified by reverse phase chromatography eluted with ACN and water and dried using lyophilization to afford the title products as white solids. ESI-MS, m/z 418.2 (MH)$^+$.

Example 66: Synthesis of N-(4-fluoro-3-methylphenyl)-5-(2-((2-hydroxy-2-methylpropyl)amino)-2-oxoacetyl)-1,2,4-trimethyl-1H-pyrrole-3-carboxamide

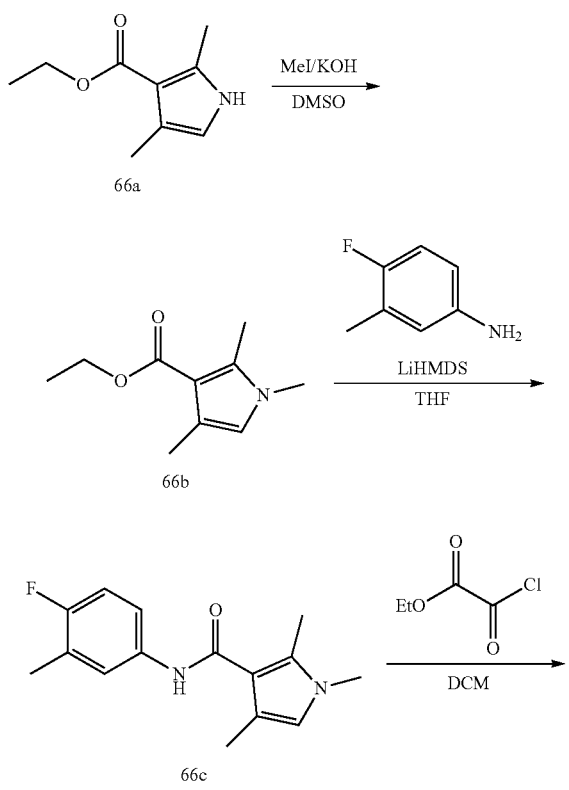

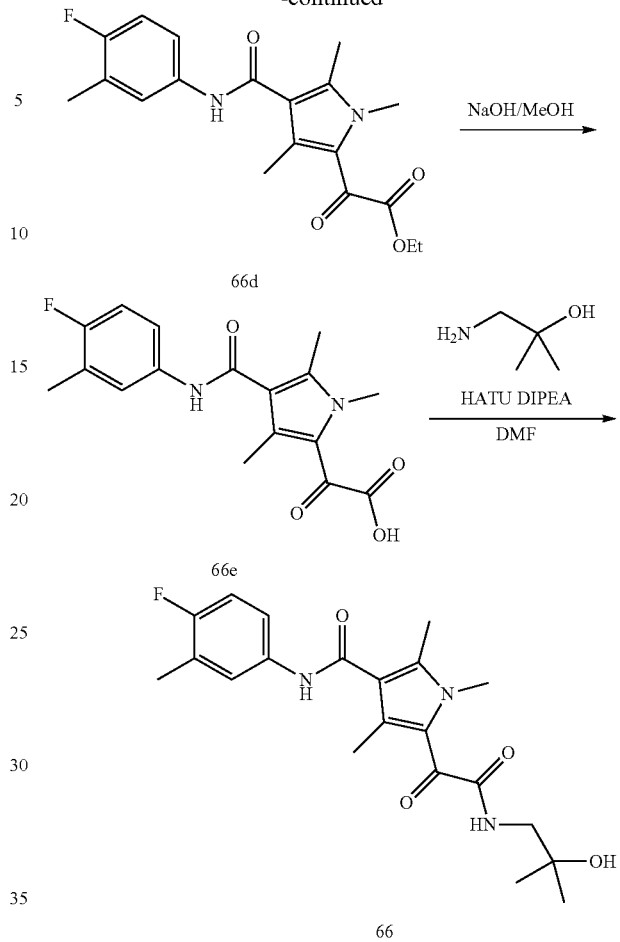

Step 1: Synthesis of ethyl 1,2,4-trimethyl-1H-pyrrole-3-carboxylate (66b)

MeI (31.8 g, 224.3 mmol) was added to a mixture of 66a (25 g, 149.5 mmol) and KOH (16.8 g, 299 mmol) in DMSO (250 mL) at 0° C. The reaction mixture was warmed to rt for 16 hrs. The reaction mixture was extracted with 4× Et$_2$O. The combined extracts were washed with water and brine, dried over Na$_2$SO$_4$, filtered and concentrated in vacuo to afford the title compound 66b as brown solid (24.6 g, 91%) which was used without further purification. ESI-MS, m/z 182 (MH)$^+$.

Step 2: Synthesis of N-(4-fluoro-3-methylphenyl)-1,2,4-trimethyl-1H-pyrrole-3-carboxamide (66c)

LiHMDS (272 mL, 1 N in THF) was added dropwise over 45 min to a solution of 66b (24.6 g, 135.73 mmol) and 3-methyl-4-fluoroaniline (18.83 g, 149.3 mmol) in THF (270 mL) at 0° C. The reaction mixture was allowed to warm slowly to ambient temperature. After 16 h the reaction mixture was quenched with NH$_4$Cl (sat) and water. The layers were separated and the aqueous was extracted 3× EtOAc. The combined organics were washed with NH$_4$Cl (sat) and brine, dried over Na$_2$SO$_4$, filtered and concentrated. The crude residue was suspended in 1:1 EtOAc/hexanes and stirred for 1 h at 40° C., then cooled to ambient temperature and filtered. The filter cake was washed with

445 hexanes and dried to afford the title compound 66c as tan solid (31.85 g, 90%). $^1$H NMR (300 MHz, DMSO-d$_6$) δ 9.25 (s, 1H), 7.58 (d, J=7.2 Hz, 1H), 7.45 (m, 1H), 7.02 (t, J=9.6 Hz, 1H), 6.44 (s, 1H), 3.43 (s, 3H), 2.26 (s, 3H), 2.19 (s, 3H), 2.06 (s, 3H). ESI-MS, m/z 261 (MH)$^+$.

Step 3: Synthesis of ethyl 2-(4-((4-fluoro-3-methylphenyl)carbamoyl)-1,3,5-trimethyl-1H-pyrrol-2-yl)-2-oxoacetate (66d)

To a solution of 66c (31.85 g, 121.89 mmol) in DCM (500 mL) at 0° C. was added ethyl chlorooxoacetate (24.96 g, 182.84 mmol) dropwise over 30 mins and the reaction mixture was allowed to warm slowly to ambient temperature. After 16 h the reaction mixture was washed with H$_2$O and NaHCO$_3$ (sat) and then concentrated in vacuo to afford the title compound 66d (44 g, quant) as a brown solid which was used without any further purification. ESI-MS, m/z 361 (MH)$^+$.

Step 4: Synthesis of 2-(4-((4-fluoro-3-methylphenyl)carbamoyl)-1,3,5-trimethyl-1H-pyrrol-2-yl)-2-oxoacetic acid (66e)

To a solution of 66d (43.9 g, 121.89 mmol) in THF (200 mL) and MeOH (200 mL) was added 1N NaOH (300 mL). After 15 min the reaction mixture was partially concentrated to remove organics, diluted with EtOAc and partially concentrated again. The heterogeneous mixture was diluted with water and washed 4× EtOAc. The heterogeneous aqueous was acidified with conc. HCl to pH=1 and extracted with 4× EtOAc. The heterogeneous organic layer was washed with brine, filtered and the filter cake was washed with hexanes. The crude solids were suspended in EtOAc (200 mL) and hexanes (200 mL) and stirred for 1 h at 45° C., then cooled to ambient temperature, filtered and washed with hexanes. The solids were further dried in vacuo to provide the title compound 66e (34.21 g, 84%) as an off-white solid. $^1$H NMR (300 MHz, DMSO-d$_6$) δ 9.96 (s, 1H), 7.60 (d, J=6.9 Hz, 1H), 7.46 (m, 1H), 7.07 (t, J=9.6 Hz, 1H), 3.78 (s, 3H), 2.32 (s, 3H), 2.23 (s, 3H), 2.20 (s, 3H). ESI-MS, m/z 333 (MH)$^+$.

Step 5: Synthesis of N-(4-fluoro-3-methylphenyl)-5-(2-((1-hydroxy-2-methylpropan-2-yl)amino)-2-oxoacetyl)-1,2,4-trimethyl-1H-pyrrole-3-carboxamide To a solution of 66e (20 g, 60.18 mmol), 1-amino-2-methylpropan-2-ol (5.9 g, 66.20 mmol)) and HATU (27.46 g, 72.22 mmol) in DMF (200 mL) at ambient temperature was added DIPEA (23.3 g, 180.54 mmol). After 2 h the reaction mixture was diluted with 1N HCl and extracted 4× EtOAc. The combined organics were washed sequentially with 1 N HCl, NaHCO$_3$ (sat), and brine, then dried over Na$_2$SO$_4$, filtered and concentrated. The crude solids were suspended in MeCN (100 mL) and water (100 mL) and stirred at 40° C. After 1 h the mixture was cooled to ambient temperature and filtered. The filter cake was washed with 1:1 MeCN/water and dried in vacuo. The resultant tan solids were slurried in MeCN (60 mL) and stirred at 45° C. After 1 h the mixture was cooled to ambient temperature, filtered and washed with cold MeCN. The resultant solids were dried in vacuo to provide the title compound (17.5 g, 72%) as an off white solid. $^1$H NMR (300 MHz, DMSO-d$_6$) δ 9.90 (s, 1H), 8.51 (t, J=5.1 Hz, 1H), 7.60 (d, J=6.9 Hz, 1H), 7.45 (t, J=3 Hz, 1H), 7.06 (t, J=9.3 Hz, 1H), 4.50 (s, 1H), 3.74 (s, 3H), 3.14 (d, J=5.7 Hz, 2H), 2.31 (s, 3H), 2.19 (m, 6H), 1.10 (m, 1H). ESI-MS, m/z 404.2 (MH)$^+$.

Example 67: Synthesis of (S)—N-(4-fluoro-3-methylphenyl)-5-(2-((1-hydroxy-3,3-dimethylbutan-2-yl)amino)-2-oxoacetyl)-1,2,4-trimethyl-1H-pyrrole-3-carboxamide

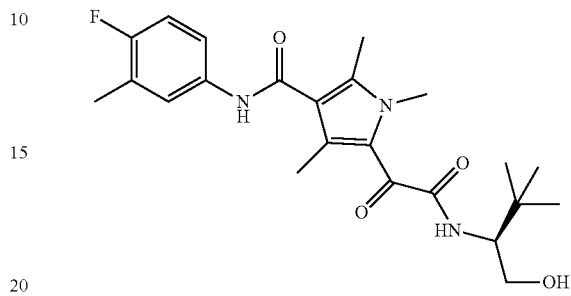

The title compounds were prepared following the procedure described in Example 2, Step 5, using L-tert-leucinol. The final product was purified by reverse phase chromatography eluted with ACN and water and dried using lyophilization to afford the title products as white solids. ESI-MS, m/z 432.2 (MH)$^+$.

Example 70: Synthesis of 5-(2-(tert-butoxyamino)-2-oxoacetyl)-N-(4-fluoro-3-methylphenyl)-1,2,4-trimethyl-1H-pyrrole-3-carboxamide

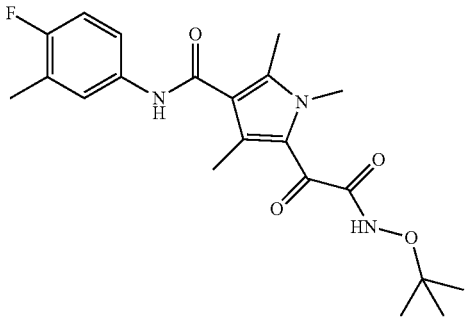 [SMILES: Cc1cc(NC(=O)c2c(C)c(C(=O)C(=O)NOC(C)(C)C)n(C)c2C)ccc1F]

The title compounds were prepared following the procedure described in Example 2, Step 5, using O-(tert-butyl) hydroxylamine. The final product was purified by flash chromatography on silica gel eluted with ethyl acetate and hexane to afford the title products as pale yellow solids. ESI-MS, m/z 404 (MH)$^+$.

Example 71: 5-(2-(tert-butylamino)-2-oxoacetyl)-N-(4-fluoro-3-methylphenyl)-1-(2-hydroxyethyl)-2,4-dimethyl-1H-pyrrole-3-carboxamide

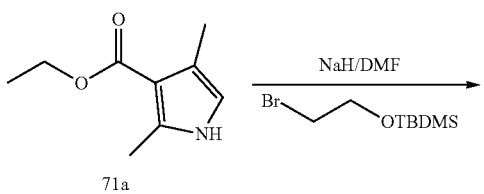

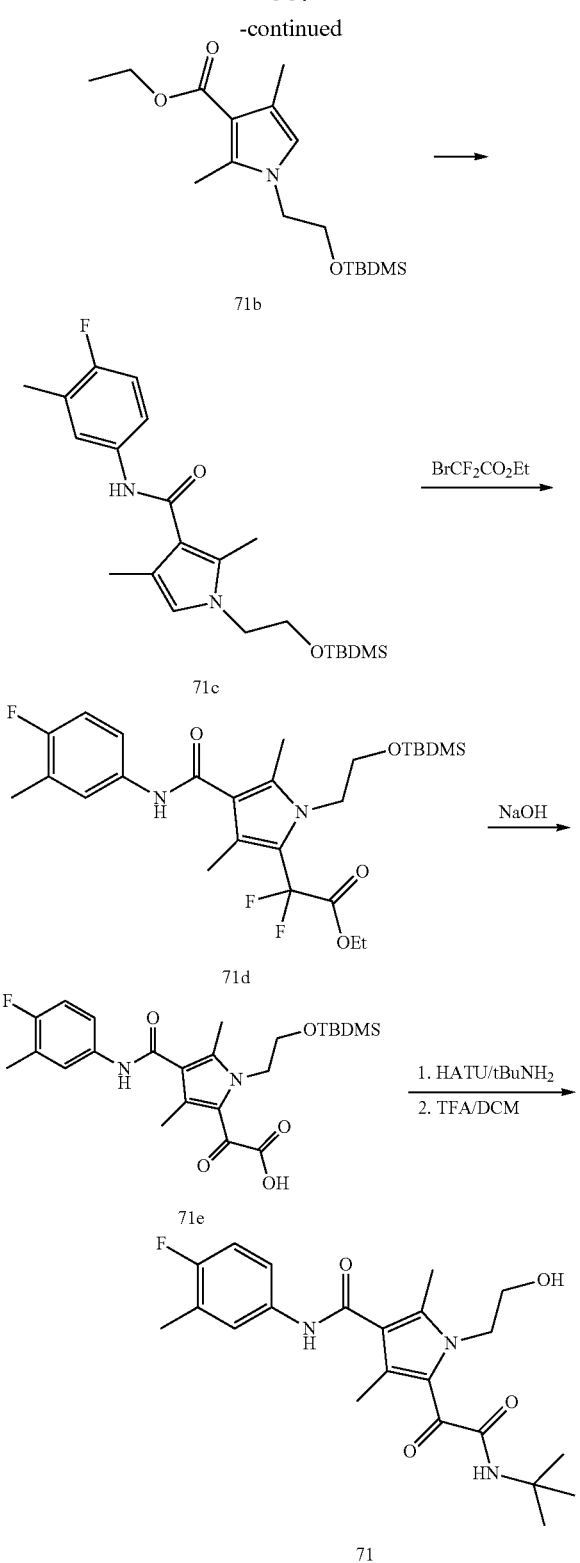

30 min., (2-bromoethoxy)(tert-butyl)dimethylsilane (3 g, 12.5 mmol in DMF 10 mL) was added dropwise. The mixture was stirred at 0° C. for 4 hrs. The reaction was carefully quenched with saturated NH$_4$Cl at 0° C., then, extracted with EtOAc (3×50 mL). The combined extractions were washed with water/brine, concentrated in vacuo, and purified by flash chromatography on silica gel (EtOAc/Hexanes 0~100%) to afford the product as brown oil (3 g). ESI-MS, m/z 326 (MH)+.

Step 2: Synthesis of 1-(2-((tert-butyldimethylsilyl)oxy)ethyl)-N-(4-fluoro-3-methylphenyl)-2,4-dimethyl-1H-pyrrole-3-carboxamide (71c)

The title compounds were prepared following the procedure described in Example 2, Step 2. The final product was purified by flash chromatography on silica gel (EtOAc/Hexanes 0~100%) as brown solid. ESI-MS, m/z 405 (MH)$^+$.

Step 3: Synthesis of ethyl 2-(1-(2-((tert-butyldimethylsilyl)oxy)ethyl)-4-((4-fluoro-3-methylphenyl)carbamoyl)-3,5-dimethyl-1H-pyrrol-2-yl)-2,2-difluoroacetate (71d)

A mixture of 71c (0.4 g, 0.99 mmol), K$_2$CO$_3$ (0.5 g, 3.6 mmol), Xantphos (0.15 g, 0.26 mmol) and tetrakis(triphenylphosphine)palladium(0) (40 mg) in 1,4-dioxane (5 mL) was flushed with argon, then, ethyl 2-bromo-2,2-difluoroacetate (0.5 g) was added under argon. The mixture was stirred at 100° C. for 20 hrs. After cooling to rt, the reaction mixture was diluted with EtOAc and washed with water/brine, concentrated in vacuo, and purified by flash chromatography on silica gel (EtOAc/Hexanes 0~40%) to afford the product as brown oil (0.25 g). ESI-MS, m/z 527 (MH)$^+$.

Step 4: Synthesis of 2-(1-(2-((tert-butyldimethylsilyl)oxy)ethyl)-4-((4-fluoro-3-methylphenyl)carbamoyl)-3,5-dimethyl-1H-pyrrol-2-yl)-2-oxoacetic acid (71e)

NaOH (2N, 2 mL) was added to a solution of 71d (0.25 g) in MeOH (4 mL) at rt. The mixture was stirred at rt for 2 hrs, then, carefully neutralized with HCl (0.5 N aqueous) to pH ~2 at 0° C. The mixture was concentrated and lyophilized to afford crude product as white solid. ESI-MS, m/z 477 (MH)$^+$.

Step 5: Synthesis of N-(4-fluoro-3-methylphenyl)-1-(2-hydroxyethyl)-5-(2-(isopropylamino)-2-oxoacetyl)-2,4-dimethyl-1H-pyrrole-3-carboxamide (71)

HATU (60 mg, 0.16 mmol) was added to a solution of crude 71e (40 mg, 0.08 mmol) in DMA (0.75 mL) at 0° C. After 20 min, tert-butylamine (10 mg, 0.14) and DIPEA (25 mg, 0.19 mmol) in DMA (0.4 mL) were added. The reaction mixture was stirred at rt for 20 hrs. The reaction mixture was quenched with aqueous HCl (0.2N, 2 mL), then, extracted with EtOAc (10 mL). The organic layer was washed with water and brine, and concentrated in vacuo. The residue was dissolved in DCM (1 mL) at 0° C., then, added TFA (0.6 mL). After 4 hrs, the mixture was concentrated, and purified by reverse phase chromatography eluted with ACN and water, and dried using lyophilization to afford the title product as white solid. ESI-MS, m/z 418 (MH)$^+$.

Step 1: Synthesis of ethyl 1-(2-((tert-butyldimethylsilyl)oxy)ethyl)-2,4-dimethyl-1H-pyrrole-3-carboxylate (71b)

NaH (65% mineral oil, 1 g) was added to a solution of 71a (2 g, 12 mmol) in DMF (100 mL) at 0° C. under argon. After

Example 72: 5-(2-((1-amino-2-methyl-1-oxopropan-2-yl)amino)-2-oxoacetyl)-N-(4-fluoro-3-methylphenyl)-1-(2-hydroxyethyl)-2,4-dimethyl-1H-pyrrole-3-carboxamide

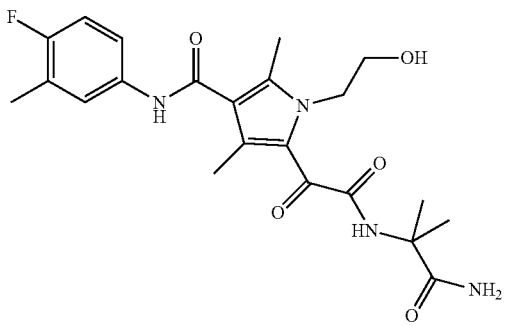 [SMILES: Cc1cc(NC(=O)c2c(C)c(C(=O)C(=O)NC(C)(C)C(N)=O)n(CCO)c2C)ccc1F]

The title compounds were prepared following the procedure described in Example 71, Step 5, using 2-amino-2-methylpropanamide. The final product was purified by reverse phase chromatography eluted with ACN and water and dried using lyophilization to afford the title products as white solids. ESI-MS, m/z 447 (MH)+.

Example 73: N-(4-fluoro-3-methylphenyl)-5-(2-(((1r,3s,5R,7S)-3-hydroxyadamantan-1-yl)amino)-2-oxoacetyl)-1-(2-hydroxyethyl)-2,4-dimethyl-1H-pyrrole-3-carboxamide

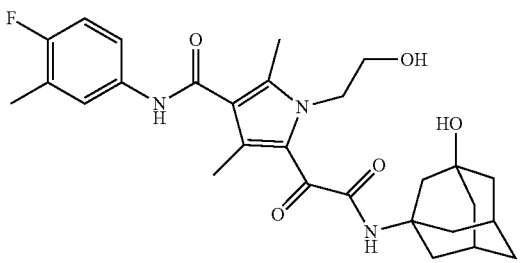 [SMILES: Cc1cc(NC(=O)c2c(C)c(C(=O)C(=O)NC34CC5CC(CC(O)(C5)C3)C4)n(CCO)c2C)ccc1F]

The title compounds were prepared following the procedure described in Example 71, Step 5, using 3-aminoadamantan-1-ol. The final product was purified by reverse phase chromatography eluted with ACN and water and dried using lyophilization to afford the title products as white solids. ESI-MS, m/z 512 (MH)+.

Example 74: N-(4-fluoro-3-methylphenyl)-5-(2-(((1R,2s,3S,5s,7s)-5-hydroxyadamantan-2-yl)amino)-2-oxoacetyl)-1,2,4-trimethyl-M-pyrrole-3-carboxamide

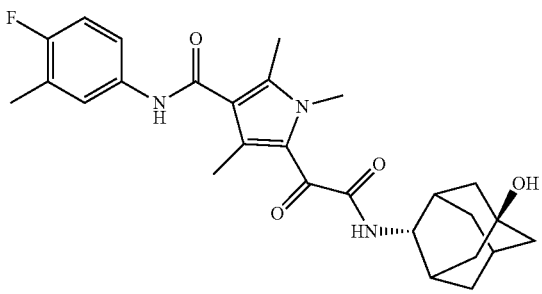 [SMILES: Cc1cc(NC(=O)c2c(C)c(C(=O)C(=O)N[C@H]3C4CC5CC3C[C@](O)(C5)C4)n(C)c2C)ccc1F]

The title compounds were prepared following the procedure described in Example 2, Step 5, using trans-4-aminoadamantan-1-ol. The final product was purified by reverse phase chromatography eluted with ACN and water and dried using lyophilization to afford the title products as white solids. ESI-MS, m/z 482 (MH)+.

Example 75: (S)-5-(2-((2-amino-4,5,6,7-tetrahydrobenzo[d]thiazol-6-yl)amino)-2-oxoacetyl)-N-(4-fluoro-3-methylphenyl)-1,2,4-trimethyl-1H-pyrrole-3-carboxamide

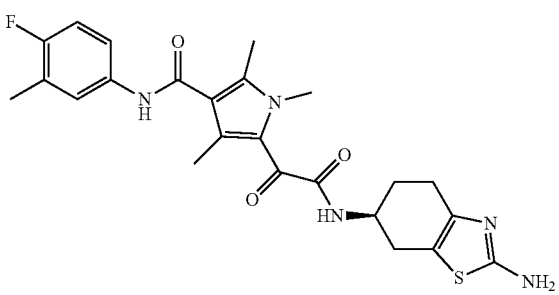 [SMILES: Cc1cc(NC(=O)c2c(C)c(C(=O)C(=O)N[C@H]3CCc4nc(N)sc4C3)n(C)c2C)ccc1F]

The title compounds were prepared following the procedure described in Example 2, Step 5, using (S)-4,5,6,7-tetrahydrobenzo[d]thiazole-2,6-diamine. The final product was purified by reverse phase chromatography eluted with ACN and water and dried using lyophilization to afford the title products as white solids. ESI-MS, m/z 484 (MH)+.

Example 76: (R)-5-(2-((2-amino-4,5,6,7-tetrahydrobenzo[d]thiazol-6-yl)amino)-2-oxoacetyl)-N-(4-fluoro-3-methylphenyl)-1,2,4-trimethyl-1H-pyrrole-3-carboxamide

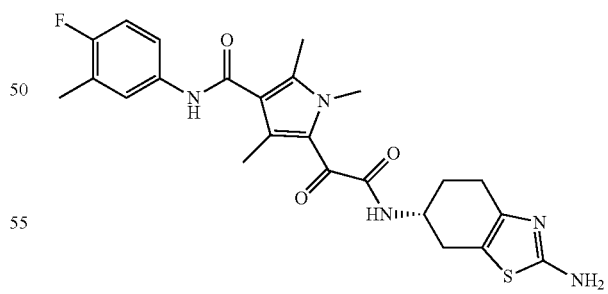

The title compounds were prepared following the procedure described in Example 2, Step 5, using (R)-4,5,6,7-tetrahydrobenzo[d]thiazole-2,6-diamine. The final product was purified by reverse phase chromatography eluted with ACN and water and dried using lyophilization to afford the title products as white solids. ESI-MS, m/z 484 (MH)+.

Example 77: 5-(2-((2-amino-4,5,6,7-tetrahydrobenzo[d]thiazol-6-yl)amino)-2-oxoacetyl)-N-(6-fluoropyridin-3-yl)-1,2,4-trimethyl-1H-pyrrole-3-carboxamide

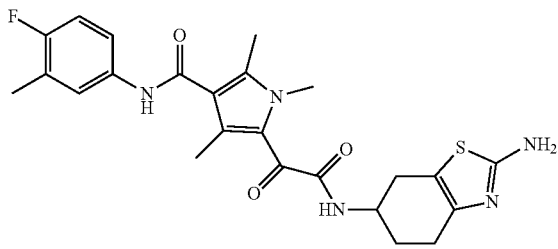 [SMILES: Cc1cc(NC(=O)c2c(C)c(C(=O)C(=O)NC3CCc4nc(N)sc4C3)n(C)c2C)ccc1F]

The title compounds were prepared following the procedure described in Example 5, Step 5, using 4,5,6,7-tetrahydrobenzo[d]thiazole-2,6-diamine. The final product was purified by reverse phase chromatography eluted with ACN and water and dried using lyophilization to afford the title products as white solids. ESI-MS, m/z 471 (MH)+.

Example 78: Synthesis of (R)—N-(4-fluoro-3-methylphenyl)-5-(2-((1-hydroxy-3,3-dimethylbutan-2-yl)amino)-2-oxoacetyl)-1,2,4-trimethyl-1H-pyrrole-3-carboxamide

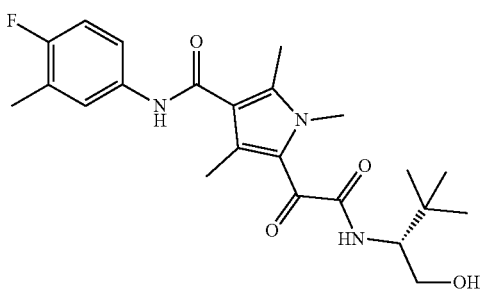 [SMILES: Cc1cc(NC(=O)c2c(C)c(C(=O)C(=O)N[C@@H](CO)C(C)(C)C)n(C)c2C)ccc1F]

The title compounds were prepared following the procedure described in Example 2, Step 5, using D-tert-leucinol. The final product was purified by reverse phase chromatography eluted with ACN and water and dried using lyophilization to afford the title products as white solids. ESI-MS, ink 432.2 (MH)+.

Example 79: Synthesis of 5-(2-((1-(2H-tetrazol-5-yl)ethyl)amino)-2-oxoacetyl)-N-(4-fluoro-3-methylphenyl)-1,2,4-trimethyl-1H-pyrrole-3-carboxamide

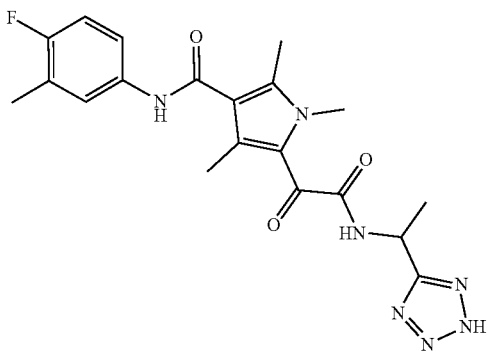 [SMILES: Cc1cc(NC(=O)c2c(C)c(C(=O)C(=O)NC(C)c3nn[nH]n3)n(C)c2C)ccc1F]

The title compounds were prepared following the procedure described in Example 2, Step 5, using 1-(2H-tetrazol-5-yl)ethan-1-amine. The final product was purified by reverse phase chromatography eluted with ACN and water and dried using lyophilization to afford the title products as white solids. ESI-MS, m/z 428 (MH)+.

Example 80: Synthesis of N-(4-fluoro-3-methylphenyl)-1,2,4-trimethyl-5-(2-((3-methyl-1-(2H-tetrazol-5-yl)butyl)amino)-2-oxoacetyl)-1H-pyrrole-3-carboxamide

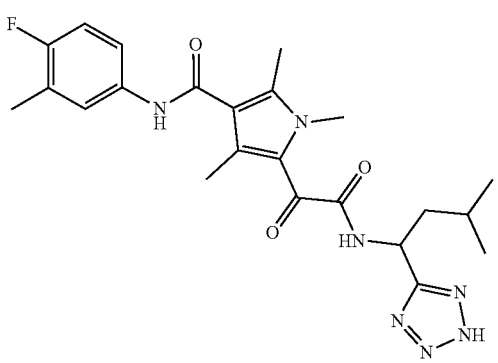 [SMILES: Cc1cc(NC(=O)c2c(C)c(C(=O)C(=O)NC(CC(C)C)c3nn[nH]n3)n(C)c2C)ccc1F]

The title compounds were prepared following the procedure described in Example 2, Step 5, using 3-methyl-1-(2H-tetrazol-5-yl)butan-1-amine. The final product was purified by reverse phase chromatography eluted with ACN and water and dried using lyophilization to afford the title products as white solids. ESI-MS, m/z 470 (MH)+.

Example 81: Synthesis of N-(4-fluoro-3-methylphenyl)-1,2,4-trimethyl-5-(2-((2-methyl-1-(3-methyl-1,2,4-oxadiazol-5-yl)propyl)amino)-2-oxoacetyl)-1H-pyrrole-3-carboxamide

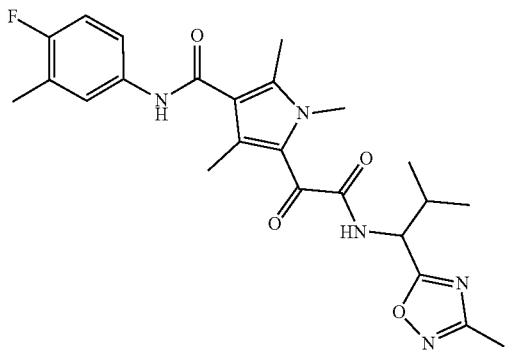 [SMILES: Cc1noc(C(NC(=O)C(=O)c2c(C)c(C(=O)Nc3ccc(F)c(C)c3)c(C)n2C)C(C)C)n1]

The title compounds were prepared following the procedure described in Example 2, Step 5, using 2-methyl-1-(3-methyl-1,2,4-oxadiazol-5-yl)propan-1-amine. The final product was purified by flash chromatography on silica gel eluted with ethyl acetate and hexane to afford the title products as white solids. ESI-MS, m/z 470 (MH)+.

Example 82: Synthesis of N-(4-fluoro-3-methylphenyl)-1,2,4-trimethyl-5-(2-((1-(3-methyl-1,2,4-oxadiazol-5-yl)ethyl)amino)-2-oxoacetyl)-1H-pyrrole-3-carboxamide

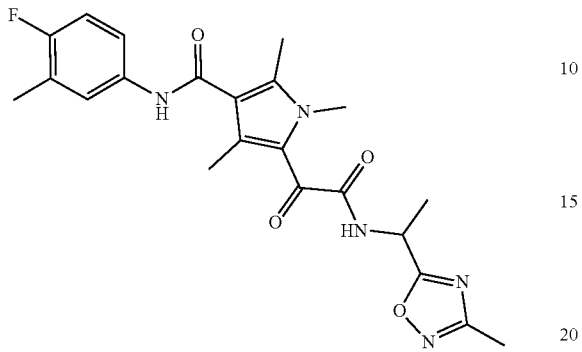

The title compounds were prepared following the procedure described in Example 2, Step 5, using 1-(3-methyl-1,2,4-oxadiazol-5-yl)ethan-1-amine. The final product was purified by flash chromatography on silica gel eluted with ethyl acetate and hexane to afford the title products as white solids. ESI-MS, m/z 470 (MH)+.

Example 83: Synthesis of 5-(2-((cyclopropyl(5-methylthiazol-2-yl)methyl)amino)-2-oxoacetyl)-N-(4-fluoro-3-methylphenyl)-1,2,4-trimethyl-1H-pyrrole-3-carboxamide

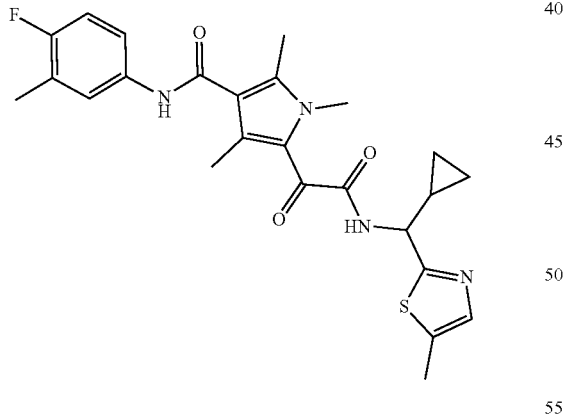

The title compounds were prepared following the procedure described in Example 2, Step 5, using cyclopropyl(5-methylthiazol-2-yl)methanamine. The final product was purified by reverse phase chromatography eluted with ACN and water and dried using lyophilization to afford the title products as white solids. ESI-MS, m/z 483 (MH)+.

Example 84: Synthesis of N-(4-fluoro-3-methylphenyl)-1,2,4-trimethyl-5-(2-((2-(5-methylthiazol-2-yl)propan-2-yl)amino)-2-oxoacetyl)-1H-pyrrole-3-carboxamide

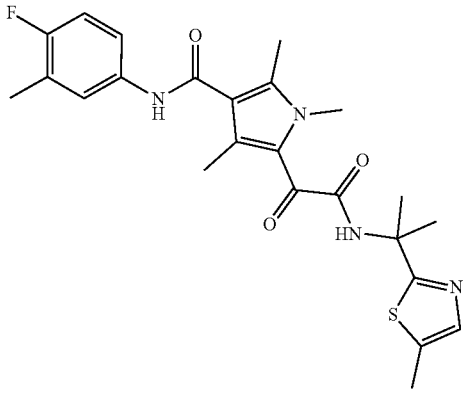 [SMILES: Cc1cnc(C(C)(C)NC(=O)C(=O)c2c(C)c(C(=O)Nc3ccc(F)c(C)c3)c(C)n2C)s1]

The title compounds were prepared following the procedure described in Example 2, Step 5, using 2-(5-methylthiazol-2-yl)propan-2-amine. The final product was purified by flash chromatography on silica gel eluted with ethyl acetate and hexane to afford the title products as pale yellow solids. ESI-MS, m/z 471 (MH)+.

Example 85: Synthesis of N-(4-fluoro-3-methylphenyl)-1,2,4-trimethyl-5-(2-(((3-methyl-1,2,4-oxadiazol-5-yl)(tetrahydro-2H-pyran-4-yl)methyl)amino)-2-oxoacetyl)-1H-pyrrole-3-carboxamide

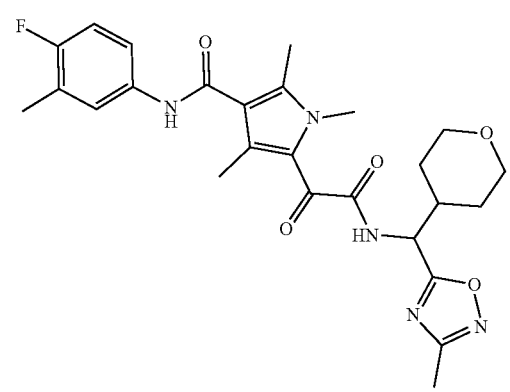 [SMILES: Cc1noc(C(NC(=O)C(=O)c2c(C)c(C(=O)Nc3ccc(F)c(C)c3)c(C)n2C)C2CCOCC2)n1]

The title compounds were prepared following the procedure described in Example 2, Step 5, using (3-methyl-1,2,4-oxadiazol-5-yl)(tetrahydro-2H-pyran-4-yl)methanamine The final product was purified by flash chromatography on silica gel eluted with ethyl acetate and hexane to afford the title products as white solids. ESI-MS, m/z 512 (MH)+.

Example 115: Synthesis of 5-(2-(tert-butylamino)-2-oxoacetyl)-N-(4-fluoro-3-methylphenyl)-1-(2-fluoroethyl)-2,4-dimethyl-1H-pyrrole-3-carboxamide

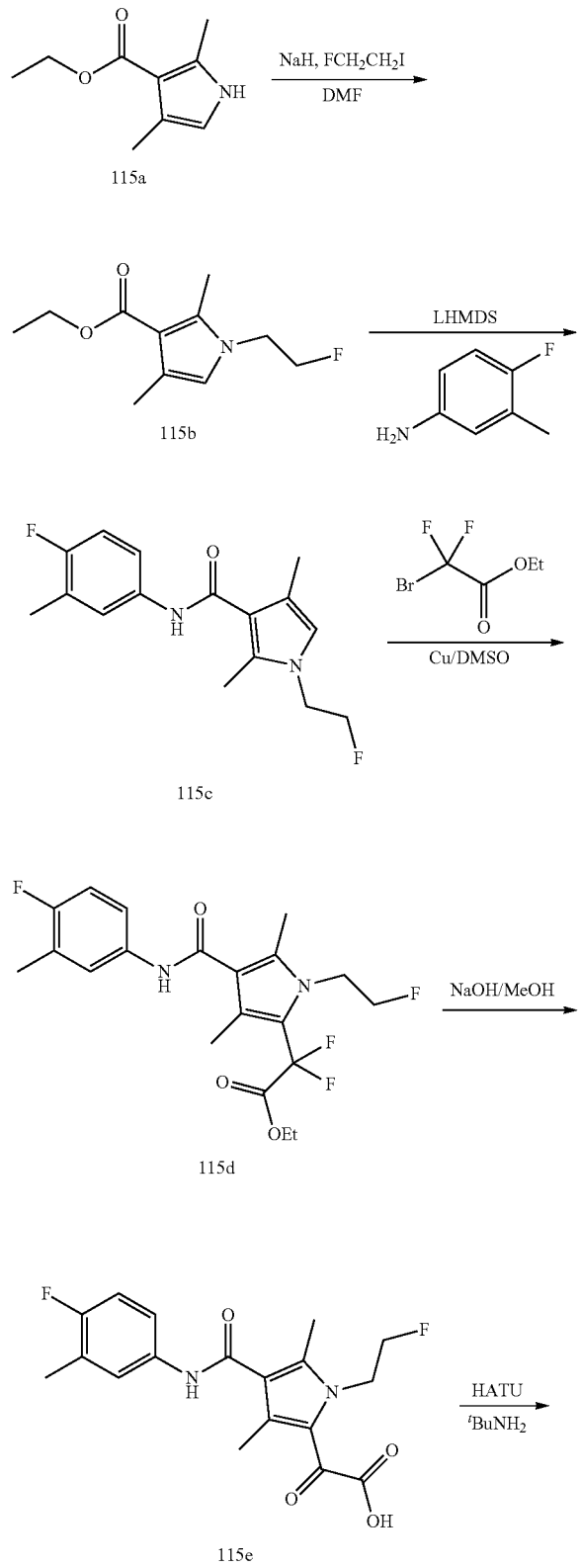

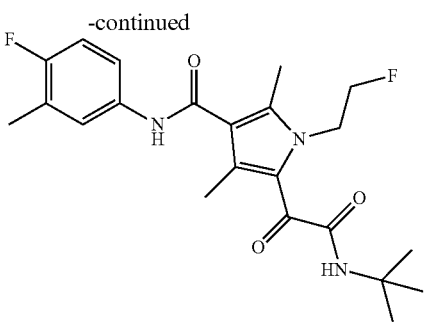

115

Step 1: Synthesis of ethyl 1-(2-fluoroethyl)-2,4-dimethyl-1H-pyrrole-3-carboxylate (115b)

The title compounds were prepared following the procedure described in Example 71, Step 1 using 1-fluoro-2-iodoethane instead of (2-bromoethoxy)(tert-butyl)dimethylsilane. The final product was purified by flash chromatography on silica gel (EtOAc/Hexanes 0~100%) as white solid (3 g): ESI-MS, m/z 214.1 (MH)$^+$.

Step 2: Synthesis of N-(4-fluoro-3-methylphenyl)-1-(2-fluoroethyl)-2,4-dimethyl-1H-pyrrole-3-carboxamide (115c)

The title compounds were prepared following the procedure described in Example 71, Step 2. The final product was purified by flash chromatography on silica gel (EtOAc/Hexanes 0~100%) as yellow solid (3 g): $^1$HNMR (300 MHz, CDCl$_3$) δ 7.46 (dd, 1H, J=2.4 & 6.6 Hz), 7.24-7.28 (m, 1H), 6.95 (dd, 1H, J=8.7 & 9.3 Hz), 6.42 (s, 1H), 4.68 (dd, 1H, J=4.2 & 5.1 Hz), 4.53 (dd, 1H, J=4.5 & 5.4 Hz), 4.13 (dd, 1H, J=4.8 & 5.4 Hz), 4.04 (dd, 1H, J=4.8 & 5.7 Hz), 2.49 (s, 3H), 2.29 (s, 3H), 2.27 (s, 3H); ESI-MS, m/z 293.1 (MH)$^+$.

Step 3: Synthesis of ethyl 2,2-difluoro-2-(4-((4-fluoro-3-methylphenyl)carbamoyl)-1-(2-fluoroethyl)-3,5-dimethyl-1H-pyrrol-2-yl)acetate (115d)

Ethyl 2-bromo-2,2-difluoroacetate (0.6 mL) was added to a mixture of 115c (0.6 g, 2.1 mmol) and Cu (0.6 g, 9.4 mmol) in DMSO (10 mL) at rt. The mixture was flushed with argon, then, heated at 60° C. for 24 hrs. After cooled to rt, the reaction mixture was diluted with EtOAc, washed with aqueous NH$_4$Cl and brine. The organic layer was dried over Na$_2$SO$_4$, filtered, concentrated in vacuo, and purified by flash chromatography on silica gel (EtOAc/Hexanes 0~100%) to afford the product as white solid (0.6 g, 70%). ESI-MS, m/z 415.1 (MH)$^+$.

Step 4: Synthesis of 2-(4-((4-fluoro-3-methylphenyl)carbamoyl)-1-(2-fluoroethyl)-3,5-dimethyl-1H-pyrrol-2-yl)-2-oxoacetic acid (115e)

NaOH (2 N, 3 mL) was added to a solution of 115d (0.2 g, 0.48 mmol) in MeOH (3 mL) at 0° C. The mixture was warmed to rt for 20 hrs. The reaction mixture was diluted with EtOAc, cooled with ice-water and carefully neutralized with aqueous HCl (0.5 N) to pH ~2. The organic layer was washed with brine, concentrated and dried to afford crude product 115e as white solid: ESI-MS, m/z 365.1 (MH)$^+$.

Step 5: Synthesis of 5-(2-(tert-butylamino)-2-oxoacetyl)-N-(4-fluoro-3-methylphenyl)-1-(2-fluoroethyl)-2,4-dimethyl-1H-pyrrole-3-carboxamide HATU (90 mg, 0.24 mmol) was added to a solution of 115e (60 mg) in DMA (0.75 mL) at 0° C., then, a solution of tert-butylamine (20 mg, 0.28) and DIPEA (50 mg, 0.38 mmol) in DMA (0.4 mL) was added dropwise. The reaction mixture was warmed to rt for 20 hrs. The reaction mixture was quenched with aqueous HCl (0.2 N), and extracted with EtOAc. The organic layer was washed with water and brine, concentrated in vacuo, then, purified by reverse phase chromatography eluted with ACN and water, and dried using lyophilization to afford the title product as white solid. ESI-MS, m/z 420.2 (MH)+.

Example 137: Synthesis of N-(4-fluoro-3-methylphenyl)-5-(2-(((1s,4s)-4-hydroxycyclohexyl)amino)-2-oxoacetyl)-1,2,4-trimethyl-1H-pyrrole-3-carboxamide

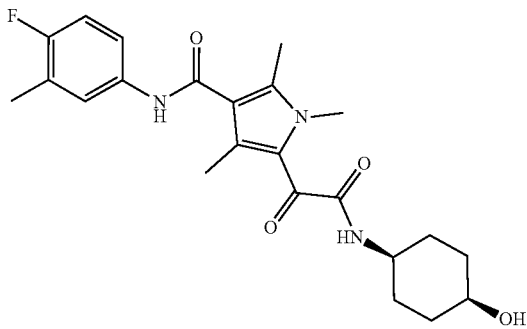 [SMILES: Cc1cc(NC(=O)c2c(C)c(C(=O)C(=O)N[C@H]3CC[C@@H](O)CC3)n(C)c2C)ccc1F]

To a mixture of intermediate 66e from Example 66 (3.2 g, 9.63 mmol), cis-4-hydroxycyclohexylamine hydrochloride (1.61 g, 10.59 mmol) and HATU (4.39 g, 11.56 mmol) in DMF (40 mL) at ambient temperature was added DIPEA (6.22 g, 48.15 mmol). After 2 h the reaction mixture was diluted into 1N HCl and extracted 3× EtOAc. The combined organics were washed sequentially with 1 N HCl, NaHCO$_3$ (sat), and brine, dried over Na$_2$SO$_4$, filtered and concentrated. The crude solids were concentrated from MeCN then suspended in MeCN and warmed to 40° C. After 1 h the mixture was cooled to ambient temperature, filtered and washed with MeCN and the resultant solids were dried in vacuo. The solids were again suspended in MeCN and warmed to 40° C. After 1 h the mixture was cooled to ambient temperature, filtered and washed with MeCN and the resultant solids were dried in vacuo to provide the title compound (2.52 g, 61%) as an off-white solid. $^1$H NMR (400 MHz, DMSO-d$_6$) δ 9.91 (s, 1H), 8.60 (d, J=7.5 Hz, 1H), 7.59 (d, J=6.9 Hz, 1H). 7.46 (m, 1H), 7.06 (t, J=9.3 Hz, 1H), 4.38 (m, 1H), 3.75 (s, 3H), 3.68 (m, 2H), 2.31 (s, 3H), 2.20 (m, 6H), 1.70-1.40 (m, 8H). ESI-MS, m/z 430.2 (MH)+.

Example 170: Synthesis of (R)—N-(2-fluoropyridin-4-yl)-1,2,4-trimethyl-5-(2-oxo-2-(((1,1,1-trifluoropropan-2-yl)amino)acetyl)-1H-pyrrole-3-carboxamide

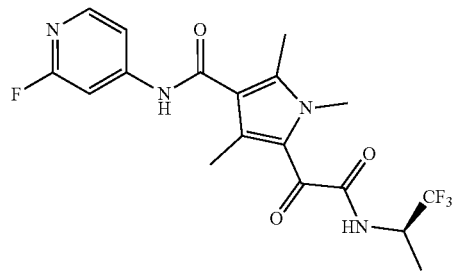 [SMILES: Cc1c(C(=O)Nc2ccnc(F)c2)c(C)n(C)c1C(=O)C(=O)N[C@H](C)C(F)(F)F]

The title compound was prepared following the procedure described in Example 2, substituting 2-fluoro-4-aminopyridine for 4-fluoro-3-methylaniline in Step 2, and substituting (R)-1,1,1-trifluoropropan-2-amine for tert-butylamine in Step 5. The final product was purified by reverse phase chromatography eluted with ACN and water and dried using lyophilization to afford the title products as white solids. $^1$H NMR (400 MHz, CD$_3$OD) δ 8.06 (d, 1H, J=9.3 Hz), 7.52 (s, 1H), 7.42 (d, 1H, J=6.1 Hz), 4.7-4.8 (m, 1H), 3.84 (s, 3H), 2.4 (s, 3H), 2.31 (s, 3H), 1.4 (d, 3H, J=6.9 Hz). ESI-MS, m/z 415.1 (MH)+.

Example 213: Synthesis of N-(4-fluoro-3-methylphenyl)-5-(2-(((1r,4r)-4-hydroxy-4-methylcyclohexyl)amino)-2-oxoacetyl)-1,2,4-trimethyl-1H-pyrrole-3-carboxamide

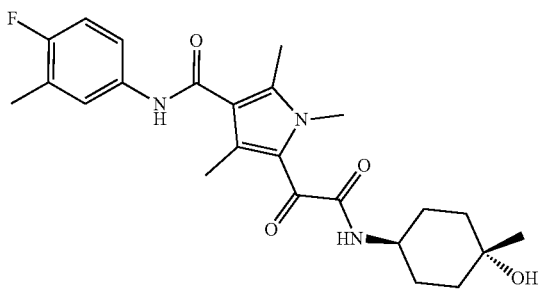

The title compound was prepared following the procedure described in Example 2, Step 5, using (1r,4r)-4-amino-1-methylcyclohexan-1-ol. The final product was purified by reverse phase chromatography eluted with ACN and water and dried using lyophilization to afford the title product as a white solid. $^1$H NMR (300 MHz, CD$_3$OD) δ 8.69 (d, J=7.5 Hz, 1H), 7.59-7.42 (m, 2H), 7.00 (t, J=9.0 Hz, 1H), 3.86-3.81 (m, 4H), 2.38 (s, 3H), 2.32 (s, 3H), 2.26 (s, 3H), 1.97-1.91 (m, 2H), 1.72-1.49 (m, 6H), 1.24 (s, 3H). ESI-MS, m/z 444.2 (MH)+.

Example 228: Synthesis of N-(4-fluoro-3-methylphenyl)-5-(2-(((1s,4s)-4-hydroxy-1-methylcyclohexyl)amino)-2-oxoacetyl)-1,2,4-trimethyl-1H-pyrrole-3-carboxamide

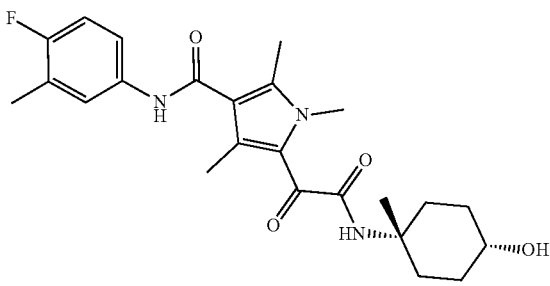 [SMILES: Cc1cc(NC(=O)c2c(C)c(C(=O)C(=O)N[C@]3(C)CC[C@H](O)CC3)n(C)c2C)ccc1F]

The title compound was prepared following the procedure described in Example 2, using (1s,4s)-4-amino-4-methylcyclohexan-1-ol in Step 5. The final product was purified by reverse phase chromatography eluted with ACN and water and dried using lyophilization to afford the title product as a white solid. $^1$H NMR (400 MHz, CD$_3$OD) δ 7.4-7.5 (m, 2H), 6.99 (dd, 1H, J=7.8, 9.3 Hz), 3.81 (s, 3H), 3.80 (br m, 1H), 2.38 (s, 3H), 2.36 (s, 3H), 2.26 (s, 3H), 1.8-2.0 (m, 6H), 1.5-1.6 (m, 2H), 1.46 (s, 3H). ESI-MS, m/z 444.2 (MH)$^+$.

Example 267: Synthesis of N-(4-fluoro-3-methylphenyl)-5-(2-(((1s,3s)-3-hydroxy-1-methylcyclobutyl)amino)-2-oxoacetyl)-1,2,4-trimethyl-1H-pyrrole-3-carboxamide

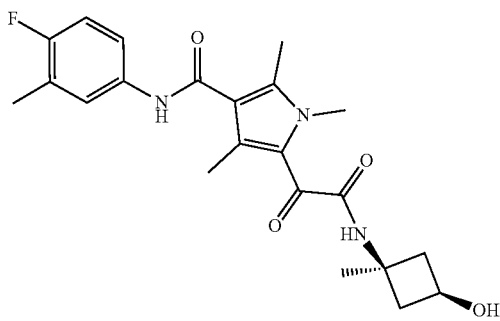 [SMILES: Cc1cc(NC(=O)c2c(C)c(C(=O)C(=O)N[C@]3(C)C[C@H](O)C3)n(C)c2C)ccc1F]

The title compound was prepared following the procedure described in Example 2, using (1s,3s)-3-amino-3-methylcyclobutan-1-ol in Step 5. The final product was purified by reverse phase chromatography eluted with ACN and water and dried using lyophilization to afford the title product as a white solid. $^1$H NMR (400 MHz, CD$_3$OD) δ 7.43-7.49 (m, 2H), 7.0 (dd, 1H, J=8.7, 9.3 Hz), 4.1-4.2 (m, 1H), 3.82 (s, 3H), 2.5-2.6 (m, 2H), 2.38 (s, 3H), 2.37 (s, 3H), 2.2-2.3 (m, 5H), 1.47 (s, 3H). ESI-MS, m/z 416 (MH)$^+$.

Example 273: Synthesis of N-(4-fluoro-3-methylphenyl)-5-(2-(((1r,4r)-4-hydroxy-1-methylcyclohexyl)amino)-2-oxoacetyl)-1,2,4-trimethyl-1H-pyrrole-3-carboxamide

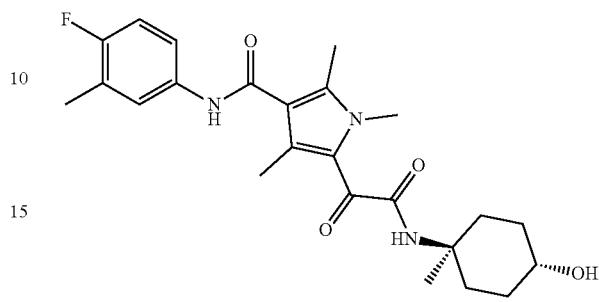

The title compound was prepared following the procedure described in Example 2, using (1r,4r)-4-amino-4-methylcyclohexan-1-ol in Step 5. The final product was purified by reverse phase chromatography eluted with ACN and water and dried using lyophilization to afford the title product as a white solid. $^1$H NMR (400 MHz, CD$_3$OD) δ 7.4-7.5 (m, 2H), 6.99 (dd, 1H, J=7.8, 9.3 Hz), 3.82 (s, 3H), 3.5-3.7 (m, 1H), 2.38 (s, 3H), 2.37 (s, 3H), 2.2-2.3 (m, 2H), 1.5-1.8 (m, 6H), 1.42 (s, 3H). ESI-MS, m/z 445 (MH)$^+$.

Synthesis of Example Compounds 23-26, 28, 30-33, 35, 39-41, 44-46, 51, 52, 54-58, 60-62, 68, 69, 86-114, 116-136, 138-169, 171-212, 214-227, 229-266, 268-272, 274-359 (Structures Shown in Table 1)

Examples 23-26, 28, 30-33, 35, 39-41, 44-46, 51, 52, 54-58, 60-62, 68, 69, 86-114, 119-129, 131-136, 138-169, 171-176, 181-193, 199-200, 204-209, 211, 212, 214-221, 223, 231-240, 242-266, 268-272, and 274-359 (structures shown in Table 1) were prepared in analogy to the procedures described above for Example 2, utilizing the appropriate aryl amine in Step 2, and requisite amine in Step 5. The observed MS data for these Examples are shown in Table 1.

Example compounds 116-118, 130, 177-180, 194-198, 201-203, 210, 222, 224-227, 229, 230, and 241 (structures shown in Table 1), bearing a 1-(2-fluoroethyl) pyrrole moiety were prepared in analogy to the procedures described above for Example 115, utilizing the appropriate aryl amine in Step 2, and requisite amine in Step 5. The observed MS data for these Examples are shown in Table 1.

Synthesis of Example compounds 360 and 361 (structures shown in Table 1)

These Example compounds bearing a 1-(2-hydroxyethyl) pyrrole moiety may be prepared in analogy to the procedures described above for Example 50, utilizing the requisite amine in Step 5.

Example 362: Synthesis of 5-(2-(tert-butylamino)-2-oxoacetyl)-N-(5-fluoropyridin-2-yl)-1,2,4-trimethyl-1H-pyrrole-3-carboxamide (structure shown in Table 1)

The title compound may be prepared according to the procedure of Example 2, utilizing 5-fluoro-2-aminopyridine in Step 2, and tert-butyl amine in Step 5.

461

Example 363: Synthesis of 5-(2-(tert-butylamino)-2-oxoacetyl)-4-chloro-N-(4-fluoro-3-methylphenyl)-1,2-dimethyl-1H-pyrrole-3-carboxamide

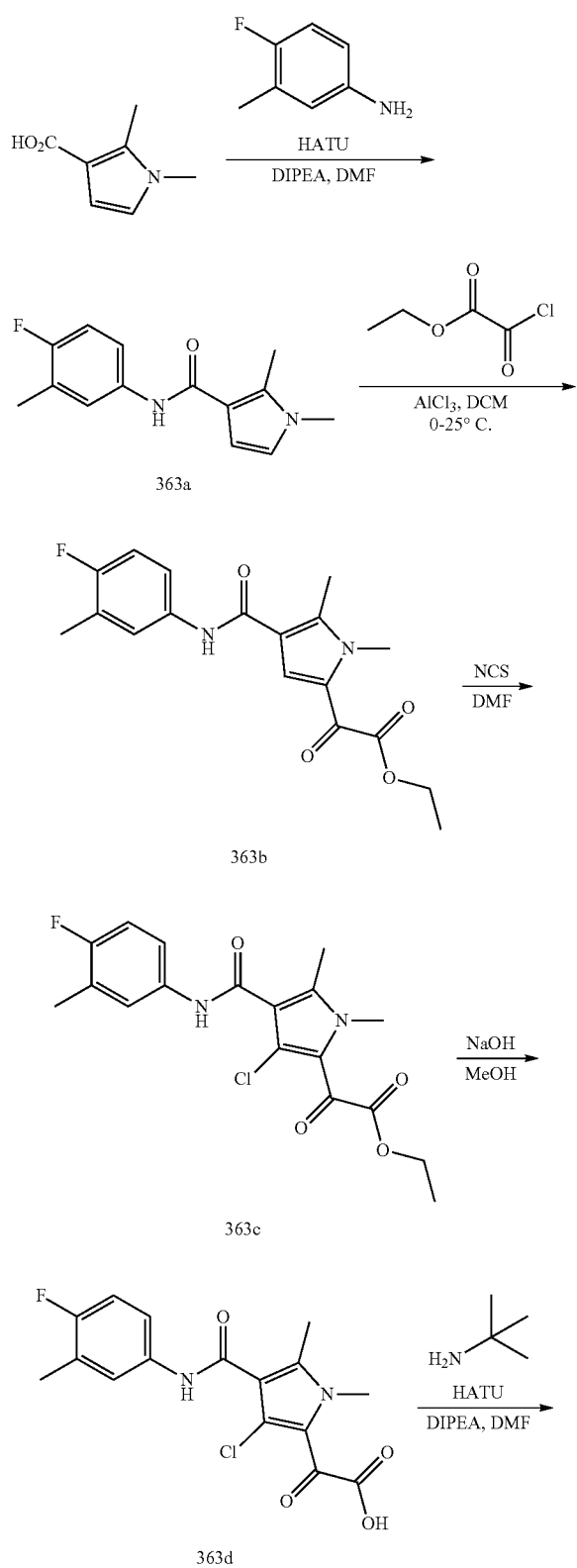

462

-continued

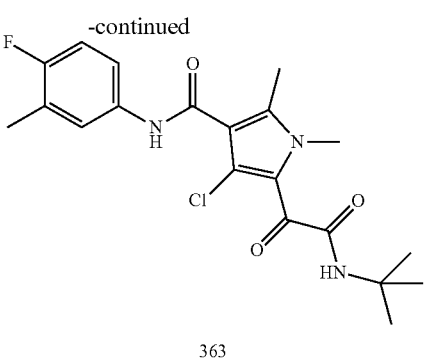

363

Step 1: Synthesis of N-(4-fluoro-3-methylphenyl)-1,2-dimethyl-1H-pyrrole-3-carboxamide (363a)

To a solution of 1,2-dimethyl-1H-pyrrole-3-carboxylic acid (1.0 g, 7.19 mmol), 3-methyl-4-fluoroaniline (989 mg, 7.91 mmol) and HATU (3.28 g, 8.63 mmol) in DMF (20 mL) was added DIPEA (3.76 mL, 21.57 mmol). After 96 h, the reaction mixture was warmed to 50° C. After an additional 16 h, the reaction mixture was cooled to ambient temperature, diluted with EtOAc and washed successively with 1N HCl, NaHCO₃ (sat), and brine. The organic layer was dried over Na₂SO₄, filtered and concentrated in vacuo. The crude residue was purified via flash chromatography on silica gel (EtOAc/hexanes 5-60%) to afford the title compound (690 mg, 39%) as an off-white solid ESI-MS, m/z 247.2 (MH)⁺

Step 2: Synthesis of ethyl 2-(4-((4-fluoro-3-methylphenyl)carbamoyl)-1,5-dimethyl-1H-pyrrol-2-yl)-2-oxoacetate (363b)

To a solution of 363a (690 mg, 2.8 mmol) in DCM (30 mL) at 0° C. was added ethyl 2-chloro-2-oxoacetate (847 µL, 7.56 mmol). After 15 min, AlCl₃ (933 mg, 7.0 mmol) was added in several portions and then the reaction mixture was allowed to warm slowly to ambient temperature. After 16 h, the reaction mixture was quenched slowly with ice, diluted with water and separated. The aqueous layer was further extracted with DCM, then the combined organics were washed with water, NaHCO₃ (sat) and brine, dried over Na₂SO₄, filtered and concentrated in vacuo. The crude residue was purified via flash chromatography on silica gel (EtOAc/hexanes 5-80%) to afford the title compound (600 mg, 62%) as an off-white solid ESI-MS, m/z 347.1 (MH)⁺

Step 3: Synthesis of ethyl 2-(3-chloro-4-((4-fluoro-3-methylphenyl)carbamoyl)-1,5-dimethyl-1H-pyrrol-2-yl)-2-oxoacetate (363c)

To a solution of 363b (600 mg, 1.73 mmol) in DMF (10 mL) was added N-chlorosuccinimide (694 mg, 5.2 mmol). After 16 h, the reaction mixture was diluted with EtOAc and washed successively with 2×1 N HCl, NaHCO₃ (sat) and brine, dried over Na₂SO₄, filtered and concentrated. The crude residue was purified via flash chromatography on silica gel (EtOAc/hexanes 5-70%) to afford the title compound (400 mg, 61%) as an pale yellow solid ESI-MS, m/z 415.1 (MH)⁺

Step 4: Synthesis of 2-(3-chloro-4-((4-fluoro-3-methylphenyl)carbamoyl)-1,5-dimethyl-1H-pyrrol-2-yl)-2-oxoacetic acid (363d)

To a solution of 363c (400 mg, 1.05 mmol) in MeOH (10 mL) was added 1 N NaOH (2.1 mL). After 2 h, the reaction mixture was diluted with 1 N HCl to pH ~1 then concentrated three times from MeOH. Salts were triturated with DCM and the mixture was filtered and concentrated to afford the title compound (370 mg, quant) and an off-white solid ESI-MS, m/z 353.1 (MH)⁺

Step 5: Synthesis 5-(2-(tert-butylamino)-2-oxoacetyl)-4-chloro-N-(4-fluoro-3-methylphenyl)-1,2-dimethyl-1H-pyrrole-3-carboxamide (363)

To a solution of 363d (50 mg, 0.14 mmol), tert-butyl amine (12 mg, 0.16 mmol), and HATU (64 mg, 0.17 mmol) in DMF (1 mL) was added DIPEA (73 µL, 0.42 mmol). After 1 h the reaction mixture was diluted into 1 N HCl and extracted 3× with EtOAc. The combined organics were washed with 1 N HCl, NaHCO₃ (sat) and brine, dried over Na₂SO₄, filtered and concentrated. The crude residue was purified via reverse phase chromatography eluted with ACN and water and dried using lyophilization to afford the title products as white solids. ESI-MS, m/z 406.2 (MH)⁺.

Synthesis of Example Compounds 364-376
(Structures Shown in Table 1)

Examples 374-376 were prepared in analogy to the procedures described above for Example 363, utilizing the appropriate aryl amine in Step 1, and requisite amine in Step 5. The observed MS data for these Examples are shown in Table 1.

Example 377: Synthesis of N-(3,4-difluorophenyl)-4-methoxy-1,2-dimethyl-5-(2-oxo-2-((1-(trifluoromethyl)cyclopropyl)amino)acetyl)-1H-pyrrole-3-carboxamide

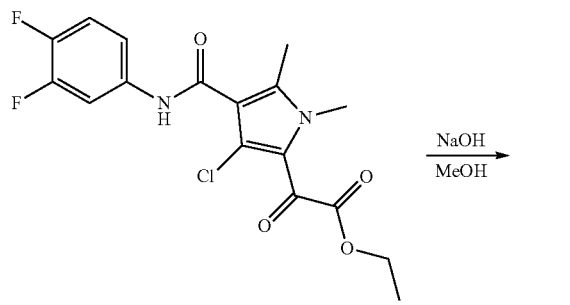

377a

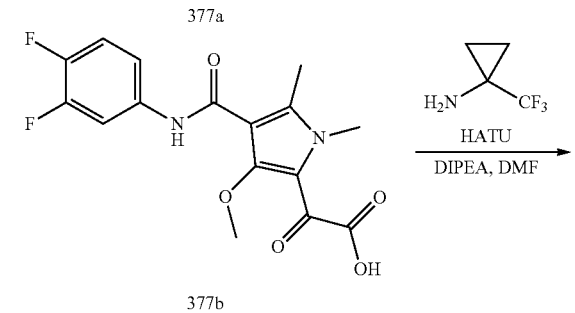

377b

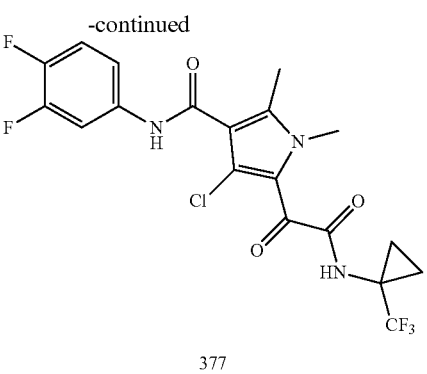

377

Compound 377a was prepared in analogy to the procedures described above for Example 363, utilizing 3,4-difluoroaniline in Step 1.

Step 1: Synthesis of 2-(4-((3,4-difluorophenyl)carbamoyl)-3-methoxy-1,5-dimethyl-1H-pyrrol-2-yl)-2-oxoacetic acid (377b)

To a solution of 377a (2.31 g, 6.0 mmol) in MeOH (20 mL) and THF (20 mL) was added 1 N NaOH (7 mL). After 2 h the reaction mixture was concentrated to remove organics, diluted with water and washed with EtOAc. The aqueous layer was acidified to pH ~1 using conc. HCl and extracted 3× with EtOAc. The combined organics were washed with brine, dried over Na₂SO₄, filtered and concentrated to afford the title compound (1.28 g, 60%) as a foamy tan solid which was taken forward without further purification ESI-MS, m/z 353.1 (MH)⁺

Step 2: Synthesis of N-(4-fluoro-3-methylphenyl)-4-methoxy-1,2-dimethyl-5-(2-oxo-2-((1-(trifluoromethyl)cyclopropyl)amino)acetyl)-1H-pyrrole-3-carboxamide (377)

To a solution of 377b (50 mg, 0.14 mmol), 1-(trifluoromethyl)cyclopropan-1-amine hydrochloride (24 mg, 0.15 mmol) and HATU (65 mg, 0.17 mmol) in DMF (1 mL) was added DIPEA (122 µL, 0.7 mmol). After 2 h the reaction mixture was purified directly via reverse phase HPLC eluted with ACN and water and dried using lyophilization to afford the title product as a white solid. ESI-MS, m/z 460.2 (MH)⁺.

Synthesis of Example Compounds 378-385
(Structures Shown in Table 1)

Examples 378-385 were prepared in analogy to the procedures described above for Example 377, utilizing the requisite amine in Step 2. The observed MS data for these Examples are shown in Table 1.

Example 386: Synthesis of 5-(2-(tert-butylamino)-2-oxoacetyl)-2-chloro-N-(4-fluoro-3-methylphenyl)-1,4-dimethyl-1H-pyrrole-3-carboxamide

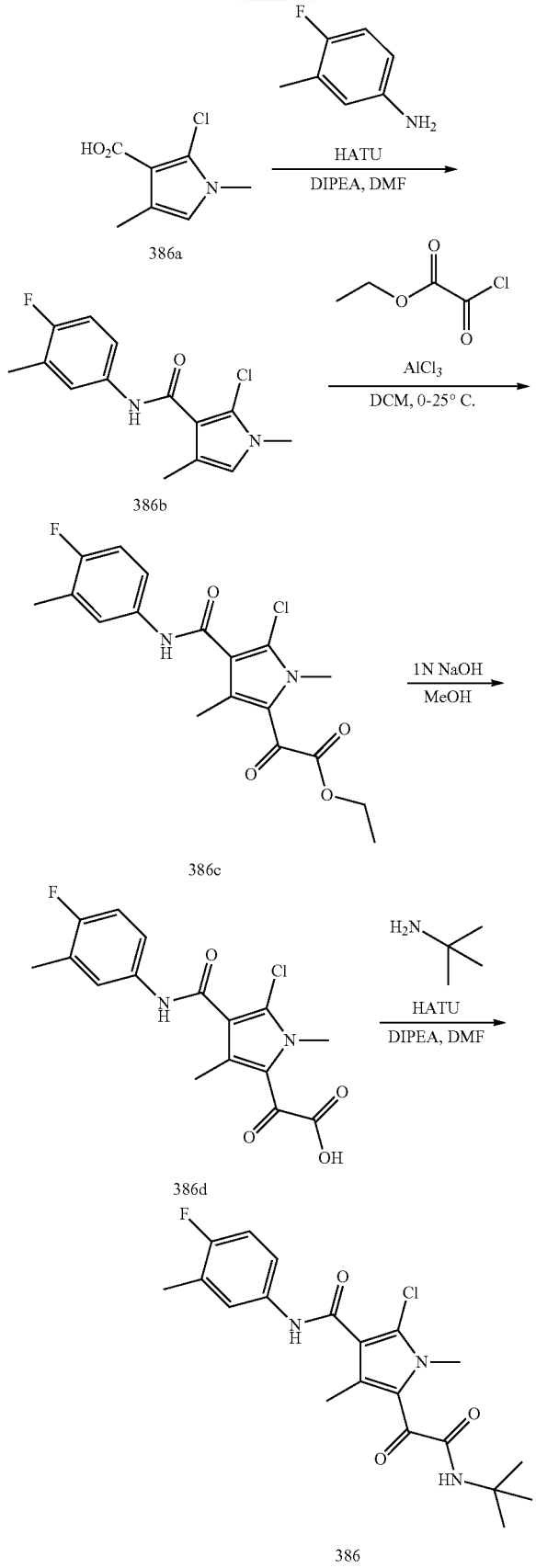

Step 1: Synthesis of
2-chloro-1,4-dimethyl-1H-pyrrole-3-carboxylic acid
(386a)

To a solution of 1,4-dimethyl-1H-pyrrole-3-carboxylic acid (1.0 g, 7.19 mmol) in THF (50 mL) at −78° C. was added LDA (7.9 mL, 15.8 mmol, 2 M THF/benzene) dropwise over 20 min. After 2 h, a solution of NCS (1.15 g, 8.63 mmol) in THF (20 mL) was added dropwise over 20 min and the cooling bath was removed. After 16 h, the reaction mixture was diluted with 1N HCl and extracted 3× EtOAc. The combined organics were washed with 2× water, $NaHCO_3$ (sat) and brine, dried over $Na_2SO_4$, filtered and concentrated. The crude residue was purified via reverse phase HPLC eluting with ACN and water and dried using lyophilization to afford the title product (770 mg, 62%) as an off-white solid. ESI-MS, m/z 174.1 $(MH)^+$.

Step 2: Synthesis of 2-chloro-N-(4-fluoro-3-methylphenyl)-1,4-dimethyl-1H-pyrrole-3-carboxamide
(386b)

To a solution of 386b (770 mg, 4.44 mmol), 3-methyl-4-fluoroaniline (666 mg, 5.32 mmol) and HATU (2.19 g, 5.77 mmol) in DMF (12 mL) was added DIPEA (2.32 mL, 13.3 mmol). After 1 h, the reaction mixture was heated to 50° C. After 5 h reaction mixture was cooled to ambient temperature, diluted with EtOAc and washed successively with 1 N HCl, $NaHCO_3$ (sat) and brine, dried over $Na_2SO_4$, filtered and concentrated. The crude residue was precipitated from EtOAc, filtered, and the solids were washed with hexanes and dried in vacuo to afford the title product (750 mg, 60%) as an off-white solid. ESI-MS, m/z 281.1 $(MH)^+$.

Step 3: Synthesis of ethyl 2-(5-chloro-4-((4-fluoro-3-methylphenyl)carbamoyl)-1,3-dimethyl-1H-pyrrol-2-yl)-2-oxoacetate (386c)

To a solution of 386b (750 mg, 2.67 mmol) in DCM (20 mL) at 0° C. were added ethyl 2-chloro-2-oxoacetate (807 μL, 7.21 mmol) and $AlCl_3$ (890 mg, 6.68 mmol). After 16 h additional quantities of ethyl 2-chloro-2-oxoacetate (807 μL, 7.21 mmol) and $AlCl_3$ (890 mg, 6.68 mmol) were added. After 4 h, the reaction mixture was quenched with ice and water, and separated. The aqueous layer was extracted twice with DCM. The combined organics were washed with water, $NaHCO_3$ (sat) and brine, dried over $Na_2SO_4$, filtered and concentrated. The crude residue was purified via flash chromatography on silica gel (5-80% EtOAc/hexanes) to afford the title product (570 mg, 56%) as a yellow foam. ESI-MS, m/z 381.2 $(MH)^+$.

Step 4: Synthesis of 2-(5-chloro-4-((4-fluoro-3-methylphenyl)carbamoyl)-1,3-dimethyl-1H-pyrrol-2-yl)-2-oxoacetic acid (386d)

To a suspension of 386c (570 mg, 1.5 mmol) in MeOH (10 mL) was added 1N NaOH (3 mL) and a solution was formed. After 2 h the reaction mixture was diluted with 1 N HCl and concentrated 3× from MeOH. The resultant solids were suspended in DCM, filtered, and washed with DCM. The solids were then dissolved in MeOH, filtered and concentrated to afford the title product (525 mg, 99%) as a tan solid. ESI-MS, m/z 353.1 (MH)+.

Step 5: Synthesis of 5-(2-(tert-butylamino)-2-oxoacetyl)-2-chloro-N-(4-fluoro-3-methylphenyl)-1,4-dimethyl-1H-pyrrole-3-carboxamide (386)

To a solution of 386d (50 mg, 0.14 mmol), tert-butylamine (12 mg, 0.16 mmol) and HATU (65 mg, 0.17 mmol) in DMF (1 mL) was added DIPEA (73 µL, 0.42 mmol). After 2 h, the reaction mixture was purified directly via reverse phase HPLC eluting with ACN and water and dried using lyophilization to afford the title product (33 mg, 58%) as an off-white solid. ESI-MS, m/z 430.2 (MNa)+.

Synthesis of Example Compounds 387-391
(Structures Shown in Table 1)

Examples 387-391 were prepared in analogy to the procedures described above for Example 386, utilizing the appropriate aryl amine in Step 2 and requisite amine in Step 5. The observed MS data for these Examples are shown in Table 1.

Example 392: Synthesis of 3-(2-(tert-butylamino)-2-oxoacetyl)-N-(3-cyano-4-fluorophenyl)-5,6,7,8-tetrahydroindolizine-1-carboxamide

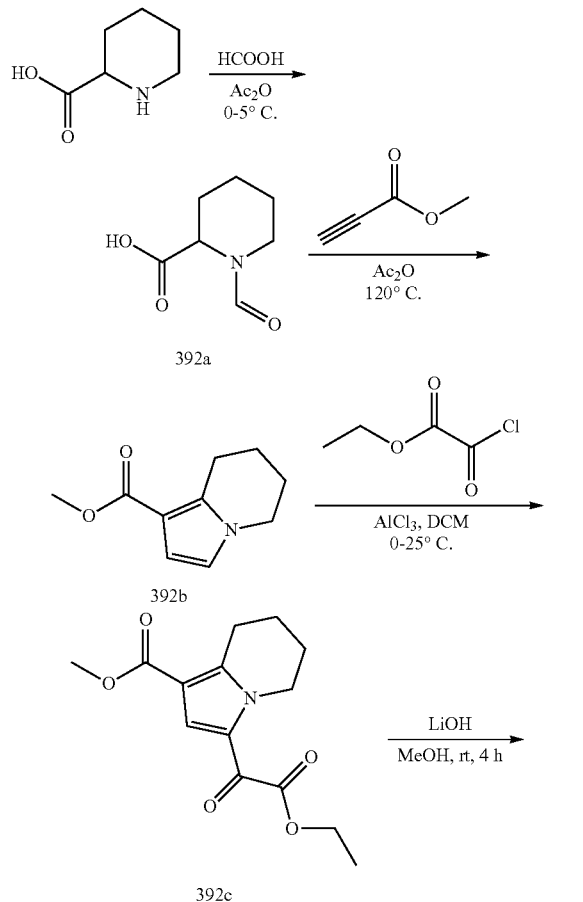
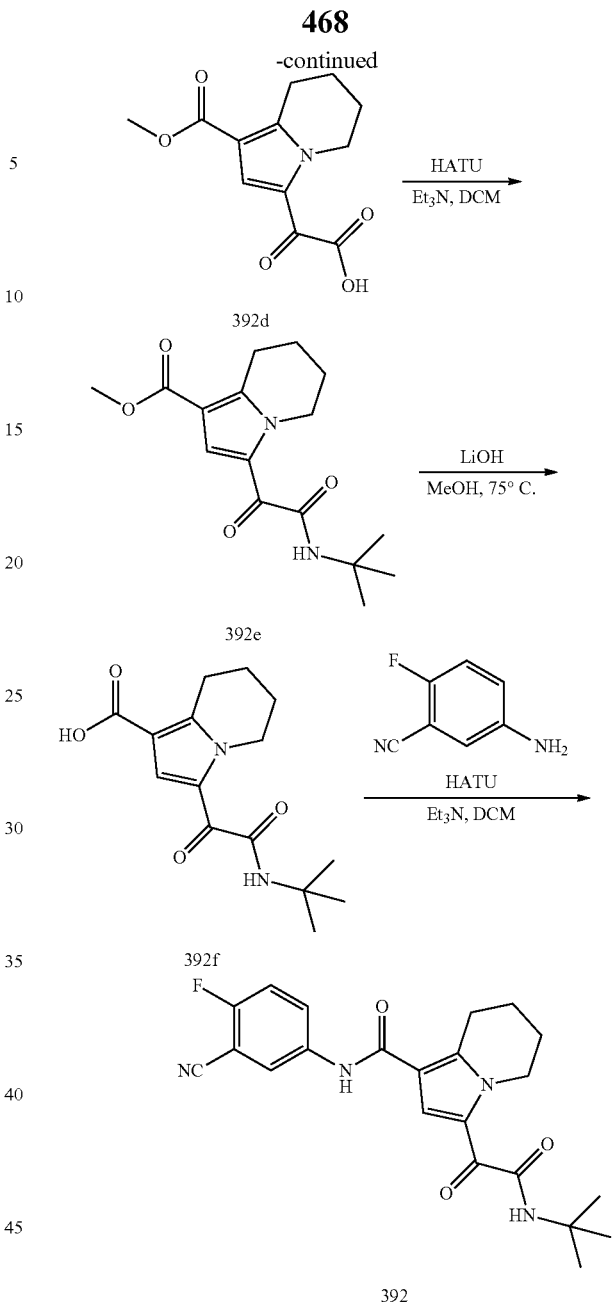

Step 1. Synthesis of 1-formylpiperidine-2-carboxylic acid (392a)

To a solution of piperidine-2-carboxylic acid (4.9 g, 38 mmol) in formic acid (30 mL) was added acetic anhydride (50 mL) at 0° C. The resulting mixture was stirred 0 to 5° C. for 4 h. LCMS showed the reaction was complete. The mixture was concentrated in vacuo to obtain crude product 80a (7.1 g) as colorless oil. MS (ESI): mass calcd. for $C_7H_{11}NO_3$ 157.07, m/z found 158.1 [M+H]+.

Step 2. Synthesis of methyl 5,6,7,8-tetrahydroindolizine-1-carboxylate (392b)

To a solution of intermediate 392a (7.1 g, 45 mmol) in acetic anhydride (70 mL) was added methyl propiolate (5.04 g, 60 mmol). The resulting mixture was stirred at 120° C. for 2 h under $N_2$. MS showed the desired product, and the reaction was concentrated in vacuo. The residue was purified by column chromatography (EtOAc/petroleum ether: 0-10%) to obtain the title compound (1.4 g, 17%) as white solid. MS (ESI): mass calcd. for $C_{10}H_{13}NO_2$ 179.09, m/z found 179.8 [M+H]$^+$.

Step 3. Synthesis of methyl 3-(2-ethoxy-2-oxoacetyl)-5,6,7,8-tetrahydroindolizine-1-carboxylate (392c)

To a solution of compound 392b (538 mg, 3 mmol) and ethyl 2-chloro-2-oxoacetate (620 mg, 4.5 mmol) in DCM (15 mL), $AlCl_3$ (790 mg, 6 mmol) was added slowly at 0° C. The resulting mixture was warmed to RT and stirred for 5 h. Water (20 mL) was added slowly, and the mixture was extracted with DCM (3×20 mL), the combined organic extract was dried over $Na_2SO_4$, and concentrated. The residue was purified by column chromatography (EtOAc/petroleum ether: 0-20%) to obtain the title compound (930 mg crude) as a colorless oil. MS (ESI): mass calcd. for $C_{14}H_{17}NO_5$ 279.11, m/z found 280.1 [M+H]$^+$.

Step 4. Synthesis of 2-(1-(methoxycarbonyl)-5,6,7,8-tetrahydroindolizin-3-yl)-2-oxoacetic acid (392d)

To a solution of 392c (930 mg, 3.3 mmol) in MeOH (30 mL) was added 1 N LiOH aq. (60 mL). The resulting mixture was stirred for 5 h at RT. The mixture was poured into ice water (30 mL) and acidified using 1 N aqueous HCl to pH=3. The resulting solid was isolated by filtration to obtain the titled compound (530 mg, 63%) as white solid. MS (ESI): mass calcd. for $C_{12}H_{13}NO_5$ 251.08, m/z found 252.1 [M+H]$^+$.

Step 5. Synthesis of methyl 3-(2-(tert-butylamino)-2-oxoacetyl)-5,6,7,8-tetrahydroindolizine-1-carboxylate (392e)

To a solution of 392d (500 mg, 2 mmol), HATU (1.1 g, 4 mmol), DIPEA (520 mg, 4 mmol) in DCM (30 mL), 2-methylpropan-2-amine (500 mg, 2 mmol) was added. The resulting mixture was stirred for 2 h at rt. The mixture was concentrated and purified by column chromatography (EtOAc/petroleum ether: 0-15%) to obtain the title compound (480 mg, 79%) as white solid. MS (ESI): mass calcd. for $C_{16}H_{22}N_2O_4$ 306.1, m/z found 307.1 [M+H]$^+$.

Step 6. Synthesis of 3-(2-(tert-butylamino)-2-oxoacetyl)-5,6,7,8-tetrahydroindolizine-1-carboxylic acid (392f)

To a solution of 392e (480 mg, 1.6 mmol) in MeOH (20 mL), LiOH aq. (30 mL) was added. The resulting mixture was stirred for 2 h at 80° C. The mixture was concentrated and water (30 mL) was added and acidified using 1 N aqueous HCl to pH=3. The resulting solid was isolated by filtration to obtain the title compound (340 mg, 74%) as white solid. MS (ESI): mass calcd. for $C_{15}H_{20}N_2O_4$ 292.14, m/z found 293.1 [M+H]$^+$.

Step 7. Synthesis of 3-(2-(tert-butylamino)-2-oxoacetyl)-N-(3-cyano-4-fluorophenyl)-5,6,7,8-Tetrahydroindolizine-1-carboxamide To a solution of 392f (120 mg, 0.4 mmol), HATU (310 mg, 0.8 mmol), and $Et_3N$ (520 mg, 4 mmol) in DCM (20 mL), 5-amino-2-fluorobenzonitrile (82 mg, 1.5 mmol) was added. The resulting mixture was stirred for 13 h at RT. The mixture was concentrated and purified by column chromatography (EtOAc/petroleum ether: 0-10%) to obtain the title compound (14 mg, 9%) as white solid. MS (ESI): mass calcd. for $C_{22}H_{23}FN_4O_3$ 410.18, m/z found 411.1 [M+H]$^+$. $^1$H NMR (400 MHz, CDCl3) δ 8.80 (s, 1H), 8.74 (d, J=4.3 Hz, 1H), 8.46 (d, J=8.3 Hz, 1H), 7.46 (dd, J=8.3, 4.5 Hz, 1H), 7.13 (s, 1H), 4.43 (t, J=5.8 Hz, 2H), 3.21 (t, J=6.2 Hz, 2H), 2.06-1.91 (m, 4H), 1.47 (s, 9H).

Example 393: Synthesis of 3-(2-(tert-butylamino)-2-oxoacetyl)-N-(4-fluoro-3-methylphenyl)-5,6,7,8-tetrahydroindolizine-1-carboxamide

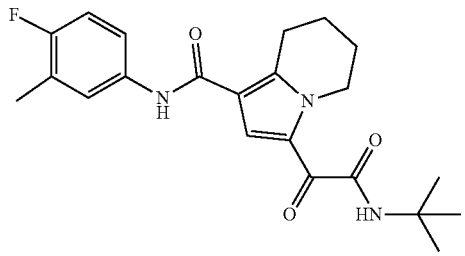 [SMILES: Cc1cc(NC(=O)c2cc(C(=O)C(=O)NC(C)(C)C)n3c2CCCC3)ccc1F]

The title compound was prepared according to the procedure of Example 392, substituting 4-fluoro-3-methylaniline for 5-amino-2-fluorobenzonitrile in Step 7. MS (ESI): mass calcd. for $C_{22}H_{26}FN_3O_3$ 399.20, m/z found 401.1 [M+H]$^+$. $^1$H NMR (400 MHz, CDCl$_3$) δ 8.40 (s, 1H), 7.61 (s, 1H), 7.51 (d, J=6.8 Hz, 1H), 7.31 (s, 1H), 6.98 (t, J=9.0 Hz, 1H), 4.39 (t, J=6.0 Hz, 2H), 3.30 (t, J=6.4 Hz, 2H), 2.30 (s, 3H), 2.06-1.95 (m, 2H), 1.95-1.80 (m, 2H), 1.47 (s, 9H).

Synthesis of Example Compounds 394-433
(Structures Shown in Table 1)

Examples 394-433 were prepared in analogy to the procedures described above for Example 392, utilizing the requisite amine in Step 5, and the appropriate aryl amine in Step 7. The observed MS data for these Examples are shown in Table 1.

Example 434: Synthesis of 3-(2-(tert-butylamino)-2-oxoacetyl)-N-(4-fluoro-3-methylphenyl)-2-methyl-5,6,7,8-tetrahydroindolizine-1-carboxamide

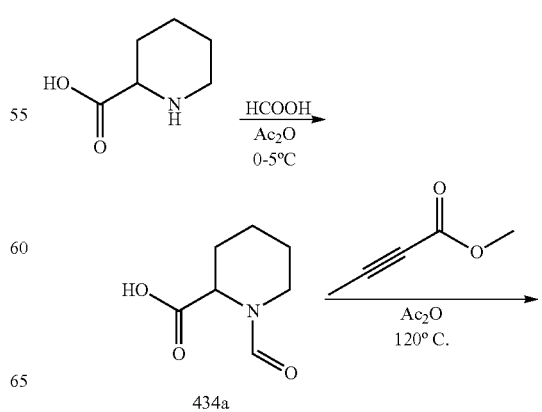

434a

471
-continued

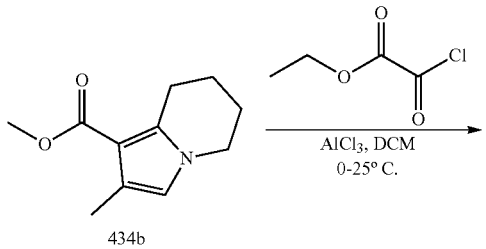
434b

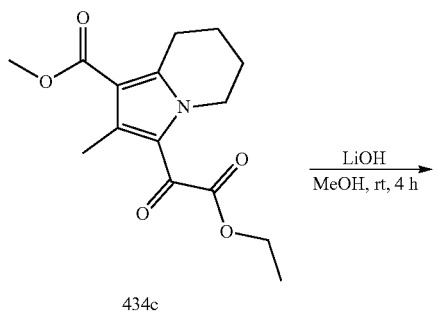
434c

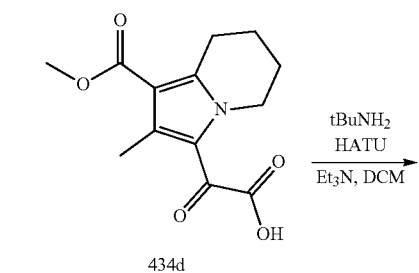
434d

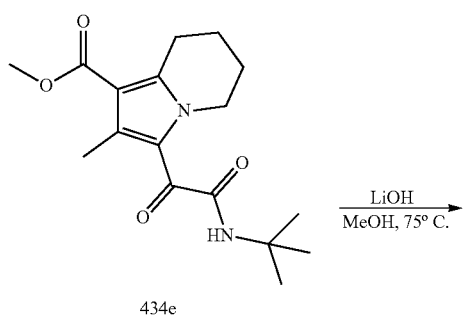
434e

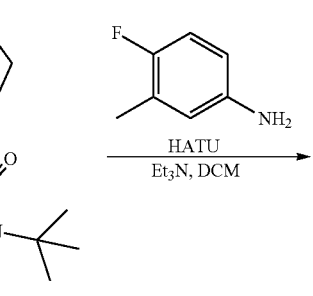
434f

472
-continued

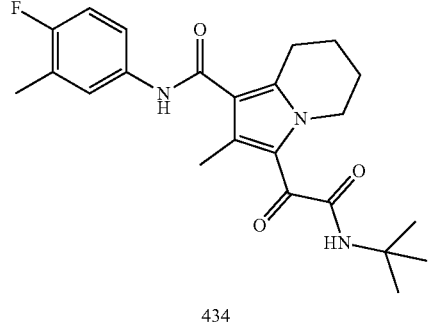
434

The title compound was prepared according to the procedure of Example 392, substituting methyl but-2-ynoate for methyl propionate in Step 2, and 4-fluoro-3-methylaniline for 5-amino-2-fluorobenzonitrile in Step 7. $^1$H NMR (400 MHz, CDCl$_3$) δ 7.46 (d, J=6.2 Hz, 1H), 7.19 (s, 1H), 6.99 (t, J=9.1 Hz, 1H), 6.41 (s, 1H), 4.23 (t, J=5.8 Hz, 2H), 3.09 (t, J=6.2 Hz, 2H), 2.47 (s, 3H), 2.30 (s, 3H), 1.95 (d, J=5.4 Hz, 2H), 1.85 (d, J=5.5 Hz, 2H), 1.48 (s, 9H). MS (ESI): mass calcd. for C$_{23}$H$_{28}$FN$_3$O$_3$ 413.21, m/z found 414.1 [M+H]$^+$.

Example 435: Synthesis of 3-(2-(tert-butylamino)-2-oxoacetyl)-N-(3-cyano-4-fluorophenyl)-2-methyl-5,6,7,8-tetrahydroindolizine-1-carboxamide

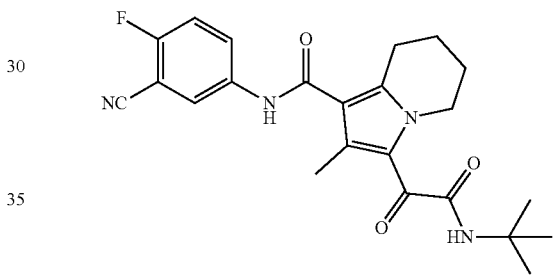

The title compound was prepared according to the procedure of Example 392, substituting methyl but-2-ynoate for methyl propionate in Step 2. MS (ESI): mass calcd. for C$_{23}$H$_{25}$FN$_4$O$_3$ 424.19, m/z found 425.1 [M+H]+. $^1$H NMR (400 MHz, CDCl$_3$) δ 8.75 (d, J=4.2 Hz, 1H), 8.46 (d, J=8.4 Hz, 1H), 7.46 (dd, J=8.2, 4.3 Hz, 1H), 6.43 (s, 1H), 4.23 (d, J=5.8 Hz, 2H), 3.30 (t, J=6.1 Hz, 2H), 2.98 (s, 1H), 2.91 (s, 1H), 2.58 (s, 3H), 1.94 (dd, J=15.7, 6.7 Hz, 2H), 1.48 (s, 9H).

Example 444: Synthesis of N-(4-fluoro-3-methylphenyl)-3-(2-((2-hydroxy-2-methylpropyl)amino)-2-oxoacetyl)-2-methyl-5,6,7,8-tetrahydroindolizine-1-carboxamide The title compound was prepared according to the procedure for Example 434, utilizing 2-amino-2-methylpropan-1-ol in Step 5, and 4-fluoro-3-methylaniline in Step 7, to provide a white solid. $^1$H NMR (300 MHz, DMSO-d$_6$) δ 9.78 (s, 1H), 8.53-8.49 (m, 1H), 7.62-7.58 (m, 1H), 7.49-7.45 (m, 1H), 7.08 (t, J=8 Hz, 2H), 4.51 (s, 1H), 4.24-4.20 (m, 2H), 3.16 (d, J=8 Hz, 2H), 2.92-2.88 (m, 2H), 2.22 (s, 6H), 1.90-1.86 (m, 2H), 1.76-1.72 (m, 2H), 1.12 (s, 6H). ESI-MS, m/z 430.1 (MH)$^+$. Synthesis of Example compounds 436-443 and 445-488 (structures shown in Table 1).

Examples 436-488 were prepared in analogy to the procedures described above for Example 434, utilizing the requisite amine and the appropriate aryl amine for preparation of the required intermediates. The observed MS data for these Examples are shown in Table 1.

Example 489: Synthesis of 3-(2-(tert-butylamino)-2-oxoacetyl)-N-(3-cyano-4-fluorophenyl)-5,6,7,8-tetrahydroindolizine-1-carboxamide

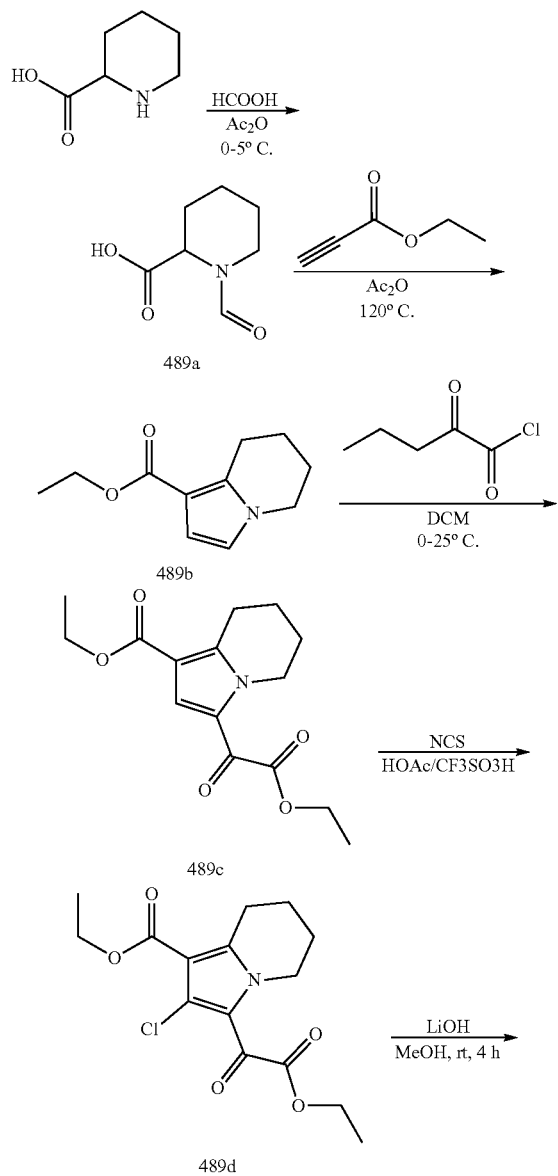
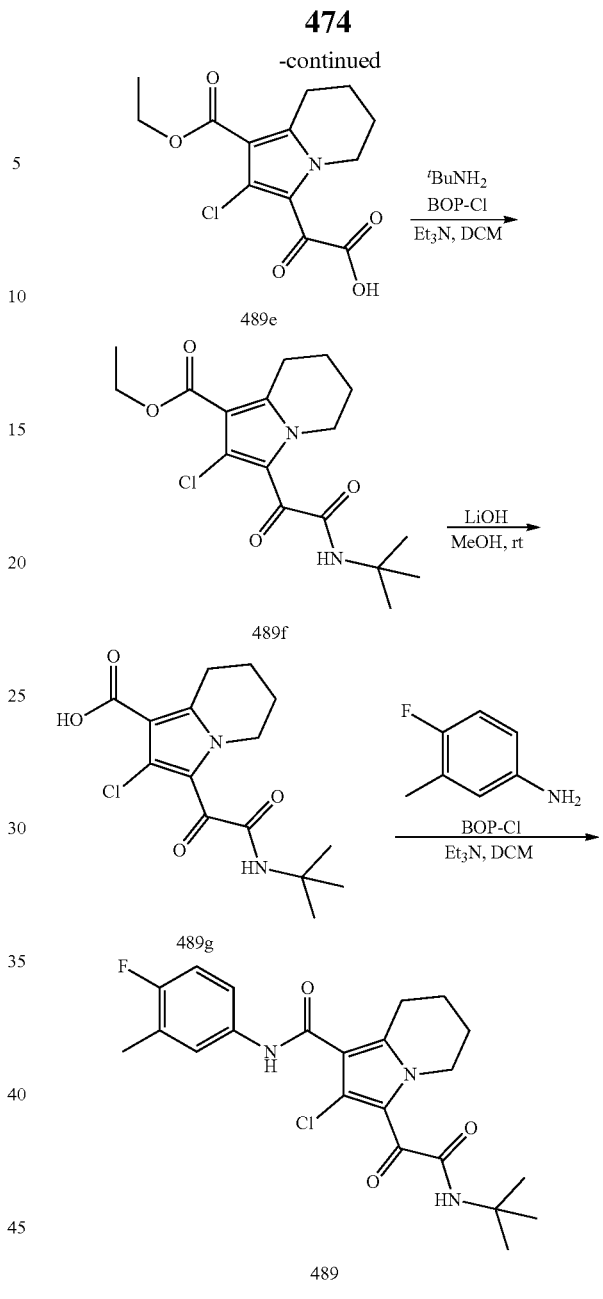

Step 1. Synthesis of 1-formylpiperidine-2-carboxylic acid (489a)

To a solution of piperidine-2-carboxylic acid (4.9 g, 38 mmol) in formic acid (30 mL) was added acetic anhydride (50 mL) at 0° C. The resulting mixture was stirred 0 to 5° C. for 4 h. LCMS showed the reaction was complete. The mixture was concentrated in vacuo to obtain crude product 489a (7.1 g) as colorless oil. MS (ESI): mass calcd. for C$_7$H$_{11}$NO$_3$ 157.07, m/z found 158.1 [M+H]$^+$.

Step 2. Synthesis of ethyl 5,6,7,8-tetrahydroindolizine-1-carboxylate (489b)

To a solution of intermediate 489a (7.1 g, 45 mmol) in acetic anhydride (70 mL) was added ethyl propiolate (5.88 g, 60 mmol). The resulting mixture was stirred at 120° C. for 2 h under N$_2$. MS showed the desired product, and the reaction was concentrated in vacuo. The residue was purified by column chromatography (EtOAc/petroleum ether: 0-10%) to obtain the title compound (1.5 g, 17%) as white solid. MS (ESI): mass calcd. for $C_{11}H_{15}NO_2$ 193.11, m/z found 194.1[M+H]$^+$.

Step 3. Synthesis of ethyl 3-(2-ethoxy-2-oxoacetyl)-5,6,7,8-tetrahydroindolizine-1-carboxylate (489c)

To a solution of compound 489b (579 mg, 3 mmol) and ethyl 2-chloro-2-oxoacetate (620 mg, 4.5 mmol) in DCM (15 mL), AlCl$_3$ (790 mg, 6 mmol) was added slowly at 0° C. The resulting mixture was warmed to RT and stirred for 5 h. Water (20 mL) was added slowly, and the mixture was extracted with DCM (3×20 mL), the combined organic extract was dried over Na$_2$SO$_4$, and concentrated. The residue was purified by column chromatography (EtOAc/petroleum ether: 0-20%) to obtain the title compound (967 mg crude) as a colorless oil. MS (ESI): mass calcd. for $C_{14}H_{17}NO_5$ 293.13, m/z found 294.1 [M+H]$^+$. $^1$H NMR (400 MHz, CDCl$_3$) δ 7.68 (s, 1H), 4.50-4.36 (m, 4H), 4.29 (q, J=7.1 Hz, 2H), 3.18 (t, J=6.3 Hz, 2H), 2.02-1.97 (m, 2H), 1.94-1.80 (m, 2H), 1.43 (t, J=7.1 Hz, 3H), 1.36 (t, J=7.1 Hz, 3H).

Step 4. Synthesis of ethyl 2-chloro-3-(2-ethoxy-2-oxoacetyl)-5,6,7,8-tetrahydroindolizine-1-carboxylate (489d)

To a solution of compound 489c (967 mg, 3.3 mmol) in CH$_3$COOH (25 mL), CF$_3$SO$_3$H (2.3 mg, 0.015 mmol) and NCS (661 mg, 4.95 mmol) was added at 0° C. The resulting mixture was warmed to RT and stirred overnight. Water (100 mL) was added slowly, and the mixture was extracted with CH$_3$COOEt (3×50 mL), the combined organic extract was dried over Na$_2$SO$_4$, and concentrated. The residue was purified by column chromatography (EtOAc/petroleum ether: 0-10%) to obtain the title compound (252 mg) as a light yellow solide. MS (ESI): mass calcd. for $C_{15}H_{15}ClNO_5$ 327.09, m/z found 327.9 [M+H]$^+$ Step 5. Synthesis of 2-(2-chloro-1-(ethoxycarbonyl)-5,6,7,8-tetrahydroindolizin-3-yl)-2-oxoacetic acid (489e)

To a solution of 489d (252 mg, 0.77 mmol) in MeOH (10 mL) was added 1 N LiOH aq. (20 mL). The resulting mixture was stirred for 5 h at RT. The mixture was poured into ice water (30 mL) and acidified using 1 N aqueous HCl to pH=3. The resulting solid was isolated by filtration to obtain the titled compound (219 mg, 95%) as white solid. MS (ESI): mass calcd. for $C_{13}H_{14}C_1NO_5$ 299.06, m/z found 300.1 [M+H]$^+$.

Step 6. Synthesis of ethyl 3-(2-(tert-butylamino)-2-oxoacetyl)-2-chloro-5,6,7,8-tetrahydroindolizine-1-carboxylate (489f).

To a solution of 489e (219 mg, 0.73 mmol), BOP—Cl (280 mg, 1.1 mmol), DIPEA (194 mg, 1.5 mmol) in DCM (15 mL), 2-methylpropan-2-amine (64 mg, 0.88 mmol) was added. The resulting mixture was stirred for 2 h at rt. The mixture was concentrated and purified by column chromatography (EtOAc/petroleum ether: 0-15%) to obtain the title compound (223 mg, 86%) as white solid. MS (ESI): mass calcd. for $C_{17}H_{23}C_1N_2O_4$ 354.1, m/z found 355.0 [M+H]$^+$.

Step 7. Synthesis of 3-(2-(tert-butylamino)-2-oxoacetyl)-2-chloro-5,6,7,8-tetrahydroindolizine-1-carboxylic acid (489g)

To a solution of 489f (223 mg, 0.63 mmol) in MeOH (20 mL), 1 N LiOH aq. (30 mL) was added. The resulting mixture was stirred for 2 h at 80° C. The mixture was concentrated and water (30 mL) was added and acidified using 1 N aqueous HCl to pH=3. The resulting solid was isolated by filtration to obtain the title compound (174 mg, 85%) as white solid. MS (ESI): mass calcd. for $C_{15}H_{19}C_1N_2O_4$ 326.1, m/z found 327.0 [M+H]$^+$. $^1$H NMR (400 MHz, DMSO-d$_6$) δ 12.57 (s, 1H), 8.25 (s, 1H), 4.19 (t, J=5.4 Hz, 2H), 3.03 (t, J=6.0 Hz, 2H), 1.89 (brs, 2H), 1.76 (br s, 2H), 1.33 (s, 9H).

Step 8. Synthesis of 3-(2-(tert-butylamino)-2-oxoacetyl)-N-(3-cyano-4-fluorophenyl)-5,6,7,8-Tetrahydroindolizine-1-carboxamide To a solution of 489g (110 mg, 0.3 mmol), BOP—Cl (129 mg, 0.5 mmol), and Et$_3$N (91 mg, 0.9 mmol) in DCM (20 mL), 4-fluoro-3-methylaniline (42 mg, 1.5 mmol) was added. The resulting mixture was stirred for 13 h at RT. The mixture was concentrated and purified by column chromatography (EtOAc/petroleum ether: 0-10%) to obtain the title compound (35 mg, 73%) as white solid. MS (ESI): mass calcd. for $C_{22}H_{25}ClFN_3O_3$ 433.1, m/z found 433.7 [M+H]$^+$. $^1$H NMR (400 MHz, DMSO-d$_6$) δ 9.94 (s, 1H), 8.30 (s, 1H), 7.60 (dd, J=7.0, 2.2 Hz, 1H), 7.54-7.46 (m, 1H), 7.10 (t, J=9.2 Hz, 1H), 4.23 (t, J=6.0 Hz, 2H), 2.93 (t, J=6.2 Hz, 2H), 2.22 (d, J=1.6 Hz, 3H), 1.97-1.87 (m, 2H), 1.81-1.71 (m, 2H), 1.34 (s, 9H).

Example 492: Synthesis of 2-chloro-N-(3,4-difluorophenyl)-3-(2-((1-hydroxy-2-methylpropan-2-yl)amino)-2-oxoacetyl)-5,6,7,8-tetrahydroindolizine-1-carboxamide

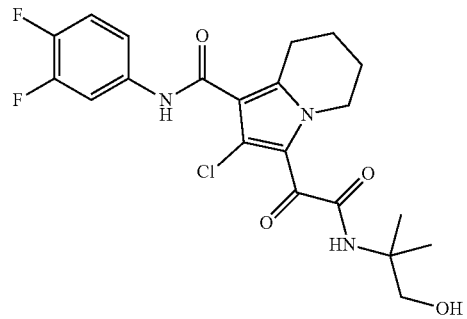 [SMILES: CC(C)(CO)NC(=O)C(=O)c1c(Cl)c(C(=O)Nc2ccc(F)c(F)c2)c2n1CCCC2]

The title compound was prepared according to the procedure for Example 489, utilizing 2-amino-2-methylpropan-1-ol in Step 6, and 3,4-difluoroaniline in Step 8, to provide a white solid. $^1$H NMR (300 MHz, DMSO-d$_6$) δ 10.19 (s, 1H), 8.14 (s, 1H), 7.84-7.80 (m, 1H), 7.75-7.40 (m, 2H), 4.87-4.84 (m, 1H), 4.25-4.21 (m, 2H), 3.45 (s, 2H), 2.93-2.90 (m, 2H), 1.94-1.90 (m, 2H), 1.79-1.74 (m, 2H), 1.29 (s, 6H). ESI-MS, m/z 454.1 (MH)$^+$.

Synthesis of Example compounds 489-491 and 493-534 (structures shown in Table 1)

Examples 489-534 were prepared in analogy to the procedures described above for Example 489, utilizing the requisite amine for Step 6, and the appropriate aryl amine in Step 8. The observed MS data for these Examples are shown in Table 1.

Example 535: Synthesis of 5-(2-(tert-butylamino)-2-oxoacetyl)-N-(3-chloro-4-fluorophenyl)-2,3-dihydro-1H-pyrrolizine-7-carboxamide

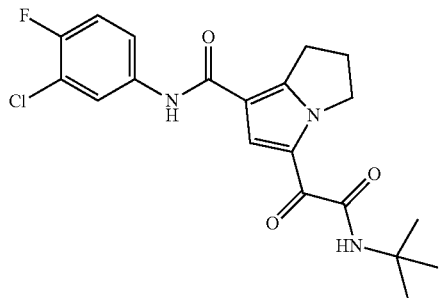 [SMILES: CC(C)(C)NC(=O)C(=O)c1cc(C(=O)Nc2ccc(F)c(Cl)c2)c2n1CCC2]

The title compound was prepared according to the procedure of Example 392, substituting proline for piperidine-2-carboxylic acid in Step 1, and substituting 4-fluoro-3-chloroaniline for 5-amino-2-fluorobenzonitrile in Step 7. MS (ESI): mass calcd. for $C_{20}H_{21}ClFN_3O_3$ 405.13, m/z found 406.1 [M+H]$^+$. $^1$H NMR (400 MHz, CDCl$_3$) δ 8.29 (s, 1H), 7.92 (d, J=6.6 Hz, 1H), 7.62 (s, 1H), 7.35 (d, J=8.6 Hz, 2H), 7.14 (d, J=8.7 Hz, 1H), 4.39 (t, J=7.3 Hz, 2H), 3.24 (t, J=7.6 Hz, 2H), 2.69-2.57 (m, 2H), 1.47 (s, 9H).

Example 536: Synthesis of 5-(2-(tert-butylamino)-2-oxoacetyl)-N-(4-fluoro-3-methylphenyl)-2,3-dihydro-1H-pyrrolizine-7-carboxamide

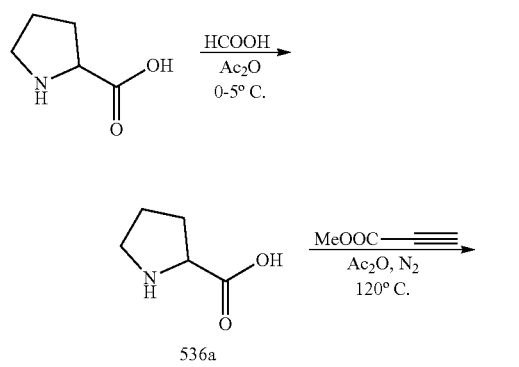

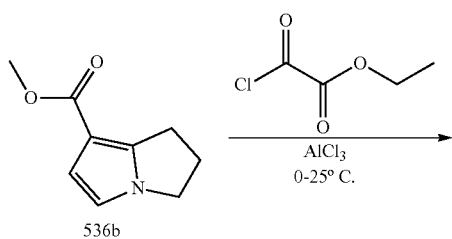

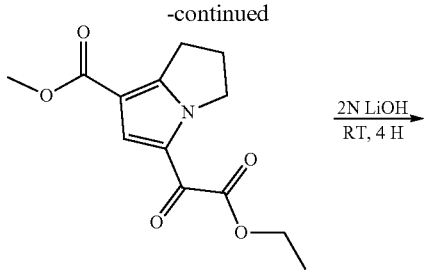

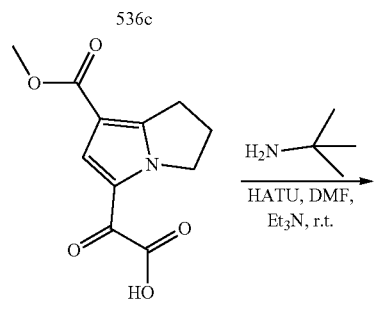

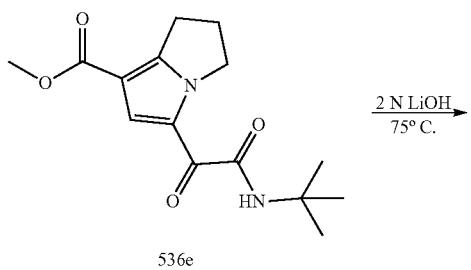

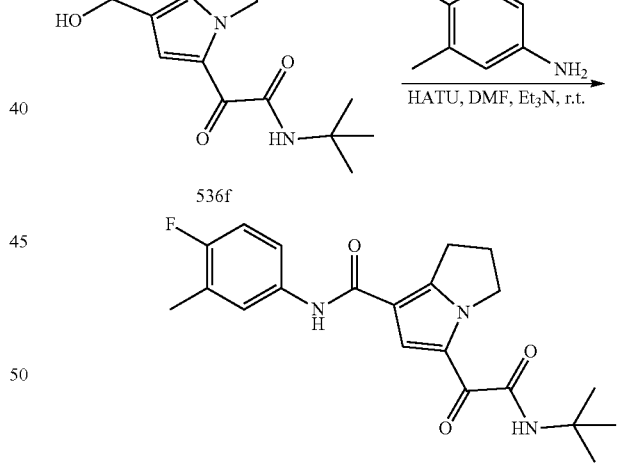

Step 1. Synthesis of formylproline (536a)

To a solution of proline (10.3 g, 89 mmol) in formic acid (60 mL) was added acetic anhydride (100 mL) at 0° C. The resulting mixture was stirred 0 to 5° C. for 4 h. LCMS showed the reaction was complete. The mixture was concentrated in vacuo to obtain crude product 536a (12 g) as colorless oil. MS (ESI): mass calcd. for $C_6H_9NO_3$ 143.03, m/z found 144.1 [M+H]$^+$.

Step 2. Synthesis of methyl 2,3-dihydro-1H-pyrrolizine-7-carboxylate (536b)

To a solution of intermediate 536a (12 g, 84 mmol) in acetic anhydride (120 mL) was added methyl propiolate (10.58 g, 126 mmol). The resulting mixture was stirred at 120° C. for 2 h under $N_2$. MS showed the desired product, and the reaction was concentrated in vacuo. The residue was purified by column chromatography (EtOAc/petroleum ether: 0-10%) to obtain the title compound (2.5 g, 18%) as white solid. MS (ESI): mass calcd. for $C_9H_{11}NO_2$ 165.08, m/z found 165.8 [M+H]$^+$.

Step 3. Synthesis of methyl 5-(2-ethoxy-2-oxoacetyl)-2,3-dihydro-1H-pyrrolizine-7-carboxylate (536c)

To a solution of compound 536b (2.5 g, 15 mmol) and ethyl 2-chloro-2-oxoacetate (3 g, 7.5 mmol) in DCM (50 mL), AlCl$_3$ (790 mg, 6 mmol) was added slowly at 0° C. The resulting mixture was warmed to RT and stirred for 5 h. Water (80 mL) was added slowly, and the mixture was extracted with DCM (3×50 mL), the combined organic extract was dried over Na$_2$SO$_4$, and concentrated. The residue was purified by column chromatography (EtOAc/petroleum ether: 0-20%) to obtain the title compound (1.6 g, crude) as a colorless oil. MS (ESI): mass calcd. for $C_{13}H_{15}NO_5$ 265.10, m/z found 266.1 [M+H]$^+$.

Step 4. Synthesis of 2-(7-(methoxycarbonyl)-2,3-dihydro-1H-pyrrolizin-5-yl)-2-oxoacetic acid (536d)

To a solution of 536c (1 g, 3.7 mmol) in MeOH (30 mL) was added 1 N LiOH aq. (50 mL). The resulting mixture was stirred for 5 h at RT. The mixture was poured into ice water (200 mL) and acidified using 1 N aqueous HCl to pH=3. The resulting solid was isolated by filtration to obtain the title compound (640 mg, 71%) as white solid. MS (ESI): mass calcd. for $C_{11}H_{11}NO_5$ 237.06, m/z found 238.1 [M+H]$^+$.

Step 5. Synthesis of methyl 5-(2-(tert-butylamino)-2-oxoacetyl)-2,3-dihydro-1H-pyrrolizine-7-carboxylate (536e)

To a solution of 536d (640 mg, 2.7 mmol), HATU (1.1 g, 4 mmol), Et$_3$N (1.09 g, 4 mmol) in DCM (30 mL), 2-methylpropan-2-amine (197 mg, 2.7 mmol) was added. The resulting mixture was stirred for 2 h at rt. The mixture was concentrated and purified by column chromatography (EtOAc/petroleum ether: 0-30%) to obtain the title compound (567 mg, 72%) as white solid. MS (ESI): mass calcd. for $C_{15}H_{20}N_2O_4$ 292.14, m/z found 293.1 [M+H]$^+$.

Step 6. Synthesis of 5-(2-(tert-butylamino)-2-oxoacetyl)-2,3-dihydro-1H-pyrrolizine-7-carboxylic acid (536f)

To a solution of 536e (567 mg, 1.9 mmol) in MeOH (20 mL), LiOH aq. (30 mL) was added. The resulting mixture was stirred for 2 h at 75° C. The mixture was concentrated and water (30 mL) was added and acidified using 1 N aqueous HCl to pH=3. The resulting solid was isolated by filtration to obtain the title compound (454 mg, 84%) as white solid. MS (ESI): mass calcd. for $C_{14}H_{18}N_2O_4$ 278.13, m/z found 279.2 [M+H]$^+$.

Step 7. Synthesis of 5-(2-(tert-butylamino)-2-oxoacetyl)-N-(4-fluoro-3-methylphenyl)-2,3-dihydro-1H-pyrrolizine-7-carboxamide To a solution of 536f (120 mg, 0.4 mmol), HATU (310 mg, 0.8 mmol), and Et$_3$N (520 mg, 4 mmol) in DCM (20 mL), 4-fluoro-3-methylaniline (187 mg, 1.5 mmol) was added. The resulting mixture was stirred for 13 h at RT. The mixture was concentrated and purified by column chromatography (EtOAc/petroleum ether: 0-50%) to obtain the title compound (27 mg, 16%) as white solid. MS (ESI): mass calcd. for $C_{21}H_{24}FN_3O_3$ 385.18 m/z found 386.2 [M+H]$^+$. $^1$H NMR (400 MHz, DMSO) δ 9.90 (s, 1H), 8.13 (s, 1H), 8.05 (s, 1H), 7.68 (dd, J=7.1, 2.4 Hz, 1H), 7.57 (dd, J=7.7, 4.0 Hz, 1H), 7.07 (t, J=9.2 Hz, 1H), 4.26 (t, J=7.2 Hz, 2H), 3.07 (t, J=7.5 Hz, 2H), 2.23 (s, 3H), 1.38 (s, 9H).

Example 537: Synthesis of N-(4-fluoro-3-methylphenyl)-5-(2-((1-hydroxy-2-methylpropan-2-yl)amino)-2-oxoacetyl)-2,3-dihydro-1H-pyrrolizine-7-carboxamide

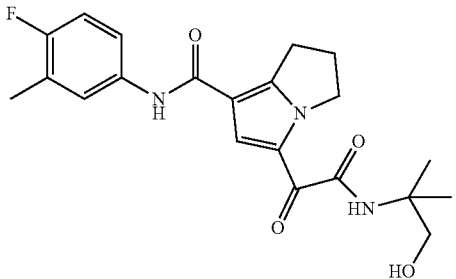 [SMILES: Cc1cc(NC(=O)c2cc(C(=O)C(=O)NC(C)(C)CO)n3c2CCC3)ccc1F]

The title compounds was prepared according to the procedure of Example 536, substituting 2-amino-2-methylpropan-1-ol for tert-butylamine in Step 5. MS (ESI): mass calcd. for $C_{21}H_{24}FN_3O_4$ 401.18 m/z found 401.9 [M+H]$^+$.

Example 538: Synthesis of 5-(2-amino-2-oxoacetyl)-N-(3-chloro-4-fluorophenyl)-6-methyl-2,3-dihydro-1H-pyrrolizine-7-carboxamide

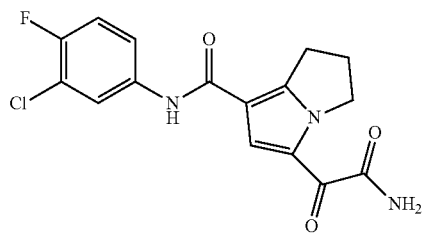 [SMILES: NC(=O)C(=O)c1cc(C(=O)Nc2ccc(F)c(Cl)c2)c2n1CCC2]

The title compound may be prepared according to the procedure of Example 536, substituting ammonia for tert-butylamine in Step 5, and 3-chloro-4-fluoroaniline in Step 7.

481

Example 539: Synthesis of 5-(2-(tert-butylamino)-2-oxoacetyl)-6-chloro-N-(4-fluoro-3-methylphenyl)-2,3-dihydro-1H-pyrrolizine-7-carboxamide

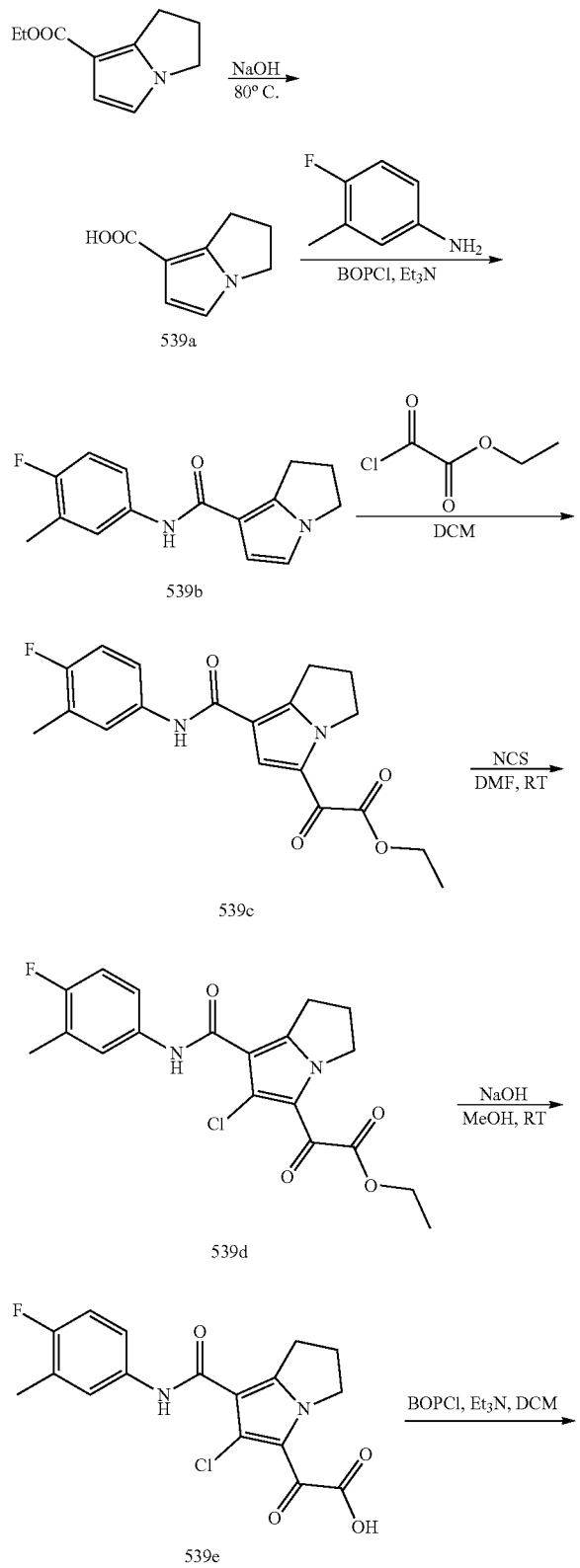

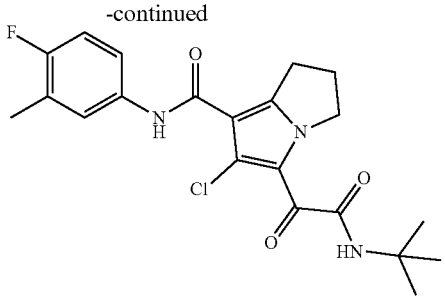

Step 1. Synthesis of 2,3-dihydro-1H-pyrrolizine-7-carboxylic acid (539a)

To a solution of ethyl 2,3-dihydro-1H-pyrrolizine-7-carboxylate (12 g, 67 mmol) in MeOH (150 mL) was added 3 N LiOH aq. (50 mL). The resulting mixture was stirred for 5 h at 80° C. The mixture was poured into ice water (400 mL) and acidified using 1 N aqueous HCl to pH=3. The resulting solid was isolated by filtration to obtain the title compound (10.1 g, 100%) as white solid. MS (ESI): mass calcd. for $C_8H_9NO_2$ 151.06, m/z found 152.1 [M+H]$^+$.

Step 2. Synthesis of N-(4-fluoro-3-methylphenyl)-2,3-dihydro-1H-pyrrolizine-7-carboxamide (539b)

To a solution of 539a (10.3 g, 68 mmol), BOP—Cl (26 g, 102 mmol), Et$_3$N (27.5 g, 272 mmol) in DCM (300 mL), 4-fluoro-3-methylaniline (8.5 g, 68 mmol) was added. The resulting mixture was stirred for 20 h at rt. The mixture was concentrated and purified by column chromatography (EtOAc/petroleum ether: 0-50%) to obtain the title compound (6.5 g, 37%) as white solid. MS (ESI): mass calcd. for $C_{15}H_{15}FN_2O$ 258.12, m/z found 259.1 [M+H]$^+$.

Step 3 Synthesis of ethyl 2-(7-((4-fluoro-3-methylphenyl)carbamoyl)-2,3-dihydro-1H-pyrrolizin-5-yl)-2-oxoacetate (539c)

To a solution of compound 539b (6 g, 23 mmol) and ethyl 2-chloro-2-oxoacetate (4.7 g, 35 mmol) in DCM (150 mL) was added slowly at 0° C. The resulting mixture was warmed to RT and stirred for 5 h. Water (80 mL) was added slowly, and the mixture was extracted with DCM (3×50 mL), the combined organic extract was dried over Na$_2$SO$_4$, and concentrated. The residue was purified by column chromatography (EtOAc/petroleum ether: 0-20%) to obtain the title compound (2.3 g and 4 g crude) as yellow solid. MS (ESI): mass calcd. for $C_{19}H_{19}FN_2O_4$ 358.13, m/z found 359.1 [M+H]+.

Step 4 Synthesis of ethyl 2-(6-chloro-7-((4-fluoro-3-methylphenyl)carbamoyl)-2,3-dihydro-1H-pyrrolizin-5-yl)-2-oxoacetate (539d)

To a solution of compound 539c (2.3 g, 6 mmol) in DMF (50 mL), NCS (1.03 g, 67.8 mmol) was added at 25° C. The resulting mixture was stirred for 25 h. Water (80 mL) was added, and the mixture was extracted with EA (3×50 mL), the combined organic extract was dried over Na$_2$SO$_4$, and concentrated. The residue was purified by column chromatography (EtOAc/petroleum ether: 0-30%) to obtain the title compound (0.4 g and 1.1 g crude) as brown solid. MS (ESI): mass calcd. for $C_{19}H_{18}ClFN_2O_4$ 392.09 m/z found 393.1 [M+H]$^+$.

Step 5. Synthesis of 2-(6-chloro-7-((4-fluoro-3-methylphenyl)carbamoyl)-2,3-dihydro-1H-pyrrolizin-5-yl)-2-oxoacetic acid (539e)

To a solution of 539d (400 mg, 1.02 mmol) in MeOH (20 mL), NaOH aq. (30 mL) was added. The resulting mixture was stirred for 2 h at 25° C. The mixture was concentrated and water (30 mL) was added and acidified using 1 N aqueous HCl to pH=3. The resulting solid was isolated by filtration to obtain the title compound (320 mg, 86%) as white solid. MS (ESI): mass calcd. for $C_{17}H_{14}ClFN_2O_4$ 364.06, m/z found 365.1 [M+H]$^+$.

Step 7. Synthesis of 5-(2-(tert-butylamino)-2-oxoacetyl)-6-chloro-N-(4-fluoro-3-methylphenyl)-2,3-dihydro-1H-pyrrolizine-7-carboxamide To a solution of 539e (50 mg, 0.14 mmol), BOP—Cl (70 mg, 0.27 mmol), and Et$_3$N (40 mg, 0.4 mmol) in DCM (10 mL), 2-methylpropan-2-amine (51 mg, 0.7 mmol) was added. The resulting mixture was stirred for 13 h at RT. The mixture was concentrated and purified by column chromatography (EtOAc/petroleum ether: 0-50%) to obtain the title compound (12 mg, 20%) as white solid. MS (ESI): mass calcd. for $C_{21}H_{23}ClFN_3O_3$ 419.14 m/z found 420.1 [M+H]$^+$. $^1$H NMR (400 MHz, DMSO-d$_6$) δ 9.67 (s, 1H), 8.39 (s, 1H), 7.60 (dd, J=7.1, 2.5 Hz, 1H), 7.53-7.45 (m, 1H), 7.10 (t, J=9.2 Hz, 1H), 4.28 (t, J=7.3 Hz, 2H), 3.08 (t, J=7.5 Hz, 2H), 2.49-2.39 (m, 2H), 2.23 (d, J=1.6 Hz, 3H), 1.35 (s, 9H).

Synthesis of Example Compounds 540-581 (Structures Shown in Table 1)

Examples 540-581 were prepared in analogy to the procedures described above for Example 539, utilizing the appropriate aryl amine in Step 2, and the requisite amine for Step 6. The observed MS data for these Examples are shown in Table 1.

Example 582: Synthesis of 6-(2-(tert-butylamino)-2-oxoacetyl)-N-(3-cyano-4-fluorophenyl)-3,4-dihydro-1H-pyrrolo[2,1-c][1,4]oxazine-8-carboxamide

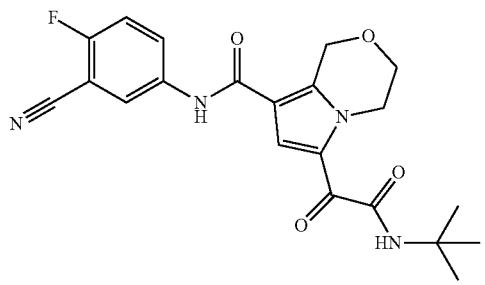 [SMILES: CC(C)(C)NC(=O)C(=O)c1cc(C(=O)Nc2ccc(F)c(C#N)c2)c2n1CCOC2]

The title compound was prepared according to the procedure of Example 392, substituting morpholine-3-carboxylic acid for piperidine-2-carboxylic acid in Step 1. MS (ESI): mass calcd. for $C_{21}H_{21}FN_4O_4$ 412.15, m/z found 412.8 [M+H]$^+$. $^1$H NMR (400 MHz, DMSO-d$_6$) δ 8.85 (d, J=4.5 Hz, 1H), 8.75 (d, J=8.4 Hz, 1H), 8.29 (s, 1H), 7.98 (s, 1H), 7.67 (dd, J=8.3, 4.4 Hz, 1H), 5.12 (s, 2H), 4.41 (s, 2H), 4.08 (t, J=4.9 Hz, 2H), 1.38 (s, 9H).

Example 583: Synthesis of 6-(2-(tert-butylamino)-2-oxoacetyl)-N-(4-fluoro-3-methylphenyl)-3,4-dihydro-1H-pyrrolo[2,1-c][1,4]oxazine-8-carboxamide

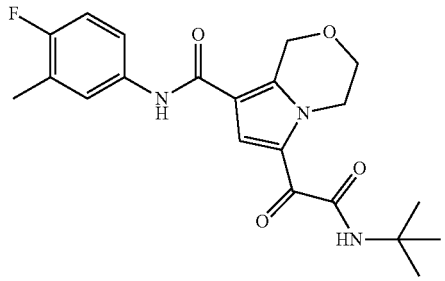 [SMILES: Cc1cc(NC(=O)c2cc(C(=O)C(=O)NC(C)(C)C)n3c2COCC3)ccc1F]

The title compound was prepared according to the procedure of Example 392, substituting morpholine-3-carboxylic acid for piperidine-2-carboxylic acid in Step 1, and substituting 4-fluoro-3-methylaniline for 5-amino-2-fluorobenzonitrile in Step 7. MS (ESI): mass calcd. for $C_{21}H_{24}FN_3O_4$ 401.18, m/z found 401.9 [M+H]$^+$. $^1$H NMR (400 MHz, DMSO-d$_6$) δ 10.03 (s, 1H), 8.13 (s, 1H), 8.10 (s, 1H), 7.65 (d, J=7.0 Hz, 1H), 7.59-7.50 (m, 1H), 7.08 (t, J=9.2 Hz, 1H), 5.09 (s, 2H), 4.32 (t, J=4.7 Hz, 2H), 4.00 (t, J=4.9 Hz, 2H), 2.23 (s, 3H), 1.39 (s, 9H).

Synthesis of Example Compound 584 (Structures Shown in Table 1)

Example 584 was prepared in analogy to the procedures described above for Example 539, utilizing the appropriate aryl amine in Step 2.

Synthesis of Example Compounds 585 and 586 (Structures Shown in Table 1)

Examples 591 and 592 (structures shown in Table 1) may be prepared in analogy to the procedures described above for Example 584.

Example 587: Synthesis of tert-butyl 6-(2-(tert-butylamino)-2-oxoacetyl)-8-((4-fluoro-3-methylphenyl)carbamoyl)-3,4-dihydropyrrolo[1,2-a]pyrazine-2 (1B)-carboxylate

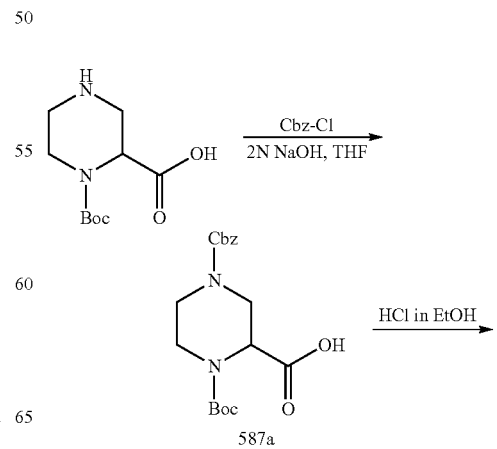

587a

485
-continued

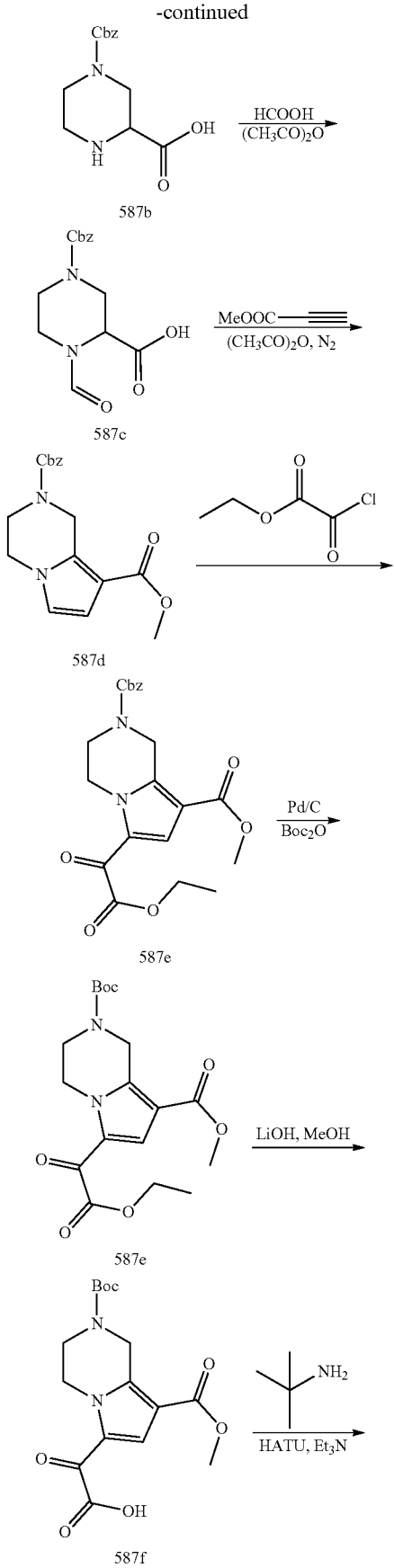

486
-continued

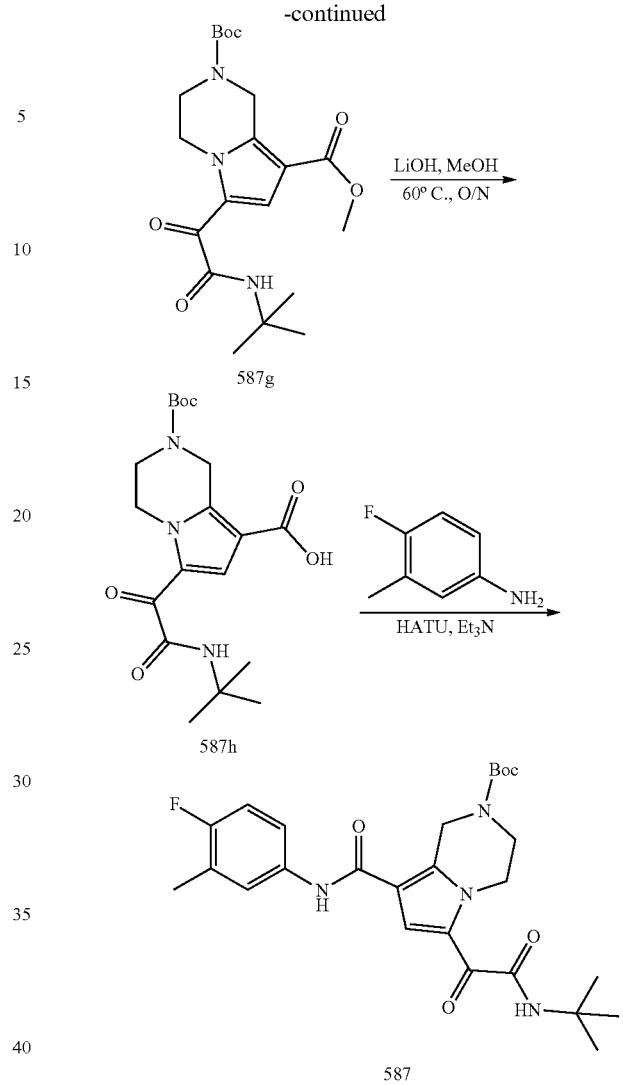

Step 1. Synthesis of 4-((benzyloxy)carbonyl)-1-(tert-butoxycarbonyl)piperazine-2-carboxylic acid (587a)

A mixture of 1-(tert-butoxycarbonyl)piperazine-2-carboxylic acid (23 g, 100 mmol) in THF (200 mL) was added NaOH (1 mol/L in H$_2$O, 200 mL, 200 mmol), followed by added Cbz-Cl (19 g, 110 mmol) dropwise. The mixture was stirred at 25° C. for 4 hours. HCl (1N in H$_2$O) was added to pH=5, the organic phase was washed with H$_2$O, brine, dried and evaporated to afford product as yellow oil (25 g, 69%). MS (ESI): mass calcd. for C$_{18}$H$_{24}$N$_2$O$_6$ 364.16, m/z found 365.1 [M+H]$^+$.

Step 2. Synthesis of 4-((benzyloxy)carbonyl)piperazine-2-carboxylic acid (587b)

A mixture of 4-((benzyloxy)carbonyl)-1-(tert-butoxycarbonyl)piperazine-2-carboxylic acid 587a (25 g, 69 mmol) in EtOH (50 mL) was added HCl.EtOH (35%, 50 mL). The mixture was stirred at 25° C. for 4 hours. The mixture was evaporated to afford product as white solid (18 g, 100%). MS (ESI): mass calcd. for $C_{13}H_{16}N_2O_4$ 264.11, m/z found 265.1 $[M+H]^+$.

Step 3. Synthesis of 4-((benzyloxy)carbonyl)-1-formylpiperazine-2-carboxylic acid (587c)

The title compound was prepared from compound 587b following the procedure described in Example 392, Step 1, using 4-((benzyloxy)carbonyl)piperazine-2-carboxylic acid. Title product (20 g, crude) as white solid was obtained. MS (ESI): mass calcd. for $C_{14}H_{16}N_2O_5$ 292.11, m/z found 293.1 [M+H]+.

Step 4. Synthesis of 2-benzyl 8-methyl 3,4-dihydropyrrolo[1,2-a]pyrazine-2,8(1H)-dicarboxylate (587d)

The title compound was prepared from 587c following the procedure described in Example 392, Step 2, using 4-((benzyloxy)carbonyl)-1-formylpiperazine-2-carboxylic acid, to provide 587d (16 g, 74%) as white solid. MS (ESI): mass calcd. for $C_{14}H_{16}N_2O_5$ 292.11, m/z found 293.1 $[M+H]^+$.

Step 5. Synthesis of 2-benzyl 8-methyl 6-(2-ethoxy-2-oxoacetyl)-3,4-dihydropyrrolo[1,2-a]pyrazine-2,8(1H)-dicarboxylate (587e)

To a solution of 587d (3.14 g, 10 mmol), ethyl 2-chloro-2-oxoacetate (2.04 g, 15 mmol) in DCM (15 mL) was stirred for 15 h. 20 mL water was added slowly, and the mixture was extracted with DCM (3×20 mL), dried over $Na_2SO_4$, concentrated. The residue was purified by FCC (EA/PE: 0-20%) to obtain the title compound (2 g, 48%) as colorless oil. MS (ESI): mass calcd. for $C_{21}H_{22}N_2O_7$ 414.14, m/z found 415.1 $[M+H]^+$.

Step 6. Synthesis of 2-(tert-butyl) 8-methyl 6-(2-ethoxy-2-oxoacetyl)-3,4-dihydropyrrolo[1,2-a]pyrazine-2,8(1H)-dicarboxylate (587f)

A mixture of 587e (2 g, 4.8 mmol) in EtOH (20 mL) was added $Boc_2O$ (1.09 g, 5 mmol) and Pd/C (50 mg), the mixture was stirred under $H_2$ with a balloon for 20 min, then the mixture was filtered and evaporated to afford product as white solid (1.2 g, 67%). MS (ESI): mass calcd. for $C_{18}H_{24}N_2O_7$ 380.16, m/z found 381.1 $[M+H]^+$.

Step 7. Synthesis of 2-(2-(tert-butoxycarbonyl)-8-(methoxycarbonyl)-1,2,3,4-tetrahydropyrrolo[1,2-a]pyrazin-6-yl)-2-oxoacetic acid (587g)

The title compounds were prepared following the procedure described in Example 392, Step 4, using 2-(tert-butyl) 8-methyl 6-(2-ethoxy-2-oxoacetyl)-3,4-dihydropyrrolo[1,2-a]pyrazine-2,8(1H)-dicarboxylate (587f). Title product (800 mg, 85%) as white solid was obtained. MS (ESI): mass calcd. for $C_{16}H_{20}N_2O_7$ 352.13, m/z found 353.1 $[M+H]^+$.

Step 8. Synthesis of 2-(tert-butyl) 8-methyl 6-(2-(tert-butylamino)-2-oxoacetyl)-3,4-dihydropyrrolo[1,2-a]pyrazine-2,8(1H)-dicarboxylate (587h)

The title compounds were prepared from compound 587g following the procedure described in Example 392, Step 5. The title product (480 mg, 75%) was obtained as yellow solid. MS (ESI): mass calcd. for $C_{20}H_{29}N_3O_6$ 407.21, m/z found 408.0 $[M+H]^+$.

Step 9. Synthesis of 2-(tert-butoxycarbonyl)-6-(2-(tert-butylamino)-2-oxoacetyl)-1,2,3,4-tetrahydropyrrolo[1,2-a]pyrazine-8-carboxylic acid (587i)

The title compounds were prepared from compound 344h, following the procedure described in Example 392, Step 6. The title product (400 mg, 77%) was obtained as yellow solid. MS (ESI): mass calcd. for $C_{19}H_{27}N_3O_6$ 393.19, m/z found 394.0 $[M+H]^+$.

Step 10. Synthesis of tert-butyl 6-(2-(tert-butylamino)-2-oxoacetyl)-8-((4-fluoro-3-methylphenyl)carbamoyl)-3,4-dihydropyrrolo[1,2-a]pyrazine-2 (1H)-carboxylate The title compounds were prepared from compound 587i following the procedure described in Example 392, Step 6. The title product (280 mg, 65%) was obtained as yellow solid. MS (ESI): mass calcd. for $C_{26}H_{33}FN_4O_5$ 500.24, m/z found 501.0 $[M+H]^+$.

Example 588: Synthesis of 6-(2-(tert-butylamino)-2-oxoacetyl)-N-(4-fluoro-3-methylphenyl)-1,2,3,4-tetrahydropyrrolo[1,2-a]pyrazine-8-carboxamide

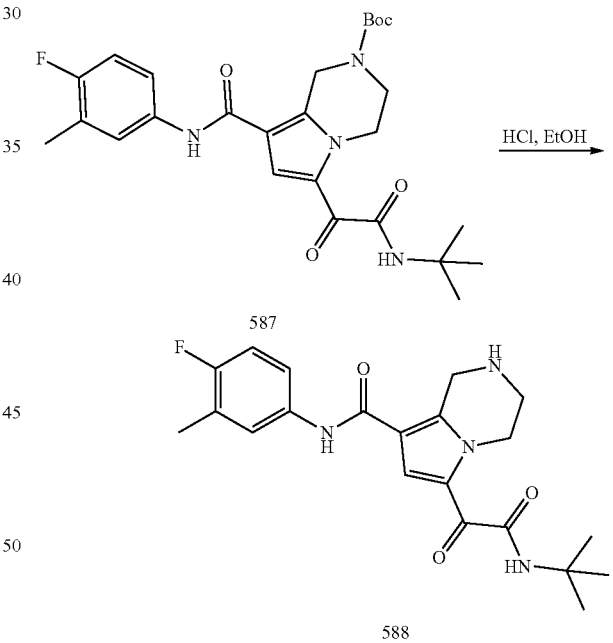

To a solution of Example 587 (260 mg, 0.52 mmol) in EtOH (5 mL) was added 35% HCl in EtOH (5 mL), and the solution was stirred at 20° C. for 1 h. The solution was evaporated and purified by preparative HPLC to afford the title compound as white solid (190 mg, 91%). MS (ESI): mass calcd. for $C_{21}H_{25}FN_4O_3$ 400.19, m/z found 401.0 $[M+H]^+$. $^1H$ NMR (400 MHz, DMSO-$d_6$) δ 10.02 (s, 1H), 8.14 (s, 2H), 8.07 (s, 1H), 7.64 (d, J=7.0 Hz, 1H), 7.55 (br s, 1H), 7.09 (t, J=9.2 Hz, 1H), 4.43 (s, 2H), 4.34 (s, 2H), 3.28 (s, 2H), 2.23 (s, 3H), 1.39 (s, 9H).

489

Example 589: Synthesis of 6-(2-(tert-butylamino)-2-oxoacetyl)-N-(4-fluoro-3-methylphenyl)-2-(methylsulfonyl)-1,2,3,4-tetrahydropyrrolo[1,2-a]pyrazine-8-carboxamide

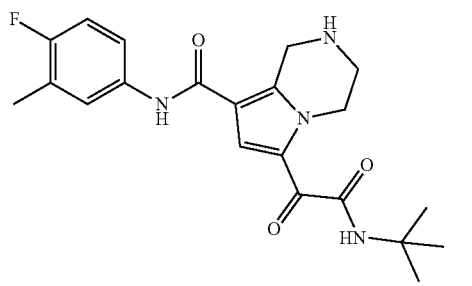

588

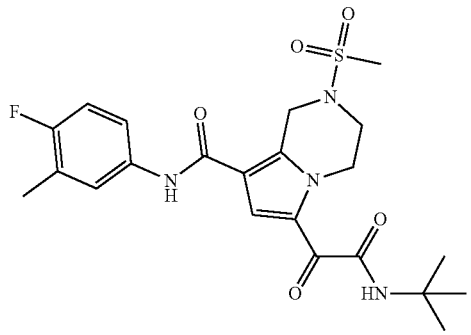

589

To a mixture of Example 588 (90 mg, 0.225 mmol) in DCM (5 mL) was added Et₃N (0.5 mmol) and methanesulfonyl chloride (31 mg, 0.27 mmol), and the mixture was stirred at 25° C. for 2 h and then evaporated in vacuo. The residue was purified by preparative HPLC to afford the title compound (20 mg, 21%) as white solid. MS (ESI): mass calcd. for $C_{22}H_{27}FN_4O_5S$ 478.17, m/z found 479.0 [M+H]⁺. ¹H NMR (400 MHz, DMSO-d₆) δ 10.08 (s, 1H), 8.16 (s, 1H), 8.12 (s, 1H), 7.69 (d, J=5.6 Hz, 1H), 7.55 (brs, 1H), 7.09 (t, J=9.2 Hz, 1H), 4.83 (s, 2H), 4.46 (s, 2H), 3.65 (s, 2H), 3.07 (s, 3H), 2.24 (s, 3H), 1.39 (s, 9H).

Example 590: Synthesis of 2-acetyl-6-(2-(tert-butylamino)-2-oxoacetyl)-N-(4-fluoro-3-methylphenyl)-1,2,3,4-tetrahydropyrrolo[1,2-a]pyrazine-8-carboxamide

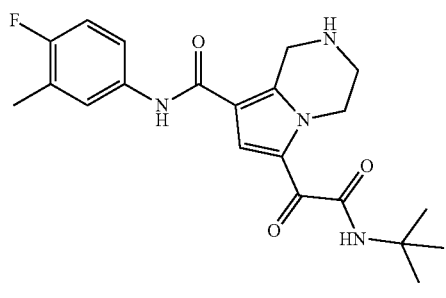

588

490

-continued

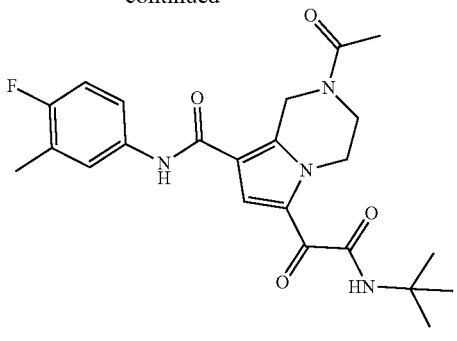

590

To a mixture of Example 588 (90 mg, 0.225 mmol) in DCM (5 mL) was added Et₃N (0.5 mmol) and acetyl chloride (18 mg, 0.225 mmol), and the mixture was stirred at 25° C. for 2 h, and then evaporated in vacuo. The residue was purified by preparative HPLC to afford the title compound as white solid (20 mg, 20%). MS (ESI): mass calcd. for $C_{23}H_{27}FN_4O_4$ 442.20, m/z found 443.0 [M+H]⁺. ¹H NMR (400 MHz, DMSO-d₆) δ 10.06-10.03 (m, 1H), 8.13-8.09 (m, 2H), 7.69 (d, J=6.6 Hz, 1H), 7.56 (s, 1H), 7.09 (t, J=9.4 Hz, 1H), 5.09-5.01 (m, 2H), 4.43-4.33 (m, 2H), 3.88 (br s, 2H), 2.24 (s, 3H), 2.13 (d, J=8.4 Hz, 3H), 1.39 (s, 9H).

Synthesis of Example Compounds 591 and 592 (Structures Shown in Table 1)

Examples 591 and 592 (structures shown in Table 1) may be prepared in analogy to the procedures described above for Example 590.

Synthesis of Example Compounds 593 and 594 (Structures Shown in Table 1)

Examples 593 and 594 (structures shown in Table 1) may be prepared in analogy to the procedures described above for Example 392, utilizing azepane-2-carboxylic acid in Step 1.

Synthesis of Example Compounds 595-612 (Structures Shown in Table 1)

Examples 595-611, and 613-XXX were prepared in analogy to the procedures described above for Example Examples 639, 641, 643, 645, 664, 666, 668, 670, 708, and 709 were prepared in analogy to the procedures described above for Example 612, utilizing the requisite acids.

Example 612: 5-(2-((1-acetyl-4-methylpiperidin-4-yl)amino)-2-oxoacetyl)-N-(4-fluoro-3-methylphenyl)-1,2,4-trimethyl-1H-pyrrole-3-carboxamide

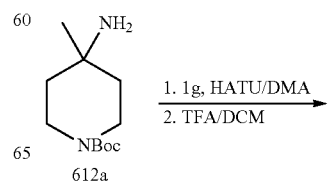

612a 1. 1g, HATU/DMA
2. TFA/DCM

491

-continued

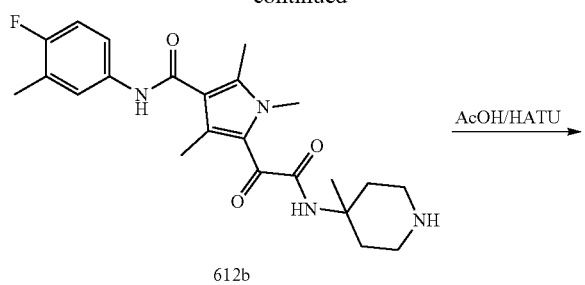

612b

F
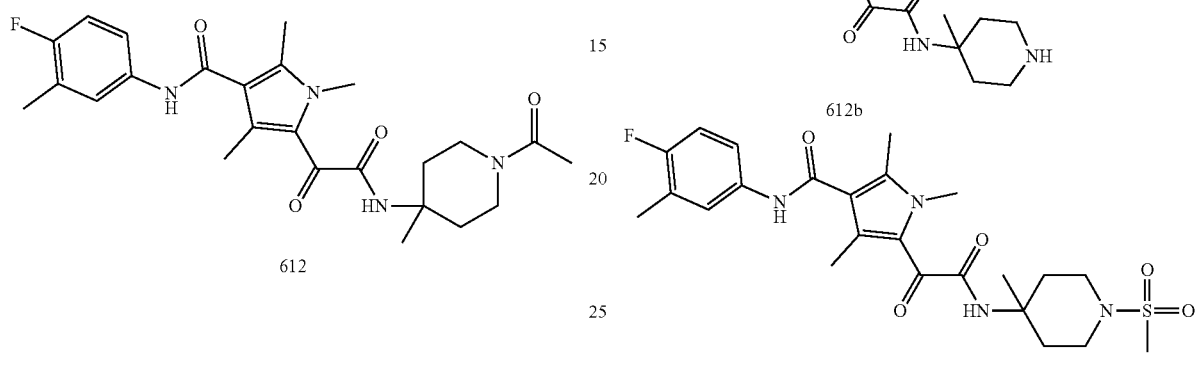

612

Step 1: Synthesis of N-(4-fluoro-3-methylphenyl)-1,2,4-trimethyl-5-(2-((4-methylpiperidin-4-yl)amino)-2-oxoacetyl)-1H-pyrrole-3-carboxamide To a mixture of Example 612a (110 mg, 0.5 mmol), Example 1 g (170 mg, 0.5 mmol) and HATU (200 mg, 0.52 mmol) in DMF (1 mL) was added DIPEA at 0° C. The reaction mixture was warmed to rt overnight. The reaction mixture was quenched with 0.5 N HCl and extracted with EtOAc. The combined extracts was washed with brine, and concentrated under vacuum. The residues was dissolved in DCM (2 mL), then, TFA (1.5 mL) was added at 0° C. The mixture was warmed to rt for 2 hrs. The solvent was evaporated and purified by reverse phase chromatography eluted with ACN and water and dried using lyophilization to afford the title products as TFA-salt pink solids. ESI-MS, m/z 551.3 (M+23)⁺.

Step 2: Synthesis of 5-(2-((1-acetyl-4-methylpiperidin-4-yl)amino)-2-oxoacetyl)-N-(4-fluoro-3-methylphenyl)-1,2,4-trimethyl-1H-pyrrole-3-carboxamide To a solution of Example 612b (30 mg, 0.07 mmol), HATU (60 mg, 0.15 mmol) and DIPEA (20 μL). in DMF (1 mL) was added AcOH (30 mg) 0° C. The reaction mixture was stirred at rt for 20 hrs. The reaction mixture was quenched with aqueous TFA (4%, 0.4 mL), and purified by reverse phase chromatography eluted with ACN and water, and dried using lyophilization to afford the title product as white solid. ESI-MS, m/z 471.2 (MH)⁺.

492

Example 613: N-(4-fluoro-3-methylphenyl)-1,2,4-trimethyl-5-(2-((4-methyl-1-(methylsulfonyl)piperidin-4-yl)amino)-2-oxoacetyl)-1H-pyrrole-3-carboxamide DIPEA was added to a solution of 612b (30 mg, 0.07 mmol) and methanesulfonyl chloride (20 mg, 0.17 mmol) in DCM (1 mL) at 0° C. After 2 hrs at rt, the solvent was removed and the residue was purified by reverse phase chromatography eluted with ACN and water, and dried using lyophilization to afford the title product as white solid. ESI-MS, m/z 507.2 (MH)⁺.

Examples 640, 642, 644, 665, 667 and 669 were prepared in analogy to the procedures described above for Example 612, utilizing the requisite amines.

Example 614: N-ethyl-4-(2-(4-((4-fluoro-3-methylphenyl)carbamoyl)-1,3,5-trimethyl-1H-pyrrol-2-yl)-2-oxoacetamido)-4-methylpiperidine-1-carboxamide

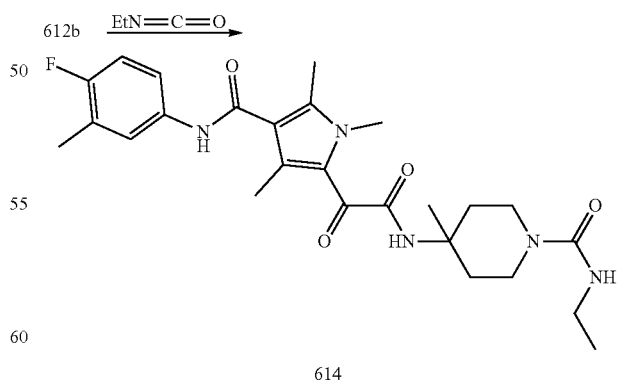

DIPEA was added to a solution of Example 612b (30 mg, 0.07 mmol) and isocyanatoethane (10 mg, 0.14 mmol) in DMA (1 mL) at 0° C. After 24 hrs at rt, the reaction mixture was purified by reverse phase chromatography eluted with ACN and water, and dried using lyophilization to afford the title product as white solid. ESI-MS, m/z 500.3 (MH)+.

Example 681: N-(4-fluoro-3-methylphenyl)-5-(2-((4-((1-hydroxy-2-methylpropan-2-yl)carbamoyl)tetrahydro-2H-pyran-4-yl)amino)-2-oxoacetyl)-1,2,4-trimethyl-1H-pyrrole-3-carboxamide

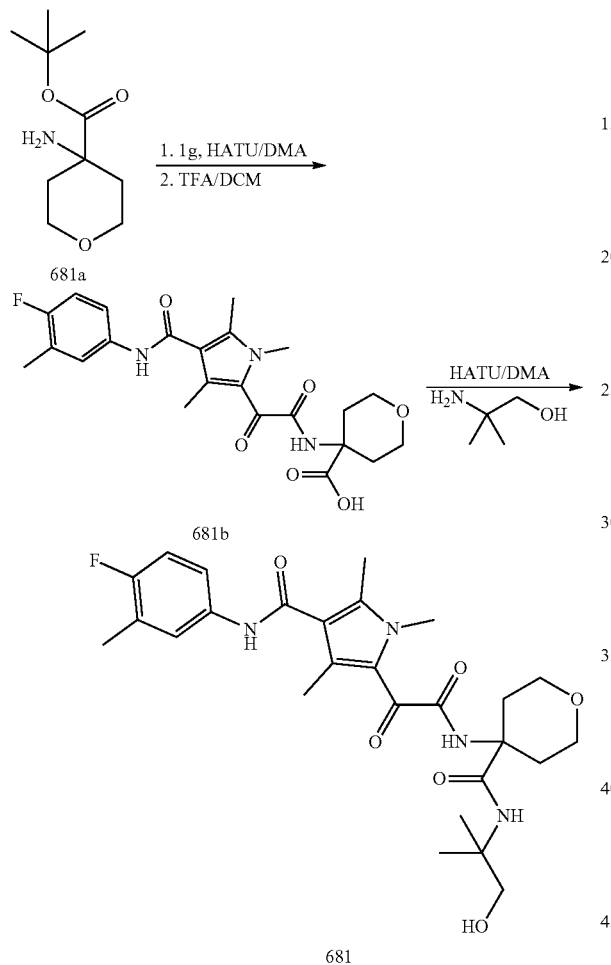

Step 1: Synthesis of 4-(2-(4-((4-fluoro-3-methylphenyl)carbamoyl)-1,3,5-trimethyl-1H-pyrrol-2-yl)-2-oxoacetamido)tetrahydro-2H-pyran-4-carboxylic acid To a mixture of 681a (100 mg, 0.5 mmol), 1 g (170 mg, 0.5 mmol) and HATU (200 mg, 0.52 mmol) in DMF (1 mL) was added DIPEA at 0° C. The reaction mixture was warmed to rt overnight. The reaction mixture was diluted with water, and extracted with EtOAc (2×10 mL). The combined extracts was washed with water and brine, and concentrated under vacuum. The residues was dissolved in DCM (2 mL), then, TFA (1.2 mL) was added at 0° C. The mixture was warmed to rt for 4 hrs, then, the solvent was evaporated and the residue was purified by reverse phase chromatography eluted with ACN and water and dried using lyophilization to afford the title products as white solids. ESI-MS, m/z 460.2 (MH)+.

Step 2: Synthesis N-(4-fluoro-3-methylphenyl)-5-(2-((4-((1-hydroxy-2-methylpropan-2-yl)carbamoyl)tetrahydro-2H-pyran-4-yl)amino)-2-oxoacetyl)-1,2,4-trimethyl-1H-pyrrole-3-carboxamide DIEPA (20 mg) was added to a solution of 681b (50 mg, 0.11 mmol), 2-amino-2-methylpropan-1-ol (12 mg) and HATU (60 mg, 0.16 mmol) in DMF at 0° C. The mixture was warmed to rt for 12 hrs. The reaction was quenched with aqueous HCl (0.2 N), and extracted with EtOAc. The organic layer was washed with water and brine, concentrated in vacuo, then, purified by reverse phase chromatography eluted with ACN and water, and dried using lyophilization to afford the title product as white solid. ESI-MS, m/z 531.3 (MH)+.

Examples 605, 682, and 683 were prepared in analogy to the procedures described above for Example 681, utilizing the requisite amines.

Example 695 and 712: N-(4-fluoro-3-methylphenyl)-5-(2-M3aS,4R,6S,6aR)-6-hydroxy-2,2-dimethyltetrahydro-4H-cyclopenta[d][1,3]dioxol-4-yl)amino)-2-oxoacetyl)-1,2,4-trimethyl-1H-pyrrole-3-carboxamide and N-(4-fluoro-3-methylphenyl)-1,2,4-trimethyl-5-(2-oxo-2-(((1R,2S,3R,4S)-2,3,4-trihydroxycyclopentyl)amino)acetyl)-1H-pyrrole-3-carboxamide

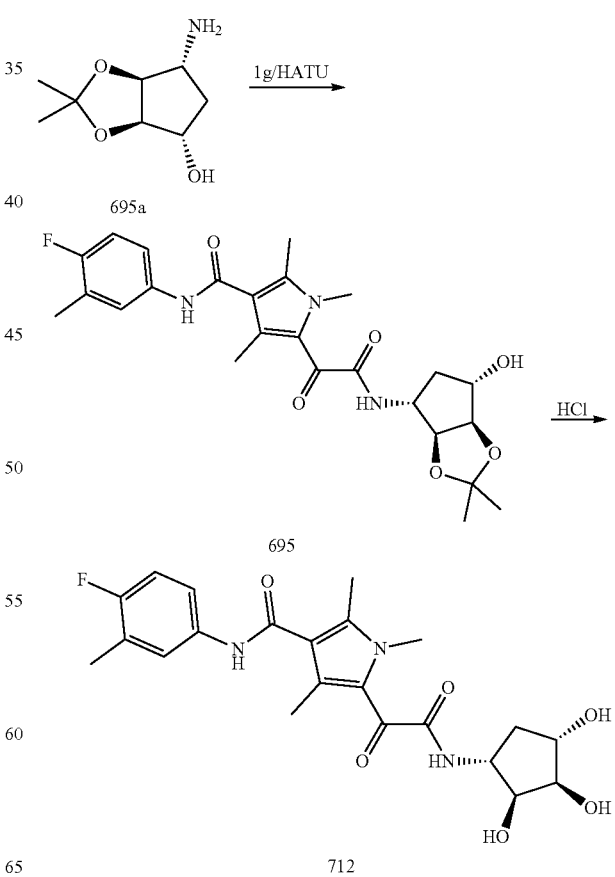

Step 1: Synthesis of N-(4-fluoro-3-methylphenyl)-5-(2-(((3aS,4R,6S,6aR)-6-hydroxy-2,2-dimethyltetrahydro-4H-cyclopenta[d][1,3]dioxol-4-yl)amino)-2-oxoacetyl)-1,2,4-trimethyl-1H-pyrrole-3-carboxamide The title compound was prepared from compound 695 following the procedure described in Example 2 Step 5, using 695a. The final product was purified by reverse phase chromatography eluted with ACN and water and dried using lyophilization to afford the title product as white solid. ESI-MS, m/z 488.2 (MH)⁺.

Step 2: Synthesis of N-(4-fluoro-3-methylphenyl)-1,2,4-trimethyl-5-(2-oxo-2-(((1R,2S,3R,4S)-2,3,4-trihydroxycyclopentyl)amino)acetyl)-1H-pyrrole-3-carboxamide HCl (2 N aqueous, 0.2 mL) was added to a solution of 695 (20 mg, 0.04 mmol) in MeOH/CH₃CN (1/1, 1 mL) at rt. After 20 hrs at rt, the reaction mixture was purified by reverse phase chromatography eluted with ACN and water and dried using lyophilization to afford the title product as white solid. ESI-MS, m/z 448.2 (MH)⁺.

Example 702 and 703: 5-(2-(((3S,4R)-3,4-dihydroxy-1-methylcyclohexyl)amino)-2-oxoacetyl)-N-(4-fluoro-3-methylphenyl)-1,2,4-trimethyl-1H-pyrrole-3-carboxamide and 5-(2-(((3R,4S)-3,4-dihydroxy-1-methylcyclohexyl)amino)-2-oxoacetyl)-N-(4-fluoro-3-methylphenyl)-1,2,4-trimethyl-1H-pyrrole-3-carboxamide

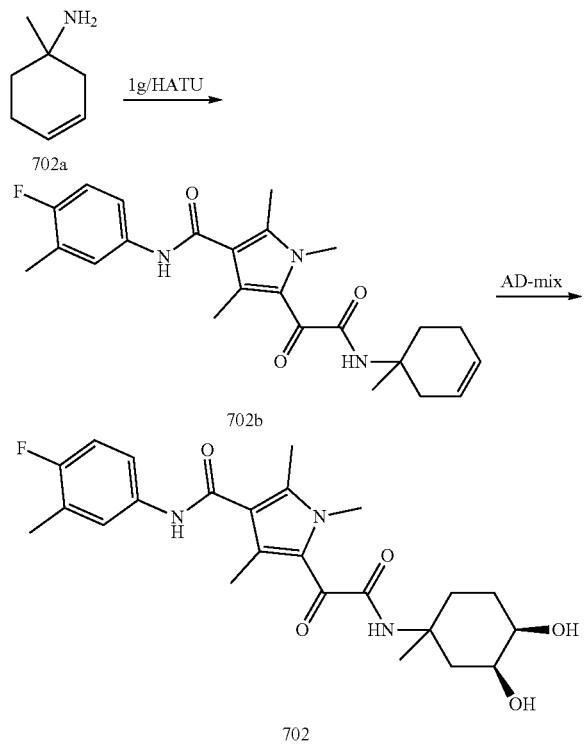

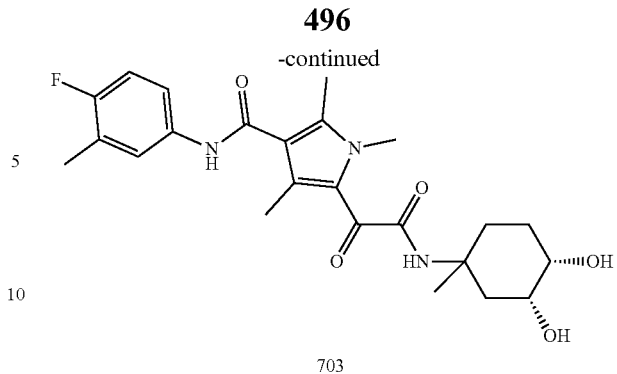

703

Step 1: Synthesis of N-(4-fluoro-3-methylphenyl)-1,2,4-trimethyl-5-(2-((1-methylcyclohex-3-en-1-yl)amino)-2-oxoacetyl)-1H-pyrrole-3-carboxamide The title compound was prepared from compound 702b following the procedure described in Example 2 Step 5, using 702a. The final product was purified by reverse phase chromatography eluted with ACN and water and dried using lyophilization to afford the title product as white solid. ESI-MS, m/z 426.2 (MH)⁺.

Step 2:

AD-mix-beta (1 g) was added to a solution of 702b (60 mg) in tBuOH/water (1/1, 10 mL) at 0° C. The reaction was stirred at rt for 36 hrs. The reaction was quenched with water and extracted with EtOAc. The organic layer was washed with water and brine, concentrated in vacuo, and purified by reverse phase chromatography eluted with ACN and water, and dried using lyophilization to afford 702 and 703 as white solid. ESI-MS, m/z 531.3 (MH)⁺.

Example 707 was prepared in the same procedure as described for Example 614, using 1,2-difluoro-4-isocyanatobenzene instead of isocyanatoethane.

Example 722 and 723: N-(4-fluoro-3-methylphenyl)-5-(2-(((1S,3R)-3-hydroxy-1-methylcyclopentyl)amino)-2-oxoacetyl)-1,2,4-trimethyl-1H-pyrrole-3-carboxamide and N-(4-fluoro-3-methylphenyl)-5-(2-(((1S,3S)-3-hydroxy-1-methylcyclopentyl)amino)-2-oxoacetyl)-1,2,4-trimethyl-1H-pyrrole-3-carboxamide

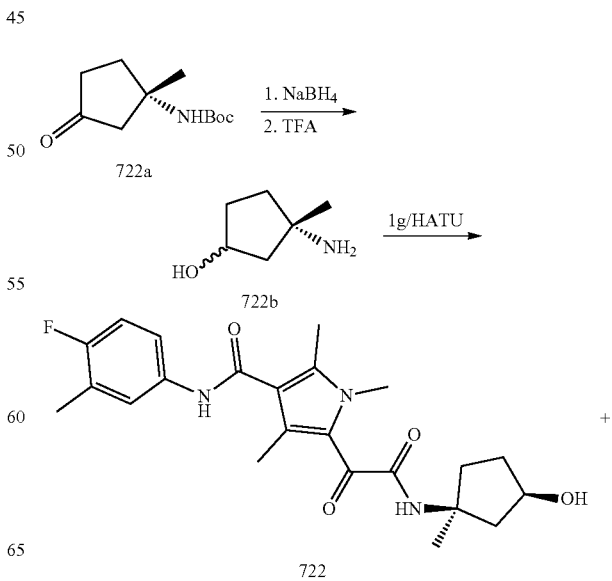

-continued

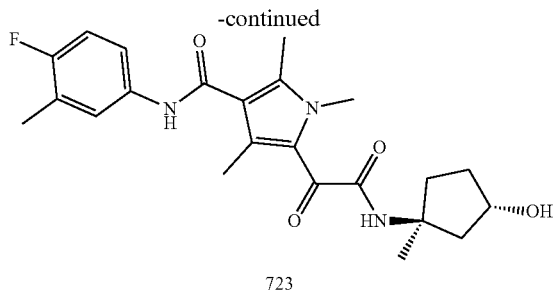

723

Step 1: Synthesis of
(3S)-3-amino-3-methylcyclopentan-1-ol

NaBH$_4$ (0.1 g) was added to a solution of 722a (0.25 g, 1.2 mmol) in 6 mL of THF/MeOH (20/1) at 0° C. The reaction mixture was warmed to rt for 2 hrs, then, concentrated. TFA (2 mL) was added to the residue in DCM (2 mL) at 0° C. The reaction mixture was stirred at rt for 12 hrs, then, concentrated and purified by reverse phase chromatography eluted with ACN and water and dried using lyophilization to afford the title product as white solid. ESI-MS, m/z 116.2 (MH)$^+$.

Step 2: Synthesis of 722 and 723

DIPEA was added to a solution of 722b (30 mg, 0.07 mmol), HATU (125 mg, 0.33 mmol) and 1g (90 mg, 0.27 mmol) in DMF (1 mL) at 0° C. The reaction mixture was stirred at rt for 20 hrs. The reaction mixture was quenched with aqueous TFA (4%, 0.4 mL), and purified by reverse phase chromatography eluted with ACN and water, and dried using lyophilization to afford 722 and 723 product as white solid. ESI-MS, m/z 430.2 (MH)$^+$.

Examples 729-759 were prepared in analogy to the procedures of Example 434, utilizing the requisite amine and the appropriate aryl amine for preparation of the required intermediates. The observed MS data for these Examples are shown in Table 1.

Example I: Oral Composition of a Compounds of Formula (I), (Ia)-(Id), or a Pharmaceutically Acceptable Salt, Solvate, or Stereoisomer Thereof To prepare a pharmaceutical composition for oral delivery, 400 mg of compound described herein, or a pharmaceutically acceptable salt, solvate, or stereoisomer thereof and the following ingredients are mixed intimately and pressed into single scored tablets.

| Tablet Formulation | |
| --- | --- |
| Ingredient | Quantity per tablet (mg) |
| compound | 400 |
| cornstarch | 50 |
| croscarmellose sodium | 25 |
| lactose | 120 |
| magnesium stearate | 5 |

The following ingredients are mixed intimately and loaded into a hard-shell gelatin capsule.

| Capsule Formulation | |
| --- | --- |
| Ingredient | Quantity per capsule (mg) |
| compound | 200 |
| lactose spray dried | 148 |
| magnesium stearate | 2 |

Example II: In Vitro Antiviral Assays

The anti-HBV activity of the Capsid Assembly Modulators (CAMs) was evaluated in a cell based assay utilizing the human hepatoma cell line HepAD38 (Ladner, S K., et al., 1998). HepAD38 cells were derived from the parental line, HepG2, that were stably transfected with a construct containing an HBV genome (genotype D, serotype ayw) under the control of a tetracycline repressible CMV promoter. Upon removal of tetracycline, viral pre-genomic RNA (pgRNA) and mRNAs are expressed and infectious viral particles are assembled and secreted into the culture medium providing a reliable, robust system to measure multiple steps of the HBV life cycle. Disruption of capsid formation results in reduced levels of DNA-containing virus particles that are released into the culture supernatant. To quantify the effect of CAMs on HBV replication, we developed a sensitive QPCR-based assay that measures extracellular HBV DNA levels upon treatment of HepAD38 cells with various concentrations of test compounds.

HepAD38 cells were maintained in DMEM/F12 medium containing 10% FBS, 400 μg/mL G418 and 0.3 μg/mL tetracycline (tet+ media) to maintain repression of HBV replication. To evaluate each compound, HepAD38 cells were seeded into 24-well collagen coated culture plates (Corning BioCoat) at a density of 200,000 cells per well in 1 mL of medium without tetracycline (tet-media) and allowed to adhere overnight at 37° C., 5% CO$_2$ in a humidified incubator. The following day, media was refreshed and a dose range of each compound was prepared by performing 1 log$_{10}$ serial dilutions in 100% DMSO at 200× the desired assay concentration. Dilutions were then added to the cells resulting in a final dose range of 1 μM to 10 pM and the plates were returned to the incubator. Following 7 days of incubation, culture supernatants were harvested and HBV DNA levels were evaluated by QPCR and compared to the vehicle treated control wells (i.e. DMSO alone).

To quantify HBV DNA levels, cell culture supernatants were diluted 1:10 in sterile, nuclease-free water (Gibco). The diluted supernatants were subsequently added to a PCR master mix containing 1× Roche Light Cycler Master Mix, 0.5 μM forward primer, 0.5 μM reverse primer (Fwd: 5'-TTGGTGTCTTTCGGAGTGTG (SEQ ID NO 1); Rev: 5'-AGGGGCATTTGGTGGTCTAT (SEQ ID NO 2)), 0.2 μM Roche Universal Probe Library Probe 25. The volume was brought to 20 μL with nuclease-free water and amplification of the HBV target sequence was performed using a Roche LightCycler 480 QPCR instrument. PCR extended out to 45 cycles with each cycle consisting of a denaturation step at 95° C. for 10 sec., followed by an annealing step at 60° C. for 10 sec. and a brief extension step at 72° C. for 1 sec.

Extracellular HBV DNA levels, expressed in copies/mL, were determined by comparison to a standard curve (10$^2$-10$^9$ copies/mL) using the Roche LightCycler analysis software. These values were subsequently converted to percent inhibition of HBV replication by dividing the HBV DNA levels in the experimental samples with those obtained from the vehicle control (~1-2×105 copies/mL). Potency, expressed as an $EC_{50}$ (the effective concentration required to inhibit 50% of HBV replication), was calculated from the dose-response curve using a 4-parameter non-linear regression analysis (GraphPad Prism). The nucleoside analog inhibitor entecavir was used as a positive control to validate each assay run. The $EC_{50}$ value of entecavir in the HepAD38 assay was 0.5 nM, as previously reported in the literature.

Table 2 summarizes the antiviral activity of the exemplary compounds. A: $EC_{50}$>1 μM; B: $EC_{50}$ values between 0.5 μM and 1 μM, inclusive; C: $EC_{50}$ values between 0.05 μM and 0.499 μM, inclusive; D: $EC_{50}$ values <0.05 μM. NT=not tested. NA=not available.

TABLE 2

Summary of anti-HBV replication in HepAD38 cells.

| Ex. | Anti-HBV $EC_{50}$ | Ex. | Anti-HBV $EC_{50}$ | Ex. | Anti-HBV $EC_{50}$ | Ex. | Anti-HBV $EC_{50}$ | Ex. | Anti-HBV $EC_{50}$ |
|---|---|---|---|---|---|---|---|---|---|
| 1 | D | 2 | D | 3 | D | 4 | D | 5 | C |
| 6 | D | 7 | D | 8 | D | 9 | D | 10 | D |
| 11 | D | 12 | D | 13 | D | 14 | D | 15 | D |
| 16 | C | 17 | D | 18 | D | 19 | D | 20 | D |
| 21 | C | 22 | D | 23 | C | 24 | D | 25 | C |
| 26 | D | 27 | A | 28 | D | 29 | B | 30 | A |
| 31 | C | 32 | A | 33 | A | 34 | A | 35 | A |
| 36 | D | 37 | D | 38 | D | 39 | B | 40 | B |
| 41 | D | 42 | D | 43 | D | 44 | D | 45 | B |
| 46 | D | 47 | C | 48 | C | 49 | C | 50 | A |
| 51 | C | 52 | A | 53 | C | 54 | C | 55 | B |
| 56 | D | 57 | C | 58 | B | 59 | D | 60 | D |
| 61 | C | 62 | D | 63 | D | 64 | D | 65 | D |
| 66 | D | 67 | D | 68 | A | 69 | B | 70 | D |
| 71 | A | 72 | A | 73 | A | 74 | D | 75 | D |
| 76 | D | 77 | C | 78 | D | 79 | C | 80 | C |
| 81 | D | 82 | D | 83 | D | 84 | D | 85 | D |
| 86 | D | 87 | D | 88 | D | 89 | D | 90 | D |
| 91 | D | 92 | C | 93 | C | 94 | D | 95 | D |
| 96 | D | 97 | D | 98 | D | 99 | C | 100 | A |
| 101 | A | 102 | D | 103 | D | 104 | D | 105 | D |
| 106 | D | 107 | D | 108 | D | 109 | D | 110 | D |
| 111 | D | 112 | C | 113 | D | 114 | D | 115 | D |
| 116 | D | 117 | C | 118 | D | 119 | D | 120 | B |
| 121 | D | 122 | D | 123 | C | 124 | D | 125 | D |
| 126 | D | 127 | D | 128 | D | 129 | D | 130 | C |
| 131 | C | 132 | C | 133 | C | 134 | C | 135 | C |
| 136 | D | 137 | D | 138 | D | 139 | D | 140 | D |
| 141 | D | 142 | D | 143 | D | 144 | D | 145 | D |
| 146 | D | 147 | D | 148 | D | 149 | D | 150 | D |
| 151 | D | 152 | D | 153 | D | 154 | D | 155 | D |
| 156 | D | 157 | C | 158 | D | 159 | D | 160 | C |
| 161 | D | 162 | C | 163 | A | 164 | B | 165 | D |
| 166 | D | 167 | D | 168 | C | 169 | D | 170 | D |
| 171 | D | 172 | D | 173 | D | 174 | C | 175 | C |
| 176 | C | 177 | C | 178 | C | 179 | D | 180 | D |
| 181 | D | 182 | D | 183 | B | 184 | D | 185 | B |
| 186 | C | 187 | A | 188 | C | 189 | D | 190 | D |
| 191 | D | 192 | B | 193 | A | 194 | C | 195 | D |
| 196 | C | 197 | C | 198 | C | 199 | D | 200 | C |
| 201 | C | 202 | C | 203 | D | 204 | D | 205 | D |
| 206 | D | 207 | D | 208 | D | 209 | D | 210 | D |
| 211 | D | 212 | D | 213 | D | 214 | D | 215 | D |
| 216 | D | 217 | D | 218 | D | 219 | D | 220 | D |
| 221 | D | 222 | A | 223 | D | 224 | C | 225 | B |
| 226 | B | 227 | D | 228 | D | 229 | D | 230 | D |
| 231 | D | 232 | D | 233 | C | 234 | D | 235 | NT |
| 236 | D | 237 | NT | 238 | D | 239 | B | 240 | C |
| 241 | D | 242 | C | 243 | D | 244 | C | 245 | D |
| 246 | D | 247 | D | 248 | C | 249 | D | 250 | D |
| 251 | D | 252 | C | 253 | D | 254 | D | 255 | D |
| 256 | C | 257 | C | 258 | D | 259 | D | 260 | D |
| 261 | D | 262 | D | 263 | D | 264 | D | 265 | C |
| 266 | C | 267 | D | 268 | D | 269 | D | 270 | D |
| 271 | D | 272 | D | 273 | D | 274 | D | 275 | D |
| 276 | D | 277 | D | 278 | D | 279 | C | 280 | D |
| 281 | D | 282 | D | 283 | D | 284 | D | 285 | D |
| 286 | D | 287 | D | 288 | D | 289 | D | 290 | D |
| 291 | D | 292 | C | 293 | D | 294 | B | 295 | D |
| 296 | D | 297 | D | 298 | D | 299 | C | 300 | C |
| 301 | D | 302 | D | 303 | D | 304 | D | 305 | A |
| 306 | D | 307 | D | 308 | B | 309 | C | 310 | D |
| 311 | D | 312 | D | 313 | D | 314 | D | 315 | D |
| 316 | D | 317 | A | 318 | C | 319 | D | 320 | D |
| 321 | D | 322 | D | 323 | D | 324 | D | 325 | C |
| 326 | D | 327 | D | 328 | C | 329 | B | 330 | D |
| 331 | D | 332 | D | 333 | D | 334 | D | 335 | D |
| 336 | D | 337 | B | 338 | B | 339 | B | 340 | B |
| 341 | C | 342 | B | 343 | C | 344 | C | 345 | D |
| 346 | D | 347 | D | 348 | D | 349 | A | 350 | B |
| 351 | C | 352 | C | 353 | C | 354 | D | 355 | D |
| 356 | D | 357 | D | 358 | C | 359 | D | 360 | NA |
| 361 | NA | 362 | NA | 363 | D | 364 | D | 365 | D |
| 366 | D | 367 | D | 368 | C | 369 | D | 370 | D |
| 371 | C | 372 | D | 373 | D | 374 | D | 375 | D |
| 376 | D | 377 | D | 378 | D | 379 | C | 380 | D |
| 381 | C | 382 | A | 383 | B | 384 | A | 385 | A |
| 386 | A | 387 | A | 388 | A | 389 | A | 390 | C |
| 391 | A | 392 | A | 393 | C | 394 | C | 395 | A |
| 396 | C | 397 | C | 398 | C | 399 | C | 400 | C |
| 401 | A | 402 | C | 403 | C | 404 | C | 405 | C |
| 406 | B | 407 | C | 408 | C | 409 | C | 410 | C |
| 411 | C | 412 | C | 413 | C | 414 | C | 415 | A |
| 416 | A | 417 | C | 418 | C | 419 | A | 420 | C |
| 421 | A | 422 | A | 423 | A | 424 | C | 425 | C |
| 426 | C | 427 | C | 428 | C | 429 | C | 430 | C |
| 431 | C | 432 | C | 433 | B | 434 | D | 435 | A |
| 436 | C | 437 | C | 438 | C | 439 | C | 440 | C |
| 441 | D | 442 | D | 443 | D | 444 | D | 445 | D |
| 446 | C | 447 | D | 448 | D | 449 | C | 450 | C |
| 451 | C | 452 | D | 453 | C | 454 | C | 455 | D |
| 456 | B | 457 | C | 458 | B | 459 | C | 460 | D |
| 461 | D | 462 | C | 463 | C | 464 | C | 465 | D |
| 466 | C | 467 | B | 468 | C | 469 | B | 470 | B |
| 471 | B | 472 | A | 473 | B | 474 | B | 475 | B |
| 476 | A | 477 | A | 478 | A | 479 | NA | 480 | NA |
| 481 | NA | 482 | NA | 483 | NA | 484 | NA | 485 | NA |
| 486 | NA | 487 | NA | 488 | NA | 489 | D | 490 | D |
| 491 | D | 492 | D | 493 | D | 494 | D | 495 | D |
| 496 | D | 497 | C | 498 | C | 499 | D | 500 | D |
| 501 | C | 502 | C | 503 | D | 504 | C | 505 | B |
| 506 | B | 507 | C | 508 | B | 509 | B | 510 | A |
| 511 | C | 512 | B | 513 | C | 514 | C | 515 | D |
| 516 | C | 517 | C | 518 | C | 519 | C | 520 | D |
| 521 | A | 522 | A | 523 | C | 524 | C | 525 | A |
| 526 | A | 527 | B | 528 | B | 529 | A | 530 | A |
| 531 | C | 532 | B | 533 | B | 534 | C | 535 | D |
| 536 | D | 537 | C | 538 | NA | 539 | D | 540 | D |
| 541 | D | 542 | D | 543 | D | 544 | D | 545 | D |
| 546 | D | 547 | C | 548 | D | 549 | B | 550 | D |
| 551 | C | 552 | D | 553 | D | 554 | D | 555 | C |
| 556 | C | 557 | D | 558 | D | 559 | C | 560 | D |
| 561 | D | 562 | D | 563 | D | 564 | D | 565 | D |
| 566 | D | 567 | D | 568 | D | 569 | D | 570 | D |
| 571 | C | 572 | D | 573 | C | 574 | B | 575 | B |
| 576 | C | 577 | A | 578 | B | 579 | B | 580 | D |
| 581 | D | 582 | A | 583 | D | 584 | D | 587 | C |
| 588 | C | 589 | B | 590 | B | 595 | B | 596 | C |
| 597 | D | 598 | D | 599 | D | 600 | D | 601 | D |
| 602 | D | 603 | D | 604 | D | 605 | D | 606 | D |
| 607 | D | 608 | D | 609 | D | 610 | D | 611 | D |
| 612 | D | 613 | D | 614 | D | 615 | D | 616 | D |
| 617 | D | 618 | D | 619 | D | 620 | D | 621 | D |
| 622 | D | 623 | D | 624 | D | 625 | D | 626 | D |
| 627 | D | 628 | D | 629 | D | 630 | D | 631 | D |
| 632 | D | 633 | D | 634 | D | 635 | D | 636 | D |
| 637 | D | 638 | D | 639 | D | 640 | D | 641 | D |
| 642 | D | 643 | C | 644 | D | 645 | D | 646 | D |
| 647 | D | 648 | D | 649 | D | 650 | C | 651 | D |
| 652 | D | 653 | C | 654 | D | 655 | D | 656 | D |

TABLE 2-continued

Summary of anti-HBV replication in HepAD38 cells.

| Ex. | Anti-HBV EC$_{50}$ | Ex. | Anti-HBV EC$_{50}$ | Ex. | Anti-HBV EC$_{50}$ | Ex. | Anti-HBV EC$_{50}$ | Ex. | Anti-HBV EC$_{50}$ |
|---|---|---|---|---|---|---|---|---|---|
| 657 | D | 658 | D | 659 | D | 660 | D | 661 | D |
| 662 | D | 663 | D | 664 | D | 665 | D | 666 | D |
| 667 | D | 668 | D | 669 | D | 670 | D | 671 | D |
| 672 | D | 673 | D | 674 | C | 675 | D | 676 | D |
| 677 | D | 678 | D | 679 | D | 680 | D | 681 | D |
| 682 | D | 683 | D | 684 | D | 685 | D | 686 | D |
| 687 | D | 688 | D | 689 | D | 690 | D | 691 | D |
| 692 | D | 693 | D | 694 | D | 695 | D | 696 | D |
| 697 | D | 698 | C | 699 | D | 700 | D | 701 | D |
| 702 | D | 703 | D | 704 | D | 705 | D | 706 | D |
| 707 | D | 708 | D | 709 | D | 710 | D | 711 | D |
| 712 | D | 713 | D | 714 | D | 715 | D | 716 | D |
| 717 | D | 718 | D | 719 | D | 720 | D | 721 | D |
| 722 | D | 723 | D | 724 | D | 725 | D | 726 | D |
| 727 | D | 728 | D | 729 | C | 730 | C | 731 | D |
| 732 | C | 733 | D | 734 | D | 735 | D | 736 | D |
| 737 | D | 738 | C | 739 | C | 740 | D | 741 | C |
| 742 | C | 743 | C | 744 | C | 745 | C | 746 | C |
| 748 | C | 749 | C | 750 | C | 751 | C | 752 | C |
| 753 | C | 754 | C | 756 | C | 757 | C | 758 | C |
| 759 | C | | | | | | | | |

Example III: In Vitro Cytotoxicity Assays

To evaluate antiviral selectivity, the cytotoxic activity of each compound was determined using a standard cell viability assay performed on the parental HepG2 cell line. Cell viability was determined by measuring the conversion of 3-(4,5-dimethylthiazol-2-yl)-2,5-diphenyltetrazolium bromide (MTT) to the insoluble formazan salt crystal that occurs in live cells. Briefly, HepG2 cells were seeded in 96-well plates at a density of 20,000 cells per well in EMEM+10% FBS (complete growth medium) and allowed to adhere overnight in a 37° C., 5% CO$_2$ humidified incubator. The next day, test agents were prepared by performing 8 half-log$_{10}$ serial dilutions in 100% DMSO at 200× the final desired concentration in the assay. Compounds were tested over a range of concentrations from 30 μM to 1.0 nM in the assay. HepG2 cells were incubated in the presence of various concentrations of CAMs for 7 days in a 37° C., 5% CO$_2$ humidified incubator. At the completion of the 7-day incubation period, MTT reagent was added to each well and the mixture was incubated for an additional 3-4 hours. At the completion of the incubation period, all wells were aspirated to remove the culture medium. The formazan crystals were solubilized from the cell monolayers with 100% DMSO. Plates were briefly mixed on an orbital shaker and absorbance was measured at 492 nm using a Perkin-Elmer EnVision multi-label plate reader. All absorbance values were converted to a percentage of the signal obtained from the vehicle treated controls. Absorbance values at 492 nm are directly proportional to the number of viable cells present in the sample. A CC$_{50}$ value (cytotoxic concentration that results in loss of 50% cell viability) was calculated from the dose-response curve by 4-parameter, non-linear regression analysis using the GraphPad Prism software. The positive control compound, staurosporine, reduced the viability of HepG2 cells in a dose-dependent manner (CC$_{50}$=100 nM).

Table 3 summarizes the cytotoxicity assay data in the hepatocyte cell line HepG2 for the example compounds. A: CC$_{50}$>30 μM; B: CC$_{50}$ values between 5 μM and 30 μM, inclusive; C: CC$_{50}$ values between 0.5 μM and 4.99 μM, inclusive; D: CC$_{50}$ values <0.5 μM. NT=not tested. NA=not available.

TABLE 3

Summary of cytotoxicity results in HepG2 cells for example compounds.

| Ex. | HepG2 CC$_{50}$ | Ex. | HepG2 CC$_{50}$ | Ex. | HepG2 CC$_{50}$ | Ex. | HepG2 CC$_{50}$ | Ex. | HepG2 CC$_{50}$ |
|---|---|---|---|---|---|---|---|---|---|
| 1 | A | 2 | A | 3 | B | 4 | A | 5 | A |
| 6 | A | 7 | A | 8 | A | 9 | A | 10 | B |
| 11 | A | 12 | A | 13 | A | 14 | B | 15 | A |
| 16 | B | 17 | C | 18 | A | 19 | B | 20 | C |
| 21 | A | 22 | A | 23 | A | 24 | A | 25 | A |
| 26 | A | 27 | A | 28 | A | 29 | A | 30 | A |
| 31 | A | 32 | A | 33 | A | 34 | A | 35 | A |
| 36 | A | 37 | A | 38 | A | 39 | A | 40 | C |
| 41 | C | 42 | A | 43 | C | 44 | A | 45 | A |
| 46 | A | 47 | C | 48 | A | 49 | A | 50 | A |
| 51 | A | 52 | A | 53 | A | 54 | A | 55 | C |
| 56 | C | 57 | A | 58 | A | 59 | A | 60 | A |
| 61 | A | 62 | A | 63 | A | 64 | B | 65 | A |
| 66 | A | 67 | A | 68 | A | 69 | A | 70 | A |
| 71 | A | 72 | A | 73 | A | 74 | A | 75 | B |
| 76 | B | 77 | A | 78 | A | 79 | A | 80 | A |
| 81 | A | 82 | A | 83 | B | 84 | A | 85 | A |
| 86 | B | 87 | A | 88 | B | 89 | A | 90 | B |
| 91 | A | 92 | A | 93 | A | 94 | A | 95 | A |
| 96 | A | 97 | A | 98 | A | 99 | A | 100 | B |
| 101 | B | 102 | C | 103 | A | 104 | A | 105 | B |
| 106 | C | 107 | A | 108 | C | 109 | A | 110 | A |
| 111 | A | 112 | A | 113 | A | 114 | A | 115 | A |
| 116 | A | 117 | A | 118 | A | 119 | A | 120 | A |
| 121 | A | 122 | A | 123 | A | 124 | B | 125 | C |
| 126 | A | 127 | A | 128 | A | 129 | A | 130 | A |
| 131 | A | 132 | A | 133 | A | 134 | A | 135 | B |
| 136 | A | 137 | A | 138 | C | 139 | A | 140 | A |
| 141 | A | 142 | A | 143 | A | 144 | A | 145 | A |
| 146 | A | 147 | A | 148 | A | 149 | A | 150 | A |
| 151 | A | 152 | A | 153 | B | 154 | A | 155 | A |
| 156 | A | 157 | A | 158 | A | 159 | A | 160 | A |
| 161 | A | 162 | A | 163 | A | 164 | A | 165 | A |
| 166 | A | 167 | A | 168 | A | 169 | A | 170 | A |
| 171 | A | 172 | A | 173 | A | 174 | A | 175 | A |
| 176 | A | 177 | B | 178 | B | 179 | B | 180 | B |
| 181 | A | 182 | A | 183 | A | 184 | A | 185 | A |
| 186 | A | 187 | A | 188 | A | 189 | A | 190 | A |
| 191 | A | 192 | A | 193 | A | 194 | A | 195 | A |
| 196 | A | 197 | A | 198 | A | 199 | A | 200 | A |
| 201 | A | 202 | A | 203 | A | 204 | A | 205 | A |
| 206 | A | 207 | A | 208 | A | 209 | A | 210 | A |
| 211 | A | 212 | B | 213 | A | 214 | A | 215 | A |
| 216 | B | 217 | A | 218 | B | 219 | A | 220 | B |
| 221 | B | 222 | A | 223 | B | 224 | A | 225 | A |
| 226 | A | 227 | A | 228 | A | 229 | A | 230 | A |
| 231 | B | 232 | A | 233 | A | 234 | A | 235 | NT |
| 236 | B | 237 | NT | 238 | A | 239 | A | 240 | A |
| 241 | A | 242 | A | 243 | B | 244 | B | 245 | A |
| 246 | B | 247 | B | 248 | B | 249 | B | 250 | B |
| 251 | A | 252 | A | 253 | A | 254 | B | 255 | B |
| 256 | B | 257 | B | 258 | B | 259 | A | 260 | B |
| 261 | C | 262 | B | 263 | A | 264 | B | 265 | A |
| 266 | A | 267 | A | 268 | B | 269 | B | 270 | A |
| 271 | A | 272 | A | 273 | A | 274 | A | 275 | A |
| 276 | A | 277 | A | 278 | A | 279 | A | 280 | A |
| 281 | B | 282 | A | 283 | A | 284 | A | 285 | A |
| 286 | A | 287 | A | 288 | A | 289 | B | 290 | A |
| 291 | A | 292 | A | 293 | B | 294 | A | 295 | B |
| 296 | A | 297 | B | 298 | A | 299 | A | 300 | A |
| 301 | A | 302 | A | 303 | A | 304 | B | 305 | A |
| 306 | A | 307 | A | 308 | A | 309 | A | 310 | E |
| 311 | A | 312 | B | 313 | B | 314 | B | 315 | A |
| 316 | A | 317 | B | 318 | A | 319 | B | 320 | A |
| 321 | B | 322 | B | 323 | B | 324 | B | 325 | A |
| 326 | A | 327 | A | 328 | A | 329 | A | 330 | A |
| 331 | A | 332 | A | 333 | A | 334 | A | 335 | A |
| 336 | B | 337 | B | 338 | A | 339 | A | 340 | A |
| 341 | A | 342 | A | 343 | A | 344 | A | 345 | A |

TABLE 3-continued

Summary of cytotoxicity results in HepG2 cells for example compounds.

| Ex. | HepG2 CC$_{50}$ | Ex. | HepG2 CC$_{50}$ | Ex. | HepG2 CC$_{50}$ | Ex. | HepG2 CC$_{50}$ | Ex. | HepG2 CC$_{50}$ |
|---|---|---|---|---|---|---|---|---|---|
| 346 | A | 347 | A | 348 | A | 349 | A | 350 | A |
| 351 | A | 352 | A | 353 | A | 354 | A | 355 | A |
| 356 | A | 357 | A | 358 | A | 359 | A | 360 | NA |
| 361 | NA | 362 | NA | 363 | A | 364 | B | 365 | A |
| 366 | A | 367 | B | 368 | A | 369 | A | 370 | A |
| 371 | A | 372 | C | 373 | C | 374 | C | 375 | A |
| 376 | B | 377 | A | 378 | A | 379 | A | 380 | A |
| 381 | A | 382 | A | 383 | A | 384 | A | 385 | A |
| 386 | B | 387 | B | 388 | B | 389 | B | 390 | A |
| 391 | A | 392 | B | 393 | A | 394 | A | 395 | C |
| 396 | B | 397 | B | 398 | A | 399 | A | 400 | A |
| 401 | A | 402 | A | 403 | A | 404 | A | 405 | A |
| 406 | A | 407 | A | 408 | A | 409 | A | 410 | A |
| 411 | A | 412 | B | 413 | A | 414 | A | 415 | A |
| 416 | A | 417 | A | 418 | A | 419 | A | 420 | A |
| 421 | A | 422 | A | 423 | B | 424 | A | 425 | A |
| 426 | A | 427 | A | 428 | A | 429 | A | 430 | A |
| 431 | A | 432 | A | 433 | A | 434 | A | 435 | B |
| 436 | A | 437 | A | 438 | A | 439 | A | 440 | A |
| 441 | B | 442 | B | 443 | B | 444 | B | 445 | B |
| 446 | B | 447 | B | 448 | B | 449 | A | 450 | A |
| 451 | B | 452 | B | 453 | A | 454 | A | 455 | B |
| 456 | A | 457 | A | 458 | B | 459 | B | 460 | B |
| 461 | B | 462 | B | 463 | B | 464 | A | 465 | B |
| 466 | A | 467 | A | 468 | A | 469 | B | 470 | B |
| 471 | A | 472 | A | 473 | A | 474 | A | 475 | A |
| 476 | B | 477 | A | 478 | A | 489 | A | 490 | A |
| 491 | A | 492 | B | 493 | B | 494 | B | 495 | B |
| 496 | B | 497 | C | 498 | A | 499 | A | 500 | B |
| 501 | B | 502 | A | 503 | A | 504 | B | 505 | A |
| 506 | B | 507 | A | 508 | A | 509 | A | 510 | A |
| 511 | A | 512 | A | 513 | A | 514 | B | 515 | B |
| 516 | A | 517 | B | 518 | B | 519 | B | 520 | A |
| 521 | A | 522 | A | 523 | B | 524 | B | 525 | A |
| 526 | A | 527 | C | 528 | C | 529 | A | 530 | A |
| 531 | A | 532 | C | 533 | A | 534 | B | 535 | C |
| 536 | A | 537 | A | 538 | NA | 539 | B | 540 | A |
| 541 | A | 542 | A | 543 | A | 544 | A | 545 | B |
| 546 | A | 547 | B | 548 | B | 549 | A | 550 | A |
| 551 | A | 552 | B | 553 | B | 554 | B | 555 | B |
| 556 | B | 557 | B | 558 | A | 559 | A | 560 | A |
| 561 | A | 562 | B | 563 | B | 564 | B | 565 | B |
| 566 | B | 567 | A | 568 | B | 569 | A | 570 | A |
| 571 | A | 572 | A | 573 | B | 574 | B | 575 | A |
| 576 | B | 577 | A | 578 | A | 579 | A | 580 | B |
| 581 | B | 582 | A | 583 | A | 584 | B | 585 | NA |
| 586 | NA | 587 | A | 588 | B | 589 | A | 590 | A |
| 595 | A | 596 | A | 597 | A | 598 | A | 599 | A |
| 600 | A | 601 | A | 602 | A | 603 | B | 604 | B |
| 605 | A | 606 | A | 607 | A | 608 | A | 609 | A |
| 610 | A | 611 | A | 612 | A | 613 | A | 614 | A |
| 615 | A | 616 | A | 617 | A | 618 | A | 619 | A |
| 620 | A | 621 | A | 622 | A | 623 | A | 624 | A |
| 625 | A | 626 | A | 627 | A | 628 | A | 629 | A |
| 630 | A | 631 | A | 632 | A | 633 | A | 634 | A |
| 635 | A | 636 | A | 637 | A | 638 | A | 639 | A |
| 640 | B | 641 | A | 642 | B | 643 | A | 644 | B |
| 645 | A | 646 | B | 647 | A | 648 | A | 649 | A |
| 650 | A | 651 | A | 652 | A | 653 | A | 654 | A |
| 655 | A | 656 | B | 657 | B | 658 | B | 659 | A |
| 660 | A | 661 | B | 662 | A | 663 | A | 664 | A |
| 665 | B | 666 | A | 667 | C | 668 | A | 669 | A |
| 670 | A | 671 | A | 672 | A | 673 | A | 674 | B |
| 675 | A | 676 | A | 677 | A | 678 | B | 679 | A |
| 680 | A | 681 | A | 682 | A | 683 | A | 684 | A |
| 685 | A | 686 | C | 687 | B | 688 | A | 689 | A |
| 690 | A | 691 | A | 692 | A | 693 | A | 694 | A |
| 695 | A | 696 | A | 697 | A | 698 | A | 699 | B |
| 700 | A | 701 | A | 702 | A | 703 | A | 704 | A |
| 705 | A | 706 | A | 707 | C | 708 | A | 709 | A |
| 710 | A | 711 | A | 712 | A | 713 | A | 714 | A |
| 715 | B | 716 | A | 717 | B | 718 | B | 719 | A |
| 720 | A | 721 | A | 722 | A | 723 | A | 724 | A |
| 725 | A | 726 | A | 727 | A | 728 | A | 729 | A |
| 730 | A | 731 | B | 732 | A | 733 | B | 734 | A |
| 735 | B | 736 | B | 737 | A | 738 | A | 739 | A |
| 740 | A | 741 | A | 742 | A | 743 | A | 744 | A |
| 745 | A | 746 | A | 748 | A | 749 | A | 750 | A |
| 751 | A | 752 | A | 753 | A | 754 | A | 756 | A |
| 757 | A | 758 | A | 759 | A | | | | |

What is claimed is:

1. A compound of Formula (Ia), or a pharmaceutically acceptable salt, solvate, or stereoisomer thereof:

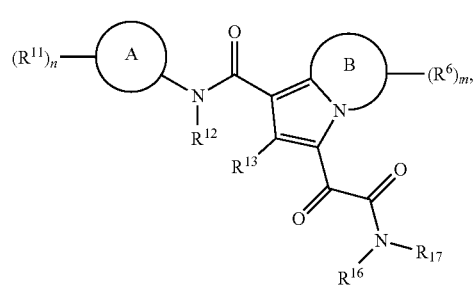

wherein:
Ring A is aryl;
each $R^{11}$ is independently halogen;
n is 2 or 3;
$R^{12}$ is hydrogen;

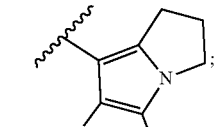

is

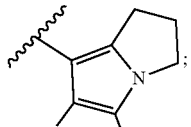

$R^{13}$ is hydrogen, halogen, or $C_1$-$C_6$alkyl;
$R^{16}$ is hydrogen or $C_1$-$C_6$alkyl;
$R^{17}$ is cycloalkyl optionally substituted with one, two, or three $R^7$;
each $R^7$ is independently $C_1$-$C_6$alkyl optionally substituted with one, two, or three $R^{7a}$;
each $R^{7a}$ is independently halogen, —CN, —OH, —OR$^a$, —NR$^b$R$^c$, —C(=O)R$^a$, —C(=O)OR$^b$, or —C(=O)NR$^b$R$^c$;
each R$^a$ is independently $C_1$-$C_6$alkyl or $C_1$-$C_6$haloalkyl; and each $R^b$ and $R^c$ are independently hydrogen, $C_1$-$C_6$alkyl, or $C_1$-$C_6$haloalkyl.

2. The compound of claim 1, or a pharmaceutically acceptable salt, solvate, or stereoisomer thereof, wherein:
Ring A is phenyl; n is 2 or 3; and each $R^{11}$ is independently fluorine.

3. The compound of claim 1, or a pharmaceutically acceptable salt, solvate, or stereoisomer thereof, wherein:

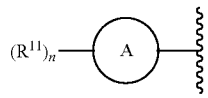

is

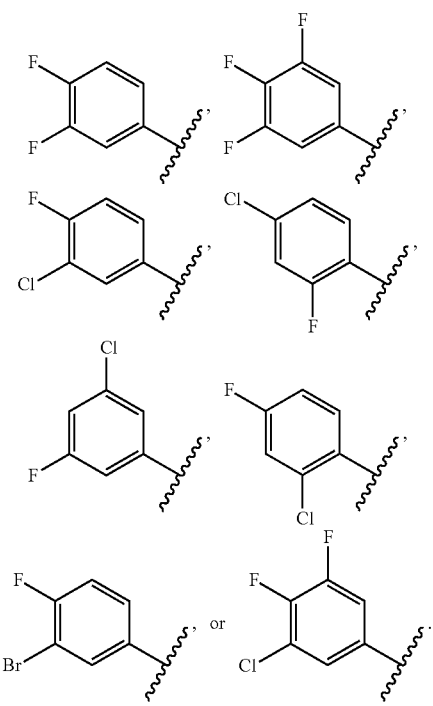

4. The compound of claim 1, or a pharmaceutically acceptable salt, solvate, or stereoisomer thereof, wherein:

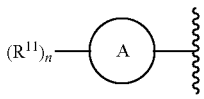

is

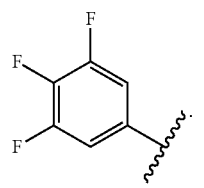

5. The compound of claim 1, or a pharmaceutically acceptable salt, solvate, or stereoisomer thereof, wherein:
$R^{13}$ is halogen.

6. The compound of claim 1, or a pharmaceutically acceptable salt, solvate, or stereoisomer thereof, wherein:
$R^{16}$ is hydrogen.

7. The compound of claim 1, or a pharmaceutically acceptable salt, solvate, or stereoisomer thereof, wherein:
$R^{17}$ is cyclohexyl optionally substituted with one, two, or three $R^7$.

8. The compound of claim 1, or a pharmaceutically acceptable salt, solvate, or stereoisomer thereof, wherein:
each $R^7$ is independently $C_1$-$C_6$alkyl optionally substituted with one $R^{7a}$.

9. The compound of claim 1, or a pharmaceutically acceptable salt, solvate, or stereoisomer thereof, wherein:
each $R^{7a}$ is independently —C(=O)$OR^b$.

10. A pharmaceutical composition comprising a compound of claim 1, or a pharmaceutically acceptable salt, solvate, or stereoisomer thereof, and a pharmaceutically acceptable excipient.

11. A method of treating hepatitis B in a subject, comprising administering to the subject a compound of claim 1, or a pharmaceutically acceptable salt, solvate, or stereoisomer thereof.

* * * * *